(12) United States Patent
Tseng et al.

(10) Patent No.: US 10,717,763 B2
(45) Date of Patent: *Jul. 21, 2020

(54) COMPOSITIONS CONTAINING HC-HA/PTX3 COMPLEXES AND METHODS OF USE THEREOF

(71) Applicant: TissueTech, Inc., Miami, FL (US)

(72) Inventors: Scheffer Tseng, Pinecrest, FL (US); Hua He, Miami, FL (US); Sean Tighe, Tampa, FL (US); Suzhen Zhang, Miami, FL (US); Ying-Tieng Zhu, Homestead, FL (US)

(73) Assignee: TISSUETECH, INC., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/274,123

(22) Filed: Feb. 12, 2019

(65) Prior Publication Data

US 2019/0169231 A1 Jun. 6, 2019

Related U.S. Application Data

(63) Continuation of application No. 15/214,706, filed on Jul. 20, 2016, now Pat. No. 10,253,065, which is a continuation of application No. 14/414,047, filed as application No. PCT/US2013/049983 on Jul. 10, 2013, now Pat. No. 10,040,821.

(60) Provisional application No. 61/670,571, filed on Jul. 11, 2012.

(51) Int. Cl.
| | |
|---|---|
| C07K 1/36 | (2006.01) |
| C07K 19/00 | (2006.01) |
| A61L 27/54 | (2006.01) |
| A61K 47/55 | (2017.01) |
| A61L 31/16 | (2006.01) |
| C07K 14/47 | (2006.01) |
| A61L 31/10 | (2006.01) |
| A61L 27/34 | (2006.01) |
| A61K 47/69 | (2017.01) |
| A61L 29/16 | (2006.01) |
| A61L 29/08 | (2006.01) |
| C07K 14/525 | (2006.01) |
| A61K 38/19 | (2006.01) |
| A61K 38/00 | (2006.01) |
| C07K 14/81 | (2006.01) |

(52) U.S. Cl.
CPC ............. *C07K 1/36* (2013.01); *A61K 38/191* (2013.01); *A61K 47/55* (2017.08); *A61K 47/69* (2017.08); *A61K 47/6957* (2017.08); *A61L 27/34* (2013.01); *A61L 27/54* (2013.01); *A61L 29/085* (2013.01); *A61L 29/16* (2013.01); *A61L 31/10* (2013.01); *A61L 31/16* (2013.01); *C07K 14/47* (2013.01); *C07K 14/525* (2013.01); *C07K 19/00* (2013.01); *A61K 38/00* (2013.01); *A61L 2300/236* (2013.01); *A61L 2300/252* (2013.01); *A61L 2300/41* (2013.01); *A61L 2300/412* (2013.01); *A61L 2300/426* (2013.01); *C07K 14/81* (2013.01)

(58) Field of Classification Search
CPC ...... A61K 38/00; A61K 38/191; A61K 47/55; A61K 47/69; A61K 47/6957; A61L 2300/236; A61L 2300/252; A61L 2300/41; A61L 2300/412; A61L 2300/426; A61L 27/34; A61L 27/54; A61L 29/085; A61L 29/16; A61L 31/10; A61L 31/16; C07K 14/47; C07K 14/525; C07K 14/81; C07K 19/00; C07K 1/36

See application file for complete search history.

(56) References Cited

U.S. PATENT DOCUMENTS

| | | | |
|---|---|---|---|
| 3,598,122 A | 8/1971 | Zaffaroni et al. |
| 3,598,123 A | 8/1971 | Zaffaroni et al. |
| 3,710,795 A | 1/1973 | Higuchi et al. |
| 3,731,683 A | 5/1973 | Zaffaroni et al. |
| 3,742,951 A | 7/1973 | Zaffaroni et al. |
| 3,814,097 A | 6/1974 | Ganderton et al. |
| 3,921,636 A | 11/1975 | Zaffaroni et al. |
| 3,972,995 A | 8/1976 | Tsuk et al. |
| 3,993,072 A | 11/1976 | Zaffaroni et al. |
| 3,993,073 A | 11/1976 | Zaffaroni et al. |
| 3,996,934 A | 12/1976 | Zaffaroni et al. |
| 4,031,894 A | 6/1977 | Urquhart et al. |
| 4,060,084 A | 11/1977 | Chandrasekaran et al. |
| 4,069,307 A | 1/1978 | Higuchi et al. |

(Continued)

FOREIGN PATENT DOCUMENTS

| | | |
|---|---|---|
| CN | 101316602 A | 12/2008 |
| KR | 20010098716 A | 11/2001 |

(Continued)

OTHER PUBLICATIONS

Roubelakis et al. (Stem Cells International vol. 2012, Article ID 107836 9 pages) (Year: 2012).*

(Continued)

*Primary Examiner* — Anna R Falkowitz
(74) *Attorney, Agent, or Firm* — Wilson Sonsini Goodrich & Rosati

(57) ABSTRACT

Provided herein are methods for the production of native and reconstituted hyaluronan (HA) complexes containing pentraxin-3 (PTX3) and heavy chain 1 (HC1) of inter alpha inhibitor (IαI). Compositions containing the complexes and therapeutic methods using the complexes are provided. Combinations and kits for use in practicing the methods also are provided.

20 Claims, 123 Drawing Sheets

Specification includes a Sequence Listing.

(56) References Cited

U.S. PATENT DOCUMENTS

| | | | |
|---|---|---|---|
| 4,077,407 A | 3/1978 | Theeuwes et al. | |
| 4,201,211 A | 5/1980 | Chandrasekaran et al. | |
| 4,230,105 A | 10/1980 | Harwood et al. | |
| 4,292,299 A | 9/1981 | Suzuki et al. | |
| 4,292,303 A | 9/1981 | Keith et al. | |
| 4,327,725 A | 5/1982 | Cortese et al. | |
| 4,476,116 A | 10/1984 | Anik | |
| 4,624,848 A | 11/1986 | Lee | |
| 4,871,549 A | 10/1989 | Ueda et al. | |
| 4,968,509 A | 11/1990 | Radebaugh et al. | |
| 5,011,692 A | 4/1991 | Fujioka et al. | |
| 5,017,381 A | 5/1991 | Maruyama et al. | |
| 5,033,252 A | 7/1991 | Carter | |
| 5,052,558 A | 10/1991 | Carter | |
| 5,093,487 A | 3/1992 | Brown et al. | |
| 5,116,817 A | 5/1992 | Anik | |
| 5,229,135 A | 7/1993 | Philippon et al. | |
| 5,260,068 A | 11/1993 | Chen | |
| 5,260,069 A | 11/1993 | Chen | |
| 5,294,446 A | 3/1994 | Schlameus et al. | |
| 5,323,907 A | 6/1994 | Kalvelage | |
| 5,336,168 A | 8/1994 | Sibalis | |
| 5,437,287 A | 8/1995 | Phillips et al. | |
| 5,456,923 A | 10/1995 | Nakamichi et al. | |
| 5,461,140 A | 10/1995 | Heller et al. | |
| 5,508,040 A | 4/1996 | Chen | |
| 5,516,527 A | 5/1996 | Curatolo | |
| 5,567,441 A | 10/1996 | Chen | |
| 5,622,721 A | 4/1997 | Dansereau et al. | |
| 5,665,378 A | 9/1997 | Davis et al. | |
| 5,686,105 A | 11/1997 | Kelm et al. | |
| 5,700,410 A | 12/1997 | Nakamichi et al. | |
| 5,837,280 A | 11/1998 | Kenealy et al. | |
| 5,837,284 A | 11/1998 | Mehta et al. | |
| 5,840,329 A | 11/1998 | Bai | |
| 5,869,090 A | 2/1999 | Rosenbaum | |
| 5,932,545 A | 8/1999 | Henkin et al. | |
| 5,977,175 A | 11/1999 | Lin | |
| 6,203,755 B1 | 3/2001 | Odland | |
| 6,391,452 B1 | 5/2002 | Antonsen et al. | |
| 6,465,014 B1 | 10/2002 | Moroni et al. | |
| 6,521,179 B1 | 2/2003 | Girardot et al. | |
| 6,632,648 B1 | 10/2003 | Kampinga et al. | |
| 6,923,983 B2 | 8/2005 | Morgan et al. | |
| 6,929,801 B2 | 8/2005 | Klose et al. | |
| 6,932,983 B1 | 8/2005 | Straub et al. | |
| 6,946,144 B1 | 9/2005 | Jordan | |
| 8,093,365 B2 | 1/2012 | Wisniewski et al. | |
| 8,460,714 B2 | 6/2013 | Tseng et al. | |
| 9,175,066 B2 | 11/2015 | Tseng et al. | |
| 9,956,252 B2 | 5/2018 | Tseng et al. | |
| 10,040,821 B2 | 8/2018 | Tseng et al. | |
| 10,253,065 B2 * | 4/2019 | Tseng | C07K 14/47 |
| 10,314,688 B2 | 6/2019 | Shepard et al. | |
| 2001/0041684 A1 | 11/2001 | Lezdey et al. | |
| 2003/0180181 A1 | 9/2003 | Greib et al. | |
| 2004/0181240 A1 | 9/2004 | Tseng et al. | |
| 2007/0071740 A1 | 3/2007 | Tseng et al. | |
| 2008/0102135 A1 | 5/2008 | Ollivier | |
| 2008/0193554 A1 | 8/2008 | Dua et al. | |
| 2009/0226499 A1 | 9/2009 | Wisniewski et al. | |
| 2011/0311491 A1 | 12/2011 | Edinger et al. | |
| 2012/0263731 A1 | 10/2012 | Fraunhofer et al. | |
| 2016/0095076 A1 | 4/2016 | Tseng et al. | |
| 2016/0339061 A1 | 11/2016 | Tseng et al. | |
| 2018/0126036 A1 | 5/2018 | Early | |
| 2018/0127721 A1 | 5/2018 | Phan | |
| 2018/0140641 A1 | 5/2018 | Harrell | |
| 2018/0163177 A1 | 6/2018 | Lo et al. | |
| 2018/0177716 A1 | 6/2018 | Noh et al. | |
| 2018/0177989 A1 | 6/2018 | Prentice | |
| 2018/0264049 A1 | 9/2018 | Wagner et al. | |
| 2018/0271914 A1 | 9/2018 | Steed et al. | |
| 2018/0271917 A1 | 9/2018 | Fu | |
| 2018/0338998 A1 | 11/2018 | Petrucci | |
| 2018/0344777 A1 | 12/2018 | Harris et al. | |
| 2018/0346874 A1 | 12/2018 | Harris et al. | |
| 2018/0362920 A1 | 12/2018 | Guo | |
| 2018/0362923 A1 | 12/2018 | Guo | |
| 2018/0362932 A1 | 12/2018 | Guo | |
| 2019/0070335 A1 | 3/2019 | Karagianis | |
| 2019/0127702 A1 | 5/2019 | Kerkis et al. | |
| 2019/0134100 A1 | 5/2019 | Cao et al. | |
| 2019/0141987 A1 | 5/2019 | Patel et al. | |
| 2019/0177684 A1 | 6/2019 | Ha et al. | |

FOREIGN PATENT DOCUMENTS

| | | | | |
|---|---|---|---|---|
| WO | WO-03097809 A2 | | 11/2003 | |
| WO | WO 2007/038686 | * | 4/2007 | ............ A61K 38/43 |
| WO | WO-2012149486 A1 | | 11/2012 | |
| WO | WO-2014011813 A1 | | 1/2014 | |
| WO | WO-2016187555 A1 | | 11/2016 | |

OTHER PUBLICATIONS

Zhang etc. (J. Biol Chem. May 9, 2014, 289(19)) (Year: 2014).*

Bae et al. Characterization of the Promoter Region of the Human Transforming Growth Factor-β Type II Receptor Gene. J. Biol. Chem. 270(49):29460-29468 (1995).

Bhutto et al. Localization of Collagen XVIII and the Endostatin Portion of Collagen XVIII in Ages Human Control Eyes and Eyes with Age-Related Macular Degeneration. Invest. Ophthalmol. Vis. Sci. 45(5):1544-1552 (2004).

Border et al. Transforming Growth Factor-β in Disease: The Dark Side of Tissue Repair. J. Clin. Invest. 90:1-7 (1992).

Chen et al. Functions of hyaluronan in wound repair. Wound Rep Reg 7:79-89 (1999).

Chen et al. Recombinant Adenovirus Coexpressing Covalent Peptide/ MHC Class II Complex and B7-1: In Vitro and In Vivo Activation of Myelin Basic Protein-Specific T Cells. J. Immunol. 167:1297-1305 (2001).

Colon et al. Transfer of Inter-α-inhibitor Heavy Chains to Hyaluronan by Surface-linked Hyaluronan-TSG-6 Complexes. J. Biol. Chem. 2009. 284:2320-2331.

Derynk et al. TGF-β receptor signaling. Biochem. Biophys. Acta. 1333:F105-F150 (1997).

Fortunato et al. Interleukin-10 and transforming growth factor-β inhibit amniochorion tumor necrosis factor-α production by contrasting mechanisms of action: Therapeutic implications in prematurity. Am. J. Obstet. Gynecol. 177(4):803-809 (1997).

Fortunato et al. Interleukin-10 inhibition of interleukin-6 in human amniochorionic membrane: Transcriptional regulation. Am. J. Obstet. Gynecol. 175:1057-1065 (1996).

Fortunato et al. The effect of transforming growth factor and interleukin-10 on interleukin-8 release by human amniochorion may regulate histologic chorioamnionitis. Am. J. Obstet. Gynecol. 179(3):794-799 (1998).

Fries et al. Inter-alpha-inhibitor, hyaluronan and inflammation. Acta Biochim Polonica 50(3):735-742 (2003).

Gabbiani. The myofibroblast in wound healing and fibrocontractive diseases. J. Pathol. 200:500-503 (2003).

Grande. Role of Transforming Growth Factor-β in Tissue Injury and Repair. Proc. Soc. Exp. Biol. Med. 214:27-40 (1997).

Guo. Carbopol® Polymers for Pharmaceutical Drug Delivery Applications. Drug Delivery Technology 3(6):1-4 (2003).

Hales et al. TGF-β-1 induces lens cells to accumulate α-smooth muscle actin, a marker for subcapsular cataracts. Curr. Eye Res. 13:885-890 (1994).

Hanada et al. Regulation of cytokine signaling and inflammation. Cytokine & Growth Factor Reviews 13(4-5):413-421 (2002).

He et al. A simplified system for generating recombinant adenoviruses. PNAS USA 95:2509-2514 (1998).

He et al. Biochemical Characterization and Function of Complexes formed by Hyaluronan and the Heavy Chains of Inter-α-inhibitor (HC-HA) Purified from Extracts of Human Amniotic Membrane. J Biol Chem 284(30):20136-20146 (Jul. 24, 2009).

(56) References Cited

OTHER PUBLICATIONS

He et al. Immobilized heavy chain-hyaluronic acid polarizes lipopolysaccharide-activated macrophages toward M2 phenotype. J Biol Chem 288(36):25792-25803 (2013).
He et al. Inhibition of Proliferation and Epithelial Mesenchymal Transition via Wnt and TGF-β Signaling Pathway in an in vitro Cell Culture Based-PVR Model by HC-HA/PTX3 Purified from Amniotic Membrane. The Association for Research in Vision and Ophthalmology (ARVO) May 1-May 5, 2016 (Washington State Convention Center, Seattle, Washington) Abstract No. 5384-B005 (2 pgs).
He et al. Role of Hyaluronan, Inter-Alpha-Trypsin Inhibitor, and TSG-6 Complex in Amniotic Membrane in Inhibiting TFG-Beta Transcription. ARVO Annual Meeting Abstract. Investigative Ophthalmology & Visual Science 47:599 (May 2006).
Heiligenhaus et al. Improvement of HSV-1 Necrotizing Keratitis with Amniotic Membrane Transplantation Invest Ophthalmol Vis Sci 42(9):1969-1974 (2001).
Hirashima et al. Inter-alpha-trypsin inhibitor is concentrated in the pericellular environment of mouse granulosa cells through hyaluronan-binding. Eur J Obstet Gynecol Reprod Biol. 73 :79-84 (1997).
Howes et al. Receptor for Advanced Glycation End Products and Age-Related Macular Degeneration. Invest. Ophthalmol. Vis. Sci. 45(10):3713-3720 (2004).
Huang et al. A Serum-derived Hyaluronan-associated Protein (SHAP) Is the Heavy Chain of the Inter a-Trypsin Inhibitor. J Biol Chem 268(35):26725-76730 (1993).
Jadin et al. Characterization of a Novel Recombinant Hyaluronan Binding Protein for Tissue Hyaluronan Detection. Journal of Histochemistry & Cytochemistry 62(9):672-683 (2014).
Jester et al. Corneal Stromal Wound Healing in Refractive Surgery: the Role of Myofibroblasts. Prog. Retin. Eye Res. 18(3):311-356 (1999).
Jester et al. Induction of α-Smooth Muscle Actin Expression and Myofibroblast Transformation in Cultured Cornea Keratocytes. Cornea 15(5):505-516 (1996).
Keelan et al. Activin A Exerts both Pro- and -Anti-inflammatory Effects on Human Term Gestational Tissues. Placenta 21:38-43 (2000).
Kida et al. The SHAP-HA complex in sera from patients with rheumatoid arthritis and osteoarthritis. J Rheumatol 26(6):1230-1238 (1999).
Kishida et al. Hyaluronan (HA) and serum-derived hyaluronan-associated protein (SHAP)-HA complex as predictive markers of cervical ripening in premature labor. 49(2):105-108 (2008).
Kobayashi et al. Identification of structural domains in inter-alpha-trypsin inhibitor involved in calcium oxalate crystallization. Kidney Int 53:1727-1735 (1998).
Kopp et al. Abrogation of Transforming Growth Factor-beta Signaling by SMAD7 Inhibits Collagen Gel Contraction of Human Dermal Fibroblasts. J. Biol. Chem. 280(22):21570-21576 (2005).
Kuriyan et al. A potential novel therapy for PVR: HC-HA/PTX3, an active matrix component of amniotic membrane, inhibits proliferation of rabbit RPE cells and is non-toxic intravitreally. The Association for Research in Vision and Ophthalmology (ARVO) 2015 meeting on May 3-May 7 (Colorado Convention Center Denver, CO) Abstract No. 1126-B029 (2 pgs).
Kuriyan et al. HC-HA/PTX3, an active matrix component of amniotic membrane, inhibits proliferation and epithelial mesenchymal transition of RPE cells: a potential novel therapy for PVR. The Association for Research in Vision and Ophthalmology (ARVO) 2015 meeting on May 3-May 7 (Colorado Convention Center Denver, CO) Abstract No. 2287-B0192 (2 pgs).
Lawrence. Transforming Growth Factor-β: a general review. Eur. Cytokine Netw. 7:363-374 (1996).
Lee et al. Adhesion between Amniotic Membrane and Retinal Tissue and Inhibition of Amniotic Membrane on Cell Transformation. J Korean Ophthalmol Soc. 44(2):459-471 (2003) (Abstract Only).
Lee et al. Amniotic Membrane Transplantation for Persistent Epithelial Defects with Ulceration. Am. J. Ophthalmol. 123:303-312 (1997).
Lee et al. An Agarose Gel Electrophoretic Method for Analysis of Hyaluronan Molecular Weight Distribution. Anal. Biochem. 219:278-287 (1994).
Lieberman et al. Pharmaceutical Dosage Forms. 2 Ed. 1:209-214 (1990).
Liu et al. E-cadherin engagement stimulates proliferation via Rac1. Journal of Cell Biology 173(3):431-441 (2006).
Logan et al. Decorin Attenuates Gliotic Scar Formation in the Rat Cerebral Hemisphere. Exp. Neurol. 159:504-510 (1999).
Marek et al. TGF-β-(transforming growth factor-β) in chronic inflammatory conditions—a new diagnostic and prognostic marker? Med. Sci. Monitl. 8(7):RA145-RA151 (2002).
Massague et al. Controlling TGF-β signaling. Genes and Development 14:627-644 (2000).
Milner et al. TSG-6: a multifunctional protein associated with inflammation. J. Cell Sci. 116(10):1863-1873 (2003).
Moalli et al. Pathogen Recognition by the Long Pentraxin PTX3. Journal of Biomedicine and Biotechnology 2011:Article ID 830421 (15 pgs.) (2011).
Moller-Pedersen et al. Neutralizing antibody to TGF-β modulates stromal fibrosis but not regression of photoablative effect following PRK. Curr. Eye Res. 17:736-747 (1998).
Monteleone et al. SMAD7 in TGF-β-mediated negative regulation of gut inflammation. Trends in Immunology 25(10):513-517 (2004).
Mukhopadhyay et al. Two distinct populations of tumor necrosis factor-stimulated gene-6 protein in the extracellular matrix of expanded mouse cumulus cell-oocyte complexes. Archives of Biochemistry and Biophysics 394(2):173-181 (2001).
Nakao et al. SMAD7: a new key player in TGF-b-associated disease. Trends in Molecular Medicine 8(8):361-363 (2002).
Neumann et al. High molecular weight hyaluronic acid inhibits advanced glycation endproduct-induced NF-kB activation and cytokine expression. FEBS Ltrs. 453:283-287(1999).
Obayashi et al. Role of serum-derived hyaluronan-associated protein-hyaluronan complex in ovarian cancer. Oncol Rep 19(5):1245-1251 (2008).
Ochsner et al. Decreased expression of tumor necrosis factor-alpha-stimulated gene 6 in cumulus cells of the cyclooxygenase2 and EP2 null mice. Endocrinology 144:1008-1019 (2003).
Oikawa et al. Inhibition of Angiogenesis by 15-Deoxyspergualin. J. Antibiotics 44(9):1033-1035 (1991).
PCT/US2010/032452 International Preliminary Report on Patentability dated Oct. 25, 2011.
PCT/US2010/032452 International Search Report dated Dec. 27, 2010.
PCT/US2013/049983 International Preliminary Report on Patentability dated Jan. 22, 2015.
PCT/US2013/049983 International Search Report and Written Opinion dated Nov. 29, 2013.
PCT/US2016/033558 International Search Report and Written Opinion dated Oct. 25, 2016.
Petraglia et al. Inhibin and Activin in Human Fetal Membranes: Evidence of a Local Effect on Prostaglandin Release. J. Clin. Endocrinol. Metab. 77(2):542-548 (1993).
Riley et al. Production of inhibin forms by the fetal membranes, decidua, placenta and fetus at parturition. Hum. Reprod. 15:578-583 (2000).
Romero et al. The natural interleukin-1 receptor antagonist in the fetal, maternal, and amniotic fluid compartments: The effect of gestational age, fetal gender, and intrauterine infection. Am. J. Obstet. Gynecol. 171:912-921 (1994).
Ronnov-Jessen et al. Induction of α-Smooth Muscle Actin by Transforming Growth Factor-β1 in Quiescent Human Breast Gland Fibroblasts. Lab. Invest. 68:696-707 (1993).
Rovere et al. The long pentraxin PTX3 binds to apoptotic cells and regulates their clearance by antigen-presenting dendritic cells. Blood 96(13):4300-4306 (2000).

(56) References Cited

OTHER PUBLICATIONS

Rugg et al. Characterization of complexes formed between TSG-6 and inter-alpha-inhibitor that act as intermediates in the covalent transfer of heavy chains onto hyaluronan. J Biol Chem 280(27):25674-25686 (2005).
Sakurai et al. Characterization of the Role of PTX3 in Enhancing the Anti-angiogenic Action of HC.HA Purified From the Chorion. Arvo Annual Meeting Abstract Search and Program Planner. 2011:4881 (May 2011).
Sanggaard et al, The transfer of heavy chains from bikunin proteins to hyaluronan requires both TSG-6 and HC2. J Biol Chem 283(27):18530-18537 (2008).
Serini et al. The Fibronectin Domain ED-A Is Crucial for Myofibroblastic Phenotype Induction by Transforming Growth Factor-β1. J. Cell. Biol. 142:873-881 (1998).
Shah et al. Control of scarring in adult wounds by neutralising antibody to transforming growth factor β. Lancet 339:213-214 (1992).
Shen et al. The SHAP-hyaluronan complex in serum from patients with chronic liver diseases caused by hepatitis virus infection. Hepatol Res 34(3):178-186 (2006).
Singh et al. Encyclopedia of Pharmaceutical Technology 2nd Ed. pp. 751-753 (2002).
Sun et al. Link protein as an enhancer of cumulus cell-oocyte complex expansion. Mol Reprod Dev 63:223-231 (2002).
Tan et al. Structural and Biological Comparison of Cryopreserved and Fresh Amniotic membrane Tissues. Journal Biomaterial and Tissue Engineering 4:379-388 (2014).
Travis et al. Hyaluronan Enhances Contraction of Collagen by Smooth Muscle Cells and Adventitial Fibroblasts Role of CD44 and Implications for Constrictive Remodeling. Cir. Res. 88:77-83 (2001).
Tseng et al. How Does Amniotic Membrane Work? Ocular Surface J. 2(3):177-187 (2004).
U.S. Appl. No. 13/262,725 Office Action dated Feb. 25, 2015.
U.S. Appl. No. 13/262,725 Office Action dated Jul. 17, 2014.
U.S. Appl. No. 14/414,047 Office Action dated Feb. 13, 2017.
U.S. Appl. No. 14/414,047 Office Action dated Jul. 19, 2017.
U.S. Appl. No. 14/414,047 Office Action dated Jul. 8, 2016.
U.S. Appl. No. 14/869,609 Office Action dated Jun. 2, 2017.
U.S. Appl. No. 14/869,609 Office Action dated Oct. 17, 2016.
U.S. Appl. No. 15/160,487 Office Action dated Jun. 1, 2018.
U.S. Appl. No. 15/214,706 Office Action dated Mar. 15, 2018.
Verbeek et al. Induction of alpha-smooth muscle actin expression in cultured human brain pericytes by transforming growth factor-beta 1. Am. J. Pathol. 144:372-382 (1994).
Yabushita et al. Clinicopathological Role of Serum-Derived Hyaluronan-Associated Protein (SHAP)-Hyaluronan Complex in Endometrial Cancer. Obstet Gynecol Inc. 2011:739150 (2011).
Yamaguchi et al. Negative regulation of transforming growth factor-β by the proteoglycan decorin. Nature 346(6281):281-284 (1990).
Yingsung et al. Molecular heterogeneity of the SHAP-hyaluronan complex. Isolation and characterization of the complex in synovial fluid from patients with rheumatoid arthritis. J Biol Chem 2878(35):32710-32718 (2003).
Yoneda et al. Hyaluronic acid associated with the surfaces of cultured fibroblasts is linked to a serum-derived 85-kDa protein. J Biol Chem 265(9):5247-5257 (1990).
Zhang et al. Constitutive Expression of Inter-α-inhibitor (IαI) Family Proteins and Tumor Necrosis Factor-stimulatedGene-6 (TSG-6) by Human Amniotic Membrane Epithelial and Stromal Cells Supporting Formation of the Heavy Chain-Hyaluronan (HC-HA) Complex. J of Biological Chemistry 287(15):12433-12444 (2012).
Zhao et al. Evidence for the covalent binding of SHAP, heavy chains of inter-alpha-trypsin inhibitor, to hyaluronan. J Biol Chem 270:26657-26663 (1995).
Zhuo et al. Inter-α-trypsin Inhibitor, a Covalent Protein-Glycosaminoglycan-Protein Complex. J Biol Chem 279(37):38079-38082 (2004).
Zhuo et al. SHAP potentiates the CD44-mediated leukocyte adhesion to the hyaluronan substratum. J Biol Chem 281(29):20303-20314 (2006).

* cited by examiner

FIG. 1C      FIG. 1D      FIG. 1E
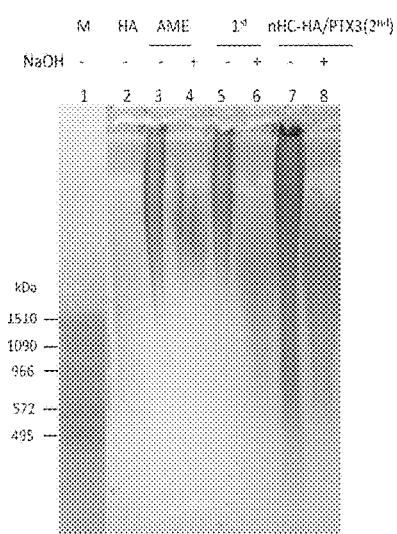
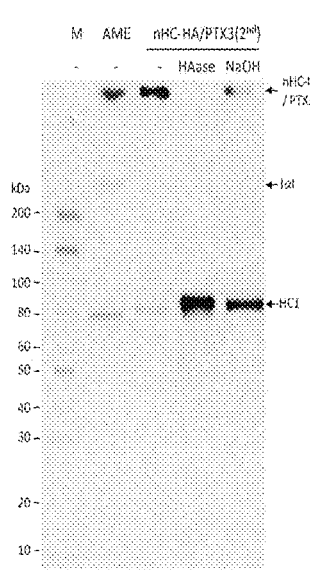
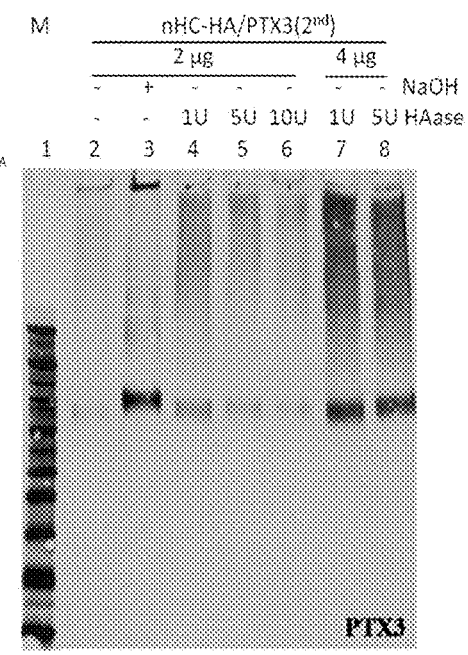
FIG. 1F   FIG. 1G   FIG. 1H   FIG. 1I
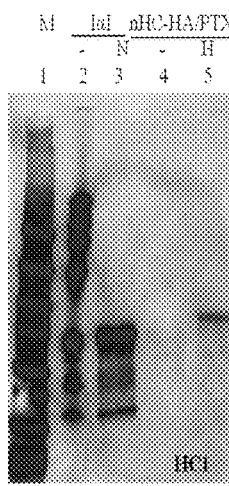
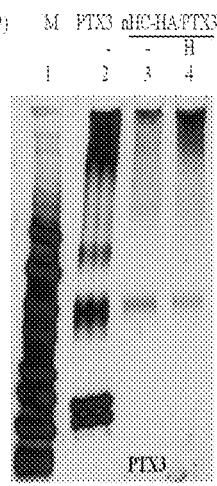
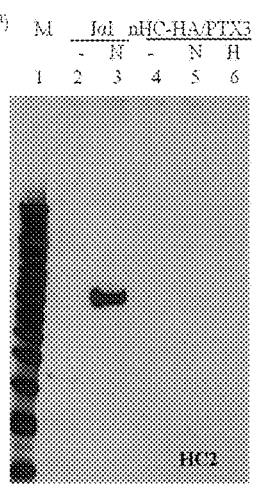
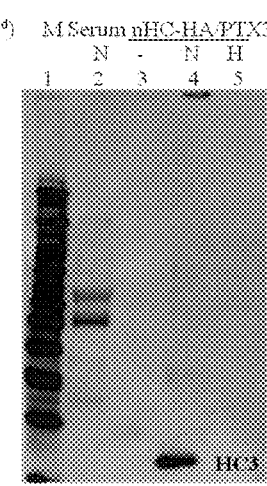

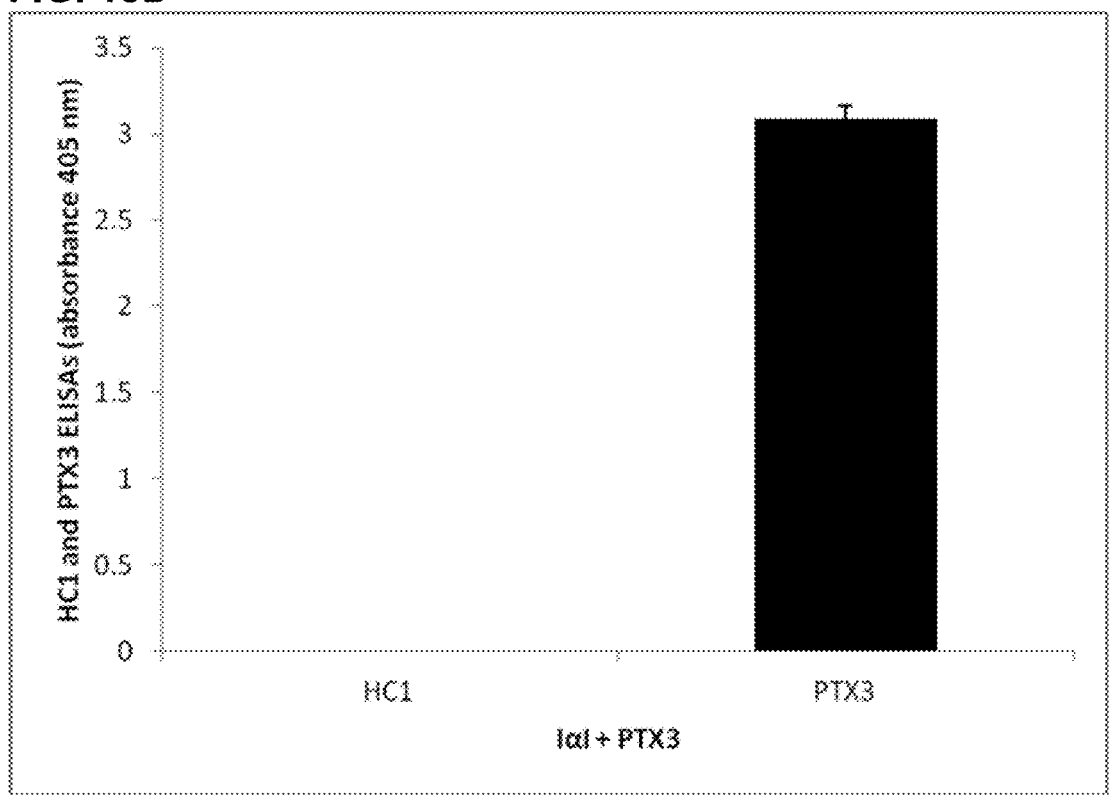

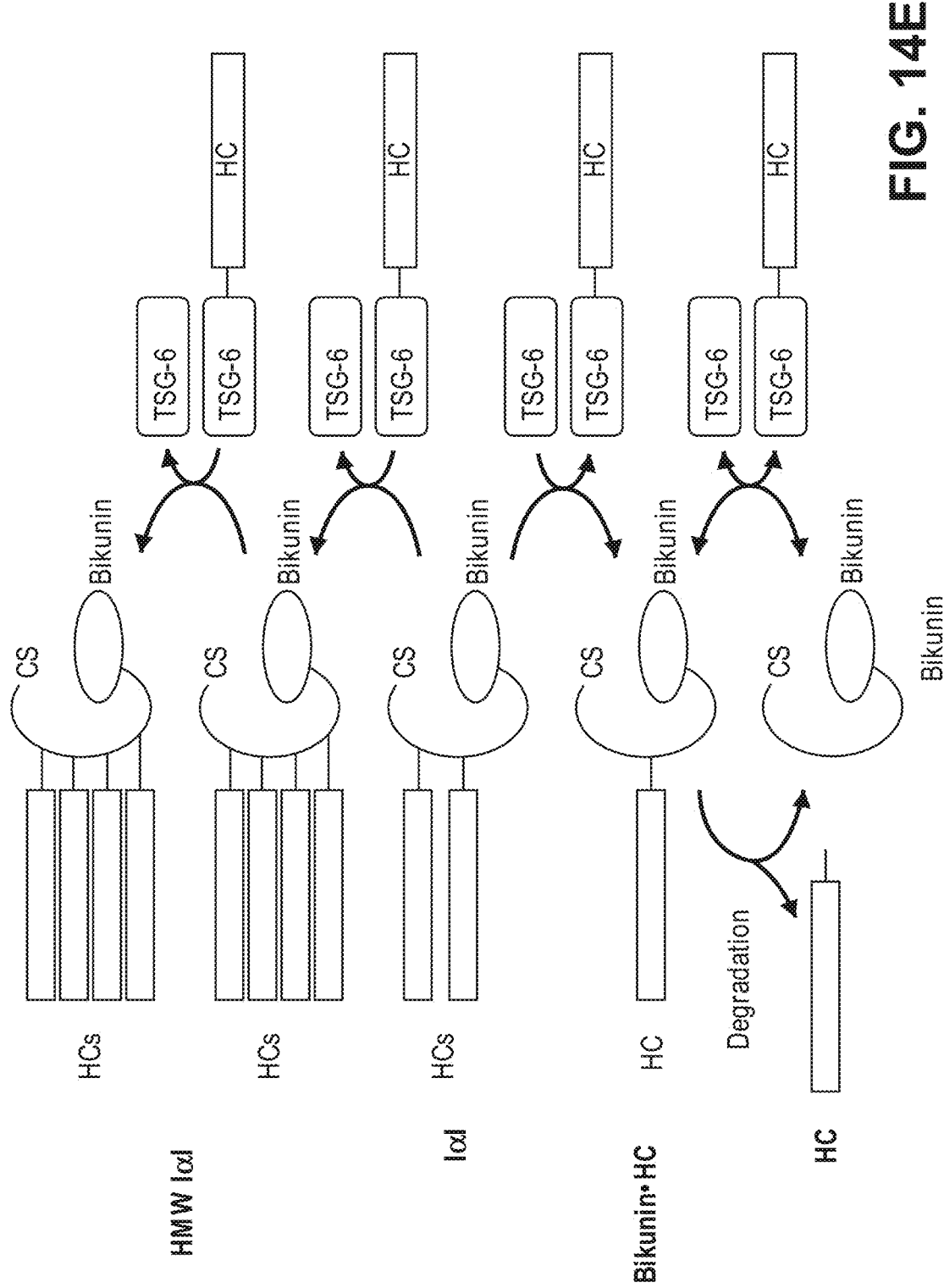

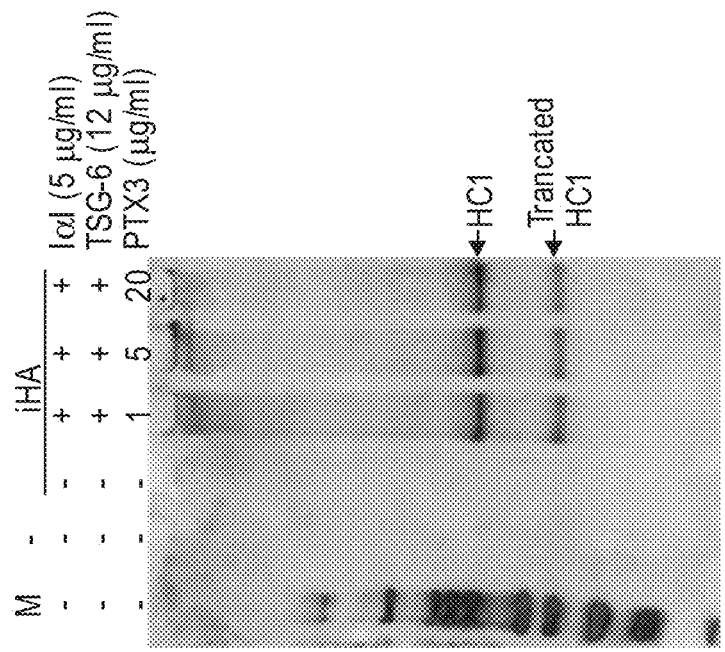
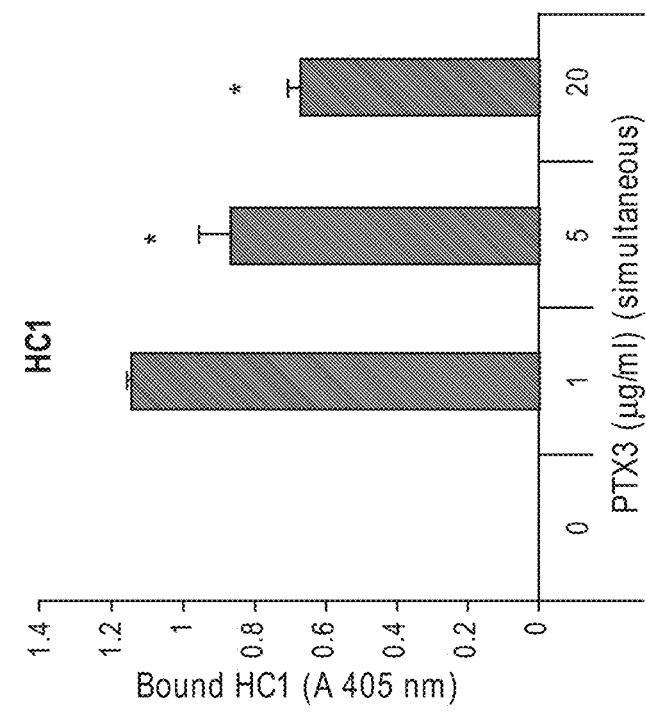
FIG. 15B
FIG. 15A

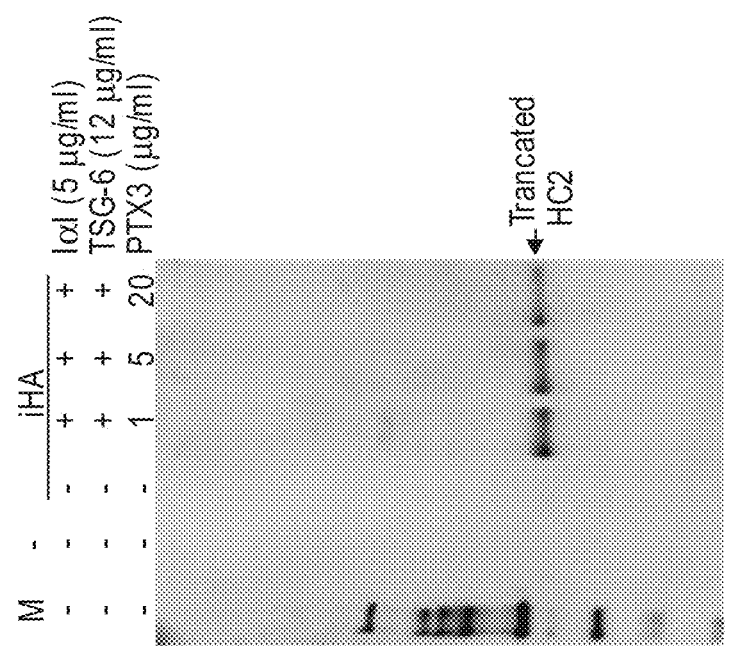

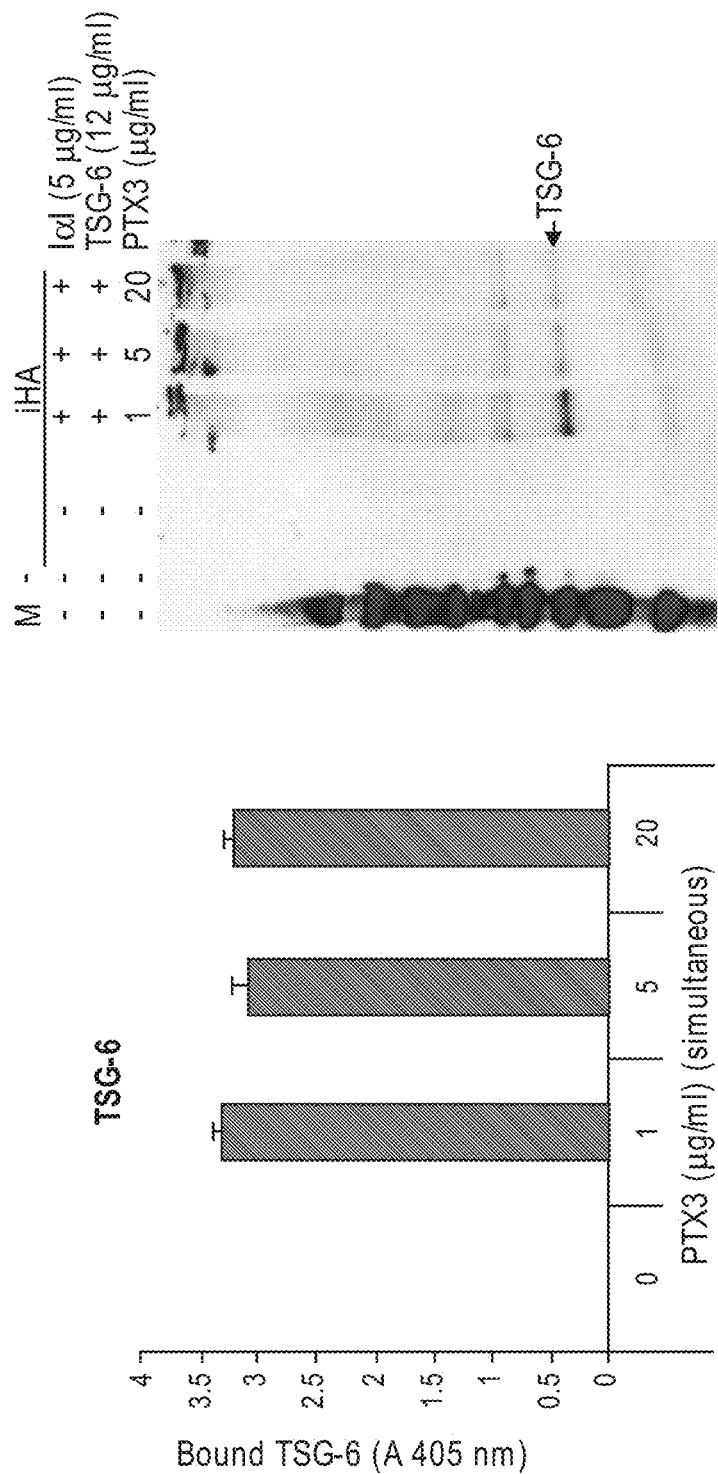

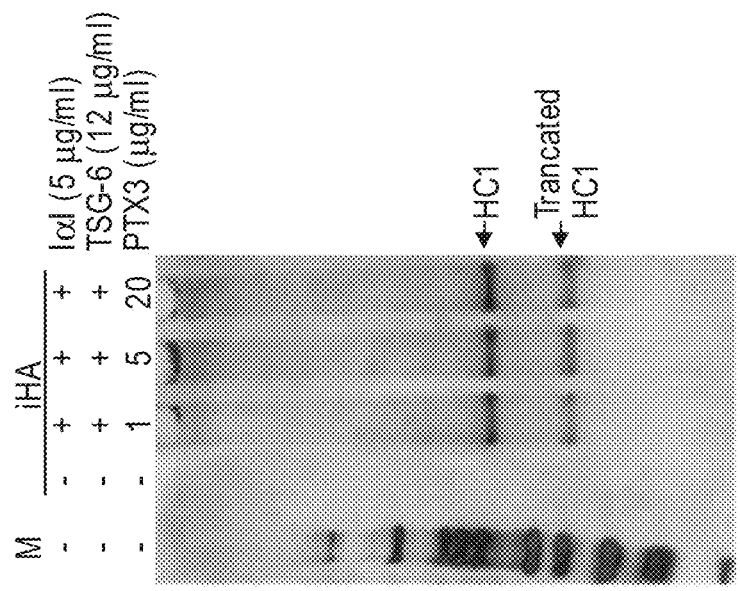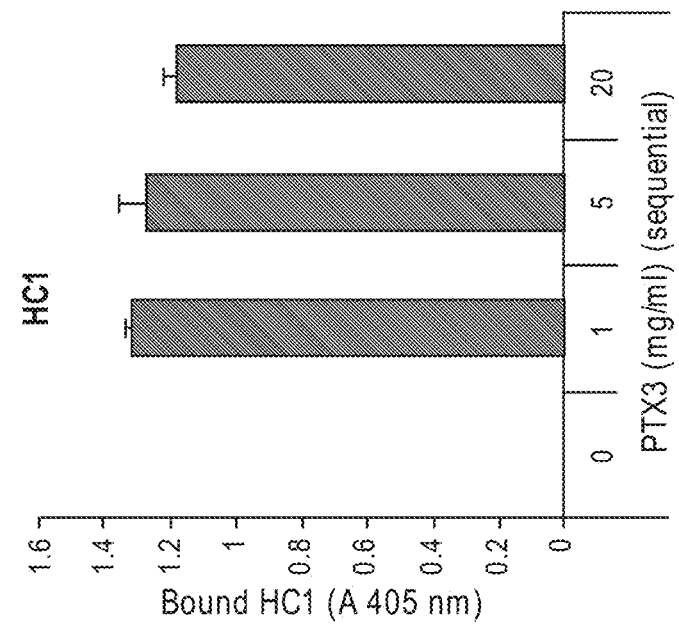
FIG. 16A
FIG. 16B

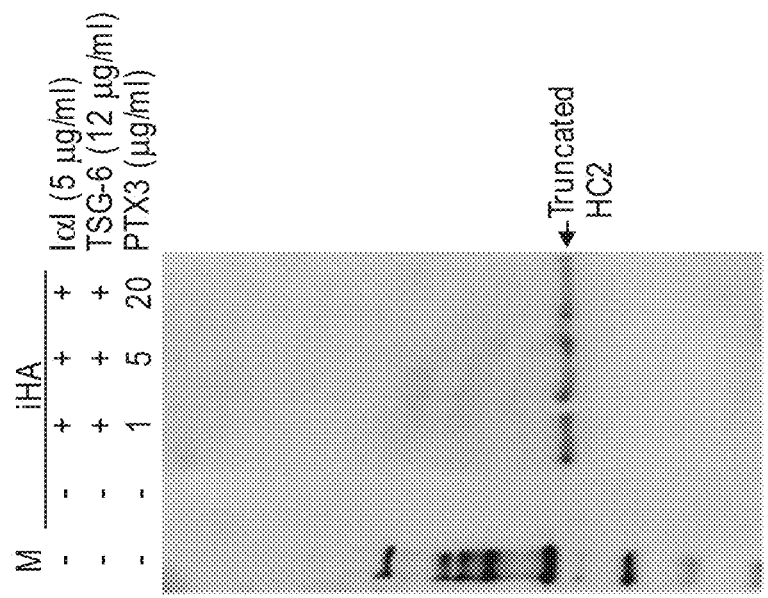

HC-HA

AMP

HC-HA

AMP

HC-HA

AMP

Negative Control

Positive Control

HC-HA

AMP

Negative Control

Positive Control

HC-HA

AMP

No Transwell

Transwell

COMPOSITIONS CONTAINING HC-HA/PTX3 COMPLEXES AND METHODS OF USE THEREOF

CROSS-REFERENCE

This application is a continuation of U.S. application Ser. No. 15/214,706, filed on Jul. 20, 2016, which is a continuation of U.S. application Ser. No. 14/414,047, filed Jan. 9, 2015, now issued as U.S. Pat. No. 10,040,821 on Aug. 7, 2018, which is the National Phase Entry of International Application No. PCT/US2013/049983, filed Jul. 10, 2013, which claims the benefit of U.S. Provisional Application No. 61/670,571, filed on Jul. 11, 2012, all of which are hereby incorporated by reference in their entireties.

STATEMENT REGARDING FEDERALLY SPONSORED RESEARCH OR DEVELOPMENT

This invention was made with government support under RO1 EY06819, R44 EY017497, and R43 EY021045 awarded by the National Eye Institute, the National Institutes of Health, Bethesda, Md., USA. The government has certain rights in the invention.

SEQUENCE LISTING

The instant application contains a Sequence Listing which has been submitted in ASCII format and is hereby incorporated by reference in its entirety. Said ASCII copy, created on Feb. 8, 2019, is named "34157832302_SL.txt" and is 473,554 bytes in size.

BACKGROUND OF THE INVENTION

The amniotic membrane (AM) is an avascular membranous sac that is filled with amniotic fluid surrounding the fetus. The AM, like the placenta, is derived from the epiblast formed during development of the fertilized egg. The AM forms the innermost membrane surrounding the fetus in the amniotic cavity. In placental mammals, the umbilical cord (i.e., the funiculus umbilicalis) connects the developing fetus to the placenta. The umbilical cord is made up of amniotic membrane (UCAM) and Wharton's Jelly. The amniotic membrane forms the outer layer of the umbilical cord. The UCAM functions to regulate the fluid pressure within the UC. Wharton's Jelly is a gelatinous substance within the umbilical cord, largely made up of mucopolysaccharides (hyaluronic acid and chondroitin sulfate). It also contains some fibroblasts and macrophages. The umbilical cord further comprises two arteries (the umbilical arteries) and one vein (the umbilical vein), buried within the Wharton's Jelly.

SUMMARY OF THE INVENTION

Described herein are methods for the identification of HC-HA/PTX3 complexes in fetal tissues, such as amniotic membrane and umbilical cord. Also, described herein are methods for the isolation of native HC-HA/PTX3 complexes from fetal tissues, such as amniotic membrane and umbilical cord. Also described herein are methods for the production of reconstituted HC-HA/PTX3 complexes. Also described herein are methods for the use of native and reconstituted HC-HA/PTX3 complexes provided herein.

Described herein, in certain embodiments, are methods of producing HC-HA/PTX3 complexes. In some embodiments, the methods comprise isolating a native HC-HA/PTX3 (nHC-HA/PTX3) complex from an extract prepared from a tissue or cell. In some embodiments, the methods comprise generating a reconstituted HC-HA/PTX3 (rcHC-HA/PTX3) complex.

Described herein, in certain embodiments, are methods of isolating native HC-HA/PTX3 (nHC-HA/PTX3) complexes from amniotic tissues, such as umbilical cord or amniotic membrane. In some embodiments, the nHC-HA/PTX3 complexes are isolated from an isolated cell. In some embodiments, the nHC-HA/PTX3 complexes are isolated from a cultured cell. In some embodiments, the nHC-HA/PTX3 complexes are isolated from a stem cell. In some embodiments, the nHC-HA/PTX3 complexes are isolated from a water soluble fraction of an extract prepared from a tissue, such as umbilical cord or amniotic membrane. In some embodiments, the water soluble fraction is extracted with an isotonic salt solution. In some embodiments, the nHC-HA/PTX3 complexes are isolated from a water insoluble fraction of an extract prepared from a tissue, such as umbilical cord or amniotic membrane. In some embodiments, the insoluble fraction is extracted with GnHCl.

Described herein, in certain embodiments, are methods of producing a reconstituted HC-HA/PTX3 (rcHC-HA/PTX3) complex in vitro, (a) contacting (i) high molecular weight hyaluronan (HMW HA) immobilized to a solid support, and (ii) pentraxin 3 (PTX3) protein, to form an immobilized complex of PTX3 and HMW HA (immobilized PTX3/HA); and (b) contacting the immobilized PTX3/HA with an inter-α-inhibitor (IαI) protein comprising heavy chain 1 (HC1) and Tumor necrosis factor α-stimulated gene 6 (TSG-6) to form an immobilized rcHC-HA/PTX3 complex. In some embodiments, steps (a) and (b) of the method are performed sequentially in order. In some embodiments of the method, the method comprises contacting high molecular weight hyaluronan (HMW HA) with a pentraxin 3 (PTX3) protein, inter-α-inhibitor (IαI) protein comprising heavy chain 1 (HC1) and Tumor necrosis factor α-stimulated gene 6 (TSG-6) simultaneously. In some embodiments of the method, TSG-6 catalyzes the covalent linkage of IαI HC1 to HA. In some embodiments, the method further comprises removing unbound PTX3 protein following step (a) and prior to performing step (b). In some embodiments, the method further comprises removing unbound TSG-6 following step (b). In some embodiments, the PTX3 protein used in the methods is a native PTX3 protein isolated from a cell. In some embodiments, the cell is a mammalian cell. In some embodiments, the cell is a human cell. In some embodiments, the cell is an amniotic membrane cell. In some embodiments, the cell is an umbilical cord cell. In some embodiments, the cell is an amniotic membrane cell from an umbilical cord. In some embodiments, the amniotic membrane cell is an amniotic epithelial cell. In some embodiments, the amniotic membrane cell is an umbilical cord epithelial cell. In some embodiments, the amniotic membrane cell is an amniotic stromal cell. In some embodiments, the amniotic membrane cell is an umbilical cord stromal cell. In some embodiments, the PTX3 protein is a recombinant protein. In some embodiments, the PTX3 protein used in the methods comprises a polypeptide having the sequence set forth in SEQ ID NO: 33 or a polypeptide having at least 75%, 80%, 85%, 90%, 95%, 96%, 97%, 98%, or 99% sequence amino acid identity to the polypeptide having the sequence set forth in SEQ ID NO: 33. In some embodiments, the PTX3 protein used in the methods comprises a polypeptide having the sequence set forth in any of SEQ ID NOS: 32-45 or a species variant or allelic variant thereof. In some embodiments, the PTX3 protein used in the methods is a multimeric protein. In some embodiments, the PTX3 protein used in the methods is a homomultimer (i.e. a multimeric protein consisting of two or more identical components). In some embodiments, the PTX3 homomultimer is a dimer, trimer, tetramer, pentamer, hexamer, or octamer. In some embodiments, the PTX3 homomultimer is an octamer. In some embodiments, the PTX3 protein comprises a modified multimerization domain or a heterogeneous multimerization domain. In some embodiments, the TSG-6 protein used in the methods is a native TSG-6 protein isolated from a cell. In some embodiments, the cell is a mammalian cell. In some embodiments, the cell is a human cell. In some embodiments, the cell is an amniotic membrane cell. In some embodiments, the cell is an umbilical cord cell. In some embodiments, the cell is an amniotic membrane cell from an umbilical cord. In some embodiments, the amniotic membrane cell is an amniotic epithelial cell. In some embodiments, the amniotic membrane cell is an umbilical cord epithelial cell. In some embodiments, the amniotic membrane cell is an amniotic stromal cell. In some embodiments, the amniotic membrane cell is an umbilical cord stromal cell. In some embodiments, the TSG-6 protein is a recombinant protein. In some embodiments, the TSG-6 protein comprises a polypeptide having the sequence set forth in SEQ ID NO: 2 or a polypeptide having at least 75%, 80%, 85%, 90%, 95%, 96%, 97%, 98%, or 99% sequence amino acid identity to the polypeptide having the sequence set forth in SEQ ID NO: 2. In some embodiments, the TSG-6 protein used in the methods comprises a polypeptide having the sequence set forth in any of SEQ ID NOS: 1-31 or a species variant or allelic variant thereof. In some embodiments, the HC1 used in the methods comprises a polypeptide having the sequence set forth in SEQ ID NO: 47 or a polypeptide having at least 75%, 80%, 85%, 90%, 95%, 96%, 97%, 98%, or 99% sequence amino acid identity to the polypeptide having the sequence set forth in SEQ ID NO: 47. In some embodiments, inter-α-inhibitor (IαI) protein used in the methods as a source of HC1 also comprises HC2 and bikunin linked by a chondroitin sulfate chain. In some embodiments, the HC1 comprises a polypeptide having the sequence set forth in any of SEQ ID NOS: 46-47 or a species variant or allelic variant thereof. In some embodiments, HC2 comprises a polypeptide having the sequence set forth in SEQ ID NO: 49 or a polypeptide having at least 75%, 80%, 85%, 90%, 95%, 96%, 97%, 98%, or 99% sequence amino acid identity to the polypeptide having the sequence set forth in SEQ ID NO: 49. In some embodiments, the HC2 used in the methods comprises a polypeptide having the sequence set forth in any of SEQ ID NOS: 48-49 or a species variant or allelic variant thereof. In some embodiments, bikunin comprises a polypeptide having the sequence set forth in SEQ ID NO: 53 or a polypeptide having at least 75%, 80%, 85%, 90%, 95%, 96%, 97%, 98%, or 99% sequence amino acid identity to the polypeptide having the sequence set forth in SEQ ID NO: 53. In some embodiments, the bikunin used in the methods comprises a polypeptide having the sequence set forth in any of SEQ ID NOS: 52-53 or a species variant or allelic variant thereof. In some embodiments, the IαI protein used in the methods is isolated from blood, serum, plasma, amniotic membrane, chorionic membrane, amniotic fluid, or a combination thereof. In some embodiments, the IαI protein used in the methods is isolated from serum. In some embodiments, the IαI protein used in the methods is isolated from human serum. In some embodiments, the IαI protein used in the methods is produced by a mammalian cell. In some embodiments, the cell is a human cell. In some embodiments, the cell is an amniotic membrane cell. In some embodiments, the cell is an umbilical cord cell. In some embodiments, the cell is an amniotic membrane cell from an umbilical cord. In some embodiments, the amniotic membrane cell is an amniotic epithelial cell. In some embodiments, the amniotic membrane cell is an umbilical cord epithelial cell. In some embodiments, the amniotic membrane cell is an amniotic stromal cell. In some embodiments, the amniotic membrane cell is an umbilical cord stromal cell. In some embodiments, the IαI and TSG-6 protein are contacted at a molar ratio of 1:1, 2:1, 3:1, 4:1, 5:1, 6:1, 7:1, 8:1, 9:1, 10:1, 15:1, or 20:1. In some embodiments, the IαI and TSG-6 protein are contacted at a molar ratio of 3:1. In some embodiments of the method, the weight average molecular weight of the HMW HA is between about 500 kDa and about 10,000 kDa, between about 800 kDa and about 8,500 kDa, between about 1100 kDa and about 5,000 kDa, or between about 1400 kDa and about 3,500 kDa. In some embodiments of the method, the weight average molecular weight of the HMW HA is 3,000 kDa. In some embodiments, HMW HA is immobilized by direct linkage to a solid support. In some embodiments of the method, HMW HA is immobilized by indirect linkage to a solid support. In some embodiments of the method, HMW HA is immobilized by covalent attachment to the solid support. In some embodiments of the method, HMW HA is immobilized by non-covalent attachment to the solid support. In some embodiments of the method, HMW HA is immobilized by linkage to a solid support via a cleavable linker. In some embodiments, the linker is a chemically or enzymatically cleavable linker. In some embodiments, the method further comprises dissociation of the rcHC-HA/PTX3 complex from the solid support following step (b). In some embodiments, dissociation comprises cleavage of a cleavable linker. In some embodiments, the method further comprises purification of the dissociated rcHC-HA/PTX3 complex. In some embodiments, purification comprises affinity purification, centrifugation, filtration, chromatography or a combination thereof. In some embodiments of the method, PTX3, IαI HC1 or TSG-6 polypeptides comprise an affinity tag. In some embodiments, the affinity tag is selected from among a hemagglutinin tag, a poly-histidine tag, a myc tag, a FLAG tag, a glutathione-S-transferase (GST) tag. In some embodiments, HMW HA is immobilized by binding HMW HA to an intermediary polypeptide. In some embodiments, the intermediary polypeptide is covalently attached to the solid support. In some embodiments, binding HMW HA to the intermediary polypeptide is non-covalent. In some embodiments, the intermediary polypeptide is an HA binding protein (HABP). In some embodiments, the intermediary polypeptide is an HABP selected from among HAPLN1, HAPLN2, HAPLN3, HAPLN4, aggrecan, versican, neurocan, brevican, phosphacan, TSG-6, CD44, stabilin-1, stabilin-2, or a portion thereof sufficient to bind HA. In some embodiments, the intermediary polypeptide is versican. In some embodiments, the intermediary polypeptide comprises a link module. In some embodiments, the intermediary polypeptide comprises a link module of HAPLN1, HAPLN2, HAPLN3, HAPLN4, aggrecan, versican, neurocan, brevican, phosphacan, TSG-6, CD44, stabilin-1, or stabilin-2. In some embodiments, the intermediary polypeptide comprises a link module of versican. In some embodiments, the intermediary polypeptide comprises a polypeptide set forth in any of SEQ ID NOS: 54-99. In some embodiments, the intermediary polypeptide comprises a polypeptide linker. In some embodiments, the linker is attached to the solid support. In some embodiments, the method further comprises dissociation of the rcHC-HA/PTX3 complex from the intermediary polypeptide following step (b). In some embodiments, dissociation of the rcHC-HA/PTX3 complex from the intermediary polypeptide comprises contacting the complex with a dissociation agent. In some embodiments, the dissociation agent is guanidine hydrochloride or urea. In some embodiments, the dissociation agent is about 4 M to about 8M guanidine hydrochloride. In some embodiments, the intermediary polypeptide or linker comprises a proteolytic cleavage sequence. In some embodiments, dissociation of the rcHC-HA/PTX3 complex comprises cleaving the intermediary polypeptide or linker at proteolytic cleavage sequence. In some embodiments, cleaving comprises contacting the proteolytic cleavage sequence with a protease. In some embodiments, the protease is selected from among furin, 3C protease, caspase, matrix metalloproteinase and TEV protease.

Described herein, in certain embodiments, are methods of producing a reconstituted HC-HA/PTX3 (rcHC-HA/PTX3) complex in vitro, comprising contacting a PTX3/HA complex immobilized to a solid support with inter-α-inhibitor (IαI) protein comprising heavy chain 1 (HC1) and TSG-6. In some embodiments, the PTX3/HA complex is produced by contacting high molecular weight hyaluronan (HMW HA) with a pentraxin 3 (PTX3) protein under conditions effective to form a complex of PTX3 and HMW HA (PTX3/HA), wherein the HMW HA is immobilized to a solid support. In some embodiments, the method further comprises removing unbound PTX3 protein prior to contacting the PTX3/HA complex with IαI and TSG-6. In some embodiments, the method further comprises removing unbound TSG-6. In some embodiments, the PTX3 protein is a recombinant protein. In some embodiments, the PTX3 protein comprises a polypeptide having the sequence set forth in SEQ ID NO: 33 or a polypeptide having at least 75%, 80%, 85%, 90%, 95%, 96%, 97%, 98%, or 99% sequence amino acid identity to the polypeptide having the sequence set forth in SEQ ID NO: 33. In some embodiments, the PTX3 protein used in the methods is a multimeric protein. In some embodiments, the PTX3 protein used in the methods is a homomultimer. In some embodiments, PTX3 homomultimer is a dimer, trimer, tetramer, pentamer, hexamer, octamer. In some embodiments, the PTX3 homomultimer is an octamer. In some embodiments, PTX3 comprises a modified multimerization domain or a heterogeneous multimerization domain. In some embodiments, TSG-6 is a recombinant protein. In some embodiments, TSG-6 comprises a polypeptide having the sequence set forth in SEQ ID NO: 2 or a polypeptide having at least 75%, 80%, 85%, 90%, 95%, 96%, 97%, 98%, or 99% sequence amino acid identity to the polypeptide having the sequence set forth in SEQ ID NO: 2. In some embodiments, HC1 comprises a polypeptide having the sequence set forth in SEQ ID NO: 47 or a polypeptide having at least 75%, 80%, 85%, 90%, 95%, 96%, 97%, 98%, or 99% sequence amino acid identity to the polypeptide having the sequence set forth in SEQ ID NO: 47. In some embodiments, IαI protein also comprises HC2. In some embodiments, HC2 comprises a polypeptide having the sequence set forth in SEQ ID NO: 49 or a polypeptide having at least 75%, 80%, 85%, 90%, 95%, 96%, 97%, 98%, or 99% sequence amino acid identity to the polypeptide having the sequence set forth in SEQ ID NO: 49. In some embodiments, the IαI protein also comprises bikunin. In some embodiments, bikunin comprises a polypeptide having the sequence set forth in SEQ ID NO: 53 or a polypeptide having at least 75%, 80%, 85%, 90%, 95%, 96%, 97%, 98%, or 99% sequence amino acid identity to the polypeptide having the sequence set forth in SEQ ID NO: 53. In some embodiments, IαI also comprises a chondroitin sulfate chain. In some embodiments, the IαI protein is a recombinant protein. In some embodiments, the IαI protein is isolated from blood, plasma, serum, amniotic membrane, chorionic membrane, amniotic fluid, or a combination thereof. In some embodiments, the IαI protein is isolated from serum. In some embodiments, the IαI protein is isolated from human serum. In some embodiments, the IαI and TSG-6 protein are contacted at a molar ratio of 1:1, 2:1, 3:1, 4:1, 5:1, 6:1, 7:1, 8:1, 9:1, 10:1, 15:1, or 20:1. In some embodiments, the IαI and TSG-6 protein are contacted at a molar ratio of 3:1. In some embodiments, the weight average molecular weight of the HMW HA is between about 500 kDa and about 10,000 kDa, between about 800 kDa and about 8,500 kDa, between about 1100 kDa and about 5,000 kDa, or between about 1400 kDa and about 3,500 kDa. In some embodiments, the weight average molecular weight of the HMW HA is 3,000 kDa. In some embodiments, HMW HA is immobilized by direct linkage to a solid support In some embodiments, HMW HA is immobilized by indirect linkage to a solid support. In some embodiments, HMW HA is immobilized by covalent attachment to the solid support. In some embodiments, HMW HA is immobilized by non-covalent attachment to the solid support. In some embodiments, the method further comprises dissociation of the rcHC-HA/PTX3 complex from the solid support. In some embodiments, the method further comprises purification of the dissociated rcHC-HA/PTX3 complex. In some embodiments, purification comprises affinity purification, centrifugation, filtration, chromatography or a combination thereof. In some embodiments, the PTX3, IαI HC1 or TSG-6 polypeptides comprise an affinity tag. In some embodiments, the affinity tag is selected from among a hemagglutinin tag, a poly-histidine tag, a myc tag, a FLAG tag, a glutathione-S-transferase (GST) tag. In some embodiments, HMW HA is immobilized by binding HMW HA to an intermediary polypeptide. In some embodiments, the intermediary polypeptide is covalently attached to the solid support. In some embodiments, the binding HMW HA to the intermediary polypeptide is non-covalent. In some embodiments, the intermediary polypeptide is an HA binding protein (HABP). In some embodiments, the intermediary polypeptide is an HABP selected from among HAPLN1, HAPLN2, HAPLN3, HAPLN4, aggrecan, versican, neurocan, brevican, phosphacan, TSG-6, CD44, stabilin-1, stabilin-2, or a portion thereof sufficient to bind HA. In some embodiments, the intermediary polypeptide is versican. In some embodiments, the intermediary polypeptide comprises a link module. In some embodiments, the intermediary polypeptide comprises a link module of HAPLN1, HAPLN2, HAPLN3, HAPLN4, aggrecan, versican, neurocan, brevican, phosphacan, TSG-6, CD44, stabilin-1, or stabilin-2. In some embodiments, the intermediary polypeptide comprises a link module of versican. In some embodiments, the intermediary polypeptide comprises a polypeptide set forth in any of SEQ ID NOS: 54-99. In some embodiments, the intermediary polypeptide comprises a polypeptide linker. In some embodiments, the linker is attached to the solid support. In some embodiments, the method further comprises dissociation of the rcHC-HA/PTX3 complex from the intermediary polypeptide. In some embodiments, dissociation of the rcHC-HA/PTX3 complex from the intermediary polypeptide comprises contacting the complex with a dissociation agent. In some embodiments, the dissociation agent is guanidine hydrochloride or urea. In some embodiments, the dissociation agent is about 4 M to about 8M guanidine hydrochloride. In some embodiments, the intermediary polypeptide or linker comprises a proteolytic cleavage sequence. In some embodiments, dissociation comprises cleaving the intermediary polypeptide or linker at proteolytic cleavage sequence. In some embodiments, cleaving comprises contacting the proteolytic cleavage sequence with a protease. In some embodiments, the protease is selected from among furin, 3C protease, caspase, matrix metalloproteinase and TEV protease.

Described herein, in certain embodiments, are reconstituted HC-HA (rcHC-HA/PTX3) complexes produced by any of the methods provided herein for generating rcHC-HA/PTX3 complexes.

Described herein, in certain embodiments, are reconstituted HC-HA/PTX3(rcHC-HA/PTX3) complexes comprising high molecular weight hyaluronan (HMW HA), PTX3, and IαI HC1, wherein the rcHC-HA/PTX3 complexes promote the M2 polarization of a macrophage. Described herein, in certain embodiments, are native HC-HA/PTX3 (nHC-HA/PTX3) complexes comprising high molecular weight hyaluronan (HMW HA), PTX3, and IαI HC1, wherein the nHC-HA/PTX3 complexes promote the M2 polarization of a macrophage. Described herein, in certain embodiments, are methods for inducing the M2 polarization of macrophages comprising contacting a macrophage with an rcHC-HA/PTX3 or isolated nHC-HA/PTX3 complex.

Described herein, in certain embodiments, are reconstituted HC-HA/PTX3(rcHC-HA/PTX3) complexes comprising high molecular weight hyaluronan (HMW HA), PTX3, and IαI HC1, wherein the rcHC-HA/PTX3 complexes reduce the expression of IL-12p40 in LPS-stimulated macrophages, wherein the level of IL-12p40 expressed by LPS-stimulated macrophages is lower when the LPS-stimulated macrophages are contacted the rcHC-HA/PTX3 complexes compared to the level of IL-12p40 expressed by LPS-stimulated macrophages in the absence of the rcHC-HA/PTX3 complexes. In some embodiments, the level of IL-12p40 mRNA is reduced. In some embodiments, the level of IL-12p40 protein is reduced.

Described herein, in certain embodiments, are native HC-HA/PTX3(nHC-HA/PTX3) complexes comprising high molecular weight hyaluronan (HMW HA), PTX3, and IαI HC1, wherein the nHC-HA/PTX3 complexes reduce the expression of IL-12p40 in LPS-stimulated macrophages, wherein the level of IL-12p40 expressed by LPS-stimulated macrophages is lower when the LPS-stimulated macrophages are contacted the nHC-HA/PTX3 complexes compared to the level of IL-12p40 expressed by LPS-stimulated macrophages in the absence of the nHC-HA/PTX3 complexes. In some embodiments, the level of IL-12p40 mRNA is reduced. In some embodiments, the level of IL-12p40 protein is reduced.

Described herein, in certain embodiments, are methods for reducing the level of IL-12p40 expressed by LPS-stimulated macrophages comprising, contacting an LPS-stimulated macrophages with an rcHC-HA/PTX3 or isolated nHC-HA/PTX3 complex. In some embodiments, the level of IL-12p40 mRNA is reduced. In some embodiments, the level of IL-12p40 protein is reduced.

Described herein, in certain embodiments, are reconstituted HC-HA/PTX3 (rcHC-HA/PTX3) complexes comprising high molecular weight hyaluronan (HMW HA), PTX3, and IαI HC1, wherein the rcHC-HA/PTX3 complexes reduce the expression of IL-12p70 protein in LPS-stimulated macrophages, wherein the amount of IL-12p70 protein expressed by LPS-stimulated macrophages is lower when the LPS-stimulated macrophages are contacted the rcHC-HA/PTX3 complexes compared to the amount of IL-12p70 protein expressed by LPS-stimulated macrophages in the absence of the rcHC-HA/PTX3 complexes.

Described herein, in certain embodiments, are native HC-HA/PTX3 (nHC-HA/PTX3) complexes comprising high molecular weight hyaluronan (HMW HA), PTX3, and IαI HC1, wherein the nHC-HA/PTX3 complexes reduces the expression of IL-12p70 protein in LPS-stimulated macrophages, wherein the amount of IL-12p70 protein expressed by LPS-stimulated macrophages is lower when the LPS-stimulated macrophages are contacted the nHC-HA/PTX3 complexes compared to the amount of IL-12p70 protein expressed by LPS-stimulated macrophages in the absence of the nHC-HA/PTX3 complexes.

Described herein, in certain embodiments, are methods for reducing the level of IL-12p70 protein expressed by LPS-stimulated macrophages comprising, contacting an LPS-stimulated macrophages with an rcHC-HA/PTX3 or isolated nHC-HA/PTX3 complex.

Described herein, in certain embodiments, are reconstituted HC-HA/PTX3 (rcHC-HA/PTX3) complexes comprising high molecular weight hyaluronan (HMW HA), PTX3, and IαI HC1, wherein the rcHC-HA/PTX3 complexes reduce the expression of IL-23 in LPS-stimulated macrophages, wherein the level of IL-23 expressed by LPS-stimulated macrophages is lower when the LPS-stimulated macrophages are contacted the rcHC-HA/PTX3 complexes compared to the level of IL-23 expressed by LPS-stimulated macrophages in the absence of the rcHC-HA/PTX3 complexes. In some embodiments, the level of IL-23 mRNA is reduced. In some embodiments, the level of IL-23 protein is reduced.

Described herein, in certain embodiments, are native HC-HA/PTX3 (rcHC-HA/PTX3) complexes comprising high molecular weight hyaluronan (HMW HA), PTX3, and IαI HC1, wherein the complexes reduces the expression of IL-23 in LPS-stimulated macrophages, wherein the level of IL-23 expressed by LPS-stimulated macrophages is lower when the LPS-stimulated macrophages are contacted the nHC-HA/PTX3 complexes compared to the level of IL-23 expressed by LPS-stimulated macrophages in the absence of the nHC-HA/PTX3 complex. In some embodiments, the level of IL-23 mRNA is reduced. In some embodiments, the level of IL-23 protein is reduced.

Described herein, in certain embodiments, are methods for reducing the level of IL-23 expressed by LPS-stimulated macrophages comprising, contacting an LPS-stimulated macrophages with an rcHC-HA/PTX3 or isolated nHC-HA/PTX3 complex. In some embodiments, the level of IL-23 mRNA is reduced. In some embodiments, the level of IL-23 protein is reduced.

Described herein, in certain embodiments, are reconstituted HC-HA/PTX3 (rcHC-HA/PTX3) complexes comprising high molecular weight hyaluronan (HMW HA), PTX3, and IαI HC1, wherein the rcHC-HA/PTX3 complexes increase the expression of IL-10 in LPS-stimulated macrophages, wherein the level of IL-10 expressed by LPS-stimulated macrophages is higher when the LPS-stimulated macrophages are contacted the rcHC-HA/PTX3 complexes compared to the level of IL-10 expressed by LPS-stimulated macrophages in the absence of the rcHC-HA/PTX3 complexes. In some embodiments, the level of IL-10 mRNA is increased. In some embodiments, the level of IL-10 protein is increased.

Described herein, in certain embodiments, are native HC-HA/PTX3 (nHC-HA/PTX3) complexes comprising high molecular weight hyaluronan (HMW HA), PTX3, and IαI HC1, wherein the complexes increase the expression of IL-10 in LPS/IFNγ-stimulated macrophages, wherein the amount of IL-10 expressed by LPS/IFNγ-stimulated macrophages is higher when the LPS-stimulated macrophages are contacted with the nHC-HA/PTX3 complexes compared to the amount of IL-10 expressed by LPS/IFNγ-stimulated macrophages in the absence of the nHC-HA/PTX3 complexes. In some embodiments, the level of IL-10 mRNA is increased. In some embodiments, the level of IL-10 protein is increased.

Described herein, in certain embodiments, are methods for increasing the level of IL-10 expressed by LPS-stimulated macrophages comprising, contacting an LPS-stimulated macrophages with an rcHC-HA/PTX3 or isolated nHC-HA/PTX3 complex. In some embodiments, the level of IL-10 mRNA is increased. In some embodiments, the level of IL-10 protein is increased.

Described herein, in certain embodiments, are reconstituted HC-HA/PTX3 (rcHC-HA/PTX3) complexes comprising high molecular weight hyaluronan (HMW HA), PTX3, and IαI HC1, wherein the rcHC-HA/PTX3 complexes promote apoptosis of LPS-stimulated neutrophils but do not promote apoptosis in resting neutrophils. In some embodiments, a reconstituted HC-HA/PTX3 (rcHC-HA/PTX3) complex, comprising high molecular weight hyaluronan (HMW HA), PTX3, and IαI HC1, promotes apoptosis of LPS-stimulated neutrophils wherein the number of LPS-stimulated neutrophils that are apoptotic in a sample of LPS-stimulated neutrophils is higher when the sample is contacted the rcHC-HA/PTX3 complex compared to the number of LPS-stimulated neutrophils that are apoptotic in the sample in the absence of the rcHC-HA/PTX3 complex.

Described herein, in certain embodiments, are native HC-HA/PTX3 (nHC-HA/PTX3) complex comprising high molecular weight hyaluronan (HMW HA), PTX3, and IαI HC1, wherein the nHC-HA/PTX3 complexes promote apoptosis of LPS-stimulated neutrophils but do not promote apoptosis in resting neutrophils. In some embodiments, a nHC-HA/PTX3 complex, comprising high molecular weight hyaluronan (HMW HA), PTX3, and IαI HC1, promotes apoptosis of LPS-stimulated neutrophils wherein the number of LPS-stimulated neutrophils that are apoptotic in a sample of LPS-stimulated neutrophils is higher when the sample is contacted the nHC-HA/PTX3 complex compared to the number of LPS-stimulated neutrophils that are apoptotic in the sample in the absence of the nHC-HA/PTX3 complex.

Described herein, in certain embodiments, are methods for inducing apoptosis of LPS-stimulated neutrophils comprising, contacting an LPS-stimulated neutrophil with an rcHC-HA/PTX3 or isolated nHC-HA/PTX3 complex.

Described herein, in certain embodiments, are reconstituted HC-HA/PTX3 (rcHC-HA/PTX3) complexes comprising high molecular weight hyaluronan (HMW HA), PTX3, and IαI HC1, wherein the rcHC-HA/PTX3 complexes promote phagocytosis of apoptotic neutrophils, wherein the number of apoptotic neutrophils that are phagocytosed by LPS-stimulated macrophages in a sample of apoptotic neutrophils and LPS-stimulated macrophages is higher when the sample is contacted with the rcHC-HA/PTX3 complexes compared to the number of neutrophils that are phagocytosed by LPS-stimulated macrophages in the sample in the absence of the rcHC-HA/PTX3 complexes. Described herein, in certain embodiments, are reconstituted HC-HA/PTX3 (rcHC-HA/PTX3) complexes comprising high molecular weight hyaluronan (HMW HA), PTX3, and IαI HC1, wherein the complexes promote phagocytosis of apoptotic neutrophils, wherein the number of apoptotic neutrophils that are phagocytosed by resting macrophages in a sample of apoptotic neutrophils and resting macrophages is higher when the sample is contacted with the rcHC-HA/PTX3 complexes compared to the number of neutrophils that are phagocytosed by resting macrophages in the sample in the absence of the rcHC-HA/PTX3 complexes.

Described herein, in certain embodiments, are native HC-HA/PTX3 (nHC-HA/PTX3) complexes comprising high molecular weight hyaluronan (HMW HA), PTX3, and IαI HC1, wherein the nHC-HA/PTX3 complexes promotes phagocytosis of apoptotic neutrophils, wherein the number of apoptotic neutrophils that are phagocytosed by LPS-stimulated macrophages in a sample of apoptotic neutrophils and LPS-stimulated macrophages is higher when the sample is contacted with the nHC-HA/PTX3 complexes compared to the number of neutrophils that are phagocytosed by LPS-stimulated macrophages in the sample in the absence of the nHC-HA/PTX3 complexes. Described herein, in certain embodiments, are native HC-HA/PTX3 (nHC-HA/PTX3) complexes comprising high molecular weight hyaluronan (HMW HA), PTX3, and IαI HC1, wherein the nHC-HA/PTX3 complexes promotes phagocytosis of apoptotic neutrophils, wherein the number of apoptotic neutrophils that are phagocytosed by resting macrophages in a sample of apoptotic neutrophils and LPS-stimulated macrophages is higher when the sample is contacted with the nHC-HA/PTX3 complexes compared to the number of neutrophils that are phagocytosed by resting macrophages in the sample in the absence of the nHC-HA/PTX3 complexes.

Described herein, in certain embodiments, are methods inducing phagocytosis of apoptotic neutrophils comprising, contacting a sample containing apoptotic neutrophils and LPS-stimulated or resting macrophages with an rcHC-HA/PTX3 or isolated nHC-HA/PTX3 complex.

Described herein, in certain embodiments, are reconstituted HC-HA/PTX3 (rcHC-HA/PTX3) complexes comprising high molecular weight hyaluronan (HMW HA), PTX3, and IαI HC1, wherein the rcHC-HA/PTX3 complexes promote attachment of LPS-stimulated macrophages to at least the same level as a native HC-HA/PTX3 (nHC-HA/PTX3) complex isolated from human umbilical cord, human amniotic membrane, or a combination of nHC-HA/PTX3 complexes from both human umbilical cord and human amniotic membrane, wherein attachment comprises the contacting LPS-stimulated macrophages to the rcHC-HA/PTX3 or nHC-HA/PTX3 complexes immobilized to a solid support. In some embodiments, the nHC-HA/PTX3 is isolated from human umbilical cord. In some embodiments, the nHC-HA/PTX3 is isolated from human amniotic membrane. In some embodiments, the nHC-HA/PTX3 is isolated from a combination of nHC-HA/PTX3 complexes from both human umbilical cord and human amniotic membrane.

In some embodiments, the weight average molecular weight of the HMW HA of the nHC-HA/PTX3 or rcHC-HA/PTX3 complex is between about 500 kDa and about 10,000 kDa, between about 800 kDa and about 8,500 kDa, between about 1100 kDa and about 5,000 kDa, or between about 1400 kDa and about 3,500 kDa. In some embodiments, contains, the weight average molecular weight of the HMW HA of the nHC-HA/PTX3 or rcHC-HA/PTX3 complex is about 3,000 kDa.

In some embodiments, HC1 of the nHC-HA/PTX3 or rcHC-HA/PTX3 complex is covalently linked to HA.

In some embodiments, the PTX3 protein of the rcHC-HA/PTX3 complex is a recombinant protein. In some embodiments, PTX3 of the rcHC-HA/PTX3 complex comprises a polypeptide having the sequence set forth in SEQ ID NO: 33 or a polypeptide having at least 75%, 80%, 85%, 90%, 95%, 96%, 97%, 98%, or 99% sequence amino acid identity to the polypeptide having the sequence set forth in SEQ ID NO: 33. In some embodiments, the PTX3 protein used in the methods is a multimeric protein. In some embodiments, the PTX3 protein used in the methods is a homomultimer. In some embodiments, the PTX3 homomultimer is a dimer, trimer, tetramer, pentamer, hexamer, or octamer. In some embodiments, the PTX3 homomultimer is a trimer, tetramer, or octamer. In some embodiments, the PTX3 homomultimer is an octamer.

In some embodiments, the IαI HC1 of the rcHC-HA/PTX3 complex comprises a polypeptide having the sequence set forth in SEQ ID NO: 47 or a polypeptide having at least 75%, 80%, 85%, 90%, 95%, 96%, 97%, 98%, or 99% sequence amino acid identity to the polypeptide having the sequence set forth in SEQ ID NO: 47. In some embodiments, the IαI HC1 of the rcHC-HA/PTX3 complex is a recombinant protein.

In some embodiments, the rcHC-HA/PTX3 complex comprises TSG-6. In some embodiments, the TSG-6 protein is a recombinant protein. In some embodiments, the TSG-6 protein comprises a polypeptide having the sequence set forth in SEQ ID NO: 2 or a polypeptide having at least 75%, 80%, 85%, 90%, 95%, 96%, 97%, 98%, or 99% sequence amino acid identity to the polypeptide having the sequence set forth in SEQ ID NO: 2.

In some embodiments, the PTX3, IαI HC1 or TSG-6 polypeptides of the rcHC-HA/PTX3 complex comprise an affinity tag. In some embodiments, the affinity tag is selected from among is selected from among a hemagglutinin tag, a poly-histidine tag, a myc tag, a FLAG tag, a glutathione-S-transferase (GST) tag.

Described herein, in certain embodiments, is a pharmaceutical composition, comprising an nHC-HA/PTX3 or rcHC-HA/PTX3 complex described herein or produced by the methods provided herein. In some embodiments, pharmaceutical composition further comprises a pharmaceutically acceptable carrier or excipient. In some embodiments, pharmaceutical composition is in the form of a solution, suspension, powder, ointment, tablet, capsule, or an aerosol. In some embodiments, pharmaceutical composition is in the form of a solid, a cross-linked gel, or a liposome. In some embodiments, pharmaceutical composition is in the form of a cross-linked hyaluronan hydrogel. In some embodiments, pharmaceutical composition comprises a natural polymer. In some embodiments, natural polymer comprises fibronectin, collagen, laminin, keratin, fibrin, fibrinogen, hyaluronic acid, heparan sulfate, chondroitin sulfate, or combinations thereof. In some embodiments, pharmaceutical composition further comprises an anti-inflammatory agent, an anti-scarring agent, an anti-neoplastic agent, a chemotherapeutic agent, an immunosuppressive agent, a cytotoxic agent, an antimicrobial agent, or a combination thereof.

Described herein, in certain embodiments, is a use of an nHC-HA/PTX3 or rcHC-HA/PTX3 complex described herein or produced by the methods provided herein for the production of a medicament.

Described herein, in certain embodiments, is a combination comprising: (a) an nHC-HA/PTX3 or rcHC-HA/PTX3 complex described herein or produced by the methods provided herein; and (b) an anti-inflammatory agent, an anti-scarring agent, an anti-neoplastic agent, a chemotherapeutic agent, an immunosuppressive agent, a cytotoxic agent, an antimicrobial agent or a combination thereof.

Described herein, in certain embodiments, are methods of treatment, comprising administering a pharmaceutical composition comprising an nHC-HA/PTX3 or rcHC-HA/PTX3 complex described herein or produced by the methods provided herein.

Described herein, in certain embodiments, are methods of preventing or reversing scar formation or fibrosis in a tissue, comprising administering to the subject in need thereof an effective amount of an nHC-HA/PTX3 or rcHC-HA/PTX3 complex described herein or produced by the methods provided herein. In some embodiments, the method comprises contacting the tissue with an effective amount of the nHC-HA/PTX3 or rcHC-HA/PTX3 complex. In some embodiments, the scar is a dermatitis scar, a keloid scar, contracture scar, a hypertrophic scar, or a scar resulting from acne. Described herein, in certain embodiments, is a use of an nHC-HA/PTX3 or rcHC-HA/PTX3 complex described herein or produced by the methods provided herein to reduce or prevent scarring. In some embodiments, administration of an nHC-HA/PTX3 or rcHC-HA/PTX3 complex described herein or produced by the methods provided herein reduces or prevents scarring or fibrosis by decreasing or inhibiting TGF-β signaling in the tissue.

Described herein, in certain embodiments, are methods of preventing or reducing inflammation in a subject in need thereof, comprising administering to the subject an effective amount of an nHC-HA/PTX3 or rcHC-HA/PTX3 complex described herein or produced by the methods provided herein. In some embodiments, the method comprises contacting inflamed tissues with the nHC-HA/PTX3 or rcHC-HA/PTX3 complex. In some embodiments, the inflammation is acute inflammation or chronic inflammation. In some embodiments, the subject has an inflammatory disorder. In some embodiments, the inflammatory disorder is a macrophage-mediated inflammatory disorder, a Th-17-mediated immune disorder or a T-cell mediated inflammatory disorder. In some embodiments, the subject has an autoimmune disorder, an allergy, a leukocyte defect, an infection, graft versus host disease, tissue transplant rejection, or combinations thereof. In some embodiments, the inflammatory disorder is rheumatoid arthritis. In some embodiments, the inflammatory disorder is an inflammatory disorder of the eye. In some embodiments, the inflammatory disorder is conjunctivitis, keratitis, blepharitis, blepharoconjunctivitis, scleritis, episcleritis, uveitis, retinitis, or choroiditis. In some embodiments, the acute inflammation is caused by myocardial infarction, stroke, endotoxin shock or sepsis. In some embodiments, the subject has atherosclerosis. In some embodiments, the subject has cancer. In some embodiments, the subject has inflammation of a solid tumor. In some embodiments, the subject is administered the nHC-HA/PTX3 or rcHC-HA/PTX3 complex in combination with an additional anti-inflammatory agent. In some embodiments, the additional anti-inflammatory agent is selected from among an anti-TGF-β antibody, an anti-TGF-β receptor blocking antibody, an anti-TNF antibody, an anti-TNF receptor blocking antibody, an anti-IL1β antibody, an anti-IL1β receptor blocking antibody, an anti-IL-2 antibody, an anti-IL-2 receptor blocking antibody, an anti-IL-6 antibody, an anti-IL-6 receptor blocking antibody, an anti IL-12 antibody, an anti IL-12 receptor blocking antibody, an anti-IL-17 antibody, anti-IL-17 receptor blocking antibody, an anti-IL-23 antibody, or an anti-IL-23 receptor blocking antibody. In some embodiments, the Type 1 interferon is IFN-α or IFN-β. Described herein, in certain embodiments, is a use of an nHC-HA/PTX3 or rcHC-HA/PTX3 complex described herein or produced by the methods provided herein to reduce or prevent inflammation.

Described herein, in certain embodiments, are methods of treating a skin wound or ulcer in a subject in need thereof, comprising administering to the subject an effective amount of an nHC-HA/PTX3 or rcHC-HA/PTX3 complex described herein or produced by the methods provided herein. In some embodiments, the methods comprise contacting the skin wound or ulcer with an effective amount of the nHC-HA/PTX3 or rcHC-HA/PTX3 complex. Described herein, in certain embodiments, is a use of an nHC-HA/PTX3 or rcHC-HA/PTX3 complex described herein or produced by the methods provided herein to treat a skin wound or ulcer. In some embodiments, the skin wound or ulcer is a non-healing ulcer.

Described herein, in certain embodiments, are methods of promoting or inducing bone formation in a subject in need thereof, comprising administering to the administering to the subject an effective amount of the rcHC-HA/PTX3 complex or nHC-HA/PTX3 complex described herein or produced by the methods provided herein. In some embodiments, the subject has arthritis, osteoporosis, alveolar bone degradation, Paget's disease, or a bone tumor. Described herein, in certain embodiments, is a use of an nHC-HA/PTX3 or rcHC-HA/PTX3 complex described herein or produced by the methods provided herein to promote or induce bone formation in a subject.

Described herein, in certain embodiments, are methods of preventing or reducing abnormal angiogenesis in a subject in need thereof, comprising administering to the subject an effective amount of an nHC-HA/PTX3 or rcHC-HA/PTX3 complex described herein or produced by the methods provided herein. In some embodiments, the subject has wet age-related macular degeneration (wARMD) or diabetic proliferative retinopathy. In some embodiments, the subject has cancer. In some embodiments, the subject has a solid tumor. In some embodiments, the subject is administered the nHC-HA/PTX3 or rcHC-HA/PTX3 complex in combination with an anti-cancer therapy. In some embodiments, the anticancer therapy comprises administration of an antineoplastic agent, a cytotoxic agent, an anti-angiogenic agent, a chemotherapeutic agent, or radiation therapy. In some embodiments, the anticancer therapy is administered sequentially, concurrently or intermittently with the nHC-HA/PTX3 or rcHC-HA/PTX3 complex. Described herein, in certain embodiments, is a use of an nHC-HA/PTX3 or rcHC-HA/PTX3 complex described herein or produced by the methods provided herein to reduce or prevent angiogenesis.

Described herein, in certain embodiments, are methods of preventing transplant rejection in a transplant recipient, comprising administering to the transplant recipient an effective amount of an nHC-HA/PTX3 or rcHC-HA/PTX3 complex described herein or produced by the methods provided herein. In some embodiments, the method comprise contacting the transplant with the nHC-HA/PTX3 or rcHC-HA/PTX3 complex. In some embodiments, the nHC-HA/PTX3 or rcHC-HA/PTX3 complex is administered before a transplantation procedure, after a transplantation procedure, or during a transplantation procedure. In some embodiments, the nHC-HA/PTX3 or rcHC-HA/PTX3 complex is administered in combination with an immunosuppressive agent. Described herein, in certain embodiments, is a use of an nHC-HA/PTX3 or rcHC-HA/PTX3 complex described herein or produced by the methods provided herein to prevent transplant rejection in a transplant recipient. In some embodiments, the transplant is a corneal transplant.

Described herein, in certain embodiments, are methods of inducing stem cell expansion in a subject in need thereof, comprising administering to the subject an effective amount of an nHC-HA/PTX3 or rcHC-HA/PTX3 complex described herein or produced by the methods provided herein. In some embodiments, the method comprise contacting the stem cell with the nHC-HA/PTX3 or rcHC-HA/PTX3 complex. Described herein, in certain embodiments, is a use of an nHC-HA/PTX3 or rcHC-HA/PTX3 complex described herein or produced by the methods provided herein to induce stem cell expansion. In some embodiments, administration of an nHC-HA/PTX3 or rcHC-HA/PTX3 complex described herein or produced by the methods provided herein induces stem cell expansion by suppression of TGF-$\beta$ signaling and/or upregulation of BMP signaling pathways. In some embodiments, administration of an nHC-HA/PTX3 or rcHC-HA/PTX3 complex described herein or produced by the methods provided herein induces stem cell expansion by reprogramming differentiated cells into stem cells (or induced progenitor cells, iPSCs).

Described herein, in certain embodiments, is a use of an nHC-HA/PTX3 or rcHC-HA/PTX3 complex described herein or produced by the methods provided herein for cell therapy.

Described herein, in certain embodiments, are methods of cell therapy in a subject in need thereof, comprising administering to the subject a composition comprising an effective amount of an nHC-HA/PTX3 or rcHC-HA/PTX3 complex described herein or produced by the methods provided herein in combination with a therapeutic cell. In some embodiments, the therapeutic cell and the nHC-HA/PTX3 or rcHC-HA/PTX3 complex are administered locally to a damaged tissue. In some embodiments, the therapeutic cell and the nHC-HA/PTX3 or rcHC-HA/PTX3 complex are administered systemically. In some embodiments, the therapeutic cell is a stem cell. In some embodiments, the therapeutic is a stem cell. In some embodiments, the cell therapy comprises administration of a stem cell. In some embodiments, the stem cell is a mesenchymal stem cell. In some embodiments, the stem cells are induced progenitor stem cells. In some embodiments, the cell therapy comprises administration of differentiated cells. In some embodiments, therapeutic cell is an insulin producing cell. In some embodiments, the insulin producing cell is an islet cell. In some embodiments, the subject has diabetes mellitus type 1.

Described herein, in certain embodiments, are methods of cell therapy in a subject in need thereof, comprising administering to the administering to the subject an effective amount of an nHC-HA/PTX3 or rcHC-HA/PTX3 complex described herein or produced by the methods provided herein in combination with a cell contained in a cell delivery device. In some embodiments, the cell is contained in a microcapsule. In some embodiments, the nHC-HA/PTX3 or rcHC-HA/PTX3 complex is attached to the microcapsule. In some embodiments, the microcapsule is administered locally to a damaged tissue. In some embodiments, the therapeutic cell and the nHC-HA/PTX3 or rcHC-HA/PTX3 complex are administered systemically. In some embodiments, the therapeutic cell is a stem cell. In some embodiments, the therapeutic is a stem cell. In some embodiments, the cell therapy comprises administration of a stem cell. In some embodiments, the stem cell is a mesenchymal stem cell. In some embodiments, the stem cells are induced progenitor stem cells. In some embodiments, the cell therapy comprises administration of differentiated cells. In some embodiments, therapeutic cell is an insulin producing cell.

In some embodiments, the insulin producing cell is an islet cell. In some embodiments, the subject has diabetes mellitus type 1.

Described herein, in certain embodiments, are methods of preventing or reducing pain in a subject in need thereof, comprising administering to the subject an effective amount of an nHC-HA/PTX3 or rcHC-HA/PTX3 complex described herein or produced by the methods provided herein, wherein the pain is caused by chemical burn, severe bacterial keratitis, Stevens-Johnson syndrome, toxic epidermal necrolysis, irradiation of ocular tumors. Described herein, in certain embodiments, is a use of an nHC-HA/PTX3 or rcHC-HA/PTX3 complex described herein or produced by the methods provided herein to reduce pain in a subject, wherein the pain is caused by chemical burn, severe bacterial keratitis, Stevens-Johnson syndrome, toxic epidermal necrolysis, irradiation of ocular tumors.

Described herein, in certain embodiments, are methods of inducing or promoting tissue regeneration in a subject in need thereof, comprising administering to the subject an effective amount of an nHC-HA/PTX3 or rcHC-HA/PTX3 complex described herein or produced by the methods provided herein. In some embodiments, the methods comprise contacting damaged tissue of the subject with an effective amount of the nHC-HA/PTX3 or rcHC-HA/PTX3 complex. In some embodiments, the tissue is bone or gum, corneal tissue, or conjunctival tissue. In some embodiments, the nHC-HA/PTX3 or rcHC-HA/PTX3 complex is administered in combination with a therapeutic cell, a plurality of therapeutic cells or a tissue transplant. In some embodiments, the tissue transplant is an allograft or an autograft. In some embodiments, the nHC-HA/PTX3 or rcHC-HA/PTX3 complex is administered in combination with a tissue based therapy. Described herein, in certain embodiments, is a use of an nHC-HA/PTX3 or rcHC-HA/PTX3 complex described herein or produced by the methods provided herein to induce or promote tissue regeneration in a subject.

Described herein, in certain embodiments, are methods of treating fibrosis in a subject in need thereof, comprising administering to the subject an effective amount of an nHC-HA/PTX3 or rcHC-HA/PTX3 complex described herein or produced by the methods provided herein. In some embodiments, the treatment inhibits or prevents scarring. Described herein, in certain embodiments, is a use of an nHC-HA/PTX3 or rcHC-HA/PTX3 complex described herein or produced by the methods provided herein to treat fibrosis in a subject.

Described herein, in certain embodiments, are methods of treating obesity or insulin resistance in a subject in need thereof, comprising administering to the subject an effective amount of an nHC-HA/PTX3 or rcHC-HA/PTX3 complex described herein or produced by the methods provided herein. In some embodiments, the treatment inhibits or decreases the amount of M1 adipose tissue macrophages in the subject. Described herein, in certain embodiments, are methods of inhibiting or decreasing the amount of M1 adipose tissue macrophages in a subject in need thereof, administering to the subject an effective amount of an nHC-HA/PTX3 or rcHC-HA/PTX3 complex described herein or produced by the methods provided herein. In some embodiments, the subject has been diagnosed with obesity or insulin-resistance. Described herein, in certain embodiments, is a use of an nHC-HA/PTX3 or rcHC-HA/PTX3 complex described herein or produced by the methods provided herein to treat obesity or insulin resistance in a subject.

Described herein, in certain embodiments, are methods of treating conjunctivochalasis in a subject in need thereof, comprising administering to the subject an effective amount of an nHC-HA/PTX3 or rcHC-HA/PTX3 complex described herein or produced by the methods provided herein. In some embodiments, the methods comprise contacting the conjunctiva of the subject with an effective amount of the nHC-HA/PTX3 or rcHC-HA/PTX3 complex. Described herein, in certain embodiments, is a use of an nHC-HA/PTX3 or rcHC-HA/PTX3 complex described herein or produced by the methods provided herein to treat conjunctivochalasis in a subject.

Described herein, in certain embodiments, are cell cultures comprising a substrate suitable for culturing a cell and a rcHA/PTX3 complex or the nHC-HA/PTX3 complex described herein or produced by the methods provided herein, In some embodiments, the rcHA/PTX3 complex or the nHC-HA/PTX3 complex immobilized to the substrate.

Described herein, in certain embodiments, are methods of treatment, wherein the subject is administered an effective amount of an nHC-HA/PTX3 or rcHC-HA/PTX3 complex described herein or produced by the methods provided herein in combination with an additional therapeutic agent. In some embodiments, the additional therapeutic agent is selected from an interferon, an anti-tumor necrosis factor, an interleukin-1 (IL-1) receptor antagonist, an interleukin-2 (IL-2) receptor antagonist, an interleukin-6 (IL-6) receptor antagonist, an interleukin-12 (IL-12) receptor antagonist, an interleukin-17 (IL-17) receptor antagonist, an interleukin-23 (IL-23) receptor antagonist, a cytotoxic agent, an antimicrobial agent, an interleukin, an immunomodulatory agent, an antibiotic, a T-cell co-stimulatory blocker, a disorder-modifying anti-rheumatic agent, an immunosuppressive agent, an anti-lymphocyte antibody, an anti-angiogenesis agent, a chemotherapeutic agent, an anti-neoplastic agent, an anti-metabolite, an Akt inhibitor, an IGF-1 inhibitor, an angiotensin II antagonist, a cyclooxygenase inhibitor, an heparanase inhibitor, a lymphokine inhibitor, a cytokine inhibitor, an IKK inhibitor, a P38MAPK inhibitor, an anti-apoptotic pathway inhibitor, an apoptotic pathway agonist, a PPAR agonist, an inhibitors of Ras, a telomerase inhibitor, a protease inhibitor, a metalloproteinase inhibitor, an aminopeptidase inhibitor, a SHIP activator and combinations thereof. In some embodiments, the antimicrobial agent is an antiviral, antibacterial or antifungal agent.

Described herein, in certain embodiments, are methods of treatment, wherein the subject is administered an effective amount of an nHC-HA/PTX3 or rcHC-HA/PTX3 complex described herein or produced by the methods provided herein and the subject is a mammal. In some embodiments, the mammal is a human.

Described herein, in certain embodiments, are methods of treatment, wherein the nHC-HA/PTX3 or rcHC-HA/PTX3 complex is attached to a solid surface. In some embodiments, the solid surface is a surface or a portion thereof of a nanoparticle, a bead, a microcapsule or implantable medical device.

Described herein, in certain embodiments, is are medical devices, comprising a substrate coated with an nHC-HA/PTX3 or rcHC-HA/PTX3 complex described herein or produced by the methods provided herein. In some embodiments, the substrate comprises at least one of a stent, a joint, a screw, a rod, a pin, a plate, a staple, a shunt, a clamp, a clip, a suture, a suture anchor, an electrode, a catheter, a lead, a graft, a dressing, a pacemaker, a pacemaker housing, a cardioverter, a cardioverter housing, a defibrillator, a defibrillator housing, a prostheses, an ear drainage tube, an ophthalmic implant, an orthopedic device, a vertebral disk, a bone substitute, an anastomotic device, a perivascular wrap, a colostomy bag attachment device, a hemostatic barrier, a vascular implant, a vascular support, a tissue adhesive, a tissue sealant, a tissue scaffold, and an intraluminal device.

Described herein, in certain embodiments, is a device comprising an nHC-HA/PTX3 or rcHC-HA/PTX3 complex described herein or produced by the methods provided herein immobilized on a surface. In some embodiments, the surface is a polystyrene, polyethylene, silica, metallic or polymeric surface. In some embodiments, the nHC-HA/PTX3 or rcHC-HA/PTX3 complex is attached to a microcapsule. In some embodiments, the nHC-HA/PTX3 or rcHC-HA/PTX3 complex is attached to a nanoparticle. In some embodiments, the nHC-HA/PTX3 or rcHC-HA/PTX3 complex is attached to a bead, a chip, a glass slide, or a filter. In some embodiments, the nHC-HA/PTX3 or rcHC-HA/PTX3 complex is attached to a contact lens. In some embodiments, the nHC-HA/PTX3 or rcHC-HA/PTX3 complex is attached to a surgical implant or prosthesis. In some embodiments, the implant or prosthesis is an artificial joint, a bone implant, a suture, or a stent. In some embodiments, the artificial joint is an artificial hip joint, an artificial knee, an artificial glenohumeral joint, or an artificial knee. In some embodiments, the stent is a coronary stent, a ureteral stent, a urethral stent, a prostatic stent, esophageal stent, or a bone stent.

Described herein, in certain embodiments, is are medical devices comprising: a structure adapted for implantation into a patient, wherein a surface or a portion of a surface of the structure is attached to comprising an nHC-HA/PTX3 or rcHC-HA/PTX3 complex described herein or produced by the methods provided herein. In some embodiments, attachment comprises covalent or non-covalent attachment of the nHC-HA/PTX3 or rcHC-HA/PTX3 complex to the surface or portion of a surface of the structure In some embodiments, attachment comprises coating the surface or a portion of a surface of the structure with a composition containing the nHC-HA/PTX3 or rcHC-HA/PTX3 complex. In some embodiments, the structure is a vascular stent, an artificial joint, a suture, or a microcapsule. In some embodiments, the nHC-HA/PTX3 or rcHC-HA/PTX3 complex inhibits the formation of a bacterial biofilm. In some embodiments, the microcapsule contains a therapeutic cell. In some embodiments, the therapeutic cell is a stem cell.

Described herein, in certain embodiments, are methods for modulating macrophage activity comprising contacting a macrophage with an nHC-HA/PTX3 or rcHC-HA/PTX3 complex described herein or produced by the methods provided herein in an amount sufficient to reduce or inhibit the expression of IL-12 or IL-23 but also promote the expression of IL-10 in polarizing macrophages from M1 to M2 phenotype. In some embodiments, the macrophage has been stimulated with a pro-inflammatory mediator. In some embodiments, the pro-inflammatory mediator is lipopolysaccharide (LPS), tumor necrosis factor α (TNF-α), interferon-gamma (IFN γ) or a combination thereof. In some embodiments, the nHC-HA/PTX3 or rcHC-HA/PTX3 complex contacts the macrophage in vivo in a subject. In some embodiments, the subject is a mammal. In some embodiments, the mammal is a human. In some embodiments, the method is performed in vitro. Described herein, in certain embodiments, are methods of treatment comprising administration of macrophages that have been modulated by the method for modulating macrophage activity provided herein.

Described herein, in certain embodiments, is a kit, comprising an nHC-HA/PTX3 or rcHC-HA/PTX3 complex described herein or produced by the methods provided herein, a device for administration of the composition and, optionally, instructions for administration.

Described herein, in certain embodiments, is a combination or mixture comprising: (a) a complex of PTX3 pre-bound to HMW HA (PTX3/HA); (b) an inter-α-inhibitor (IαI) protein comprising heavy chain 1 (HC1); and (c) TSG-6.

Described herein, in certain embodiments, is a combination or a mixture comprising: (a) a complex of TSG-6 pre-bound to HC-HA; and (b) PTX3.

Described herein, in certain embodiments, are methods of producing a reconstituted HC-HA/PTX3 (rcHC-HA/PTX3) complex in vitro, comprising: (a) contacting (i) high molecular weight hyaluronan (HMW HA) immobilized to a solid support, (ii) an inter-α-inhibitor (IαI) protein comprising heavy chain 1 (HC1) and (iii) TSG-6 to form an rcHC-HA complex pre-bound to TSG-6; and (b) contacting rcHC-HA complex pre-bound to TSG-6 with a pentraxin 3 (PTX3) protein to form an rcHC-HA/PTX3 complex.

Described herein, in certain embodiments, are methods of producing a reconstituted HC-HA/PTX3 (rcHC-HA/PTX3) complex in vitro, comprising contacting (i) high molecular weight hyaluronan (HMW HA) immobilized to a solid support, (ii) pentraxin 3 (PTX3) protein, (iii) inter-α-inhibitor (IαI) protein comprising heavy chain 1 (HC1) and (iv) Tumor necrosis factor α-stimulated gene 6 (TSG-6) to form an immobilized rcHC-HA/PTX3 complex.

Described herein, in certain embodiments, is a complex comprising immobilized HA bound to PTX3.

Described herein, in certain embodiments, are methods of producing a complex comprising immobilized HA bound to PTX3 in vitro, comprising contacting high molecular weight hyaluronan (HMW HA) with a PTX3 protein under conditions effective to form a complex of PTX3 and HMW HA (PTX3/HA), wherein the HMW HA is immobilized to a solid support. In some embodiments, the PTX3 protein is a native PTX3 protein isolated from a cell. In some embodiments, the cell is a mammalian cell. In some embodiments, the cell is a human cell. In some embodiments, the cell is an amniotic membrane cell. In some embodiments, the cell is an umbilical cord cell. In some embodiments, the cell is an amniotic membrane cell from an umbilical cord. In some embodiments, the amniotic membrane cell is an amniotic epithelial cell. In some embodiments, the amniotic membrane cell is an umbilical cord epithelial cell. In some embodiments, the amniotic membrane cell is an amniotic stromal cell. In some embodiments, the amniotic membrane cell is an umbilical cord stromal cell. In some embodiments, the PTX3 protein is a recombinant protein. In some embodiments, the PTX3 protein comprises a polypeptide having the sequence set forth in SEQ ID NO: 2 or a polypeptide having at least 75%, 80%, 85%, 90%, 95%, 96%, 97%, 98%, or 99% sequence amino acid identity to the polypeptide having the sequence set forth in SEQ ID NO: 2. In some embodiments, the PTX3 protein used in the methods is a multimeric protein. In some embodiments, the PTX3 protein used in the methods is a homomultimer. In some embodiments, the PTX3 homomultimer is a dimer, trimer, tetramer, pentamer, hexamer, octamer. In some embodiments, the PTX3 homomultimer is a trimer, tetramer, or octamer. In some embodiments, the PTX3 homomultimer is an octamer. In some embodiments, the PTX3 comprises a modified multimerization domain or a heterogeneous multimerization domain. In some embodiments, the immobilizing HMW HA comprises non-covalent attachment to the solid support. In some embodiments, the immobilizing HMW HA comprises binding HMW HA to an intermediary polypeptide. In some embodiments, the intermediary polypeptide is covalently attached to the solid support. In some embodiments, binding HMW HA to the intermediary polypeptide is non-covalent. In some embodiments, the intermediary polypeptide is an HA binding protein (HABP). In some embodiments, the intermediary polypeptide is an HABP selected from among HAPLN1, HAPLN2, HAPLN3, HAPLN4, aggrecan, versican, neurocan, brevican, phosphacan, TSG-6, CD44, stabilin-1, stabilin-2, or a portion thereof sufficient to bind HA. In some embodiments, the intermediary polypeptide is versican. In some embodiments, the intermediary polypeptide comprises a link module. In some embodiments, the intermediary polypeptide comprises a link module of HAPLN1, HAPLN2, HAPLN3, HAPLN4, aggrecan, versican, neurocan, brevican, phosphacan, TSG-6, CD44, stabilin-1, or stabilin-2. In some embodiments, the intermediary polypeptide comprises a link module of versican. In some embodiments, the intermediary polypeptide comprises a polypeptide set forth in any of SEQ ID NOS: 54-99. Described herein, in certain embodiments, is a PTX3/HA complex produced by the preceding method. Described herein, in certain embodiments, is a pharmaceutical composition, comprising the PTX3/HA complex produced by the preceding method. Described herein, in certain embodiments, is a use of the PTX3/HA complex for the production of a medicament. Described herein, in certain embodiments, are methods of treatment comprising administration of the PTX3/HA complex for the prevention or inhibition of scarring, inflammation, angiogenesis, cancer, diabetes, obesity, or fibrosis.

Described herein, in certain embodiments, are methods for inducing or maintaining pluripotency in a cell, comprising culturing the cell with an nHC-HA/PTX3 complex or rcHC-HA/PTX3 complex, thereby inducing or maintaining pluripotency in a cell. In some embodiments, the cell heterogeneously expresses a protein selected from among Sox2, myc, Oct4 and KLF4. In some embodiments, the cell heterogeneously expresses one, two, or three proteins selected from among Sox2, myc, Oct4 and KLF4. In some embodiments, the nHC-HA/PTX3 complex or rcHC-HA/PTX3 complex is immobilized. In some embodiments, the cell is an adult differentiated cell. In some embodiments, the cell is a fibroblast. In some embodiments, the cell is a human corneal fibroblast. In some embodiments, the cell is an embryonic stem cell, an adult stem cell, a fetal stem cell, or an induced pluripotent stem cell. In some embodiments, the cell is a limbal epithelial progenitor cell, a limbal stromal niche cell, an umbilical cord stem cell, an amniotic membrane stem cell or an adipose stem cell. In some embodiments, the nHC-HA/PTX3 complex is an amniotic membrane nHC-HA/PTX3 complex. In some embodiments, the nHC-HA/PTX3 is an umbilical cord nHC-HA/PTX3 complex. In some embodiments, the methods further comprise purifying the nHC-HA/PTX3 complex by performing ultracentrifugation on an amniotic membrane extract. In some embodiments, the methods further comprise purifying the nHC-HA/PTX3 complex by performing ultracentrifugation on an amniotic membrane extract prepared in a PBS buffer to produce a nHC-HA/PTX3 extract (i.e. nHC-HA/PTX3 soluble). In some embodiments, the methods further comprise purifying the nHC-HA/PTX3 complex by performing ultracentrifugation on an amniotic membrane extract prepared in a GnHC1 buffer to produce an nHC-HA/PTX3 extract (i.e. nHC-HA/PTX3 soluble). In some embodiments, the methods further comprise purifying the nHC-HA/PTX3 complex by performing ultracentrifugation on an umbilical cord extract. In some embodiments, the umbilical cord extract comprises umbilical cord amniotic membrane, umbilical cord stroma, Wharton's jelly, or any combination thereof. In some embodiments, the methods further comprise purifying the nHC-HA/PTX3 complex by performing ultracentrifugation on an umbilical cord extract prepared in a PBS buffer to produce a nHC-HA/PTX3 extract (i.e. nHC-HA/PTX3 soluble). In some embodiments, the methods further comprise purifying the nHC-HA/PTX3 complex by performing ultracentrifugation on an umbilical cord extract prepared in a GnHC1 buffer to produce an nHC-HA/PTX3 extract (i.e. nHC-HA/PTX3 soluble). In some embodiments, the methods further comprise performing two, three or four rounds of ultracentifugation. In some embodiments, the methods further comprise performing four rounds of ultracentifugation. In some embodiments, the nHC-HA/PTX3 or rcHC-HA/PTX3 complex comprises PTX3. In some embodiments, the nHC-HA/PTX3 or rcHC-HA/PTX3 complex comprises a small leucine rich proteoglycan (SLRP). In some embodiments, the nHC-HA/PTX3 or rcHC-HA/PTX3 complex comprises PTX3 and a small leucine rich proteoglycan (SLRP). In some embodiments, the small leucine-rich proteoglycan is selected from among decorin, biglycan, fibromodulin, lumican, PRELP (proline arginine rich end leucine-rich protein), keratocan, osteoadherin, epipycan, and osteoglycin. In some embodiments, the small leucine-rich proteoglycan is covalently attached to a glycosaminoglycan. In some embodiments, the glycosaminoglycan is keratan sulfate.

It is to be understood that the foregoing general description and the following detailed description are exemplary and explanatory only and are not restrictive of any subject matter claimed.

BRIEF DESCRIPTION OF THE DRAWINGS

FIG. 1A-M exemplifies purification of native HC-HA/PTX3 (nHC-HA/PTX3) complexes from amniotic membrane extract (AME) and analysis of protein composition and the size of HA. (A-B) Total protein and HA concentrations in fractions obtained by CsCl/4 M guanidine HC1 ultracentifugation. (C) HA stained by Stains-all dye in 0.5% agarose gel. (D-J) Analysis of proteins present in nHC-HA/PTX3 by Western blot using antibodies against HC1 (D and F), PTX3 (E and G), HC2 (H), HC3 (I), bikunin (J), TSG-6 (K) or TSP-1 (L). NaOH or N=Treatment with 0.05 N NaOH at 25° C. for 1 h. HAase or H=Treatment with 20 units/ml HAase at 60° C. for 2 h (F-K). Bar graph of relative protein amount (M) determined by dot assays using antibodies against various antigens including IGFBP 1-3, PF4 or TIMP-1.

FIG. 13A-D exemplifies efficiency of TSG-6 free in solution versus bound TSG-6 for transferring HC1 and HC2 from I$\alpha$I to iHA. (A, B) Relative bound HC1 (A) or I$\alpha$I (B) following simultaneous or sequential addition of TSG-6 and I$\alpha$I to iHA as determined by respective ELISA. An asterisk (*) indicates p<0.05 in the same TSG-6 concentration when added simultaneously and sequentially. (C) Western blot of samples from A digested with hyaluronidase (HAase) and analyzed with anti-TSG-6 antibody. (D) Relative HC1 and PTX3 bound to iHA following simultaneous incubation of PTX3 and I$\alpha$I with iHA as determined by ELISA.

FIG. 14A-G exemplifies complexes formed in solution following simultaneous incubation of I$\alpha$I and TSG-6 with or without PTX3. (A-D) Western blot with antibodies against HC1 (A), HC2 (B), TSG-6 (C), or bikunin (D). HAase=treatment with hyaluronidase. (E) Illustration of TSG-6 interaction with I$\alpha$I. (F) Illustration of the inhibition of HC2•TSG-6 formation by PTX3. (G) Western blot with antibody against I$\alpha$I.

FIG. 15A-G exemplifies complexes formed on iHA following simultaneous incubation of I$\alpha$I and TSG-6 with or without PTX3. After washes with 8 M GnHCl and PBS, bound HC1, TSG-6, and PTX3 were measured by respective ELISAs (A, D, F). An asterisk (*) indicates p<0.05 compared to PTX3 at 1 µg/ml. The complexes were washed again with 8 M GnHCl and PBS and bound components were digested with 1 unit/ml of hyaluronidase for 2 h. The digested samples were analyzed by Western blot with antibodies against HC1 (B), HC2 (C), TSG-6 (E), and PTX3 (G).

FIG. 16A-G exemplifies complexes formed on iHA following sequential addition of I$\alpha$I with TSG-6 followed by PTX3. Bound HC1, TSG-6, and PTX3 were measured by respective ELISAs (A, D, F). The complexes were washed again with 8 M GnHCl and PBS and bound components were digested with 1 unit/ml of hyaluronidase for 2 h. The digested samples were analyzed by Western blot with antibodies against HC1 (B), HC2 (C), TSG-6 (E), PTX3 (G).

FIG. 59A-B exemplifies phase contrast microscopy of morphological changes in MC3T3-E1 cells following induction from Day 3. (A) Uninduced cells were cultured in αMEM w/10% FBS for 7 days. (B) MC3T3-E1 cells were cultured to confluence in flat bottom 96-well plates one day after seeding (Day 0). Cells were then induced with ascorbic acid and β-glycerophosphate.

DETAILED DESCRIPTION OF THE INVENTION

Certain Terminology

Figure 1A:
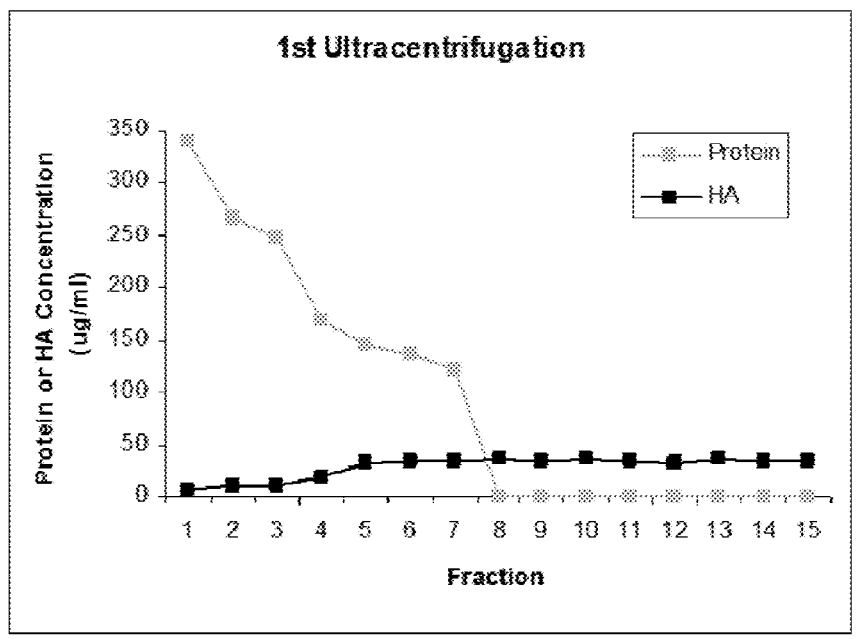
Figure 1B:
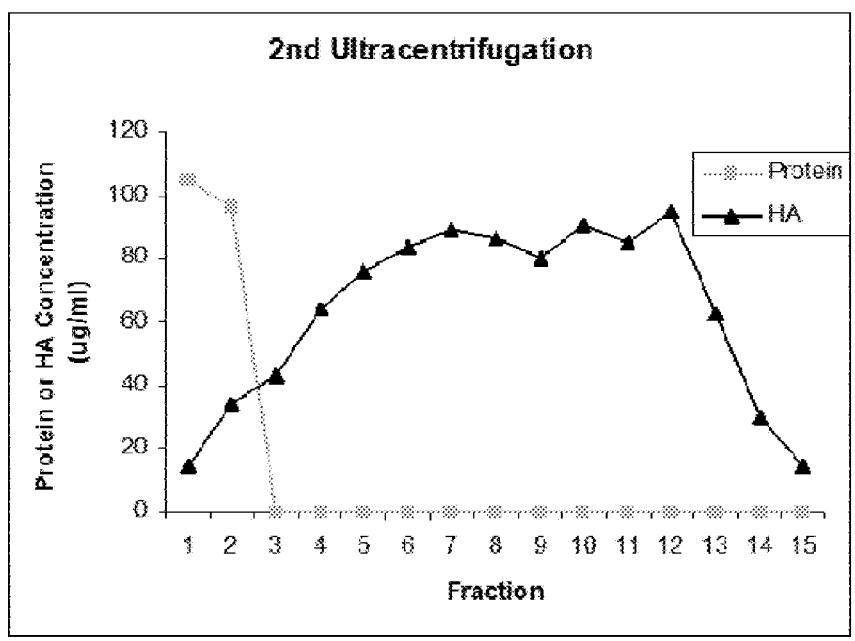
Figure 1J:
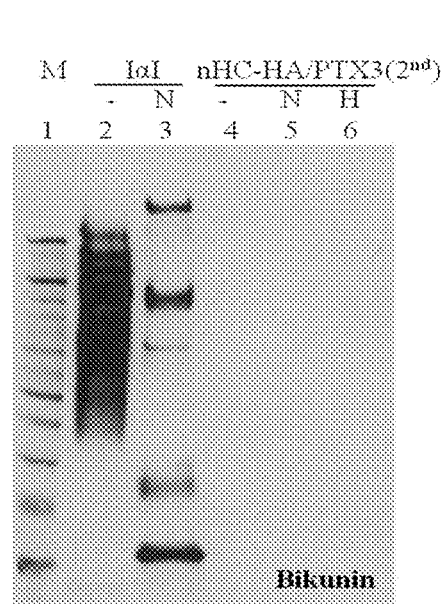
Figure 1K:
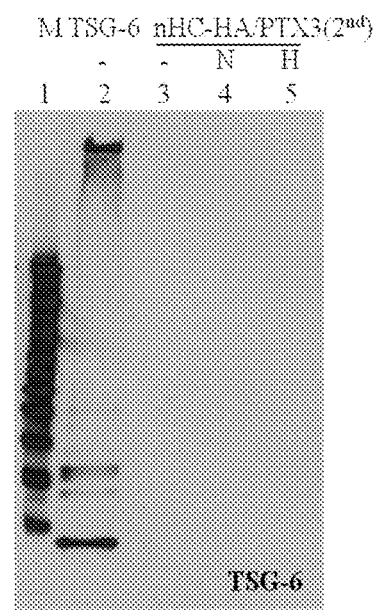

Unless defined otherwise, all technical and scientific terms used herein have the same meaning as is commonly understood by one of skill in the art to which the claimed subject matter belongs. All patents, patent applications, published applications and publications, GENBANK sequences, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, ranges and amounts can be expressed as "about" a particular value or range. About also includes the exact amount. Hence "about 5 μg" means "about 5 μg" and also "5 μg." Generally, the term "about" includes an amount that would be expected to be within experimental error.

As used herein, a reconstituted HC-HA/PTX3 (rcHC-HA/PTX3) complex is an HC-HA/PTX3 complex that is formed by assembly of the component molecules of the complex in vitro. The process of assembling the rcHC-HA/PTX3 includes reconstitution with purified native proteins or molecules from biological source, recombinant proteins generated by recombinant methods, or synthesis of molecules by in vitro synthesis. In some instances, the purified native proteins used for assembly of the rcHC-HA/PTX3 are proteins in a complex with other proteins (i.e. a multimer, a multichain protein or other complex). In some instances, PTX3 is purified as a multimer (e.g. a homomultimer) from a cell and employed for assembly of the rcHC-HA/PTX3 complex.

As used herein, a purified native HC-HA/PTX3 (nHC-HA/PTX3) complex refers to an HC-HA/PTX3 complex that is purified from a biological source such as a cell, a tissue or a biological fluid. Such complexes are generally assembled in vivo in a subject or ex vivo in cells, tissues, or biological fluids from a subject, including a human or other animal.

As used herein, a PTX3/HA complex refers to an intermediate complex that is formed by contacting PTX3 with immobilized HA. In the methods provided herein, the PTX3/HA complex is the generated prior to the addition of HC1 to HA.

As used herein, "hyaluronan," "hyaluronic acid," or "hyaluronate" (HA) are used interchangeably to refer to a substantially non-sulfated linear glycosaminoglycan (GAG) with repeating disaccharide units of D-glucuronic acid and N-acetylglucosamine (D-glucuronosyl-N-acetylglucosamine).

As used herein, the term "high molecular weight" or "HMW," as in high molecular weight hyaluronan (HMW HA), is meant to refer to HA that has a weight average molecular weight that is greater than about 500 kilodaltons (kDa), such as, for example, between about 500 kDa and about 10,000 kDa, between about 800 kDa and about 8,500 kDa, between about 1100 kDa and about 5,000 kDa, or between about 1400 kDa and about 3,500 kDa. In some embodiments, the HMW HA has a weight average molecular weight of 3000 kDa or greater. In some embodiments, the HMW HA has a weight average molecular weight of 3000 kDa. In some embodiments, the HMW HA is Healon® with a weight average molecular weight of about 3000 kDa. In some embodiments, HMW HA has a molecular weight of between about 500 kDa and about 10,000 kDa. In some embodiments, HMW HA has a molecular weight of between about 800 kDa and about 8,500 kDa. In some embodiments, HMW HA has a molecular weight of about 3,000 kDa.

As used herein, the term "low molecular weight" or "LMW," as in low molecular weight hyaluronan (LMW HA), is meant to refer to HA that has a weight average molecular weight that is less than 500 kDa, such as for example, less than about 400 kDa, less than about 300 kDa, less than about 200 kDa, about 200-300 kDa, or about 1-300 kDa.

As used herein, pentraxin 3, or PTX3, protein or polypeptide refers to any PTX3 protein, including but not limited to, a recombinantly produced protein, a synthetically produced protein, a native PTX3 protein, and a PTX3 protein extracted from cells or tissues. PTX3 include multimeric forms (e.g. homomultimer) of PTX3, including, but not limited to, dimeric, trimeric, tetrameric, pentameric, hexameric, tetrameric, octameric, and other multimeric forms naturally or artificially produced.

As used herein, Tumor necrosis factor Stimulated Gene-6 (TSG-6) refers to any TSG-6 protein or polypeptide, including but not limited to, a recombinantly produced protein, a synthetically produced protein, a native TSG-6 protein, and a TSG-6 protein extracted from cells or tissues.

As used herein, inter-α-inhibitor (IαI) refers to the IαI protein comprised of light chain (i.e., bikunin) and one or both heavy chains of type HC1 or HC2 covalently connected by a chondroitin sulfate chain. In some embodiments, the source of IαI is from serum or from cells producing IαI e.g., hepatic cells or amniotic epithelial or stromal cells or umbilical epithelial or stromal cells under a constitutive mode stimulation by proinflammatory cytokines such as IL-1 or TNF-α.

As used herein, a "hyaluronan binding protein", "HA binding protein", or "HABP" refers to any protein that specifically binds to HA.

As used herein, "link module" means a hyaluronan-binding domains.

As used herein, "biological activity" refers to the in vivo activities of an nHC-HA/PTX3 or rcHC-HA/PTX3 complex or physiological responses that result upon in vivo administration of an nHC-HA/PTX3 or rcHC-HA/PTX3 complex or a composition or mixture containing an nHC-HA/PTX3 or rcHC-HA/PTX3 complex. Biological activity, thus, encompasses therapeutic effects and pharmaceutical activity of nHC-HA/PTX3 or rcHC-HA/PTX3 complexes and compositions and mixtures thereof.

As used herein, the terms "subject", "individual" and "patient" are used interchangeably. None of the terms are to be interpreted as requiring the supervision of a medical professional (e.g., a doctor, nurse, physician's assistant, orderly, hospice worker). As used herein, the subject is any animal, including mammals (e.g., a human or non-human animal) and non-mammals. In one embodiment of the methods and compositions provided herein, the mammal is a human.

As used herein, the terms "treat," "treating" or "treatment," and other grammatical equivalents, include alleviating, abating or ameliorating one or more symptoms of a disease or condition, ameliorating, preventing or reducing the appearance, severity or frequency of one or more additional symptoms of a disease or condition, ameliorating or preventing the underlying metabolic causes of one or more symptoms of a disease or condition, inhibiting the disease or condition, such as, for example, arresting the development of the disease or condition, relieving the disease or condition, causing regression of the disease or condition, relieving a condition caused by the disease or condition, or inhibiting the symptoms of the disease or condition either prophylactically and/or therapeutically. In a non-limiting example, for prophylactic benefit, an rcHC-HA/PTX3 complex or composition disclosed herein is administered to an individual at risk of developing a particular disorder, predisposed to developing a particular disorder, or to an individual reporting one or more of the physiological symptoms of a disorder.

As used herein, "placenta" refers to the organ that connects a developing fetus to the maternal uterine wall to allow nutrient uptake, waste elimination, and gas exchange via the maternal blood supply. The placenta is composed of three layers. The innermost placental layer surrounding the fetus is called amnion. The allantois is the middle layer of the placenta (derived from the embryonic hindgut); blood vessels originating from the umbilicus traverse this membrane. The outermost layer of the placenta, the chorion, comes into contact with the endometrium. The chorion and allantois fuse to form the chorioallantoic membrane.

As used herein, "chorion" refers to the membrane formed by extraembryonic mesoderm and the two layers of trophoblast. The chorion consists of two layers: an outer formed by the trophoblast, and an inner formed by the somatic mesoderm; the amnion is in contact with the latter. The trophoblast is made up of an internal layer of cubical or prismatic cells, the cytotrophoblast or layer of Langhans, and an external layer of richly nucleated protoplasm devoid of cell boundaries, the syncytiotrophoblast. The avascular amnion is adherent to the inner layer of the chorion.

As used herein, "amnion-chorion" refers to a product comprising amnion and chorion. In some embodiments, the amnion and the chorion are not separated (i.e., the amnion is naturally adherent to the inner layer of the chorion). In some embodiments, the amnion is initially separated from the chorion and later combined with the chorion during processing.

As used herein, "umbilical cord" refers to the organ that connects a developing fetus to the placenta. The umbilical cord is composed of Wharton's jelly, a gelatinous substance made largely from mucopolysaccharides. It contains one vein, which carries oxygenated, nutrient-rich blood to the fetus, and two arteries that carry deoxygenated, nutrient-depleted blood away.

As used herein, "placental amniotic membrane" (PAM) refers to amniotic membrane derived from the placenta. In some embodiments, the PAM is substantially isolated.

As used herein, "umbilical cord amniotic membrane" (UCAM) means amniotic membrane derived from the umbilical cord. UCAM is a translucent membrane. The UCAM has multiple layers an epithelial layer, a basement membrane; a compact layer; a fibroblast layer; and a spongy layer. It lacks blood vessels or a direct blood supply. In some embodiments, the UCAM comprises Wharton's Jelly. In some embodiments, the UCAM comprises blood vessels and/or arteries. In some embodiments, the UCAM comprises Wharton's Jelly and blood vessels and/or arteries.

As used herein, the terms "purified", "and "isolated" mean a material (e.g., nHC-HA/PTX3 complex) substantially or essentially free from components that normally accompany it in its native state. In some embodiments, "purified" or "isolated" mean a material (e.g., nHC-HA/PTX3 complex) is about 50% or more free from components that normally accompany it in its native state, for example, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% free from from components that normally accompany it in its native state.

Overview: nHC-HA/PTX3 and rcHC-HA/PTX3 Complexes

Hyaluronan (HA) is a substantially non-sulfated linear glycosaminoglycan (GAG), composed of repeating disaccharide subunits units of D-glucuronic acid and N-acetyl-D-glucosamine via GlcUA-β1,3-GlcNAc-β1,4-linkages. HA is synthesized by HA synthases (e.g., HAS1, HAS2, and HAS3) and deposited into the extracellular matrix, where it contributes to the structural integrity of tissues and also regulates many cellular process via interaction with proteins, including cell surface receptors. The molecular weight of HA typically ranges in size from about 200 to about 10,000 kDa. Normal levels of HA are maintained in tissues through a balance of biosynthesis by HAS enzymes and catabolism by hyaluronidases, such as Hyal1.

High molecular weight HA (HMW HA), typically greater than 500 kDa, promotes cell quiescence and structural integrity of such tissues as the cartilage and the vitreous body (humor) in the eye, and is associated with scarless fetal wound healing. In certain instances, HMW HA inhibits the gene expression of pro-inflammatory mediators and angiogenesis.

In certain pathogenic conditions, HMW HA is degraded into smaller fragments and oligosaccharides (e.g., via hyaluronidase or free radical oxidation). LMW HA fragments stimulate vascular endothelial cell proliferation, migration, collagen synthesis, sprout formation, and angiogenesis in rat skin, myocardial infarction, and cryo-injured skin graft model by promoting the gene expression of pro-inflammatory and pro-angiogenic mediators.

The biological functions of HA are mediated though interaction of HA with HA-binding proteins (HABPs), also called hyaladherins. Such proteins include, but are not limited to, tumor necrosis factor-α-stimulated gene 6 (TSG-6), aggrecan, versican, neurocan, brevican, LYVE-1, CD44, and inter-α-inhibitor (IαI). In some instances, HABPs comprise a link module domain that binds to HA. TSG-6, aggrecan, versican, neurocan, brevican, LYVE-1 and CD44 are exemplary HABPs that contain a link module.

IαI comprises two heavy chains (HC1 and HC2), both of which are linked through ester bonds to a chondroitin sulfate chain that is attached to a light chain (i.e., Bikunin). In some instances, HA forms a covalent complex (hereinafter, "HC-HA") with one or both of the HCs of IαI by covalent linkage to the IαI heavy chains. In certain instances, the IαI is found in serum and/or obtained from cells producing IαI, e.g., hepatic cells or amniotic epithelial or stromal cells or umbilical epithelial or stromal cells under a constitutive mode stimulation by proinflammatory cytokines, such as IL-1 or TNF-α

In certain instances, TSG-6 facilitates the transfer of, catalyzes the transfer of, and/or transfers the HC1 and HC2 of IαI to HA. TSG-6 forms stable complexes with immobilized HA (TSG-6•HA) resulting in the transfer HC1 and HC2 to HA to form an HC-HA complex and release of TSG-6 from the complex. The expression of TSG-6 is often induced by inflammatory mediators such as TNF-α and interleukin-1 and during inflammatory-like processes such as ovulation and cervical ripening.

Amniotic membrane (AM) modulates adult wound healing and facilitates tissue regeneration. In certain instances, AM promotes epithelialization while suppressing stromal inflammation, angiogenesis and scarring. AM has been used successfully as a surgical graft or temporary biological patch for the treatment of ophthalmic conditions which require corneal and conjunctival surface reconstruction, including, but not limited to, persistent epithelial defect, deep corneal ulcer, infectious keratitis, symptomatic bullous keratopathy, acute Stevens Johnson Syndrome/Toxic Epidermal Necrolysis (SJS/TEN), limbal stem cell deficiency, pterygium, pinguecula, conjunctivochalasis, symblepharon, formix reconstruction, and conjunctival tumors.

The avascular stromal matrix of AM contains high amounts of HA and constitutively expresses IαI (Zhang et al. (2012) *J. Biol. Chem.* 287(15):12433-44). HMW HA in AM forms nHC-HA complexes (He et al. (2009) *J. Biol. Chem.* 284(30):20136-20146). As shown herein in the Examples provided, this nHC-HA complex also contains pentraxin 3, PTX3 (FIG. 1), and hence it is referred to herein as "nHC-HA/PTX3 complex." Native HC-HA/PTX3 complexes extracted from the AM exhibit suppression of TGF-β promoter activity, promotion of macrophage cell death, and suppression of blood vessel development. The nHC-HA/PTX3 complexes of the AM thus serve an active role in AM's anti-inflammatory, antiscarring and antiangiogenic actions.

As described herein, nHC-HA/PTX3 complexes are also found in the umbilical cord (UC). The UC HC-HA/PTX3 complexes differ in their biochemical composition with respect to HA content and the presence and/or relative abundance of various components of the complex, including proteoglycans, such as small leucine rich proteoglycans (SLRPs). In some embodiments, the SLRP is decorin, biglycan and/or osteoadherin. As described herein, the complexes also differ in content with respect to the presence of particular sulfated glycosaminoglycans, such keratan sulfate. In addition, as described herein, complexes isolated from AM or UC using different extraction methods (e.g., PBS versus GnHC1 extraction) resulted in complexes with different biochemical compositions and biological properties. In certain instances, it is found that complexes isolated from an insoluble fraction by GnHC1 extraction from umbilical cord tissue exhibit improved properties.

PTX3 is a multimeric protein that has been shown to interact directly with TSG-6 and IαI HCs. PTX3 is upregulated in response to inflammatory regulators and has been shown to play an important role in the organization of HA in the extracellular matrix of the cumulous oophorous during oocyte maturation. As demonstrated herein, PTX3 also is found within nHC-HA complexes (i.e. nHC-HA/PTX3) of the amniotic membrane and umbilical cord and plays a critical role in M2 macrophage polarization.

M1 macrophages, or classically activated proinflammatory macrophages are induced by interferon (IFN) alone or in combination with lipopolysaccharide (LPS) or tumor necrosis factor (TNF) α. M1 macrophages are typically characterized by high expression of interleukin-12 (IL-12) and IL-23 and low levels of IL-10. In contrast, M2 macrophages or "alternatively activated" macrophages display wound healing and tissue regenerative properties and are characterized by low IL-12/IL-23 and high IL-10 or about the same ratio of IL-12 to IL-10. In certain instances, M2 macrophages also have a high expression of TGF-β.

The examples provided herein demonstrate that PTX3 binds directly to immobilized HA as evidenced by resistance to dissociating agents. It is demonstrated herein that in vitro reconstituted complexes of HA bound to PTX3 exhibit different properties compared to in vitro reconstituted complexes of HA bound to TSG-6. For example, in some embodiments, a PTX3/HA complex promotes attachment of LPS-stimulated macrophages without aggregation and induces expression of IL-10 in an LPS-stimulated macrophage. In some embodiments, a PTX3/HA complex disclosed herein increases the expression of IL-10 by about 5%, 10%, 15%, 20%, 25%, 30%, 35%, 40%, 45%, 50%, 55%, 60%, 65%, 70%, 75%, 80%, 85%, 90%, 95%, or 100% in an LPS-stimulated macrophage compared to IL-10 expression the absence of a PTX3/HA complex. In contrast, in some embodiments, the TSG-6/HA complex reduces cell attachment and promotes aggregation of LPS-stimulated macrophages and does not induce the expression of IL-10 in an LPS-stimulated macrophage. In addition, in some embodiments, TSG-6 pre-bound to HA inhibits subsequent binding of PTX3 to the complex. In some embodiments, both TSG-6/HA complex and PTX3/HA complex decreased expression of IL-12 in an LPS-stimulated macrophage. In some embodiments, a PTX3/HA complex or TSG-6/HA complex disclosed herein reduces or inhibits the expression of IL-12 by about 5%, 10%, 15%, 20%, 25%, 30%, 35%, 40%, 45%, 50%, 55%, 60%, 65%, 70%, 75%, 80%, 85%, 90%, 95%, or 100% in an LPS-stimulated macrophage compared to IL-12 expression the absence of a PTX3/HA complex or TSG-6/HA complex. In some embodiments, both TSG-6/HA complex and PTX3/HA complex increased expression of IL-23 in an LPS/IFNγ-stimulated macrophage. In some embodiments, a PTX3/HA complex or TSG-6/HA complex disclosed herein reduces or inhibits the expression of IL-23 by about 5%, 10%, 15%, 20%, 25%, 30%, 35%, 40%, 45%, 50%, 55%, 60%, 65%, 70%, 75%, 80%, 85%, 90%, 95%, or 100% in an LPS/IFNγ-stimulated macrophage compared to IL-23 expression the absence of a PTX3/HA complex or TSG-6/HA complex.

In addition, it is demonstrated herein that in vitro reconstituted rcHC-HA/PTX3 complexes possess different biological activities dependent on whether the rcHC-HA/PTX3 complex is formed with HA pre-bound to TSG-6 in the presence of IαI followed by addition of PTX3 or HA pre-bound to PTX3 followed by addition of TSG-6 with IαI. Exemplary methods for reconstitution of rcHC-HA/PTX3 complexed formed with HA pre-bound to TSG-6 or HA pre-bound to PTX3 are provided herein. In some embodiments, rcHC-HA/PTX3 complexes formed with immobilized HA pre-bound to TSG-6 result in aggregation of LPS-stimulated macrophages. In some embodiments, rcHC-HA/PTX3 complexes formed with immobilized HA pre-bound to PTX3 promote attachment of LPS-stimulated macrophages without aggregation.

In some embodiments, rcHC-HA/PTX3 complexes formed with immobilized HA pre-bound to PTX3 decrease or inhibit expression of M1 macrophage markers such as IL-12 and IL-23. In some embodiments, rcHC-HA/PTX3 complexes formed with immobilized HA pre-bound to PTX3 decrease expression of IL-12 in an LPS-stimulated macrophage compared to IL-12 expression the absence of rcHC-HA/PTX3 complex. In some embodiments, an rcHC-HA/PTX3 complex disclosed herein reduces or inhibits the expression of IL-12 by about 5%, 10%, 15%, 20%, 25%, 30%, 35%, 40%, 45%, 50%, 55%, 60%, 65%, 70%, 75%, 80%, 85%, 90%, 95%, or 100% in an LPS-stimulated macrophage compared to IL-12 expression the absence of rcHC-HA/PTX3 complex. In some embodiments, rcHC-HA/PTX3 complexes formed with immobilized HA pre-bound to PTX3 decrease or inhibit expression of IL-23 in an LPS/IFNγ-stimulated macrophage compared to IL-12 expression the absence of rcHC-HA/PTX3 complex. In some embodiments, rcHC-HA/PTX3 complexes formed with immobilized HA pre-bound to PTX3 decrease or inhibit expression of IL-23 by about 5%, 10%, 15%, 20%, 25%, 30%, 35%, 40%, 45%, 50%, 55%, 60%, 65%, 70%, 75%, 80%, 85%, 90%, 95%, or 100% in an LPS/IFNγ-stimulated macrophage compared to IL-23 expression the absence of rcHC-HA/PTX3 complex. In some embodiments, rcHC-HA/PTX3 complexes formed with immobilized HA pre-bound to PTX3 replicate the activity of nHC-HA/PTX3 complexes isolated from amniotic membrane.

In some embodiments, rcHC-HA/PTX3 complexes formed with immobilized HA pre-bound to TSG-6 decrease or inhibit expression of M1 macrophage markers such as IL-12, but increase expression of IL-23. In some embodiments, rcHC-HA/PTX3 complexes formed with immobilized HA pre-bound to TSG-6 decrease or inhibit expression of IL-12. In some embodiments, rcHC-HA/PTX3 complexes formed with immobilized HA pre-bound to TSG-6 increase expression of IL-23.

Provided herein are methods of producing reconstituted HC-HA/PTX3 complexes using immobilized HA pre-bound to PTX3 and uses thereof. Also provided herein are complexes of immobilized HA pre-bound to PTX3 and uses thereof. Also provided herein are methods of producing reconstituted HC-HA/PTX3 complexes using immobilized HA pre-bound to TSG-6 and uses thereof. In some embodiments, the reconstituted HC-HA/PTX3 complexes provided herein are administered to treat a wide variety of diseases or conditions, including, but not limited to, the treatment, such as the inhibition, reduction, prevention or lowering the risk, of inflammation, immune reaction leading to autoimmune or immune rejection, adhesion, scarring, angiogenesis, conditions requiring cell or tissue regeneration, tissue reperfusion injury due to ischemia, including myocardial infarction and stroke, and the symptoms caused thereby. In some embodiments, the reconstituted HC-HA/PTX3 complexes provided herein are administered to treat inflammation. In some embodiments, the reconstituted HC-HA/PTX3 complexes provided herein are administered to treat scarring. In some embodiments, the reconstituted HC-HA/PTX3 complexes provided herein are administered to treat angiogenesis. In some embodiments, the reconstituted HC-HA/PTX3 complexes provided herein are administered to treat immune reaction leading to autoimmune or immune rejection. In some embodiments, the reconstituted HC-HA/PTX3 complexes provided herein are administered to treat conditions requiring inhibition of cell adhesion. In some embodiments, the reconstituted HC-HA/PTX3 complexes provided herein are administered to treat conditions requiring cell or tissue regeneration.

In addition, the examples provided herein demonstrate the ability of HC-HA/PTX3 complexes to maintain stem cells in an undifferentiated state as well as induce adult differentiated fibroblasts to younger progenitors in a human corneal fibroblasts model. Human corneal fibroblasts are differentiated from keratocytes and upon addition of exogenous TGF-β1, they further differentiate into scar-forming myofibroblasts. The data provided herein demonstrate that culturing the cells in the presence of HC-HA prevented cells from differentiating into myofibroblasts under TGF-β1 stimulation. In the absence of TGF-β1, HC-HA/PTX3 complexes revert human corneal fibroblasts into keratocytes expressing keratocan and CD34. In the presence of TGF-β1 human corneal fibroblasts are further reprogrammed into younger progenitors that lack of keratocan expression and but express a number of neural crest cell markers such as Osr2, FGF10, and Sox9 and embryonic stem cell markers, such as c-myc, KLF4, Nanog, nestin, Oct 4, Rex-1, Sox-2, and SSEA-4.

The transcription factors Sox2, Oct4, c-Myc, and KLF4 are known play an important role in the induction of progenitor stem cells (iPSCs) from adult differentiated cells. Accordingly, in some embodiments, HC-HA/PTX3 complexes provided herein are employed to reprogram adult differentiated cells into iPSCs. In some embodiments, induction of iPSCs using an HC-HA/PTX3 complex in combination with one or more of Sox2, Oct4, c-Myc, and KLF4 is performed with a much higher efficiency than the conventional methods that use these four transcription factors without HC-HA/PTX3. In some embodiments, addition of HC-HA/PTX3 complex facilitates stem cell induction by turning off TGF-β signaling to prevent differentiation and by turning on BMP signaling to facilitate reprogramming into young progenitor cells such as iPSCs. In some embodiments, addition of HC-HA/PTX3 complex facilitates stem cell induction by reprogramming cells into younger progenitors and induction of stem cell markers. In some embodiments, addition of HC-HA/PTX3 complex helps maintain stem cell characteristics during ex vivo expansion, thus eliminating the need of using feeder layers made of murine embryonic fibroblasts. Hence, in some embodiments, HC-HA/PTX3 complex is used as a carrier or scaffold to help deliver stem cells that have been ex vivo expanded into the human patients to promote the efficacy of said stem cell therapies.

Methods of Production of Isolated nHC-HA/PTX3 Complexes

Disclosed herein are methods of generating isolated native HC-HA/PTX3 complexes (nHC-HA/PTX3).

In some embodiments, the isolated nHC-HA/PTX3 complex is isolated from an amniotic tissue. In some embodiments, the isolated nHC-HA/PTX3 complex is isolated from an amniotic membrane or an umbilical cord. In some embodiments, the isolated nHC-HA/PTX3 complex is isolated from fresh, frozen or previously frozen placental amniotic membrane (PAM), fresh, frozen or previously frozen umbilical cord amniotic membrane (UCAM), fresh, frozen or previously frozen placenta, fresh, frozen or previously frozen umbilical cord, fresh, frozen or previously frozen chorion, fresh, frozen or previously frozen amnion-chorion, or any combinations thereof. Such tissues can be obtained from any mammal, such as, for example, but not limited to a human, non-human primate, cow or pig.

In some embodiments, the nHC-HA/PTX3 is purified by any suitable method. In some embodiments, the nHC-HA/PTX3 complex is purified by centrifugation (e.g., ultracentrifugation, gradient centrifugation), chromatography (e.g., ion exchange, affinity, size exclusion, and hydroxyapatite chromatography), gel filtration, or differential solubility, ethanol precipitation or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference).

In some embodiments, the nHC-HA/PTX3 is isolated from an extract. In some embodiments, the extract is prepared from an amniotic membrane extract. In some embodiments, the extract is prepared from an umbilical cord extract. In some embodiments, the umbilical cord extract comprises umbilical cord stroma and/or Wharton's jelly. In some embodiments, the nHC-HA/PTX3 complex is contained in an extract that is prepared by ultracentrifugation. In some embodiments, the nHC-HA/PTX3 complex is contained in an extract that is prepared by ultracentrifugation using a CsCl/4-6M guanidine HC1 gradient. In some embodiments, the extract is prepared by at least 2 rounds of ultracentrifugation. In some embodiments, the extract is prepared by more than 2 rounds of ultracentrifugation (i.e. nHC-HA/PTX3 $2^{nd}$). In some embodiments, the extract is prepared by at least 4 rounds of ultracentrifugation (i.e. nHC-HA/PTX3 $4^{th}$). In some embodiments, the nHC-HA/PTX3 complex comprises a small leucine-rich proteoglycan. In some embodiments, the nHC-HA/PTX3 complex comprises HC1, HA, PTX3 and/or a small leucine-rich proteoglycan.

In some embodiments, ultracentrifugation is performed on an extract prepared by extraction in an isotonic solution. In some embodiments, the isotonic solution is PBS. For example, in some embodiments the tissue is homogenized in PBS to produce a homogenized sample. The homogenized sample is then separated into a soluble portion and insoluble portion by centrifugation. In some embodiments, ultracentrifugation is performed on the soluble portion of the PBS-extracted tissue. In such embodiments, the nHC-HA/PTX3 purified by ultracentrifugation of the PBS-extracted tissue called an nHC-HA/PTX3 soluble complex. In some embodiments, the nHC-HA soluble complex comprises a small leucine-rich proteoglycan. In some embodiments, the nHC-HA/PTX3 soluble complex comprises HC1, HA, PTX3 and/or a small leucine-rich proteoglycan.

In some embodiments, ultracentrifugation is performed on an extract prepared by direct guanidine HC1 extraction (e.g. 4-6 M GnHC1) of the amniotic membrane and/or umbilical cord tissue. In some embodiments, the GnHC1 extract tissues is then centrifuged to produce GnHC1 soluble and GnHC1 insoluble portions. In some embodiments, ultracentrifugation is performed on the GnHC1 soluble portion. In such embodiments, the nHC-HA/PTX3 purified by ultracentrifugation of the guanidine HC1-extracted tissue is called an nHC-HA/PTX3 insoluble complex. In some embodiments, the nHC-HA insoluble complex comprises a small leucine-rich proteoglycan. In some embodiments, the nHC-HA/PTX3 insoluble complex comprises HC1, HA, PTX3 and/or a small leucine-rich proteoglycan.

In some embodiments, ultracentrifugation is performed on an extract prepared by further guanidine HC1 extraction of the insoluble portion of the PBS-extracted tissue. For example, in some embodiments the tissue is homogenized in PBS to produce a homogenized sample. The homogenized sample is then separated into a soluble portion and insoluble portion by centrifugation. The insoluble portion is then further extracted in guanidine HC1 (e.g. 4-6 M GnHC1) and centrifuged to produce a guanidine HC1 soluble and insoluble portions. In some embodiments, ultracentrifugation is performed on the guanidine HC1 soluble portion. In such embodiments, the nHC-HA/PTX3 purified by ultracentrifugation of the guanidine HC1-extracted tissue is called an nHC-HA/PTX3 insoluble complex. In some embodiments, the nHC-HA insoluble complex comprises a small leucine-rich proteoglycan. In some embodiments, the nHC-HA/PTX3 insoluble complex comprises HC1, HA, PTX3 and/or a small leucine-rich proteoglycan.

In some embodiments, the method of purifying the isolated nHC-HA/PTX3 extract comprises: (a) dissolving the isolated extract (e.g. prepared by the soluble or insoluble method described herein) in CsCl/4-6M guanidine HC1 at the initial density of 1.35 g/ml, to generate a CsCl mixture, (b) centrifuging the CsCl mixture at 125,000×g for 48 h at 15° C., to generate a first purified extract, (c) extracting the first purified extract and dialyzing it against distilled water to remove CsCl and guanidine HC1, to generate a dialysate. In some embodiments, the method of purifying the isolated extract further comprises (d) mixing the dialysate with 3 volumes of 95% (v/v) ethanol containing 1.3% (w/v) potassium acetate at 0° C. for 1 h, to generate a first dialysate/ethanol mixture, (e) centrifuging the first dialysate/ethanol mixture at 15,000×g, to generate a second purified extract, and (f) extracting the second purified extract. In some embodiments, the method of purifying the isolated extract further comprises: (g) washing the second purified extract with ethanol (e.g., 70% ethanol), to generate a second purified extract/ethanol mixture; (h) centrifuging the second purified extract/ethanol mixture, to generate a third purified extract; and (i) extracting the third purified extract. In some embodiments, the method of purifying the isolated extract further comprises: (j) washing the third purified extract with ethanol (e.g., 70% ethanol), to generate a third purified extract/ethanol mixture; (k) centrifuging the third purified extract/ethanol mixture, to generate a forth purified extract; and (l) extracting the forth purified extract. In some embodiments, the purified extract comprises an nHC-HA/PTX3 complex.

In some embodiments, the nHC-HA/PTX3 complex is purified by immunoaffinity chromatography. In some embodiments, anti HC1 antibodies, anti-HC2 antibodies, or both are generated and affixed to a stationary support. In some embodiments, the unpurified HC-HA complex (i.e., the mobile phase) is passed over the support. In certain instances, the HC-HA complex binds to the antibodies (e.g., via interaction of (a) an anti-HC1 antibody and HC1, (b) an anti-HC2 antibody and HC2, (c) an anti-PTX antibody and PTX3, (d) an anti-SLRP antibody and the SLRP, or (e) any combination thereof). In some embodiments the support is washed (e.g., with PBS) to remove any unbound or loosely bound molecules. In some embodiments, the support is then washed with a solution that enables elution of the nHC-HA/PTX3 complex from the support (e.g., 1% SDS, 6M guanidine-HCl, or 8M urea).

In some embodiments, the nHC-HA/PTX3 complex is purified by affinity chromatography. In some embodiments, HABP is generated and affixed to a stationary support. In some embodiments, the unpurified nHC-HA/PTX3 complex (i.e., the mobile phase) is passed over the support. In certain instances, the nHC-HA/PTX3 complex binds to the HABP. In some embodiments the support is washed (e.g., with PBS) to remove any unbound or loosely bound molecules. In some embodiments, the support is then washed with a solution that enables elution of the HC-HA complex from the support.

In some embodiments, the nHC-HA/PTX3 complex is purified by a combination of HABP affinity chromatography, and immunoaffinity chromatography using anti HC1 antibodies, anti-HC2 antibodies, anti-PTX3 antibodies, antibodies against a SLRP or a combination of SLRPs, or any combination of antibodies thereof.

In some embodiments, the nHC-HA/PTX3 complex is purified from the insoluble fraction as described herein using one or more antibodies. In some embodiments, the nHC-HA/PTX3 complex is purified from the insoluble fraction as described herein using anti-SLRP antibodies.

In some embodiments, the nHC-HA/PTX3 complex is purified from the soluble fraction as described herein. In some embodiments, the nHC-HA/PTX3 complex is purified from the soluble fraction as described herein using anti-PTX3 antibodies.

In some embodiments, the nHC-HA/PTX3 complex comprises a small leucine rich proteoglycan (SLRP). In some embodiments, the nHC-HA/PTX3 complex comprises a class I, class II or class II SLRP. In some embodiments, the small leucine-rich proteoglycan is selected from among class I SLRPs, such as decorin and biglycan. In some embodiments, the small leucine-rich proteoglycan is selected from among class II SLRPs, such as fibromodulin, lumican, PRELP (proline arginine rich end leucine-rich protein), keratocan, and osteoadherin. In some embodiments, the small leucine-rich proteoglycan is selected from among class III SLRPs, such as epipycan and osteoglycin. In some embodiments, the small leucine-rich proteoglycan is selected from among bikunin, decorin, biglycan, and osteoadherin. In some embodiments, the small leucine-rich proteoglycan comprises a glycosaminoglycan. In some embodiments, the small leucine-rich proteoglycan comprises keratan sulfate.

Methods of Production of rcHC-HA/PTX3 Complexes

Disclosed herein are methods of generating reconstituted HC-HA/PTX3 complexes (rcHC-HA/PTX3) with or without SLRPs. Also disclosed herein are rcHC-HA/PTX3 complexes and intermediate combinations of components generated by such methods.

In some embodiments, a method for generating reconstituted HC-HA/PTX3 complexes comprises (a) contacting immobilized high molecular weight hyaluronan (HMW HA) with pentraxin 3 (PTX3) under suitable conditions to form a PTX3/HA complex, and (b) contacting the PTX3/HA complex with IαI and Tumor necrosis factor-Stimulated Gene-6 (TSG-6). Provided herein are rcHC-HA/PTX3 complexes produced by such method. In some embodiments, TSG-6 catalyzes the transfer of heavy chain 1 (HC1) of inter-α-inhibitor (IαI) to HA. In some embodiments, HC1 of IαI forms a covalent linkage with HA. In some embodiments, the steps (a) and (b) of the method are performed sequentially in order.

In some embodiments, a method for generating reconstituted HC-HA/PTX3 complexes comprises contacting a PTX3/HA complex with IαI and TSG-6. In some embodiments, TSG-6 catalyzes the transfer of heavy chain 1 (HC1) of inter-α-inhibitor (IαI) to HA. Provided herein are rcHC-HA/PTX3 complexes produced by such method. In some embodiments, HC1 of IαI forms a covalent linkage with HA.

In some embodiments, a method for generating a complex of HA bound to PTX3 comprises contacting immobilized high molecular weight hyaluronan (HMW HA) with pentraxin 3 (PTX3) under suitable conditions to form a PTX3/HA complex. Provided herein are PTX3/HA complexes produced by such method.

In some embodiments, a method for generating reconstituted HC-HA/PTX3 complexes comprises (a) contacting immobilized high molecular weight hyaluronan (HMW HA) with IαI and TSG-6 to HA to form an HC-HA complex pre-bound to TSG-6 and (b) contacting the HC-HA complex with pentraxin 3 (PTX3) under suitable conditions to form an rcHC-HA/PTX3 complex. Provided herein are rcHC-HA/PTX3 complexes produced by such method. In some embodiments, HC1 of IαI forms a covalent linkage with HA. In some embodiments, the steps (a) and (b) of the method are performed sequentially in order. In some embodiments, the method comprises contacting an HC-HA complex pre-bound to TSG-6 with PTX3.

In some embodiments, the method comprises first contacting high molecular weight hyaluronan (HMW HA) with pentraxin 3 (PTX3) under suitable conditions to form a PTX3/HA complex, then contacting the PTX3/HA complex with IαI and TSG-6.

In some embodiments, the IαI protein and TSG-6 protein are contacted to the complex at a molar ratio of about 1:1, 2:1, 3:1, 4:1, 5:1, 6:1, 7:1, 8:1, 9:1, 10:1, 15:1, or 20:1 (IαI:TSG-6). In some embodiments the ratio of IαI:TSG-6 ranges from about 1:1 to about 20:1, such as about 1:1 to about 10:1, such as about 1:1 to 5 about:1, such as about 1:1 to about 3:1. In some embodiments, the ratio of IαI:TSG-6 is 3:1 or higher. In some embodiments, the ratio of IαI:TSG-6 is 3:1.

In some embodiments, the steps (a) and (b) of the method are performed sequentially in order. In some embodiments, the method comprises contacting a PTX3/HA complex with IαI and TSG-6.

In certain instances, TSG-6 interacts with IαI and forms covalent complexes with HC1 and HC2 of IαI (i.e. HC1•TSG-6 and HC2•TSG-6). In certain instances, in the presence of HA, the HCs are transferred to HA to form rcHC-HA. In some embodiments, a TSG-6•HC1 complex is added to pre-bound PTX3/HA complex to catalyze the transfer of HC1 to HA. In some embodiments, the method comprises first contacting immobilized high molecular weight hyaluronan (HMW HA) with pentraxin 3 (PTX3) under suitable conditions to form a PTX3/HA complex, then contacting the PTX3/HA complex with a HC1•TSG-6 complex. In some embodiments, a combination of HC1•TSG-6 complex and HC2•TSG-6 complex is added to a PTX3/HA complex.

In some embodiments, the step of contacting PTX3 to immobilized HMW HA occurs for at least 10 minutes, at least 30 minutes, at least 1 hour, at least 2 hours, at least 3 hours, at least 4 hours, at least 5 hours, at least 6 hours, at least 12 hours, or at least 24 hours or longer. In some embodiments, the step of contacting PTX3 to immobilized HMW HA occurs for at least 2 hours or longer. In some embodiments, the step of contacting PTX3 to immobilized HMW HA occurs for at least 2 hours. In some embodiments, the step of contacting PTX3 to immobilized HMW HA occurs at 37° C. In some embodiments, the step of contacting PTX3 to immobilized HMW HA occurs in 5 mM $MgCl_2$ in PBS.

In some embodiments, the step of contacting the PTX3/HA complex with IαI and TSG-6 to HA occurs for at least 10 minutes, at least 30 minutes, at least 1 hour, at least 2 hours, at least 3 hours, at least 4 hours, at least 5 hours, at least 6 hours, at least 12 hours, or at least 24 hours or longer. In some embodiments the step of contacting the PTX3/HA complex with a HC1•TSG-6 complex and/or a HC2•TSG-6 complex occurs for at least 10 minutes, at least 30 minutes, at least 1 hour, at least 2 hours, at least 3 hours, at least 4 hours, at least 5 hours, at least 6 hours, at least 12 hours, or at least 24 hours or longer. In some embodiments the step of contacting the PTX3/HA complex with a HC1•TSG-6 complex and/or a HC2•TSG-6 complex occurs for at least 2 hours or longer. In some embodiments the step of contacting the PTX3/HA complex with a HC1•TSG-6 complex and/or a HC2•TSG-6 complex occurs for at least 2 hours. In some embodiments the step of contacting the PTX3/HA complex with a HC1•TSG-6 complex and/or a HC1•TSG-6 complex occurs at 37° C. In some embodiments the step of contacting the PTX3/HA complex with a HC1•TSG-6 complex and/or a HC1•TSG-6 complex occurs in 5 mM $MgCl_2$ in PBS.

In some embodiments, the method comprises contacting high molecular weight hyaluronan (HMW HA) with a pentraxin 3 (PTX3) protein, inter-α-inhibitor (IαI) protein comprising heavy chain 1 (HC1) and Tumor necrosis factor α-stimulated gene 6 (TSG-6) simultaneously under suitable conditions to form a HC-HA/PTX3 complex. In some embodiments, the contacting the HMW HA with PTX3, IαI and TSG-6 occurs for at least 10 minutes, at least 30 minutes, at least 1 hour, at least 2 hours, at least 3 hours, at least 4 hours, at least 5 hours, at least 6 hours, at least 12 hours, or at least 24 hours or longer. In some embodiments the step of contacting the HMW HA, PTX3, IαI, and TSG-6 occurs at 37° C. In some embodiments the step of contacting the HMW HA, PTX3, IαI, and TSG-6 occurs in 5 mM $MgCl_2$ in PBS.

In some embodiments, the method comprises contacting high molecular weight hyaluronan (HMW HA) with a pentraxin 3 (PTX3) protein, inter-α-inhibitor (IαI) protein comprising heavy chain 1 (HC1) and Tumor necrosis factor α-stimulated gene 6 (TSG-6) sequentially, in any order, under suitable conditions to form a HC-HA/PTX3 complex. In some embodiments, the contacting the HMW HA with PTX3, IαI and TSG-6 occurs for at least 10 minutes, at least 30 minutes, at least 1 hour, at least 2 hours, at least 3 hours, at least 4 hours, at least 5 hours, at least 6 hours, at least 12 hours, or at least 24 hours or longer. In some embodiments the step of contacting the HMW HA, PTX3, IαI, and TSG-6 occurs at 37° C. In some embodiments the step of contacting the HMW HA, PTX3, IαI, and TSG-6 occurs in 5 mM $MgCl_2$ in PBS.

In some embodiments, the methods for production of an rcHC-HA/PTX3 complex further comprises addition of one or more small leucine rich proteoglycans (SLRPs). In some embodiments, a method for generating reconstituted HC-HA/PTX3 complexes comprises (a) contacting immobilized high molecular weight hyaluronan (HMW HA) with pentraxin 3 (PTX3) under suitable conditions to form a PTX3/HA complex, (b) contacting the PTX3/HA complex with IαI and Tumor necrosis factor-Stimulated Gene-6 (TSG-6) and (c) contacting the PTX3/HA complex with one or more SLRPS. Provided herein are rcHC-HA/PTX3 complexes produced by such method. In some embodiments, TSG-6 catalyzes the transfer of heavy chain 1 (HC1) of inter-α-inhibitor (IαI) to HA. In some embodiments, HC1 of IαI forms a covalent linkage with HA. In some embodiments, the steps (a), (b), and (c) of the method are performed sequentially in order. In some embodiments, the steps (a), (b), and (c) of the method are performed simultaneously. In some embodiments, the step (a) of the method is performed and then steps (b) and (c) of the method are performed sequentially in order. In some embodiments, the step (a) of the method is performed and then steps (b) and (c) of the method are performed simultaneously.

In some embodiments, a method for generating reconstituted HC-HA/PTX3 complexes comprises (a) contacting immobilized high molecular weight hyaluronan (HMW HA) with IαI and TSG-6 to HA to form an HC-HA complex pre-bound to TSG-6, (b) contacting the HC-HA complex with pentraxin 3 (PTX3) and (c) contacting the HC-HA complex with one or more SLRPS under suitable conditions to form an rcHC-HA/PTX3 complex. Provided herein are rcHC-HA/PTX3 complexes produced by such method. In some embodiments, HC1 of IαI forms a covalent linkage with HA. In some embodiments, the method comprises contacting an HC-HA complex pre-bound to TSG-6 with PTX3. In some embodiments, the steps (a), (b), and (c) of the method are performed sequentially in order. In some embodiments, the steps (a), (b), and (c) of the method are performed simultaneously. In some embodiments, the step (a) of the method is performed and then steps (b) and (c) of the method are performed sequentially in order. In some embodiments, the step (a) of the method is performed and then steps (b) and (c) of the method are performed simultaneously.

In some embodiments, the SLRP is selected from among a class I, class II or class II SLRP. In some embodiments, the SLRP is selected from among class I SLRPs, such as decorin and biglycan. In some embodiments, the small leucine-rich proteoglycan is selected from among class II SLRPs, such as fibromodulin, lumican, PRELP (proline arginine rich end leucine-rich protein), keratocan, and osteoadherin. In some embodiments, the small leucine-rich proteoglycan is selected from among class III SLRPs, such as epipycan and osteoglycin. In some embodiments, the small leucine-rich proteoglycan is selected from among bikunin, decorin, biglycan, and osteoadherin. In some embodiments, the small leucine-rich protein comprises a glycosaminoglycan. In some embodiments, the small leucine-rich proteoglycan comprises keratan sulfate.

PTX3

In some embodiments, PTX3 for use in the methods is isolated from a cell or a plurality of cells (e.g., a tissue extract). Exemplary cells suitable for the expression of PTX3 include, but are not limited to, animal cells including, but not limited to, mammalian cells, primate cells, human cells, rodent cells, insect cells, bacteria, and yeast, and plant cells, including, but not limited to, algae, angiosperms, gymnosperms, pteridophytes and bryophytes. In some embodiments, PTX3 for use in the methods is isolated from a human cell. In some embodiments, PTX3 for use in the methods is isolated from a cell that is stimulated with one or more proinflammatory cytokines to upregulate PTX3 expression. In some embodiments, the proinflammatory cytokine is IL-1 or TNF-α.

In some embodiments, PTX3 for use in the methods is isolated from an amniotic membrane cell. In some embodiments, PTX3 for use in the methods is isolated from an amniotic membrane cell from an umbilical cord. In some embodiments, the amniotic membrane cell is stimulated with or more proinflammatory cytokines to upregulate PTX3 expression. In some embodiments, the proinflammatory cytokine is IL-1 or TNF-α.

In some embodiments, PTX3 for use in the methods is isolated from an umbilical cord cell. In some embodiments, the umbilical cord cell is stimulated with or more proinflammatory cytokines to upregulate PTX3 expression. In some embodiments, the proinflammatory cytokine is IL-1 or TNF-α.

In some embodiments, PTX3 for use in the methods is isolated from an amniotic epithelial cell. In some embodiments, PTX3 for use in the methods is isolated from an umbilical cord epithelial cell. In some embodiments, the amniotic epithelial cell or umbilical cord epithelial cell is stimulated with or more proinflammatory cytokines to upregulate PTX3 expression. In some embodiments, the proinflammatory cytokine is IL-1 or TNF-α.

In some embodiments, PTX3 for use in the methods is isolated from an amniotic stromal cell. In some embodiments, PTX3 for use in the methods is isolated from an umbilical cord stromal cell. In some embodiments, the amniotic stromal cell or umbilical cord stromal cell is stimulated with or more proinflammatory cytokines to upregulate PTX3 expression. In some embodiments, the proinflammatory cytokine is IL-1 or TNF-α.

In some embodiments, PTX3 for use in the methods is a native PTX3 protein isolated from a cell. In some embodiments, the cell is stimulated with or more proinflammatory cytokines to upregulate PTX3 expression. In some embodiments, the proinflammatory cytokine is IL-1 or TNF-α.

In some embodiments, PTX3 is prepared by recombinant technology. In some embodiments, PTX3 is expressed from a recombinant expression vector. In some embodiments, nucleic acid encoding PTX3 is operably linked to a constitutive promoter. In some embodiments, nucleic acid encoding PTX3 is operably linked to an inducible promoter. In some embodiments, PTX3 is expressed in a transgenic animal. In some embodiments, PTX3 is a recombinant protein. In some embodiments, PTX3 is a recombinant protein isolated from a cell. In some embodiments, PTX3 is a recombinant protein produced in a cell-free extract.

In some embodiments, PTX3 is purified from amniotic membrane, umbilical cord, umbilical cord amniotic membrane, chorionic membrane, amniotic fluid, or a combination thereof. In some embodiments, PTX3 is purified from amniotic membrane cells. In some embodiments, the amniotic membrane cell is an amniotic epithelial cell. In some embodiments, the amniotic membrane cell is an umbilical cord epithelial cell. In some embodiments, the amniotic membrane cell is an amniotic stromal cell. In some embodiments, the amniotic membrane cell is an umbilical cord stromal cell. In some embodiments, the amniotic membrane cell is stimulated with or more proinflammatory cytokines to upregulate PTX3 expression. In some embodiments, the proinflammatory cytokine is IL-1 or TNF-α.

In some embodiments, PTX3 is not isolated from a cell or a plurality of cells (e.g., a tissue extract).

In some embodiments, PTX3 comprises a polypeptide having the sequence set forth in SEQ ID NO: 33 or a variant thereof having at least 65%, 70%, 75%, 80%, 85%, 90%, 95%, 96%, 97%, 98%, or 99% sequence amino acid identity to the polypeptide having the sequence set forth in SEQ ID NO: 33. Exemplary variants include, for example, species variants, allelic variants and variants that contain conservative and non-conservative amino acid mutations. In some embodiments, PTX3 comprises a fragment of PTX3 sufficient to bind to HA and facilitate the formation of rcHC-HA/PTX3 complex. In some embodiments, PTX3 comprises Glu18 to Ser277 of human PTX3. Variants of PTX3 for use in the provided methods include variants with an amino acid modification that is an amino acid replacement (substitution), deletion or insertion. In some embodiments, such modification improves one or more properties of the PTX3 polypeptides such as improving the one or more therapeutic properties of the rcHC-HA/PTX3 complex (e.g., anti-inflammatory, anti-immune, anti-angiogenic, anti-scarring, anti-adhesion, regeneration or other therapeutic activities as described herein).

In some embodiments PTX3 protein is obtained from a commercial source. An exemplary commercial source for PTX3 is, but is not limited to, PTX3 (Catalog No. 1826-TS; R&D Systems, Minneapolis, Minn.).

In some embodiments, the PTX3 protein used in the methods is a multimeric protein. In some embodiments, the PTX3 protein used in the methods is a homomultimer. In some embodiments, the homomultimer is a dimer, trimer, tetramer, hexamer, pentamer, or octamer. In some embodiments, the PTX3 homomultimer is a trimer, tetramer, or octamer. In particular embodiments, the PTX3 homomultimer is an octamer. In some embodiments, the multimerization domain is modified to improve multimerization of the PTX3 protein. In some embodiments, the multimerization domain is replaced with a heterogeneous multimerization domain (e.g., an Fc multimerization domain or leucine zipper) that when fused to PTX3 improves the multimerization of PTX3.

TSG-6

In some embodiments, TSG-6 for use in the methods is isolated from a cell or a plurality of cells (e.g., a tissue extract). Exemplary cells suitable for the expression of TSG-6 include, but are not limited to, animal cells including, but not limited to, mammalian cells, primate cells, human cells, rodent cells, insect cells, bacteria, and yeast, and plant cells, including, but not limited to, algae, angiosperms, gymnosperms, pteridophytes and bryophytes. In some embodiments, TSG-6 for use in the methods is isolated from a human cell. In some embodiments, TSG-6 for use in the methods is isolated from a cell that is stimulated with one or more proinflammatory cytokines to upregulate TSG-6 expression. In some embodiments, the proinflammatory cytokine is IL-1 or TNF-α.

In some embodiments, TSG-6 for use in the methods is isolated from an amniotic membrane cell. In some embodiments, TSG-6 for use in the methods is isolated from an amniotic membrane cell from an umbilical cord. In some embodiments, TSG-6 for use in the methods is isolated from an amniotic membrane cell that is stimulated with one or more proinflammatory cytokines to upregulate TSG-6 expression. In some embodiments, the proinflammatory cytokine is IL-1 or TNF-α.

In some embodiments, TSG-6 for use in the methods is isolated from an umbilical cord cell. In some embodiments, TSG-6 for use in the methods is isolated from an umbilical cord cell that is stimulated with one or more proinflammatory cytokines to upregulate TSG-6 expression. In some embodiments, the proinflammatory cytokine is IL-1 or TNF-α.

In some embodiments, TSG-6 for use in the methods is isolated from an amniotic epithelial cell. In some embodiments, TSG-6 for use in the methods is isolated from an umbilical cord epithelial cell. In some embodiments, TSG-6 for use in the methods is isolated from an amniotic epithelial cell or an umbilical cord epithelial cell that is stimulated with one or more proinflammatory cytokines to upregulate TSG-6 expression. In some embodiments, the proinflammatory cytokine is IL-1 or TNF-α.

In some embodiments, TSG-6 for use in the methods is isolated from an amniotic stromal cell. In some embodiments TSG-6 for use in the methods is isolated from an umbilical cord stromal cell. In some embodiments, TSG-6 for use in the methods is isolated from an amniotic stromal cell or an umbilical cord stromal cell that is stimulated with one or more proinflammatory cytokines to upregulate TSG-6 expression. In some embodiments, the proinflammatory cytokine is IL-1 or TNF-α.

In some embodiments, TSG-6 for use in the methods is a native TSG-6 protein isolated from a cell. In some embodiments, the cell is stimulated with or more proinflammatory cytokines to upregulate TSG-6 expression. In some embodiments, the proinflammatory cytokine is IL-1 or TNF-α.

In some embodiments, TSG-6 is prepared by recombinant technology. In some embodiments, TSG-6 is expressed from a recombinant expression vector. In some embodiments, nucleic acid encoding TSG-6 is operably linked to a constitutive promoter. In some embodiments, nucleic acid encoding TSG-6 is operably linked to an inducible promoter. In some embodiments, TSG-6 is expressed in a transgenic animal. In some embodiments, TSG-6 is a recombinant protein. In some embodiments, TSG-6 is a recombinant protein isolated from a cell. In some embodiments, TSG-6 is a recombinant protein produced in a cell-free extract.

In some embodiments, TSG-6 is purified from amniotic membrane, amniotic membrane, chorionic membrane, amniotic fluid, or a combination thereof. In some embodiments, PTX3 is purified from amniotic membrane cells. In some embodiments, the amniotic membrane cell is an amniotic epithelial cell. In some embodiments, the amniotic epithelial cell is an umbilical cord epithelial cell. In some embodiments, the amniotic membrane cell is an amniotic stromal cell. In some embodiments, the amniotic membrane cell is an umbilical cord stromal cell. In some embodiments, the amniotic membrane cell is stimulated with or more proinflammatory cytokines to upregulate TSG-6 expression. In some embodiments, the proinflammatory cytokine is IL-1 or TNF-α.

In some embodiments, TSG-6 is not isolated from a cell or a plurality of cells (e.g., a tissue extract).

In some embodiments, TSG-6 comprises a fragment of TSG-6 that is sufficient to facilitate or catalyze the transfer HC1 of IαI to HA. In some embodiments, TSG-6 comprises the link module of TSG-6. In some embodiments, TSG-6 comprises amino acids Trp18 through Leu277 of TSG-6. In some embodiments, TSG-6 comprises a polypeptide having the sequence set forth in SEQ ID NO: 2 or a variant thereof having at least 65%, 70%, 75%, 80%, 85%, 90%, 95%, 96%, 97%, 98%, or 99% sequence amino acid identity to the polypeptide having the sequence set forth in SEQ ID NO: 2. Exemplary variants include, for example, species variants, allelic variants and variants that contain conservative and non-conservative amino acid mutations. Natural allelic variants of human TSG-6 include, for example, TSG-6 containing the amino acid replacement Q144R. Variants of TSG-6 or HA binding fragments thereof for use in the provided methods include variants with an amino acid modification that is an amino acid replacement (substitution), deletion or insertion. In some embodiments, such modification improve one or more properties of the TSG-6 polypeptides such as improved transfer of HC1 of IαI to HA or improved release of the TSG-6 polypeptide from the rcHC-HA/PTX3 complex following transfer of HC1 of IαI to HA.

In some embodiments, TSG-6 comprises an affinity tag. Exemplary affinity tags include but are not limited to a hemagglutinin tag, a poly-histidine tag, a myc tag, a FLAG tag, a glutathione-S-transferase (GST) tag. Such affinity tags are well known in the art for use in purification. In some embodiments, such an affinity tag incorporated into the TSG-6 polypeptide as a fusion protein or via a chemical linker. In some embodiments, TSG-6 comprises an affinity tag and the unbound TSG-6 is removed from the rcHC-HA/PTX3 complex by affinity purification.

In some embodiments TSG-6 protein is obtained from a commercial source. An exemplary commercial source for TSG-6 is, but is not limited to, TSG-6 (Catalog No. 2104-TS R&D Systems, Minneapolis, Minn.).

IαI

In some embodiments, the IαI comprises an HC1 chain. In some embodiments, the IαI comprises an HC1 and an HC2 chain. In some embodiments, the IαI comprises an HC1 and bikunin. In some embodiments, the IαI comprises an HC1, and HC2 chain and bikunin. In some embodiments, the IαI comprises an HC1, and HC2 chain and bikunin linked by a chondroitin sulfate chain.

In some embodiments, IαI is isolated from a biological sample. In some embodiments the biological sample is a biological sample from a mammal. In some embodiments, the mammal is a human. In some embodiments, the biological sample is a blood, serum, plasma, liver, amniotic membrane, chorionic membrane or amniotic fluid sample. In some embodiments, the biological sample is a blood, serum, or plasma sample. In some embodiments, the biological sample is a blood sample. In some embodiments, the biological sample is a serum sample. In some embodiments, the biological sample is a plasma sample. In some embodiments, the IαI is purified from human blood, plasma or serum. In some embodiments, IαI is isolated from human serum. In some embodiments, IαI is not isolated from serum. In some embodiments, IαI for use in the methods is produced in an amniotic membrane cell. In some embodiments, IαI for use in the methods is produced in an umbilical cord cell. In some embodiments, IαI for use in the methods is produced in an amniotic membrane cell from an umbilical cord. In some embodiments, IαI for use in the methods is produced in an amniotic epithelial cell. In some embodiments, IαI for use in the methods is produced in an umbilical cord epithelial cell. In some embodiments, IαI for use in the methods is produced in an amniotic stromal cell. In some embodiments, IαI for use in the methods is produced in an umbilical cord stromal cell. In some embodiments, IαI for use in the methods is produced in a hepatic cell. In some embodiments, IαI is prepared by recombinant technology.

In some embodiments, HC1 of IαI is isolated from a biological sample. In some embodiments the biological sample is a biological sample from a mammal. In some embodiments, the mammal is a human. In some embodiments, the biological sample is a blood, serum, plasma, liver, amniotic membrane, chorionic membrane or amniotic fluid sample. In some embodiments, the biological sample is a blood, serum, or plasma sample. In some embodiments, the biological sample is a blood sample. In some embodiments, the biological sample is a serum sample. In some embodiments, the biological sample is a plasma sample. In some embodiments, the HC1 of IαI is purified from human blood, plasma or serum. In some embodiments, IαI is isolated from human serum. In some embodiments, HC1 of IαI is not purified from serum. In some embodiments, HC1 of IαI is prepared by recombinant technology. In some embodiments, HC1 of IαI is purified from hepatic cells. In some embodiments, HC1 of IαI is purified from amniotic membrane cells. In some embodiments, HC1 of IαI is purified from amniotic epithelial cells or umbilical cord epithelial cells. In some embodiments, HC1 of IαI is purified from amniotic stromal cells or umbilical cord stromal cells.

In some embodiments, HC1 comprises a polypeptide having the sequence set forth in SEQ ID NO: 47 or a polypeptide having at least 75%, 80%, 85%, 90%, 95%, 96%, 97%, 98%, or 99% sequence amino acid identity to the polypeptide having the sequence set forth in SEQ ID NO: 47.

In some embodiments, HC2 of IαI is isolated from a biological sample. In some embodiments the biological sample is a biological sample from a mammal. In some embodiments, the mammal is a human. In some embodiments, the biological sample is a blood, serum, plasma, liver, amniotic membrane, chorionic membrane or amniotic fluid sample. In some embodiments, the biological sample is a blood, serum, or plasma sample. In some embodiments, the biological sample is a blood sample. In some embodiments, the biological sample is a serum sample. In some embodiments, the biological sample is a plasma sample. In some embodiments, the HC2 of IαI is purified from human blood, plasma or serum. In some embodiments, HC2 of IαI is isolated from human serum. In some embodiments, HC2 of IαI is not isolated from blood serum. In some embodiments, HC2 of IαI is prepared by recombinant technology. In some embodiments, HC2 of IαI is purified from hepatic cells. In some embodiments, HC2 of IαI is purified from amniotic membrane cells. In some embodiments, HC2 of IαI is purified from amniotic epithelial cells or umbilical cord epithelial cells. In some embodiments, HC2 of IαI is purified from amniotic stromal cells or umbilical cord stromal cells.

In some embodiments, HC2 comprises a polypeptide having the sequence set forth in SEQ ID NO: 49 or a polypeptide having at least 75%, 80%, 85%, 90%, 95%, 96%, 97%, 98%, or 99% sequence amino acid identity to the polypeptide having the sequence set forth in SEQ ID NO: 49.

In some embodiments, IαI comprises bikunin. In some embodiments, bikunin comprises a polypeptide having the sequence set forth in SEQ ID NO: 53 or a polypeptide having at least 75%, 80%, 85%, 90%, 95%, 96%, 97%, 98%, or 99% sequence amino acid identity to the polypeptide having the sequence set forth in SEQ ID NO: 53. In some embodiments, IαI comprises a chondroitin sulfate chain.

HA

In some embodiments, HA is purified from a cell, tissue or a fluid sample. In some embodiments, HA is obtained from a commercial supplier (e.g., Sigma Aldrich or Advanced Medical Optics, Irvine, Calif. (e.g., Healon)). In some embodiments, HA is obtained from a commercial supplier as a powder. In some embodiments, HA is expressed in a cell. Exemplary cells suitable for the expression of HA include, but are not limited to, animal cells including, but not limited to, mammalian cells, primate cells, human cells, rodent cells, insect cells, bacteria, and yeast, and plant cells, including, but not limited to, algae, angiosperms, gymnosperms, pteridophytes and bryophytes. In some embodiments, HA is expressed in a human cell. In some embodiments, HA is expressed in a transgenic animal. In some embodiments, HA is obtained from a cell that expresses a hyaluronan synthase (e.g., HAS1, HAS2, and HAS3). In some embodiments, the cell contains a recombinant expression vector that expresses an HA synthase. In certain instances, an HA synthase lengthens hyaluronan by repeatedly adding glucuronic acid and N-acetylglucosamine to the nascent polysaccharide as it is extruded through the cell membrane into the extracellular space.

HA for use in the methods is typically high molecular weight (HMW) HA. In some embodiments, the weight average molecular weight of HMW HA is greater than about 500 kilodaltons (kDa), such as, for example, between about 500 kDa and about 10,000 kDa, between about 800 kDa and about 8,500 kDa, between about 1100 kDa and about 5,000 kDa, or between about 1400 kDa and about 3,500 kDa. In some embodiments, the weight average molecular weight of HMW HA is about 3000 kDa.

Additional Components

In some embodiments, one or more additional components are added to generate an rcHC-HA/PTX3 complex. In some embodiments, a small leucine rich proteoglycan (SLRP) is added to generate an rcHC-HA/PTX3 complex. In some embodiments, the SLRP is a class I, class II or class II SLRP. In some embodiments, the SLRP is selected from among class I SLRPs, such as decorin and biglycan. In some embodiments, the SLRP is selected from among class II SLRPs, such as fibromodulin, lumican, PRELP (proline arginine rich end leucine-rich protein), keratocan, and osteoadherin. In some embodiments, the SLRP is selected from among class III SLRPs, such as epipycan and osteoglycin. In some embodiments, the SLRP is selected from among bikunin, decorin, biglycan, and osteoadherin. In some embodiments, the SLRP comprises a glycosaminoglycan. In some embodiments, the SLRP comprises keratan sulfate.

HA Immobilization

In some embodiments, HMW HA is immobilized by any suitable method. In some embodiments, HMW HA is immobilized to a solid support, such as culture dish, bead, a column or other suitable surfaces, such as, for example, a surface of an implantable medical device or a portion thereof or on a surface that is subsequently connected to or combined with an implantable medical device as described herein. In some embodiments, HMW HA is immobilized directly to the solid support, such a by chemical linkage. In some embodiments, HMW HA is attached indirectly to the solid support via a linker or an intermediary protein. Numerous heterobifunctional cross-linking reagents that are used to form covalent bonds between amino groups and thiol groups and to introduce thiol groups into proteins, are known to those of skill in this art. In some embodiments, HMW HA is immobilized directly to the solid support via crosslinking to the solid support. In some embodiments, HMW HA is immobilized directly to the solid support without crosslinking to the solid support. In some embodiments, HMW HA is immobilized directly to the solid support as a coating. In some embodiments, HMW HA is immobilized to a Covalink™-NH surface. In some embodiments, HMW HA is immobilized directly to the solid support as a coating. In some embodiments, HMW HA is immobilized to a Covalink™-NH surface for about 16 h at 4° C.

In some embodiments, the method comprises immobilizing HMW HA to a solid surface via direct linkage to a solid support (i.e. without an intermediary protein). In some embodiments, the solid support is washed to remove unbound HMW HA prior to contacting the immobilized HA with PTX3. In some embodiments, the solid support is washed with washes of 8M GnHCl and PBS to remove unbound HMW HA prior to contacting the immobilized HA with PTX3.

In some embodiments, the method comprises immobilizing HA to a solid surface via an intermediary protein or a linker. In some embodiments, the linker is a peptide linker. In some embodiments, the intermediary protein is an HA binding protein (HABP). In some embodiments, HABP is first attached to a solid support (e.g., by cross-linking, chemical linkage or via a chemical linker). In some embodiments, the solid support comprising HABP is then contacted with HA (e.g., HMW HA) to immobilize HA to the solid support via binding of the HABP to HA. In some embodiments, the solid support is washed to remove unbound HMW HA prior to contacting the immobilized HMW HA with PTX3. In some embodiments, the solid support is washed with washes of 8M GnHCl and PBS to remove unbound HMW HA prior to contacting the immobilized HA with PTX3.

In some embodiments, the method comprises immobilizing HA to a solid surface via attachment of a peptide linker to the solid support and attachment HA to the peptide linker. In some embodiments, the peptide linker comprises a protease cleavage site.

In some embodiments, the method comprises immobilizing HA to a solid surface via attachment of a cleavable chemical linker, such as, but not limited to a disulfide chemical linker.

In some embodiments, the HABP selected for use in the methods is an HABP that is dissociated from HA following formation of the rcHC-HA/PTX3 complex. In some embodiments, the HABP non-covalently binds to HA. In some embodiments, the method further comprises dissociating the rcHC-HA/PTX3 complex from HABP using one or more dissociating agents. Dissociating agents for the disruption of non covalent interactions (e.g., guanidine hydrochloride, urea and various detergents, e.g., SDS) are known in the art. In some embodiments the dissociating agent is urea. In some embodiments the dissociating agent is guanidine hydrochloride. In some embodiments, the dissociation agent is about 4M to about 8M guanidine-HCl. In some embodiments, the dissociation agent is about 4M, about 5M, about 6M, about 7M, about 8M guanidine-HCl. In some embodiments, the dissociation agent is about 4M to about 8M guanidine-HCl in PBS at pH 7.5.

In some embodiments, such dissociating agents are employed to dissociate the rcHC-HA/PTX3 complex from an intermediary HABP. An HABP for use in the methods typically is selected such that the binding affinity for HA is strong enough to permit assembly of the rcHC-HA/PTX3 complex but is dissociated from the rcHC-HA/PTX3 complex with a suitable dissociation agent. In some embodiments the dissociating agent is guanidine hydrochloride.

Exemplary HABPs for use with the methods provided herein include, but are not limited to, HAPLN1, HAPLN2, HAPLN3, HAPLN4, aggrecan, versican, neurocan, brevican, phosphacan, TSG-6, CD44, stabilin-1, stabilin-2, or portions thereof (e.g., link modules thereof) sufficient to bind HA. In some embodiments, the HABP comprises a polypeptide having the sequence set forth in any of SEQ ID NOS: 54-99 or a polypeptide having at least 75%, 80%, 85%, 90%, 95%, 96%, 97%, 98%, or 99% sequence amino acid identity to the polypeptide having the sequence set forth in any of SEQ ID NOS: 54-99. In some embodiments, the HABP is versican. In some embodiments, the HABP is a recombinant protein. In some embodiments, the HABP is a recombinant mammalian protein. In some embodiments, the HABP is a recombinant human protein. In some embodiments, the HABP is a recombinant versican protein or a portion thereof sufficient to bind to HA. In some embodiments, the HABP is a recombinant aggrecan protein or a portion thereof sufficient to bind to HA. In some embodiments, the HABP is a native HABP or a portion thereof sufficient to bind to HA. In some embodiments, the native HABP is isolated from mammalian tissue or cells. In some embodiments, the HABP is isolated from bovine nasal cartilage (e.g. HABP from Seikagaku which contains the HA binding domains of aggrecan and link protein).

In some embodiments, the HABP comprises a link module of HAPLN1, HAPLN2, HAPLN3, HAPLN4, aggrecan, versican, neurocan, brevican, phosphacan, TSG-6, CD44, stabilin-1, or stabilin-2. In some embodiments, the HABP comprising a link module comprises a polypeptide having the sequence set forth in any of link domains of SEQ ID NOS: 54-99 or a polypeptide having at least 75%, 80%, 85%, 90%, 95%, 96%, 97%, 98%, or 99% sequence amino acid identity to the polypeptide having the sequence set forth in any of link domains of SEQ ID NOS: 54-99. In some embodiments, the HABP comprises a link module of versican. In some embodiments, the HABP comprising a link module is a recombinant protein. In some embodiments, the HABP comprising a link module of versican is a recombinant protein.

In some embodiments, the or intermediary protein, such as an HABP, contains a proteolytic cleavage sequence that is recognized by and is hydrolyzed by a site specific protease, such as furin, 3C protease, caspase, matrix metalloproteinase or TEV protease. In such embodiments, assembled rcHC-HA/PTX3 complexes are released from the solid support by contacting the immobilized complexes with a protease that cleaves the specific cleavage sequence.

In some embodiments, the rcHC-HA/PTX3 complex is purified. In some embodiments, the rcHC-HA/PTX3 complex is purified by any suitable method or combination of methods. The embodiments described below are not intended to be exclusive, only exemplary.

In some embodiments, the rcHC-HA/PTX3 complex is purified by chromatography (e.g., ion exchange, affinity, size exclusion, and hydroxyapatite chromatography), gel filtration, centrifugation (e.g., gradient centrifugation), or differential solubility, ethanol precipitation or by any other available technique for the purification of proteins.

In some embodiments, the rcHC-HA/PTX3 complex is purified by immunoaffinity chromatography. In some embodiments antibodies are generated against a component of the rcHC-HA/PTX3 complex (e.g., anti-HC1, anti-PTX, an antibody against one or more SLRPs of the rcHC-HA/PTX3 complex, e.g., anti-bikunin, anti-decorin, anti-biglycan, or anti-osteoadherin) and affixed to a solid support. In some embodiments, the unpurified rcHC-HA/PTX3 complex (i.e., the mobile phase) is passed over the support. In certain instances, the rcHC-HA/PTX3 complex binds to the antibodies. In some embodiments, the support is washed (e.g., with PBS) to remove any unbound or loosely bound molecules. In some embodiments, the support is then washed with a solution that enables elution of the rcHC-HA/PTX3 complex from the support (e.g., 1% SDS, 6M guanidine-HC1, or 8M urea). In some embodiments, the dissociating agent is removed from the dissociated rcHC-HA/PTX3 complex. In some embodiments, the dissociating agent is removed from the dissociated rcHC-HA/PTX3 complex by a method including, but not limited to, ion-exchange chromatography, dialysis, gel filtration chromatography, ultrafiltration, or diafiltration.

In some embodiments, the rcHC-HA/PTX3 complex is purified by affinity chromatography. In some embodiments, an HABP is employed to bind to the rcHC-HA/PTX3 complex for purification of the complex and affixed to a stationary support. In some embodiments, the unpurified rcHC-HA/PTX3 complex (i.e., the mobile phase) is passed over the support. In certain instances, the rcHC-HA/PTX3 complex binds to the HABP. In some embodiments the support is washed (e.g., with PBS) to remove any unbound or loosely bound molecules. In some embodiments, the support is then washed with a solution (e.g., a dissociating agent) that enables elution of the rcHC-HA/PTX3 complex from the support. In some embodiments, the dissociating agent is removed from the dissociated rcHC-HA/PTX3 complex by a method including, but not limited to, ion-exchange chromatography, dialysis, gel filtration chromatography, ultrafiltration, or diafiltration.

In some embodiments, the rcHC-HA/PTX3 complex is purified by a combination of HABP affinity chromatography, and immunoaffinity chromatography using antibodies against one or more components of the rcHC-HA/PTX3 complex.

In some embodiments, one or more components of the rcHC-HA/PTX3 complex disclosed herein comprise an affinity tag (e.g., a fusion protein of PTX3 or HC1 with an affinity tag). Exemplary affinity tags that are incorporated into one or more components of the rcHC-HA/PTX3 complex in some embodiments include, but are not limited to, a hemagglutinin tag, poly-histidine, a myc tag, a FLAG tag, or glutathione-S-transferase sequence. In some embodiments, the ligand for the affinity tag is affixed to the solid support. In some embodiments, the unpurified rcHC-HA/PTX3 complex is passed over the support. In certain instances, the rcHC-HA/PTX3 complex binds to the ligand. In some embodiments the support is washed (e.g., with PBS) to remove any unbound or loosely bound molecules. In some embodiments, the support is then washed with a solution that enables elution of an rcHC-HA/PTX3 complex disclosed herein from the support. In some embodiments, the elution agent is removed from the dissociated rcHC-HA/PTX3 complex by a method including, but not limited to, ion-exchange chromatography, dialysis, gel filtration chromatography, ultrafiltration, or diafiltration.

In some embodiments, the PTX3, TSG-6, and/or HC1 are conjugated to a label. A "label" refers to a detectable compound or composition which is conjugated directly or indirectly to a polypeptide so as to generate a labeled polypeptide. In some embodiments, the label is detectable by itself (e.g., radioisotope labels or fluorescent labels) or, in the case of an enzymatic label, catalyzes chemical alteration of a substrate compound composition which is detectable. Non-limiting examples of labels include fluorogenic moieties, dyes, fluorescent tags, green fluorescent protein, or luciferase.

Methods of Assessing the Activity of nHC-HA/PTX3 and rcHC-HA/PTX3 Complexes

The properties of nHC-HA/PTX3 and rcHC-HA/PTX3 complexes provided herein are assessed by any suitable method including, in vitro and in vivo methods. Exemplary in vitro methods are provided herein and include, but are not limited, to cell culture methods that assess the ability of nHC-HA/PTX3 or rcHC-HA/PTX3 complexes to promote attachment of macrophages to the immobilized nHC-HA/PTX3 or rcHC-HA/PTX3 complexes, to inhibit or reduce aggregation of macrophages, to promote apoptosis of neutrophils, macrophage phagocytosis of apoptotic neutrophils, and M2 polarization of stimulated macrophages. In some embodiments, the macrophages used in the assay are stimulated, such as by exposure to LPS or IFN-γ. In some embodiments, the gene or protein expression in stimulated macrophages is assessed following contact with nHC-HA/PTX3 or rcHC-HA/PTX3 complexes. In such methods of assessing activity of nHC-HA/PTX3 or rcHC-HA/PTX3 complex, a suitable control is employed for comparison. In some embodiments, the control is the absence of treatment with an nHC-HA/PTX3 or rcHC-HA/PTX3 complex (i.e. a negative control).

In some embodiments, the activity of an rcHC-HA/PTX3 complex is compared to the activity of a native HC-HA/PTX3 complex. In some embodiments the native HC-HA/PTX3 is isolated from amniotic membrane.

In some embodiments, gene expression in treated macrophages is assessed by PCR, RT-PCR, Northern blotting, western blotting, dot blotting, immunohistochemistry, chromatography or other suitable method of detecting proteins or nucleic acids. In some embodiments, the level of expression of IL-10, IL-12, IL23, LIGHT and SPHK1 is assessed.

Exemplary in vitro methods for assessing the activity of an nHC-HA/PTX3 or rcHC-HA/PTX3 complex provided herein include, but are not limited to, animal models of various disease and conditions. A variety of animal models are available and well-known in the art for diseases and conditions, including, but not limited to, animal models (e.g. rodent and primate models) for various inflammatory and autoimmune diseases and disorders including, but not limited to, ischemia reperfusion injury, type 1 and type 2 diabetes, inflammatory diseases, collagen induced arthritis, rheumatoid arthritis, antigen induced autoimmune disease such as collagen induced arthritis and myelin peptide-induced experimental allergic encephalomyelitis, inflammatory bowel disease (IBD)/ulcerative colitis, multiple sclerosis, surgically induced osteoarthritis and nephritis, psoriasis, inflammatory skin diseases, LPS-induced endotoxic shock, LPS-induced lung injury, allergic rhinitis, liver injury, chronic stress, asthma, and xenograft and allograft models for various cancers.

In some embodiments, the animal model is a rodent model of inflammation such as chronic graft-versus-host disease (cGVHD), HSV1-induced necrotizing stromal keratitis, or high-risk corneal transplantation. In some embodiments, reduction of inflammation by nHC-HA/PTX3 or rcHC-HA/PTX3 treatment is assessed by the measuring the proliferation and activation of T cells and the production of immune cytokines such as IL-1α, IL-2, IL-6, IFN-γ, and TNF-α. In some embodiments, the animal model is a rodent model of scarring such as excimer laser-assisted photorefractive keratectomy (PRK). Exemplary methods for the use of such animal models are provided in the Examples provided herein.

In some embodiments, the animal model is a genetic model of inflammatory and autoimmune diseases and disorder that contains one or more genetic modifications that cause the disease or disorder. In some embodiments, such models are obtained from a commercial source. In some embodiments, an nHC-HA/PTX3 or rcHC-HA/PTX3 complex provided herein is administered to an animal model of a particular disease or condition and the ability of the rcHC-HA/PTX3 complex to inhibit or reduce one or more symptoms of the disease or condition is assessed.

Pharmaceutical Compositions

Disclosed herein, in certain embodiments, are pharmaceutical compositions comprising nHC-HA/PTX3 or rcHC-HA/PTX3 complexes described herein. Disclosed herein, in certain embodiments, are pharmaceutical compositions comprising nHC-HA/PTX3 or rcHC-HA/PTX3 complexes produced by the methods provided herein. In some embodiments, the pharmaceutical compositions are formulated in a conventional manner using one or more physiologically acceptable carriers including excipients and auxiliaries which facilitate processing of an nHC-HA/PTX3 or rcHC-HA/PTX3 complex into preparations which are suitable for pharmaceutical use. Proper formulation is dependent upon the route of administration selected. Any of the well-known techniques, carriers, and excipients can be used as suitable and as understood in the art.

Disclosed herein, in certain embodiments, is a pharmaceutical composition comprising an nHC-HA/PTX3 or rcHC-HA/PTX3 complex disclosed herein. In some embodiments, the pharmaceutical composition further comprises at least one pharmaceutically acceptable carrier. In some embodiments, the pharmaceutical composition further comprises an adjuvant, excipient, preservative, agent for delaying absorption, filler, binder, adsorbent, buffer, and/or solubilizing agent. Exemplary pharmaceutical compositions that are formulated to contain an nHC-HA/PTX3 or rcHC-HA/PTX3 complex provided herein include, but are not limited to, a solution, suspension, emulsion, syrup, granule, powder, ointment, tablet, capsule, pill or an aerosol.

Dosage Forms

In some embodiments, an nHC-HA/PTX3 or rcHC-HA/PTX3 complex disclosed herein is administered as an aqueous suspension. In some embodiments, an aqueous suspension comprises water, Ringer's solution and/or isotonic sodium chloride solution. In some embodiments, an aqueous suspension comprises a sweetening or flavoring agent, coloring matters or dyes and, if desired, emulsifying agents or suspending agents, together with diluents water, ethanol, propylene glycol, glycerin, or combinations thereof. In some embodiments, an aqueous suspension comprises a suspending agent. In some embodiments, an aqueous suspension comprises sodium carboxymethylcellulose, methylcellulose, hydroxypropylmethyl-cellulose, sodium alginate, polyvinylpyrrolidone, gum tragacanth and/or gum acacia. In some embodiments, an aqueous suspension comprises a dispersing or wetting agent. In some embodiments, an aqueous suspension comprises a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. In some embodiments, an aqueous suspension comprises a preservative. In some embodiments, an aqueous suspension comprises ethyl, or n-propyl p-hydroxybenzoate. In some embodiments, an aqueous suspension comprises a sweetening agent. In some embodiments, an aqueous suspension comprises sucrose, saccharin or aspartame.

In some embodiments, an nHC-HA/PTX3 or rcHC-HA/PTX3 complex disclosed herein is administered as an oily suspension. In some embodiments, an oily suspension is formulated by suspending the active ingredient in a vegetable oil (e.g., arachis oil, olive oil, sesame oil or coconut oil), or in mineral oil (e.g., liquid paraffin). In some embodiments, an oily suspension comprises a thickening agent (e.g., beeswax, hard paraffin or cetyl alcohol). In some embodiments, an oily suspension comprises sweetening agents (e.g., those set forth above). In some embodiments, an oily suspension comprises an anti-oxidant (e.g., butylated hydroxyanisol or alpha-tocopherol).

In some embodiments, an nHC-HA/PTX3 or rcHC-HA/PTX3 complex disclosed herein is formulated for parenteral injection (e.g., via injection or infusion, including intraarterial, intracardiac, intradermal, intraduodenal, intramedullary, intramuscular, intraosseous, intraperitoneal, intrathecal, intravascular, intravenous, intravitreal, epidural and/or subcutaneous). In some embodiments, an nHC-HA/PTX3 or rcHC-HA/PTX3 complex disclosed herein is administered as a sterile solution, suspension or emulsion.

In some embodiments, a formulation for parenteral administration includes aqueous and/or non-aqueous (oily) sterile injection solutions of an nHC-HA/PTX3 or rcHC-HA/PTX3 complex disclosed herein, which in some embodiments, contain antioxidants, buffers, bacteriostats and/or solutes which render the formulation isotonic with the blood of the intended recipient; and/or aqueous and/or non-aqueous sterile suspensions which in some embodiments, include a suspending agent and/or a thickening agent. In some embodiments, a formulation for parenteral administration includes suitable stabilizers or agents which increase the solubility of an nHC-HA/PTX3 or rcHC-HA/PTX3 complex disclosed herein to allow for the preparation of highly concentrated solutions.

In some embodiments, an nHC-HA/PTX3 or rcHC-HA/PTX3 complex disclosed herein is administered as an oil-in-water micro-emulsion where the active ingredient is dissolved in the oily phase. In some embodiments, an nHC-HA/PTX3 or rcHC-HA/PTX3 complex disclosed herein is dissolved in a fatty oil (e.g., sesame oil, or synthetic fatty acid esters, (e.g., ethyl oleate or triglycerides, or liposomes. In some embodiments, an nHC-HA/PTX3 or rcHC-HA/PTX3 complex disclosed herein is dissolved in a mixture of soybean oil and/or lecithin. In some embodiments, the oil solution is introduced into a water and glycerol mixture and processed to form a micro-emulsion.

In some embodiments, a composition formulated for parenteral administration is administered as a single bolus shot. In some embodiments, a composition formulated for parenteral administration is administered via a continuous intravenous delivery device (e.g., Deltec CADD-PLUS™ model 5400 intravenous pump).

In some embodiments, a formulation for injection is presented in unit dosage form, e.g., in ampoules or in multi-dose containers, with an added preservative. In some embodiments, a formulation for injection is stored in powder form or in a freeze-dried (lyophilized) condition requiring only the addition of the sterile liquid carrier, for example, saline or sterile pyrogen-free water, immediately prior to use.

In some embodiments, an nHC-HA/PTX3 or rcHC-HA/PTX3 complex disclosed herein is formulated for topical administration. Topical formulations include, but are not limited to, ointments, creams, lotions, solutions, pastes, gels, films, sticks, liposomes, nanoparticles. In some embodiments, a topical formulation is administered by use of a patch, bandage or wound dressing.

In some embodiments, an nHC-HA/PTX3 or rcHC-HA/PTX3 complex disclosed herein is formulated as composition is in the form of a solid, a cross-linked gel, or a liposome. In some embodiments, an nHC-HA/PTX3 or rcHC-HA/PTX3 complex disclosed herein is formulated as an insoluble cross-linked hydrogel.

In some embodiments, a topical formulation comprises a gelling (or thickening) agent. Suitable gelling agents include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum, acacia (gum arabic), agar, aluminum magnesium silicate, sodium alginate, sodium stearate, bladderwrack, bentonite, carbomer, carrageenan, carbopol, xanthan, cellulose, microcrystalline cellulose (MCC), ceratonia, chondrus, dextrose, furcellaran, gelatin, ghatti gum, guar gum, hectorite, lactose, sucrose, maltodextrin, mannitol, sorbitol, honey, maize starch, wheat starch, rice starch, potato starch, gelatin, sterculia gum, polyethylene glycol (e.g. PEG 200-4500), gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), or combinations thereof.

In some embodiments, a topical formulation disclosed herein comprises an emollient. Emollients include, but are not limited to, castor oil esters, cocoa butter esters, safflower oil esters, cottonseed oil esters, corn oil esters, olive oil esters, cod liver oil esters, almond oil esters, avocado oil esters, palm oil esters, sesame oil esters, squalene esters, kikui oil esters, soybean oil esters, acetylated monoglycerides, ethoxylated glyceryl monostearate, hexyl laurate, isohexyl laurate, isohexyl palmitate, isopropyl palmitate, methyl palmitate, decyloleate, isodecyl oleate, hexadecyl stearate decyl stearate, isopropyl isostearate, methyl isostearate, diisopropyl adipate, diisohexyl adipate, dihexyldecyl adipate, diisopropyl sebacate, lauryl lactate, myristyl lactate, and cetyl lactate, oleyl myristate, oleyl stearate, and oleyl oleate, pelargonic acid, lauric acid, myristic acid, palmitic acid, stearic acid, isostearic acid, hydroxystearic acid, oleic acid, linoleic acid, ricinoleic acid, arachidic acid, behenic acid, erucic acid, lauryl alcohol, myristyl alcohol, cetyl alcohol, hexadecyl alcohol, stearyl alcohol, isostearyl alcohol, hydroxystearyl alcohol, oleyl alcohol, ricinoleyl alcohol, behenyl alcohol, erucyl alcohol, 2-octyl dodecanyl alcohol, lanolin and lanolin derivatives, beeswax, spermaceti, myristyl myristate, stearyl stearate, carnauba wax, candelilla wax, lecithin, and cholesterol.

In some embodiments, an nHC-HA/PTX3 or rcHC-HA/PTX3 complex disclosed herein is formulated with one or more natural polymers. In some embodiments, an nHC-HA/PTX3 or rcHC-HA/PTX3 complex disclosed herein is formulated with a natural polymer that is fibronectin, collagen, laminin, keratin, fibrin, fibrinogen, hyaluronic acid, heparan sulfate, chondroitin sulfate. In some embodiments, an nHC-HA/PTX3 or rcHC-HA/PTX3 complex disclosed herein is formulated with a polymer gel formulated from a natural polymer. In some embodiments, an nHC-HA/PTX3 or rcHC-HA/PTX3 complex disclosed herein is formulated with a polymer gel formulated from a natural polymer, such as, but not limited to, fibronectin, collagen, laminin, keratin, fibrin, fibrinogen, hyaluronic acid, heparan sulfate, chondroitin sulfate, and combinations thereof. In some embodiments, an nHC-HA/PTX3 or rcHC-HA/PTX3 complex disclosed herein is formulated with a cross-linked polymer. In some embodiments, an nHC-HA/PTX3 or rcHC-HA/PTX3 complex disclosed herein is formulated with a non-cross-linked polymer. In some embodiments, an nHC-HA/PTX3 or rcHC-HA/PTX3 complex disclosed herein is formulated with a non-cross-linked polymer and a cross-linked polymer. In some embodiments, an nHC-HA/PTX3 or rcHC-HA/PTX3 complex disclosed herein is formulated with cross-linked hyaluronan gel. In some embodiments, an nHC-HA/PTX3 or rcHC-HA/PTX3 complex disclosed herein is formulated with an insoluble cross-linked HA hydrogel. In some embodiments, an nHC-HA/PTX3 or rcHC-HA/PTX3 complex disclosed herein is formulated with non-cross-linked hyaluronan gel. In some embodiments, an nHC-HA/PTX3 or rcHC-HA/PTX3 complex disclosed herein is formulated with a collagen matrix. In some embodiments, an nHC-HA/PTX3 or rcHC-HA/PTX3 complex disclosed herein is formulated with a fibrin matrix. In some embodiments, an nHC-HA/PTX3 or rcHC-HA/PTX3 complex disclosed herein is formulated with a fibrin/collagen matrix.

In some embodiments, an nHC-HA/PTX3 or rcHC-HA/PTX3 complex disclosed herein is formulated for administration to an eye or a tissue related thereto. Formulations suitable for administration to an eye include, but are not limited to, solutions, suspensions (e.g., an aqueous suspension), ointments, gels, creams, liposomes, niosomes, pharmacosomes, nanoparticles, or combinations thereof. In some embodiments, an nHC-HA/PTX3 or rcHC-HA/PTX3 complex disclosed herein for topical administration to an eye is administered spraying, washing, or combinations thereof. In some embodiments, an nHC-HA/PTX3 or rcHC-HA/PTX3 complex disclosed herein is administered to an eye via an injectable depot preparation.

As used herein, a "depot preparation" is a controlled-release formulation that is implanted in an eye or a tissue related thereto (e.g., the sclera) (for example subcutaneously, intramuscularly, intravitreally, or within the subconjunctiva). In some embodiments, a depot preparation is formulated by forming microencapsulated matrices (also known as microencapsulated matrices) of an nHC-HA/PTX3 or rcHC-HA/PTX3 complex disclosed herein in biodegradable polymers. In some embodiments, a depot preparation is formulated by entrapping an nHC-HA/PTX3 or rcHC-HA/PTX3 complex disclosed herein in liposomes or microemulsions.

A formulation for administration to an eye has an ophthalmically acceptable tonicity. In certain instances, lacrimal fluid has an isotonicity value equivalent to that of a 0.9% sodium chloride solution. In some embodiments, an isotonicity value from about 0.6% to about 1.8% sodium chloride equivalency is suitable for topical administration to an eye. In some embodiments, a formulation for administration to an eye disclosed herein has an osmolarity from about 200 to about 600 mOsm/L. In some embodiments, a formulation for administration to an eye disclosed herein is hypotonic and thus requires the addition of any suitable to attain the proper tonicity range. Ophthalmically acceptable substances that modulate tonicity include, but are not limited to, sodium chloride, potassium chloride, sodium thiosulfate, sodium bisulfite and ammonium sulfate.

A formulation for administration to an eye has an ophthalmically acceptable clarity. Examples of ophthalmically-acceptable clarifying agents include, but are not limited to, polysorbate 20, polysorbate 80, or combinations thereof.

In some embodiments, a formulation for administration to an eye comprises an ophthalmically acceptable viscosity enhancer. In some embodiments, a viscosity enhancer increases the time a formulation disclosed herein remains in an eye. In some embodiments, increasing the time a formulation disclosed herein remains in the eye allows for greater drug absorption and effect. Non-limiting examples of mucoadhesive polymers include carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, a formulation for administration to an eye is administered or delivered to the posterior segments of an eye (e.g., to the retina, choroid, vitreous and optic nerve). In some embodiments, a topical formulation for administration to an eye disclosed herein for delivery to the posterior of the eye comprises a solubilizing agent, for example, a glucan sulfate and/or a cyclodextrin. Glucan sulfates which are used in some embodiments include, but are not limited to, dextran sulfate, cyclodextrin sulfate and β-1,3-glucan sulfate, both natural and derivatives thereof, or any compound which temporarily binds to and be retained at tissues which contain fibroblast growth factor (FGF), which improves the stability and/or solubility of a drug, and/or which improves penetration and ophthalmic absorption of a topical formulation for administration to an eye disclosed herein. Cyclodextrin derivatives which are used in some embodiments as a solubilizing agent include, but are not limited to, α-cyclodextrin, β-cyclodextrin, γ-cyclodextrin, hydroxyethyl β-cyclodextrin, hydroxypropyl γ-cyclodextrin, hydroxypropyl β-cyclodextrin, sulfated α-cyclodextrin, sulfated β-cyclodextrin, sulfobutyl ether β-cyclodextrin.

In some embodiments, an nHC-HA/PTX3 or rcHC-HA/PTX3 complex disclosed herein is formulated for rectal or vaginal administration. In some embodiments, an nHC-HA/PTX3 or rcHC-HA/PTX3 complex disclosed herein is administered as a suppository. In some embodiments, a composition suitable for rectal administration is prepared by mixing an nHC-HA/PTX3 or rcHC-HA/PTX3 complex disclosed herein with a suitable non-irritating excipient which is solid at ordinary temperatures but liquid at the rectal temperature and will therefore melt in the rectum to release the drug. In some embodiments, a composition suitable for rectal administration is prepared by mixing an nHC-HA/PTX3 or rcHC-HA/PTX3 complex disclosed herein with cocoa butter, glycerinated gelatin, hydrogenated vegetable oils, mixtures of polyethylene glycols of various molecular weights or fatty acid esters of polyethylene glycol.

In certain embodiments, an nHC-HA/PTX3 or rcHC-HA/PTX3 complex described herein is optionally incorporated within controlled release particles, lipid complexes, liposomes, nanoparticles, microspheres, microparticles, nanocapsules or other agents which enhance or facilitate localized delivery to the skin. An example of a conventional microencapsulation process for pharmaceutical preparations is described in U.S. Pat. No. 3,737,337, incorporated herein by reference for such disclosure.

Dosages

The amount of pharmaceutical compositions administered is dependent in part on the individual being treated. In instances where pharmaceutical compositions are administered to a human subject, the daily dosage will normally be determined by the prescribing physician with the dosage generally varying according to the age, sex, diet, weight, general health and response of the individual, the severity of the individual's symptoms, the precise disease or condition being treated, the severity of the disease or condition being treated, time of administration, route of administration, the disposition of the composition, rate of excretion, drug combination, and the discretion of the prescribing physician.

In some embodiments, the dosage of an nHC-HA/PTX3 or rcHC-HA/PTX3 complex is between about 0.001 to about 1000 mg/kg body weight/day. In some embodiments, the amount of nHC-HA/PTX3 or rcHC-HA/PTX3 complex disclosed herein is in the range of about 0.5 to about 50 mg/kg/day. In some embodiments, the amount of nHC-HA/PTX3 or rcHC-HA/PTX3 complex disclosed herein is about 0.001 to about 7 g/day. In some embodiments, the amount of nHC-HA/PTX3 or rcHC-HA/PTX3 complex disclosed herein is about 0.01 to about 7 g/day. In some embodiments, the amount of nHC-HA/PTX3 or rcHC-HA/PTX3 complex disclosed herein is about 0.02 to about 5 g/day. In some embodiments, the amount of nHC-HA/PTX3 or rcHC-HA/PTX3 complex disclosed herein is about 0.05 to about 2.5 g/day. In some embodiments, the amount of nHC-HA/PTX3 or rcHC-HA/PTX3 complex disclosed herein is about 0.1 to about 1 g/day.

In some embodiments, an nHC-HA/PTX3 or rcHC-HA/PTX3 complex disclosed herein is administered, before, during or after the occurrence of a disease or condition. In some embodiments, a combination therapy is administered before, during or after the occurrence of a disease or condition. In some embodiments, an nHC-HA/PTX3 or rcHC-HA/PTX3 complex disclosed herein is administered with a combination therapy before, during or after the occurrence of a disease or condition. In some embodiments, the timing of administering the composition containing an nHC-HA/PTX3 or rcHC-HA/PTX3 disclosed herein varies. Thus, in some examples, an nHC-HA/PTX3 or rcHC-HA/PTX3 complex disclosed herein is used as a prophylactic and is administered continuously to subjects with a propensity to develop conditions or diseases in order to prevent the occurrence of the disease or condition. In some embodiments, an nHC-HA/PTX3 or rcHC-HA/PTX3 complex disclosed herein is administered to a subject during or as soon as possible after the onset of the symptoms. In some embodiments, the administration of an nHC-HA/PTX3 or rcHC-HA/PTX3 complex disclosed herein is initiated within the first 48 hours of the onset of the symptoms, preferably within the first 48 hours of the onset of the symptoms, more preferably within the first 6 hours of the onset of the symptoms, and most preferably within 3 hours of the onset of the symptoms. In some embodiments, the initial administration is via any route practical, such as, for example, an intravenous injection, a bolus injection, infusion over 5 minutes to about 5 hours, a pill, a capsule, transdermal patch, buccal delivery, or combination thereof. An nHC-HA/PTX3 or rcHC-HA/PTX3 complex disclosed herein is preferably administered as soon as is practicable after the onset of a disease or condition is detected or suspected, and for a length of time necessary for the treatment of the disease, such as, for example, from about 1 month to about 3 months. In some embodiments, the length of treatment varies for each subject, and the length is determined using the known criteria. In some embodiments, an nHC-HA/PTX3 or rcHC-HA/PTX3 complex disclosed herein or a formulation containing a complex is administered for at least 2 weeks, preferably about 1 month to about 5 years, and more preferably from about 1 month to about 3 years.

In some embodiments, an nHC-HA/PTX3 or rcHC-HA/PTX3 complex disclosed herein is administered in a single dose, once daily. In some embodiments, an nHC-HA/PTX3 or rcHC-HA/PTX3 complex disclosed herein is administered in multiple doses, more than once per day. In some embodiments, an nHC-HA/PTX3 or rcHC-HA/PTX3 complex disclosed herein is administered twice daily. In some embodiments, an nHC-HA/PTX3 or rcHC-HA/PTX3 complex disclosed herein is administered three times per day. In some embodiments, an nHC-HA/PTX3 or rcHC-HA/PTX3 complex is administered four times per day. In some embodiments, an nHC-HA/PTX3 or rcHC-HA/PTX3 complex disclosed herein is administered more than four times per day.

In some embodiments, an nHC-HA/PTX3 or rcHC-HA/PTX3 complex disclosed herein is administered for prophylactic and/or therapeutic treatments. In therapeutic applications, in some embodiments, an nHC-HA/PTX3 or rcHC-HA/PTX3 complex disclosed herein is administered to an individual already suffering from a disease or condition, in an amount sufficient to cure or at least partially arrest the symptoms of the disease or condition. Amounts effective for this use will depend on the severity and course of the disease or condition, previous therapy, the individual's health status, weight, and response to the drugs, and the judgment of the treating physician.

In prophylactic applications, in some embodiments, an nHC-HA/PTX3 or rcHC-HA/PTX3 complex disclosed herein is administered to an individual that is at risk of a particular disorder. Such an amount is defined to be a "prophylactically effective amount or dose." In such use, the precise amounts also depend on the individual's state of health, weight, and other physical parameters of the individual.

In the case wherein the individual's condition does not improve, upon the doctor's discretion an nHC-HA/PTX3 or rcHC-HA/PTX3 complex disclosed herein is administered chronically, that is, for an extended period of time, including throughout the duration of the individual's life in order to ameliorate or otherwise control or limit the symptoms of the individual's disease or condition.

In some embodiments, in cases where the individual's status does improve, upon the doctor's discretion, an nHC-HA/PTX3 or rcHC-HA/PTX3 complex disclosed herein is administered continuously or the dose of drug being administered is temporarily reduced or temporarily suspended for a certain length of time (i.e., a "drug holiday"). In some embodiments, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. In some embodiments the dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the individual's conditions has occurred, a maintenance dose is administered if necessary. In some embodiments, subsequently, the dosage or the frequency of administration, or both, is reduced, as a function of the symptoms, to a level at which the improved disease, disorder or condition is retained. In some embodiments, individuals require intermittent treatment on a long-term basis upon any recurrence of symptoms.

In some embodiments, the pharmaceutical composition described herein is in unit dosage forms suitable for single administration of precise dosages. In unit dosage form, the formulation is divided into unit doses containing appropriate quantities of an nHC-HA/PTX3 or rcHC-HA/PTX3 complex disclosed herein. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. In some embodiments, multiple-dose reclosable containers are used, in which case it is typical to include a preservative in the composition. In some embodiments, formulations for parenteral injection are presented in unit dosage form, which include, but are not limited to ampoules, or in multi dose containers, with an added preservative.

The daily dosages appropriate for an nHC-HA/PTX3 or rcHC-HA/PTX3 complex disclosed herein are, for example, from about 0.01 to 2.5 mg/kg per body weight. An indicated daily dosage in the larger mammal, including, but not limited to, humans, is in the range from about 0.5 mg to about 100 mg, conveniently administered in divided doses, including, but not limited to, up to four times a day or in extended release form. Suitable unit dosage forms for oral administration include from about 1 to 50 mg active ingredient. The foregoing ranges are merely suggestive, as the number of variables in regard to an individual treatment regime is large, and considerable excursions from these recommended values are not uncommon. In some embodiments, the dosages are altered depending on a number of variables, not limited to the activity of an nHC-HA/PTX3 or rcHC-HA/PTX3 complex used, the disease or condition to be treated, the mode of administration, the requirements of the individual subject, the severity of the disease or condition being treated, and the judgment of the practitioner.

In some embodiments, the toxicity and therapeutic efficacy of such therapeutic regimens are determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). In some embodiments, the dose ratio between the toxic and therapeutic effects is the therapeutic index and it is expressed as the ratio between $LD_{50}$ and $ED_{50}$. nHC-HA/PTX3 or rcHC-HA/PTX3 complexes exhibiting high therapeutic indices are preferred. In some embodiments, the data obtained from cell culture assays and animal studies is used in formulating a range of dosage for use in human. The dosage of an nHC-HA/PTX3 or rcHC-HA/PTX3 complex disclosed herein lies preferably within a range of circulating concentrations that include the $ED_{50}$ with minimal toxicity. In some embodiments, the dosage varies within this range depending upon the dosage form employed and the route of administration utilized.

In some embodiments, the pharmaceutical compositions of nHC-HA/PTX3 or rcHC-HA/PTX3 complexes are packaged as articles of manufacture containing packaging material, a pharmaceutical composition which is effective for prophylaxis and/or treating a disease or condition, and a label that indicates that the pharmaceutical composition is to be used for treating the disease or condition. In some embodiments, the pharmaceutical compositions are packaged in unit dosage forms contain an amount of the pharmaceutical composition for a single dose or multiple doses. In some embodiments, the packaged compositions contain a lyophilized powder of the pharmaceutical compositions, which is reconstituted (e.g., with water or saline) prior to administration.

Medical Device and Biomaterials Compositions

In some embodiments, an nHC-HA/PTX3 or rcHC-HA/PTX3 complex disclosed herein is assembled directly on a surface of or formulated as a coating for an implantable medical device. Methods for covalent attachment of hyaluronan to surfaces such as, but not limited to, metallic, polymeric, ceramic, silica and composite surfaces is well-known in the art and in some embodiments, is employed in conjunction with the methods provided herein for the assembly of nHC-HA/PTX3 or rcHC-HA/PTX3 complexes on such surfaces (see e.g., U.S. Pat. Nos. 5,356,433; 5,336,518, 4,613,665, 4,810,784, 5,037,677, 8,093,365). In some embodiments, an nHC-HA/PTX3 or rcHC-HA/PTX3 complex is assembled directly on a surface of an implantable medical device or a portion thereof. In some embodiments, an nHC-HA/PTX3 or rcHC-HA/PTX3 complex that has been generated according the methods provided herein is purified and then attached directly on a surface of an implantable medical device or a portion thereof. In some embodiments, an nHC-HA/PTX3 or rcHC-HA/PTX3 complex that has been generated according the methods provided herein is purified and then formulated as a coating for attachment to the medical device or a portion thereof. In some embodiments, the coating is applied directly to the surfaces or is applied to a pretreated or coated surface where the pretreatment or coating is designed to aid adhesion of the coating to the substrate. In some embodiments, an nHC-HA/PTX3 or rcHC-HA/PTX3 complex that has been generated according the methods provided herein is purified and then attached to a medical device or a portion thereof that has been coated with a substance that promotes the attachment of the nHC-HA/PTX3 or rcHC-HA/PTX3 complex. For example, in some embodiments, the medical device or a portion thereof is coated with an adhesive polymer that provides functional groups on its surface for the covalent attachment of hyaluronan of the nHC-HA/PTX3 or rcHC-HA/PTX3 complex. In some embodiments, a coupling agent, such as, but not limited to carbodiimide is employed to attach the nHC-HA/PTX3 or rcHC-HA/PTX3 complex to the polymer coating. In some embodiments, photoimmobilization is employed to covalently attach an nHC-HA/PTX3 or rcHC-HA/PTX3 complex that has been generated according the methods provided herein to medical device or a portion thereof. In some embodiments, an nHC-HA/PTX3 or rcHC-HA/PTX3 complex that has been generated according the methods provided herein is attached to a medical device or a portion thereof using a spacer molecule that comprises a photochemically or thermochemically reactive group.

In some embodiments, the coating formulations comprising an nHC-HA/PTX3 or rcHC-HA/PTX3 complex are applied to the substrate by for example dip-coating. Other methods of application include, but are not limited to, spray, wash, vapor deposition, brush, roller, curtain, spin coating and other methods known in the art.

Exemplary implantable medical devices include, but not limited to an artificial joint, orthopedic device, bone implant, contact lenses, suture, surgical staple, surgical clip, catheter, angioplasty balloon, sensor, surgical instrument, electrode, needle, syringe, wound drain, shunt, urethral insert, metal or plastic implant, heart valve, artificial organ, lap band, annuloplasty ring, guide wire, K-wire or Denham pin, stent, stent graft, vascular graft, pacemaker, pellets, wafers, medical tubing, infusion sleeve, implantable defibrillator, neurostimulator, glucose sensor, cerebrospinal fluid shunt, implantable drug pump, spinal cage, artificial disc, ocular implant, cochlear implant, breast implant, replacement device for nucleus pulposus, ear tube, intraocular lens, drug delivery system, microparticle, nanoparticle, and microcapsule.

In particular embodiments, the implantable medical device is an implant or prosthesis comprising an nHC-HA/PTX3 or rcHC-HA/PTX3 complex disclosed herein. In particular embodiments, the prosthesis is an artificial joint. In some embodiments, the prosthesis is an artificial hip joint, artificial knee, an artificial glenohumeral joint, an artificial ankle.

In particular embodiments, the implant is a stent. In particular embodiments, the implant is a coronary stent, a ureteral stent, a urethral stent, a prostatic stent, a bone stent, or an esophageal stent. In particular embodiments, the implant is a bone implant, such as, but not limited to, an osseointegrated implant or a craniofacial prosthesis (e.g., an artificial ear, orbital prosthesis, nose prosthesis).

In some embodiments, an nHC-HA/PTX3 or rcHC-HA/PTX3 complex disclosed herein is assembled directly on a microparticle or a nanoparticle for delivery of the nHC-HA/PTX3 or rcHC-HA/PTX3 complex to a subject (see, e.g., WO 03/015755 and US2004/0241248).

In some embodiments, the nHC-HA/PTX3 or rcHC-HA/PTX3 complexes provided herein are attached to, assembled on, or provided as a coating on the surfaces of or portions thereof of any such implantable medical devices as described herein or known in the art. In some embodiments the nHC-HA/PTX3 or rcHC-HA/PTX3 complex elutes from the coating and into the surrounding tissue following implantation.

In some embodiments, an nHC-HA/PTX3 or rcHC-HA/PTX3 complex disclosed herein is assembled directly on a scaffold, a microparticle, a microcapsule or microcarrier employed for the delivery of a biomaterial, such as a stem cell or an insulin producing cell. In some embodiments, an nHC-HA/PTX3 or rcHC-HA/PTX3 complex disclosed herein is attached to the microcapsule or assembled directly on a microcapsule. In some embodiments, the nHC-HA/PTX3 or rcHC-HA/PTX3 complex is combined with a material used to form the microcapsule and a microcapsule is generated that contains the nHC-HA/PTX3 or rcHC-HA/PTX3 complex. In some embodiments, the nHC-HA/PTX3 or rcHC-HA/PTX3 complex is used to coat the inner surface of the microcapsule. In some embodiments, the nHC-HA/PTX3 or rcHC-HA/PTX3 complex is used to coat the outer surface of the microcapsule. In some embodiments, the nHC-HA/PTX3 or rcHC-HA/PTX3 complex is used to coat the inner and outer surface of the microcapsule.

Exemplary materials for encapsulating cells include, but are not limited to, thermosetting hydrogels, such as agarose, alginate, and artificial polymers such as poly(NiPAAm-co-AAC), poly(ethylene glycol) (PEG) and PEG derivatives such as PEG diacrylate and oligo(poly(ethylene glycol)) fumerate. Methods for the culturing and microencapsulation of stem cells are known in the art in some embodiments, are employed to generate microcapsules containing an nHC-HA/PTX3 or rcHC-HA/PTX3 complex provided herein.

In some embodiments the microcapsule contains a cell, a plurality of cells or other biological material. In some embodiments, the cell or cells are stem cells, such as, but not limited to, mesenchymal stem cells. In some embodiments, the cell or cells are differentiated cells, such as, but not limited to, insulin-producing cells. In some embodiments, the cell or cells are autologous cells (i.e. cells that are from or derived from the recipient of the cells). In some embodiments, the cell or cells are allogeneic cells (i.e. cells that are not from or derived from the recipient of the cells). In some embodiments, the microcapsule contains a cell, a plurality of cells or other biological material and the inner surfaces of the microcapsule are coated with nHC-HA/PTX3 or rcHC-HA/PTX3 complex provided herein. In some embodiments the microcapsule contains a cell, a plurality of cells or other biological material and the outer surfaces of the microcapsule are coated with nHC-HA/PTX3 or rcHC-HA/PTX3 complex provided herein. In some embodiments the microcapsule contains a cell, a plurality of cells or other biological material and the outer and inner surfaces of the microcapsule are coated with nHC-HA/PTX3 or rcHC-HA/PTX3 complex provided herein. In some embodiments the microcapsule is administered to treat a disease or condition. Exemplary diseases and conditions and methods of treatment for which a microcapsule can be administered are described elsewhere herein and include but are not limited to inflammatory and immune related diseases.

Methods of Treatment

Disclosed herein, in certain embodiments, are methods of treating an individual in need thereof, comprising administering to the individual nHC-HA/PTX3 or rcHC-HA/PTX3 complexes described herein. Disclosed herein, in certain embodiments, are methods of treating an individual in need thereof, comprising administering to the individual nHC-HA/PTX3 or rcHC-HA/PTX3 complexes produced by the methods described herein. The following are non-limiting examples of methods of treatment comprising administration of an nHC-HA/PTX3 or rcHC-HA/PTX3 complex disclosed herein. In some embodiments, an nHC-HA/PTX3 or rcHC-HA/PTX3 complex disclosed herein is used to inhibit at least one of the following: scarring, inflammation, immune reaction leading to autoimmune or immune rejection, adhesion, angiogenesis and conditions requiring cell or tissue regeneration. In some embodiments, an nHC-HA/PTX3 or rcHC-HA/PTX3 complex disclosed herein is used to promote wound healing. In some embodiments, an nHC-HA/PTX3 or rcHC-HA/PTX3 complex disclosed herein is used to promote stem cell expansion. In some embodiments, an nHC-HA/PTX3 or rcHC-HA/PTX3 complex disclosed herein is used to promote tissue regeneration.

In some embodiments, the methods of treating an individual in need thereof, comprising administering to the individual nHC-HA/PTX3 or rcHC-HA/PTX3 complexes described herein by any suitable method. In some embodiments, the methods of treating an individual in need thereof, comprising administering to the individual nHC-HA/PTX3 or rcHC-HA/PTX3 complexes described herein by any suitable route of administration. Suitable methods for administration will depend on the disease or condition to be treated. In some embodiments, the nHC-HA/PTX3 or rcHC-HA/PTX3 complexes are administered locally to the site of treatment. In some embodiments, the nHC-HA/PTX3 or rcHC-HA/PTX3 complexes are administered systemically. Exemplary methods for administration of the nHC-HA/PTX3 or rcHC-HA/PTX3 complexes provided herein include but are not limited to parenteral, enteral, subcutaneous, percutaneous, transdermal, intradermal, intravenous, topical, inhalation, or implantation.

Scarring

Described herein, in certain embodiments, are methods of preventing, reducing, or reversing scarring in a subject in need thereof, comprising administering to the subject a composition comprising an nHC-HA/PTX3 or rcHC-HA/PTX3 complex disclosed herein.

As used herein, "scarring" refers to the formation of a scar. In one aspect, the scar is a hypertrophic scar, or keloid scar, or a scar resulting from acne. As used herein, a "scar" is an area of fibrous tissue that results from the overproduction of collagen. In certain instances, wound healing comprises the migration of fibroblasts to the site of injury. In certain instances, fibroblasts deposit collagen. In certain instances, fibroblasts deposit excess collagen at the wound site, resulting in a scar.

In certain instances, an nHC-HA/PTX3 or rcHC-HA/PTX3 complex disclosed herein prevents or inhibits TGF-β signaling. In certain instances, TGF-β regulates the extracellular matrix by stimulating fibroplasia and collagen deposition and inhibiting extracellular matrix degradation (by up-regulating the synthesis of protease inhibitors). In certain instances, preventing or inhibiting the expression of TGF-β results in the prevention of or a reduction in intensity of a scar. In some embodiments, administering an nHC-HA/PTX3 or rcHC-HA/PTX3 complex disclosed herein prevents or reduces scarring.

In some embodiments, an nHC-HA/PTX3 or rcHC-HA/PTX3 complex disclosed herein inhibits or prevents the ability of fibroblasts to differentiate into myofibroblasts. In some embodiments, an nHC-HA/PTX3 or rcHC-HA/PTX3 complex disclosed herein reverts differentiated myofibroblasts to fibroblasts.

In some embodiments, a method disclosed herein is used to prevent, reduce or reverse the formation of a scar. In some embodiments, a method disclosed herein comprises administering an nHC-HA/PTX3 or rcHC-HA/PTX3 complex disclosed herein to an individual with a disorder that results in scarring (e.g., dermatitis scar, a keloid scar, contracture scar, a hypertrophic scar, or a scar resulting from acne). In some embodiments, a method disclosed herein comprises administering an nHC-HA/PTX3 or rcHC-HA/PTX3 complex disclosed herein to an individual in need thereof before or after trauma. In some embodiments, a method disclosed herein comprises administering an nHC-HA/PTX3 or rcHC-HA/PTX3 complex disclosed herein to an individual in need thereof before or after surgery.

In some embodiments, a method disclosed herein is used to prevent or reduce the formation of a scar on an eye or on the surrounding tissue. In some embodiments, a method disclosed herein comprises administering an nHC-HA/PTX3 or rcHC-HA/PTX3 complex disclosed herein to an individual with a disorder that results in scarring of the eye or surrounding tissue (e.g., retinopathy of prematurity). In some embodiments, a method disclosed herein comprises administering an nHC-HA/PTX3 or rcHC-HA/PTX3 complex disclosed herein to an individual in need thereof before or after trauma to an eye or the surrounding tissue. In some embodiments, a method disclosed herein comprises administering an nHC-HA/PTX3 or rcHC-HA/PTX3 complex disclosed herein to an individual in need thereof before or after surgery to an eye or the surrounding tissue.

Inflammation

Described herein, in certain embodiments, are methods of preventing or reducing inflammation in a subject in need thereof, comprising administering to the subject a composition comprising an nHC-HA/PTX3 or rcHC-HA/PTX3 complex disclosed herein. As used herein, "inflammation" means physiological responses resulting from the migration of plasma and/or leukocytes (e.g., lymphocytes, macrophages, granulocytes, and neutrophils) to the site of an infection or trauma (e.g., blunt force trauma, penetrating trauma, or surgery).

In certain instances, leukocytes secrete cytokines following contact with an antigen. As used herein, "cytokines" are signaling proteins or glycoproteins. In certain instances, a cytokine binds to a cell-surface receptor. In certain instances, cytokines induces the chemotaxis of leukocytes to the site of an infection. In certain instances, cell surface receptors on a leukocyte detect chemical gradients of a cytokine. In certain instances, a leukocyte follows the gradient to the site of infection. In certain instances, the binding of a cytokine to a cell-surface receptor results in the upregulation or downregulation of certain genes and their transcription factors. In certain instances, changes in gene expression results in the production of cytokines, an increase in the production of cytokines, or an increase in the presentation of cell surface receptors.

By way of non-limiting example, cytokines include interleukins IL-1, IL-6, IL-8, MCP-1 (also known as CCL2), and TNF-α. Interleukin 1 is present in the body in two isoforms: IL-1α and IL-1β. In certain instances, the presence of IL-1 increases the expression of adhesion factors on endothelial cells. This, in turn, enables the transmigration of leukocytes to the site of infection. In certain instances, IL-8 induces the chemotaxis of leukocytes. In certain instances, TNF-α induces the chemotaxis of leukocytes. In certain instances, MCP-1 recruits leukocytes to sites of tissue injury and infection.

In some embodiments, an nHC-HA/PTX3 or rcHC-HA/PTX3 complex disclosed herein suppresses the production of and/or activity of cytokines. In certain instances, a decrease in the concentration cytokines reduces or prevents inflammation by decreasing the number of leukocytes and/or the rate at which leukocytes migrate to the site of an injury.

In some embodiments, an nHC-HA/PTX3 or rcHC-HA/PTX3 complex disclosed herein induces apoptosis of a leukocyte (e.g., a macrophage, neutrophil, or lymphocyte). In some embodiments, an nHC-HA/PTX3 or rcHC-HA/PTX3 complex disclosed herein decreases the number of activated leukocytes or the rate at which leukocytes are activated. In certain instances, a decrease in the concentration of leukocytes reduces or prevents inflammation by decreasing the number (e.g., facilitate death of such cells via apoptosis) of cells that migrate to the site of an injury.

In some embodiments, an nHC-HA/PTX3 or rcHC-HA/PTX3 complex disclosed herein inhibits the polarization of a macrophage to an inflammatory phenotype (i.e. an M1 phenotype). In some embodiments, an nHC-HA/PTX3 or rcHC-HA/PTX3 complex disclosed herein reduces or inhibits the expression of IL-12 or IL-23 in stimulated macrophages. In some embodiments, an nHC-HA/PTX3 or rcHC-HA/PTX3 complex disclosed herein promotes the polarization of stimulated macrophages to a regulatory or wound healing M2 phenotype. In some embodiments, an nHC-HA/PTX3 or rcHC-HA/PTX3 complex disclosed herein inhibits or reduces inflammation in a subject. In some embodiments, an nHC-HA/PTX3 or rcHC-HA/PTX3 complex disclosed herein inhibits or reduces tissue damage caused by an inflammatory response in a subject. In some embodiments, an nHC-HA/PTX3 or rcHC-HA/PTX3 complex inhibits or reduces tissue damage caused by a condition or disease that induces inflammation in a subject.

In some embodiments, an nHC-HA/PTX3 or rcHC-HA/PTX3 complex disclosed herein is administered to a subject having inflammation. In some embodiments, an nHC-HA/PTX3 or rcHC-HA/PTX3 complex disclosed herein is administered to a subject having acute inflammation. In some embodiments, an nHC-HA/PTX3 or rcHC-HA/PTX3 complex disclosed herein is administered to a subject having chronic inflammation. In some embodiments, an nHC-HA/PTX3 or rcHC-HA/PTX3 complex disclosed herein is administered to a subject having an inflammatory disorder. In some embodiments, the inflammatory disorder is a macrophage mediated inflammatory disorder. In some embodiments, the inflammatory disorder is a T-cell mediated inflammatory disorder. In some embodiments, the inflammatory disorder is a Th-17 mediated immune disorder.

In some embodiments, an nHC-HA/PTX3 or rcHC-HA/PTX3 complex disclosed herein is administered to a subject having an acute inflammatory response. In some embodiments, the acute inflammatory response is caused by, for example, an allergy, sepsis, endotoxic shock or ischemia, such as but not limited to, myocardial infarction and stroke. In some embodiments, the acute inflammatory response is the result of bacterial infection, a protozoal infection, a protozoal infection, a viral infection, a fungal infection, or combinations thereof. In some embodiments, an nHC-HA/PTX3 or rcHC-HA/PTX3 complex inhibits or reduces acute inflammation. In some embodiments, an nHC-HA/PTX3 or rcHC-HA/PTX3 complex inhibits or reduces tissue damage caused by acute inflammation. In some embodiments, an nHC-HA/PTX3 or rcHC-HA/PTX3 complex inhibits or reduces tissue reperfusion injury due to ischemia, including myocardial infarction and stroke, In some embodiments, an nHC-HA/PTX3 or rcHC-HA/PTX3 complex disclosed herein is administered to a subject having chronic inflammation that is associated with the activation of lymphocytes via adaptive immunity. In some embodiments, an nHC-HA/PTX3 or rcHC-HA/PTX3 complex disclosed herein is administered to a subject having a Th1 response. In some embodiments the Th1 response leads to immune rejection of biological transplant. In some embodiments, the transplant is an allograft transplant. In some embodiments, the transplant is an autologous transplant. In some embodiments, the inflammatory disorder is graft versus host disease or tissue transplant rejection. In some embodiments, an nHC-HA/PTX3 or rcHC-HA/PTX3 complex inhibits or reduces chronic inflammation in a subject.

In some embodiments, an nHC-HA/PTX3 or rcHC-HA/PTX3 complex disclosed herein is administered to a subject having chronic inflammation that is associated with a Th17 immune response associated with an inflammatory disorder. In some embodiments, the inflammatory disorder is an autoimmune disorder or a leukocyte defect.

In some embodiments, an nHC-HA/PTX3 or rcHC-HA/PTX3 complex disclosed herein is administered to a subject having an inflammatory disorder that is acute disseminated encephalomyelitis; Addison's disease; ankylosing spondylitis; antiphospholipid antibody syndrome; autoimmune hemolytic anemia; autoimmune hepatitis; autoimmune inner ear disease; bullous pemphigoid; Chagas disease; chronic obstructive pulmonary disease; coeliac disease; dermatomyositis; diabetes mellitus type 1; diabetes mellitus type 2; endometriosis; Goodpasture's syndrome; Graves' disease; Guillain-Barré syndrome; Hashimoto's disease; idiopathic thrombocytopenic purpura; interstitial cystitis; systemic lupus erythematosus (SLE); metabolic syndrome, multiple sclerosis; myasthenia gravis; myocarditis, narcolepsy; obesity; pemphigus vulgaris; pernicious anemia; polymyositis; primary biliary cirrhosis; rheumatoid arthritis; schizophrenia; scleroderma; Sjögren's syndrome; vasculitis; vitiligo; Wegener's granulomatosis; allergic rhinitis; prostate cancer; non-small cell lung carcinoma; ovarian cancer; breast cancer; melanoma; gastric cancer; colorectal cancer; brain cancer; metastatic bone disorder; pancreatic cancer; a lymphoma; nasal polyps; gastrointestinal cancer; ulcerative colitis; Crohn's disorder; collagenous colitis; lymphocytic colitis; ischaemic colitis; diversion colitis; Behçet's syndrome; infective colitis; indeterminate colitis; inflammatory liver disorder, ischemia, myocardial infarction, stroke, endotoxin shock, septic shock; rheumatoid spondylitis, ankylosing spondylitis, Gouty arthritis, polymyalgia rheumatica, Alzheimer's disorder, Parkinson's disorder, epilepsy, AIDS dementia, asthma, adult respiratory distress syndrome, bronchitis, cystic fibrosis, acute leukocyte-mediated lung injury, distal proctitis, Wegener's granulomatosis, fibromyalgia, uveitis, conjunctivitis, psoriasis, eczema, dermatitis, smooth muscle proliferation disorders, meningitis, shingles, encephalitis, nephritis, tuberculosis, retinitis, atopic dermatitis, pancreatitis, periodontal gingivitis, coagulative Necrosis, liquefactive necrosis, fibrinoid necrosis, neointimal hyperplasia, or combinations thereof.

In some embodiments, the inflammatory disorder is an inflammatory disorder of an eye or the surrounding tissue. In some embodiments, the inflammatory disorder is conjunctivitis. In certain instances, conjunctivitis results from exposure to an allergen. In certain instances, conjunctivitis results from a bacterial infection. In some embodiments, the inflammatory disorder is keratitis. As used herein, "keratitis" is a disorder characterized by inflammation of the cornea. In some embodiments, the inflammatory disorder is keratoconjunctivitis (i.e., a combination of conjunctivitis and keratitis (i.e., corneal inflammation)). In some embodiments, the inflammatory disorder is blepharitis. As used herein, "blepharitis" is an ophthalmic disorder characterized by inflammation of the eyelid margins. In some embodiments, the inflammatory disorder is blepharoconjunctivitis (i.e., a combination of conjunctivitis and blepharitis (i.e., inflammation of an eyelid)). In some embodiments, the inflammatory disorder is scleritis. As used herein, "scleritis" is a disorder characterized by inflammation of the sclera. In some embodiments, the inflammatory disorder is episcleritis. As used herein, "episcleritis" is an inflammatory disorder of the episclera characterized by hyperaemia, and chemosis. In some embodiments, the inflammatory disorder is uveitis. As used herein, "uveitis" is an inflammatory disorder of the uvea. In some embodiments, the disorder is retinitis. As used herein, "retinitis" is an inflammatory disorder of a retina. In some embodiments, the disorder is choroiditis. As used herein, "choroiditis" is an inflammatory disorder of the uvea, ciliary body and the choroid.

Abnormal Angiogenesis

Disclosed herein, in certain embodiments, are methods of preventing or reducing angiogenesis in a subject in need thereof, comprising administering to the subject a composition comprising an nHC-HA/PTX3 or rcHC-HA/PTX3 complex disclosed herein. As used herein, "angiogenesis" means the formation of new blood vessels. In certain instances, angiogenesis facilitates the growth and metastasis of a tumor. Further, in certain instances, abnormal angiogenesis is the basis of wet age-related macular degeneration (wARMD) and diabetic proliferative retinopathy. In certain instances, an nHC-HA/PTX3 or rcHC-HA/PTX3 complex disclosed herein prevents or reduces angiogenesis.

In certain instances, the binding of a ligand to the VEGF receptor-2 (VEGFR-2) starts a tyrosine kinase signaling cascade that stimulates the production of factors that variously stimulate vessel permeability (eNOS, producing NO), proliferation/survival (bFGF), migration (ICAMs/VCAMs/MMPs) and finally differentiation into mature blood vessels. In certain instances, following binding of VEGFR-2 to its ligand, endothelial cells form tube structures resembling capillaries.

As used herein, "wet Age Related Macular Degeneration", "wARMD", or "wet ARMD" means a disorder of an eye characterized by the proliferation of blood vessels from the choroid. In certain instances, wet ARMD causes vision loss due blood and protein leakage below the macula. In certain instances, bleeding, leaking, and scarring from these blood vessels cause irreversible damage to the photoreceptors and rapid vision loss if left untreated.

As used herein, "diabetic proliferative retinopathy" means a disorder of an eye characterized by incompetence of the vascular walls. In certain instances, the lack of oxygen in the retina results in angiogenesis along the retina and in the vitreous humour. In certain instances, the new blood vessels bleed, cloud vision, and destroy the retina.

In certain instances, the proliferation of capillaries supplies a tumor with nutrients, allowing the tumor to expand. In certain instances, the proliferation of capillaries enables the rapid removal of cellular waste enabling tumor growth. In certain instances, angiogenesis facilitates metastasis. In certain instances, the proliferation of capillaries increases the chances that a cancerous cell will be able to enter a blood vessel and thus establish a new tumor at a new site.

Exemplary cancer types that are treated in some embodiments using an nHC-HA/PTX3 or rcHC-HA/PTX3 complex described herein include, but are not limited to, Acute Lymphoblastic Leukemia, Acute Myeloid Leukemia, Adrenocortical Carcinoma, AIDS-Related Cancers, AIDS-Related Lymphoma, Anal Cancer, Astrocytoma, Basal Cell Carcinoma, Bile Duct Cancer, Bladder Cancer, Bladder Cancer, Bone Cancer, Brain Stem Glioma, Brain Tumor, Breast Cancer, Bronchial Adenomas, Burkitt's Lymphoma, Carcinoid Tumor, Carcinoma, Central Nervous System Lymphoma, Cerebellar Astrocytoma, Cervical Cancer, Chronic Lymphocytic Leukemia, Chronic Myelogenous Leukemia, Chronic Myeloproliferative Disorders, Colon Cancer, Colorectal Cancer, Cutaneous T-Cell Lymphoma, Endometrial Cancer, Ependymoma, Esophageal Cancer, Extragonadal Germ Cell Tumor, Eye Cancer, Intraocular Melanoma, Eye Cancer, Retinoblastoma, Gallbladder Cancer, Gastrointestinal Carcinoid Tumor, Gastrointestinal Stromal Tumor (GIST), Germ Cell Tumor (Extracranial), Germ Cell Tumor (Extragonadal), Germ Cell Tumor (Ovarian), Gestational Trophoblastic Tumor, Glioma, Hairy Cell Leukemia, Head and Neck Cancer, Hepatocellular (Liver) Cancer, Hodgkin's Lymphoma, Hypopharyngeal Cancer, Hypothalamic and Visual Pathway Glioma, Intraocular Melanoma, Islet Cell Carcinoma (Endocrine Pancreas), Kaposi's Sarcoma, Kidney (Renal Cell) Cancer, Laryngeal Cancer, Leukemia (Acute Lymphoblastic), Leukemia (Acute Myeloid), Leukemia (Chronic Lymphocytic), Leukemia (Chronic Myelogenous), Lip and Oral Cavity Cancer, Liver Cancer, Lung Cancer (Non-Small Cell), Lung Cancer (Small Cell), Lymphoma, (Cutaneous T-Cell), Lymphoma (Non-Hodgkin's), Malignant Fibrous Histiocytoma of Bone/Osteosarcoma, Medulloblastoma, Melanoma, Merkel Cell Carcinoma, Mesothelioma, Metastatic Squamous Neck Cancer with Occult Primary, Multiple Endocrine Neoplasia Syndrome, Multiple Myeloma/Plasma Cell Neoplasm, Mycosis Fungoides, Myelodysplastic Syndromes, Myelodysplastic/Myeloproliferative Diseases, Myelogenous Leukemia, Myeloid Leukemia, Myeloproliferative Disorders, Nasal Cavity and Paranasal Sinus Cancer, Nasopharyngeal Cancer, Neuroblastoma, Oral Cancer, Oropharyngeal Cancer, Osteosarcoma/Malignant Fibrous Histiocytoma of Bone, Ovarian Cancer, Ovarian Epithelial Cancer, Ovarian Germ Cell Tumor, Ovarian Low Malignant Potential Tumor, Pancreatic Cancer, Parathyroid Cancer, Penile Cancer, Pheochromocytoma, Pineoblastoma and Supratentorial Primitive Neuroectodermal Tumors, Pituitary Tumor, Plasma Cell Neoplasm/Multiple Myeloma, Pleuropulmonary Blastoma, Prostate Cancer, Rectal Cancer, Retinoblastoma, Rhabdomyosarcoma, Salivary Gland Cancer, Sarcoma (Kaposi's), Sarcoma (uterine), Sezary Syndrome, Skin Cancer (non-Melanoma), Skin Cancer (Melanoma), Skin Carcinoma (Merkel Cell), Small Intestine Cancer, Soft Tissue Sarcoma, Squamous Cell Carcinoma, Stomach (Gastric) Cancer, T-Cell Lymphoma, Testicular Cancer, Thymoma, Thyroid Cancer, Trophoblastic Tumor, Gestational, Urethral Cancer, Uterine Cancer, Endometrial, Uterine Sarcoma, Vaginal Cancer, Visual Pathway and Hypothalamic Glioma, Vulvar Cancer, Waldenstrom's Macroglobulinemia, and Wilms' Tumor.

Wound Repair and Tissue Regeneration

In some embodiments, a pharmaceutical compositions containing an nHC-HA/PTX3 or rcHC-HA/PTX3 complex disclosed herein is used as a wound covering or is used to facilitate wound repair. In some embodiments, the tissue was damaged, compromised, or lost due to an injury (e.g., a burn; a surgical incision; an area of necrosis resulting from an infection, trauma, or a toxin; a laceration). In some embodiments, the tissue was damaged, compromised, or lost due to a burn. In some embodiments, the tissue was damaged, compromised, or lost due to a wound (e.g., an incision, laceration, abrasion). In some embodiments, the tissue was damaged, compromised, or lost due to necrosis. In some embodiments, the tissue was damaged, compromised, or lost due to ulceration.

Burns

In some embodiments, a pharmaceutical composition containing an nHC-HA/PTX3 or rcHC-HA/PTX3 complex disclosed herein is applied to a burn. In some embodiments, a pharmaceutical composition containing an nHC-HA/PTX3 or rcHC-HA/PTX3 complex disclosed herein is applied to a first degree burn. In some embodiments, a pharmaceutical composition containing an nHC-HA/PTX3 or rcHC-HA/PTX3 complex disclosed herein is applied to a second degree burn. In some embodiments, a pharmaceutical composition containing an nHC-HA/PTX3 or rcHC-HA/PTX3 complex disclosed herein is applied to a third degree burn. In some embodiments, the pharmaceutical composition containing an nHC-HA/PTX3 or rcHC-HA/PTX3 complex is applied to a substrate prior to be placed on the burn.

Wounds

In some embodiments, a pharmaceutical composition containing an nHC-HA/PTX3 or rcHC-HA/PTX3 complex disclosed herein is applied to a wound in the skin (e.g., an incision, laceration, abrasion, ulcer, puncture, penetration). In some embodiments, the wound is an ischemic wound. In some embodiments, the pharmaceutical composition containing an nHC-HA/PTX3 or rcHC-HA/PTX3 complex is applied to a substrate prior to being placed on the wound. In some embodiments, a pharmaceutical composition containing an nHC-HA/PTX3 or rcHC-HA/PTX3 complex disclosed herein treats the wound.

In some embodiments, a pharmaceutical composition containing an nHC-HA/PTX3 or rcHC-HA/PTX3 complex disclosed herein is applied to an incision in an organ (e.g., the skin, brain, stomach, kidneys, liver, intestines, lungs, bladder, trachea, esophagus, vagina, ureter, and blood vessel walls). In some embodiments, a pharmaceutical composition containing an nHC-HA/PTX3 or rcHC-HA/PTX3 complex disclosed herein is applied to a surgical incision. In some embodiments, a pharmaceutical composition containing an nHC-HA/PTX3 or rcHC-HA/PTX3 complex disclosed herein is applied to the site of a colon resection. In some embodiments, a pharmaceutical composition containing an nHC-HA/PTX3 or rcHC-HA/PTX3 complex disclosed herein is applied to the site of a gastrectomy. In some embodiments, a pharmaceutical composition containing an nHC-HA/PTX3 or rcHC-HA/PTX3 complex disclosed herein is applied to the site of a breast surgery (e.g., breast reduction surgery, breast augmentation surgery, and mastectomy). In some embodiments, the pharmaceutical composition containing nHC-HA/PTX3 or rcHC-HA/PTX3 complex is applied to a substrate prior to being placed on the wound.

In some embodiments, a pharmaceutical composition containing an nHC-HA/PTX3 or rcHC-HA/PTX3 complex disclosed herein is used as a covering over an incision in the skin (e.g., an incision to the epidermis, dermis, and/or hypodermis). In some embodiments, a pharmaceutical composition containing an nHC-HA/PTX3 or rcHC-HA/PTX3 complex disclosed herein is used to repair or supplement the skin following hemorrhoid surgery. In some embodiments, the pharmaceutical composition containing nHC-HA/PTX3 or rcHC-HA/PTX3 complex is applied to a substrate prior to being placed on the wound. In some embodiments, a pharmaceutical composition containing an nHC-HA/PTX3 or rcHC-HA/PTX3 complex disclosed herein treats the wound.

Necrosis

In some embodiments, a pharmaceutical composition containing an nHC-HA/PTX3 or rcHC-HA/PTX3 complex disclosed herein is used as a protective graft over an area of necrotic tissue (e.g., from an infection). In some embodiments, a pharmaceutical composition containing an nHC-HA/PTX3 or rcHC-HA/PTX3 complex disclosed herein is used as a protective graft over an area of necrotic skin. In some embodiments, a pharmaceutical composition containing an nHC-HA/PTX3 or rcHC-HA/PTX3 complex disclosed herein is placed on an area of necrotic tissue. In some embodiments, the pharmaceutical composition containing nHC-HA/PTX3 or rcHC-HA/PTX3 complex is applied to a substrate prior to being placed on the necrotic tissue. In some embodiments, a pharmaceutical composition containing an nHC-HA/PTX3 or rcHC-HA/PTX3 complex disclosed herein treats the necrotic tissue.

Ulcer

In some embodiments, a pharmaceutical composition containing an nHC-HA/PTX3 or rcHC-HA/PTX3 complex disclosed herein is used as a protective covering over an ulcer. In some embodiments, a pharmaceutical composition containing an nHC-HA/PTX3 or rcHC-HA/PTX3 complex disclosed herein treats the ulcer. In some embodiments, the ulcer is a diabetic ulcer, such as a diabetic foot or leg ulcer. In some embodiments, the ulcer is an ischemic wound. In some embodiments, the pharmaceutical composition containing an nHC-HA/PTX3 or rcHC-HA/PTX3 complex is applied to a substrate prior to being placed on the ulcer. In some embodiments, a pharmaceutical composition containing an nHC-HA/PTX3 or rcHC-HA/PTX3 complex disclosed herein treats the ulcer. In some embodiments the ulcer is a non-healing ulcer. For example, in some embodiments that non-healing ulcer is a wound or ulcer on the skin that has been present for about 3-4 weeks duration without healing.

In some embodiments, the ulcer is a foot ulcer (e.g., a diabetic foot ulcer or an arterial insufficiency ulcer). In some embodiments, treating a foot ulcer comprises (a) preparing the wound (e.g., debriding the wound); and (b) placing a pharmaceutical composition containing an nHC-HA/PTX3 or rcHC-HA/PTX3 complex disclosed herein on the wound. In some embodiments, treating a foot ulcer comprises (a) preparing the wound (e.g., debriding the wound); (b) placing a pharmaceutical composition containing an nHC-HA/PTX3 or rcHC-HA/PTX3 complex disclosed herein on the wound; and (c) covering the pharmaceutical composition with a protective barrier (e.g., a silvercell dressing, metipel, gauze, or a bandage). In some embodiments, the pharmaceutical composition containing nHC-HA/PTX3 or rcHC-HA/PTX3 complex is applied to a substrate prior to be placed on the ulcer. In some embodiments, a pharmaceutical composition containing an nHC-HA/PTX3 or rcHC-HA/PTX3 complex disclosed herein treats the ulcer.

In some embodiments, the ulcer is a venous stasis (VS) ulcer. In some embodiments, treating a VS ulcer comprises (a) preparing the wound (e.g., debriding the wound); and (b) placing a pharmaceutical composition containing an nHC-HA/PTX3 or rcHC-HA/PTX3 complex disclosed herein on the wound. In some embodiments, treating a VS ulcer comprises (a) preparing the wound (e.g., debriding the wound); (b) placing a pharmaceutical composition containing an nHC-HA/PTX3 or rcHC-HA/PTX3 complex disclosed herein on the wound; and (c) covering the pharmaceutical composition with a protective barrier (e.g., a wound veil, antimicrobial dressing, gauze, or a bandage). In some embodiments, the pharmaceutical composition containing nHC-HA/PTX3 or rcHC-HA/PTX3 complex is applied to a substrate prior to being placed on the wound. In some embodiments, a pharmaceutical composition containing an nHC-HA/PTX3 or rcHC-HA/PTX3 complex disclosed herein treats the ulcer.

In some embodiments, the ulcer is a corneal ulcer (i.e., ulcerative keratitis). In some embodiments, treating a corneal ulcer comprises (a) preparing the wound (e.g., debriding the wound); and (b) placing a pharmaceutical composition containing an nHC-HA/PTX3 or rcHC-HA/PTX3 complex disclosed herein on the wound. In some embodiments, treating a corneal ulcer comprises (a) preparing the wound (e.g., debriding the wound); (b) placing a pharmaceutical composition containing an nHC-HA/PTX3 or rcHC-HA/PTX3 complex disclosed herein on the wound; and (c) covering the pharmaceutical composition with a protective barrier (e.g., a contact lens or a bandage). In some embodiments, the pharmaceutical composition containing nHC-HA/PTX3 or rcHC-HA/PTX3 complex is applied to a substrate prior to being placed on the wound. In some embodiments, a pharmaceutical composition containing an nHC-HA/PTX3 or rcHC-HA/PTX3 complex disclosed herein treats the ulcer.

Therapeutic Cell Therapies

In some embodiments, an nHC-HA/PTX3 or rcHC-HA/PTX3 complex disclosed herein is administered in combination with a cell therapy. In some embodiments, an nHC-HA/PTX3 or rcHC-HA/PTX3 complex disclosed herein is co-administered with a therapeutic cell. Therapeutic cells include any cell that exhibits a therapeutic property for treatment of a disease or disorder. In some embodiments, the therapeutic cell is a recombinant cell that heterologously expresses one or more therapeutic gene products. In some embodiments, the therapeutic cell is a transplanted cell. In some embodiments, the therapeutic cell is a stem cell. In some embodiments, the therapeutic cell is a cell that expresses one or more stem cell markers (e.g. Oct-3/4 (Pou5f1), Sox2, c-Myc, and Klf4).

In some embodiments, the cell therapy is a stem cell transplant. In some embodiments, the nHC-HA/PTX3 or rcHC-HA/PTX3 complex is administered to promote expansion of stem cells of the transplant and tissue regeneration. In some examples, the nHC-HA/PTX3 or rcHC-HA/PTX3 complex is employed to reduces or inhibit inflammation, scarring, and abnormal angiogenesis caused by a stem cell transplant. In some embodiments, nHC-HA/PTX3 or rcHC-HA/PTX3 complex is employed to maintain the stem cell characteristics during ex vivo expansion by substituting feeder layers. In some embodiments, nHC-HA/PTX3 or rcHC-HA/PTX3 complex is employed to reprogram a differentiated cell to a stem cell. In some embodiments, an nHC-HA/PTX3 or rcHC-HA/PTX3 complex disclosed herein is employed to expand and culture stem cells in vitro for subsequent transplant into a subject.

In some embodiments, the stem cell therapy is an embryonic stem cell therapy. In some embodiments, the stem cell therapy is an adult stem cell therapy. In some embodiments, the stem cell therapy is a mesenchymal stem cell therapy. In some embodiments, the stem cell therapy is administered for the treatment of a disease or disorder, such as, but not limited to, cardiovascular disease, cancer, diabetes, spinal cord injury, neurodegenerative disease, Alzheimer's disease, Parkinson's disease, multiple sclerosis, Amytrophic lateral sclerosis, Duchenne Muscular Dystrophy, muscle damage or dystrophy, stroke, burns, lung disease, retinal disease, kidney disease, osteoarthritis, and rheumatoid arthritis.

In some embodiments, stem cells are used to treat diabetes mellitus. Type 1 diabetes results from autoimmune-mediated destruction of insulin-secreting β cells in the islets of Langerhans of the pancreas. Type 2 diabetes results from systemic insulin resistance and reduced insulin secretion by pancreatic β cells. Stem cells have been shown in vitro to differentiate into insulin-producing cells (see e.g., Schuldiner et al. (2000) *Proc. Natl. Acad. Sci. USA.* 97:11307-11312; Guo et al., (2009) *Endocr Rev* 30:214-227). Thus, in some embodiments, stem cells, including ESCs and ASCs, and their derivatives, such as partially differentiated stem cells, are used in stem cell therapy for regeneration of pancreatic β cells.

In some embodiments, stem cells or differentiated cells employed for therapy are encapsulated in a microcapsule device. In some embodiments, the microcapsule comprises an nHC-HA/PTX3 or rcHC-HA/PTX3 complex disclosed herein. In some embodiments the nHC-HA/PTX3 or rcHC-HA/PTX3 complex is covalently attached to the microcapsule. In some embodiments the nHC-HA/PTX3 or rcHC-HA/PTX3 complex is assembled on the surface of the microcapsule, such as the inner or out surface, or both. In some embodiments the nHC-HA/PTX3 or rcHC-HA/PTX3 is formulated to coat the microcapsule. In some embodiments, the microcapsule comprises pores to allow the passage of nutrients to cells into the microcapsule and/or allows secreted proteins and molecules (e.g., insulin) by the encapsulated cells to flow out of the microcapsule. In some embodiments, the cells are first immobilized on a microcarrier, such as a bead coated with Matrigel® and then encapsulated within the microcapsule. Methods for the encapsulation of cells, such as stem cells are known in the art and are described, for example, in Serra et al. (2011) *PLoS ONE*

6(8):e23212. In some embodiments, any method for the encapsulation of cells is employed in conjunction with the methods provided herein.

In some embodiments, allogeneic therapeutic stem cells (e.g., insulin producing islet cells) are encapsulated in a microcapsule device for production of insulin. In some embodiments, the nHC-HA/PTX3 or rcHC-HA/PTX3 complex promotes the expansion of the stem cells. In some embodiments, the nHC-HA/PTX3 or rcHC-HA/PTX3 complex, inhibits or reduces an inflammatory response against the microcapsule containing the stem cells employed for therapy of diabetes mellitus. In some embodiments, the micro capsule comprises an nHC-HA/PTX3 or rcHC-HA/PTX3 complex disclosed herein. In some embodiments, the nHC-HA/PTX3 or rcHC-HA/PTX3 complex inhibits or reduces an inflammatory response against the microcapsule containing the stem cells.

Soft Tissue Uses

Disclosed herein, in certain embodiments, is the use of an nHC-HA/PTX3 or rcHC-HA/PTX3 complex disclosed herein for repairing, reconstructing, replacing, or supplementing a recipient's damaged, compromised, or missing soft tissue (e.g., tendons). In some embodiments, a pharmaceutical composition containing an nHC-HA/PTX3 or rcHC-HA/PTX3 complex disclosed herein is applied directly to the tissue. In some embodiments, a pharmaceutical composition containing an nHC-HA/PTX3 or rcHC-HA/PTX3 complex disclosed herein is administered in conjunction with cell or tissue based therapies. In some embodiments, a pharmaceutical composition containing an nHC-HA/PTX3 or rcHC-HA/PTX3 complex disclosed herein is mixed with a cell, a plurality of cells, or a tissue and is administered as part of a tissue based therapy. In some embodiments, a pharmaceutical composition containing an nHC-HA/PTX3 or rcHC-HA/PTX3 complex disclosed herein is used to coat a cell, a plurality of cells, or a tissue and is administered as part of a tissue based therapy.

In some embodiments, a pharmaceutical composition containing an nHC-HA/PTX3 or rcHC-HA/PTX3 complex disclosed herein is used as a covering over an incision in soft tissue (e.g., eyelids form the tissue plane between different layers of soft tissue). In some embodiments, the pharmaceutical composition containing nHC-HA/PTX3 or rcHC-HA/PTX3 complex is applied to a substrate and then used as a covering over an incision in soft tissue (e.g., eyelids form the tissue plane between different layers of soft tissue).

In some embodiments, a pharmaceutical composition containing an nHC-HA/PTX3 or rcHC-HA/PTX3 complex disclosed herein is used as structural (tectonic) support for soft tissue. In some embodiments, a pharmaceutical composition containing an nHC-HA/PTX3 or rcHC-HA/PTX3 complex disclosed herein prevents adhesion in joint or tendon repairs.

In some embodiments, a pharmaceutical composition containing an nHC-HA/PTX3 or rcHC-HA/PTX3 complex disclosed herein is used in the repair a tendon or joint (such as rotator cuff repairs, hand tendon repairs). In some embodiments, a pharmaceutical composition containing an nHC-HA/PTX3 or rcHC-HA/PTX3 complex disclosed herein is used to reinforce a tendon or joint. In some embodiments, a pharmaceutical composition containing an nHC-HA/PTX3 or rcHC-HA/PTX3 complex disclosed herein is used to prevent adhesion of a healing tendon to surrounding tissue, tendons or joints. In some embodiments, a pharmaceutical composition containing an nHC-HA/PTX3 or rcHC-HA/PTX3 complex disclosed herein is used to prevent the formation of scar tissue on a tendon.

In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used to augment smaller tendons and ligaments of the foot and ankle, including the posterior tibial tendon, the peroneal tendons, the flexor and extensor tendons, and the ligaments of the lateral ankle complex. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used to reinforce primary repair of the quadriceps and patellar tendons surrounding the knee. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as a periosteal patch for bone graft in joint replacement. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used to augment deficient hip and knee capsular tissue following total joint revision surgery.

In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used in the repair of a torn rotator cuff. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as a patch over a rotator cuff muscle or tendon (e.g., the supraspinatus tendon). In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used to reconstruct a rotator cuff muscle or tendon (e.g., the supraspinatus tendon). In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used to augment a rotator cuff muscle or tendon (e.g., the supraspinatus tendon). In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used to reinforce a rotator cuff muscle or tendon (e.g., the supraspinatus tendon). In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used to prevent adhesion of soft tissue to a rotator cuff muscle or tendon (e.g., the supraspinatus tendon).

In some embodiments, a pharmaceutical composition containing an nHC-HA/PTX3 or rcHC-HA/PTX3 complex disclosed herein is used in the repair gingiva. In some embodiments, a pharmaceutical composition containing an nHC-HA/PTX3 or rcHC-HA/PTX3 complex disclosed herein is used in the repair gingival recession. In some embodiments, a pharmaceutical composition containing an nHC-HA/PTX3 or rcHC-HA/PTX3 complex disclosed herein is applied to a substrate and used as a patch over gingiva. In some embodiments, a pharmaceutical composition containing an nHC-HA/PTX3 or rcHC-HA/PTX3 complex disclosed herein is applied to substrate and used as a patch over an exposed tooth root surface. In some embodiments, a pharmaceutical composition containing an nHC-HA/PTX3 or rcHC-HA/PTX3 complex disclosed herein is used to reconstruct gingiva. In some embodiments, a pharmaceutical composition containing an nHC-HA/PTX3 or rcHC-HA/PTX3 complex disclosed herein is used to augment gingiva. In some embodiments, a pharmaceutical composition containing an nHC-HA/PTX3 or rcHC-HA/PTX3 complex disclosed herein is used to reinforce gingiva. In some embodiments, a pharmaceutical composition containing an nHC-HA/PTX3 or rcHC-HA/PTX3 complex disclosed herein is used to prevent adhesion of soft tissue to gingiva.

In some embodiments, a pharmaceutical composition containing an nHC-HA/PTX3 or rcHC-HA/PTX3 complex described herein is applied to a substrate and the substrate/nHC-HA/PTX3 or substrate/rcHC-HA/PTX3 complex is used as a protective graft over an incision or tear in the fascia. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as structural (tectonic) support the fascia. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as a replacement or supplement for the fascia. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used to repair a hernia (e.g., to repair the fascia). In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used to repair an inguinal hernia. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used to repair a femoral hernia. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used to repair an umbilical hernia. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used to repair an incisional hernia. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used to repair a diaphragmatic hernia. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used to repair a Cooper's hernia, an epigastric hernia, an hiatal hernia, a Littre's hernia, a lumbar hernia, a Maydl's hernia, an obturator hernia, a pantaloon hernia, a paraesophageal hernia, a paraumbilical hernia, a perineal hernia, a properitoneal hernia, a Richter's hernia, a sliding hernia, a sciatic hernia, a spigelian hernia, a sports hernia, a Velpeau hernia, or a Amyand's hernia.

In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used to repair a spinal disc herniation. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as a protective graft over an incision or tear in a spinal disc. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as a protective graft over an incision or tear in an annulus fibrosis. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as structural (tectonic) support a spinal disc. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as structural (tectonic) support an annulus fibrosis. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as a replacement or supplement for a spinal disc. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as structural (tectonic) support a spinal disc. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as a replacement or supplement for an annulus fibrosis.

In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used over an incision in the brain, or in one (or all) of the meninges (i.e., the dura mater, the pia mater, and/or the arachnoid mater). In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as structural (tectonic) support for one (or all) of the meninges (i.e., the dura mater, the pia mater, and/or the arachnoid mater). In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as a replacement for one (or all) of the meninges (i.e., the dura mater, the pia mater, and/or the arachnoid mater).

In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used over an incision in a lung or in the pleura. In some embodiments, a pharmaceutical composition containing an nHC-HA/PTX3 or rcHC-HA/PTX3 complex disclosed herein is applied to a substrate and the substrate/nHC-HA/

PTX3 or substrate/rcHC-HA/PTX3 complex is used as structural (tectonic) support for the pleura. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as a replacement for the pleura.

In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used over an incision in a tympanic membrane. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as structural (tectonic) support for a tympanic membrane. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as a replacement for a tympanic membrane.

In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as a protective graft over an incision in the heart or the pericardium. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as structural (tectonic) support for the pericardium. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as a replacement for the pericardium.

In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as a protective graft over an incision in the peritoneum. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as structural (tectonic) support for the peritoneum. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as a replacement for the peritoneum.

Ophthalmic Uses

Disclosed herein, in certain embodiments, is the use of a pharmaceutical composition containing an nHC-HA/PTX3 or rcHC-HA/PTX3 complex disclosed herein for repairing, reconstructing, replacing, or supplementing a recipient's damaged, compromised, or missing ocular tissue.

Treatment of Glaucoma

As used herein, "Glaucoma" means a disorder characterized by the loss of retinal ganglion cells in the optic nerve. In certain instances, glaucoma partially or fully results from an increase in intraocular pressure in the anterior chamber (AC). Intraocular pressure varies depending on the production of liquid aqueous humor by the ciliary processes of the eye and the drainage of the aqueous humor through the trabecular meshwork.

Glaucoma Drainage Devices (GDD) are medical devices that are implanted into an eye to relieve intraocular pressure by providing an alternative pathway for the aqueous humor to drain. If left uncovered, a GDD tube will erode and leave the eye susceptible to intraocular infection. Thus, the GDD tube needs to be covered. Currently, patches used to cover GDD tubes are made from pericardium, sclera and cornea. These patches are about 400-550 microns thick. The thinness of these patches results in their melting by 25% in 2 years potentially leaving the shunt tube exposed again.

In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used to cover GDD tubes. In some embodiments, the substrate/nHC-HA/PTX3 or rcHC-HA/PTX3 complex is 300-600 microns thick. In some embodiments, the substrate/nHC-HA/PTX3 or substrate/rcHC-HA/PTX3 complex does not melt by 25% in 2 years.

Treatment of Ocular Ulcers

In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used to cover persistent epithelial defects and/or ulcers in eyes.

In some embodiments, the base of the ulcer is debrided with surgical sponges and the poorly adherent epithelium adjacent to the edge of the ulcer is removed (e.g., to the section of the eye where the epithelium becomes quite adherent). In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is transferred to the recipient eye. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is then secured to the eye by sutures (e.g., interrupted 10-0 nylon sutures or running 10-0 nylon sutures) with the suture knots being buried. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is secured to the eye by use of fibrin glue. In some embodiments, a protective layer is applied over the substrate/nHC-HA/PTX3 or substrate/rcHC-HA/PTX3 complex or the entire eye (e.g., a contact lens). In some embodiments, the substrate/nHC-HA/PTX3 or substrate/rcHC-HA/PTX3 complex further comprises an antibiotic (e.g., neomycin, polymyxin b sulfate and dexamethasone).

Conjunctival, Scleral, Lid, and Orbital Rim Surface Reconstruction

In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used in conjunctival, scleral, lid, and orbital rim surface reconstruction. In some embodiments, damage to the conjunctival surface results from symblepharon lysis; surgical removal of tumor, lesion, and/or scar tissue; excimer laser photorefractive keratectomy and therapeutic keratectomy; or combinations thereof.

Coronary Uses

Disclosed herein, in certain embodiments, is the use of a pharmaceutical composition containing an nHC-HA/PTX3 or rcHC-HA/PTX3 complex disclosed herein for repairing, reconstructing, replacing, or supplementing a recipient's damaged, compromised, or missing coronary tissue.

Prevention of Ischemia Reperfusion Damage

Disclosed herein, is the use of a pharmaceutical composition containing an nHC-HA/PTX3 or rcHC-HA/PTX3 complex described herein for the inhibition or reduction of tissue damage resulting from acute inflammation caused by ischemia, such as, for example myocardial infarction or stroke. In some embodiments, a pharmaceutical composition containing an nHC-HA/PTX3 or rcHC-HA/PTX3 complex disclosed herein is administered to a subject having an ischemic condition, such as, but not limited to myocardial infarction or stroke.

Coronary Artery Bypass

Disclosed herein, is the use of a pharmaceutical composition containing an nHC-HA/PTX3 or rcHC-HA/PTX3 complex described herein in coronary artery bypass surgery. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is grafted onto a coronary artery to bypass a section of the artery that is characterized by atherosclerosis.

Heart Valves

In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is applied over a heart valve. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as structural (tectonic) support for a heart valve. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as a replacement for a heart valve.

Veins and Arteries

In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is applied to a vein or artery. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as structural (tectonic) support for a vein or artery.

Nerve Uses

Disclosed herein, in certain embodiments, is the use of a pharmaceutical composition containing an nHC-HA/PTX3 or rcHC-HA/PTX3 complex disclosed herein for repairing, reconstructing, replacing, or supplementing a recipient's damaged, compromised, or missing nerve tissue.

In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as a covering over a nerve (e.g., a peripheral nerve). In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as a covering over a nerve graft, nerve transfer, or a repaired nerve. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as a covering over an incision in a nerve (e.g., a peripheral nerve). In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as structural (tectonic) support for a nerve (e.g., a peripheral nerve). In some embodiments, a pharmaceutical composition containing an nHC-HA/PTX3 or rcHC-HA/PTX3 complex disclosed herein prevents adhesion in nerve repair.

In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as a non-constricting encasement for injured nerves. In some embodiments, a pharmaceutical composition containing an nHC-HA/PTX3 or rcHC-HA/PTX3 complex described herein prevents or minimizes scar formation, encapsulation, chronic compression, tethering of a nerve, and nerve entrapment. In some embodiments, a pharmaceutical composition containing an nHC-HA/PTX3 or rcHC-HA/PTX3 complex described herein prevents or minimizes neuroma formation. In some embodiments, a pharmaceutical composition containing an nHC-HA/PTX3 or rcHC-HA/PTX3 complex described herein prevents or minimizes the migration of endogenous growth factors (i.e. Nerve Growth Factor) present during nerve repair.

Spinal Uses

Disclosed herein, in certain embodiments, is the use of a pharmaceutical composition containing an nHC-HA/PTX3 or rcHC-HA/PTX3 complex described herein during spinal surgery.

In some embodiments, a pharmaceutical composition containing an nHC-HA/PTX3 or rcHC-HA/PTX3 complex described herein is used during a laminectomy. In some embodiments, a pharmaceutical composition containing an nHC-HA/PTX3 or rcHC-HA/PTX3 complex described herein is used to reduce or prevent epidural fibrosis and/or scar adhesions following spinal surgery (e.g., laminectomy). In some embodiments, a pharmaceutical composition containing an nHC-HA/PTX3 or rcHC-HA/PTX3 complex described herein is implanted between dura mater and overlying tissue following spinal surgery (e.g., laminectomy). In some embodiments, implanting a pharmaceutical composition containing an nHC-HA/PTX3 or rcHC-HA/PTX3 complex described herein between dura mater and overlying tissue following spinal surgery (e.g., laminectomy) reduces or prevents migration of fibroblasts to the dura mater and collagen deposition on the dura mater.

In some embodiments, a pharmaceutical composition containing an nHC-HA/PTX3 or rcHC-HA/PTX3 complex described herein is used to reduce or prevent the development of proliferative scarring following spinal surgery (e.g., laminectomy). In some embodiments, a pharmaceutical composition containing an nHC-HA/PTX3 or rcHC-HA/PTX3 complex described herein is used to reduce or prevent the development of a postoperative (e.g., postlaminectomy) epidural/peridural/perineural scar. In some embodiments, a pharmaceutical composition containing an nHC-HA/PTX3 or rcHC-HA/PTX3 complex described herein is used to reduce or prevent the development of proliferative scarring following spinal surgery (e.g., laminectomy). In some embodiments, a pharmaceutical composition containing an nHC-HA/PTX3 or rcHC-HA/PTX3 complex disclosed herein is used to reduce or prevent the development of a postlaminectomy membrane.

In some embodiments, a pharmaceutical composition containing an nHC-HA/PTX3 or rcHC-HA/PTX3 complex described herein is used to reduce or prevent the development of extradural compression or dural tethering following spinal surgery (e.g., laminectomy). In some embodiments, a pharmaceutical composition containing an nHC-HA/PTX3 or rcHC-HA/PTX3 complex described herein is used to reduce or prevent the development of tethered nerve roots following spinal surgery (e.g., laminectomy). In some embodiments, a pharmaceutical composition containing an nHC-HA/PTX3 or rcHC-HA/PTX3 complex described herein is used to reduce or prevent the development of arachnoiditis following spinal surgery (e.g., laminectomy).

In some embodiments, a pharmaceutical composition containing an nHC-HA/PTX3 or rcHC-HA/PTX3 complex disclosed herein further comprises morselized bone tissue. In some embodiments, a pharmaceutical composition containing an nHC-HA/PTX3 or rcHC-HA/PTX3 complex disclosed herein comprising morselized bone tissue is used during a spinal fusion procedure. In some embodiments, a pharmaceutical composition containing an nHC-HA/PTX3 or rcHC-HA/PTX3 complex disclosed herein comprising morselized bone tissue is implanted between adjacent vertebrae. In some embodiments, implantation of a pharmaceutical composition containing an nHC-HA/PTX3 or rcHC-HA/PTX3 complex disclosed herein comprising morselized bone tissue between two adjacent vertebrae promotes fusion of the vertebrae.

In some embodiments, a pharmaceutical composition containing an nHC-HA/PTX3 or rcHC-HA/PTX3 complex disclosed herein is used as a protective graft over an incision in the dura mater. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as structural (tectonic) support for the dura mater. In some embodiments, a pharmaceutical composition containing an nHC-HA/PTX3 or rcHC-HA/PTX3 complex disclosed herein is applied to a substrate and the substrate/nHC-HA/PTX3 or substrate/rcHC-HA/PTX3 complex is used as a replacement for the dura mater.

Miscellaneous Uses of an nHC-HA/PTX3 or rcHC-HA/PTX3 Complex

In some embodiments, a pharmaceutical composition containing an nHC-HA/PTX3 or rcHC-HA/PTX3 complex disclosed herein is applied to a patch or wound dressing.

In some embodiments, a pharmaceutical composition containing an nHC-HA/PTX3 or rcHC-HA/PTX3 complex disclosed herein is used as a dermal filler. In some embodiments, a pharmaceutical composition containing an nHC-HA/PTX3 or rcHC-HA/PTX3 complex disclosed herein is injected into subdermal facial tissues. In some embodiments, a pharmaceutical composition containing an nHC-HA/PTX3 or rcHC-HA/PTX3 complex disclosed herein is injected under wrinkles and aging lines of the face (e.g., nasolabial folds, melomental folds, "crow's feet" and forehead wrinkles). In some embodiments, a pharmaceutical composition containing an nHC-HA/PTX3 or rcHC-HA/PTX3 complex disclosed herein is used for lip augmentation. In some embodiments, a pharmaceutical composition containing an nHC-HA/PTX3 or rcHC-HA/PTX3 complex disclosed herein is injected into the lips.

In some embodiments, a pharmaceutical composition containing an nHC-HA/PTX3 or rcHC-HA/PTX3 complex disclosed herein is used to treat arthritis (e.g., osteoarthritis, rheumatoid arthritis, septic arthritis, ankylosing spondylitis, spondylosis). In some embodiments, a pharmaceutical composition containing an nHC-HA/PTX3 or rcHC-HA/PTX3 complex disclosed herein is injected into an arthritic joint (e.g., a knee).

In some embodiments, a pharmaceutical composition containing an nHC-HA/PTX3 or rcHC-HA/PTX3 complex disclosed herein is used to treat arthritis in the foot. In some embodiments, a pharmaceutical composition containing an nHC-HA/PTX3 or rcHC-HA/PTX3 complex disclosed herein is used to treat arthritis of the first metatarsophalangeal (MTP) joint (e.g., hallux rigidus). In some embodiments, a pharmaceutical composition containing an nHC-HA/PTX3 or rcHC-HA/PTX3 complex disclosed herein is administered to a MTP joint following dorsal cheilectomy. In some embodiments, administration of the pharmaceutical composition containing an nHC-HA/PTX3 or rcHC-HA/PTX3 complex disclosed herein reduces one or more adverse symptoms associated with hallux rigidus or a dorsal cheilectomy procedure (e.g., scarring, joint stiffness, swelling, inflammation, and pain).

In some embodiments, a pharmaceutical composition containing an nHC-HA/PTX3 or rcHC-HA/PTX3 complex disclosed herein is used to treat one or more symptoms associated with a bone spur (e.g., scarring, joint stiffness, swelling, inflammation, and pain).

In some embodiments, a pharmaceutical composition containing an nHC-HA/PTX3 or rcHC-HA/PTX3 complex disclosed herein is used to inhibit bone resorption in an individual in need thereof. In some embodiments, the individual has arthritis, osteoporosis, alveolar bone degradation, Paget's disease, or a bone tumor. In some embodiments, a pharmaceutical composition containing an nHC-HA/PTX3 or rcHC-HA/PTX3 complex is injected into a joint. In some embodiments, a pharmaceutical composition containing an nHC-HA/PTX3 or rcHC-HA/PTX3 complex is contacted with a bone (e.g., by use of a wound dressing or bandage). In some embodiments, a pharmaceutical composition containing an nHC-HA/PTX3 or rcHC-HA/PTX3 complex coats a bone stent, bone implant, or bone prosthesis (e.g., an osseointegrated implant). As used herein, an "osseointegrated implant" means a three dimensional implant containing pores into which osteoblasts and supporting connective tissue migrates. In some embodiments, the bone stents are inserted into the intramedullary canal of a bone. In some embodiments, the bone stent is placed in the sinus tarsi. In some embodiments, the bone stent in placed in a knee or joint. In some embodiments, the bone stent is placed in a bone fracture. In some embodiments, the bone stent is expandable or contractible.

In some embodiments, a pharmaceutical composition containing an nHC-HA/PTX3 or rcHC-HA/PTX3 complex disclosed herein is used to promote or induce bone formation in an individual in need thereof in an individual in need thereof. In some embodiments, the individual has arthritis, osteoporosis, alveolar bone degradation, Paget's disease, or a bone tumor. In some embodiments, a pharmaceutical composition containing an nHC-HA/PTX3 or rcHC-HA/PTX3 complex is injected into a joint. In some embodiments, a pharmaceutical composition containing an nHC-HA/PTX3 or rcHC-HA/PTX3 complex is contacted with a bone (e.g., by use of a wound dressing or bandage). In some embodiments, a pharmaceutical composition containing an nHC-HA/PTX3 or rcHC-HA/PTX3 complex coats a bone stent, bone implant, or bone prosthesis (e.g., an osseointegrated implant). As used herein, an "osseointegrated implant" means a three dimensional implant containing pores into which osteoblasts and supporting connective tissue migrates. In some embodiments, the bone stents are inserted into the intramedullary canal of a bone. In some embodiments, the bone stent is placed in the sinus tarsi. In some embodiments, the bone stent in placed in a knee or joint. In some embodiments, the bone stent is placed in a bone fracture. In some embodiments, the bone stent is expandable or contractible.

In some embodiments, a pharmaceutical composition containing an nHC-HA/PTX3 or rcHC-HA/PTX3 complex disclosed herein is used to inhibit osteoclast differentiation. In some embodiments, the individual has arthritis, osteoporosis, alveolar bone degradation, Paget's disease, or a bone tumor. In some embodiments, a pharmaceutical composition containing an nHC-HA/PTX3 or rcHC-HA/PTX3 complex is injected into a joint. In some embodiments, a pharmaceutical composition containing an nHC-HA/PTX3 or rcHC-HA/PTX3 complex is contacted with a bone (e.g., by use of a wound dressing or bandage). In some embodiments, a pharmaceutical composition containing an nHC-HA/PTX3 or rcHC-HA/PTX3 complex coats a bone stent, bone implant, or bone prosthesis (e.g., an osseointegrated implant). As used herein, an "osseointegrated implant" means a three dimensional implant containing pores into which osteoblasts and supporting connective tissue migrates. In some embodiments, the bone stents are inserted into the intramedullary canal of a bone. In some embodiments, the bone stent is placed in the sinus tarsi. In some embodiments, the bone stent in placed in a knee or joint. In some embodiments, the bone stent is placed in a bone fracture. In some embodiments, the bone stent is expandable or contractible.

In some embodiments, a pharmaceutical composition containing an nHC-HA/PTX3 or rcHC-HA/PTX3 complex disclosed herein is used to promote mineralization by osteoblasts in an individual in need thereof. In some embodiments, the individual has arthritis, osteoporosis, alveolar bone degradation, Paget's disease, or a bone tumor. In some embodiments, a pharmaceutical composition containing an nHC-HA/PTX3 or rcHC-HA/PTX3 complex is injected into a joint. In some embodiments, a pharmaceutical composition containing an nHC-HA/PTX3 or rcHC-HA/PTX3 complex is contacted with a bone (e.g., by use of a wound dressing or bandage). In some embodiments, a pharmaceutical composition containing an nHC-HA/PTX3 or rcHC-HA/PTX3 complex coats a bone stent, bone implant, or bone prosthesis (e.g., an osseointegrated implant). As used herein, an "osseointegrated implant" means a three dimensional implant containing pores into which osteoblasts and supporting connective tissue migrates. In some embodiments, the bone stents are inserted into the intramedullary canal of a bone. In some embodiments, the bone stent is placed in the sinus tarsi. In some embodiments, the bone stent in placed in a knee or joint. In some embodiments, the bone stent is placed in a bone fracture. In some embodiments, the bone stent is expandable or contractible.

In some embodiments, a pharmaceutical composition containing an nHC-HA/PTX3 or rcHC-HA/PTX3 complex disclosed herein is used to balance bone resorption and bone formation in an individual in need thereof. In some embodiments, the individual has arthritis, osteoporosis, alveolar bone degradation, Paget's disease, or a bone tumor. In some embodiments, a pharmaceutical composition containing an nHC-HA/PTX3 or rcHC-HA/PTX3 complex is injected into a joint. In some embodiments, a pharmaceutical composition containing an nHC-HA/PTX3 or rcHC-HA/PTX3 complex is contacted with a bone (e.g., by use of a wound dressing or bandage). In some embodiments, a pharmaceutical composition containing an nHC-HA/PTX3 or rcHC-HA/PTX3 complex coats a bone stent, bone implant, or bone prosthesis (e.g., an osseointegrated implant). As used herein, an "osseointegrated implant" means a three dimensional implant containing pores into which osteoblasts and supporting connective tissue migrates. In some embodiments, the bone stents are inserted into the intramedullary canal of a bone. In some embodiments, the bone stent is placed in the sinus tarsi. In some embodiments, the bone stent in placed in a knee or joint. In some embodiments, the bone stent is placed in a bone fracture. In some embodiments, the bone stent is expandable or contractible.

In some embodiments, a pharmaceutical composition containing an nHC-HA/PTX3 or rcHC-HA/PTX3 complex disclosed herein is used to treat an orthodontic or a periodontal condition. In some embodiments, the periodontal condition is selected from gingivitis, gingival recession or periodontitis. In some embodiments, a pharmaceutical composition containing an nHC-HA/PTX3 or rcHC-HA/PTX3 complex disclosed herein is used as an anti-inflammatory or used to promote osseointegration or healing. In some embodiments, a pharmaceutical composition containing an nHC-HA/PTX3 or rcHC-HA/PTX3 complex disclosed herein is used in combination with a dental implant to promote implant osseointegration, anti-inflammation, and healing.

In some embodiments, a pharmaceutical composition containing an nHC-HA/PTX3 or rcHC-HA/PTX3 complex disclosed herein to treat hoarseness or voice disorders. In some embodiments, a pharmaceutical composition containing an nHC-HA/PTX3 or rcHC-HA/PTX3 complex disclosed herein is used for injection laryngoplasty to repair vocal cords.

In some embodiments, a pharmaceutical composition containing an nHC-HA/PTX3 or rcHC-HA/PTX3 complex disclosed herein is coated onto a medical implant (e.g., a stent). In some embodiments, a medical implant/nHC-HA/PTX3 or implant/rcHC-HA/PTX3 complex disclosed herein is implanted into an individual in need thereof, wherein the nHC-HA/PTX3 or rcHC-HA/PTX3 complex is partially or fully released into the individual. In some embodiments, the medical implant is a stent (e.g., a bone stent or a coronary stent). In some embodiments, the medical implant is a bone stent. In some embodiments, the medical implant is a coronary stent.

Combinations

In some embodiments, the compositions and methods described herein are used in conjunction with a second therapeutic agent. In some embodiments, the compositions and methods described herein are used in conjunction with two or more therapeutic agents. In some embodiments, the compositions and methods described herein are used in conjunction with one or more therapeutic agents. In some embodiments, the compositions and methods described herein are used in conjunction with 2, 3, 4, 5, 6, 7, 8, 9, 10 or more therapeutic agents.

In some embodiments, an nHC-HA/PTX3 or rcHC-HA/PTX3 complex disclosed herein and a second therapeutic agent are administered in the same dosage form. In some embodiments, an nHC-HA/PTX3 or rcHC-HA/PTX3 complex disclosed herein and a second therapeutic agent are administered in separate dosage forms.

In some embodiments, an nHC-HA/PTX3 or rcHC-HA/PTX3 complex disclosed herein and a second therapeutic agent are administered concurrently (e.g., simultaneously, essentially simultaneously or within the same treatment protocol).

In some embodiments, an nHC-HA/PTX3 or rcHC-HA/PTX3 complex disclosed herein and a second therapeutic agent are administered sequentially. In some embodiments, an nHC-HA/PTX3 or rcHC-HA/PTX3 complex disclosed herein is administered before or after the second therapeutic agent. In some embodiments, the time period between administration of an nHC-HA/PTX3 or rcHC-HA/PTX3 complex disclosed herein and a second active agent ranges from a few minutes to several hours, depending upon the properties of each pharmaceutical agent, such as potency, solubility, bioavailability, plasma half-life and kinetic profile of the pharmaceutical agent. In some embodiments, circadian variation of the target molecule concentration determines the optimal dose interval. In some embodiments, the timing between the administration of an nHC-HA/PTX3 or rcHC-HA/PTX3 complex disclosed herein and a second active agent is about an hour, about 2 hours, about 3 hours, about 4 hours, about 5 hours, about 6 hours, about 7 hours, about 8 hours, about 9 hours, about 10 hours, about 11 hours, about a day, about 2 days, about 3 days, about 4 days, about 5 days, about 6 days, about a week, about 2 weeks, about 3 weeks, about a month, or longer.

In some embodiments, the co-administration of an nHC-HA/PTX3 or rcHC-HA/PTX3 complex disclosed herein results in a lower required dosage for the nHC-HA/PTX3 or rcHC-HA/PTX3 complex than the required dosage when administering an nHC-HA/PTX3 or rcHC-HA/PTX3 complex alone. In some embodiments, the co-administration of a second therapeutic agent results in a lower required dosage for the second agent than the required dosage when administering the second agent alone. Methods for experimentally determining therapeutically-effective dosages of drugs and other agents for use in combination treatment regimens are known and described in the art. For example, the use of metronomic dosing, i.e., providing more frequent, lower doses in order to minimize toxic side effects, has been described extensively in the art. Combination treatment further includes periodic treatments that start and stop at various times to assist with the clinical management of the individual.

In some embodiments, the combination treatment nHC-HA/PTX3 or rcHC-HA/PTX3 complex and one or more additional therapeutic agents is modified. In some embodiments, the combination treatment is modified, whereby the amount of the nHC-HA/PTX3 or rcHC-HA/PTX3 complex is increased relative to the amount of a second therapeutic agent. In some embodiments, the combination treatment is modified, whereby the amount of the nHC-HA/PTX3 or rcHC-HA/PTX3 complex is decreased relative to the amount of a second therapeutic agent. In some embodiments, the combination treatment is modified, whereby the amount of is a second therapeutic agent increased relative to the amount of the nHC-HA/PTX3 or rcHC-HA/PTX3 complex. In some embodiments, the combination treatment is modified, whereby the amount of is a second therapeutic agent decreased relative to the amount of the nHC-HA/PTX3 or rcHC-HA/PTX3 complex.

In some embodiments, the second therapeutic agent is selected from cytotoxic agents, an antimicrobial agents, anti-angiogenesis agents, a chemotherapeutic agent, antineoplastic agents or radiation therapy. In some embodiments, the second therapeutic agent is selected from alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, hematopoietic growth factors, aromatase inhibitors, anti-estrogens, anti-androgens, corticosteroids, gonadorelin agonists, microtubule active agents, nitrosoureas, lipid or protein kinase targeting agents, immunomodulatory drugs (IMiDs), protein or lipid phosphatase targeting agents, anti-angiogenic agents, Akt inhibitors, IGF-I inhibitors, FGF3 modulators, mTOR inhibitors, Smac mimetics, HDAC inhibitors, agents that induce cell differentiation, bradykinin 1 receptor antagonists, angiotensin II antagonists, cyclooxygenase inhibitors, heparanase inhibitors, lymphokine inhibitors, cytokine inhibitors, IKK inhibitors, P38MAPK inhibitors, HSP90 inhibitors, multikinase inhibitors, bisphosphonate, rapamycin derivatives, anti-apoptotic pathway inhibitors, apoptotic pathway agonists, PPAR agonists, RAR agonists, inhibitors of Ras isoforms, telomerase inhibitors, protease inhibitors, metalloproteinase inhibitors, aminopeptidase inhibitors, SHIP activators—AQX-MN100, Humax-CD20 (ofatumumab), CD20 antagonists, IL2-diptheria toxin fusions, or combinations thereof. In some embodiments, the antimicrobial agent is an antiviral, antibacterial or antifungal agent. Non-limiting exemplary antibacterial agent(s) include those classified as aminoglycosides, beta lactams, quinolones or fluoroquinolones, macrolides, sulfonamides, sulfamethaxozoles, tetracyclines, streptogramins, oxazolidinones (such as linezolid), clindamycins, lincomycins, rifamycins, glycopeptides, polymxins. lipo-peptide antibiotics, as well as pharmacologically acceptable sodium salts, pharmacologically acceptable calcium salts, pharmacologically acceptable potassium salts, lipid formulations, derivatives and/or analogs of the above. Non-limiting exemplary classes of antifungal agents include imidazoles or triazoles such as clotrimazole, miconazole, ketoconazole, econazole, butoconazole, omoconazole, oxiconazole, terconazole, itraconazole, fluconazole, voriconazole (UK 109,496), posaconazole, ravuconazole or flutrimazole; the polyene antifungals such as amphotericin B, liposomal amphoterecin B, natamycin, nystatin and nystatin lipid formualtions; the cell wall active cyclic lipopeptide antifungals, including the echinocandins such as caspofungin, micafungin, anidulfungin, cilofungin; LY121019; LY303366; the allylamine group of antifungals such as terbinafine. Yet other non-limiting examples of antifungal agents include naftifine, tolnaftate, mediocidin, candicidin, trichomycin, hamycin, aurefungin, ascosin, ayfattin, azacolutin, trichomycin, levorin, heptamycin, candimycin, griseofulvin, BF-796, MTCH 24, BTG-137586, pradimicins (MNS 18184), benanomicin; ambisome; nikkomycin Z; flucytosine, or perimycin. Non-limiting examples of antiviral agents include cidofovir, amantadine, rimantadine, acyclovir, gancyclovir, pencyclovir, famciclovir, foscamet, ribavirin, or valcyclovir. In some embodiments, the antimicrobial agent is an innate immune peptide or proteins. Some exemplary classes of innate peptides or proteins are transferrins, lactoferrins, defensins, phospholipases, lysozyme, cathelicidins, serprocidins, bacteriocidal permeability increasing proteins, amphipathic alpha helical peptides, and other synthetic antimicrobial proteins. In some embodiments, the antimicrobial agent is an antiseptic agent.

In some embodiments, the second therapeutic agent is selected from ARRY-797, dacarbazine (DTIC), actinomycins $C_2$, $C_3$, D, and $F_1$, cyclophosphamide, melphalan, estramustine, maytansinol, rifamycin, streptovaricin, doxorubicin, daunorubicin, epirubicin, idarubicin, detorubicin, carminomycin, esorubicin, mitoxantrone, bleomycins A, $A_2$, and B, camptothecin, Irinotecan, Topotecan, 9-aminocamptothecin, 10,11-methylenedioxycamptothecin, 9-nitrocamptothecin, bortezomib, temozolomide, TAS103, NPI0052, combretastatin, combretastatin A-2, combretastatin A-4, calicheamicins, neocarcinostatins, epothilones A B, C, and semi-synthetic variants, Herceptin, Rittman, CD40 antibodies, asparaginase, interleukins, interferons, leuprolide, and pegaspargase, 5-fluorouracil, fluorodeoxyuridine, ptorafur, 5'-deoxyfluorouridine, UFT, MITC, S-1 capecitabine, diethylstilbestrol, tamoxifen, toremefine, tolmudex, thymitaq, flutamide, fluoxymesterone, bicalutamide, finasteride, estradiol, trioxifene, dexamethasone, leuproelin acetate, estramustine, droloxifene, medroxyprogesterone, megesterol acetate, aminoglutethimide, testolactone, testosterone, diethylstilbestrol, hydroxyprogesterone, mitomycins A, B and C, porfiromycin, cisplatin, carboplatin, oxaliplatin, tetraplatin, platinum-DACH, ormaplatin, thalidomide, lenalidomide, CI-973, telomestatin, CHIR258, Rad 001, SAHA, Tubacin, 17-AAG, sorafenib, JM-216, podophyllotoxin, epipodophyllotoxin, etoposide, teniposide, Tarceva, Iressa, Imatinib, Miltefosine, Perifosine, aminopterin, methotrexate, methopterin, dichloro-methotrexate, 6-mercaptopurine, thioguanine, azattuoprine, allopurinol, cladribine, fludarabine, pentostatin, 2-chloroadenosine, deoxycytidine, cytosine arabinoside, cytarabine, azacitidine, 5-azacytosine, gencitabine, 5-azacytosine-arabinoside, vincristine, vinblastine, vinorelbine, leurosine, leurosidine and vindesine, paclitaxel, taxotere and/or docetaxel.

In some embodiments, the second active agent is niacin, a fibrate, a statin, a Apo-A1 mimetic polypeptide (e.g., DF-4, Novartis), an apoA-I transcriptional up-regulator, an ACAT inhibitor, a CETP modulator, Glycoprotein (GP) IIb/IIIa receptor antagonists, P2Y12 receptor antagonists, Lp-PLA2-inhibitors, an anti-tumor necrosis factor (TNF) agent, an interleukin-1 (IL-1) receptor antagonist, an interleukin-2 (IL-2) receptor antagonist, an interleukin-6 (IL-6) receptor antagonist, an interleukin-12 (IL-12) receptor antagonist, an interleukin-17 (IL-17) receptor antagonist, an interleukin-23 (IL-23) receptor antagonist, a cytotoxic agent, an antimicrobial agent, an immunomodulatory agent, an antibiotic, a T-cell co-stimulatory blocker, a disorder-modifying anti-rheumatic agent, a B cell depleting agent, an immunosuppressive agent, an anti-lymphocyte antibody, an alkylating agent, an anti-metabolite, a plant alkaloid, a terpenoids, a topoisomerase inhibitor, an anti-tumor antibiotic, a monoclonal antibody, a hormonal therapy (e.g., aromatase inhibitors), or combinations thereof.

In some embodiments, the second active agent is an anti-TGF-β antibody, an anti-TGF-β receptor blocking antibody, an anti-TNF antibody, an anti-TNF receptor blocking antibody, an anti-IL1β antibody, an anti-IL1β receptor blocking antibody, an anti-IL-2 antibody, an anti-IL-2 receptor blocking antibody, an anti-IL-6 antibody, an anti-IL-6 receptor blocking antibody, an anti IL-12 antibody, an anti IL-12 receptor blocking antibody, an anti-IL-17 antibody, anti-IL-17 receptor blocking antibody, an anti-IL-23 antibody, or an anti-IL-23 receptor blocking antibody.

In some embodiments, the second active agent is niacin, bezafibrate; ciprofibrate; clofibrate; gemfibrozil; fenofibrate; DF4 (Ac-D-W-F-K-A-F-Y-D-K-V-A-E-K-F-K-E-A-F-NH2); DF5; RVX-208 (Resverlogix); avasimibe; pactimibe sulfate (CS-505); CI-1011 (2,6-diisopropylphenyl [(2,4,6-triisopropylphenyl)acetyl]sulfamate); CI-976 (2,2-dimethyl-N-(2,4,6-trimethoxyphenyl)dodecanamide); VULM1457 (1-(2,6-diisopropyl-phenyl)-3-[4-(4'-nitrophenylthio)phenyl] urea); CI-976 (2,2-dimethyl-N-(2,4,6-trimethoxyphenyl)dodecanamide); E-5324 (n-butyl-N'-(2-(3-(5-ethyl-4-phenyl-1H-imidazol-1-yl)propoxy)-6-methylphenyl)urea); HL-004 (N-(2,6-diisopropylphenyl) tetradecylthioacetamide); KY-455 (N-(4,6-dimethyl-1-pentylindolin-7-yl)-2,2-dimethylpropanamide); FY-087 (N-[2-[N'-pentyl-(6,6-dimethyl-2,4-heptadiynyl)amino]ethyl]-(2-methyl-1-naphthyl-thio)acetamide); MCC-147 (Mitsubishi Pharma); F 12511 ((S)-2',3',5'-trimethyl-4'-hydroxy-alpha-dodecylthioacetanilide); SMP-500 (Sumitomo Pharmaceuticals); CL 277082 (2,4-difluoro-phenyl-N[[4-(2,2-dimethylpropyl) phenyl]methyl]-N-(hepthylurea); F-1394 ((1s,2s)-2-[3-(2,2-dimethylpropyl)-3-nonylureido]aminocyclohexane-1-yl 3-[N-(2,2,5,5-tetramethyl-1,3-dioxane-4-carbonyl)amino] propionate); CP-113818 (N-(2,4-bis(methylthio)-6-methyl-pyridin-3-yl)-2-(hexylthio)decanoic acid amide); YM-750; torcetrapib; anacetrapid; JTT-705 (Japan Tobacco/Roche); abciximab; eptifibatide; tirofiban; roxifiban; variabilin; XV 459 (N(3)-(2-(3-(4-formamidinophenyl)isoxazolin-5-yl) acetyl)-N(2)-(1-butyloxycarbonyl)-2,3-diaminopropionate); SR 121566A (3-[N-{4-[4-(aminoiminomethyl)phenyl]-1,3-thiazol-2-yl}-N-(1-carboxymethylpiperid-4-yl) aminol propionic acid, trihydrochloride); FK419 ((S)-2-acetylamino-3-[(R)[1-[3-(piperidin-4-yl) propionyl] piperidin-3-ylcarbonyl] amino] propionic acid trihydrate); clopidogrel; prasugrel; cangrelor; AZD6140 (AstraZeneca); MRS 2395 (2,2-Dimethyl-propionic acid 3-(2-chloro-6-methylaminopurin-9-yl)-2-(2,2-dimethyl-propionyloxymethyl)-propyl ester); BX 667 (Berlex Biosciences); BX 048 (Berlex Biosciences); darapladib (SB 480848); SB-435495 (GlaxoSmithKline); SB-222657 (GlaxoSmithKline); SB-253514 (GlaxoSmithKline); alefacept, efalizumab, methotrexate, acitretin, isotretinoin, hydroxyurea, mycophenolate mofetil, sulfasalazine, 6-Thioguanine, Dovonex, Taclonex, betamethasone, tazarotene, hydroxychloroquine, sulfasalazine, etanercept, adalimumab, infliximab, abatacept, rituximab, trastuzumab, anti-CD45 monoclonal antibody AHN-12 (NCI), Iodine-131 Anti-B1 Antibody (Corixa Corp.), anti-CD66 monoclonal antibody BW 250/183 (NCI, Southampton General Hospital), anti-CD45 monoclonal antibody (NCI, Baylor College of Medicine), antibody anti-anb3 integrin (NCI), BIW-8962 (BioWa Inc.), antibody BC8 (NCI), antibody muJ591 (NCI), indium In 111 monoclonal antibody MN-14 (NCI), yttrium Y 90 monoclonal antibody MN-14 (NCI), F105 Monoclonal Antibody (NIAID), Monoclonal Antibody RAV12 (Raven Biotechnologies), CAT-192 (Human Anti-TGF-Beta1 Monoclonal Antibody, Genzyme), antibody 3F8 (NCI), 177Lu-J591 (Weill Medical College of Cornell University), TB-403 (Biolnvent International AB), anakinra, azathioprine, cyclophosphamide, cyclosporine A, leflunomide, d-penicillamine, amitriptyline, or nortriptyline, chlorambucil, nitrogen mustard, prasterone, LJP 394 (abetimus sodium), LJP 1082 (La Jolla Pharmaceutical), eculizumab, belibumab, rhuCD40L (NIAID), epratuzumab, sirolimus, tacrolimus, pimecrolimus, thalidomide, antithymocyte globulin-equine (Atgam, Pharmacia Upjohn), anti-thymocyte globulin-rabbit (Thymoglobulin, Genzyme), Muromonab-CD3 (FDA Office of Orphan Products Development), basiliximab, daclizumab, riluzole, cladribine, natalizumab, interferon beta-1b, interferon beta-1a, tizanidine, baclofen, mesalazine, asacol, pentasa, mesalamine, balsalazide, olsalazine, 6-mercaptopurine, AIN457 (Anti IL-17 Monoclonal Antibody, Novartis), theophylline, D2E7 (a human anti-TNF mAb from Knoll Pharmaceuticals), Mepolizumab (Anti-IL-5 antibody, SB 240563), Canakinumab (Anti-IL-1 Beta Antibody, NIAMS), Anti-IL-2 Receptor Antibody (Daclizumab, NHLBI), CNTO 328 (Anti IL-6 Monoclonal Antibody, Centocor), ACZ885 (fully human anti-interleukin-lbeta monoclonal antibody, Novartis), CNTO 1275 (Fully Human Anti-IL-12 Monoclonal Antibody, Centocor), (3S)-N-hydroxy-4-({4-[(4-hydroxy-2-butynyl)oxy]phenyl}sulfonyl)-2,2-dimet-hyl-3-thiomorpholine carboxamide (apratastat), golimumab (CNTO 148), Onercept, BG9924 (Biogen Idec), Certolizumab Pegol (CDP870, UCB Pharma), AZD9056 (AstraZeneca), AZD5069 (AstraZeneca), AZD9668 (AstraZeneca), AZD7928 (AstraZeneca), AZD2914 (AstraZeneca), AZD6067 (AstraZeneca), AZD3342 (AstraZeneca), AZD8309 (AstraZeneca), [(1R)-3-methyl-1-({(2S)-3-phenyl-2-[(pyrazin-2-ylcarbonyl)amino]propanoyl}amino)butyl]boronic acid (Bortezomib), AMG-714, (Anti-IL 15 Human Monoclonal Antibody, Amgen), ABT-874 (Anti IL-12 monoclonal antibody, Abbott Labs), MRA(Tocilizumab, an Anti IL-6 Receptor Monoclonal Antibody, Chugai Pharmaceutical), CAT-354 (a human anti-interleukin-13 monoclonal antibody, Cambridge Antibody Technology, MedImmune), aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, flurobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, celecoxib, rofecoxib, valdecoxib, parecoxib, etoricoxib, lumiracoxib, CS-502 (Sankyo), JTE-522 (Japan Tobacco Inc.), L-745,337 (Almirall), NS398 (Sigma), betamethasone (Celestone), prednisone (Deltasone), alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, formoterol, halcinonide, halometasone, hydrocortisone, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone, rimexolone, tixocortol, triamcinolone, ulobetasol; cisplatin; carboplatin; oxaliplatin; mechlorethamine; cyclophosphamide; chlorambucil; vincristine; vinblastine; vinorelbine; vindesine; azathioprine; mercaptopurine; fludarabine; pentostatin; cladribine; 5-fluorouracil (5FU); floxuridine (FUDR); cytosine arabinoside; methotrexate; trimethoprim; pyrimethamine; pemetrexed; paclitaxel; docetaxel; etoposide; teniposide; irinotecan; topotecan; amsacrine; etoposide; etoposide phosphate; teniposide; dactinomycin; doxorubicin; daunorubicin; valrubicine; idarubicine; epirubicin; bleomycin; plicamycin; mitomycin; trastuzumab; cetuximab; rituximab; bevacizumab; finasteride; goserelin; aminoglutethimide; anastrozole; letrozole; vorozole; exemestane; 4-androstene-3,6,17-trione ("6-OXO"; 1,4,6-androstatrien-3,17-dione (ATD); formestane; testolactone; fadrozole; or combinations thereof.

In some embodiments, the second therapeutic agent is an antibiotic. In some embodiments, the second therapeutic agent is an anti-bacterial agent. In some embodiments, the second therapeutic agent is amikacin, gentamicin, kanamycin, neomycin, netilmicin, streptomycin, tobramycin, paromomycin, geldanmycin, herbimycin, loracarbef, ertapenem, doripenem, imipenem, cilastatin, meropenem, cefadroxil, cefazolin, cefalotin, cefalexin, cefaclor, cefamandole, cefoxitin, defprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillan, bacitracin, colistin, polymyxin B, ciprofloxacin, enoxacin, gatifloxacin, levofloxacin, lomefloxacin, moxifloxacin, norfloxacin, ofloxacin, trovfloxacin, mafenide, prontosil, sulfacetamide, sulfamethizole, sulfanimilimde, sulfsalazine, sulfsioxazole, trimethoprim, demeclocycline, doxycycline, minocycline, oxtetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinuspristin/dalfopristin, rifampin, tinidazole, and combinations thereof.

In some embodiments, the second therapeutic agent is an anti-viral agent. In some embodiments, the second therapeutic agent is acyclovir, famciclovir, valacyclovir, abacavir, aciclovir, adfovir, amantadine, amprenavir, arbidol, atazanavir, artipla, brivudine, cidofovir, combivir, edoxudine, efavirenz, emtricitabine, enfuvirtide, entecavir, fomvirsen, fosamprenavir, foscarnet, fosfonet, ganciclovir, gardasil, ibacitabine, imunovir, idoxuridine, imiquimod, indinavir, inosine, integrase inhibitors, interferons, including interferon type I (e.g. IFN α and IFN β), interferon type II, interferon type III, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, tenofovir, tenofovir disoproxil, tipranavir, trifluridine, trizivir, tromantadine, truvada, valganciclovir, vicriviroc, vidarabine, viramidine, zalcitabine, zanamivir, zidovudine, and combinations thereof.

In some embodiments, the second therapeutic agent is an anti-fungal agent. In some embodiments, the second therapeutic agent is amrolfine, utenafine, naftifine, terbinafine, flucytosine, fluconazole, itraconazole, ketoconazole, posaconazole, ravuconazole, voriconazole, clotrimazole, econazole, miconazole, oxiconazole, sulconazole, terconazole, tioconazole, nikkomycin Z, caspofungin, micafungin, anidulafungin, amphotericin B, liposomal nystastin, pimaricin, griseofulvin, ciclopirox olamine, haloprogin, tolnaftate, undecylenate, clioquinol, and combinations thereof.

In some embodiments, the second therapeutic agent is an anti-parasitic agent. In some embodiments, the second therapeutic agent is amitraz, amoscanate, avermectin, carbadox, diethylcarbamizine, dimetridazole, diminazene, ivermectin, macrofilaricide, malathion, mitaban, oxamniquine, permethrin, praziquantel, prantel pamoate, selamectin, sodium stibogluconate, thiabendazole, and combinations thereof.

Combinations with Cells and Tissues

In some embodiments, an nHC-HA/PTX3 or rcHC-HA/PTX3 complex disclosed herein is co-administered with a cell, a plurality of cells or a tissue.

In some embodiments, an nHC-HA/PTX3 or rcHC-HA/PTX3 complex disclosed herein is co-administered with a therapeutic cell. In some embodiments, an nHC-HA/PTX3 or rcHC-HA/PTX3 complex disclosed herein is co-administered with a tissue transplant. In some embodiments, an nHC-HA/PTX3 or rcHC-HA/PTX3 complex disclosed herein is co-administered with a stem cell transplant. In some embodiments, an nHC-HA/PTX3 or rcHC-HA/PTX3 complex disclosed herein is co-administered with an organ transplant.

In some embodiments, an nHC-HA/PTX3 or rcHC-HA/PTX3 complex disclosed herein is administered concurrently (e.g., simultaneously, essentially simultaneously or within the same treatment protocol) with a tissue transplant. In some embodiments, an nHC-HA/PTX3 or rcHC-HA/PTX3 complex disclosed herein is administered before or after a tissue transplant. In some embodiments, the time period between administration of an nHC-HA/PTX3 or rcHC-HA/PTX3 complex disclosed herein and the tissue transplant ranges from a few minutes to several hours, depending upon the properties of each pharmaceutical agent, such as potency, solubility, bioavailability, plasma half-life and kinetic profile of the pharmaceutical agent. In some embodiments, circadian variation of the target molecule concentration determines the optimal dose interval. In some embodiments, the timing between the administration of an nHC-HA/PTX3 or rcHC-HA/PTX3 complex disclosed herein and a second active agent is about less than an hour, less than a day, less than a week, or less than a month.

In some embodiments, an nHC-HA/PTX3 or rcHC-HA/PTX3 complex disclosed herein is co-administered with a tissue transplant and an immunosuppressive agent. In some embodiments, an nHC-HA/PTX3 or rcHC-HA/PTX3 complex disclosed herein is co-administered with a tissue transplant and a calcineurin inhibitor (e.g., cyclosporin or tacrolimus); an mTOR inhibitor (sirolimus; everolimus); an antiproliferative agent (azathioprine or mycophenolic acid); a corticosteroid (e.g., prednisolone or hydrocortisone); a monoclonal anti-IL-2Rα receptor antibody (e.g., basiliximab or daclizumab); a polyclonal anti-T-cell antibodies (e.g., anti-thymocyte globulin (ATG) or anti-lymphocyte globulin (ALG)); or combinations thereof.

In some embodiments, a tissue is coated with an nHC-HA/PTX3 or rcHC-HA/PTX3 complex disclosed herein. In some embodiments, a plurality of stem cells are coated with an nHC-HA/PTX3 or rcHC-HA/PTX3 complex disclosed herein. In some embodiments, an organ is coated with an nHC-HA/PTX3 or rcHC-HA/PTX3 complex disclosed herein. In some embodiments, coating a tissue with an nHC-HA/PTX3 or rcHC-HA/PTX3 complex disclosed herein prevent a tissue from being acted upon by the host immune system.

In some embodiments, an organ, tissue, or plurality of stem cells is contacted with an nHC-HA/PTX3 or rcHC-HA/PTX3 complex disclosed herein. In some embodiments, an organ, tissue, or plurality of stem cells is contacted with a composition comprising an nHC-HA/PTX3 or rcHC-HA/PTX3 complex disclosed herein. In some embodiments, the composition has a pH of about 7.0 to about 7.5. In some embodiments, the composition has a pH of 7.4. In some embodiments, the composition further comprises potassium, magnesium, and raffinose. In some embodiments, the composition further comprises at least one of adenosine, glutathione, allopurinol, and hydroxyethyl starch. In some embodiments, the composition is UW solution supplemented with an nHC-HA/PTX3 or rcHC-HA/PTX3 complex disclosed herein.

In some embodiments, the organ, tissue, or plurality of stem cells are contacted with an nHC-HA/PTX3 or rcHC-HA/PTX3 complex disclosed herein for about 30 minutes, about 1 hour, about 2 hours, about 3 hours, about 4 hours, about 5 hours, about 6 hours, about 12 hours, about 24 hours, about 36 hours, or about 48 hours. In some embodiments, the contacting occurs at a temperature that protects tissues and vascular conditioning (e.g., less than ambient temperature). In some embodiments, the contacting occurs at 4° C.

Medical Device Combinations

In some embodiments, an nHC-HA/PTX3 or rcHC-HA/PTX3 complex disclosed herein is co-administered with a medical device. In some embodiments, medical device or a portion thereof is contacted with an nHC-HA/PTX3 or rcHC-HA/PTX3 complex disclosed herein. In some embodiments, an nHC-HA/PTX3 or rcHC-HA/PTX3 complex disclosed herein is use to coat a medical device or a portion thereof as described elsewhere herein. In some embodiment, administration of an nHC-HA/PTX3 or rcHC-HA/PTX3 complex disclosed herein in combination with a medical device reduces, inhibits or prevents inflammatory reactions against the implanted medical device. In some embodiment, administration of an nHC-HA/PTX3 or rcHC-HA/PTX3 complex disclosed herein in combination with a medical device reduces, inhibits or prevents the formation of infectious biofilms that are produce by microorganism growth on the implanted medical device (i.e. chronic biofilm infection). Exemplary of such biofilms are those produce by bacteria, such as but not limited to, *Staphylococcus aureus*.

Articles of Manufacture and Kits

The articles of manufacture provided herein contain packaging materials. Packaging materials for use in packaging pharmaceutical products are well known to those of skill in the art. Examples of pharmaceutical packaging materials include, but are not limited to, blister packs, bottles, tubes, inhalers, inhalers (e.g., pressurized metered dose inhalers (MDI), dry powder inhalers (DPI), nebulizers (e.g., jet or ultrasonic nebulizers) and other single breath liquid systems), pumps, bags, vials, containers, syringes, bottles, and any packaging material suitable for a selected formulation and intended mode of administration and treatment. In some embodiments, the pharmaceutical composition is incorporated in, applied to or coated on a medical devices, such as implants, catheters, artificial joints, stents, valves, nanoparticles, or microcapsules.

In some embodiments, the pharmaceutical compositions or combinations provided herein are provided as kits. Kits optionally include one or more components such as instructions for use, devices and additional reagents (e.g., sterilized water or saline solutions for dilution of the compositions and/or reconstitution of lyophilized protein), and components, such as tubes, containers and syringes for practice of the methods. Exemplary kits include the pharmaceutical compositions or combinations provided herein, and optionally include instructions for use, a device for administering the pharmaceutical compositions or combinations to a subject, a device for detecting the nHC-HA/PTX3 or rcHC-HA/PTX3 complexes in a subject, a device for detecting the nHC-HA/PTX3 or rcHC-HA/PTX3 complexes in samples obtained from a subject, and a device for administering an additional therapeutic agent to a subject.

The kit can, optionally, include instructions. Instructions typically include a tangible expression describing the nHC-HA/PTX3 or rcHC-HA/PTX3 complexes and, optionally, other components included in the kit, and methods for administration, including methods for determining the proper state of the subject, the proper dosage amount, dosing regimens, and the proper administration method for administering the nHC-HA/PTX3 or rcHC-HA/PTX3 complexes. In some embodiments, instructions include guidance for monitoring the subject over the duration of the treatment time.

In some embodiments, kits include a pharmaceutical composition described herein and an item for diagnosis. For example, such kits include an item for measuring the concentration, amount or activity of the selected nHC-HA/PTX3 or rcHC-HA/PTX3 complexes in a subject.

In some embodiments, kits provided herein include a device for administering the nHC-HA/PTX3 or rcHC-HA/PTX3 complexes to a subject. In some embodiments, any of a variety of devices known in the art for administering medications to a subject—is included in the kits provided herein. Exemplary devices include, but are not limited to, an inhaler (e.g., pressurized metered dose inhaler (MDI), dry powder inhaler (DPI), nebulizer (e.g., jet or ultrasonic nebulizers) and other single breath liquid system), a hypodermic needle, an intravenous needle, a catheter, and a liquid dispenser such as an eyedropper. Typically the device for administering the nHC-HA/PTX3 or rcHC-HA/PTX3 complexes of the kit will be compatible with the desired method of administration of the nHC-HA/PTX3 or rcHC-HA/PTX3 complexes.

Expansion of Stem Cell Cultures

Disclosed herein, in certain embodiments, are methods of expanding an isolated stem cell on a substrate that comprises an nHC-HA/PTX3 or rcHC-HA/PTX3 complex provided herein. As described herein, HC-HA/PTX3 complexes promote the aggregation of stem cells, prevent differentiation of the cells and preserves expression of stem cell markers.

In some embodiments, the expansion on an nHC-HA/PTX3 complex or rcHC-HA/PTX3 complex preserves expression of one or more of embryonic stem cell (ESC) markers (e.g. Oct4, Nanog, Sox2 (SRY (sex determining region Y)-box 2), Rexl (Zfp42), SSEA4 (stage-specific embryonic antigen-4), MYC/c-Myc and KLF4, pericyte markers (e.g. NG2 (neuron-glial antigen 2/Chondroitin sulfate proteoglycan 4(CSPG4)), PDGFR-β (Platelet-derived growth factor receptor B), and α-SMA (α-smooth muscle actin)), and angiogenic markers (e.g. CD133/2, FLK-1 (VEGF-R2, Ly-73), vWF (von Willebrand factor), CD34, CD31 (PECAM-1) and CD146). In some embodiments, the expression of the stem cell marker is determined by conventional methods, such as for example, protein expression analysis (e.g. Western blotting, immunofluorescence, immunohistochemistry, fluorescence activated cell sorting) or mRNA analysis (e.g. polymerase chain reaction (PCR) or Northern).

In some embodiments, nHC-HA/PTX3 or rcHC-HA/PTX3 suppresses TGF-β signaling in a cultured cell. In some embodiments, nHC-HA/PTX3 or rcHC-HA/PTX3 suppresses TGF-β signaling in a cultured stem cell. In some embodiments, suppression of TGF-β signaling refers to a decrease in the activity or expression of one or more proteins or markers in the TGF-β cell signaling pathway such as pSMAD 2/3 signaling, a smooth muscle formation, in a cell in the presence of the nHC-HA/PTX3 or rcHC-HA/PTX3 complex compared to the absence of the nHC-HA/PTX3 or rcHC-HA/PTX3 complex.

In some embodiments, nHC-HA/PTX3 or rcHC-HA/PTX3 induces BMP signaling in a cultured cell. In some embodiments, nHC-HA/PTX3 or rcHC-HA/PTX3 induces BMP signaling in a cultured stem cell. In some embodiments, suppression of TGF-β signaling refers to an increase in the activity or expression of one or more proteins in the BMP signaling pathway, such as BMP-2, BMP-4, BMP-6 and pSMAD1/5/8, in a cell in the presence of the nHC-HA/PTX3 or rcHC-HA/PTX3 complex compared to the absence of the nHC-HA/PTX3 or rcHC-HA/PTX3 complex.

In some embodiments, the isolated stem cell cultured on nHC-HA/PTX3 or rcHC-HA/PTX3 is an embryonic stem cell. In some embodiments, the isolated stem cell cultured on nHC-HA/PTX3 or rcHC-HA/PTX3 is an adult stem cell. In some embodiments, the isolated stem cell cultured on nHC-HA/PTX3 or rcHC-HA/PTX3 is a fetal stem cell. In some embodiments, the isolated stem cell cultured on nHC-HA/PTX3 or rcHC-HA/PTX3 is an induced pluripotent/progenitor stem cell (iPSC).

In some embodiments, the isolated stem cell cultured on nHC-HA/PTX3 or rcHC-HA/PTX3 is a mesenchymal stem cell. In some embodiments, the isolated stem cell cultured on nHC-HA/PTX3 or rcHC-HA/PTX3 is an adipose stem cell (ASC). In some embodiments, the isolated stem cell cultured on nHC-HA/PTX3 or rcHC-HA/PTX3 is an umbilical cord stem cell. In some embodiments, the isolated stem cell cultured on nHC-HA/PTX3 or rcHC-HA/PTX3 is an amniotic membrane stem cell. In some embodiments, the isolated stem cell cultured on nHC-HA/PTX3 or rcHC-HA/PTX3 is a limbal cell, such as a limbal niche cell or a limbal epithelial progenitor cell. In some embodiments, the isolated stem cell cultured on nHC-HA/PTX3 or rcHC-HA/PTX3 is an endothelial stem cell. In some embodiments, the isolated stem cell cultured on nHC-HA/PTX3 or rcHC-HA/PTX3 is a hematopoietic stem cell. In some embodiments, the isolated stem cell is a bone marrow stem cell. In some embodiments, the isolated stem cell cultured on nHC-HA/PTX3 or rcHC-HA/PTX3 is a neural stem cell. In some embodiments, the isolated stem cell cultured on nHC-HA/PTX3 or rcHC-HA/PTX3 is an endothelial progenitor cell. In some embodiments, the isolated stem cell cultured on nHC-HA/PTX3 or rcHC-HA/PTX3 is a skeletal muscle stem cell. In some embodiments, the isolated stem cell cultured on nHC-HA/PTX3 or rcHC-HA/PTX3 is a mammary stem cell. In some embodiments, the isolated stem cell cultured on nHC-HA/PTX3 or rcHC-HA/PTX3 is an intestinal stem cell.

In some embodiments, the isolated stem cell cultured on nHC-HA/PTX3 or rcHC-HA/PTX3 is an induced pluripotent/progenitor stem cell (iPSC). In some embodiments, the isolated stem cell cultured on nHC-HA/PTX3 or rcHC-HA/PTX3 is an induced pluripotent stem cell derived from an adult differentiated or partially differentiated cell. In some embodiments, the isolated stem cell cultured on nHC-HA/PTX3 or rcHC-HA/PTX3 is an induced pluripotent stem cell derived from a fibroblast. In some embodiments, the isolated stem cell cultured on nHC-HA/PTX3 or rcHC-HA/PTX3 is an induced pluripotent stem cell derived from a human corneal fibroblast.

In some embodiments, the isolated stem cell cultured on nHC-HA/PTX3 or rcHC-HA/PTX3 is derived from a fetal tissue, such as placental tissue or an umbilical cord tissue. In some embodiments, the isolated stem cell cultured on nHC-HA/PTX3 or rcHC-HA/PTX3 is derived from amniotic membrane. In some embodiments, the isolated stem cell cultured on nHC-HA/PTX3 or rcHC-HA/PTX3 is derived from adipose tissue. In some embodiments, the isolated stem cell cultured on nHC-HA/PTX3 or rcHC-HA/PTX3 is derived from limbal tissue. In some embodiments, the isolated stem cell cultured on nHC-HA/PTX3 or rcHC-HA/PTX3 is derived from bone marrow. In some embodiments, the isolated stem cell cultured on nHC-HA/PTX3 or rcHC-HA/PTX3 is derived from endothelial tissue. In some embodiments, the isolated stem cell cultured on nHC-HA/PTX3 or rcHC-HA/PTX3 is derived from limbal tissue. In some embodiments, the isolated stem cell cultured on nHC-HA/PTX3 or rcHC-HA/PTX3 is derived from neural tissue, In some embodiments, the isolated stem cell cultured on nHC-HA/PTX3 or rcHC-HA/PTX3 is derived from limbal tissue. In some embodiments, the isolated stem cell cultured on nHC-HA/PTX3 or rcHC-HA/PTX3 is derived from skeletal muscle. In some embodiments, the isolated stem cell cultured on nHC-HA/PTX3 or rcHC-HA/PTX3 is derived from the skin. In some embodiments, the isolated stem cell cultured on nHC-HA/PTX3 or rcHC-HA/PTX3 is derived from the digestive system. In some embodiments, the isolated stem cell cultured on nHC-HA/PTX3 or rcHC-HA/PTX3 is derived from the pancreas. In some embodiments, the isolated stem cell cultured on nHC-HA/PTX3 or rcHC-HA/PTX3 is derived from the liver. In some embodiments, the isolated stem cell cultured on nHC-HA/PTX3 or rcHC-HA/PTX3 is derived from the olfactory mucosa. In some embodiments, the isolated stem cell cultured on nHC-HA/PTX3 or rcHC-HA/PTX3 is derived from a germ cell population. In some embodiments, the isolated stem cell cultured on nHC-HA/PTX3 or rcHC-HA/PTX3 is derived from blood. In some embodiments, the isolated stem cell cultured on nHC-HA/PTX3 or rcHC-HA/PTX3 is derived from umbilical cord blood.

In some embodiments, the HC-HA/PTX3 complex is an nHC-HA/PTX3 isolated from amniotic membrane or umbilical cord. In some embodiments, the HC-HA/PTX3 complex is a reconstituted HC-HA complex. In some embodiments, HA is covalently linked to HC. In some embodiments, the HC of IαI is heavy chain 1 (HC1). In some embodiments, the HC-HA complex comprises pentraxin 3 (PTX3).

In some embodiments, the nHC-HA/PTX3 or rcHC-HA/PTX3 complex comprises a small leucine rich proteoglycan (SLRP). In some embodiments, the nHC-HA/PTX3 or rcHC-HA/PTX3 complex comprises a class I, class II or class II SLRP. In some embodiments, the nHC-HA/PTX3 or rcHC-HA/PTX3 complex comprises PTX3 and a small leucine rich proteoglycan (SLRP). In some embodiments, the small leucine-rich proteoglycan is selected from among class I SLRPs, such as decorin and biglycan. In some embodiments, the small leucine-rich proteoglycan is selected from among class II SLRPs, such as fibromodulin, lumican, PRELP (proline arginine rich end leucine-rich protein), keratocan, and osteoadherin. In some embodiments, the small leucine-rich proteoglycan is selected from among class III SLRPs, such as epipycan and osteoglycin.

In some embodiments, the isolated stem cell is expanded on a substrate comprising immobilized nHC-HA/PTX3 or rcHC-HA/PTX3. In some embodiments, the immobilized nHC-HA/PTX3 or rcHC-HA/PTX3 comprises one or more small leucine rich proteoglycans (SLRPs). In some embodiments, the SLRP is selected from among bikunin, decorin, biglycan, and osteoadherin. In some embodiments, the small leucine-rich protein comprises a glycosaminoglycan. In some embodiments, the small leucine-rich proteoglycan comprises keratan sulfate.

In some embodiments, the isolated stem cell is expanded in a culture medium comprising nHC-HA/PTX3 or rcHC-HA/PTX3 complex. In some embodiments, the nHC-HA/PTX3 or rcHC-HA/PTX3 comprises one or more small leucine rich proteoglycans (SLRPs). In some embodiments, the SLRP is selected from among bikunin, decorin, biglycan, and osteoadherin. In some embodiments, the small leucine-rich protein comprises a glycosaminoglycan. In some embodiments, the small leucine-rich proteoglycan comprises keratan sulfate. In some embodiments, the medium is embryonic stem cell medium, modified embryonic stem cell medium, supplemented hormonal epithelial medium, and/or a combination thereof. In some embodiments, the medium is supplemented with one or more growth factors. In some embodiments, the medium is supplemented with EGF, bFGF and/or LIF. In some embodiments, the medium is supplemented with an inhibitor of Rho-associated kinase (ROCK inhibitor).

Inducing and Maintaining Pluripotency

Disclosed herein, in certain embodiments, are methods of inducing pluripotency in a cell or maintaining pluripotency of a stem cell on a substrate that comprises an nHC-HA/PTX3 or rcHC-HA/PTX3 complex. As described herein, HC-HA/PTX3 complexes assist in the maintenance of stem cell marker expression and prevent differentiation of the cells over successive passages of a stem cell population. In addition, as described herein, HC-HA/PTX3 complexes promote the induction of stem cell properties in a differentiated or partially differentiated population of cells.

In certain embodiments, an nHC-HA/PTX3 or rcHC-HA/PTX3 complex promotes or induces pluripotency of a differentiated or partially differentiated cell. In certain embodiments, an nHC-HA/PTX3 or rcHC-HA/PTX3 complex promotes or induces pluripotency of a differentiated or partially differentiated cell compared to a differentiated or partially differentiated cell cultured in the absence of an nHC-HA/PTX3 or rcHC-HA/PTX3 complex. In an exemplary method, a differentiated cell or partially differentiated cell is cultured on a substrate comprising nHC-HA/PTX3 or rcHC-HA/PTX3 complex, whereby pluripotency is induced in the cell.

In certain embodiments, an nHC-HA/PTX3 or rcHC-HA/PTX3 complex further promotes or induces pluripotency of a stem cell. In certain embodiments, an nHC-HA/PTX3 or rcHC-HA/PTX3 complex further promotes or induces pluripotency of a stem cell compared to a stem cultured in the absence of an nHC-HA/PTX3 or rcHC-HA/PTX3 complex. In an exemplary method, a stem cell is cultured on a substrate comprising nHC-HA/PTX3 or rcHC-HA/PTX3 complex, whereby pluripotency is maintained in the stem cell. In an exemplary method, a stem cell is cultured on a substrate comprising nHC-HA/PTX3 or rcHC-HA/PTX3 complex, whereby pluripotency is further induced in the stem cell.

Using genetic reprogramming with protein transcription factors, pluripotent stem cells equivalent to embryonic stem cells have been derived from human adult skin tissue. iPSC cells are typically derived by transfection of certain stem cell-associated genes into non-pluripotent cells, such as adult fibroblasts. Transfection is typically achieved through viral vectors, such as retroviruses, where the pluripotency gene is operably linked to a promoter for gene expression. Four key pluripotency genes essential for the production of pluripotent stem cells are Oct-3/4 (Pou5f1), Sox2, c-Myc, and Klf4. Other genes can enhance the efficiency of induction. In some studies, Oct4, Sox2, Nanog, and Lin28 have been employed to induce pluripotency. In certain instances, after 3-4 weeks, small numbers of transfected cells begin to become morphologically and biochemically similar to pluripotent stem cells, and are typically isolated through morphological selection, doubling time, or through a reporter gene and antibiotic selection.

In some embodiments, methods are provided for inducing pluripotency in a differentiated or partially differentiated cell using heterologous expression of fewer than four of the essential transcription factors Oct-3/4 (Pou5f1), Sox2, c-Myc, and Klf4. In some embodiments, a method for inducing pluripotency is provided where use of an nHC-HA/PTX3 or rcHC-HA/PTX3 complex enhances the induction of pluripotency of a differentiated or partially differentiated cell that expresses at least one of Oct-3/4 (Pou5f1), Sox2, c-Myc, and/or Klf4 by heterologous gene transfer. In some embodiments, a method for inducing pluripotency is provided where use of an nHC-HA/PTX3 or rcHC-HA/PTX3 complex enhances the induction of pluripotency of a differentiated or partially differentiated cell that expresses one, two or three factors selected from among Oct-3/4 (Pou5f1), Sox2, c-Myc, and/or Klf4 by heterologous gene transfer. In some embodiments, a method for inducing pluripotency is provided where use of an nHC-HA/PTX3 or rcHC-HA/PTX3 complex enhances the induction of pluripotency of a differentiated or partially differentiated cell that expresses Oct-3/4 (Pou5f1) by heterologous gene transfer. In some embodiments, a method for inducing pluripotency is provided where use of an nHC-HA/PTX3 or rcHC-HA/PTX3 complex enhances the induction of pluripotency of a differentiated or partially differentiated cell that Sox2 by heterologous gene transfer. In some embodiments, a method for inducing pluripotency is provided where use of an nHC-HA/PTX3 or rcHC-HA/PTX3 complex enhances the induction of pluripotency of a differentiated or partially differentiated cell that expresses c-Myc by heterologous gene transfer. In some embodiments, a method for inducing pluripotency is provided where use of an nHC-HA/PTX3 or rcHC-HA/PTX3 complex enhances the induction of pluripotency of a differentiated or partially differentiated cell that expresses Klf4 by heterologous gene transfer.

In some embodiments, a differentiated or partially differentiated cell is transduced to express one or more of Oct-3/4 (Pou5f1), SOX2, c-Myc, and Klf4; and the transduced cell is cultured on a substrate comprising an nHC-HA/PTX3 or rcHC-HA/PTX3 complex. In some embodiments, a differentiated or partially differentiated cell is transduced to express at least one of Oct-3/4 (Pou5f1), SOX2, c-Myc, and Klf4; and the transduced cell is cultured on a substrate comprising an nHC-HA/PTX3 or rcHC-HA/PTX3 complex. In some embodiments, a differentiated or partially differentiated cell is transduced to express one, two or three of Oct-3/4 (Pou5f1), SOX2, c-Myc, and Klf4; and the transduced cell is cultured on a substrate comprising an nHC-HA/PTX3 or rcHC-HA/PTX3 complex. In some embodiments, a differentiated or partially differentiated cell is transduced to express Oct-3/4 (Pou5f1), SOX2, c-Myc, and Klf4; and the transduced cell is cultured on a substrate comprising an nHC-HA/PTX3 or rcHC-HA/PTX3 complex. In some embodiments, a differentiated or partially differentiated cell is transduced to express Oct-3/4 (Pou5f1); and the transduced cell is cultured on a substrate comprising an nHC-HA/PTX3 or rcHC-HA/PTX3 complex. In some embodiments, a differentiated or partially differentiated cell is transduced to express SOX2; and the transduced cell is cultured on a substrate comprising an nHC-HA/PTX3 or rcHC-HA/PTX3 complex. In some embodiments, a differentiated or partially differentiated cell is transduced to express c-Myc; and the transduced cell is cultured on a substrate comprising an nHC-HA/PTX3 or rcHC-HA/PTX3 complex. In some embodiments, a differentiated or partially differentiated cell is transduced to express Klf4; and the transduced cell is cultured on a substrate comprising an nHC-HA/PTX3 or rcHC-HA/PTX3 complex. In some embodiments, the cell is transduced to express one or more additional genes, such as for example, Nanog, Fbx15, ERas, ECAT15-2, Tcl1, and β-catenin.

In some embodiments, a differentiated or partially differentiated cell is transduced with a viral vector containing one or more genes encoding one or more of Oct-3/4 (Pou5f1), SOX2, c-Myc, and Klf4. In some embodiments, a differentiated or partially differentiated cell is transduced with two or more viral vectors containing one or more genes encoding one or more of Oct-3/4 (Pou5f1), SOX2, c-Myc, and Klf4.

Various methods for the induction, culturing and maintenance of induced pluripotent stem cells and assessment of the pluripotency of induced stem cells, including assessment of stem cell markers and induction of different cell lineages, are well known in the art and include, for example, methods described in U.S. Pat. Nos. 7,682,828, 8,048,999, 8,211,697, 7,951,592, and US Pat. Pubs. 2009/0191159 and 2010/000375.

In some embodiments, the nHC-HA/PTX3 or rcHC-HA/PTX3 complex reduces to time of induction of pluripotency in the transduced cell compared to a transduced cell cultured in the absence of nHC-HA/PTX3 or rcHC-HA/PTX3 complex. In some embodiments, the nHC-HA/PTX3 or rcHC-HA/PTX3 complex increases the percentage of transduced cells that are induced to pluripotency in a population of transduced cells compared to transduced cells cultured in the absence of nHC-HA/PTX3 or rcHC-HA/PTX3 complex compared to a transduced cell cultured in the absence of nHC-HA/PTX3 or rcHC-HA/PTX3 complex. In some embodiments, the nHC-HA/PTX3 or rcHC-HA/PTX3 complex enhances the level of pluripotency in the transduced cell. In some embodiments, the nHC-HA/PTX3 or rcHC-HA/PTX3 complex decreases the number of heterologous transcription factors required for induction of pluripotency in the transduced cell.

In some embodiments, an nHC-HA/PTX3 or rcHC-HA/PTX3 complex provided herein inhibits TGFβ1 signaling in a differentiated cell, a stem cell, or an iPSC. In some embodiments, an nHC-HA/PTX3 or rcHC-HA/PTX3 complex provided herein inhibits nuclear translocation of SMAD2 or SMAD3 in a differentiated cell, a stem cell, or an iPSC. In some embodiments, an nHC-HA/PTX3 or rcHC-HA/PTX3 complex provided herein inhibits alpha smooth muscle actin formation in a differentiated cell, a stem cell, or an iPSC. In some embodiments, an nHC-HA/PTX3 or rcHC-HA/PTX3 complex provided herein activates BMP4 signaling in a differentiated cell, a stem cell, or an iPSC. In some embodiments, an nHC-HA/PTX3 or rcHC-HA/PTX3 complex provided herein activates BMP6 signaling in a differentiated cell, a stem cell, or an iPSC. In some embodiments, an nHC-HA/PTX3 or rcHC-HA/PTX3 complex provided herein induces expression of an embryonic cell marker in a differentiated cell, a stem cell, or an iPSC. In some embodiments, an nHC-HA/PTX3 or rcHC-HA/PTX3 complex provided herein induces expression of c-myc, KLF-4, Nanog, nestin, Oct4, Rex-1, Sox-2, and SSEA-4 in a differentiated cell, a stem cell, or an iPSC.

EXAMPLES

The following examples are included for illustrative purposes only and are not intended to limit the scope of the claimed subject matter.

Example 1. Purification of Native HC-HA/PTX3 (nHC-HA/PTX3) Complexes from Human Amniotic Membrane Extracts (AME)

Preparation of Amniotic Membrane Extract (AME) and AM Powder (AMP)

Frozen human AM obtained from Bio-tissue (Miami, Fla.) was washed 2-3 times with PBS to remove the storage medium. To prepare AME, AM was transferred to a sterile 50 ml centrifuge tube and centrifuged at 4° C. for 5 min at 5000×g to remove the excess fluid. AM was weighed (~10 mg/cm$^2$), transferred to a 100 mm or 150 mm sterile Petri dish, and frozen in the air phase of a liquid nitrogen container for 20 min before being sliced into small pieces with a disposable scalpel and homogenized with Tissue-Tearor (Biospec Products, Inc., Bartlesville, Okla.) in PBS. The homogenate was mixed at 4° C. for 30 min and centrifuged at 48,000×g for 30 min. The supernatant was collected, designated as AME, and used for nHC-HA/PTX3 purification or stored at −80° C.

To prepare lyophilized AM powder (AMP), AM frozen in a −80° C. freezer was transferred to and lyophilized in a bench top lyophilizer (Freezone 4.5, Labconco, Kansas City, Mo.) for 16 hours. The lyophilized AM was then micronized into its matrix form (AMP) by a Mixer Mill (Retsch, Newtown, Pa.). AMP was stored at below −20° C. for further analyses.

Purification of Native HC-HA/PTX3 (nHC-HA/PTX3) Complex

AME was dissolved in CsCl/4M guanidine HCl mixture at an initial density of 1.35 g/ml, and centrifuged at 125,000×g for 48 h at 15° C. A total of 15 fractions (0.8 ml/fraction) were collected from the top to the bottom of each tube. Total protein concentration for each fraction was determined by BCA Protein Assay Kit. Hyaluronan (HA) concentration for each fraction was determined by an ELISA-based HA Quantitative Test Kit from Corgenix (Westminster, Colo.) (FIG. 1A). Fractions #8-15, which contain HA but no detectable proteins, were pooled, and used for a second ultracentrifugation. A sample of the pooled fractions (designated AM 1st) was saved for analysis. The pooled fractions were adjusted with CsCl/4M guanidine HCl at an initial density of 1.40 g/ml, centrifuged, and fractionated in the same manner as described above (FIG. 1B). Fractions #3-15, which contained HA but no detectable proteins, were pooled (designated AM 2nd) and dialyzed against distilled water to remove CsCl and guanidine HCl. The dialysate was lyophilized the same manner as for AMP describe above. Alternatively, the dialysate was mixed with 3 volumes of 95% (v/v) ethanol containing 1.3% (w/v) potassium acetate at 0° C. for 1 h. After centrifugation at 15,000×g, the pellet was washed with 70% (v/v) ethanol and centrifuged again. The pellet was briefly dried by air, stored at −80° C. The powder and pellet were designated as nHC-HA/PTX3 complex.

In some instances, the pooled sample went through three or four times of ultracentrifugation. In these ultracentrifugations, only fractions #7-12 were pooled and the initial density of CsCl/4M guanidine HCl is at 1.42 g/ml. After the third or fourth ultracentrifugation, the pooled fractions #7-12 is designated nHC-HA/PTX3 ($3^{rd}$) or nHC-HA/PTX3 ($4^{th}$).

AME pooled fractions after $1^{st}$, $2^{nd}$, $3^{rd}$, or $4^{th}$ ultracentrifugations were treated with or without 0.05 N NaOH at 25° C. for 1 h. Pooled fractions from $1^{st}$, $2^{nd}$, $3^{rd}$, or $4^{th}$ ultracentrifugation also were digested with 20 units/ml Hyaluronidase (HAase) (Seikagaku Biobusiness Corporation, Tokyo, Japan) at 60° C. for 2 h.

Samples from the pooled fractions and the NaOH and HAase treated samples were then run on 0.5% agarose gels and analyzed by staining with Stains-all dye (FIG. 1C) or by Western blot using antibodies against IαI heavy chain 1 (HC1) (FIGS. 1D and 1F), pentraxin 3 (PTX3) (FIGS. 1E and 1G), IαI heavy chain 2 (HC2) (FIG. 1H), IαI heavy chain 3 (HC3) (FIG. 1I), bikunin (FIG. 1J), TNF-stimulated gene 6 (TSG-6) (FIG. 1K), thrombospondin-1 (TSP-1) (FIG. 1L) or IGFBP 1-3 and PF4 (FIG. 1M), of which the latter two were analyzed by protein dot assays using human angiogenesis arrays (each array contains 56 different angiogenic proteins, R&D Systems, Minneapolis, Minn.). Briefly, 1.5 ml of human AM extract (25 µg/ml HA) and purified nHC-HA/PTX3($2^{nd}$) (25 µg/ml HA) were incubated separately with the detection antibodies pre-coated on the membrane overnight at 4° C., followed by incubation with the secondary antibody. Signals were detected with chemiluminescent light exposed to x-ray film. The array data on developed x-ray film were quantitated by scanning the film on a transmission-mode scanner, and the array image file was analyzed by ImageJ1.46 software (National Institutes of Health, Bethesda, Md.).

Biochemical characterization showed that nHC-HA/PTX3 is composed of high molecular weight HA (HMW HA) (FIG. 1C) covalently linked to heavy chain 1 (HC1) of IαI and PTX3. Both HC1 and PTX3 in nHC-HA/PTX3 are released only after treatment of hyaluronidase (HAase) or NaOH (FIGS. 1D-G), demonstrating that HC1 is linked to HA by ester bonds as reported.

Figure 1L:
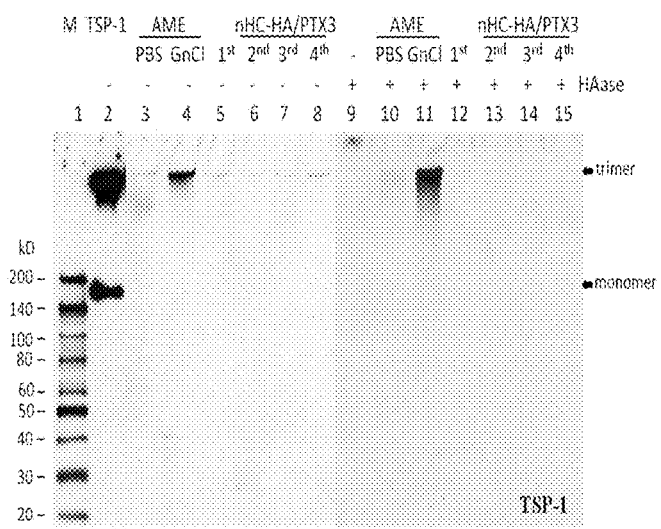
Figure 1M:
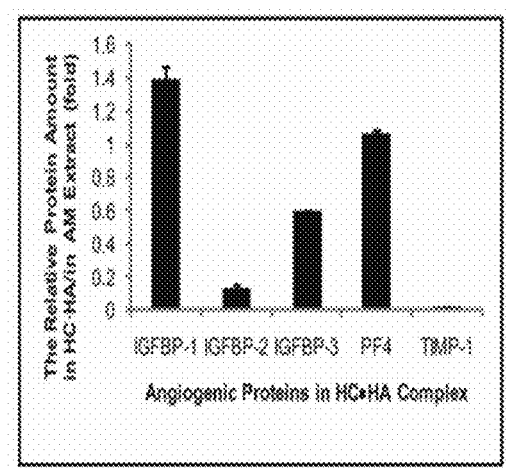

In contrast, nHC-HA/PTX3 does not contain HC2 (FIG. 1H), HC3 (FIG. 1I, a band at ~12 kDa detected only after NaOH treatment is likely non-specific), bikunin (FIG. 1J), TSG-6 (FIG. 1K) and TSP-1 (FIG. 1L). Insulin-like growth factor binding protein-1-3 (IGFBP1-3) and platelet factor 4 (PF4) are detected by protein dot assay (similar to ELISA) in nHC-HA/PTX3($2^{nd}$) (FIG. 1J); it remains unclear whether they are still in nHC-HA/PTX3($4^{th}$).

Example 2. Preparation of Immobilized HA (iHA) by Covalent Linkage

Figure 6A:
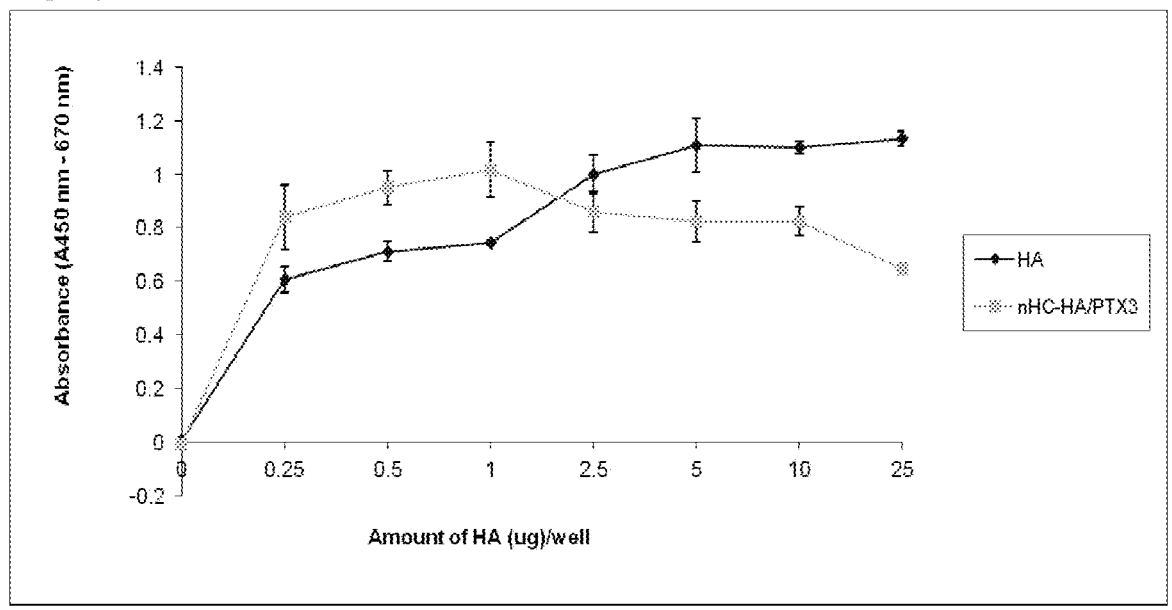
FIG. 6A-B exemplifies dose-dependent and covalent coupling of HMW HA and nHC-HA/PTX3 to surfaces of 96 well CovaLink™ plates. (A) HA ELISA of bound HMW HA and nHC-HA/PTX3 after removal of unbound HMW HA and nHC-HA/PTX3. (B) HA ELISA of bound and unbound HA from HMW HA and nHC-HA/PTX3.

A series of hyaluronan (HA) amounts (0, 0.25, 0.5, 1.0, 2.5, 5, 10, and 25 µg/well) from HMW HA (Healon, Advanced Medical Optics, Santa Ana, Calif.) or nHC-HA/PTX3($2^{nd}$) was added to the coupling solution containing Sulfo-NHS (0.184 mg/ml) and EDAC (0.123 mg/ml) (Both were from Thermo Fisher Scientific, Rockford, Ill.) and incubated in Covalink™-NH 96 well plates (Thermo Fisher Scientific Inc.), for 16 h at 4° C. After three washes of 8 M Guanidine-HCl (GnHCl) followed by washes with PBS, the coupled HA from HMW HA or nHC-HA/PTX3 was measured quantitatively by HA ELISA from Corgenix (Westminster, Colo.) according to the manufacturer's protocol (FIG. 6A). HMW HA and nHC-HA/PTX3 purified from AM are dose-dependently and covalently coupled to surfaces of Covalink-NH 96 wells. The resultant iHA or immobilized nHC-HA/PTX3 is resistant to washes by 8 M Guanidine HCl. HA of HMW HA or nHC-HA/PTX3 was maximally coupled at 2 µg/well HA equivalent input (FIG. 6A).

Figure 6B:
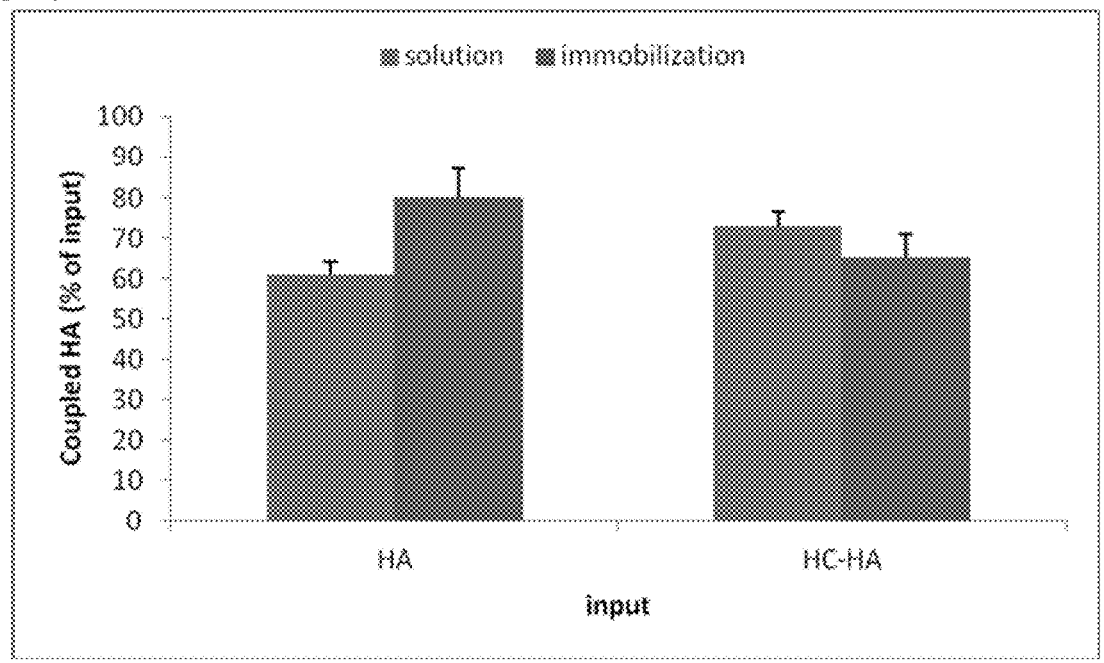

To determine coupling efficiency, HA from HMW HA or nHC-HA/PTX3 was coupled to Covalink™-NH per well of the 96 well plates, and unbound and bound HA from HMW HA or nHC-HA/PTX3 were measured by HA ELISA (FIG. 6B). 2 µg of HA from HMW HA or nHC-HA/PTX3 was added to the coupling solution containing Sulfo-NHS (0.184 mg/ml) and EDAC (0.123 mg/ml) [1-ethyl-3-(3-dimethylaminopropyl) carbodiimide] in H$_2$O and incubated in Covalink™-NH 96 well plates (Thermo Fisher Scientific, Rockford, Ill.), for 16 h at 4° C. Both HA coupled to wells or unbound in washed solution (pooled) were measured with HA ELISA from Corgenix (Westminster, Colo.) according to the manufacturer's protocol. The total amount of HA in each well in either coupled or unbound is divided by the input HA amount (2 µg/well) to calculate coupling efficiency or unbound percentage. The average coupling efficiency was determined to be 70.5±13.4% for HMW HA and 69.0±5.7% for nHC-HA/PTX3 (FIG. 6B). So, 2 μg/well input HA results in approximately 1.4 μg iHA.

Example 3. Activity of Purified Native HC-HA/PTX3(nHC-HA/PTX3) Complexes

Attachment of LPS-stimulated Macrophages to Immobilized nHC-HA/PTX3

Figure 2A:
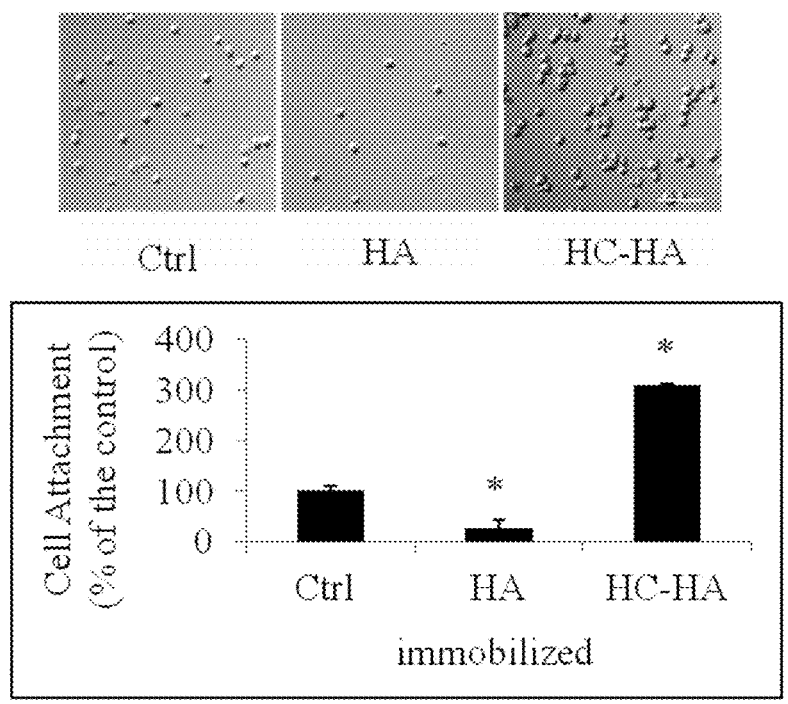
FIG. 2A-C exemplifies CD44 and TLR4 receptors mediate the attachment of LPS-Stimulated macrophages to immobilized nHC-HA/PTX3. (A) Cell attachment. RAW264.7 cells (100 µl of $2.5 \times 10^5$ cells/ml) were seeded in immobilized HA (2 µg/well) or nHC-HA/PTX3 (2 µg/well) (n=3) and stimulated with LPS (1 µg/ml). After incubation for 90 min, unattached cells were removed and attached cells were counted by the CyQuant assay. The scale bar represents 100 µm. An asterisk (*) indicates p values<0.05 (HA or nHC-HA/PTX3 vs. PBS control or nHC-HA/PTX3 vs. HA). (B) Cell viability. LPS-stimulated RAW264.7 cells were incubated on immobilized PBS control, HA, or nHC-HA/PTX3 for 24 h (n=3). The cell viability was measured by MTT assay. No significant differences (all p values>0.05) in the cell viability among cells on these immobilized substrates were observed. (C) CD44 and TLR4 Receptors are responsible for attachment of LPS-stimulated macrophages to immobilized nHC-HA/PTX3. RAW264.7 cells ($2.5 \times 10^5$/ml) were pre-incubated with the blocking antibody against CD44, TLR2, TLR4, integrin $\alpha v$, $\beta 1$, $\beta 2$, or $\beta 3$ or RGD peptides, along with the isotype control antibodies or a RGD control peptide, on ice for 30 min (n=3). After adding LPS (1 µg/ml), cells were incubated for 90 min and the cell attachment assay was done the same as described in A. An asterisk (*) indicates p value<0.05.

RAW264.7 cells (100 μl of 2.5×10$^5$ cells/ml) [American Type Culture Collection (ATCC), Manassas, Va.] in DMEM/10% FBS (Life Technologies, Grand Island, N.Y.) were seeded in 96-well plates containing immobilized HA (Advanced Medical Optics, Santa Ana, Calif., 2 μg/well), nHC-HA/PTX3(2 μg/well) or PBS control and stimulated with Lipopolysaccharide (LPS) (1 μg/ml) (n=3) [LPS-EB Ultrapure, InvivoGen, San Diego, Calif.]. Immobilization of HA and nHC-HA/PTX3 on the surface of Covalink-NH 96 well was performed similarly as described above. In brief, Covalink-NH 96-well plates were sterilized in 70% alcohol for 2 h, washed 3 times with distilled water, and added with 100 μl of 0.184 mg/ml Sulfo-NHS (Thermo Fisher Scientific, Rockford, Ill.) and 0.123 mg/ml of EDAC (Thermo Fisher Scientific, Rockford, Ill.) in distilled water containing 20 μg/ml HA or nHC-HA/PTX3 per 96-well plate (PBS control wells contain all reagents except for HA and nHC-HA/PTX3). The plate was incubated at 4° C. overnight or at 25° C. for 2 h before the coupling solution was removed, washed 3 times with PBS containing 2 M NaCl and 50 mM MgSO4, and followed by 3 washes with PBS. After incubation for 90 min, unattached cells were removed and attached cells were photographed and counted by the CyQuant assay (FIG. 2A). A greater than 3-fold increase in the attachment of LPS-stimulated macrophages was observed for the wells containing immobilized nHC-HA/PTX3 compared to the control wells. Wells containing immobilized HA inhibited the attachment of LPS-stimulated macrophages.

Figure 2B:
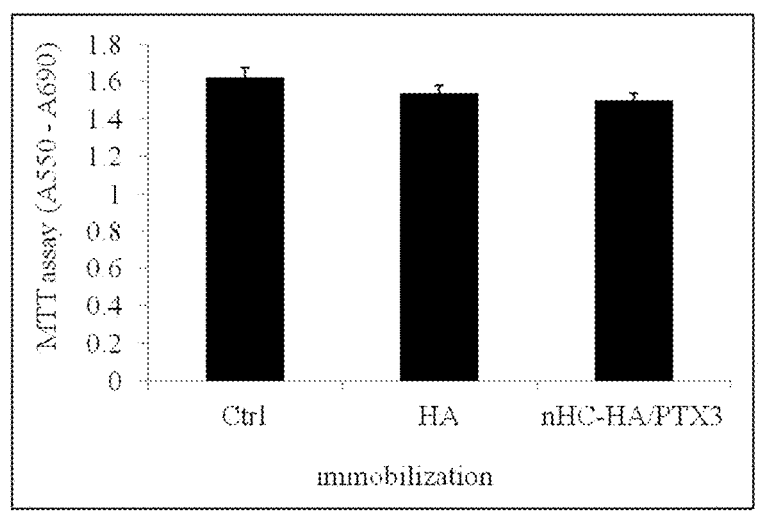

The cell viability of attached LPS-stimulated macrophages was then examined. LPS-stimulated RAW264.7 cells (100 μl of 2.5×10$^5$ cells/ml) were incubated in DMEM/10% FBS on immobilized PBS control, HA, or nHC-HA/PTX3 for 24 h as described above (n=3). Following incubation, the cell viability of the attached macrophages was measured by MTT assay. No significant differences (all p values>0.05) in the cell viability among cells on these immobilized substrates were observed (FIG. 2B).

Figure 2C:
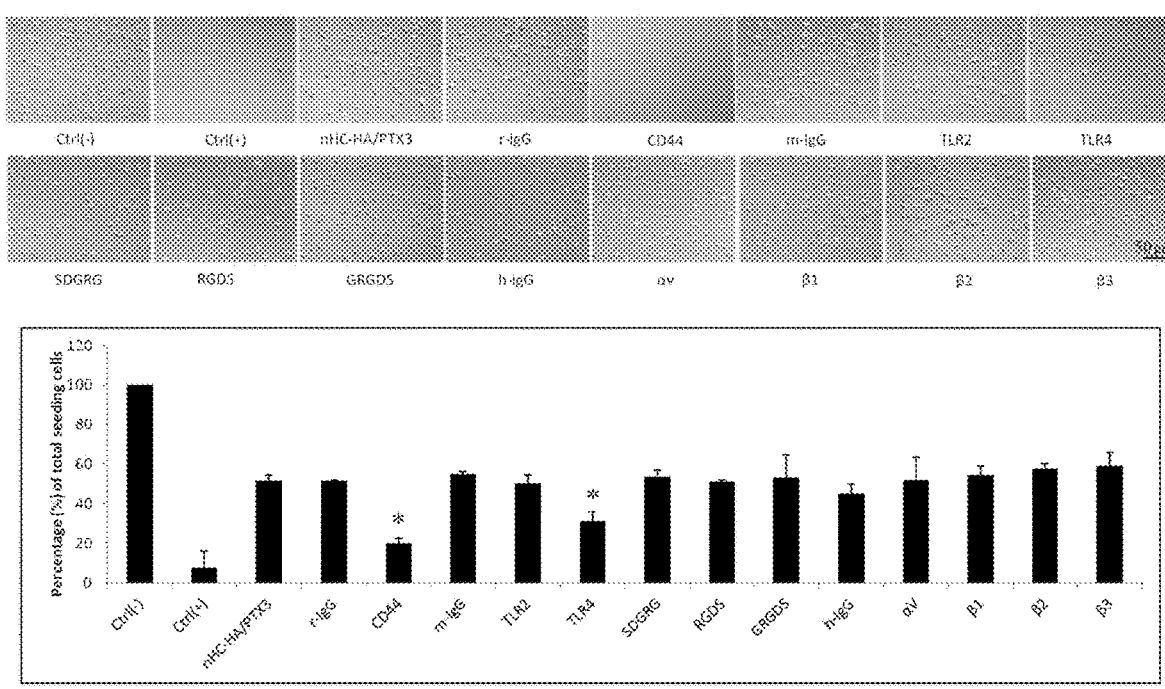

The ability of blocking antibodies and peptides to inhibit attachment of LPS-stimulated macrophages to immobilized nHC-HA/PTX3 was then examined. RAW264.7 cells (at concentration of 2.5×10$^5$ cells/ml) were pre-incubated in DMEM/10% FBS with the blocking antibodies against CD44 (10 μg/ml), TLR2 (10 μg/ml), TLR4 (10 μg/ml), integrin αv (20 μg/ml), β1 (20 μg/ml), β2 (20 μg/ml), or β3 (20 μg/ml) or RGD peptides (SDGRG, RGDS, GRGDS, all at 1 mg/ml), along with the isotype control antibodies [rat IgG (10 μg/ml), mouse IgG (10 μg/ml), or Armenian hamster IgG (20 μg/ml)] or a RGD control peptide (1 mg/ml), on ice for 30 min (n=3). (Antibodies to CD44 and rat IgG were from BD Pharmingen, San Diego, Calif.; antibodies to TLR2, TLR4, and mouse IgG were from InvivoGen, San Diego, Calif.; antibodies to integrin αv, β1, β2, β3, and Armenian hamster IgG were from Biolegend, San Diego, Calif.; RGD peptides were from Sigma-Aldrich, St Louis, Mo.). After adding LPS (1 μg/ml), cells were seeded into plates containing immobilized HA (2 μg/well), nHC-HA/PTX3(2 μg/well) or PBS control and incubated for 90 min (n=3). After incubation, unattached cells were removed and attached cells were photographed and counted by the CyQuant assay (FIG. 2C). The results showed that antibodies to CD44 and TLR4 significantly inhibited attachment of LPS-stimulated macrophages demonstrating that these receptors are involved in the attachment of LPS-stimulated macrophages to immobilized nHC-HA/PTX3.

Polarization of LPS-Stimulated Macrophages

Polarization of LPS-stimulated macrophages toward the M1 or M2 phenotype by immobilized nHC-HA/PTX3 was examined by determining the expression of genes encoding M1 and M2 markers by RNA and protein analysis.

Figure 3A:
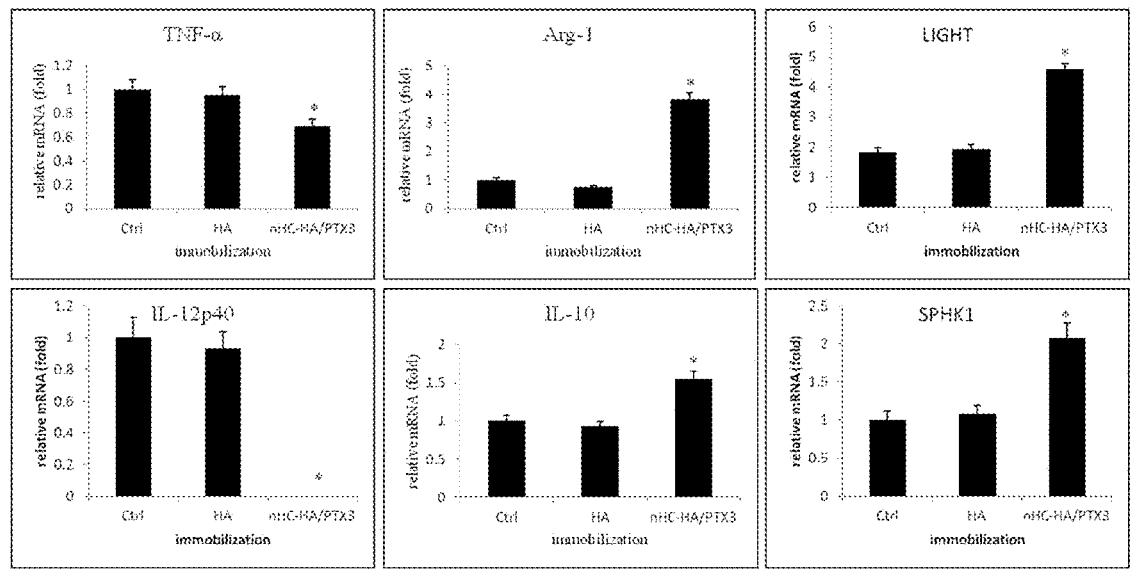
FIG. 3A-E exemplifies polarization of LPS-stimulated macrophages toward M2 phenotype by immobilized nHC-HA/PTX3. (A) Relative mRNA expression of M1 (TNF-$\alpha$, IL-12p40) or M2 (IL-10, Arg-1, LIGHT, and SPHK1) markers in macrophages bound to PBS control or immobilized HA or nHC-HA/PTX3 as determined by quantitative PCR. (B) Relative TNF-$\alpha$ protein amounts as determined by ELISA. (C) Western blot (left) and cytolocalization (right) by immunofluorescence staining of IRF5, which is a M1 marker, in macrophages bound to PBS control or immobilized nHC-HA/PTX3. (D) Apoptosis of resting, fMLP- or LPS-stimulated neutrophils following incubation with immobilized nHC-HA/PTX3. An asterisk (*) indicates p<0.05. (E) Phagocytosis of apoptotic neutrophils by resting or LPS-stimulated macrophages. An asterisk (*) indicates p<0.05.

RAW264.7 cells (100 μl of 2.5×10$^5$ cells/ml) in DMEM/10% FBS were seeded in 96-well plates containing immobilized HA (2 μg/well), nHC-HA/PTX3 (2 μg/well) or PBS control and stimulated with LPS (1 μg/ml) for 4 h (n=3). Following incubation, unattached cells were removed and total RNAs were extracted from the attached cells. The mRNA expression of M1 markers (Tumor necrosis factor alpha (TNF-α) (Mm00443258_ml) and interleukin 12 subunit p40 (IL-12p40) (Mm00434165_ml)) and M2 markers (interleukin-10 (IL-10) (Mm00439614_ml), Arginase-1 (Arg-1) (Mm00475988_ml), LIGHT/TNSF14 (Mm00444567_ml, and Sphingosine kinase-1(SPHK1) (Mm0044884_g1)) were measured by quantitative real-time PCR with glceraldehyde-3-phosphate dehydrogenase (GAPDH) (Mm99999915_g1) as the endogenous control. The real-time PCR was performed on 7300 Real-time PCR System (Applied Biosystems, Foster City, Calif.). The amplification program consisted of 10 min of initial activation at 95° C. followed by 40 cycles of 15 sec denaturation at 95° C., and 1 min annealing and extension at 60° C. The relative gene expression data was analyzed by the comparative CT method (ΔΔCT). All assays were performed in triplicate; the results were normalized by GAPDH as an internal control. All primers were from Applied Biosystems. Significant induction of expression of the M2 markers IL-10, Arg-1, LIGHT, and SPHK1 compared to the control was observed in cells attached to immobilized nHC-HA/PTX3, but not HA (FIG. 3A). In addition, expression of both M1 markers, TNF-α and IL-12p40, was reduced.

The amount of secreted TNF-α protein was measured in culture supernatants of cells treated with LPS (1 μg/ml) stimulation for 4 h in DMEM/10% FBS on plates containing immobilized HA (2 μg/well), nHC-HA/PTX3(2 μg/well) or PBS control as described above (n=3). The amount of TNF-α was measured by ELISA according to the manufacturer's protocol (R&D Systems, Minneapolis, Minn.).

Figure 3B:
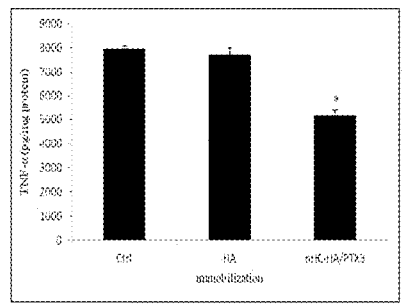

A reduced amount of TNF-α was observed in the cell culture supernatants of cells incubated on plates containing immobilized nHC-HA/PTX3 compared to PBS control (FIG. 3B). No change in the amount of TNF-α was observed on the immobilized HA plate.

Figure 3C:
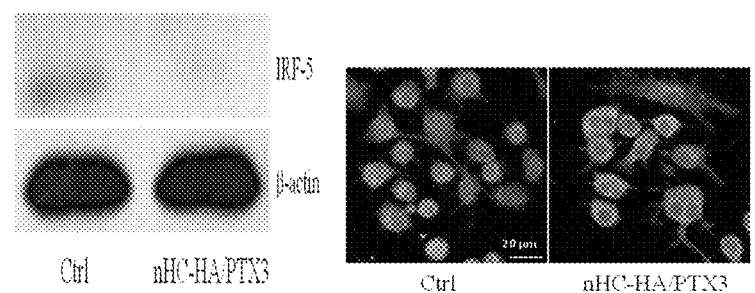

High expression of IRF-5 is characteristic of M1 macrophages. IRF-5 directly activates transcription of the genes encoding IL-12p40, IL-12p35 and IL-23p19 and represses the gene encoding IL-10. Expression of IRF-5 protein and its cytolocalization on immobilized nHC-HA/PTX3 was examined. Cells seeded on the immobilized control or nHC-HA/PTX3 were stimulated with LPS (1 μg/ml) for 4 or 24 h in DMEM/10% FBS. The expression of IRF-5 protein in cell lysates (LPS stimulation for 24 h) was detected by Western blot (FIG. 3C, left) (primary antibody: abcam, Cambridge, Mass.; secondary antibody, DAKO, Carpinteria, Calif.). In a parallel experiment, cells (LPS stimulation for 4 h) were fixed and immunostained with anti-IRF-5 antibody. The cytolocalization of IRF-5 was examined by confocal immunofluorescence microscopy (LSM 700 confocal microscope, Zeiss, Oberkochen, Germany) (FIG. 3C, right). Immobilized nHC-HA/PTX3 reduced expression and prevented nuclear localization of IRF-5. These results are consistent with the suppression of the M1 phenotype by immobilized nHC-HA/PTX3.

Figure 3D:
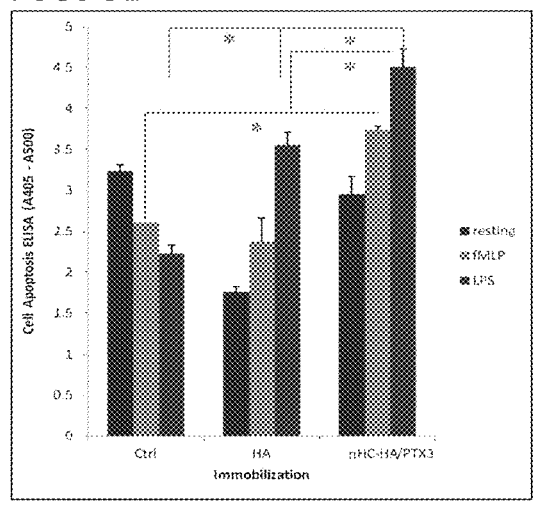

Apoptosis of Activated Neutrophils and Macrophage Phagocytosis of Apoptotic Neutrophils Neutrophils were isolated from the normal human peripheral blood using the dextran density [Lymphocyte Poly(R), Cedarlane USA, Burlington, N.C.] centrifugation according to the manufacturer's instruction. Isolated neutrophils were seeded at $2\times10^6$ cells/ml in IMDM (Iscove's Modified Dulbecco's Medium, Life Technologies, Grand Island, N.Y.) on immobilized HA (2 µg/well), nHC-HA/PTX3(2 µg/well) or PBS control and treated with PBS (resting), N-formyl-methionyl-leucyl-phenylalanine (fMLP) (1 µM) (Sigma-Aldrich, St Louis, Mo.) or LPS (1 µg/ml) for 24 h (n=3). Apoptosis of neutrophils was determined by Cell Death Detection ELISA (Roche Applied Science, Indianapolis, Ind.) in cell lysates according to the manufacturer's protocol. Immobilized nHC-HA/PTX3, but not HA, promotes apoptosis of fMLP or LPS-activated neutrophils but not resting neutrophils (FIG. 3D).

Figure 3E:
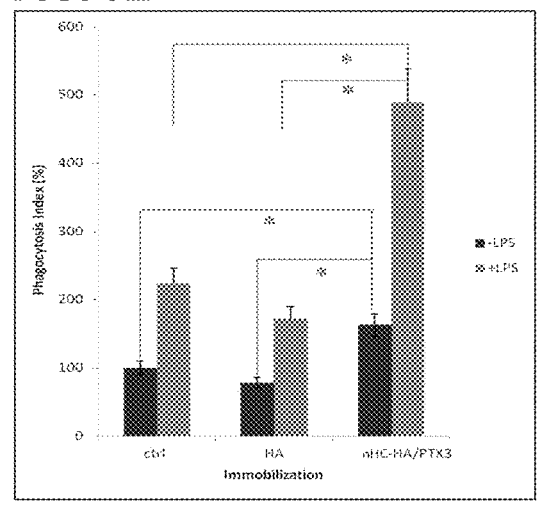

Phagocytosis of apoptotic neutrophils by resting or LPS-stimulated macrophages was then examined. RAW264.7 cells ($1\times10^5$ cells/ml) were cultivated in DMEM/10% FBS on the immobilized HA (2 µg/well), nHC-HA/PTX3 (2 µg/well) or PBS control without or with LPS (1 µg/ml) stimulation for 6 days (n=3). The cell culture medium was then removed, and 100 µl of $2\times10^6$ cells/ml of apoptotic neutrophils in IMDM (prepared by treatment of isolated resting human neutrophils with roscovitine (20 µM) (Sigma-Aldrich, St Louis, Mo.) for 8 h) were added to each well containing resting or LPS-stimulated macrophages. After incubation for 30 min at 37° C., each well was washed three times with the cold PBS, and cell lysates (including macrophages and phagocytosed neutrophils) were collected to determine human myeloperoxidase (MPO) activity by the ELISA assay to measure phagocytosed neutrophils by macrophages. Cell lysates were collected and subjected to human myeloperoxidase (MPO) ELISA assay (n=4) (R&D Systems, Minneapolis, Minn.) according to the manufacturer's protocol. MPO was then normalized with total protein measured by BCA protein assay (Thermo Fisher Scientific, Rockford, Ill.) in respective cell lysate and expressed as phagocytosis index. The phagocytosis index of resting cells without LPS (−LPS) stimulation was defined as 100% in this experiment. Immobilized nHC-HA/PTX3, but not HA, promoted phagocytosis of apoptotic neutrophils by either resting or LPS-treated macrophages (FIG. 3E).

These results demonstrate that immobilized nHC-HA/PTX3 ($2^{nd}$) enhances the apoptosis of activated neutrophils and phagocytosis of apoptotic neutrophils by macrophages.

Analysis of Receptors Involved in Polarization of M2 Macrophages by Immobilized nHC-HA/PTX3

Figure 4A:
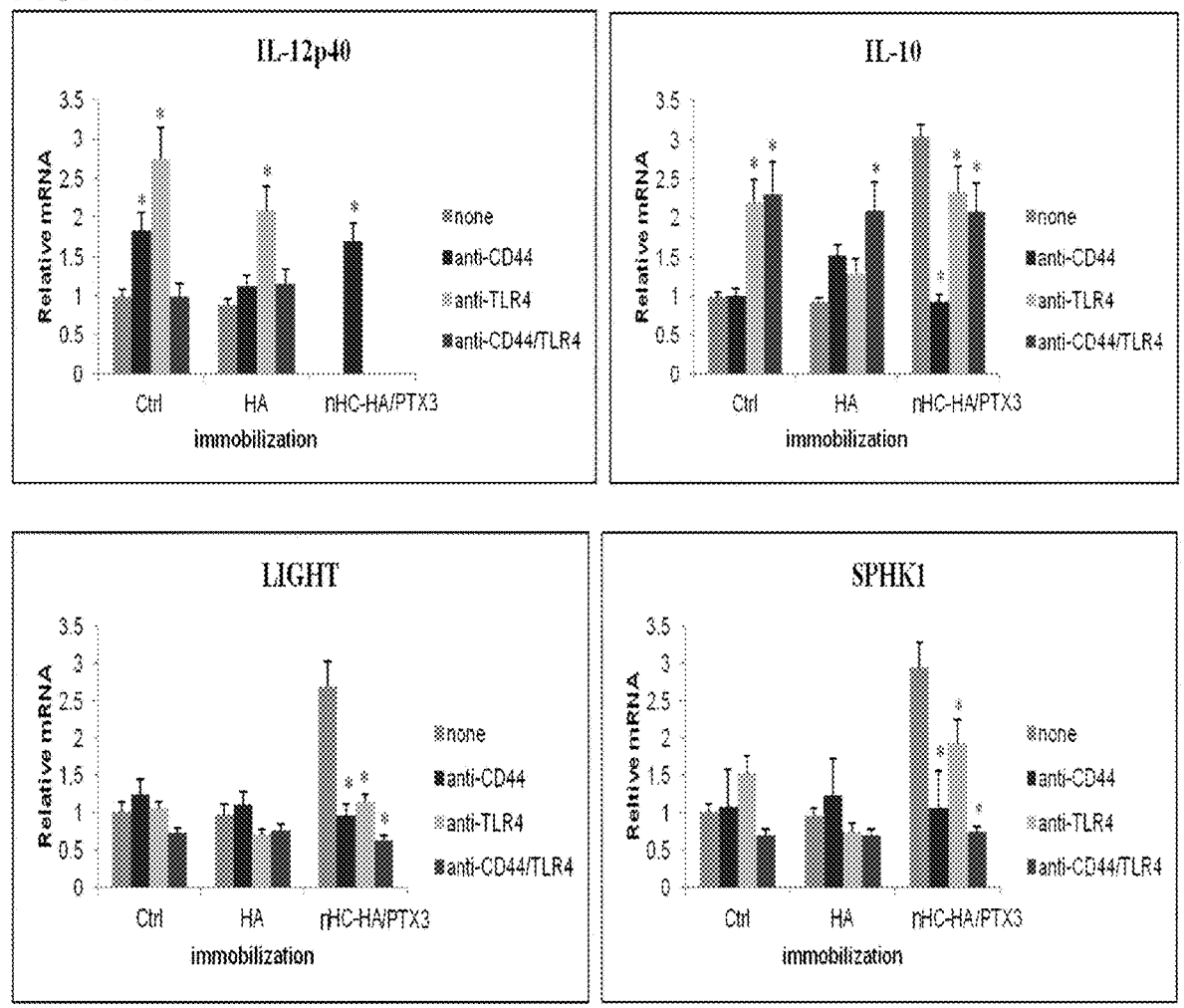
FIG. 4A-B exemplifies the role of CD44 in maintaining M2 macrophage polarization on immobilized nHC-HA/PTX3. (A) Relative mRNA expression of M1 (IL-12p40) and M2 (IL-10, LIGHT, and SPHK1) macrophage markers following binding of macrophages, pre-incubated with PBS or blocking antibodies to CD44, TLR4, or CD44/TLR4, to nHC-HA/PTX3 as determined by qPCR. An asterisk (*) indicates p<0.05 compared to no antibody treatment (none) in the same group. (B) IL-12 and IL-10 protein amounts as determined by ELISA. An asterisk (*) indicates p<0.05 compared to no antibody treatment (none) in the same group.

In order to determine the involvement of particular receptors in M2 macrophage polarization, quantitative mRNA expression of M1 and M2 macrophage markers in the presence or absence of receptor blocking antibodies was performed. RAW264.7 cells ($2.5\times10^5$ cells/ml) in DMEM/10% FBS were pre-incubated with PBS (control) or blocking antibodies to CD44 (10 µg/ml), TLR4 (10 µg/ml), or CD44/TLR4 (each at 10 µg/ml) for 30 min on ice (n=3). Cells were then stimulated with LPS (1 µg/ml) and incubated at 37° C. for 4 h on immobilized HA (2 µg/well), nHC-HA/PTX3 (2 µg/well) or PBS control. Total RNAs were extracted from the total cells. The relative mRNA expression of M1 marker (IL-12p40) and M2 markers (IL-10, LIGHT, and SPHK1) were determined by quantitative PCR with GAPDH as the endogenous control as described above (FIG. 4A). Expression of IL-12p40 was abolished while that of IL-10, LIGHT and SPHK1 was promoted by immobilized nHC-HA/PTX3, but not HA. This expression pattern was inhibited more by the CD44 blocking antibody than the TLR4 blocking antibody. In contrast, expression of IL-12p40 and IL-10 transcript by immobilized HA was affected more by the blocking antibody against TLR4 than that against CD44.

Figure 4B:
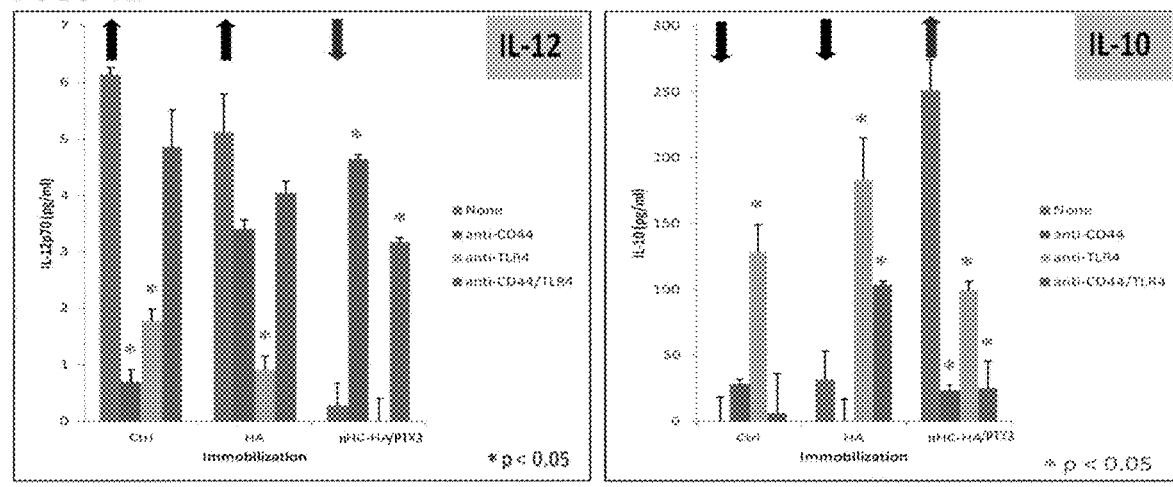

Protein expression of IL-12 and IL-10 also was determined. Cell culture supernatants were collected from cells cultivated on immobilized HA (2 µg/well), nHC-HA/PTX3 (2 µg/well) or PBS control treated as described above except for 24 h (instead of 4 h) (n=3). The amount of IL-12 or IL-10 protein in the cell culture supernatants was determined by ELISAs (Biolegend, San Diego, Calif.) according to the manufacturer's protocol (FIG. 4B). Expression of IL-12 protein is abolished while that of IL-10 protein is markedly promoted by immobilized nHC-HA/PTX3. This expression pattern is inhibited by the blocking antibody against CD44. In contrast, expression of IL-12 protein is promoted while that of IL-10 is suppressed by immobilized HA, and the expression pattern was affected more by the blocking antibody against TLR4.

Figure 5A:
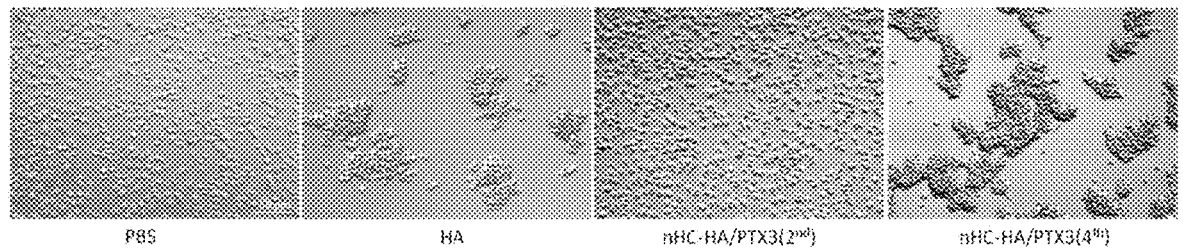
FIG. 5A-C exemplifies nHC-HA/PTX3($4^{th}$) promotes the cell aggregation, but both nHC-HA/PTX3($2^{nd}$) and nHC-HA/PTX3($4^{th}$) inhibit the production of IL-12p40 and IL-23 proteins in IFN-$\gamma$/LPS-stimulated macrophages RAW264.7 cells ($2.5 \times 10^5$/ml) were cultivated on immobilized substrates (PBS as the control) and stimulated with IFN-$\gamma$/LPS for 4 h (A) or 24 h (B and C). (A) Cell morphology at 4 h after seeding. Alternatively, cells are stimulated with LPS for 24 h and proteins of IL-10 and IL-12p70 in the cell culture supernatants were measured by respective ELISAs (B and C). p values are indicated in B and C.

Comparison of nHC-HA/PTX3(2nd) and nHC-HA/PTX3 (4th) Complexes nHC-HA/PTX3 (2nd) and nHC-HA/PTX3 (4th) complexes were compared by examining the ability of each complex to induce cell aggregation of macrophages (indicative of poor cell attachment) and/or promote M2 macrophage polarization. RAW264.7 cells ($2.5\times10^5$ cells/ml) were cultivated in DMEM/10% FBS on immobilized HA (2 µg/well), nHC-HA/PTX3 (2 µg/well) or PBS control and stimulated with 200 units/ml IFN-γ/1 µg/ml LPS (Both were from InvivoGen, San Diego, Calif.) for 4 h or 24 h (n=3). After 4 hours, cell aggregation was examined by light microscopy and photographed (FIG. 5A). Immobilized nHC-HA/PTX3 (4th), but not nHC-HA/PTX3 (2nd), promotes cell aggregation of macrophages, indicating that nHC-HA/PTX3 (4th) does not promote cell attachment to the plate while nHC-HA/PTX3(2nd) does.

Figure 5B:
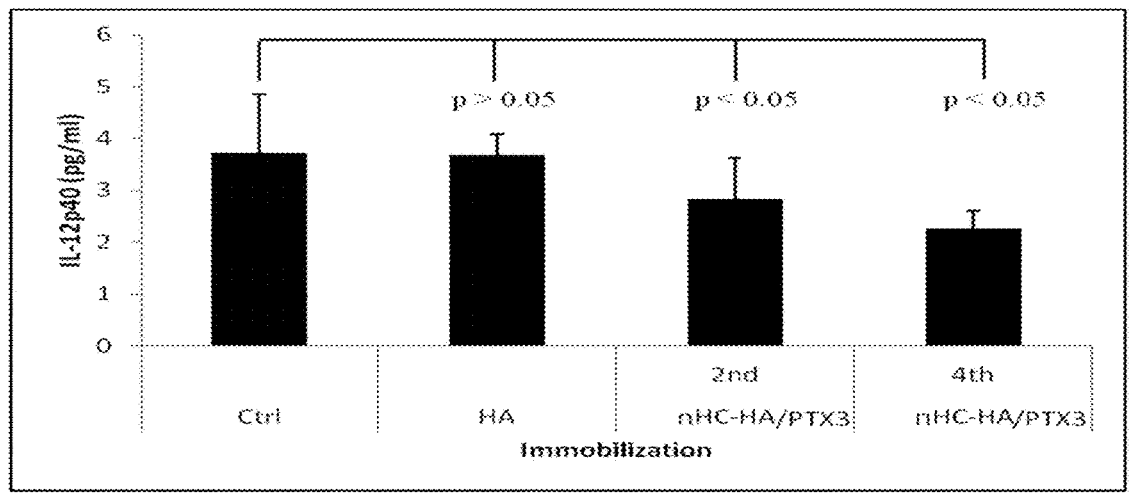
Figure 5C:
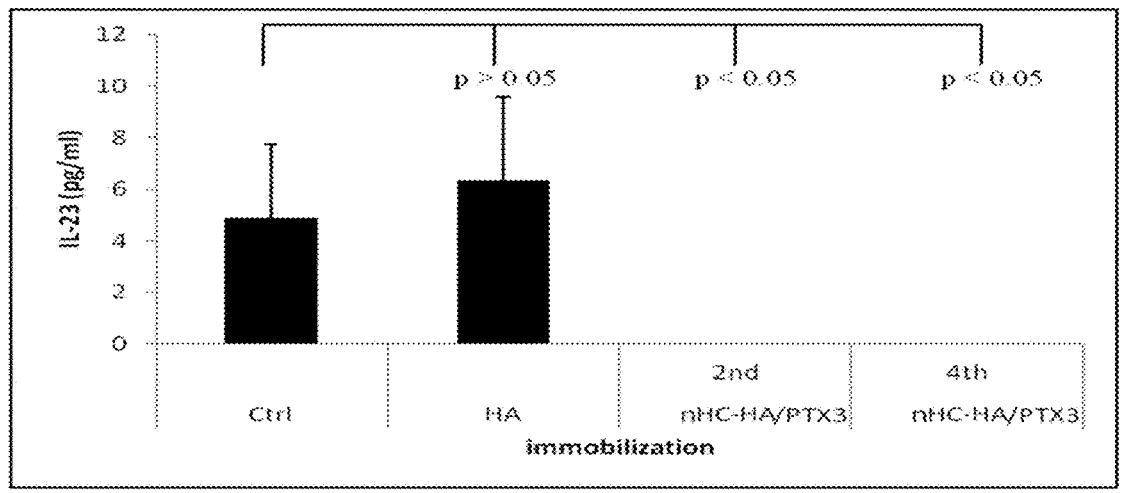

After 24 h, samples were obtained from cell culture supernatants and IL-12p40 protein and IL-23 protein concentration was measured by respective ELISAs (Biolegend, San Diego, Calif.) according to the manufacturer's protocol (FIGS. 5B and 5C). Both nHC-HA/PTX3(2nd) and nHC-HA/PTX3(4th) inhibit the production of IL-12p40 and IL-23 proteins in IFN-γ/LPS-stimulated macrophages.

Figure 7A:
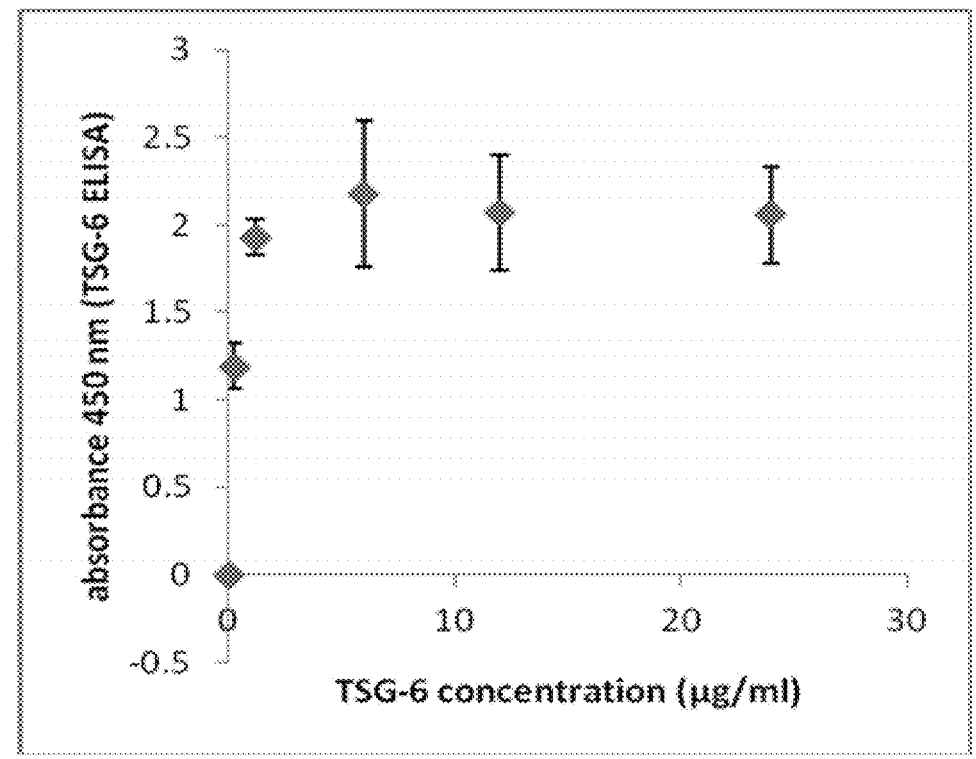
FIG. 7A-B exemplifies dose-dependent binding of TSG-6 to immobilized HA (iHA) and resistance to various dissociating and reducing agents. (A) TSG-6 bound to iHA as measured by TSG-6 ELISA. (B) TSG-6 bound to iHA as measured by TSG-6 ELISA following treatment with 6M Guanidine HCl, 8M Guanidine HCl, 2% SDS, 100 mM DTT, or 25 mM NaOH.

Example 4. In Vitro Binding of TSG-6 and PTX3 to Immobilized HA (iHA) in the Absence of IαI Binding of TSG-6 to iHA Immobilized HA (2 µg/well input) was prepared as described above. A series of human TSG-6 (overexpression in mouse myeloma cell line NS0 with Trp18 to Leu277 of human TSG-6, with a C terminal 10 His tag, Accession # P98066; R&D Systems, Minneapolis, Minn., Cat. No. 2104-TS) concentrations (0, 0.24, 1.2, 6, 12, and 24 µg/ml, 100 µl volume per well) were incubated with iHA for 2 h at 37° C. in the reaction buffer (5 mM $MgCl_2$ in PBS, pH 7.5). Unbound TSG-6 was removed by washes of 8 M Guanidine-HCl and PBS. The bound TSG-6 was measured by modified TSG-6 ELISA (R&D Systems, Minneapolis, Minn.). Because TSG-6 was already bound to iHA coupled in wells, the steps of incubating samples with pre-coated TSG-6 antibody were omitted. The subsequent steps were according to the manufacturer's protocol (FIG. 7A). TSG-6 dose-dependently bound iHA and reached its maximal binding capacity at about 6 µg/ml (or 0.6 µg in 0.1 ml of the reaction solution) when iHA was about 1.4 µg (2 µg HA per well based on the coupling efficiency of ~70%). The molar ratio of TSG-6 to HA was about 37:1 based on TSG-6 being 35 kDa and HA being 3,000 kDa.

Figure 7B:
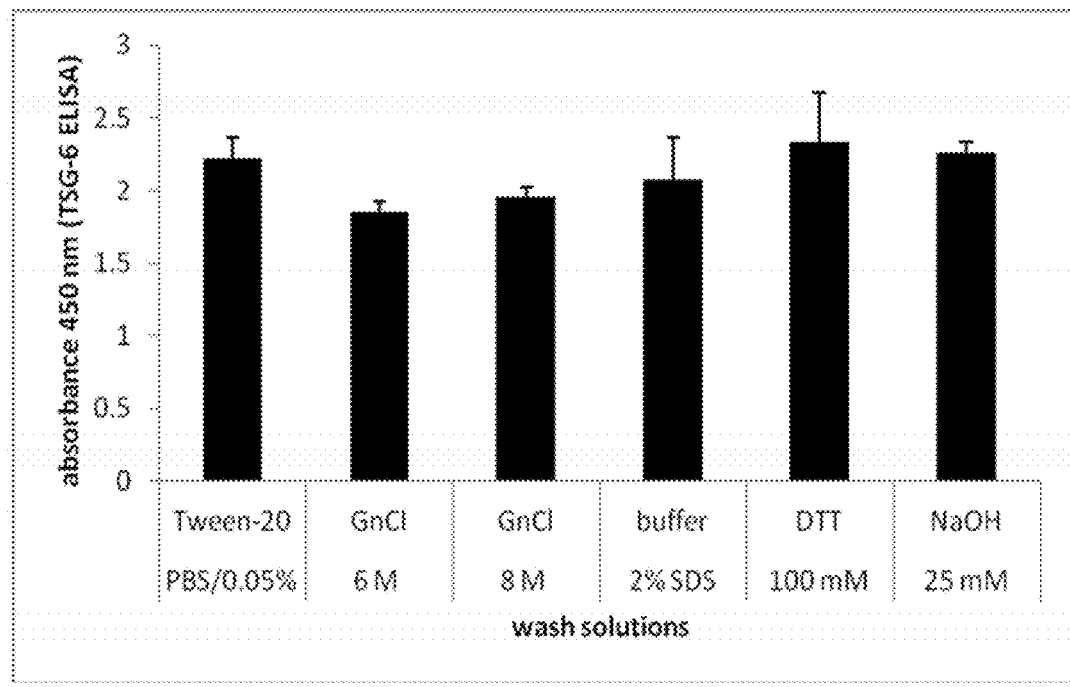

The ability of TSG-6/iHA complex to resist dissociation was then examined. iHA (2 µg/well input) was prepared as described above. TSG-6 (6 µg/ml in 100 µl) was incubated with iHA for 2 h at 37° C. Unbound TSG-6 was removed by washes with PBS (as a control) or with different dissociating or reducing agents: 6M Guanidine HC1/PBS, 8M Guanidine HC1/PBS, 2% SDS/PBS, 100 mM DTT/PBS, and 25 mM NaOH/H$_2$O. The bound TSG-6 was measured by modified TSG-6 ELISA as described above (FIG. 7B). The formed TSG-6/iHA complex was stable and was resistant to the treatment with the various dissociating or/and reducing agents. No statistical significance was noted among all groups.

Binding of PTX3 to iHA

Figure 8A:
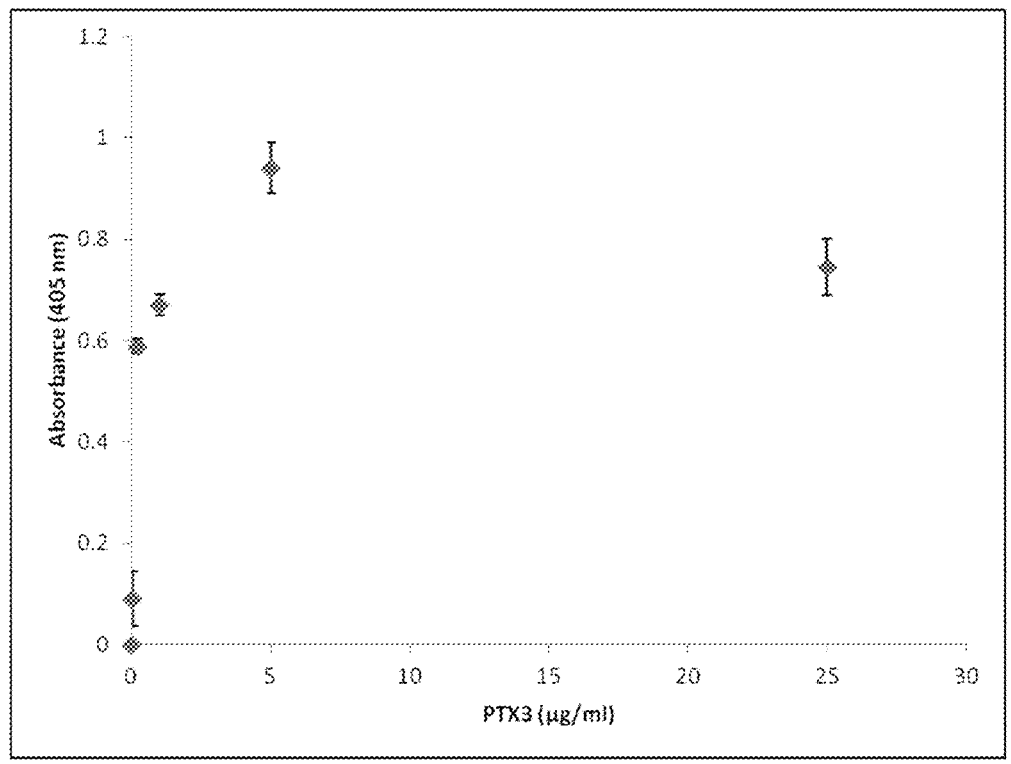
FIG. 8A-B exemplifies dose-dependent binding of PTX3 to immobilized HA (iHA) and resistance to various dissociating and reducing agents. (A) PTX3 bound to iHA as measured by PTX3 ELISA. (B) PTX3 bound to iHA as measured by PTX3 ELISA following treatment with 6M Guanidine HCl, 8M Guanidine HCl, 2% SDS, 100 mM DTT, or 25 mM NaOH.

Immobilized HA (2 µg/well input) was prepared as described above. A series of PTX3 (overexpression in mouse myeloma cell line NS0 with Glu18 to Ser277 of human PTX3, with a C terminal 6 His tag, Accession # P26022; R&D Systems, Minneapolis, Minn.) concentrations (0, 0.04, 0.2, 1, 5, and 25 µg/ml, 100 µl volume per well) were incubated with iHA for 2 h at 37° C. in the reaction buffer (5 mM MgCl$_2$ in PBS, pH 7.5). Unbound PTX3 was removed by washes with 8M GnHC1 and PBS. The bound PTX3 was measured by modified PTX3 ELISA (R&D Systems, Minneapolis, Minn.). Because PTX3 was already bound to iHA coupled in wells, the steps of incubating samples with pre-coated PTX3 antibody were omitted. The subsequent steps were according to the manufacturer's protocol (FIG. 8A). PTX3 dose-dependently bound iHA and reached the maximal binding capacity at about 5 µg/ml (or 0.5 µg in 0.1 ml of the reaction solution) when iHA was about 1.4 µg (2 µg HA per well based on the coupling efficiency of 70%) The molar ratio of PTX3 to HA was about 24:1 based on PTX3 being 45 kDa and HA being 3,000 kDa.

Figure 8B:
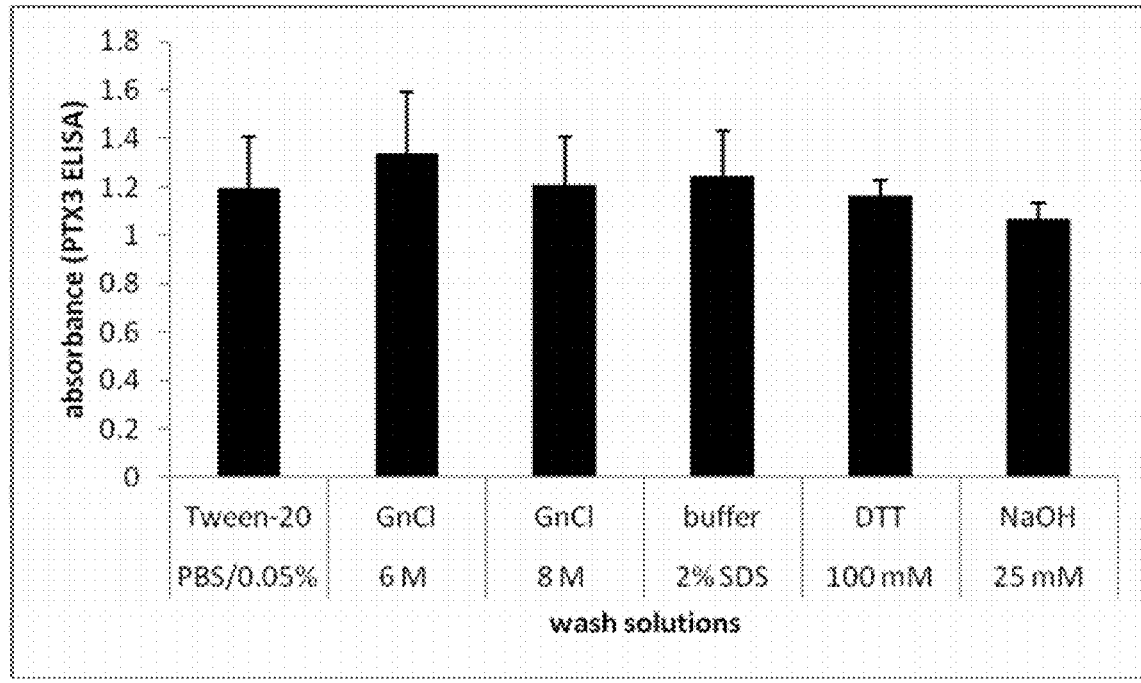

The ability of PTX3/iHA complex to resist dissociation was then examined. iHA (2 µg/well input) was prepared as described above. PTX3 (5 µg/ml in 100 µl) was incubated with iHA for 2 h at 37° C. Unbound PTX3 was removed by washes with PBS (as a control) or with different dissociating or reducing agents: 6M Guanidine HC1/PBS, 8M Guanidine HC1/PBS, 2% SDS/PBS, 100 mM DTT/PBS, and 25 mM NaOH/H$_2$O. The bound PTX3 was measured by modified PTX3 ELISA as described above (FIG. 8B). The formed PTX3/iHA complex was stable and was resistant to the treatment with the various dissociating or/and reducing agents. No statistical significance was noted among all groups.

Figure 9:
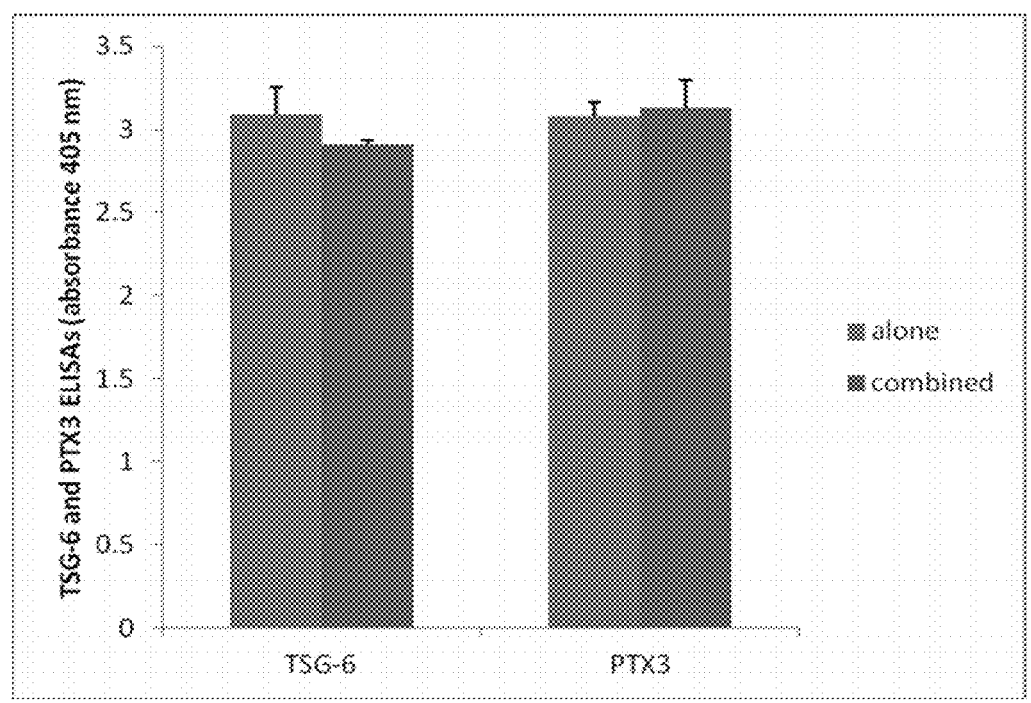
FIG. 9 exemplifies the lack of competition or synergy between TSG-6 and PTX3 for binding iHA. The relative absorbance as measured by ELISA is shown for bound TSG-6 or PTX3 for incubation of each factor alone with iHA or combined incubation with iHA. No statistical significance is found between alone and combined for either TSG-6 or PTX3 binding to iHA (p>0.05).

Simultaneous Binding of TSG-6 and PTX3 to iHA iHA (2 µg/well input) was prepared as described above. 6 µg/ml of TSG-6 and 5 µg/ml of PTX3 (concentrations for maximal binding as described above) were incubated with iHA either alone or combined in the reaction buffer (5 mM MgCl$_2$ in PBS, pH 7.5). The bound TSG-6 or PTX3 was measured by respective modified ELISA as described above. There was no competition or synergy for binding to iHA by TSG-6 or PTX3 when both proteins were incubated with iHA simultaneously as compared to that when TSG-6 or PTX3 was added alone (p>0.05). These data indicated that the binding sites on iHA for TSG-6 and PTX3 are different and might not overlap (FIG. 9).

Sequential Binding of TSG-6 and PTX3 to iHA

Sequential addition of TSG-6 and PTX3 to iHA was examined to determine whether pre-bound TSG-6 or PTX3 would inhibit binding of the other protein to iHA. 6 µg/ml of TSG-6 or 5 µg/ml of PTX3 were pre-bound to iHA, prepared as described above. After washes with 8M GnHC1 and PBS, serial concentrations of PTX3 (0, 5, or 5 µg/ml) or TSG-6 (0, 1.2, or 6 µg/ml) were subsequently incubated with pre-bound TSG-6/iHA or pre-bound PTX3/iHA in the reaction buffer (5 mM MgCl$_2$ in PBS, pH 7.5)), respectively. The subsequently bound TSG-6 and PTX3 were measured by respective modified ELISAs.

Figure 10A:
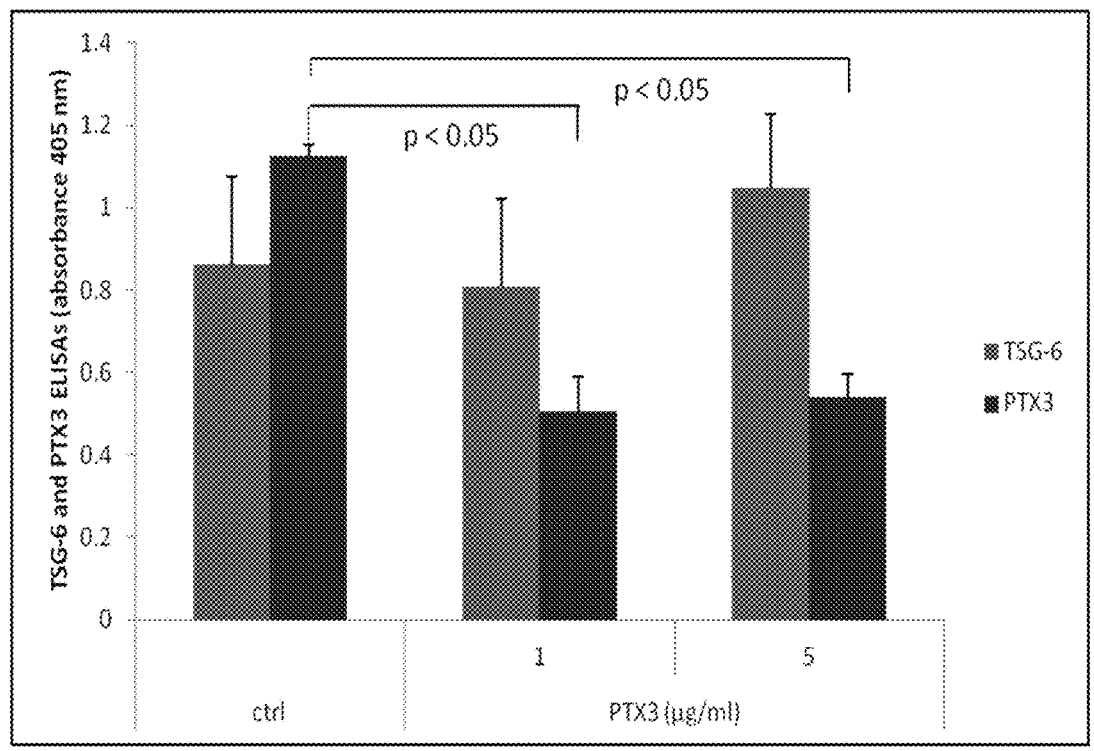
FIG. 10A-B exemplifies partial inhibition of PTX3 binding to iHA pre-bound with TSG-6 and lack of inhibition of TSG-6 binding to iHA pre-bound with PTX3. The figure shows TSG-6 and PTX3 ELISA results of subsequent binding of TSG-6 or PTX3 for pre-bound TSG-6/iHA (A) or pre-bound PTX3/iHA (B). P values are indicated in (A) and no statistical significance was found among groups in (B).
Figure 10B:
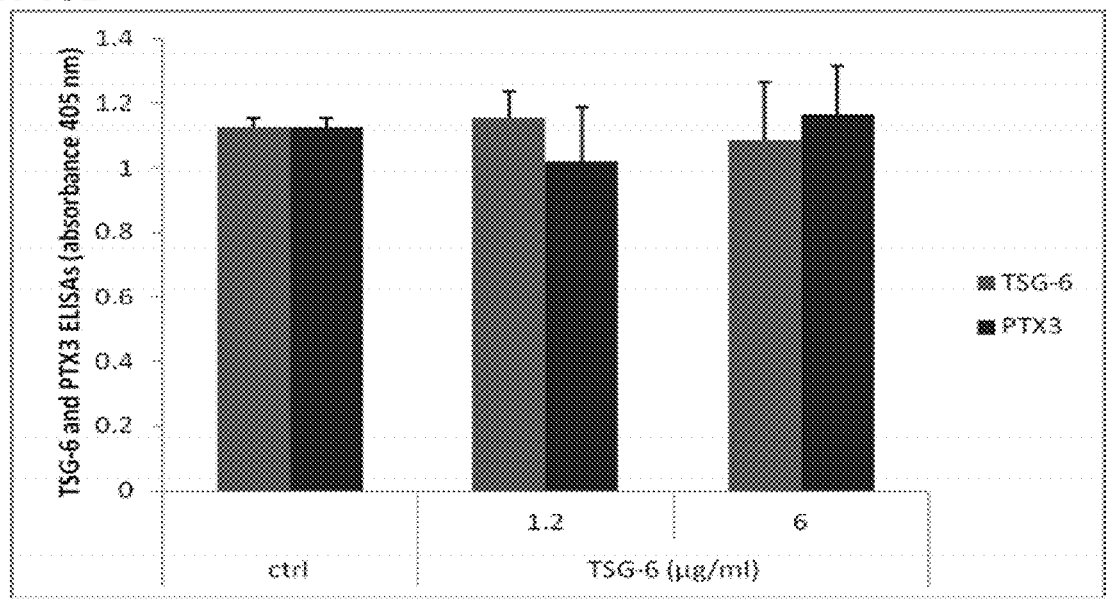

Pre-bound TSG-6 (6 µg/ml) partially prevented subsequent PTX3 from binding to iHA (FIG. 10A) (p=0.05 and 0.01 when subsequent PTX3 was added at 1 µg/ml and 5 µg/ml, respectively) (FIG. 5A). Pre-bound PTX3 (5 µg/ml) did not interfere with the subsequent TSG-6 binding to iHA (p=0.56 and 0.74 when subsequent TSG-6 was added at 1.2 µg/ml and 6 µg/ml, respectively) (FIG. 10B). These data indicate that iHA is structurally changed after TSG-6 binding so that it interferes with subsequent PTX3 binding.

Example 5. Attachment of LPS-Stimulated Macrophages to Immobilized TSG-6/iHA and PTX3/iHA Complexes Covalink-NH 96 wells were covalently coupled with PBS (control), HA (iHA), or native HC-HA/PTX3 (nHC-HA/PTX3) as described above. TSG-6 (6 µg/ml) or PTX3 (5 µg/ml) was then added and bound to iHA. RAW264.7 macrophages (100 µl of 1×10$^5$ cells/ml) in DMEM/10% FBS were seeded into each coupled well and treated with 1 µg/ml LPS. After incubation for 24 h, cell morphology was photographed.

Figure 11:
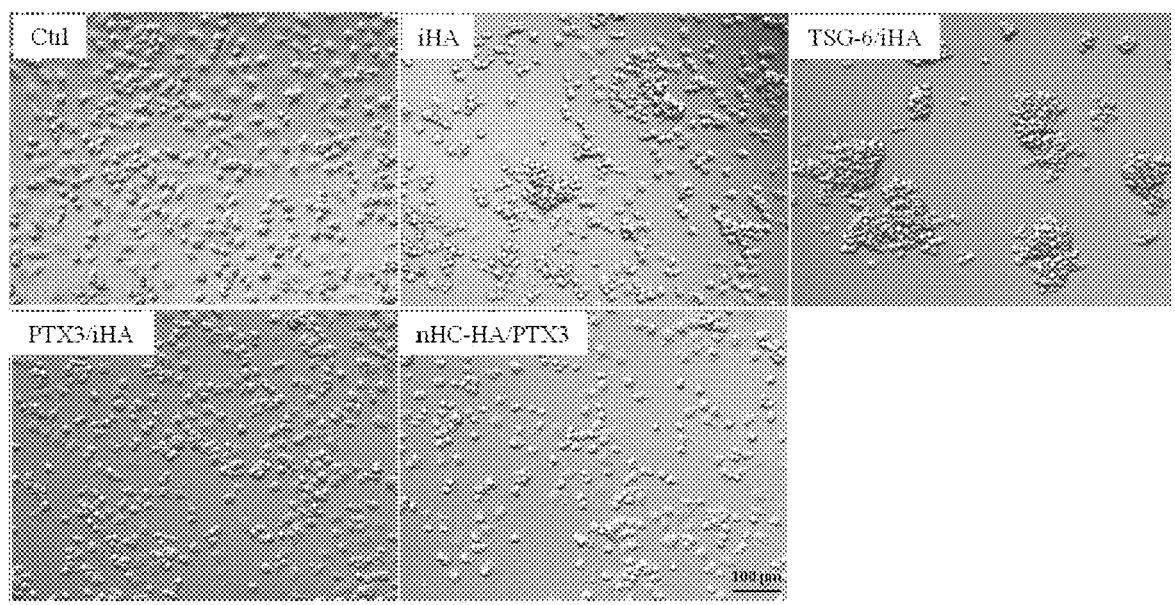
FIG. 11 exemplifies attachment of LPS-stimulated RAW264.7 macrophages to PBS (control), HA (iHA), nHC-HA/PTX3, TSG-6/iHA or PTX3/iHA. Cells were photographed 24 after incubation.

Macrophages attached poorly (i.e., resulting in more aggregated cells) to iHA when compared to the plastic control. Such attachment was further hampered by TSG-6/iHA, resulting in high number of and larger aggregations of cells. In contrast, PTX3/iHA promoted cell attachment, resulting in a similar pattern to that shown on immobilized nHC-HA/PTX3 (FIG. 11).

Example 6. Regulation of M1 and M2 Markers by TSG-6/iHA and PTX3/iHA Complexes

RAW264.7 cells were cultivated as in Example 5 and stimulated with 1 µg/ml LPS for 4 h on PBS (control), immobilized HA (iHA), TSG-6/iHA, PTX3/iHA, or nHC-HA/PTX3. Total RNAs were isolated from cells and mRNA expression of the M2 marker IL-10 and the M1 marker IL-12p40 were measured by quantitative PCR (FIGS. 12A and 12D) as described above. Alternatively, the cells were stimulated with 1 µg/ml LPS (FIGS. 12B and 12E) or IFN-γ/LPS (FIG. 12C) for 24 h, and protein expression of IL-10, IL-12p70, and IL-23 were measured in cell culture media using respective ELISAs.

Figure 12A:
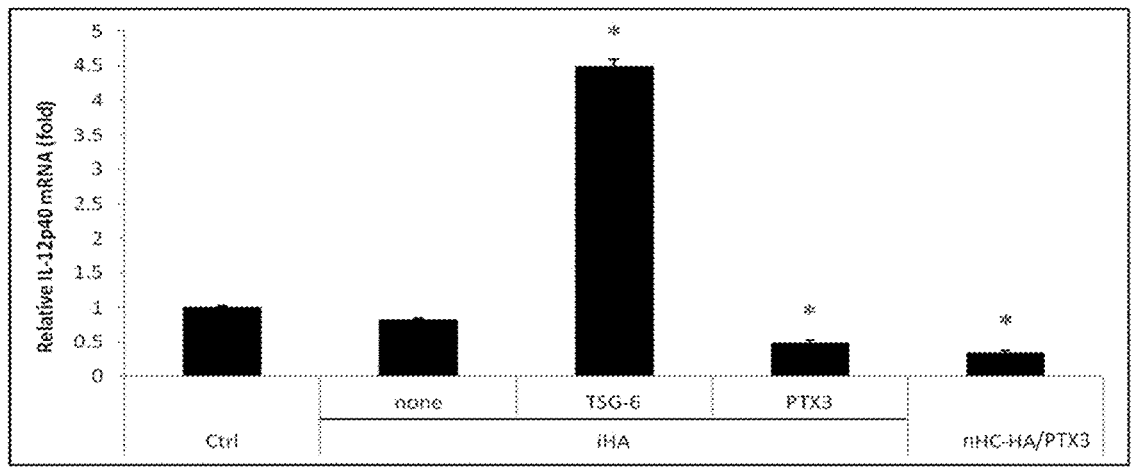
FIG. 12A-E exemplifies relative gene expression in RAW264.7 macrophages following incubation on PBS (control), HA (iHA), nHC-HA/PTX3, TSG-6/iHA or PTX3/iHA. Total RNAs were isolated and mRNA expression of IL-12p40 (A) and IL-10 (D) were measured by quantitative PCR. Alternatively, cells were stimulated with LPS (B and E) or IFN-$\gamma$/LPS (C) for 24 h, and protein expression of IL-12p70 (B), IL-23 (C), and IL-10 (E) in cell culture media were measured using respective ELISAs. An asterisk (*) indicates p<0.05 compared to the control.
Figure 12B:
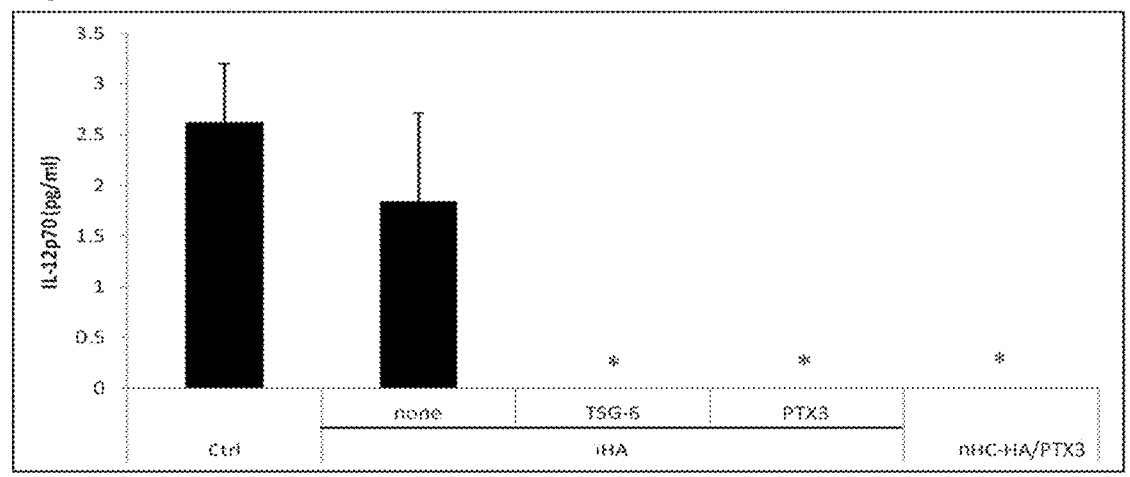
Figure 12C:
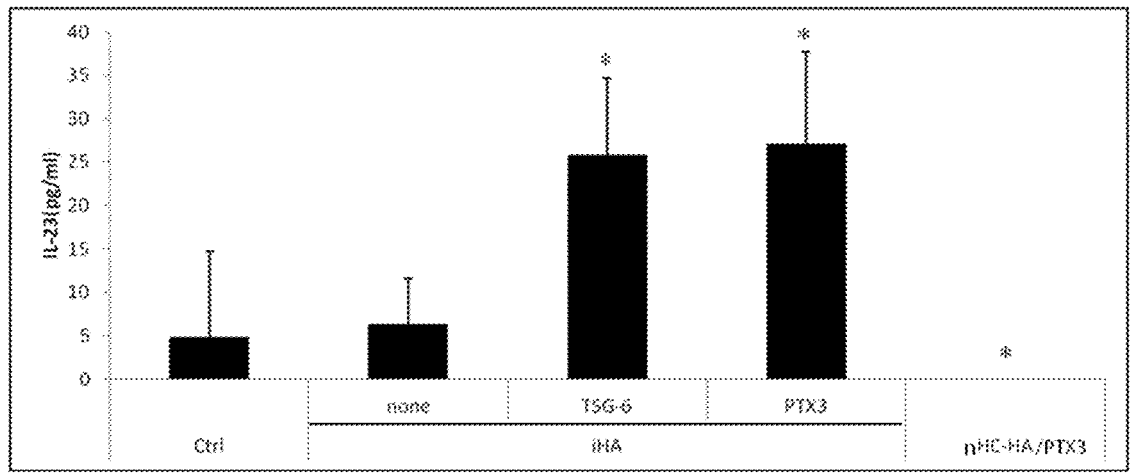

The expression of IL-12p40 mRNA (one of two subunits of IL-12p70) was not significantly changed on iHA (none) compared to that of the control (Ctrl) (p>0.05) (FIG. 12A). In contrast, IL-12p40 mRNA was significantly upregulated on TSG-6/iHA (p<0.01), but significantly downregulated on PTX3/iHA and nHC-HA/PTX3 (p<0.05) (FIG. 12A). The expression of IL-12p70 protein, however, was only detectable without any significant difference (p>0.05) on the control or iHA alone, but is undetectable on TSG-6/iHA, PTX3/iHA, and nHC-HA/PTX3 (FIG. 12B). IL-12p40 also serves as a subunit of IL-23. It was observed that expression of IL-23 protein was significantly upregulated on TSG-6/iHA and PTX3/iHA ($p<0.01$), but is undetectable on nHC-HA/PTX3 ($p<0.05$) (FIG. 12C). These data indicate that both TSG-6/iHA and PTX3/iHA are effective in suppressing IL-12 but not IL-23.

Figure 12D:
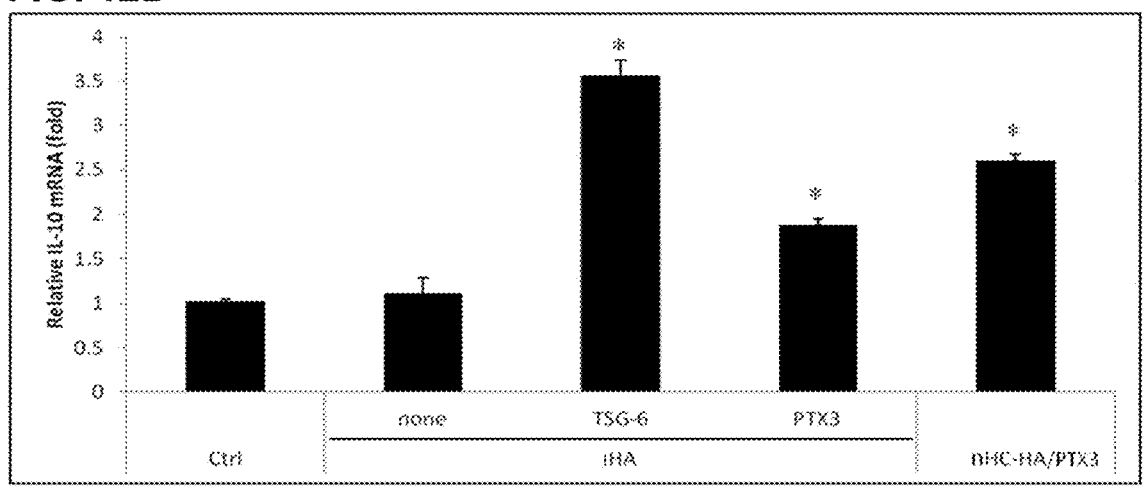
Figure 12E:
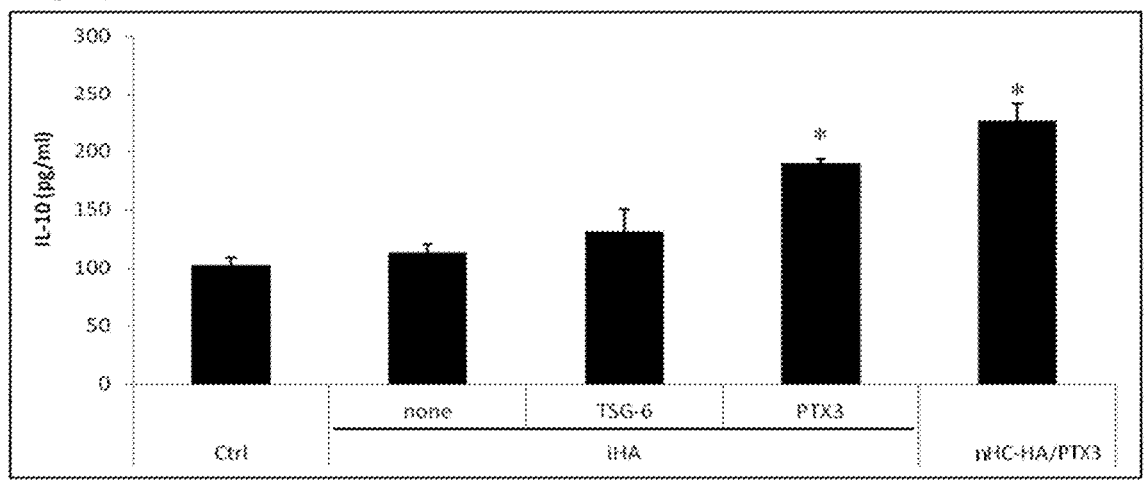

The expression of IL-10 mRNA by RAW264.7 cells was not significantly changed on iHA alone compared to the control ($p>0.05$), but was significantly upregulated on TSG-6/iHA, PTX3/iHA, and nHC-HA/PTX3 ($p<0.05$) (FIG. 12D). The expression of IL-10 protein, however, is only significantly upregulated on PTX3/iHA similar to the positive control of immobilized nHC-HA/PTX3 ($p<0.05$) (FIG. 12E). These data suggest that following different patterns of cell attachment (Example 5), resultant cells exhibit different functions, and that PTX3/iHA is more effective than TSG-6/iHA in upregulating IL-10

Example 7. In Vitro Transfer of HC1 and HC2 from IαI to Immobilized HA

Covalink-NH 96 wells were covalently coupled with PBS (control), HA (iHA), or native HC-HA/PTX3 (nHC-HA/PTX3) as described above. Serial TSG-6 concentrations (0, 0.24, 1.2, 6, 12 µg/ml in 100 µl) were individually incubated with iHA in the reaction buffer (5 mM $MgCl_2$ in PBS, pH 7.5)). Human IαI (5 µg/ml) (prepared from human plasma according to Blom et al. (1999) *J. Biol. Chem.* 274, 298-304) was added either simultaneously with TSG-6 or sequentially (2 h later). Bound HC1, HC2 (antibodies to HC1 and HC2 were from abcam, Cambridge, Mass.), or IαI (DAKO, Carpinteria, Calif.) was measured by respective modified ELISA similar to TSG-6 and PTX3 ELISAs described above.

The data show that the amount of HC1 (FIG. 13A) or IαI (FIG. 13B) bound to iHA is lower at higher TSG-6 concentrations (6 and 12 µg/ml) when TSG-6 was pre-bound to iHA with subsequent addition of IαI than when TSG-6 and IαI were added simultaneously. HC2 was not detected in the samples (data not shown). The wells were incubated with hyaluronidase to digest the bound HA and to release bound proteins from HA and these samples were analyzed by Western blot with anti-TSG-6 antibody (R&D Systems, Minneapolis, Minn.); the amount of TSG-6 bound to iHA was lower when IαI was simultaneously added with TSG-6 than when IαI was subsequently added (i.e. after TSG-6 was bound to iHA, FIG. 13C). When 5 µg/ml of PTX3 and 5 µg/ml of IαI were incubated with iHA simultaneously, PTX3 but not IαI was bound to iHA (FIG. 13D).

Figure 13A:
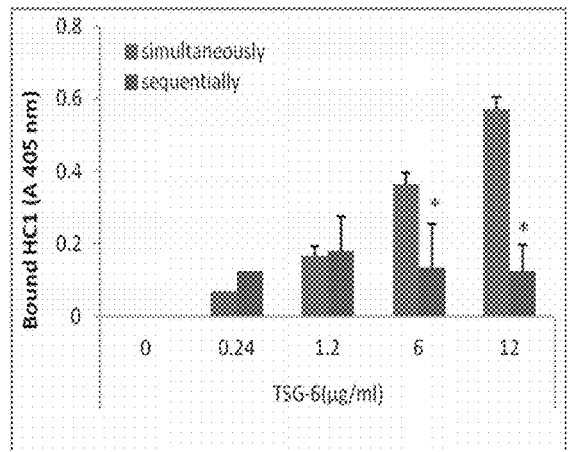
Figure 13B:
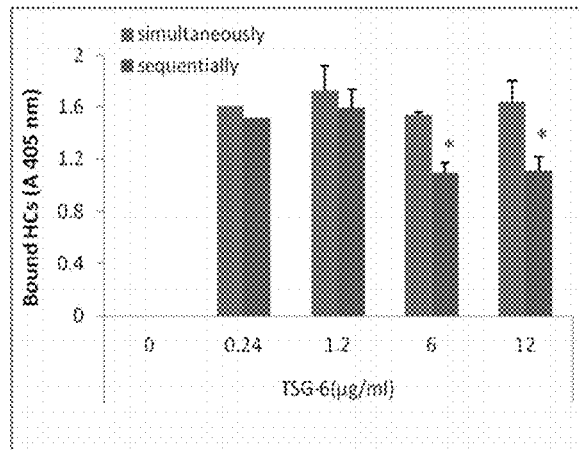
Figure 13C:
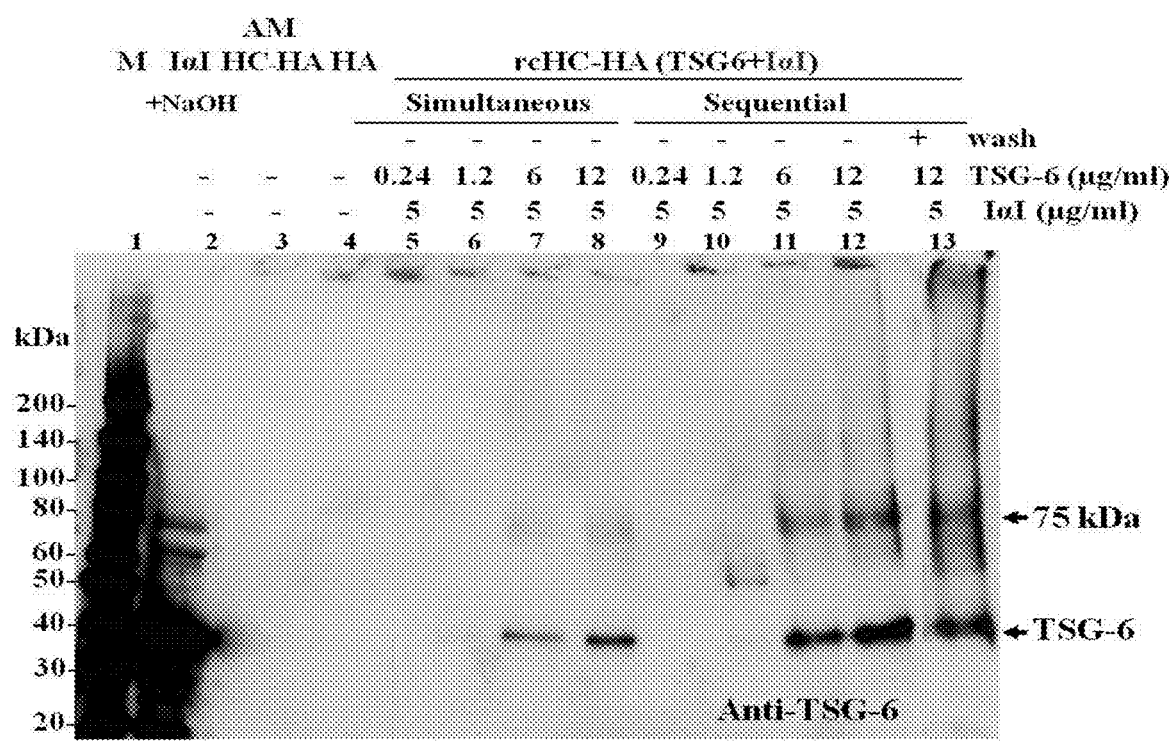

These data indicate that TSG-6 free in solution is more efficient than TSG-6 bound to iHA in transferring HC1 from IαI onto iHA (FIGS. 13A and 13B). More TSG-6 is bound to iHA when TSG-6 is pre-bound to iHA alone than when TSG-6 and IαI are incubated with iHA simultaneously (FIG. 13C), indicating that IαI prevents TSG-6 from binding to iHA if added simultaneously with TSG-6, and that TSG-6 might have a higher affinity in binding to IαI than to iHA. In addition, PTX3 free in solution or bound to iHA does not transfer HCs from IαI to iHA (FIG. 13D).

Example 8. Effect of PTX3 on the Formation of HC1•TSG-6 and HC2•TSG-6 Complexes

Figures 14A, 14B:
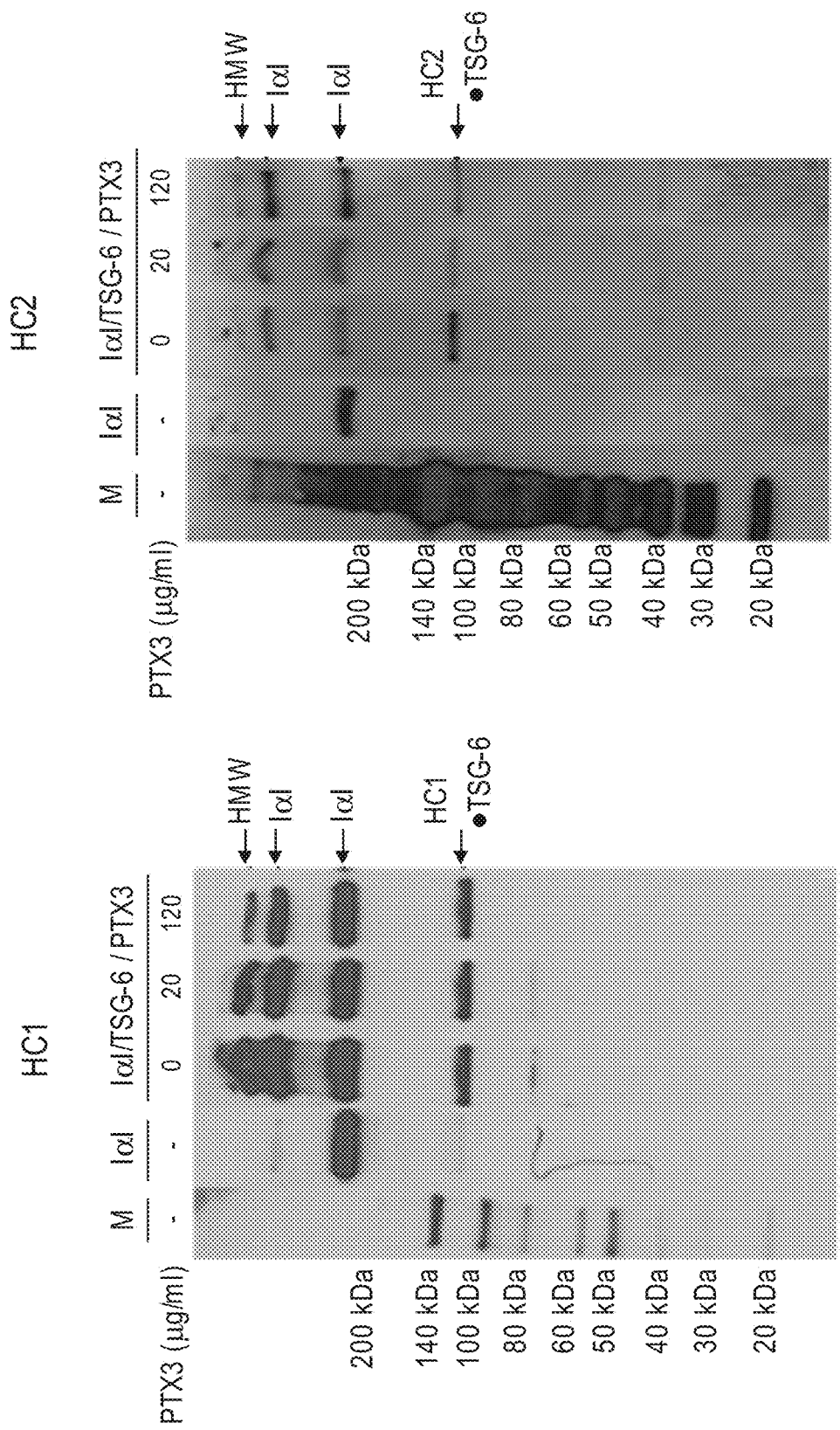

IαI (40 µg/ml) and TSG-6 (6 µg/ml) were incubated in the reaction buffer (5 mM $MgCl_2$ in PBS, pH 7.5) for 2 h at 37° C. without or with PTX3 (20 µg/ml or 120 µg/ml). The reaction samples were analyzed by Western blot with antibodies against HC1 (FIG. 14A), HC2 (FIG. 14B), TSG-6 (FIG. 14C), bikunin (abcam, Cambridge, Mass.) (FIG. 14D), and PTX3 (data not shown). In solution without HMW HA, TSG-6 forms HC1•TSG-6 and HC2•TSG-6 complexes, and generates HMW IαI (FIGS. 14A and 14B). The formation of HMW IαI is illustrated in FIG. 14E. This data indicates that both HC1 and HC2 are transferred by TSG-6 in solution to HMW HA.

Figures 14C, 14D:
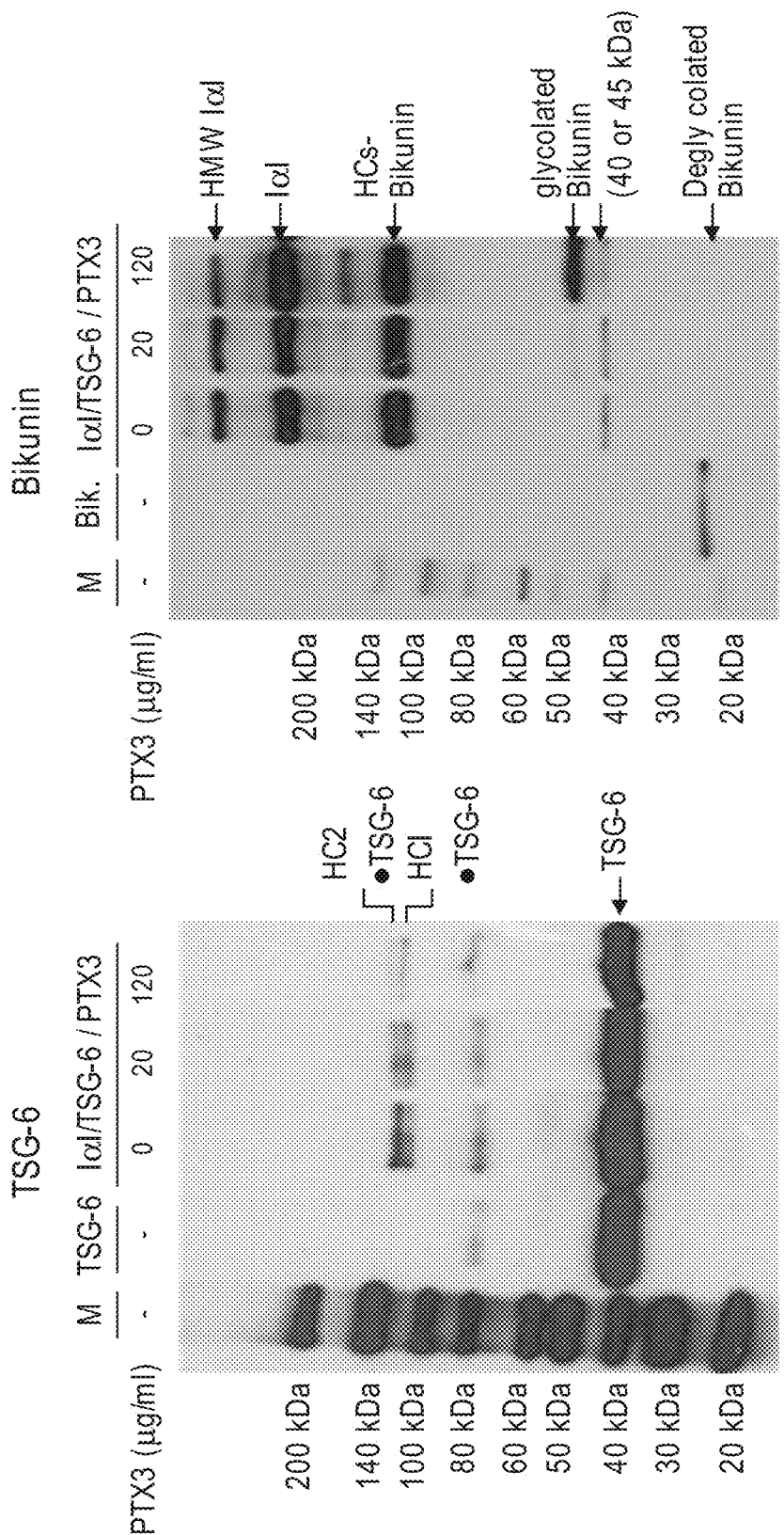
Figure 14F:
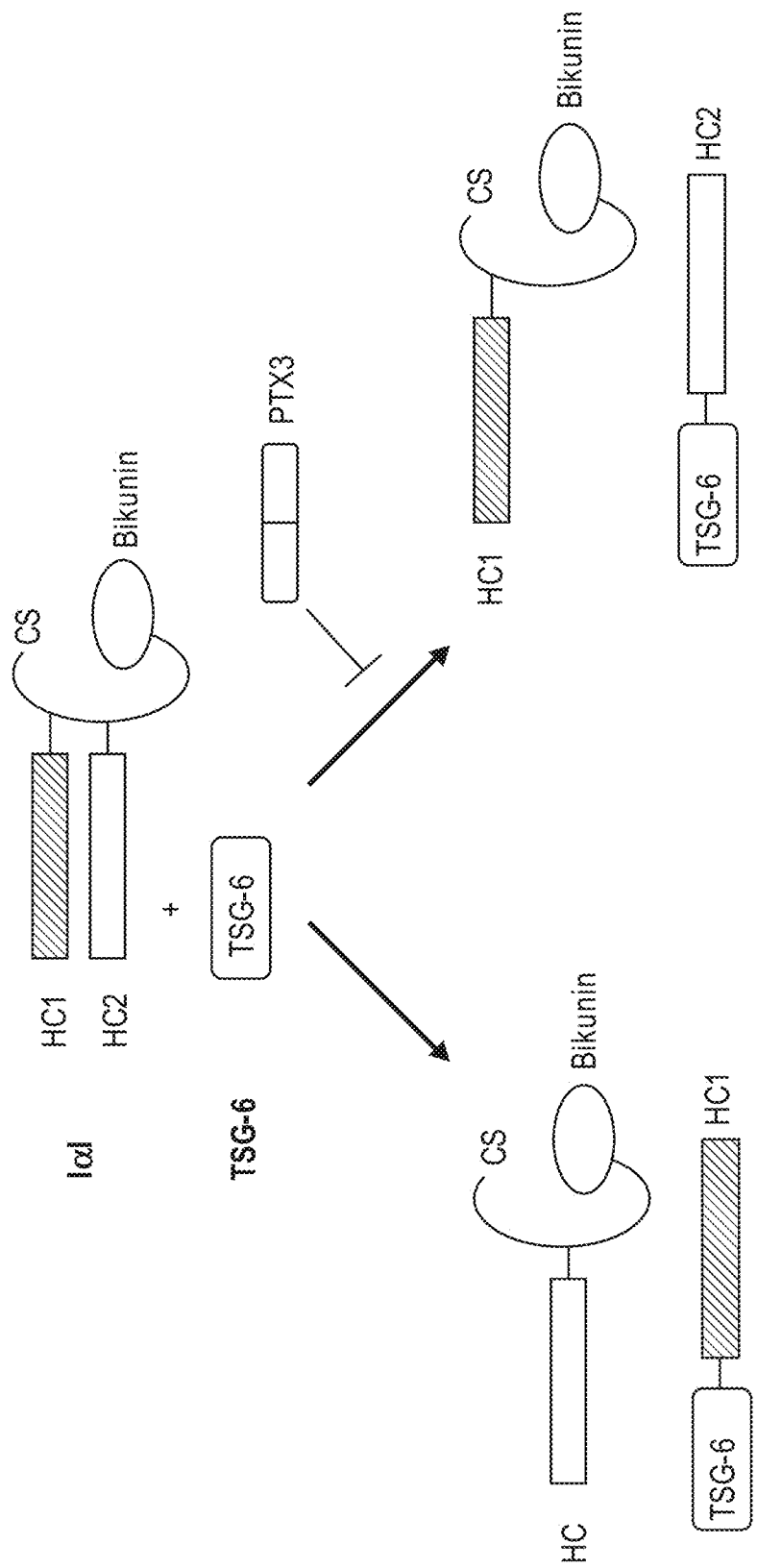

Simultaneous addition of PTX3 dose-dependently inhibits formation of HC2•TSG-6 but not HC1•TSG-6 (FIGS. 14A and 14B). In contrast, HMW IαI containing HC2 is increased while HMW IαI containing HC1 is decreased (FIGS. 14A and 14B). TSG-6 forms dimers when added in solution without HMW HA with or without PTX3 (FIG. 14C). These findings indicate that 1) both HC1 and HC2 in IαI form either a complex with TSG-6 or a HMW IαI via TSG-6's action; 2) PTX3 interferes with the above process differently regarding the transfer of HC1 and HC2 by TSG-6. There is no truncated form of HC1 or HC2. The inhibition of HC2•TSG-6 by PTX3 is illustrated in FIG. 14F.

A glycosylated form and a glycosylated and chondroitin sulfate-conjugated form of bikunin about 40 kDa and 45 kDa, respectively, were released by TSG-6 and PTX3, respectively (FIG. 14D). This data is consistent with the published data showing that both TSG-6 and PTX3 interact with IαI, and also suggests that TSG-6 and PTX3 interact differently with IαI resulting in different outcome of bikunin.

Figure 14G:
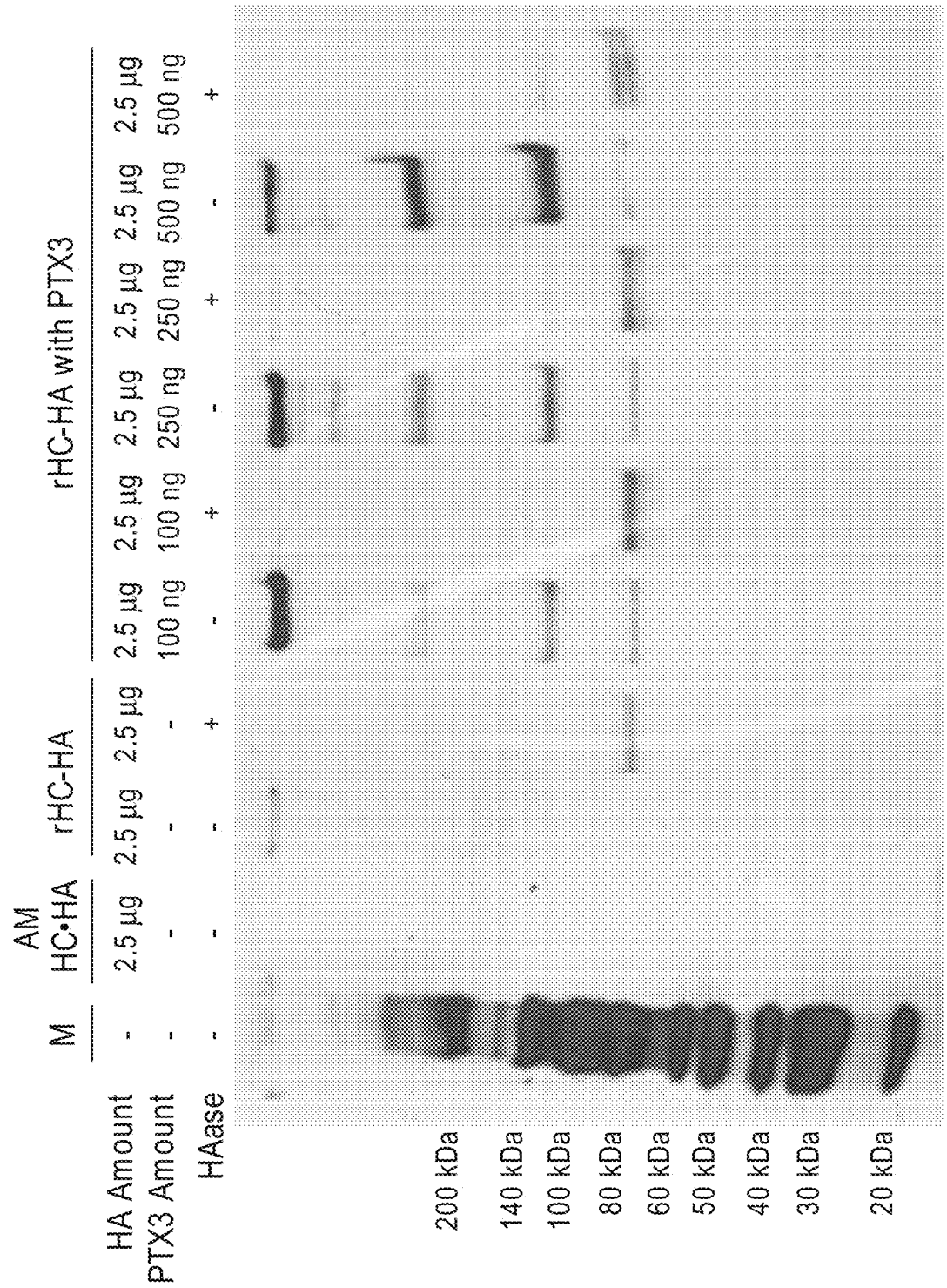

In a separate experiment, HMW HA (250 µg/ml), IαI (40 µg/ml), and TSG-6 (6 µg/ml) were incubated in solution for 24 h at 37° C. without or with PTX3 (1, 2.5, and 5 µg/ml) in the reaction buffer (5 mM $MgCl_2$ in PBS, pH 7.5). The reaction samples were analyzed by Western blot with antibodies against IαI (FIG. 14G). In solution with HMW HA but without PTX3, HCs from IαI were completely transferred to HMW HA by TSG-6. In the presence of PTX3, TSG-6-mediated HCs transfer was dose-dependently inhibited, resulting in the accumulation of LMW intermediates (~130 kDa and likely consisting of HC1-TSG-6) or unprocessed pre-IαI (~130 kDa, unprocessed IαI (220 kDa), and HMW IαI (retained in loading wells) (FIG. 14G). These data are consistent with the finding that PTX3 specifically prevents the formation of HC2-TSG-6, resulting in the inhibition of HC2 transfer and possible HC1 transfer.

Figure 15G:
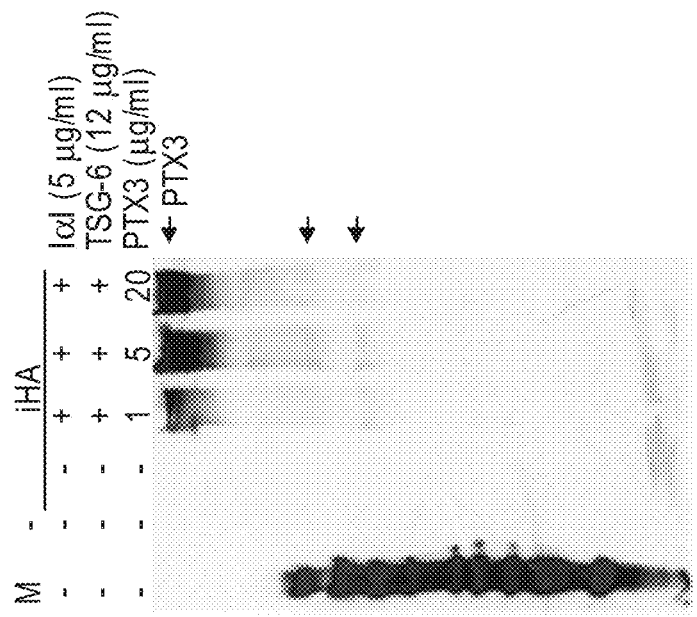
Figure 15F:
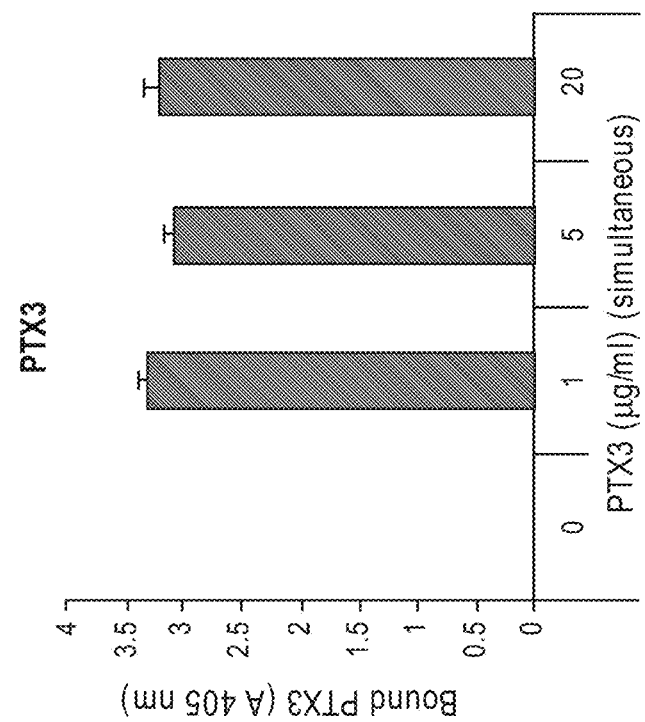

Example 9. Formation of Reconstituted HC-HA/PTX3 (rcHC-HA/PTX3) Complexes In Vitro from Immobilized HA with Simultaneous Addition of TSG-6, PTX3, and IαI Immobilized HA (~14 µg/ml or 1.4 µg in 100 µl in each well) was prepared as described in Example 3. IαI (5 µg/ml) and TSG-6 (12 µg/ml) were incubated simultaneously on iHA with or without PTX3 (1, 5, or 20 µg/ml) for 2 h at 37° C. the reaction buffer (5 mM $MgCl_2$ in PBS, pH 7.5). After washes with 8 M GnHCl and PBS, bound HC1, TSG-6, and PTX3 were measured by respective modified ELISAs (FIGS. 15A, 15D, and 15F, respectively). The wells were washed again with 8 M GnHCl and PBS, and iHA with bound components were digested with 1 unit/ml of hyaluronidase for 2 h at 60° C. in 10 mM acetate buffer with 75 mM NaCl, pH 6.0. The samples were analyzed by Western blot with antibodies against HC1 (FIG. 15B), HC2 (FIG. 15C), TSG-6 (FIG. 15E), and PTX3 (FIG. 15G).

Simultaneous addition of TSG-6, PTX3 and IαI to iHA resulted in rcHC-HA/PTX3 complexes containing HMW HC1 but not HC2, and truncated HC1 and HC2 (FIGS. 15A-C). PTX3 dose-dependently reduced the amount of HMW HC1 in the complex. The data show that PTX3 dose-dependently interfered with the transfer of HC1 and HC2 to iHA by TSG-6 (FIGS. 15A-C), resulting less HC1/truncated HC1 and truncated HC2 (FIGS. 15B and 15C). TSG-6 monomer was decreased while HMW TSG-6 (either multimeric or complexed with PTX3 and/or HCs) did not change (FIGS. 15D and E).

The data also indicate that PTX3 does not interfere with TSG-6 bound to iHA in the presence or absence of IαI. The published data suggest that TSG-6 forms dimers with iHA when a smaller MW HA is tested (Baranova et al. (2011) *J Biol Chem.* 286(29):25675-86). The data present herein indicate that TSG-6 is complexed in HMW HC-HA/PTX3 complex in the presence of Tat Because the free TSG-6 is decreased by PTX3 in a dose-dependent fashion, it further indicates that PTX3 promotes the binding of TSG-6 into HC-HA/PTX3 complex in the presence of IαI. Under this situation, the majority of PTX3 exists as multimeric forms in HC-HA/PTX3 complex, similar to what has been observed in nHC-HA/PTX3, with a declining amount of monomer, dimers or trimers (FIGS. 15F and G).

Figure 16E:
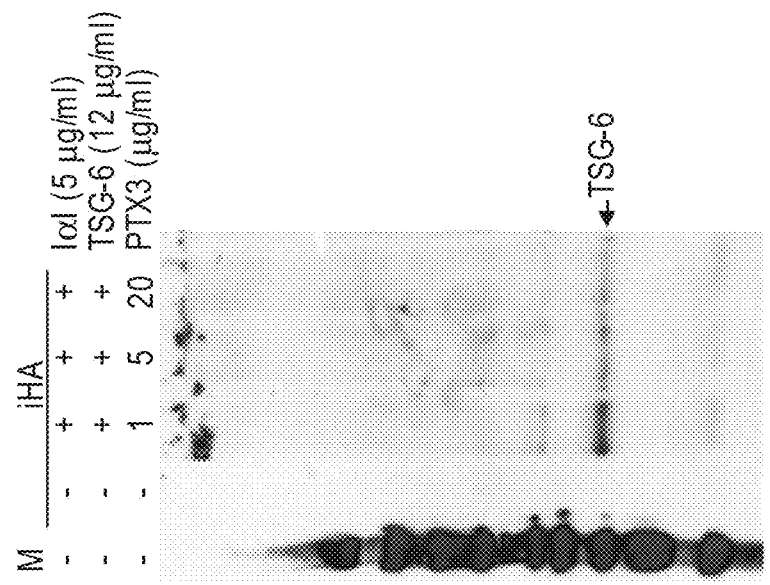
Figure 16D:
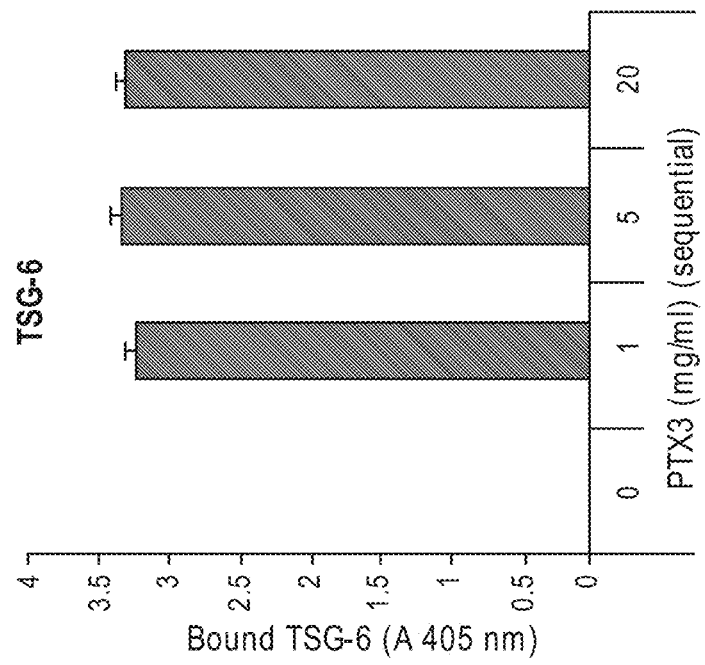
Figure 16G:
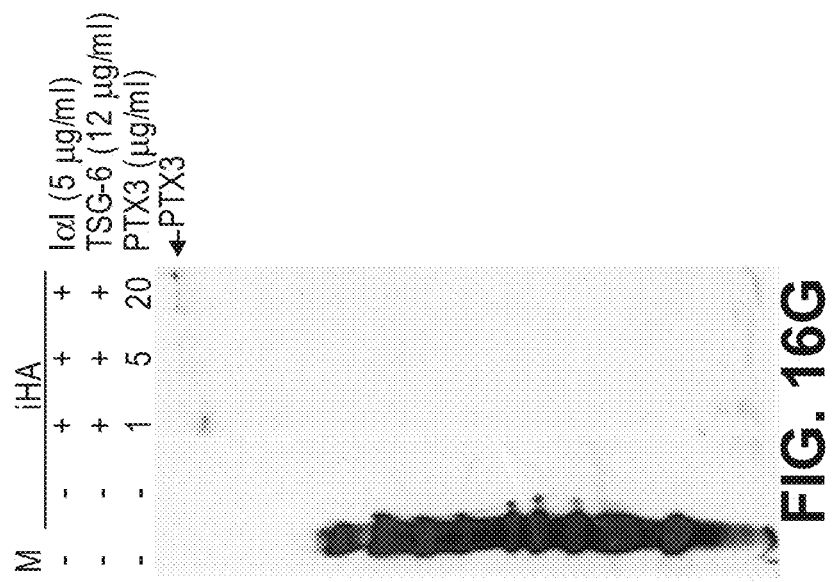
Figure 16F:
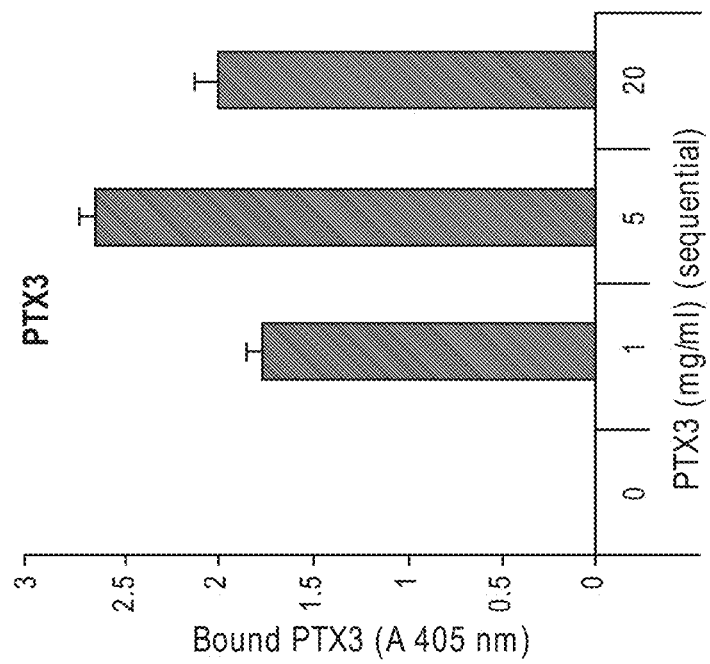

Example 10. Effect of Sequential Addition of PTX3 to Reconstituted HC-HA/PTX3 (rcHC-HA/PTX3) Complexes Formed In Vitro with TSG-6 and IαI on Immobilized HA Immobilized HA (~14 μg/ml) was prepared as described in Example 3. IαI (5 μg/ml) and TSG-6 (12 μg/ml) were incubated on iHA in the reaction buffer (5 mM MgCl$_2$ in PBS, pH 7.5) for 2 h at 37° C. After removing unbound IαI and TSG-6, reaction buffer with or without PTX3 (1, 5, or 20 μg/ml) was incubated with the pre-bound HCs and TSG-6 for 2 h at 37° C. After washes with 8 M GnHCl and PBS, bound HC1, TSG-6, and PTX3 were measured by respectively ELISAs (FIGS. 16A, 16D, and 16F, respectively). The wells were then washed again with 8 M GnHCl. PBS control and iHA with bound components were then digested with 1 unit/ml of hyaluronidase for 2 h at 60° C. The samples were analyzed by Western blot with antibodies against HC1 (FIG. 16B), HC2 (FIG. 16C), TSG-6 (FIG. 16E), PTX3 (FIG. 16G).

When PTX3 is added subsequently after TSG-6 and HCs have been pre-bound to iHA, PTX3 dose-dependently reduces HC1 transfer to the HMW complex (both intact HC1 and truncated HC1 are reduced) but increases the amount of truncated HC2 in the complex. Consistent with the data shown in Example 7, bound TSG-6 is less efficient than free TSG-6 in transferring HCs to iHA.

Similar to the data shown in Example 8, PTX3 also dose-dependently reduced the HMW TSG-6 and monomeric TSG-6 (FIGS. 16D and 16E), indicating that subsequent addition of PTX3 continuously depletes pre-bound TSG-6. PTX3, however, is no longer able to be incorporated in TSG-6/HC-HA complex (FIGS. 16F and 16G). Because pre-bound TSG-6 in iHA also partially prevents PTX3 from binding to iHA (see Example 4), this finding indicates that formation of a rcHC-HA/PTX3 complex by TSG-6 and IαI is structurally different from TSG-6/iHA in the extent that PTX3 binding to iHA is completely excluded.

Figures 17A, 17B:
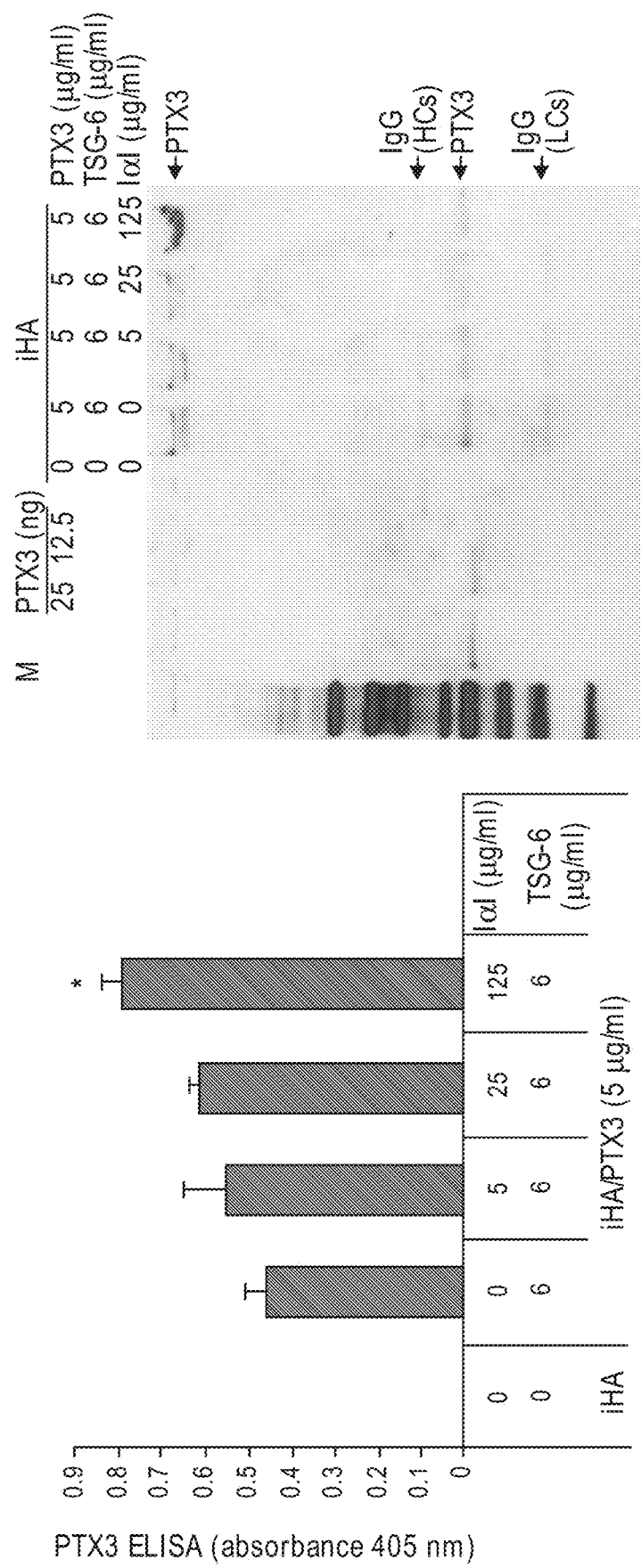
FIG. 17A-G exemplifies complexes formed on iHA following sequential addition of PTX3 followed by IαI with TSG-6. Bound HC1, TSG-6, and PTX3 were measured by respective ELISAs (A, C, E). The complexes were washed again with 8 M GnHCl and PBS and bound components were digested with 1 unit/ml of hyaluronidase for 2 h. The digested samples were analyzed by Western blot with antibodies against PTX3 (B), TSG-6 (D), HC1 (F), and HC2 (G).

Example 11. Formation of Reconstituted HC-HA/PTX3 (rcHC-HA/PTX3) Complexes In Vitro with Pre-Bound PTX3 on Immobilized HA and Sequential Addition of TSG-6 and IαI Immobilized HA (~14 μg/ml) was prepared as described in Example 3. PTX3 (5 μg/ml) and iHA were incubated in the reaction buffer for 2 h at 37° C. in the reaction buffer (5 mM MgCl$_2$ in PBS, pH 7.5). After removing unbound PTX3, the reaction buffer containing TSG-6 (6 μg/ml) and IαI (5, 25, and 125 μg/ml) were incubated for 2 h at 37° C. After washes with 8 M GnHCl and PBS, bound HC1, TSG-6, and PTX3 were measured by respectively ELISAs (FIGS. 17A, 17C, and 17E, respectively). The wells were then washed again with 8 M GnHCl. PBS or iHA with bound components were digested with 1 unit/ml of hyaluronidase for 2 h at 60° C. in 10 mM acetate buffer with 75 mM NaCl, pH 6.0. The samples were analyzed by Western blot with antibodies against PTX3 (FIG. 17B), TSG-6 (FIG. 17D), HC1 (FIG. 17F), and HC2 (FIG. 17G).

In the presence of IαI and TSG-6, pre-bound PTX3 dose-dependently increased ELISA immunoreactivity for PTX3 and the amount of multimeric PTX3 but decreased that of monomeric PTX3 in HC-HA/PTX3 complex (FIGS. 17A and 17B). This data indicates that multimeric PTX3 promotes immunoreactivity by this antibody.

Figure 17D:
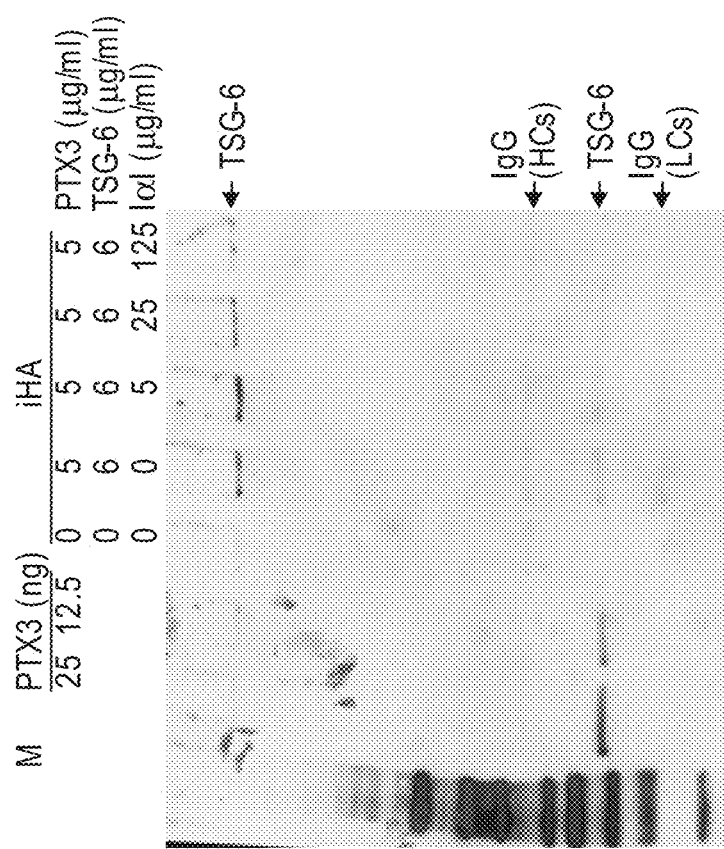
Figure 17C:
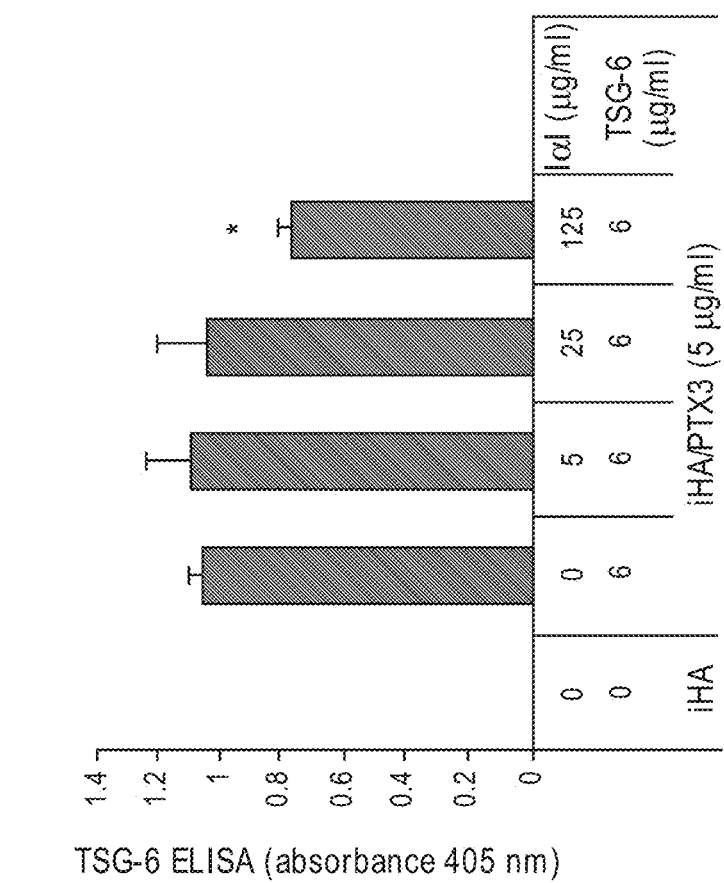
Figures 17E, 17F:
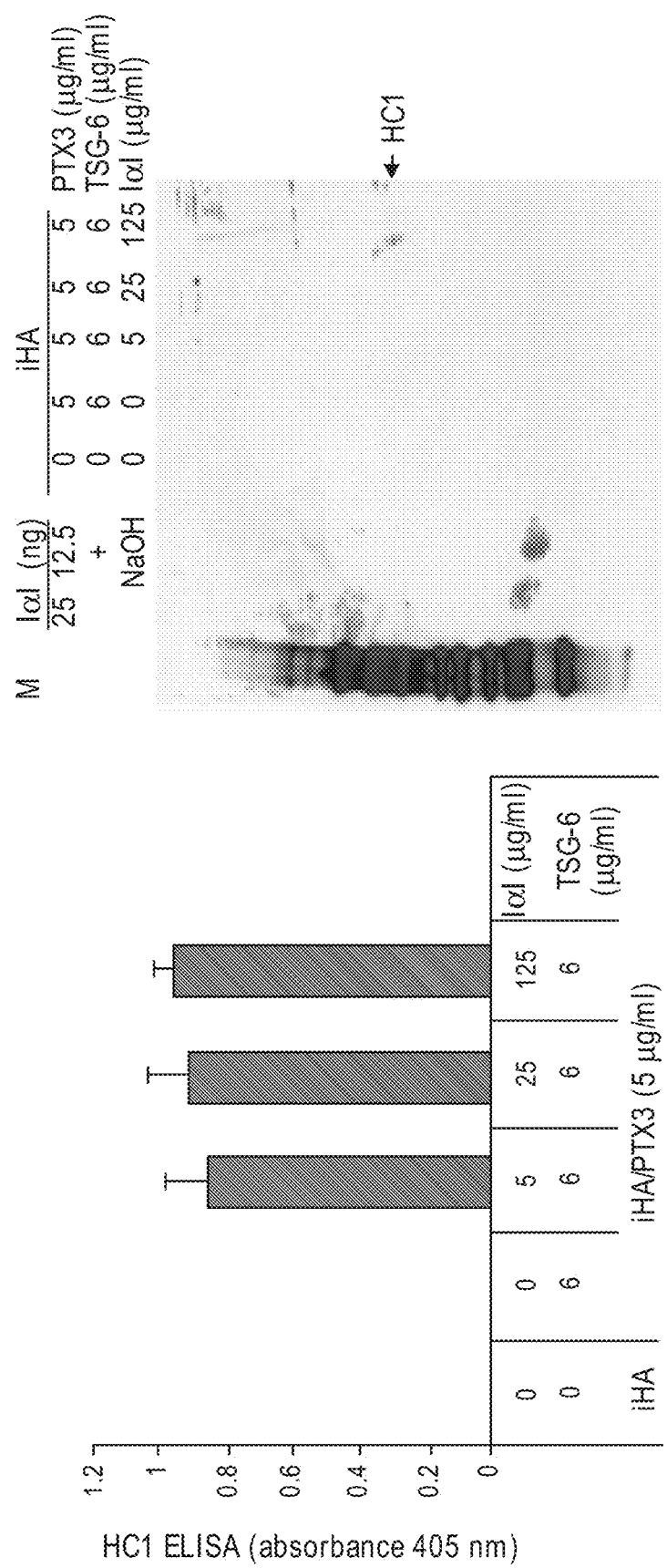
Figure 17G:
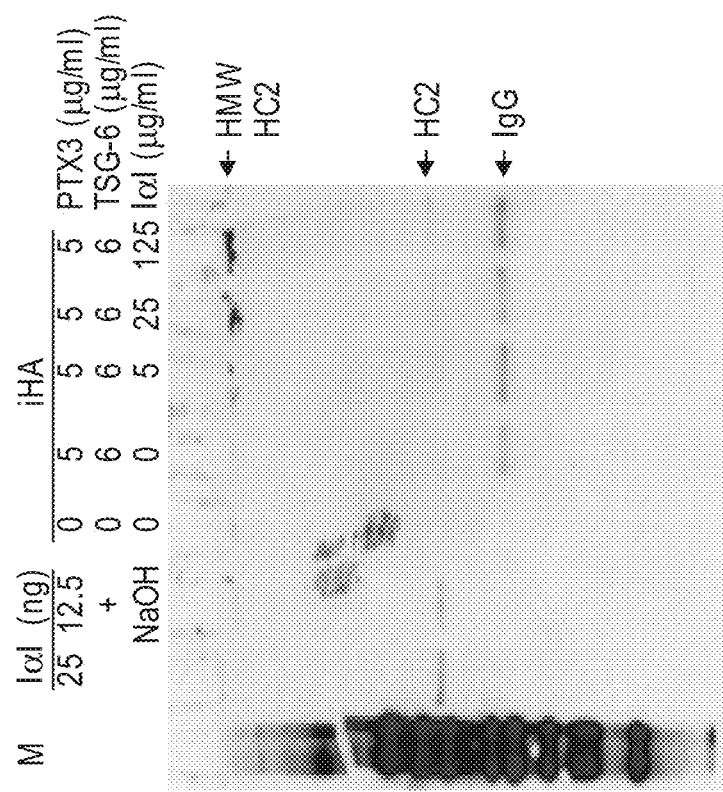

Pre-bound PTX3 dose-dependently excluded monomeric TSG-6 while decreasing TSG-6 in the rcHC-HA/PTX3 complex (FIGS. 17C and 17D). The significant reduction of bound TSG-6 (both monomer and HMW forms) is detected when a molar ratio of IαI to TSG-6 is 3:1, where bound multimeric PTX3 is maximized as well.

There was no significant change in bound HC1 based on HC1 ELISA data (FIG. 17E). The transfer of HC2 was dose-dependently increased by increasing IαI concentrations.

Example 12. Comparison of Macrophage Cell Attachment Activity Between Reconstituted HC-HA/PTX3 (rcHC-HA/PTX3) Complexes Formed In Vitro with Pre-Bound TSG-6 Versus Pre-Bound PTX3 on Immobilized HA Covalink-NH 96 wells were covalently coupled with PBS (control), HA (iHA), or nHC-HA/PTX3 as described in Example 3. IαI (5 μg/ml), TSG-6 (6 μg/ml) or PTX3 (5 μg/ml) were simultaneously or sequentially bound to iHA as follows: (1) (IαI/TSG-6/PTX3)/iHA: IαI, TSG-6, and PTX3 were simultaneously incubated with iHA for 2 h at 37° C. in the reaction buffer; (2) (IαI/TSG-6)/PTX3/iHA: IαI and TSG-6 were first incubated with iHA for 2 h at 37° C. in the reaction buffer. After removed the unbound IαI/TSG-6, washed with 8 M GnHCl and PBS, PTX3 was added and incubated for 2 h at 37° C. in the reaction buffer; (3) (PTX3)/IαI/TSG-6/iHA: PTX3 was first incubated with iHA for 2 h at 37° C. in the reaction buffer. After removed the unbound PTX3, washed with 8 M GnHCl and PBS, IαI/TSG-6 was added and incubated for 2 h at 37° C. in the reaction buffer. Following formation of the complexes, 100 μl of RAW264.7 cells (1×10$^5$ cells/ml) were seeded into each coupled well and treated with 1 μg/ml LPS. After incubation for 24 h, cell morphology was photographed.

Figure 18:
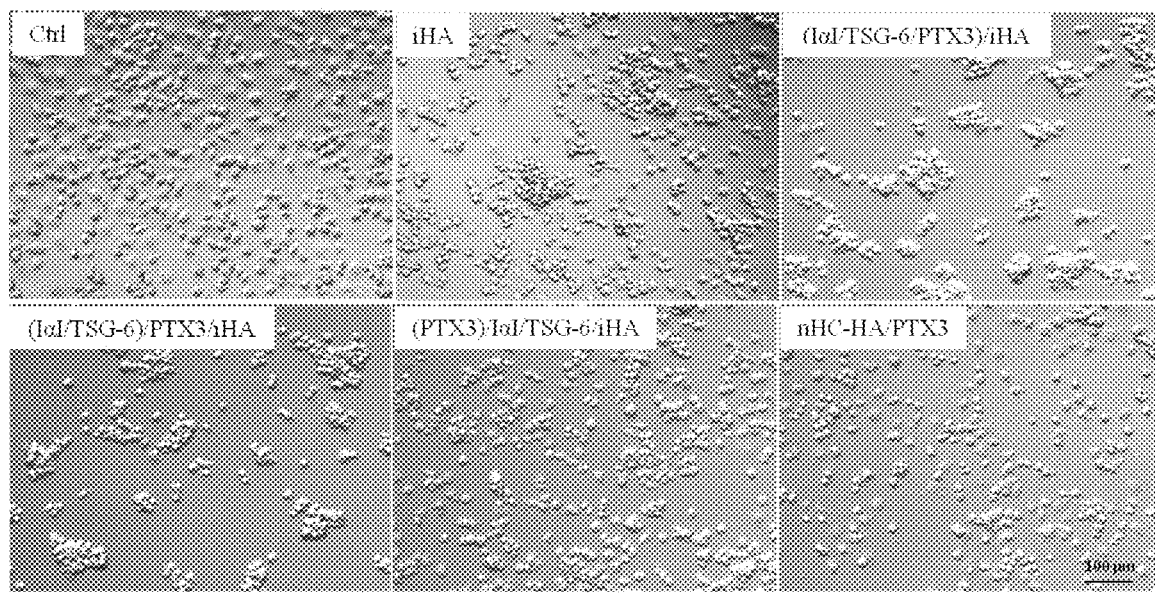
FIG. 18 exemplifies attachment of LPS-stimulated RAW264.7 macrophages to PBS (control), HA (iHA), nHC-HA/PTX3, (IαI/TSG-6/PTX3)/iHA (IαI, TSG-6 or PTX3 is simultaneously bound to iHA), (IαI/TSG-6)/PTX3/iHA (sequential addition of PTX3 to iHA pre-incubated with IαI and TSG-6), or (PTX3)/IαI/TSG-6/iHA (sequential addition of IαI and TSG-6 to iHA pre-incubated with PTX3). Cells were photographed 24 after incubation.

Macrophages attached poorly to iHA as the control. In the presence of IαI, simultaneous or pre-bound TSG-6 to iHA ((IαI/TSG-6/PTX3)/iHA or (IαI/TSG-6)/PTX3/iHA) inhibits cell attachment and promotes cell aggregation (FIG. 18) similar to the condition without IαI (see Example 5). In contrast, pre-bound PTX3 to iHA [(PTX3)/IαI/TSG-6/iHA] promotes cell attachment similar to pre-bound PTX3 without IαI as shown in Example 5. The latter resembles the positive control of nHC-HA/PTX3 (FIG. 18).

Figure 19A:
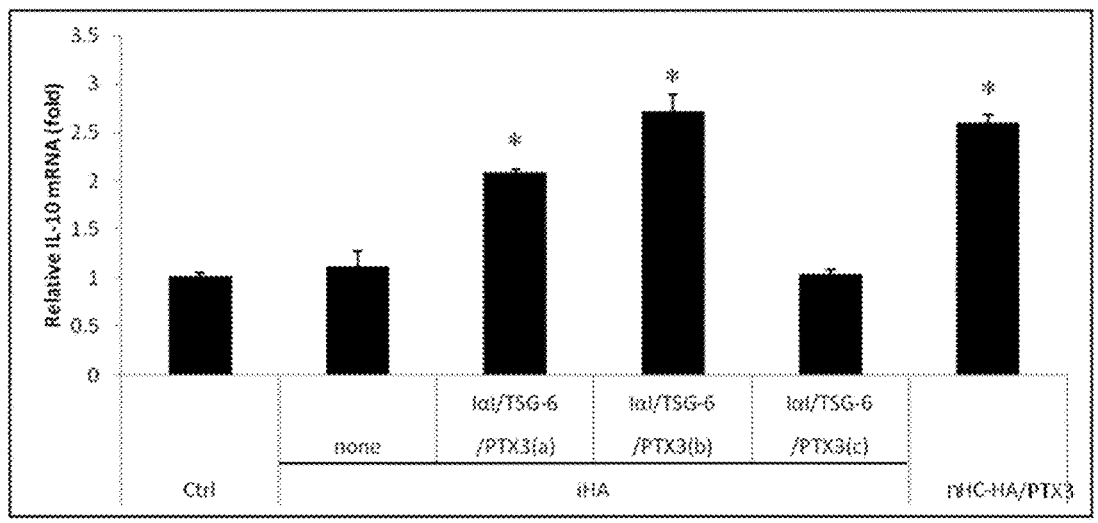
FIG. 19A-F exemplifies gene expression in RAW264.7 macrophages cultivated on immobilized substrates and stimulated with LPS. Total RNAs were isolated and expression of IL-10 and IL-12p40 mRNAs was measured by quantitative PCR (A and C). IL-10 and IL-12p70 proteins in the cell culture supernatants were measured by respective ELISAs (B and D). (E) IL-23 proteins in the cell culture supernatants of resting RAW264.7 cells (none) or with stimulation of IFN-γ (200 units/ml), LPS (1 µg/ml), IFN-γ/LPS, LPS with immune complex (LPS/IC) or IL-4 (10 ng/ml) for 24 h as measured by IL-23 ELISA. (F) IL-23 in the cell culture supernatants of RAW264.7 cells cultivated on immobilized substrates and stimulated with IFN-γ/LPS for 24 h as measured by IL-23 ELISA. An asterisk (*) indicates p<0.05.
Figure 19B:
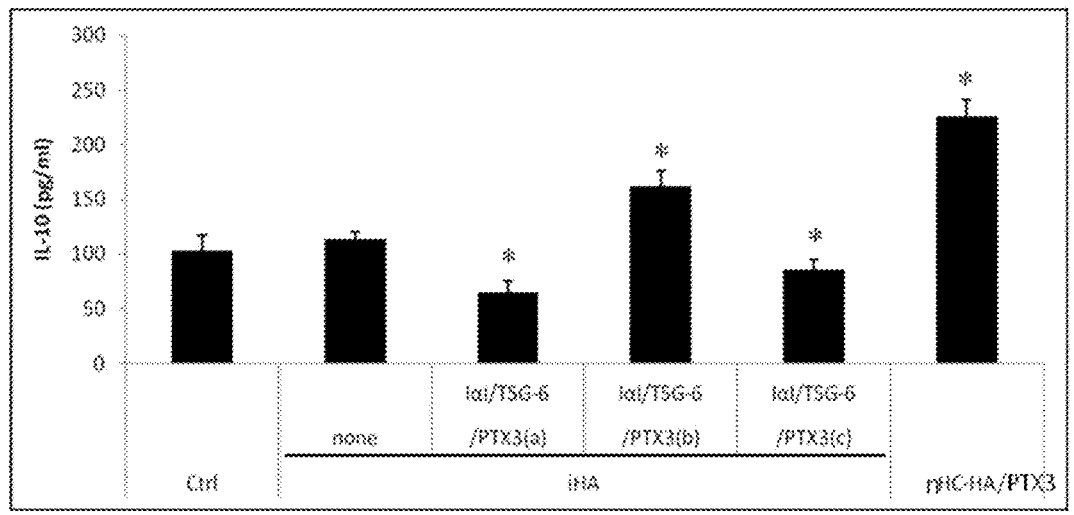
Figure 19C:
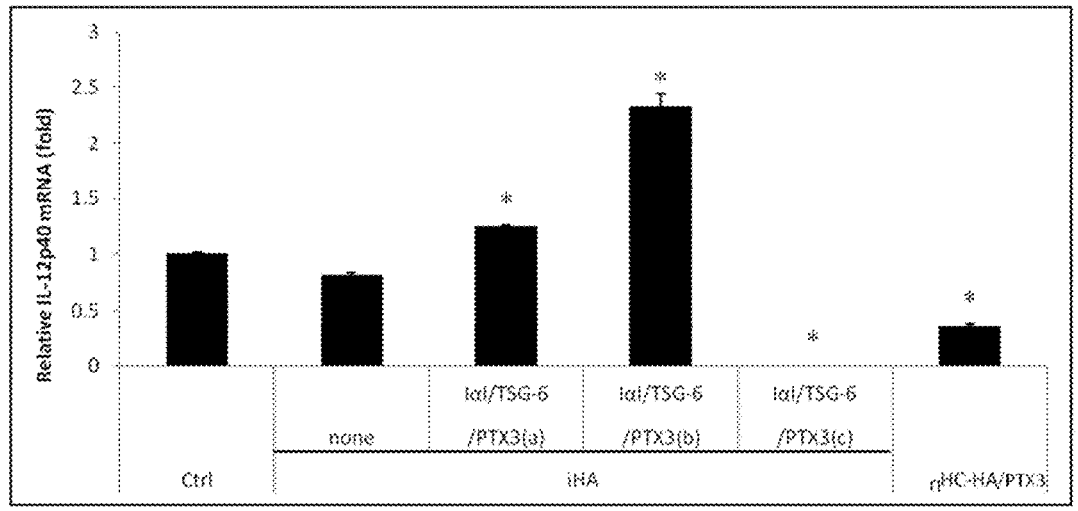
Figure 19D:
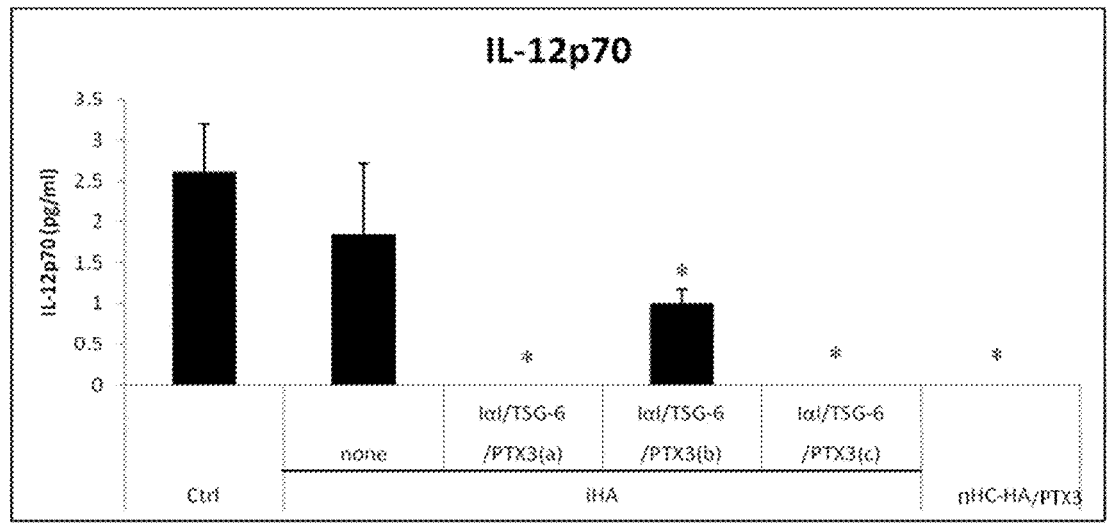

Example 13. Comparison of Regulation of M1 and M2 Marker Expression Between Reconstituted HC-HA/PTX3 (rcHC-HA/PTX3) Complexes Formed In Vitro with Pre-Bound TSG-6 Versus Pre-Bound PTX3 on Immobilized HA Expression of IL-10 and IL-12p40 in Macrophages Cultivated on rcHC-HA/PTX3 Complexes RAW264.7 cells were cultivated in DMEM/10% FBS on immobilized substrates and stimulated with 1 µg/ml LPS for 4 h as described in Example 12. Total RNAs were isolated and expression of IL-10 and IL-12p40 mRNAs was measured by quantitative PCR as described above (FIGS. 19A and 19C). Alternatively, cells were stimulated with 1 µg/ml LPS for 24 h and IL-10 and IL-12p70 proteins in the cell culture supernatants were measured by respective ELISAs (FIGS. 19B and 19D).

Compared to the PBS control, expression of IL-10 mRNA was not significantly changed by iHA (p=0.56), but was significantly upregulated on complexes formed by simultaneous addition of TSG-6, IαI, and PTX3 on iHA (IαI/TSG-6/PTX3(a) in FIG. 19) (p=0.0008). Similarly, expression of IL-10 mRNA was significantly upregulated on complexes formed by pre-bound TSG-6 to iHA with subsequent addition of IαI and PTX3 (IαI/TSG-6/PTX3(b) in FIG. 19) (p=0.04) and the positive control nHC-HA/PTX3 (p=0.008). Expression of IL-10 mRNA was significantly higher on nHC-HA/PTX3 than on IαI/TSG-6/PTX3(a) (p=0.04), but not significantly higher than on IαI/TSG-6/PTX3(b) (p=0.55). In contrast, expression of IL-10 mRNA was not significantly upregulated by on complexes formed by pre-bound PTX3 to iHA (IαI/TSG-6/PTX3(c) in FIG. 19) (p=0.74) (FIG. 19A). Expression of IL-10 protein, as measured by ELISA, was only significantly upregulated by nHC-HA/PTX3 (p=0.03) (FIG. 19B).

Compared to the control, expression of IL-12p40 (IL-12p40 is one of two subunits of IL-12p70 and the other subunit is IL-12p35) mRNA was not significantly changed by iHA (p=0.1). In contrast, expression of IL-12p40 mRNA was significantly upregulated on complexes formed by simultaneous addition of TSG-6, IαI, and PTX3 on iHA (IαI/TSG-6/PTX3(a) in FIG. 19) (p=0.05) and on complexes formed by pre-bound TSG-6 to iHA (IαI/TSG-6/PTX3(b) in FIG. 19) (p=0.04). In contrast, expression of IL-12p40 mRNA was completely abolished on complexes formed by pre-bound PTX3 (IαI/TSG-6/PTX3 (c) in FIG. 19) and significantly downregulated by nHC-HA/PTX3 (p=0.01). There was a statistical significance difference between the latter two conditions (p=0.04) (FIG. 19C). Compared to the control, expression of IL-12p70 protein was not significantly changed by iHA (p=0.32), but significantly downregulated on complexes formed by pre-bound PTX3 (IαI/TSG-6/PTX3 (c)) (p=0.03) (FIG. 19D). In contrast, expression of IL-12p70 protein was abolished on complexes formed by simultaneous addition of TSG-6, IαI, and PTX3 on iHA (IαI/TSG-6/PTX3 (a)), on complexes formed by pre-bound PTX3 (IαI/TSG-6/PTX3 (c)), and nHC-HA/PTX3 (p=0.05, 0.02, and 0.01, respectively).

Figure 19E:
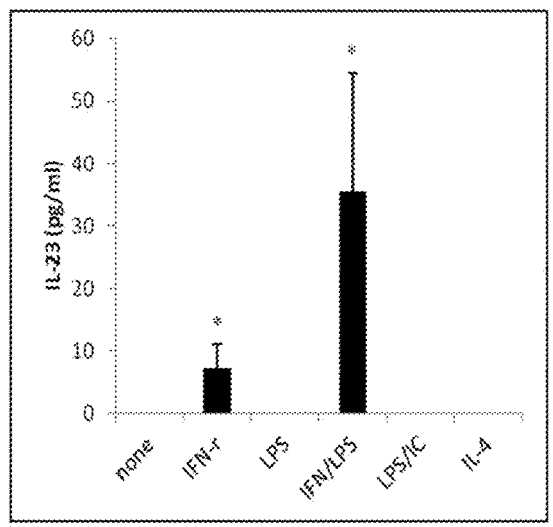

Expression of IL-23 in Macrophages Cultivated in the Presence of Various Stimuli In a separate experiment, IL-23 protein in the cell culture supernatants of resting RAW264.7 cells (none) or with stimulation of IFN-γ (200 units/ml), LPS (1 µg/ml), IFN-γ/LPS, LPS (1 µg/ml) with immune complex or IC (LPS/IC) [IC contained 150 µg/ml IgG-opsonized OVA (IgG-OVA) and was made by mixing a tenfold molar excess of rabbit anti-OVA IgG (Cappel, Durham, N.C.) to OVA (Worthington Biochemical Corp., Lakewood, N.J.) for 30 min at 25° C.], or IL-4 (10 ng/ml) (R&D Systems, Minneapolis, Minn.) in DMEM/10% FBS for 24 h was measured. IL-23 protein in the cell culture supernatants was measured by IL-23 ELISA (Biolegend, San Diego, Calif.) according to the manufacturer's protocol (FIG. 19E). IL-23 protein was undetectable in the cell culture supernatant of resting RAW264.7 cells and in those of cells under stimulation for 24 h by LPS (1 µg/ml), LPS with immune complex (LPS/IC), or IL-4 (10 ng/ml), but became detectable under stimulation for 24 h by IFN-γ (200 units/ml) and IFN-γ/LPS (FIG. 19E).

Expression of IL-23 in Macrophages Cultivated on rcHC-HA/PTX3 Complexes

In a separate experiment, RAW264.7 cells were cultivated on immobilized substrates as described above and stimulated with IFN-γ/LPS for 24 h. IL-23 in the cell culture supernatants was measured by IL-23 ELISA as described above (FIG. 19F).

Figure 19F:
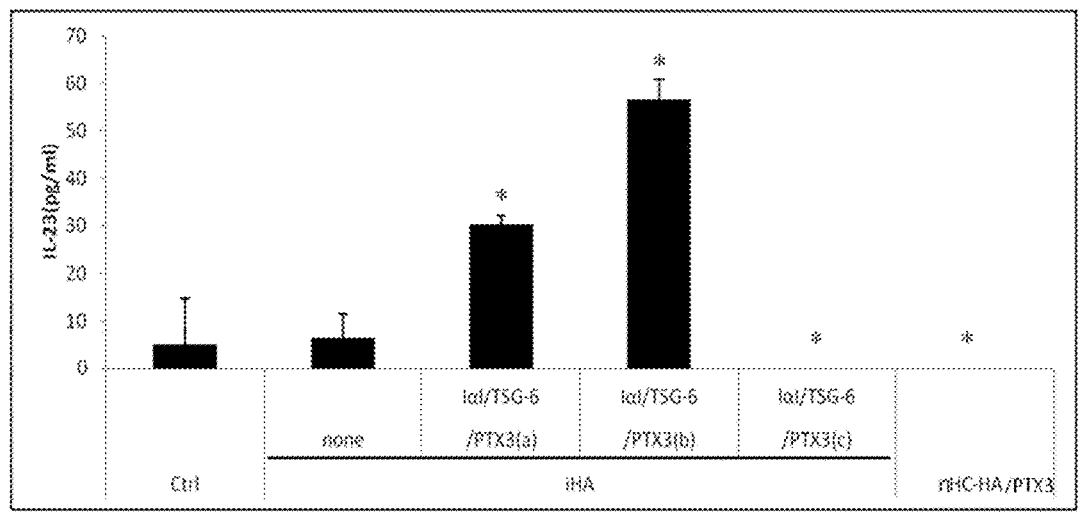

Compared to the control, IL-23 protein in the cell culture supernatant of RAW264.7 cells with stimulation of 200 units/ml IFN-γ/1 µg/ml LPS for 24 h was not significantly affected by iHA (p=0.02), but was significantly upregulated on complexes formed by simultaneous addition of TSG-6, IαI, and PTX3 on iHA (IαI/TSG-6/PTX3 (a)) (p=0.002) and on complexes formed by pre-bound TSG-6 to iHA (IαI/TSG-6/PTX3 (b)) (p=0.0005). In contrast, IL-23 protein is completely abolished on complexes formed by pre-bound PTX3 (IαI/TSG-6/PTX3 (c)) (p=0.05) similar to nHC-HA/PTX3 (p=0.05) (FIG. 19F).

Example 14. Use of HC-HA/PTX3 for the Treatment of Chronic Graft Versus Host Disease Allogeneic hematopoietic stem cell transplantation (HSCT) is a potentially curative treatment for hematological malignancies. However, chronic graft-versus-host disease (cGVHD) remains a major complication. GVHD causes several ocular manifestations in 45-60%, among which dry eye is the most frequent complication, occurring in nearly 50% of allogeneic HSCT recipients. In fact, dry eye is a distinctive sign and symptom for the diagnosis of cGVHD. Patients with cGVHD manifest either early-stage mild dry eye disease related to cGVHD or the so called 'distinctive feature of cGVHD' according to the NIH consensus conference classification. Two types of dry eye after HSCT have been noted; one had severe ocular surface and tear function damage with decreased reflex tearing that occurs soon after the onset of dry eye, whereas the other is mild with normal reflex tearing. Dry eye typically occurs 6 months after the transplantation and the severity has been reported to be correlated with the presence of cGVHD and meibomian gland disease. The onset of cGVHD-related severe dry eye is earlier than that of mild dry eye. For example, severe dry eye occurs 6.8±2.5 months after HSCT, while mild dry eye occurs 13.2±9.1 months after HSCT. A comparative study of 50 eyes of 25 post-HSCT patients and 28 eyes of 14 age-matched healthy controls showed that MG obstruction, decreased corneal sensitivity, enhanced tear evaporation rate, decreased conjunctival GCD, increased conjunctival squamous metaplasia and inflammatory cells were noted more in cGVHD-related dry eyes than the normal controls and post-HSCT without dry eye subjects. Furthermore, the conjunctival inflammatory cells were significantly higher in severe dry eyes compared with mild dry eyes (P<0.03). Moreover, most severe dry eye patients had systemic cGVHD, whereas only a few patients in the mild dry group had systemic cGVHD. Those findings indicated the different pathologic processes in cGVHD-related severe and mild dry eye disease. Because comprehensive ocular surface alteration was noted in post-HSCT patients, regardless of whether they had cGVHD-related dry eye or not, their results suggest that the extent of inflammatory process seems to have a pivotal role in the outcome of the cGVHD-related dry eye. The conjunctival brush cytology specimens showed considerably increased inflammatory cell numbers in both cGVHD-related severe dry eye and mild dry eye patients compared with normal controls and post-HSCT without dry eye subjects. Moreover, the number of inflammatory cells in severe dry eye specimens was significantly higher than in mild dry eye specimens. Furthermore, many inflammatory markers expressed in biopsy samples of the conjunctiva and lacrimal gland from cGVHD-related dry eye patients, confirming that inflammation is involved in the pathogenesis of cGVHD-related dry eye.

One likely cause of generating a number of scarring complication in cGVHD is via EMT of conjunctival basal epithelia and lacrimal gland myoepithelia as a result of cytokines released by chronic inflammation because of infiltrating donor lymphocytes. Previously, it has been recognized that inflammation and excessive fibrosis are prominent histologic features of chronic graft-versus-host disease (cGVHD), but the mechanism underlying these changes remains unknown. cGVHD manifests features resembling scleroderma, exhibiting prominent fibrosis in skin lesions, pulmonary fibrosis, and chronic immunodeficiency. Clinical features of ocular cGVHD include onset of dry, gritty, or painful eyes, cicatricial conjunctivitis including subconjunctival fibrovascular tissue formation, and scleral shortening, which is characteristic feature of conjunctival fibrosis. In addition to sclerotic features in skin lesions, mucosal atrophy in the mouth, strictures or stenosis in the upper to mid third of the esophagus, joint stiffness or contracture due to sclerosis, and bronchitis obliterans in lung together indicate the characteristic features of systemic GVHD-mediated fibrosis. The main histologic findings in the affected exocrine gland and mucosal membrane are marked fibrosis of the interstitium and a prominent increase in the number of fibroblasts, accompanied by mild lymphocytic infiltration. Clinically, the severity of the dry eye is correlated with the degree of fibrotic change, rather than with the amount of lymphocytic infiltration, indicating that excessive extracellular matrix accumulation primarily contributes to the exocrine dysfunction. The fibroblasts at the interstitium also play a role in inflammation, by attaching to lymphocytes and expressing human leukocyte antigen class II and costimulatory molecules. These findings together indicate that fibroblasts play an important role in the pathogenesis of cGVHD. Moreover, we have found that the accumulated fibroblasts in the lacrimal gland of cGVHD patients have a chimeric status. Thus, fibroblasts originating from circulating donor-derived precursors and recipient derived fibroblasts may participate in the excessive fibrosis in patients with cGVHD by interacting T cells. It remains unknown whether controlling inflammation by suppressing T cell infiltration will lead to less cicatricial complication in cGVHD.

Previously, donor-derived fibroblasts were detected by combining immunohistochemistry and Y-chromosome fluorescent in situ hybridization (FISH) methods in human cGVHD tissue samples. Using a murine model of cGVHD established by Zhang et al. ((2002) *J Immunol.* 168:3088-3098), the above finding can be reproduced. In this model, the tear volume begins to decrease at 3 weeks after transplantation. Early fibrosis around lacrimal gland ducts and progressive fibrosis are detected as early as 3 weeks after transplantation, and gradually progress for up to 8 weeks in a similar fashion to human samples. We have performed this experiments over 20 times to create both GVHD and control groups with success, resulting in overall reproducibility is 70-80% based on analysis of lacrimal gland tissue samples and tear volumes.

In a typical transplantation experiment, 7- to 8-wk-old male and female B10.D2 (H-2d) and BALB/c (H-2d, Sankyo Laboratory, Ltd) mice are used as donors and recipients, respectively, using added spleen cells as a source of mature T cells. Briefly, female recipient mice are lethally irradiated with 700 cGy from a Gammacel 137Cs source (J. L. Shepherd & Associates, San Fernando, Calif.). Approximately 6 h later they are injected by tail vein with male donor bone marrow ($1 \times 10^6$/mouse) and spleen ($2 \times 10^6$/mouse) cells suspended in RPMI 1640 (BioWhittaker, Walkersville, Md.). A control group (syngeneic BMT) consists of female BALB/c recipient mice that receive the same number of male BALB/c spleen and bone marrow cells. (Zhang et al. (2002) *J Immunol.* 168:3088-3098). For HC-HA/PTX3 treatment, HC-HA/PTX3 complexes are administered via subconjunctival injection at predetermined times following bone marrow transplantation, such as 7, 14, 21 and 28 days following bone marrow transplantation.

Effects of treatment are assessed using assays including, but not limited to measurement of lacrimal gland fibrosis using Mallory staining, determining the number of activated fibroblasts per field using HSP47, a collagen specific molecular chaperon, as a marker of activated fibroblasts, measure lacrimal tear production under pilocarpine stimulation using a cotton thread test, and determining the level of fibrogenic cytokines such as HSP47, IL-4, IL-6, and TGF-beta using RT-PCR.

It is expected that treatment with HC-HA/PTX3 complexes will result in the reduction of lacrimal gland fibrosis in the mouse model. HC-HA/PTX3 complexes are then administered in the clinical setting by means of subconjunctival injection to human subjects for the treatment of dry eye caused by cGVHD.

In some examples, the HC-HA/PTX3 complex used in the method of treatment described herein is an isolated native HC-HA/PTX3 complex (nHC-HA/PTX3). In some examples, the nHC-HA/PTX3 is isolated from umbilical cord tissue. In some examples, the nHC-HA/PTX3 is isolated from amniotic membrane. In some examples, the HC-HA/PTX3 complex used in the method of treatment described herein is a reconstituted HC-HA/PTX3 complex (rcHC-HA/PTX3).

Example 15. Use of HC-HA/PTX3 for the Treatment of Inflammation in a Mouse Model In this example, anti-inflammatory efficacy is tested in a murine model of HSV-1 necrotizing corneal stromal keratitis. A total of 240 female BALB/c mice (6-8 week old) obtained from Charles River Wiga (Sulzfeld, Germany) are anesthetized by intraperitoneal injection of 2 mg ketamine HCl and 400 ng mepivacaine HCl. For each mouse, the central cornea of one eye is then be scratched in a crisscross pattern with 8 horizontal and 8 vertical scratches using a 27-gauge needle under a surgical microscope. Each injured cornea is applied with a 5 μl suspension containing $1 \times 10^5$ plaque forming units of HSV-1 viruses (KOS strain), which are routinely propagated on Vero cells, stored at −80° C., and quantified by standard plaque assay. On Day 14 after HSV-1 inoculation, mouse corneas that have developed severe ulcerating stromal keratitis are included for the study (about 50% yield) and subdivided into three groups, each consisting of 40 corneas (n=6 for clinical examination, n=5 for histology, n=5 for immunostaining, n=6 for cytokine ELISA, n=5 for TUNEL, and n=10 for flow cytometry, and n=3 for attrition/backup). The non-infected fellow eyes are used as the negative control group. The positive control group receive tarsorrhaphy using 2 10-O nylon sutures to close eyelids. The experimental HC-HA/PTX3 group receive the same tarsorrhaphy as the positive control and topical application 4 times a day of a composition containing purified HC-HA/PTX3 complex. The experimental HA group receives the same tarsorrhaphy but topical application of composition of HA alone four times a day. After 2 days, tarsorrhaphy is removed in all three groups. Using an operation microscope (Zeiss, Germany), the severity of stromal inflammation of each cornea is evaluated by a score of 0 to 4+, with 1+ having less than 25%, 2+ less than 50%, 3+ less than 75%, and 4+ between 75 and 100% corneal opacity with corneal neovascularization, edema, and thinning. After euthanasia by $CO_2$ chamber followed by cervical dislocation, 5 corneas from each group are subjected to frozen sectioning immunostaining using primary antibodies to CD11b (neutrophils and macrophages), F4/80 (macrophages), Gr-1 (PMNs), and CD3 (T cells) (see Methods), and another 5 corneas from each group are submitted to hematoxylin-eosin staining and TUNEL staining. In addition, corneal homogenates prepared from 6 corneas from each group are subjected to ELISA measurement of IL-1α, IL-2, IL-6, IFN-γ and TNFα levels. Cells released by collagenase from 10 corneas of each group are prepared for flow cytometry to quantitate viable cells by MTT assay and apoptotic cells by the Annexin V-PE Apoptosis Detection Kit (BD-Pharmingen, Heidelberg, Germany).

It is expected that 50% mouse HSV-1-infected corneas will develop severe corneal stromal keratitis (inflammation), edema, and ulceration in two weeks after inoculation to be included for the study. Two days later, the non-infected corneas will remain normal, while infected corneas in the control group will maintain similar severe inflammation when tarsorrhaphy is removed. Similar to the control group, corneas in the experimental HA group will exhibit similar severe inflammation. In contrast, corneas of the experimental HC-HA/PTX3 group will show reduction of inflammation, which will be correlated with and substantiated by significant reduction of inflammatory (PMN/macrophages) and immune (T-cells) infiltration based on histology and immunostaining to CD11b, F4/80, Gr-1, and CD3, by significant reduction of inflammatory and immune cytokines such as IL-1α, IL-2, IL-6, IFN-γ, and TNF-α based on ELISA and by a significant increase of TUNEL-positive cells in corneal tissues and of dead (MTT) and apoptotic cells released by collagenase from the cornea (flow cytometry using Annexin-V/7-AAD) when compared to the positive control group and the experimental HA group. Collectively, these data support the notion that the HC-HA/PTX3 complex exerts a clinical anti-inflammatory efficacy in this murine HSV-1 model.

In some examples, the HC-HA/PTX3 complex used in the method of treatment described herein is an isolated native HC-HA/PTX3 complex (nHC-HA/PTX3). In some examples, the nHC-HA/PTX3 is isolated from umbilical cord tissue. In some examples, the nHC-HA/PTX3 is isolated from amniotic membrane. In some examples, the HC-HA/PTX3 complex used in the method of treatment described herein is a reconstituted HC-HA/PTX3 complex (rcHC-HA/PTX3).

Example 16. Use of HC-HA/PTX3 for the Inhibition of Scarring in a Rabbit Model

In this example, anti-scarring efficacy tested in a rabbit model of excimer laser-assisted photorefractive keratectomy (PRK). A total of 30 New Zealand white albino rabbits with body weight (BW) of 2.5-3.0 kg, either sex, are used and subdivided into three groups (n=10 each): the non-PRK control group, the PRK HA group, and the PRK HC-HA/PTX3 group. Before PRK and for all CMTF examinations, rabbits are anesthetized by intramuscular injection of 5 mg/kg BW xylazine and 30 mg/kg BW ketamine and topically by 0.5% tetracaine HC1 ophthalmic solution (Ortopics Laboratories Corp., Fairton, N.J.). For the two PRK groups, the corneal epithelium of one eye of each animal is manually be removed by gentle scraping with a blunt spatula in an area just larger than the ablation zone, the denuded stroma is irrigated with normal saline, and excess fluid is removed gently with a cellulose sponge. A standard 6 mm diameter, 9.0 D PRK myopic correction PRK is performed using a LaddarVision Excimer Laser (Alcon, Ft. Worth, Tex.) to achieve a predicted theoretical stromal ablation depth of 118 μm. Immediately following PRK and thereafter, the PRK HC-HA/PTX3 Group is applied with a composition containing the HC-HA/PTX3 complex while the PRK HA group is applied with composition containing HA alone, both four times a day thereafter for a total of 3 weeks. In addition, all PRK-treated eyes is instilled topical 0.1% sodium diclofenac (one drop immediately post-PRK) and 0.3% gentamicin sulfate (three times daily for 3 days).

In vivo CMTF is performed on all operated eyes (n=6 from each group) prior to PRK and at one, two, three, and 4 weeks, two months and 4 months post-PRK using a modified Tandem Scanning Confocal Microscope (Tandem Scanning Corporation, Reston, Va.) with a 24× surface-contact objective. Following a standard confocal examination of corneal morphology, video camera setting (gain, kilovolts, and black level) are switched to manual and kept constant during the study to allow direct comparison of all scans. CMTF is performed as a continuous, z-axis scan through the entire cornea. Corneal, epithelial, and stromal thickness are mapped within the central 3 mm zone by performing 10 consecutive CMTF-scans in areas covering all regions. Only data obtained from the thinnest stromal region corresponding to the center of the photoablation profile are used for subsequent calculations. CMTF-profiles based on image intensity depth are generated from CMTF videorecordings. Corneal light reflectivity is measured by CMTF-profiles and expressed in arbitrary units (U) defined as μm*pixel intensity as an estimate of corneal haze.

To identify and measure the presence of stromal fibrotic tissue, three PRK-treated animals from each group (control and treated) are vitally stained with 0.5% 5-(4,6-dichlorotriazinyl) aminofluorescein (DTAF) dissolved in 0.2 M sodium bicarbonate as previously reported. After 2 min staining, eyes are thoroughly rinsed to remove excess dye before administration of topical antibiotics. At 4 months post-PRK animals is euthanized by intraveneous injection of sodium pentobarbital (120 mg/kg BW). Following euthanasia, all corneas are fixed in situ by anterior chamber perfusion of 2% paraformaldehyde in PBS, pH 7.2, for 3 min, excised, placed in fresh fixative, and stored at 4° C. Tissue is then by embedded in OCT, snap frozen in liquid nitrogen and sectioned using a cryomicrotome. Tissue is serially stepped section to identify the central and deepest part of the photoablation, and subjected to immunostaining using antibodies to keratocan, CD3434, FITC-conjugated phalloidin, ED-A fibronectin, S-100A4 and α-smooth muscle actin (α-SMA) to correlate changes of corneal haze (by CMTF light reflectivity) with phenotypic changes from keratocytes to fibroblasts or myofibroblasts. Additionally, in those eyes that are stained with DTAF, the thickness of the fibrotic tissue that is deposited is measured by determining the distance between the basal epithelial cells and the DTAF stained corneal tissue which represents the original, undamaged corneal stroma.

It is expected that in vivo confocal microscopy will reveal characteristic epithelial, basal lamina, stromal and endothelial characteristics, which will correlate well with well-defined peaks that change in intensity and position over time when in vivo CMTF-profiles are analyzed for corneas of the non-PRK control as well as for those receiving PRK. According to the published data, the PRK-treated corneas will exhibit four peaks originating from the superficial epithelium, photoablated stromal surface, layers of spindle-shaped fibroblasts, and endothelium, while those of the non-PRK control will exhibit three peaks originating from superficial epithelium, basal lamina, and endothelium at one week post-PRK. It is expected that there will not be much difference between the two experimental groups at one week post-PRK. At 2 weeks post-PRK, the experimental PRK HA group will show an increasing intensity of the peak close to the photoablated stromal surface due to ongoing cell migration of spindle-shaped fibroblasts. However, it is expected that the intensity of the repopulating fibroblasts (by the height of the peak) will be much reduced in the experimental PRK HC-HA/PTX3 group. During the period from 3 weeks to four months post-PRK, the peak corresponding to the layer of spindle-shaped fibroblasts will merge with the peak originating from the photoablated stromal surface because of the completion of repopulation of the acellular anterior stroma in the experimental PRK HA group, and will result in a dramatic increase of the reflectivity of the peak corresponding to the photoablated stromal surface. In contrast, there will not be such a dramatic increase of the reflectivity in the experimental PRK HC-HA/PTX3 group. Such a difference of light reflectivity can also be quantitated by calculating the area of the CMTF-peaks originating from specific intra-corneal structures. It is expected that the experimental PRK HA group will exhibit a substantial linear increase in reflectivity intensity within the first 2 to 3 weeks post-PRK and a slow linear decline in reflectivity thereafter. In contrast, it is expected that there will be a significant decrease of reflectivity in the experimental PRK HC-HA/PTX3 group during both periods. Collectively, these CMTF data support that HC-HA/PTX3 complex exerts an inhibitory effect of keratocytes activation, migration and cell recruitment during repopulation of the acellular anterior stroma, explaining why corneal light scattering (haze) is reduced similar to anti-TGF-β antibodies previously reported. As a result, there is less cellularity and reflectivity of activated, migrating, intra-stromal wound healing keratocytes, and less deposition of new stromal extracellular matrix and a faster establishment of a normal quiescent keratocytes population in the anterior stroma. This conclusion will be corroborated by a significant reduction of activated keratocytes (F-actin in keratocan expressing cells), fibroblasts (cytoplasmic staining of S-100A4, membrane expression of ED-A fibronectin), and myofibroblasts (nuclear expression of S100A4 and cytoplasmic expression of α-SMA) in the experimental PRK HC-HA/PTX3 group when compared to the experimental PRK HA group during the period of 2 to 3 weeks post-PRK. It also is expected that there will be a significant reduction of the distance between the basal epithelial cells and the DTAF stained corneal tissue in the PRK HC-HA/PTX3 group, indicative of significantly less fibrotic tissue, when compared to the PRK HA group.

In some examples, the HC-HA/PTX3 complex used in the method of treatment described herein is an isolated native HC-HA/PTX3 complex (nHC-HA/PTX3). In some examples, the nHC-HA/PTX3 is isolated from umbilical cord tissue. In some examples, the nHC-HA/PTX3 is isolated from amniotic membrane. In some examples, the HC-HA/PTX3 complex used in the method of treatment described herein is a reconstituted HC-HA/PTX3 complex (rcHC-HA/PTX3).

Example 17. Use of HC-HA/PTX3 for the Treatment of Atherosclerosis

In this example, an HC-HA/PTX3 complex generated by the methods described herein is administered for the treatment of atherosclerosis.

Atherosclerosis includes the involvement an inflammatory cell population, in particular macrophages. A macrophage phenotypic switch is observed during disease progression. In atherosclerosis, circulating monocytes are recruited to sites of fatty deposit accumulation within the vascular intima and subintima via CCR2 and endothelial adhesion mediated mechanisms. Upon arrival these cells become activated and differentiate into macrophages. The fatty deposits then begin to mature into plaques with continued recruitment of inflammatory cells, smooth muscle cells, and the production of extracellular matrix. The initial infiltrating macrophage population in early atherosclerosis is heterogeneous, but possesses a predominantly M2-like phenotype. Concurrent with lesion progression and expansion, a switch to a predominantly M1 phenotype has been observed. This phenotypic switch may be due to the phagocytosis of excess oxidized low-density lipoproteins (LDL) within the plaque by macrophages and the production of IFN-γ by local Th1 cells, resulting in the development of foam cell macrophages. Foam cell macrophages exhibit a highly activated phenotype leading to production of pro-inflammatory mediators and MMPs that destabilize the plaques, potentially leading to thromboembolism. Therapies which prevent the M2 to M1 switch or deplete M1 macrophages selectively are of clinical utility for the stabilization of atherosclerotic plaques.

An HC-HA/PTX3 complex generated by the methods described herein is administered to a subject having atherosclerosis. The HC-HA/PTX3 complex employed, for example, to coat implantable medical devices, such as a stent, for implantation in at or near the site of inflammation. Treatment of atherosclerosis with an HC-HA/PTX3 complex is expected to decrease inflammation and prevent thromboembolism.

In some examples, the HC-HA/PTX3 complex used in the method of treatment described herein is an isolated native HC-HA/PTX3 complex (nHC-HA/PTX3). In some examples, the nHC-HA/PTX3 is isolated from umbilical cord tissue. In some examples, the nHC-HA/PTX3 is isolated from amniotic membrane. In some examples, the HC-HA/PTX3 complex used in the method of treatment described herein is a reconstituted HC-HA/PTX3 complex (rcHC-HA/PTX3).

Example 18. Use of HC-HA/PTX3 for the Treatment of Obesity and Insulin Resistance In this example, an HC-HA/PTX3 complex generated by the methods described herein is administered for the treatment of obesity and insulin resistance.

Adipose tissue macrophages (ATM) comprise a significant proportion of the cellular component of adipose tissue in both lean and obese states. In normal humans, ATMs make up as much as ten percent of the cellular constituents of the tissue. In comparison, in obese subjects that number rises to as much as 40%. In normal, non-obese subjects, ATMs have a polarized M2 phenotype characterized by increased baseline STAT6 and PPAR-γ expression. These cells play an important and beneficial role in nutrient metabolism. The deficiency in PPAR-γ leads to impaired M2 macrophage function and susceptibility to diet-induced inflammation and insulin resistance. In contrast, ATMs accumulate in the adipose tissue during obesity have a strongly polarized pro-inflammatory M1 phenotype. These cells produce high levels of TNFα, IL-6, and IL-1β, all of which are also observed in increased levels of adipose tissue from insulin resistant individuals. High levels of pro-inflammatory mediators locally impair the function of resident insulin processing cells.

An HC-HA/PTX3 complex generated by the methods described herein is administered to a subject suffering from obesity or insulin resistance. An HC-HA/PTX3 complex is administered, for example, as a solution of gel for treatment. It is expected that treatment with an HC-HA/PTX3 complex will promote a phenotypic switch of adipose tissue macrophages (ATM) from a pro-inflammatory M1 phenotype to an M2 phenotype and restore normal insulin processing.

In some examples, the HC-HA/PTX3 complex used in the method of treatment described herein is an isolated native HC-HA/PTX3 complex (nHC-HA/PTX3). In some examples, the nHC-HA/PTX3 is isolated from umbilical cord tissue. In some examples, the nHC-HA/PTX3 is isolated from amniotic membrane. In some examples, the HC-HA/PTX3 complex used in the method of treatment described herein is a reconstituted HC-HA/PTX3 complex (rcHC-HA/PTX3).

Example 19. Use of HC-HA/PTX3 for the Treatment of Type 1 Diabetes

In this example, an HC-HA/PTX3 complex generated by the methods described herein is administered for the treatment of type 1 diabetes.

Diabetes mellitus type 1 (Type 1 diabetes, T1DM, IDDM, or, formerly, juvenile diabetes) is a form of diabetes mellitus that results from autoimmune destruction of insulin-producing beta cells of the pancreas. The subsequent lack of insulin leads to increased blood and urine glucose. The classical symptoms are polyuria (frequent urination), polydipsia (increased thirst), polyphagia (increased hunger), and weight loss.

An HC-HA/PTX3 complex generated by the methods described herein is administered to a subject suffering from Type 1 diabetes in the form of a microcapsules containing autologous or allogeneic insulin-producing cells coated with HC-HA/PTX3 complex. The microcapsules are administered to a subject for example, by injection. It is expected that treatment with the HC-HA/PTX3 coated microcapsules will allow for the production of insulin that is released in the subject and prevent or reduce inflammatory responses against the cell therapy or microcapsule, thereby alleviating the Type 1 diabetes and the symptoms thereof.

In some examples, the HC-HA/PTX3 complex used in the method of treatment described herein is an isolated native HC-HA/PTX3 complex (nHC-HA/PTX3). In some examples, the nHC-HA/PTX3 is isolated from umbilical cord tissue. In some examples, the nHC-HA/PTX3 is isolated from amniotic membrane. In some examples, the HC-HA/PTX3 complex used in the method of treatment described herein is a reconstituted HC-HA/PTX3 complex (rcHC-HA/PTX3).

Example 20. Use of HC-HA/PTX3 for the Treatment of Fibrosis

In this example, an HC-HA/PTX3 complex generated by the methods described herein is administered for the treatment of fibrosis or fibrotic disorder.

The progressive fibrotic diseases, such as idiopathic pulmonary fibrosis (IPF), hepatic fibrosis and systemic sclerosis, are tightly regulated by macrophages. 'Pro-fibrotic' macrophages exhibit M1 properties and produce various mediators, including TGFβ1, PDGF and insulin-like growth factor 1, that directly activate fibroblasts and myofibroblasts, which control ECM deposition. Pro-fibrotic macrophages also produce MMPs, TIMPs, and IL-1β. IL-1β stimulates TH17 cells to produce IL-17, an important inducer of bleomycin-induced pulmonary fibrosis, a fibrotic disorder with characteristics that are similar to those of IPF. The production of IL-10, RELMα and ARG1 by M2-like macrophages suppress fibrosis.

An HC-HA/PTX3 complex generated by the methods described herein is administered to a subject suffering from fibrosis or a fibrotic disorder. An HC-HA/PTX3 complex is administered, for example, as a solution, gel or as a coating on an implantable medical device. It is expected that treatment with an HC-HA/PTX3 complex will decrease the M1 macrophages and activation of fibroblasts and myofibroblasts and increase the amount M2 macrophages present at the affected site(s) in the subject thereby suppressing the fibrosis and symptoms thereof, such as scarring.

In some examples, the HC-HA/PTX3 complex used in the method of treatment described herein is an isolated native HC-HA/PTX3 complex (nHC-HA/PTX3). In some examples, the nHC-HA/PTX3 is isolated from umbilical cord tissue. In some examples, the nHC-HA/PTX3 is isolated from amniotic membrane. In some examples, the HC-HA/PTX3 complex used in the method of treatment described herein is a reconstituted HC-HA/PTX3 complex (rcHC-HA/PTX3).

Example 21. Use of HC-HA/PTX3 for the Treatment of Chronic Inflammation

In this example, an HC-HA/PTX3 complex generated by the methods described herein is administered for the treatment of a chronic inflammatory condition, such as rheumatoid arthritis.

Many autoimmune diseases, including rheumatoid arthritis, involve inflammatory responses to autoantibodies that activate Fc receptors to trigger mast-cell and macrophage activation, and neutrophil invasion. This leads to an intense local inflammatory response and, if not resolved, to tissue damage over time with cycles of repair and destruction. In rheumatoid arthritis, CSF1 is produced constitutively by synovial fibroblasts and recruits tissue-infiltrating monocytes and macrophages. In addition, locally produced CSF1, together with RANK1, induces the differentiation of monocytes to osteoclasts, which trigger bone loss.

An HC-HA/PTX3 complex generated by the methods described herein is administered to a subject suffering from a chronic inflammatory condition, such as rheumatoid arthritis. An HC-HA/PTX3 complex is administered, for example, as a solution, gel or as a coating on an implantable medical device. It is expected that treatment with HC-HA/PTX3 will suppress M1 proinflammatory macrophages, induce neutrophil apoptosis, and inhibit osteoclast differentiation, thereby treating the inflammatory condition and the symptoms thereof.

In some examples, the HC-HA/PTX3 complex used in the method of treatment described herein is an isolated native HC-HA/PTX3 complex (nHC-HA/PTX3). In some examples, the nHC-HA/PTX3 is isolated from umbilical cord tissue. In some examples, the nHC-HA/PTX3 is isolated from amniotic membrane. In some examples, the HC-HA/PTX3 complex used in the method of treatment described herein is a reconstituted HC-HA/PTX3 complex (rcHC-HA/PTX3).

Example 22. Use of HC-HA/PTX3 for the Treatment of Acute Inflammatory Response In this example, an HC-HA/PTX3 complex generated by the methods described herein is administered for the treatment of an acute inflammatory response caused by a condition such as myocardial infarction, stroke or sepsis. An HC-HA/PTX3 complex generated by the methods described herein is administered to a subject having an acute inflammatory response caused by a condition such as myocardial infarction, stroke or sepsis. An HC-HA/PTX3 complex is administered, for example, as a solution by intravenous infusion. It is expected that the HC-HA/PTX3 complex will decrease or prevent damage caused by acute inflammation by suppression of M1 inflammatory macrophages.

In some examples, the HC-HA/PTX3 complex used in the method of treatment described herein is an isolated native HC-HA/PTX3 complex (nHC-HA/PTX3). In some examples, the nHC-HA/PTX3 is isolated from umbilical cord tissue. In some examples, the nHC-HA/PTX3 is isolated from amniotic membrane. In some examples, the HC-HA/PTX3 complex used in the method of treatment described herein is a reconstituted HC-HA/PTX3 complex (rcHC-HA/PTX3).

Example 23. Use of HC-HA/PTX3 for the Treatment of Cancer

In this example, an HC-HA/PTX3 complex generated by the methods described herein is administered for the treatment of cancer.

The participation of large numbers of inflammatory cells in tumor development and progression has been observed and is commonly described as "smoldering inflammation". These observations have led to a well-established link between inflammatory cells, macrophages in particular, and cancer. It was initially thought that development of oncogenes resulted in the hallmark microenvironment of cancer, in which transformed cells secrete cytokines and chemokines that promote tissue development and prevent apoptosis as well as suppress cytotoxic immune responses (termed the "intrinsic pathway"). It is now recognized that another pathway leading to tumorigenesis exists. This "extrinsic pathway" is initially characterized by a chronic pro-inflammatory environment resulting from a persistent microbial infection, autoimmune disease, or other etiology of unknown origin. The chronic production of large quantities of inflammatory mediators in these cases can lead to tumor cell proliferation and survival or to the induction of genetic instabilities in normal cells, with resultant expression of oncogenes and production of immune suppressive cytokines. Thus, early tumor development is, in many instances, characterized by a polarized inflammatory, M1-like macrophage environment.

An HC-HA/PTX3 complex generated by the methods described herein is administered to a subject having a cancer, such as a solid tumor cancer. An HC-HA/PTX3 complex is administered, for example, as a solution, gel or as a coating on an implantable medical device for topical, injective, or implantive application. Because HC-HA/PTX3 can suppress M1 macrophage polarization, it is expected that treatment with HC-HA/PTX3 will inhibit or prevent cancers or their progress into late stage phenotypes.

In some examples, the HC-HA/PTX3 complex used in the method of treatment described herein is an isolated native HC-HA/PTX3 complex (nHC-HA/PTX3). In some examples, the nHC-HA/PTX3 is isolated from umbilical cord tissue. In some examples, the nHC-HA/PTX3 is isolated from amniotic membrane. In some examples, the HC-HA/PTX3 complex used in the method of treatment described herein is a reconstituted HC-HA/PTX3 complex (rcHC-HA/PTX3).

Example 24. Use of HC-HA/PTX3 for the Treatment of Non-Healing Skin Wounds or Ulcers In this example, an HC-HA/PTX3 complex generated by the methods described herein is administered for the treatment of a non-healing wound or ulcer on the skin.

A non-healing wound or ulcer on the skin that has been present for about 3-4 weeks duration, without healing is called non-healing ulcer. Diseases that commonly cause non-healing ulcers are vascular disease, diabetes, skin cancers and some infections.

An HC-HA/PTX3 complex generated by the methods described herein is administered to a subject having a non-healing wound or ulcer on skin. An HC-HA/PTX3 complex is administered, for example, as a solution, gel topically or subcutaneously for the treatment at the site of the wound or ulcer. It is expected that treatment with HC-HA/PTX3 will promote the healing of the wound or ulcer by promoting the M2 phenotype of wound healing and tissue regenerative macrophages.

In some examples, the HC-HA/PTX3 complex used in the method of treatment described herein is an isolated native HC-HA/PTX3 complex (nHC-HA/PTX3). In some examples, the nHC-HA/PTX3 is isolated from umbilical cord tissue. In some examples, the nHC-HA/PTX3 is isolated from amniotic membrane. In some examples, the HC-HA/PTX3 complex used in the method of treatment described herein is a reconstituted HC-HA/PTX3 complex (rcHC-HA/PTX3).

Example 25. Use of HC-HA/PTX3 for the Treatment of High Risk Corneal Transplants In this example, HC-HA/PTX3 is administered for the treatment of high risk corneal transplants. Mafia mice, which EGFP+ macrophages are intrastromally injected with LPS (5 µg per eye) for both eyes. In each eye, OS (oculus sinister; left eye) is treated with PBS (2 or 4 injection sites) while OD (oculus dexter, right eye) is treated one time with HC-HA/PTX3 (2 or 4 injection sites; 5 µl of 1 mg/ml HA composition containing HC-HA/PTX3 per injection site) immediately after LPS injection. Images of whole corneas are taken with in vivo intravital microscopy on day 1, day 2, day 3, day 4, day 5, day 6, and day 7. EGFP-positive cells are counted based on the intensity of green fluorescence to determine the level of EGFP infiltration. In a mouse model of corneal transplantation, injection of HC-HA/PTX3 into subconjunctival sites is expected to reduce inflammation (i.e. infiltration of macrophages) and improve the survival rate of transplanted corneas when compared to PBS vehicle control.

In some examples, the HC-HA/PTX3 complex used in the method of treatment described herein is an isolated native HC-HA/PTX3 complex (nHC-HA/PTX3). In some examples, the nHC-HA/PTX3 is isolated from umbilical cord tissue. In some examples, the nHC-HA/PTX3 is isolated from amniotic membrane. In some examples, the HC-HA/PTX3 complex used in the method of treatment described herein is a reconstituted HC-HA/PTX3 complex (rcHC-HA/PTX3).

Example 26. Distribution of HA, PTX3, TSG-6, HC1, HC2, HC3 and Bikunin in Umbilical Cord (UC)

Figure 20A:
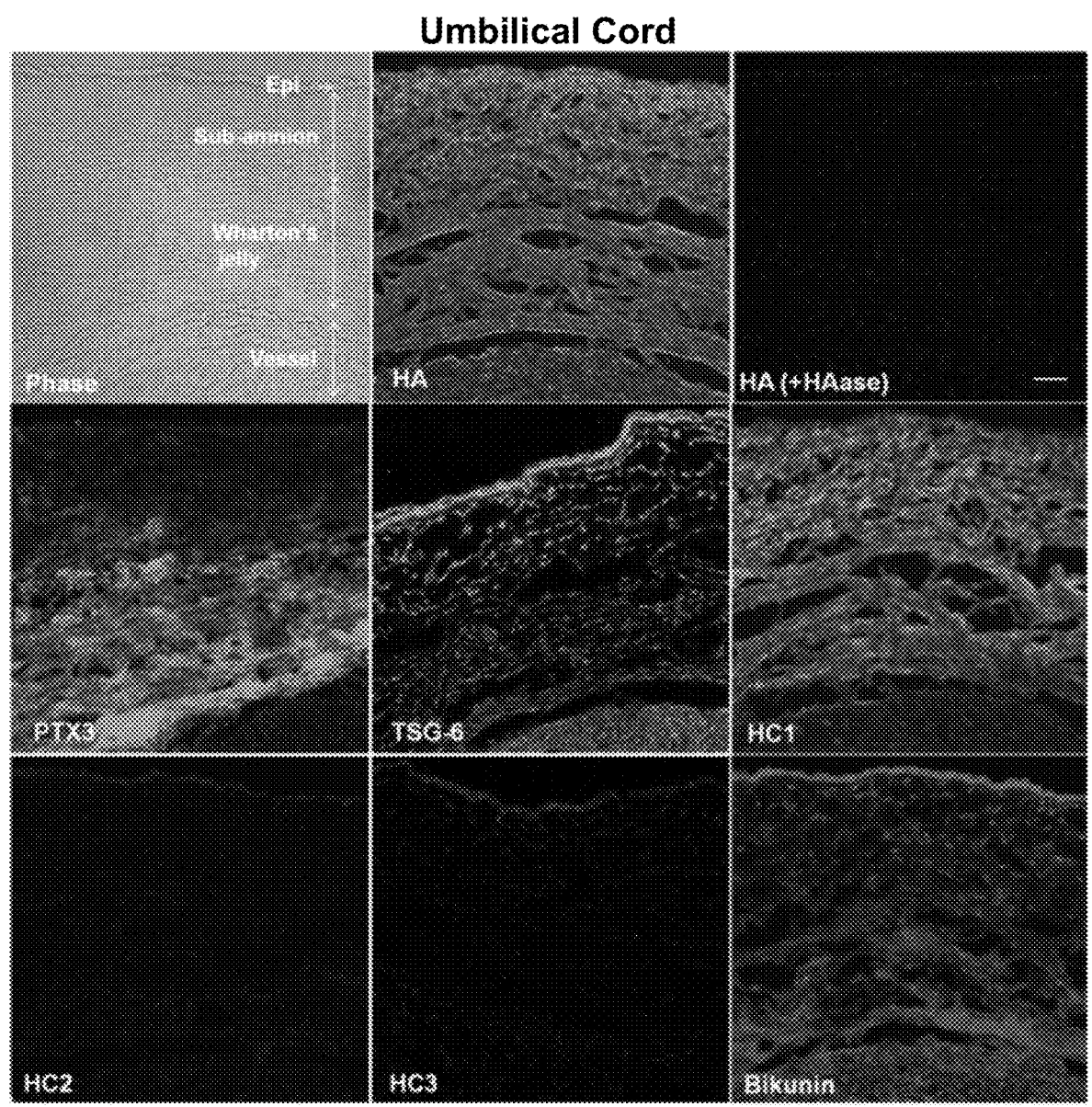
FIG. 20A-B exemplifies immunostaining of HA, PTX3, TSG-6, HCs and bikunin in human umbilical cord (A) or amniotic membrane (B). Frozen sections of human umbilical cord were probed with biotinylated HABP with or without HAase digestion and with antibodies against PTX3 and TSG-6, and chain-specific antibodies against IαI and PαI components as indicated. Nuclei were counter-stained with Hoechst 33342 (blue). Epi, Epithelium. Bar represents 100 µm.
Figure 20B:
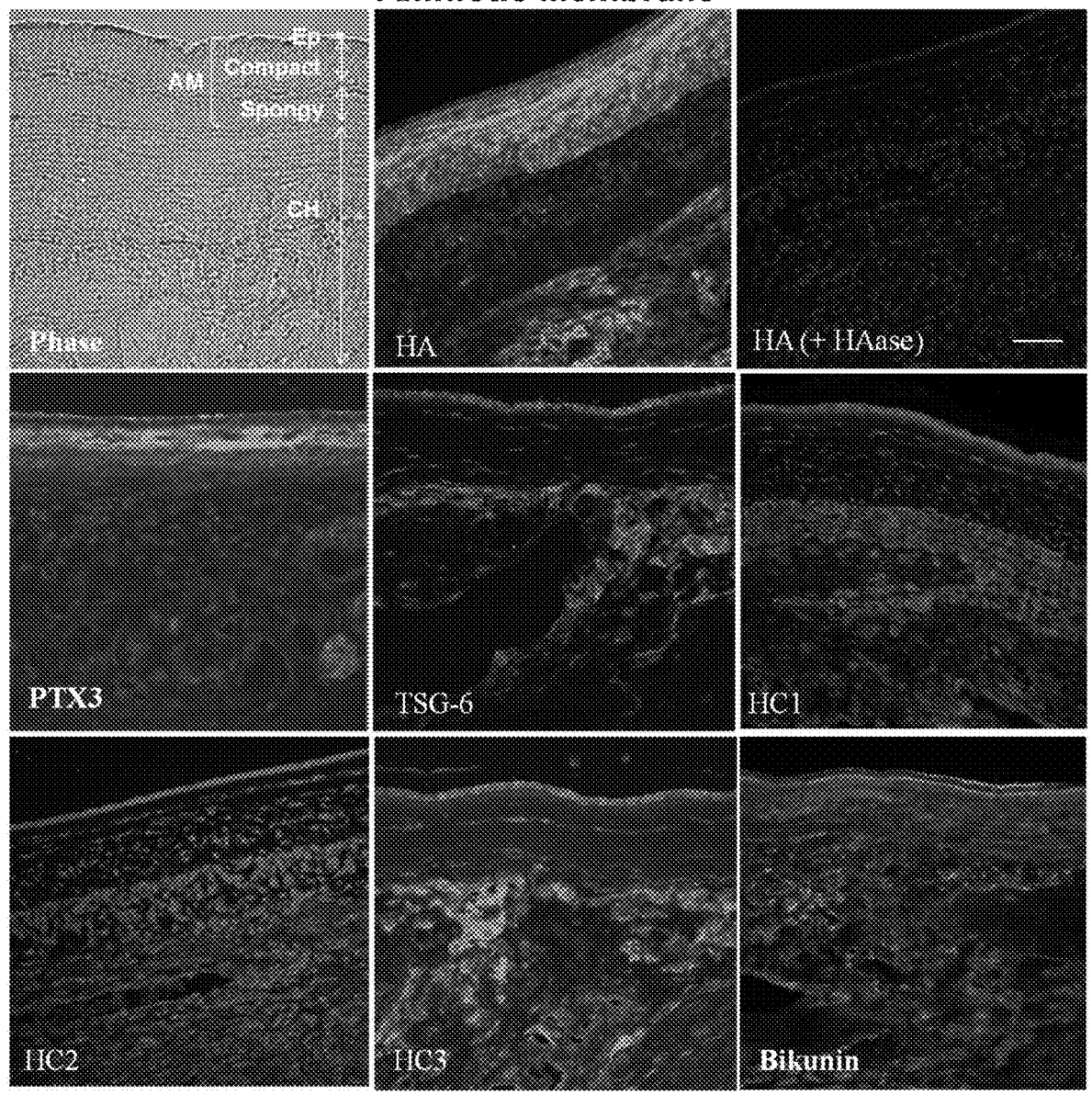

In this example, the in vivo distribution of HA, PTX3, TSG-6, HC1, HC2, HC3 and bikunin was detected in umbilical cord (UC) by immunostaining. UC tissue frozen sections were subjected to immunostaining for HA, PTX3, TSG-6 and various components of IαI including HCs and bikunin. UC consisted of a layer of epithelium and a stroma composed of a sub-amnion layer and a Wharton's jelly that contained three vessels, i.e., one vein and two arteries (FIG. 20a, with one artery vessel, phase). Strong positive HA staining was observed in the UC epithelium, sub-amnion layer and Wharton's jelly, and weak HA staining in the vessel wall (FIG. 20a, HA). With HAase digestion, the aforementioned HA staining disappeared (FIG. 20a, HA (+HAase)), conforming the specific staining for HA.

Strong positive immunostaining of PTX3 was present in Wharton's jelly, and weak PTX3 staining in sub-amnion layer and epithelium (FIG. 20a, PTX3). HAase digestion did not enhance PTX3 staining in the sub-amnion layer and the epithelium (not shown), suggesting that the weak PTX3 staining was not due to the masking effect by HA. Positive PTX3 staining was also observed in the endothelium of vessels (not shown) but not in the vessel wall of arteries and vein.

Both TSG-6 and bikunin were present in the whole UC with TSG-6 mainly present in cells and around cells and more TSG-6 was in epithelium and subamnion compared with Wharton's jelly. HC1 had a similar localization as HA except that the epithelium and the vessel wall had faint HC1 staining. Weak to no HC2 and HC3 staining was present in the epithelium but not in the stroma of UC. These results showed that UC produced abundant HA, PTX3, TSG-6, HC1 and bikunin, and disproportionally less HC2 and HC3 when compared to AM. It was determined that UC constitutively expressed the above proteins, and HC-HA/PTX3 complex.

Furthermore, PTX3 was present in UC with a different distribution pattern from what has been reported in AM. More PTX3 was present in the UC Wharton's jelly and less in epithelium and sub-amnion. In contrast, more PTX3 was in the epithelium and the stromal compact layer in AM. UC had a similar pattern to AM in the following markers: more HA was present in the whole stroma of UC and little in epithelium of UC. This was similar in the distribution pattern of HA in AM. TSG-6 was mainly localized in epithelial and subamnion cells of UC, and bikunin was found in the whole UC.

Example 27. Comparison of the Extracts of PBS and GnE Sequentially Obtained from AM and UC This example determined whether the insoluble part after PBS extract from AM still contained any PTX3, TSG-6 and IαI as well as HC-HA/PTX3 complex. Proteins were extracted from the insoluble part of AM by 4 M GnHCl after PBS extraction to see whether there was PTX3, TSG-6 and IαI. In addition, UC with PBS was also sequentially extracted with 4 M GnHCl to detect PTX3, TSG-6, HCs and bikunin in these two different extractions.

According to the method described in He et al. (2009) J. Biol. Chem. 284:20136-20146), AM, CH and UC were homogenized with a blender in cold PBS at 1:1 (g/ml) for AM or 1:1.5 (g/ml) for UC, and mixed at 4° C. for 1 h. The mixture was centrifuged at 48,000 g at 4° C. for 30 min. The supernatants of PBS extract were designated as AME, CHE and UCE, respectively. In addition, Wharton's jelly mixture from UC was also extracted by PBS and such extract was named UJE. The insoluble pellet of AM, CH, UC and UC jelly mixture after PBS extraction were further extracted by 4 M GnHCl buffer (100 mM sodium acetate, pH 5.8, 4M GnHCl, 10 mM EDTA, 1% Triton X-100) at 4° C. for 24 h. After centrifugation at 48,000 g, at 4° C. for 30 min, the supernatants were collected and named AMGnE, CHGnE, UCGnE and UJGnE, respectively. The HA and protein concentrations in each extraction were detected by HA ELISA and BCA assay, respectively.

GnHCl Further Extracted Abundant HA and Proteins from the Insoluble Pellet After PBS Extraction The HA and protein concentrations in sequential PBS and GnHCl extracts are summarized in Table 1 where the HA/protein ratio was also compared between the two extracts. In general, 4 M GnHCl further extracted abundant proteins and HA from the insoluble pellet of AM, CH, UC and UC jelly mix after PBS extraction. GnHCl buffer extracted more proteins but less HA from the insoluble pellet than PBS. However, UCGnE still contained similar amount of proteins and HA to AME and CHE. That is, UC contained more HA than AM and CH in both PBS and GnHCl extracts.

TABLE 1

Quantitation of proteins and HA in 4M GnHCl extracts (GnE) from insoluble pellets of AM, CH, UC and UC jelly mix after PBS extract

|  | HA (µg/ml) | Protein (µg/ml) | HA/protein Ratio (µg/µg) |
| --- | --- | --- | --- |
| AME I103 | 75.7 | 1014.3 | 0.074633 |
| AME J021 | 61.5 | 5353.0 | 0.011489 |
| AMGnE I103 + J021 | 47.7 | 6097.5 | 0.007823 |
| CHE I103 | 78.9 | 6161.7 | 0.012805 |
| CHGnE I103 | 24.9 | 7021.7 | 0.003546 |
| UCE 1 I103 | 453.5 | 8523.8 | 0.053204 |
| UCGnE 1 I103 | 88.2 | 1925.7 | 0.045802 |
| UCE 2 5001 | 421.3 | 7471.3 | 0.056389 |
| UCGnE 2 5001 | 79.6 | 2670.2 | 0.029811 |
| UCJE | 277.5 | 5135.1 | 0.05404 |
| UCJGnE | 57.2 | 4955.1 | 0.011544 |

Monomer, dimer, and HMW PTX3 was present at higher amounts in PBS extraction of UC cells compared to AM cells. But HMW PTX3 was present in higher amounts in GnHCl extraction in AM cells.

Figure 21A:
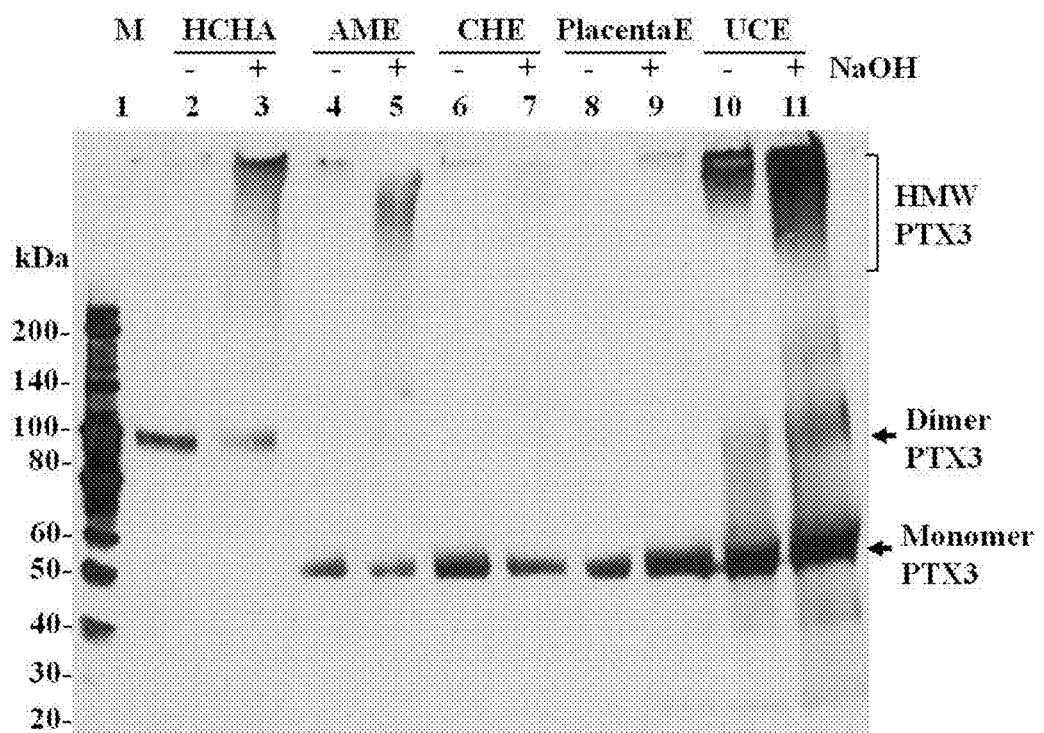
FIG. 21A-B exemplifies a comparison of PTX3 levels in sequential PBS and GnHCl extract from AM, CH and UC. A, each lane contains 2 µg HA in lanes 2 and 3 and 20 µg total proteins in lanes 4-11. B, each lane contains 40 µg total proteins in lanes 3-10.

Analysis of the AME with anti-PTX3 antibody revealed a band of ~45 kDa corresponding to the size of the native PTX3 monomer, and a HMW band at the bottom of the loading well (FIG. 21A, lane 4). NaOH treatment did not affect the 45 kDa band, but completely eliminated the HMW band, resulting in a HMW smear of PTX3 (FIG. 21A, lane 5), which is a notable feature of PTX3 in HC-HA complex with NaOH treatment where no monomer PTX3 but a 90 kD dimer was detected with or without NaOH treatment (FIG. 21A, lane 2 and 3). The HMW smear of PTX3 represented the complexes formed between PTX3 and HC-HA. CHE had the same pattern of PTX3 band, but there was less of a smear of PTX3 after NaOH treatment, consistent with the immunostaining result. Placenta extract had the same result with CHE. Notably, PTX3 existed more in a dimer and HMW smear besides monomer in UCE, and their intensity further increased after NaOH treatment. Similar to AME, UCE also generated HMW smearing pattern, more so than AME. These results showed that UCE contain more PTX3 than AME, while CHE and placenta extracts contained little PTX3.

Figure 21B:
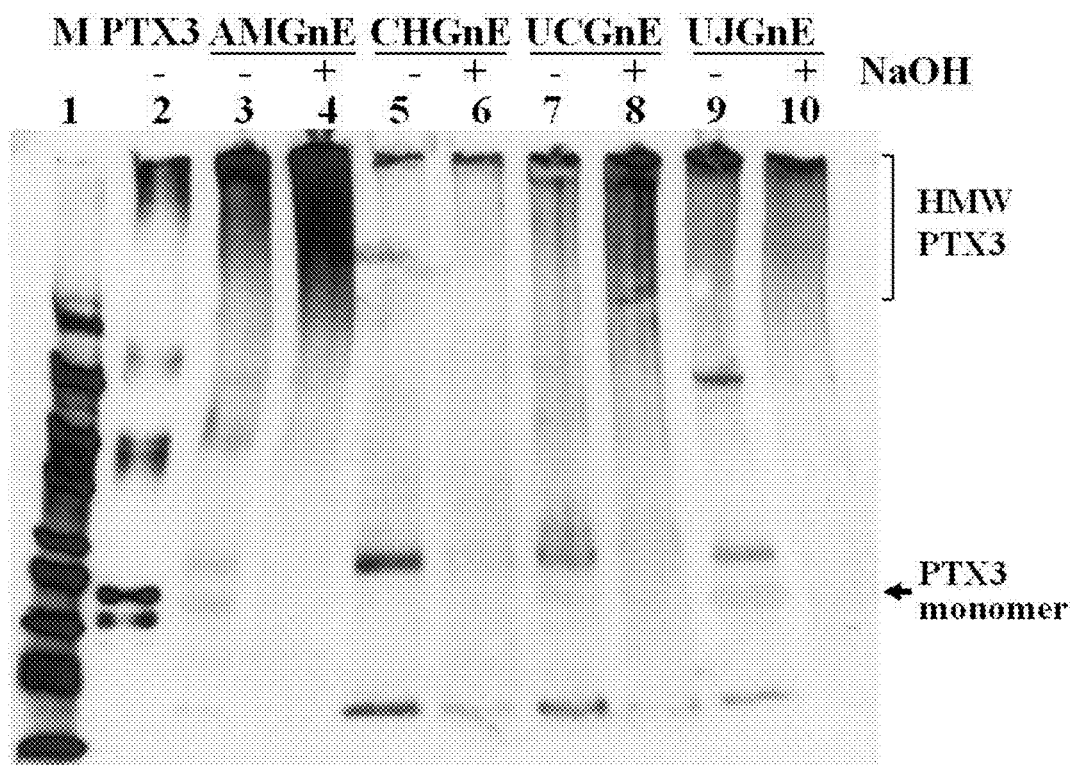

Compared with AME (FIG. 21A), AMGnE showed a strong HMW PTX3 smear, weak dimer and monomer levels of PTX3, and the intensity of HMW PTX3 smear was further increased after NaOH treatment (FIG. 21B, lane 3 and 4), which showed that AMGnE contained more HMW PTX3 than AME. More PTX3 was present in water-insoluble part of AM. CHGnE only had a HMW band in the loading well but no HMW PTX3 smear regardless of treatment with or without NaOH. UCGnE and UJGnE had the same pattern of PTX3 with or without NaOH treatment as AMGnE except the intensity of PTX3 smear was a little weaker than that in AMGnE (FIG. 21B, lane 3 and 4). The intensity of PTX3 smear in UCGnE was also lower than that in UCE, which showed that UCGnE contained less HMW PTX3 than UCE; that is more PTX3 was present in the water soluble part of UC.

The above results showed that both AM and UC contained HMW PTX3. In AM more HMW PTX3 was water-insoluble and could be extracted by GnHC1 after PBS extraction, while more HMW PTX3 in UC was water soluble that could be mostly extracted by PBS.

Figure 22A:
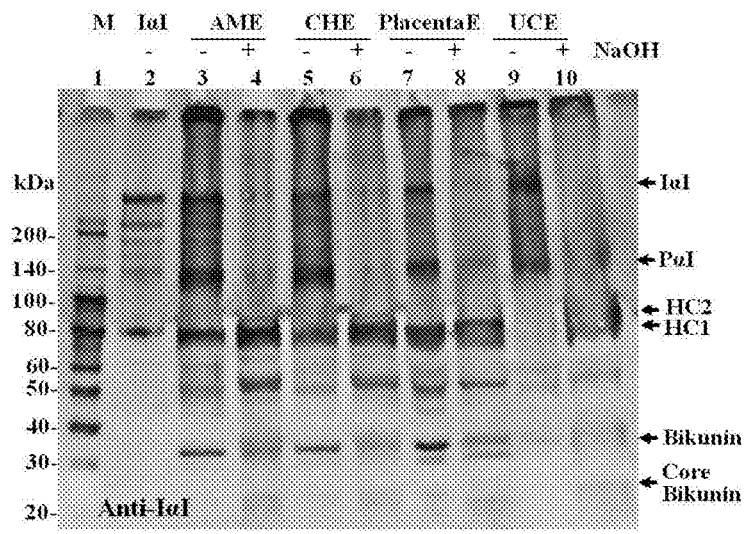
FIG. 22A-C exemplifies a comparison of HC1, bikunin and IαI in sequential PBS and GnHCl extracts from AM, CH and UC. Each lane contains 20 µg total protein in A and C and 40 µg total protein in B and D-F except positive control.
Figure 22B:
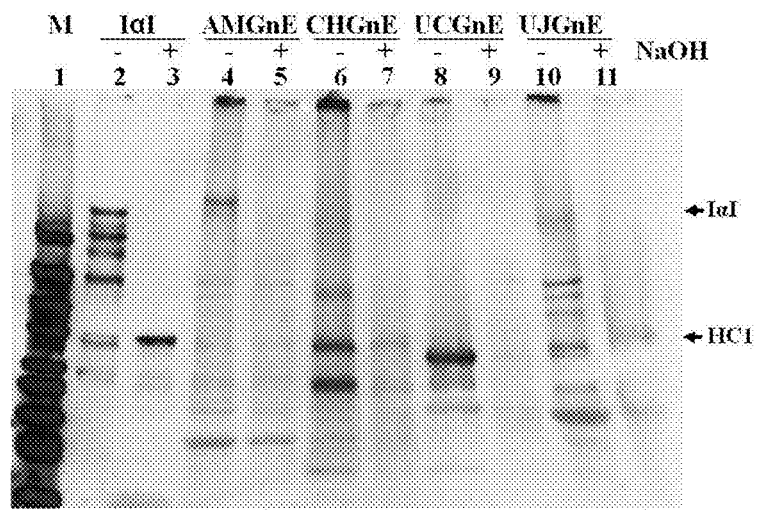
Figure 22C:
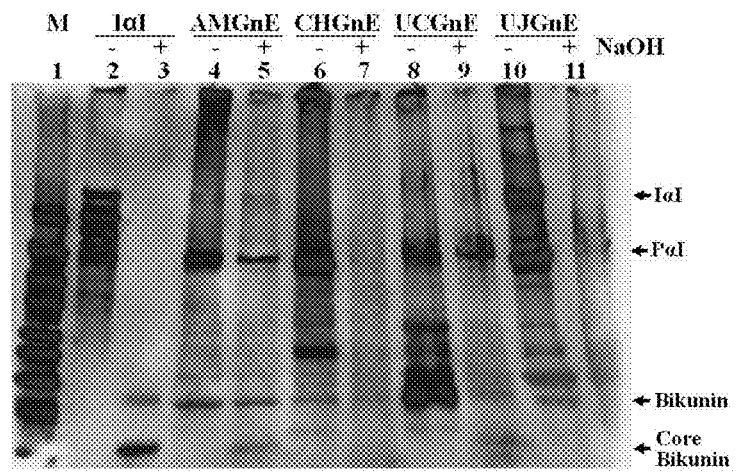

Both IαI and HC1 Mostly in AM PBS Extract but in UC Most IαI in PBS Extract while HC1 in GnHC1 Extract, while More Bikunin Present in UCGnE than in UCE with No Difference in Others' Two Extracts FIG. 22 shows that an 80 kDa HC1 band was present in all PBS extracts except UCE and in all GnE extracts except AMGnE. This band was increased by NaOH in all PBS extracts but not in GnE, showing that AM contained both free and bound water soluble HC1 (i.e. ester bound to HA in HC-HA and to bikunin in IαI) that was released by NaOH in agreement with Zhang et al. (2012) *J. Biol. Chem.* 287:12433-12444. UC contained water soluble bounded HC1 that was released by NaOH, and also contained water insoluble free HC1 bound to water insoluble extracellular components that were dissociated by SDS and 2-ME but not affected by NaOH. This was consistent with strong positive HC1 staining in UC. The HMW HC1 band was present in all PBS and GnHC1 extracts in loading wells and was decreased by NaOH, showing that it was the HC-HA complex. The HMW HC1 band was weaker in UCGnE than in UCJGnE, illustrating that Wharton's jelly contained more water insoluble HC-HA complex. Free IαI was found in all PBS extracts but not in all GnE extracts, suggesting that it was water soluble. However, free PaI was found in all PBS and GnHC1 extracts, suggesting PaI had a different interaction with IαI. More bikunin was found in UCGnE than in UCE with no difference in other two extracts, highlighting that most bikunin was bound to other water insoluble molecules in UC and that this was indicative of a unique function.

TSG-6 was Present in the HMW Complex of AM but not UC GnHC1 Extract

Figure 23:
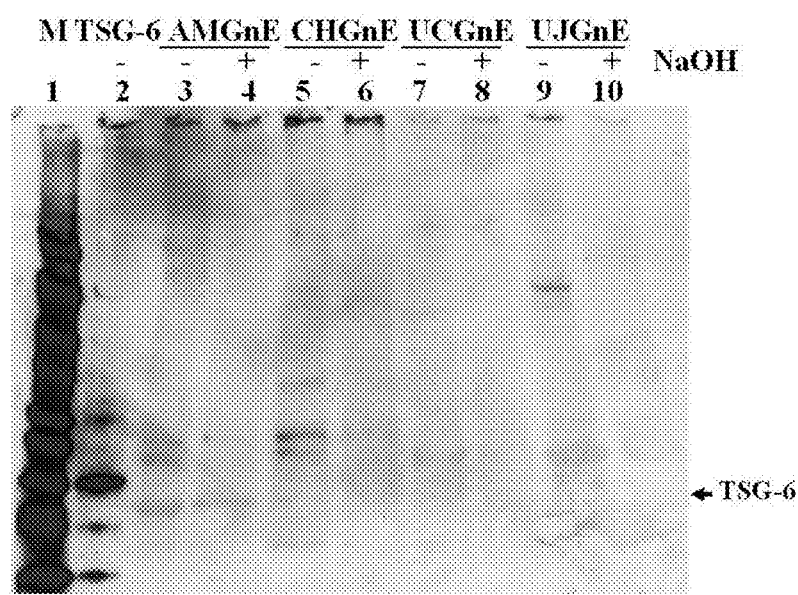
FIG. 23 exemplifies a comparison of TSG-6 in AM and UC GnHCl extract. Each lane contains 40 µg total proteins except positive TSG-6 control.

FIG. 23 showed that the 35 kDa TSG-6 band, which has been reported in AME (Zhang et al. (2012) *J. Biol. Chem.* 287:12433-12444), was present in AMGnE but not all other extracts, showing that TSG-6 was absent in GnE of UC. This band was not affected by NaOH, confirming that TSG-6 was not bound to HMW species that can be cleaved by NaOH. However, the HMW TSG-6 band was found in AMGnE and CHGnE, but not in UCGnE and UJGnE. Furthermore, this band was not changed by NaOH, showing that TSG-6 was strongly bound to HMW species. TSG-6 was not detected in HC-HA purified by 4× ultracentrifugation from GnE, suggesting that although TSG-6 is still bound in the insoluble matrix, it is separable by GnHC1 during ultracentrifugation.

In summary, GnHC1 further extracted abundant HA and proteins from the insoluble part of AM and UC after PBS extract. UC contained more HA than AM and CH in both PBS and GnHC1 extracts. HMW PTX3 were at a higher level in AM GnHC1 extract and at a higher level in UC PBS extract. More HMW PTX3 was retained in the insoluble part after PBS extract. HC1 was mostly in AM PBS extract but not in UC GnHC1 extract. HMW TSG-6 was in AMGnE but not in UCGnE and UJGnE, showing that TSG-6 was still bound in the insoluble matrix but separable by GnHC1 during ultracentrifugation.

Example 28. Purification of the HC-HA Complex by Four Successive Ultracentrifugations from AM and UC PBS Extract and Detection of the Presence of PTX3, HCs, Bikunin, and TSG-6 in the HC-HA Complexes In this example, HC-HA complex was purified by four successive ultracentrifugations from AME and UCE, and the presence of PTX3 as well as HCs, bikunin and TSG-6 were detected in the AM and UC HC-HA complex by Western blot.

The $4^{th}$ AM HC-HA Complex Contained More HMW PTX3 and HC1, and was Purer than the $2^{nd}$ and $3^{rd}$ HC-HA Complex.

Figure 24A:
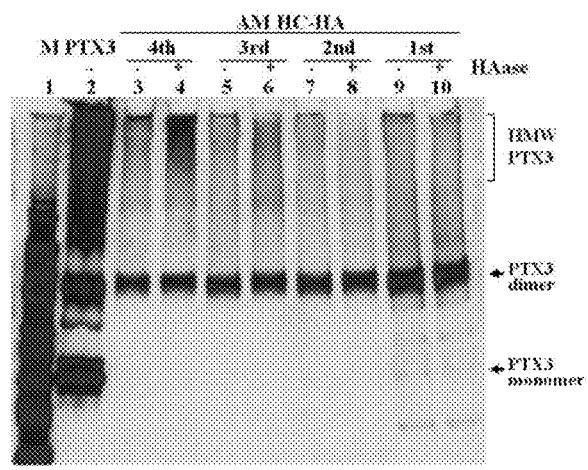
FIG. 24A-D exemplifies Western blot analysis of PTX3 (A), HC1 (B), HC2 (C), and TSG-6 (D) in 1-4th AM HC•HA complex. Each lane contains 4 µg HA except positive control.

With the anti-PTX3 antibody, Western blot analysis of $1-4^{th}$ AM HC-HA showed a 90 kDa band (dimer), compared to the monomer which was found in PBS extracts. This showed that the dimer status was resolved by further extraction in 4M GnHC1 through ultracentrifugation, revealing and a HMW band in gel top in 1st, 2nd, 3rd and $4^{th}$ HC-HA complex (FIG. 24a). Compared with purified PTX3 control, the 90 kDa band was PTX3 dimer, and the high molecular weight band was PTX3-containing HC-HA complex. After HAase treatment, the 90 kDa band did not change in all HC-HA complexes, but the HMW smear band was vaguely detected in $3^{rd}$ and $4^{th}$ fractions. That is, from $1^{st}$ to $4^{th}$, the HMW band gradually disappeared and a smear gradually appeared which was more intensified in $4^{th}$ HC-HA complex. There was no 45 kDa PTX3 monomer band in all HC-HA complexes. The results showed that HC-HA complex contained multimeric form of PTX3 that is able to bind to HC-HA, and with the number of times of ultracentrifugation increasing, the PTX3-containing HC-HA complex became more purified. The existence of 90 kDa PTX3 dimer in HC-HA complex with or without HAase showed that: 1) PTX3 dimer present in HC-HA was dissociated by SDS and 2-ME, and 2) the HMW PTX3 was resistant to SDS and 2-ME. The PTX3 dimer being a product due to 2ME is further confirmed below (FIG. 24a).

Figure 24B:
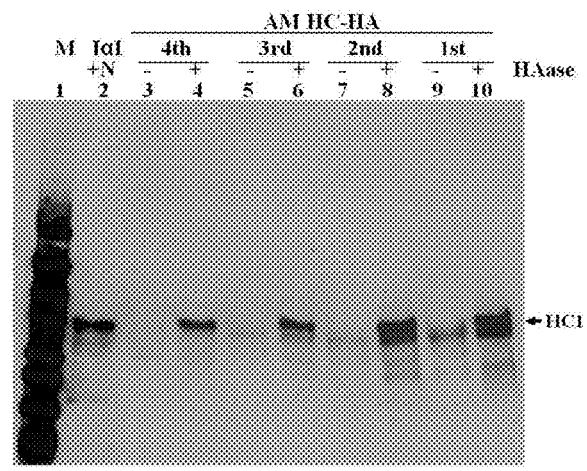
Figure 24C:
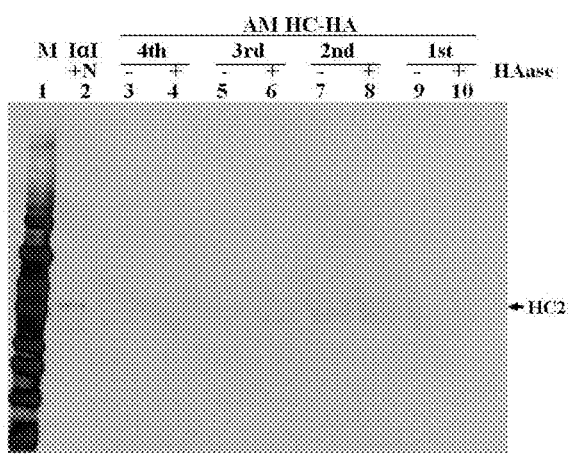
Figure 24D:
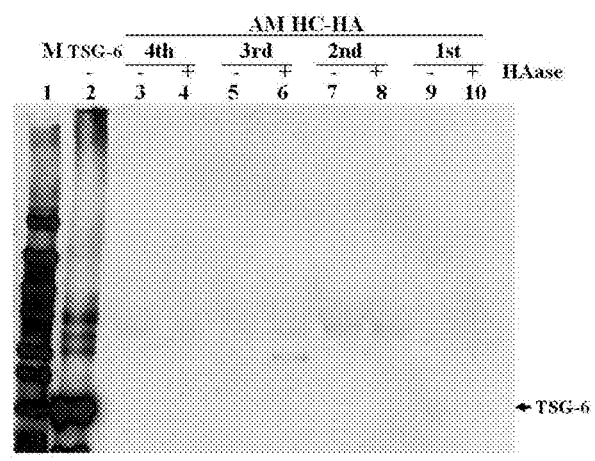

With anti-HC1 antibody, an 80 kDa HC1 band was detected only in earlier $1^{st}$ and $2^{nd}$ fractions from all the four HC-HA complexes (FIG. 24b). After HAase treatment, the HC1 band intensified, and several smaller bands also appeared in $1^{st}$ to $3^{rd}$ HC-HA complexes. The results showed that purified HC-HA complex did not contain free HC, and HC-HA was made of HC1. In agreement with above PTX3 Western blot results, with increasing times of ultracentrifugation, the HC-HA complex became more purified. No HC2 (FIG. 24c), HC3, and TSG-6 (FIG. 24d) were found in all HC-HA complexes.

Figure 25:
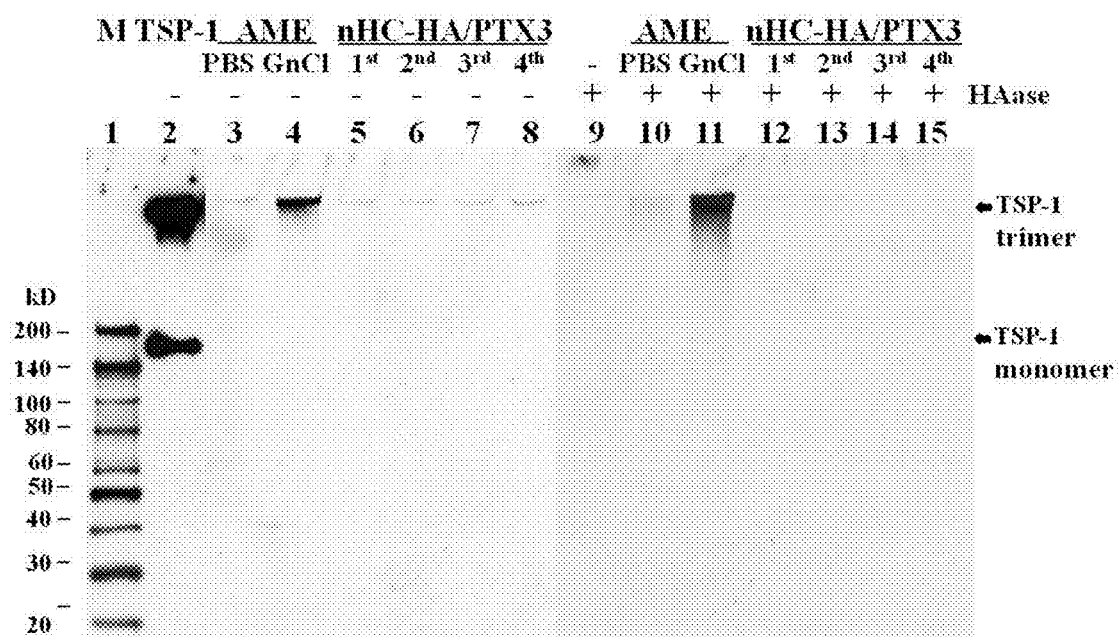
FIG. 25 exemplifies Western blot analysis of TSP-1 in AME, AM GnHCl and 1-4th HC-HA complex. Lanes 3, 4, 10 and 11, each lane contains 30 µg total proteins. Lanes 5-8 and 12-15, each lane contains 4 µg HA.

TSP-1 was Only Present in AM GnHC1 Extract but Not in PBS Extract and 1-$4^{th}$ HC-HA Complex Thrombospondin-1 (TSP-1) was only detected as trimer in AM GnHC1 extract but not in PBS extract and 1-$4^{th}$ HC-HA complex (FIG. 25). After HAase treatment it appeared as a smear, illustrating that TSP-1 was water insoluble and strongly bound to HC-HA. However, such a binding in the insoluble matrix to HC-HA can be dissociated by GnHC1 and CsCl.

Like $4^{th}$ AM HC-HA Complex, $4^{th}$ UC HC-HA Complex Contained PTX3 and HC1 but Not HC2, HC3, Bikunin and TSG-6 and the Lack of 2ME did Not Generate PTX3 Dimer but Yielded HC1

Figure 26A:
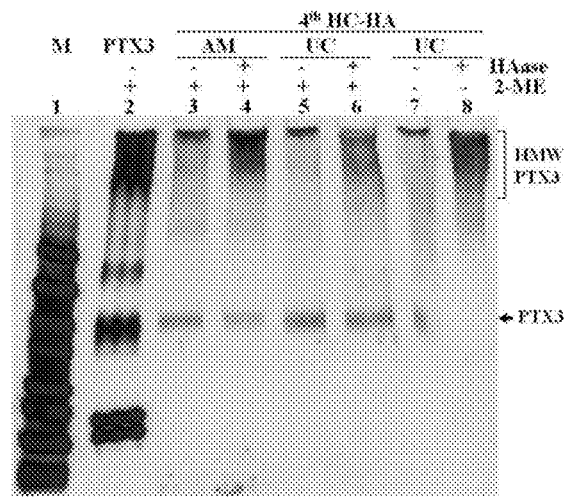
FIG. 26A-E exemplifies Western blot analysis of PTX3 (A), HC1 (B), HC2 (C), HC3 (D) and TSG-6 (E) in 4th UC HC-HA complex. Each lane contains 4 µg HA except positive control.
Figure 26B:
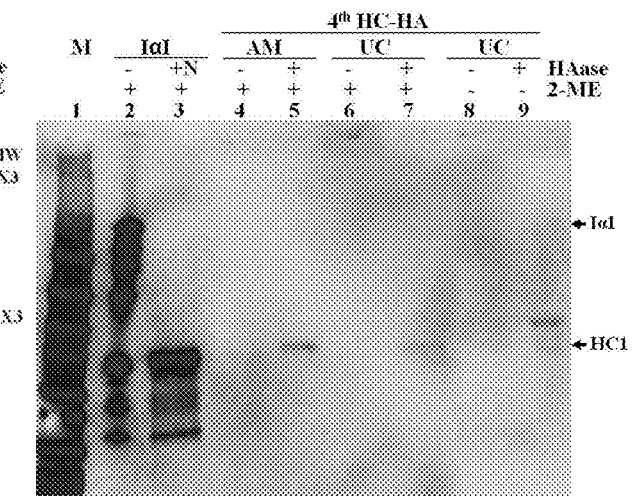
Figure 26C:
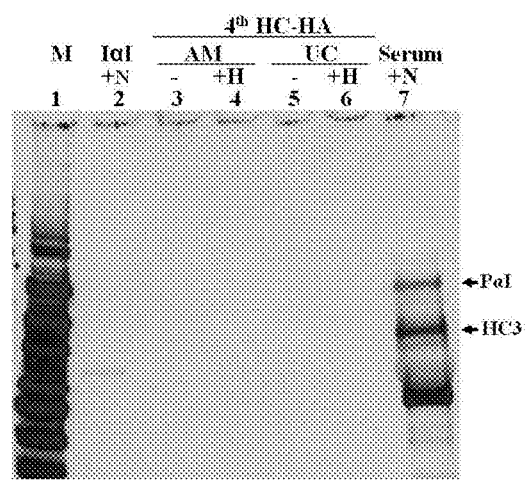
Figure 26D:
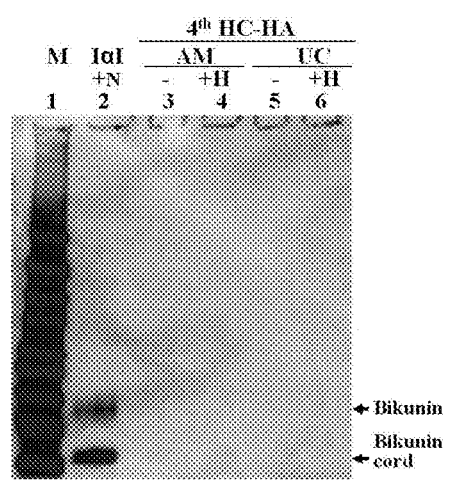
Figure 26E:
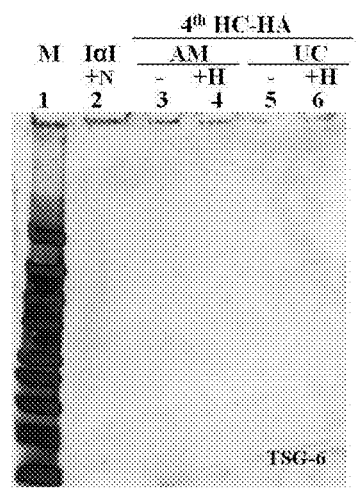

With the anti-PTX3 antibody, Western blot analysis of $4^{th}$ UC HC-HA with or without HAase treatment showed a similar PTX3 band pattern in $4^{th}$ UC HC-HA complex (FIG. 26a, lanes 5 and 6) to that in $4^{th}$ AM HC-HA complex (FIG. 26a, lanes 3 and 4). When the sample buffer did not contain 2-ME, the 90 kDa PTX3 dimer disappeared in UC HC-HA complex with or without HAase (FIG. 26a, lanes 7 and 8), showing that the appearance of 90 kDa PTX3 dimer in HC-HA complex was due to the reduction of PTX3 bound to HC-HA by 2-ME in the sample buffer. With anti-HC1 antibody, only a high molecular weight HC-HA band was detected in $4^{th}$ UC HC-HA complex (FIG. 26b, lane 6) similar to that in $4^{th}$ AM HC-HA complex (FIG. 26b, lane 4). After HAase the HC-HA band disappeared and the HC1 band increased (lane 7) like $4^{th}$ AM HC-HA complex (lane 5), though its intensity was a little weaker than that in $4^{th}$ AM HC-HA. This showed that HC1 formed a complex with S—S with PTX3. The stronger band with a MW slightly higher than generic HC1 appeared when the sample buffer did not contain 2-ME, showing that HC1 was linked to PTX3 via S—S. No HC2, HC3 (FIG. 26c), bikunin (FIG. 26d) and TSG-6 (FIG. 26e) was detected in $4^{th}$ AM and UC HC-HA complex.

Example 29. Purification of HC-HA Complex from Total AM and UC GnHC1 Extract by Four Successive Ultracentrifugations and Comparison with PBS Extractions This example determined that more HC-HA complex from AM and UC could be obtained, the HC-HA complex had a more reasonable constitution of PTX3 and HC-HA, and that it had more effective therapeutic role in the clinic. AM and UC was extracted by 6M GnHC1 buffer (200 mM Tris-HC1, pH 8.0, 6M GnHC1, 10 mM EDTA, 10 mM aminocaproic acid, 10 mM N-ethylmaleimide, 2 mM PMSF): GnHC1 extraction from AM and UC was performed by adding 6M GnHC1 buffer to AM and UC powder at 1:4 (g/ml). Samples were mixed overnight at 4° C., and centrifuged at 48,000 g, at 4° C. for 30 min. The supernatants were GnHC1 extracts. The $4^{th}$ HC-HA complex was purified from AM and UC GnHC1 extract using the same procedure as that for the $4^{th}$ HC-HA purification from PBS extract. Characterization of HC-HA complex was performed by Western blotting to examine PTX3, HCs, bikunin, TSG-6 and likely other proteins. An agarose gel of HC-HA was run to see HA content and molecular weight.

GnHC1 Extracted More HC-HA Complex from AM and UC than PBS.

The GnHC1 extracts from AM and UC were named AMEG and UCEG, and their HA and protein contents were detected by BCA assay and HA ELISA, respectively. $4^{th}$ HC-HA complex was purified from GnHC1 extract and their HA and protein contents were similarly detected. Table 2 summarizes the contents of protein and HA in both PBS and GnHC1 extracts and their $4^{th}$ HC-HA complex. The results showed that AM and UC GnHC1 extracts contained more HA and have a higher HA/protein ratio compared to relative PBS extract. Furthermore, more HC-HA complex was purified from GnHC1 extract.

TABLE 2

Quantitation of proteins and HA in extracts and $4^{th}$ HC-HA from AM and UC.

| Sample | Tissue weight/Extract buffer volume (g/ml) | HA (µg/ml) | Protein (µg/ml) | HA/protein Ratio (µg/µg) | Relative $4^{th}$ HC-HA | |
|---|---|---|---|---|---|---|
| | | | | | HA (µg/ml) | Protein (µg/ml) |
| AME-PBS J021 | 1:1 | 61.5 | 5353.0 | 0.011 | 4 | undetectable |
| AMEG G021 | 1:4 | 431.4 | 3762.5 | 0.115 | 11 | undetectable |
| UCE-PBS I103 | 1:1.5 | 453.5 | 8523.8 | 0.053 | 32 | 89.1 |
| UCEG G021 | 1:4 | 442.0 | 4750.0 | 0.093 | 44 | 13 |
| UCmixE-PBX | 1:4 | 277.5 | 5135.1 | 0.054 | 20 | undetectable |
| UCmixEG | 1:6 | 441.6 | 4730.0 | 0.093 | 40 | undetectable |

AM $4^{th}$ GnHC1 HC-HA complex contained more HC1 and HMW PTX3 but contained less than the PBS HC-HA with or without HAase or NaOH treatment, and both PBS and GnHC1 HC-HA did not contain TSP-1.

Figure 27A:
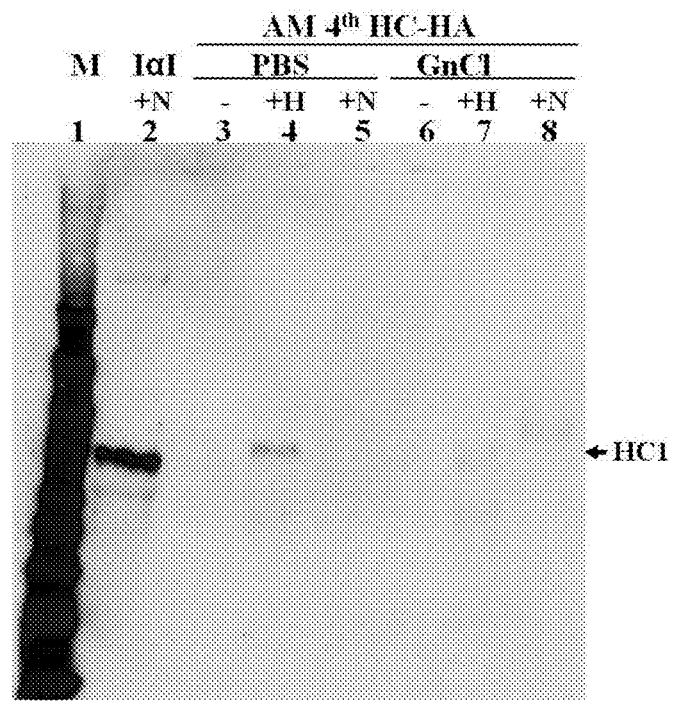
FIG. 27A-B exemplifies a comparison of HC1 (A) and PTX3 (B) in 4th HC•HA complex from PBS and GnHC1 extract. Each lane contains 4 µg HA except positive control.
Figure 27B:
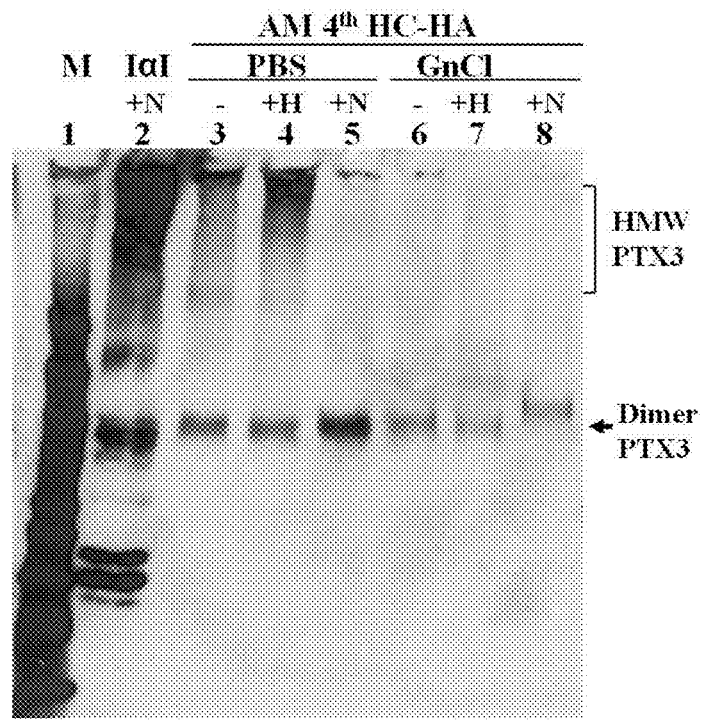

With the anti-HC1 antibody, GnHC1 HC-HA showed a HMW band in the loading well as PBS HC-HA, but HAase digestion only released weaker HC1 (FIG. 27a, lanes 6 and 7). NaOH treatment also released a weaker HC1 band that had a little higher MW than that released by HAase (FIG. 27a, lane 8), which was not seen in PBS HC-HA after NaOH treatment. These results showed that GnHC1 HC-HA contained HC1 but the amount was less than PBS HC-HA. Similarly, not like PBS HC-HA, with anti-PTX3 antibody, GnHC1 HC-HA only showed dimer PTX3 but no notable HMW PTX3 smear with or without HAase digestion (FIG. 27b, lanes 6 and 7). NaOH also resulted in a HMW and dimer PTX3 appearance. These results showed that GnHC1 HC-HA contained less HMW PTX3 than PBS HC-HA.

Similar to HC1 blot, a higher MW dimer of PTX3 occurred after NaOH than HAase in GnHC1 HC-HA. These results collectively indicated that NaOH released an ester bond that links HC1 to HA and could be associated with PTX3. Because GnHC1 HC-HA had more HA content than PBS HC-HA, the GnHC1 HC-HA complex contained HA that was not bounded by PTX3 or HC1 resulting in the decrease of actual HC-HA/PTX3 complex content in the purified products and less HC1 and HMW PTX3 in it. TSP-1 was not detected in PBS HC-HA with anti-TSP-1. It should be noted that TSP-1 was also not detected in GnHC1 HC-HA. Because GnHC1 extract contains TSP-1, these results showed that TSP-1 dissociated by ultracentrifugation, so it was not present in GnHC1 HC-HA.

Agrose Gel Showed Abundant HA in GnHC1 HC-HA

Figure 28:
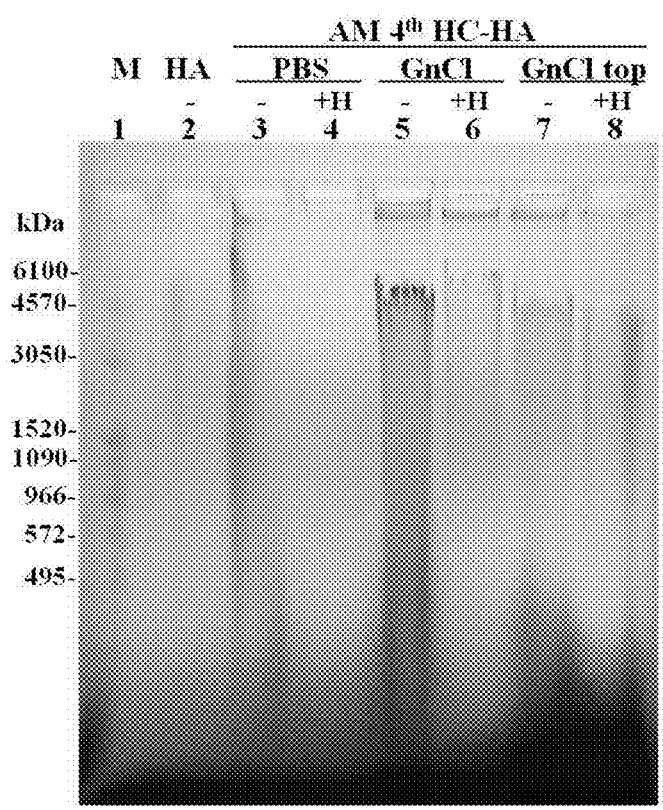
FIG. 28 exemplifies a comparison of 4th HC-HA complex from PBS and GnHC1 in agarose gel. Each lane contains 15 µg HA except positive HA control.

PBS HC-HA showed a "continuous HA smear from the top loading well to the bottom of agarose gel, and HAase completely abolished the HA smear (FIG. 28, lanes 3 and 4). GnHC1 HC-HA showed a band in the loading well and a HA smear, which started from the 4,570 kDa location to the bottom of the agarose gel (FIG. 28, lane 5). HA in GnHC1 HC-HA had a break between the loading well to the beginning of the HA smear, although its intensity was stronger than that in PBS HC-HA. Furthermore, HAase did not completely abolish the HA smear and HMW HA band in GnHC1 HC-HA (FIG. 28, lane 6). The top fractions (1-6 fractions) from GnHC1 extract after the $4^{th}$ ultracentrifugation also showed the same HA smear pattern as the "bottom fractions" of GnHC1 HC-HA (FIG. 28, lanes 7 and 8). These results showed that GnHC1 HC-HA contained more HMW HA (with a MW smaller than PBS HC-HA) but lacked a portion of HMW HA smear that corresponded to the lack of HMW PTX3 smear in the Western blot of GnHC1 HC-HA. This indicated that the missing HMW HA smear, which was present in PBS HC-HA, was at least partly formed by crosslinking of PTX3 and HC-HA, and that the HMW HA in the loading well of GnHC1 HC-HA was complexed with components other than PTX3.

GnHC1 HC-HA contained some proteins that are not found in PBS HC-HA by Coomasie blue staining.

Figure 29A:
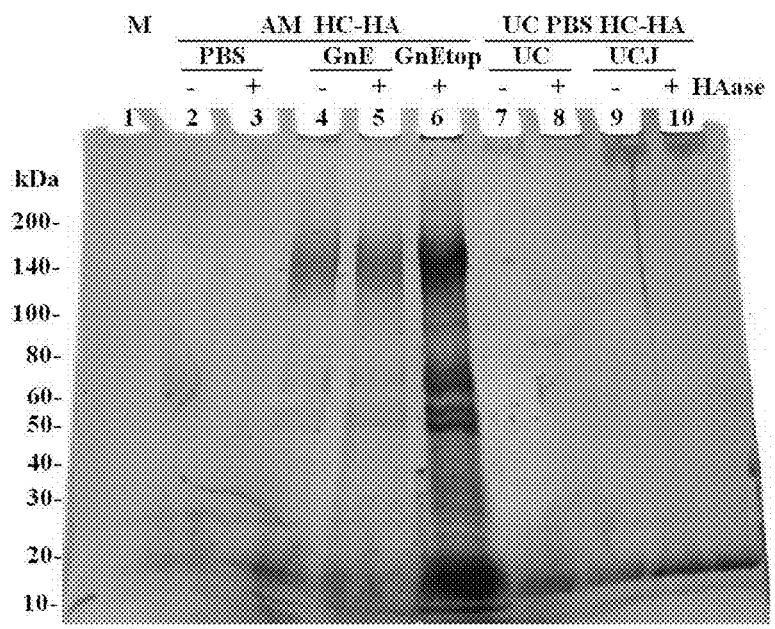
FIG. 29A-B exemplifies Coomassie blue staining for SDS-PAGE gel of GnHC1 HC-HA and PBS HC-HA. A. AM PBS and GnHC1 HC-HA. B. UC PBS and GnHC1 HC-HA. Each lane contains 30 µg HA.

FIG. 29A shows that bands in the top loading well, a major 140 kDa and some minor 70 kDa, doublet 55 kDa and 20 kDa bands, were present in AM GnHC1 HC-HA and in the top fractions of GnHC1 HC-HA but not in all other PBS HC-HA. This showed that AM GnHC1 HC-HA contained some proteins that were absent in PBS HC-HA. In addition, a 90 kDa and 25 kDa band were also visualized in the GnHC1 HC-HA top fractions. Because Western blot detected HC1 in PBS HC-HA, the HC1 should also be present in PBS HC-HA by Coomassie blue staining. The reason why it was not present in PBS HC-HA was due to the fact that the loaded HC-HA did not enter the gel due to over-loading. The 140 kDa showed as a broad band suggesting it contained sugar moieties. In addition, HAase did not affect these bands, showing that these species were dissociated by SDS and 2-ME.

Figure 29B:
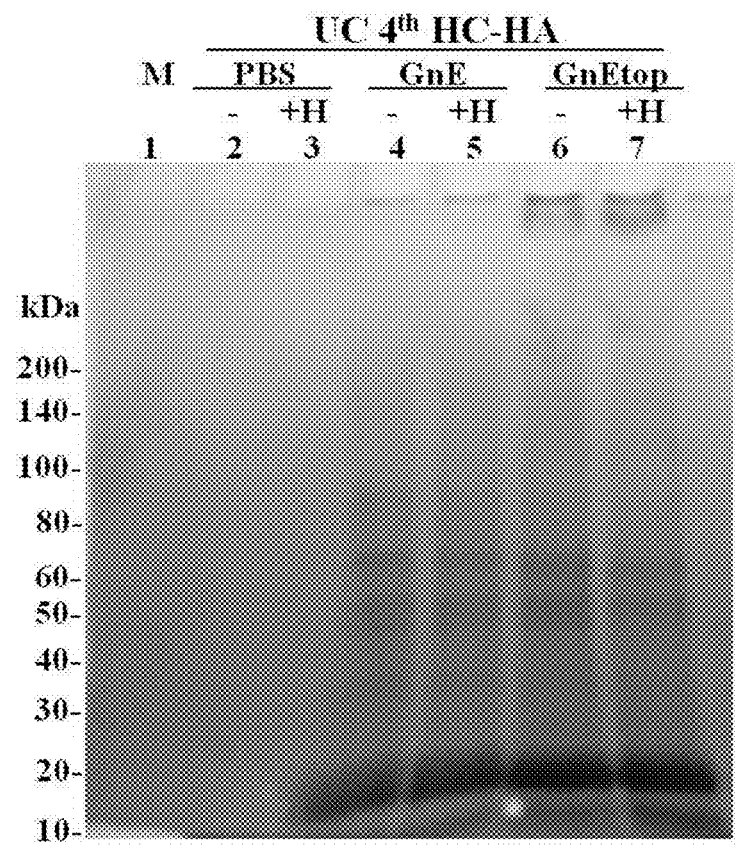

Compared to AM GnHC1 HC-HA, UC GnHC1 HC-HA showed bands in the top loading well, a 90 kDa, 70 kDa, doublet 55 kDa, 35 kDa and 20 kDa bands (FIG. 29B, lanes 4 and 5). A faint 140 kDa band was also present in it. These bands were not affected by HAase. In addition, the top fractions of GnHC1 HC-HA also showed a smear from top well to the site of 200 kDa which decreased after HAase treatment. All the bands were absent in UC PBS HC-HA. These results showed that UC GnHC1 HC-HA also contained some proteins that were absent in PBS HC-HA, and UC GnHC1 HC-HA was different from AM GnHC1 HC-HA regarding the protein bands they contained.

The above results showed that GnHC1 HC-HA was different from PBS HC-HA from both AM and UC in the following aspects: (1) GnHC1 HC-HA contained less HC1 and HMW PTX3 than PBS HC-HA (from Western blot) while like PBS HC-HA, TSG-6, HC2 and HC3 were also not present in GnHC1 HC-HA. (2) GnHC1 HC-HA contained more HMW HA but lacked a piece of HMW HA that corresponded to the HMW PTX3 smear in Western blotting shown by PBS HC-HA (from agrose gel). (3) GnHC1 HC-HA contained some proteins mainly with MW 140 kDa that were not found in PBS HC-HA (from Coomassie blue staining gel).

In summary, GnHC1 extracted more HA and proteins from AM and UC tissue, resulting in a higher HA/protein ratio compared to PBS extract. More HC-HA complex (according to HA content) was purified from the GnHC1 extract for both AM and UC. GnHC1 HC-HA contained HC1 and HMW PTX3 but much less than in PBS HC-HA for both AM and UC. GnHC1 HC-HA lacked a species of HMW HA smear in the agrose gel that corresponded to the HMW PTX3 smear in Western blotting shown by PBS HC-HA. GnHC1 HC-HA contained some proteins that are not found in PBS HC-HA.

Example 30. Determination of the Identity of Unknown Protein Bands in GnHC1 HC-HA Complex Purified from AM and UC This example determined the identify of unknown bands in GnHC1 HC-HA by running SDS-PAGE gels followed by either CB staining or Western blot analysis of GnHC1 HC-HA from AM and UC with or without deglycosylation. The sample was lyophilized AM and UC 4× HC-HA (contained 30 µg HA) from both PBS and GnHC1 extracts. Lyophilized HC-HA were incubated with 50 µl TFMS and 20 µl anisole on ice for 3 h and neutralized with TFMS with 125 µl N-ethylmorpholine. Samples were precipitated with 5-10 volumes of acetone overnight at −20 C or for 1 h at −80 C. Samples were centrifuged and the dried pellet was dissolved in SDS sample loading buffer for electrophoresis. Enzymatic deglycosylation with keratinase (Endo-β-galactosidase) was performed to remove keratan sulfate chain and N-linked oligosaccharides, or with Chondroitinase (Cabc) to remove chondroitin sulfate chain. HC-HA (contained 30 µg HA) was incubated with 0.1 U/ml keratinase in 50 mM sodium acetate, pH 5.8, at 37 C for 2 h, or incubated with 5 U/ml Cabc in PBS at 37 C for 2 h. An SDS-PAGE gel was run to test for CB staining, followed by Western blot analysis.

Keratan Sulfate and Osteoadherin were Present in AM GnHC1 HC-HA but Not in PBS HC-HA.

Figure 30A:
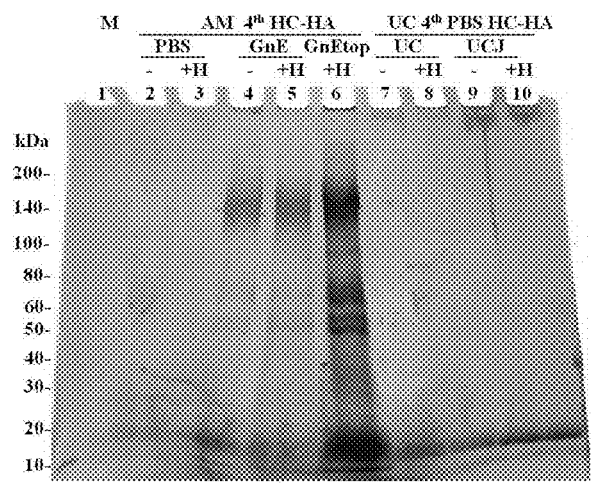
FIG. 30A-D exemplifies that keratan sulfate and osteoadherin were present in AM GnHC1 HC-HA but not in PBS HC-HA. A. Coomassie blue staining. Each lane contains 30 µg HA. B and C. Western blot for keratan sulfate (B) and osteoadherin (C). Each lane contains 4 µg HA. D, Immunostaining for keratan sulfate in AM.
Figure 30B:
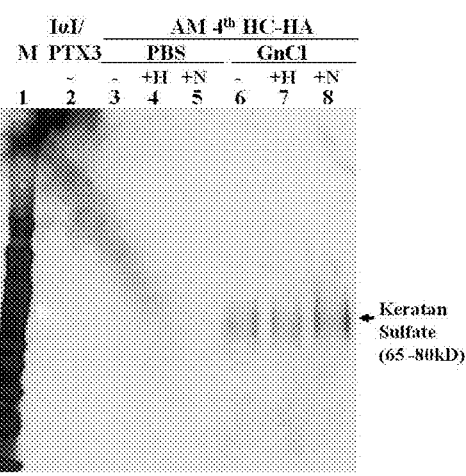
Figure 30C:
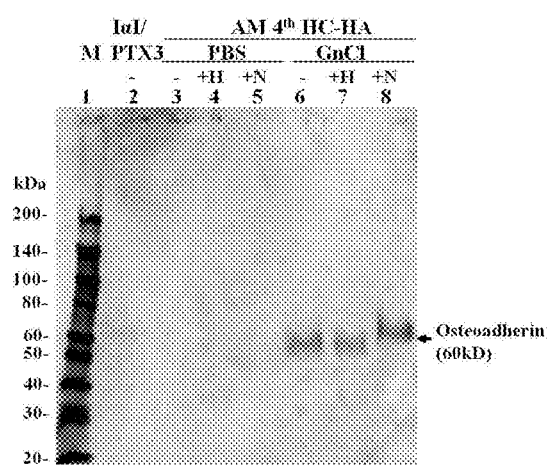
Figure 30D:

Western blot analysis was performed. The results are shown in FIGS. 30B and C. Western blot with anti-keratan sulfate antibody showed a broad 70 kDa (60-80 kDa) band in AM GnHC1 HC-HA with or without HAase digestion (FIG. 30B, lanes 6-8), but not in PBS HC-HA, which showed that this ~70 kD keratin sulfate proteoglycan was responsible for the positive immunostaining shown in FIG. 30D. This 70 kD band corresponded to the same band noted in GnHC1 HC-HA with or without HAase treatment shown in Coomassie Blue stained gel (FIG. 30A).

To further determine if this 70 kD keratin sulfate proteoglycan is a SLRPs, anti-lumican, anti-fibromodulin, and anti-osteoadherin antibodies were used in the Western blot.

The anti-osteoadherin antibody recognized a 60 kD band, but not a 70 kD band in GnHC1 HC-HA with or without HAase digestion (FIG. 30C, lanes 6-8), but not in PBS HC-HA. Osteoadherin with keratin sulfate chain has a molecular mass of ~80 kD, while its non-keratin sulfate protein is ~60 kD. A keratin sulfate band in the size of 60 kD was detected, but only in a broad size of 70 kD, which showed that the 60 kD band detected by anti-osteoadherin was non-keratan sulfate osteoadherin. AM GnHC1 HC-HA contained non-keratan sulfate osteoadherin that tightly associated with HC-HA and withstood 4 times ultracentrifugations in the presence of 6M GnHC1 and cesium chloride. But, it was released by SDS and 2-ME in the sample buffer. The results also showed that the 70 kD keratin sulfate proteoglycan was not osteoadherin. There was no lumican and fibromodulin detected in GnHC1 HC-HA, which showed that the 80 kD proteoglycan is neither lumican nor fibromodulin.

Deglycosylaton and Analysis of AM GnHC1 HC-HA

HC-HA was deglycosylated by TFMSA to remove all glycans using keratinase and chondroitinase to remove specific glycans to see whether there were any changes to the 140 kD and ~80 kD bands in AM GnHC1 HC-HA, and further determine whether the ~80 kD keratin sulfate proteoglycan was Keratocan, PRELP or Osteoglycan. As a first step confirming the effect of the above deglycosylation, Coomassie Blue staining was performed.

Figure 31A:
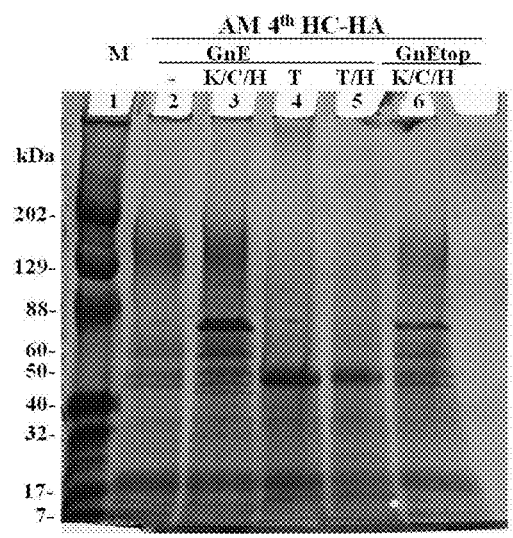
FIG. 31A-H exemplifies deglycosylation and analysis of AM GnHC1 HC-HA by SDS-PAGE with (Coomassie Blue) CB staining or Western blots. A. Coomassie blue staining. Each lane contains 30 µg HA except lane 6 which contains 5 µg HA. B-H. Western blots for Osteoadherin (B), Decorin (C, D), Biglycan (E, F), Keratan sulfate (G) and PTX3 (H). H: hyaluronidase; C: chondroitinase (Cabc); K: keratinase (keratan sulfate endo-β-galactosidase); T: TFMSA (trifluoromethanesulfonic acid). Each lane contains 4 µg HA.

In FIG. 31A, the Coomassie Blue (CB) stained gel, AM GnHC1 HC-HA (FIG. 31A, lane 2) showed the same bands of dominant 140 kDa, 70 kDa, doublet 50 kDa, 20 kDa and a weak 35 kDa band as well as a HMW band in the top of gel. K/C/H did not greatly affect these bands except for generating a major 80 kDa, a weak 100 kDa, and 30 kDa bands appearance (FIG. 31A, lane 3). This pattern was similar to that derived from the top fraction of AM GnHC1 HC-HA under C/K/H (FIG. 31A, lane 6). These results showed that the 140 kDa, 70 kDa and 55 kDa bands were not keratan sulfated and/or chondroitin sulfated, and that there were other keratan sulfated and/or chondroitin sulfated proteins in GnHC1 HC-HA that were released as a major 80 kDa species after C/K/H. TFMSA treatment led to disappearance of all of the above bands except the 20 kDa band, and generated a clear new 50 kDa band and a HMW smear (FIG. 31A, lane 4). TFMSA made the smear disappear resulting in a new 25 kDa band but did not change the 50 kDa band (FIG. 31A, lane 5). This result showed 140 kDa, 70 kDa, 55 kDa and 80 kDa band were the same species of 50 kDa that with different amounts of glycan chains.

Figure 31B:
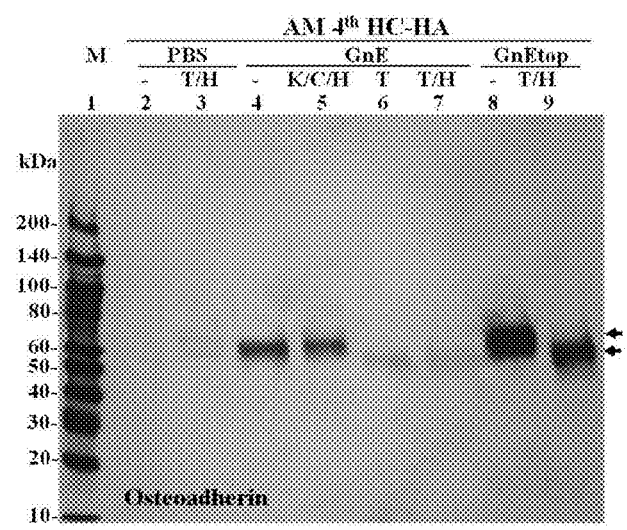

To determine whether the 50 kDa band originated from 60 kDa osteoadherin, Western blot analysis was performed with an anti-osteoadherin antibody. The result showed a 60 kDa species in AM GnHC1 HC-HA (FIG. 31B, lane 4), consistent with the finding shown in FIG. 31C. C/K/H did not change its molecular mass (FIG. 31B, lanes 5 and 6), but TFMSA with or without HAase (T/H) treatment completely changed it into a 55 kDa species with less intensity (FIG. 31, lanes 7 and 8). The top fraction of AM GnHC1 HC-HA with T/H showed a stronger band but a smaller MW without the intensity change compared to without T/H (FIG. 31B, lanes 9 and 10). These results further confirmed that AM GnHC1 HC-HA contained osteoadherin, which was free of keratan sulfate and chondroitin sulfate. The reason why the intensity of osteoadherin band decreased after TFMSA treatment was due to (1) the protein was degraded by TFMSA; (2) it was blocked by other large amount of proteins with the same MW that were also released after TFMSA treatment. Osteoadherin was not detectable in PBS HC-HA without any treatment, but a doublet bands of 60 kDa appeared after TFMSA/HAase treatment, showing that PBS HC-HA contained a minute amount of osteoadherin, which was tightly bound to HA.

Figure 31C:
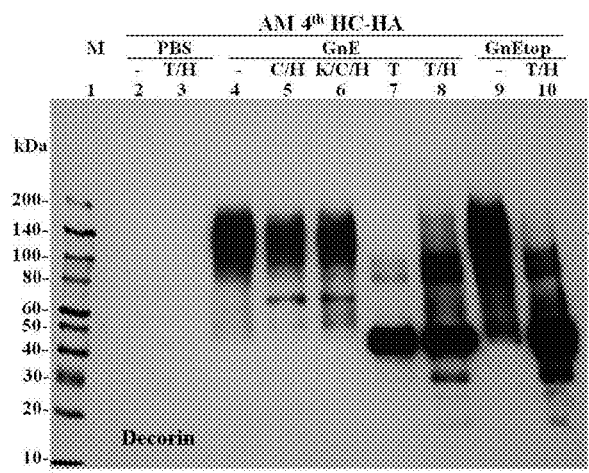

Western blot with an anti-decorin antibody showed a very strong broad 140 kDa species (80-160 kDa) and a weak doublet 50 kDa species in AM GnHC1 HC-HA (FIG. 31C, lane 4; 31D, lanes 4 and 5) but not in PBS HC-HA (FIG. 31C, lane 2; 31D, lanes 2 and 3). The broad 140 kDa species corresponded to decorin with one chondroitin sulfate or dermatan sulfate chain and different number of glycans while doublet 50 kDa species likely corresponded to the less glycosylated decorin. Because HAase did not affect decorin species, it showed they can be released by SDS and 2-ME. The above notion was confirmed by C/H, which increased a 70 kDa species (FIG. 31C, lane 5), and by C/H/K, which gave the same result (FIG. 31B, lane 6). Hence, the 70 kDa species was the chondroitin-free decorin. This 70 kDa species was a minor component because the major broad 140 kDa species was not greatly changed by either C/H or C/H/K. TFMSA treatment completely deleted the broad 140 kDa species meanwhile gave rise to a major 43 kDa species that corresponded to deglycosylated decorin core protein, and minor 95 kDa, 80 kDa and a weak 30 kDa species (FIG. 31C, lane 7). TFMSA/H treatment showed the same species pattern as TFMSA alone except that the intensity of all these species was enhanced, showing that decorin was tightly bound to HA. TFMSA/H also resulted in a release of a faint 43 kDa species from PBS HC-HA, showing that AM PBS HC-HA also contained a minute amount of decorin that was tightly bound to HA. The top fraction of AM GnHC1 HC-HA with or without TFMSA/H showed the same pattern as the bottom fraction with the intensity stronger than the latter (FIG. 31C, lanes 9 and 10), which showed that the top fraction also contained abundant decorin. The above results showed that the major 140 kDa, 70 kDa and doublet 50 kDa species in CB staining gel are formed by decorin via CS and mostly non-CS and non-KS.

Figure 31D:
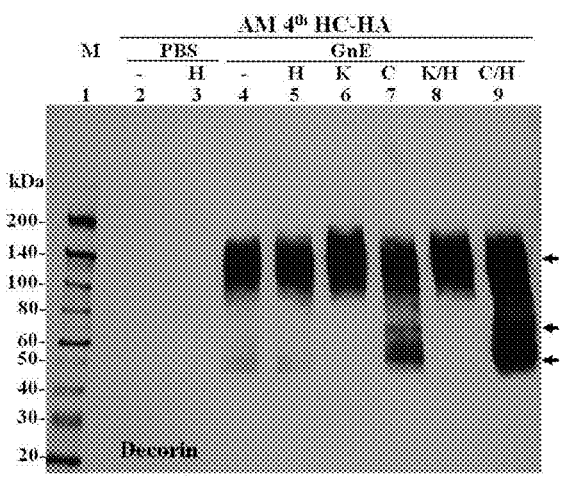
Figure 31E:
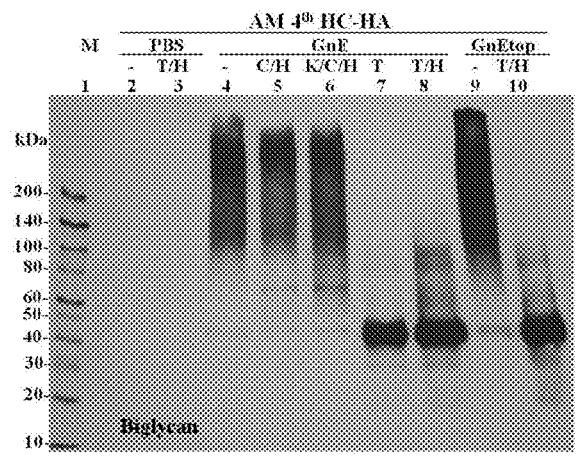
Figure 31F:
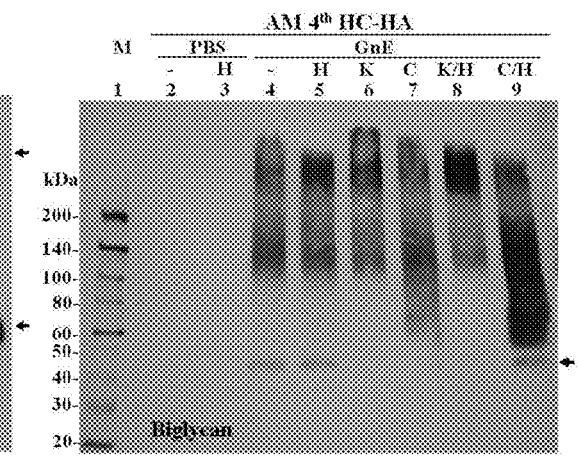
Figure 31G:
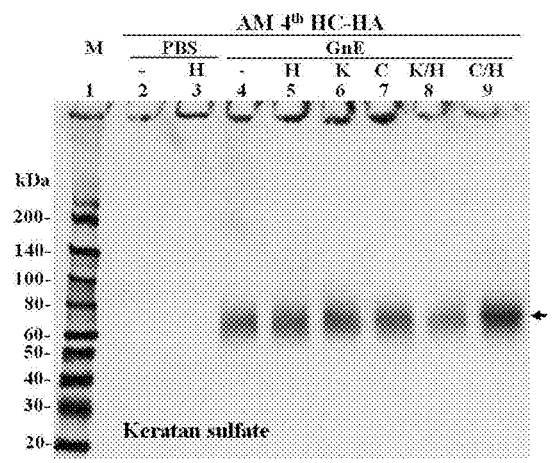
Figure 31H:
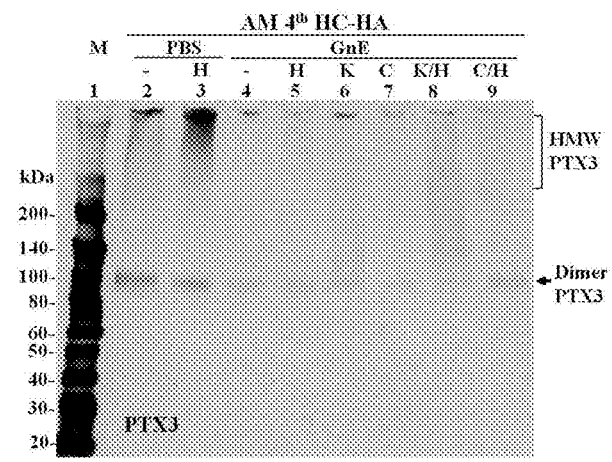

Unlike decorin, Western blot with an anti-biglycan antibody showed a HMW smear with one strong area at 400 kDa, and a weak 45 kDa species in AM GnHC1 HC-HA with or without HAase (FIG. 31E lane 4; 2F lanes 4 and 5) but not in PBS HC-HA (FIG. 31D, lane 2; F, lanes 2 and 3). The 45 kDa species corresponded to a biglycan core protein, while the HMW smear was glycosylated biglycan with two chondroitin sulfate or dermatan sulfate chains. HAase intensified the 400 kDa area with less HMW smear above 400 kDa, which showed some biglycan were also bound to HC-HA. C/H or C/K/H did not greatly change the HMW smear and 45 kDa species, but increased a 70 kDa species (FIG. 31E, lanes 5 and 6) that was likely the chondroitin-free biglycan. Because the amount of 70 kDa species was very small and the major HMW smear was not greatly changed by the above treatments, most biglycans in AM GnHC1 HC-HA were not associated with CS or KS. TFMSA treatment completely deleted the HMW smear and gave rise to a major 45 kDa species that corresponded to deglycosylated decorin core protein, and a weak 95 kDa, 80 kDa and 30 kDa species (FIG. 31E, lane 7), which suggested the existence of biglycan in AM GnHC1 HC-HA. The 95 kDa and 80 kDa species were partly deglycosylated biglycan, while the 30 kDa species was degraded biglycan. TFMSA together with HAase treatment showed the same species pattern as TFMSA alone except that the intensity of all these species enhanced, which suggested that biglycan was also tightly bound to HA. The top fraction of AM GnHC1 HC-HA with or without TFMSA/HAase showed the same species pattern as the bottom fraction with the intensity stronger than the latter (FIG. 31E, lanes 9 and 10), which showed the top fraction also contained abundant biglycan. Western blot analysis with an anti-keratan sulfate antibody showed the presence of the 70 kDa keratan sulfated protein in AM GnHC1 HC-HA with or without keratinase or chondroitinase treatment without shifting the molecular size (FIG. 31G), which suggested that keratinase did not completely eliminate the keratan sulfate or the amount of KS was minute in this species. Western blot with anti-PTX3 antibody showed an increased HMW PTX3 smear which was shown in AM GnHC1 HC-HA with K and even more with K/H (FIG. 31H, lanes 6 and 8) compared to that with or without HAase alone digestion (FIG. 31G, lanes 4 and 5). Chondroitinase had no such effect, which indicated that some KS-containing species were bound to PTX3 in GnHC1 HC-HA. The same results were also obtained from Western blot analysis of UC GnHC1 HC-HA with or without keratinase digestion (see below FIG. 32G). Western blots confirmed that there was no Fibromodulin, Lumican, Keratocan, PRELP, Osteoglycin, epiphycan, Periostin and TSG-6 as well as Bikunin in AM GnHC1 HC-HA.

In summary, AM GnHC1 HC-HA contained abundant decorin and biglycan that were bound to HC-HA, but PBS HC-HA contained only faint decorin and no biglycan. AM GnHC1 HC-HA contained osteoadherin and keratan sulfate-containing species, while PBS HC-HA did not. A very small amount of decorin and biglycan in AM GnHC1 HC-HA contained chondroitin sulfate chain.

Deglycosylaton and analysis of UC GnHC1 HC-HA showed abundant present of Decorin and biglycan in UC GnHC1 HC-HA but not in PBS HC-HA. Keratan sulfate, osteoadherin and bikunin were also present in UC GnHC1 HC-HA.

Figure 32A:
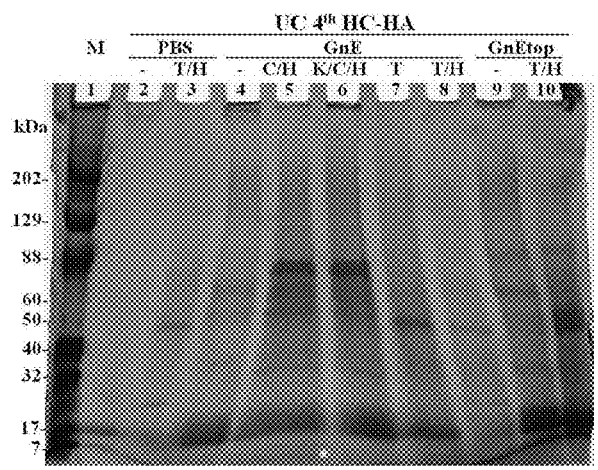
FIG. 32A-G exemplifies Decorin and biglycan were abundantly present in UC GnHC1 HC-HA but not in PBS HC-HA. Keratan sulfate, osteoadherin and bikunin also were present in UC GnHC1 HC-HA but not in PBS HC-HA except for keratan sulfate. A. Coomassie blue staining. Each lane contains 30 µg HA except lane 6 which contains 5 µg HA. B-H. Western blots for Decorin (B), Biglycan (C), Bikunin (D), PTX3 (E), Keratan sulfate (F) and Osteoadherin (G). H: hyaluronidase; C: chondroitinase (Cabc); K: keratinase (keratan sulfate endo-β-galactosidase). Each lane contains 4 µg HA.

CB staining (FIG. 32A) showed the same bands of 160 kDa, 90 kDa, 70 kDa, doublet 50 kDa, 35 kDa and 20 kDa bands in the top loading well in UC GnHC1 HC-HA (FIG. 32A, lane 4). C/H or C/H/K did not greatly affect these bands except resulting in the appearance of a major 80 kDa and a weak 30 kDa band (FIG. 32A, lanes 5 and 6). TFMSA treatment decreased all above bands except the 20 kDa band but increased a major 50 kDa band, a minor 80 kDa band and a HMW smear (FIG. 32A, lane 7). TFMSA/H made the smear and 80 kDa band disappear but resulted in a weak 25 kDa band that appeared and decreased the intensity of the newly formed 50 kDa band (FIG. 32A, lane 8). These results are similar to that obtained from AM GnHC1 HC-HA (FIG. 31A), showing that UC GnHC1 HC-HA had a similar constitution with AM GnHC1 HC-HA. The top fraction of UC GnHC1 HC-HA with or without TFMSA/H showed the same pattern as the bottom fraction (FIG. 32A, lanes 9 and 10), indicating they had the same components as the bottom fraction. UC PBS HC-HA without deglycosylation only showed a HMW band in the loading well and below it, as well as a 20 kDa band. TFMSA/H deleted the HMW band but mainly increased a 50 kDa band beside a weak 80 kDa and a 25 kDa band, suggesting that UC PBS HC-HA contained some glycosylated protein that only was released by complete deglycosylation and HA degradation.

Figure 32B:
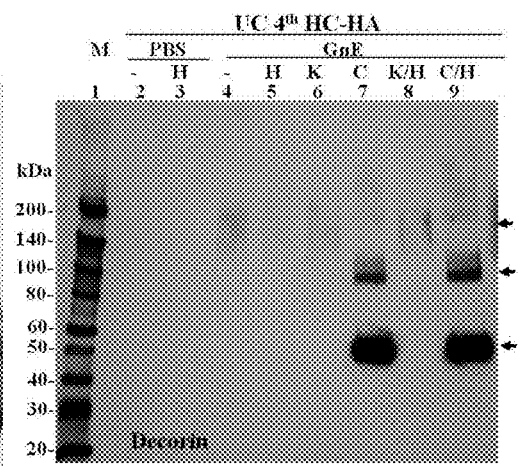

Western blot analysis with an anti-decorin antibody showed a broad 160 kDa species in UC GnHC1 HC-HA with or without HAase (FIG. 32B, lanes 4 and 5) but not in PBS HC-HA (FIG. 32B, lanes 2 and 3), indicating that UC GnHC1 HC-HA, like AM GnHC1 HC-HA, also contained decorin. Its molecular mass was different than that in AM GnHC1 HC-HA due to a different level of glycosylation. HAase greatly decreased the 160 kDa species, showing that it was bound to HC-HA. Keratinase with or without HAase also decreased the intensity of 160 kDa species, indicating it also contained some KS. Notably, C with or without HAase digestion led to the 160 kDa species and top well species disappearing, but gave rise to a strong 50 kDa and 90 kDa species as well as a HMW smear, showing the decorin in UC GnHC1 HC-HA was mainly chondroitin sulfate in comparison to that in AM GnHC1 HC-HA, where less of them contained chondroitin sulfate chain. These results further confirmed that UC GnHC1 HC-HA contained decorin, and that decorin in UC differed from AM in (1) glycosylation, (2) type of glycosaminoglycan is attached, and (3) the overall amount.

Figure 32C:
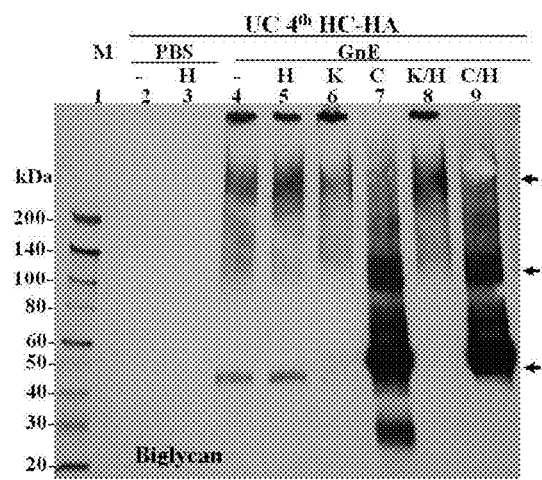

Western blot with anti-biglycan antibody showed a strong HMW species in top well, a HMW smear at 400 kDa area and 140 kDa area, and a 45 kDa species in UC GnHC1 HC-HA with or without HAase (FIG. 31C, lanes 4 and 5) but not in PBS HC-HA (FIG. 31C, lanes 2 and 3). HAase intensified the 400 kDa area without affecting the HMW species in the well, suggesting that some species was tightly bound to HA. Keratinase with or without HAase did not greatly change above species except decreasing the 45 kDa species (FIG. 32C, lanes 6 and 8), suggesting that the 45 kDa species contained KS but most others do not. Chondroitinase alone abolished the HMW species in top well and reduced the intensity of 400 kDa area, but increased a strong broad 50 kDa species, 100 kDa species and 28 kDa species with smear between them (FIG. 32C, lane 7). Chondroitinase plus HAase had the same results with the whole smear more intensified and the 28 kDa species disappeared (FIG. 32C, lane 9). These results suggested that similar to decorin, biglycan in UC GnHC1 HC-HA mainly brings chondroitin sulfate chain. This finding is different from that in AM HC-HA where less was chondroitin sulfated. Also most biglycans form HMW complex in HC-HA with some bound to HC-HA.

Figure 32D:
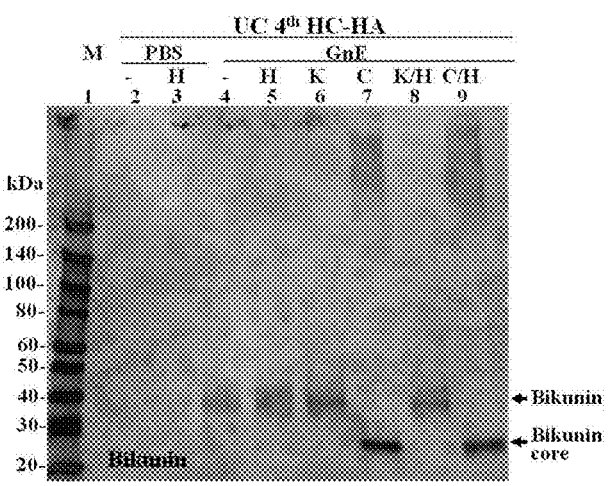

Western blot with anti-bikunin antibody showed a broad 35 kDa band in UC GnHC1 HC-HA with or without HAase digestion but not in PBS HC-HA (FIG. 32D, lanes 4 and 5). The 35 kDa band corresponds to the MW of native bikunin. Keratinase with or without HAase sharpened this 35 kDa band sharp but did not change its MW (FIG. 32D, lanes 6 and 8), while chondroitinase with or without HAase digestion changed the 35 kDa bikunin into a 25 kDa core bikunin (FIG. 32D, lanes 7 and 9), further confirming the existence of bikunin in UC GnHC1 HC-HA, and contained CS as reported. Because a HMW smear also formed after chondroitinase treatment, it suggested that bikunin is tightly bound to HC-HA via CS. These results were different from AM GnHC1 HC-HA that did not contain bikunin.

Figure 32E:
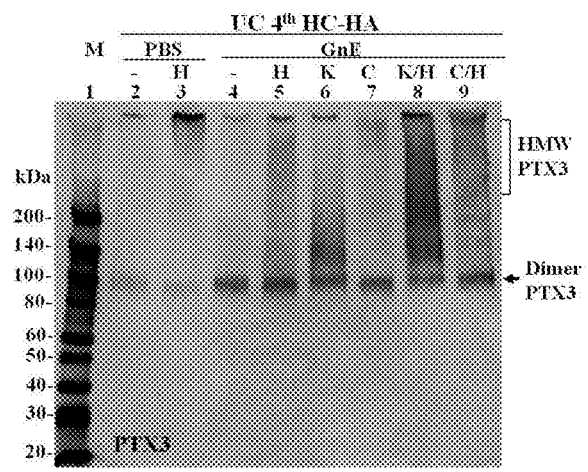

Western blot with anti-PTX3 antibody showed a increased HMW PTX3 smear in UC GnHC1 HC-HA after H, K, C, and especially with K/H (FIG. 32E, lanes 6 and 8) compared to that only with or without HAase digestion (FIG. 32E, lanes 4 and 5). These results confirmed the existence of HMW PTX3 in UC GnHC1 HC-HA, and its strong binding in GnHC1 HC-HA. Furthermore, such a strong binding was further helped by the presence of KS-containing species, of which the identity remains unclear. It also explained that our previous data (without enzymatic digestion) might have under estimated the amount of HMW PTX3 in UC GnHC1 HC-HA.

Figure 32F:
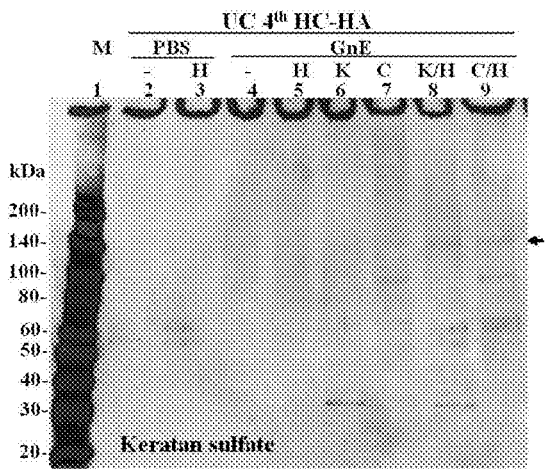
Figure 32G:
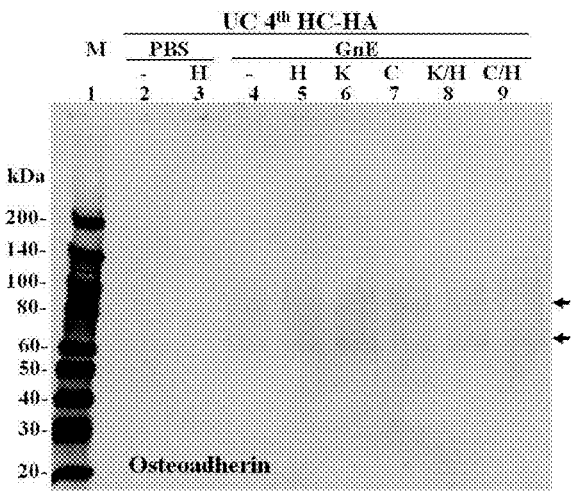

Western blot with anti-keratan sulfate antibody showed a HMW species in the well and a faint 55 kD band in UC PBS HC-HA. HAase did not change this band but made a 60 kDa band more obvious (FIG. 32F, lanes 2 and 3). However, a 140 kD band was recognized by anti-keratan sulfate antibody in UC GnHC1 HC-HA with or without HAase digestion (FIG. 32F, lanes 4 and 5). Keratinase with or without HAase treatment did not delete the 140 kDa band, but increased mainly a 35 kDa band and several other bands between them including a 60 kDa and a 55 kDa bands seen in PBS HC-HA (FIG. 32F, lanes 6 and 8).

Chondroitinase with or without HAase treatment also did not delete the 140 kDa band, but increased a 90 kDa band as well as a 60 kDa and a 55 kDa bands seen in PBS HC-HA (FIG. 32F, lanes 7 and 9). Chondroitinase treatment also resulted in a HMW smear appearance that decreased after HAase treatment, suggesting UC GnHC1 HC-HA contained abundant chondroitin sulfated proteins beside keratan sulfated proteins. It was clear that the keratan sulfated protein in UC GnHC1 HC-HA (140 kDa) had a different MW with that in AM GnHC1 HC-HA (~80 kDa), and may be it was due to the different amount of glycan in the chain.

With anti-osteoadherin antibody a major 60 kD band and a weak 80 kD band were detected in UC GnHC1 HC-HA (FIG. 32G, lanes 4) but not in PBS HC-HA. These two bands were not obviously affected by Keratinase or chondroitinase or HAase. The 80 kD should be keratin sulfated osteoadherin, while ~60 kD should be non-keratin sulfated osteoadherin. The results suggested that UC GnHC1 HC-HA contained both keratin sulfated and non-keratin sulfated osteoadherin.

In summary, no Fibromodulin, Lumican, Keratocan, PRELP, Osteoglycin, epiphycan, Periostin and TSG-6 were detected in UC GnHC1 HC-HA. UC GnHC1 HC-HA contained Decorin, biglycan, Osteoadherin, keratan sulfate and Bikunin. Biglycan and decorin were abundant in it, while PBS HC-HA did not contain an abundance of these species.

Summary

We purified HC-HA complex by 4× ultracentrifugation from both PBS and GnHC1 extract of AM and UC. The HC-HA purified from GnE was quite different from the HC-HA purified from PBS extract in yield and chemical constitution (see Table 1). In quantity, HC-HA purified from GnE contained more HA than that purified from PBS. In chemical constitution: GnHC1 HC-HA contained more HMW HA (with a MW slightly smaller than PBS HC-HA) but lacked a piece of HMW HA that corresponded to the HMW PTX3 smear in Western blotting shown by PBS HC-HA (from agarose gel). With or without HAase digestion GnHC1 HC-HA contained less HC1 and HMW PTX3 than PBS HC-HA, but after keratinase plus HAase digestion, more PTX3 was detected (from Western blot), suggesting the HMW PTX3 was tightly bound to keratin sulfated proteins in GnHC1 HC-HA. Neither PBS HC-HA nor GnHC1 HC-HA contained TSG-6, HC2 and HC3. Bikunin was present in UC GnHC1 HC-HA but not in UC PBS HC-HA and both AM PBS and GnHC1 HC-HA. AM GnHC1 HC-HA contained abundant Decorin, relatively more so than UC GnHC1 HC-HA. Both AM and UC PBS HC-HA contained a faint amount of decorin. AM and UC GnHC1 HC-HA contained abundant Biglycan, especially in UC GnHC1 HC-HA. No biglycan was present in PBS HC-HA. AM and UC GnHC1 HC-HA contained Osteoadherin. AM and UC PBS HC-HA did not contain Biglycan, keratan sulfate-containing species, Fibromodulin, Lumican, Keratocan, PRELP, Osteoglycin, epiphycan, Periostin, and Osteopondin, TSP-1. There was no Fibromodulin, Lumican, Keratocan, PRELP, Osteoglycin, epiphycan, Periostin, and Osteopondin, TSP-1, Asporin in AM and UC GnHC1 HC-HA. GnHC1 HC-HA contained visible protein bands mainly with MW 200 kDa, 80 kDa, and 60 kDa that were not found in PBS HC-HA (from Coomassie blue staining gel).

TABLE 3

Summary comparison of 4× HC-HA complex purified from PBS and GnHCl extract.

| Components | 4th PBS HC-HA | | 4th GnHC1 HC-HA | |
| --- | --- | --- | --- | --- |
| | AM | UC | AM | UC |
| Wet weight (g) from one placenta | 23.8 ± 4.7 | 48.2 ± 17.2 | 24.6 ± 9.4 | 33.5 |
| Total HA content (μg) | 208 ± 100 | 2800 ± 1697 | 872 ± 378 | 6561 |
| HC1 | +++ | ++ | + | + |
| PTX3 | +++ | ++ | ++ by keratinase | + + by keratinase |
| TSG-6, HC2, HC3 | − | − | − | − |
| Bikunin | − | − | − | + |
| Decorin | +/− | − | +++++ | ++ |
| Biglycan | − | − | ++++ | +++ |
| Keratan sulfate | − | −/+ | ++ | + |
| Osteoadherin | − | − | ++ | + |
| TSP-1* | − | − | − | − |
| Osteopondin | − | − | − | − |
| Asporin | − | − | − | − |
| Fibromodulin, | − | − | − | − |
| Lumican | − | − | − | − |
| Osteoglycan | − | − | − | − |
| Keratocan | − | − | − | − |
| Testican | − | − | − | − |
| Epiphycan | − | − | − | − |
| Periostin | − | − | − | − |

*Note that this information is not the same as extract, suggesting that there is TSP-1 that is dissociable by ultracentrifugation.

TABLE 4

Summary comparison of the extract of PBS and GnE sequentially obtained from AM and UC.

|  | PBS extract | | GnHCl extract | |
| --- | --- | --- | --- | --- |
|  | AM | UC | AM | UC |
| HA content (µg/ml) | < |  | < |  |
| HC1 | > |  | < |  |
| PTX3 | < |  | > |  |
| TSG-6 | + | unknown | + | − |
| TSP-1 | − | − | + | + |

Example 31. Constitutive Expression of PTX3 by Human Amniotic Membrane Stromal Cells Leads to HC-HA/PTX3 Complex Formation In this example, PTX3 expression in HC-HA purified from AM and its effect on HC-HA/PTX3 complex formation in AM was examined.

Experimental Procedures

1. Materials

Guanidine hydrochloride, cesium chloride, EDTA, anhydrous alcohol, potassium acetate, sodium acetate, sodium chloride, sodium hydroxide, Tris base, Triton X-100, 3-(N,N-Dimethyl palmityl ammonio) propanesulfonate (Zwittergent$^{3-16}$), protease inhibitor mixture (including 4-(2-aminoethyl)-benzenesulfonyl fluoride hydrochloride, aprotinin, bestatin hydrochloride, E-64, leupeptin, and pepstatin A) and phenylmethanesulfonyl fluoride were obtained from Sigma-Aldrich (St. Louis, Mo.). *Streptomyces* hyaluronidase (HAase) and biotinylated HA-binding protein (HABP) were from Seikagaku Biobusiness Corporation (Tokyo, Japan). Dulbecco's modified Eagle's medium, Ham's F12 nutrient mixture, fetal bovine serum, Hank's balanced salt solution, gentamicin, amphotericin B and RIPA buffer were purchased from Invitrogen (Grand Island, N.Y.). Slide-A-Lyzer Dialysis Cassettes (3.5K MWCO) was from Fisher Scientific (Pittsburgh, Pa.). BCA Protein Assay Kit was from Pierce (Rockford, Ill.). HA Quantitative Test Kit was from Corgenix (Westminster, Colo.). 4-15% gradient acrylamide ready gels and nitrocellulose membranes were from Bio-Rad (Hercules, Calif.). IαI was prepared in our laboratory from human plasma, according to the published method (1,38). PTX3 mAb (MNB4) and pAb were from Enzo Life Sciences, Inc. (Plymouth, Pa.). Recombinant human TNF, recombinant human Pentraxin 3/TSG-14 and human/mouse TSG-6 MAb (MAB2104) were from R&D Systems (Minneapolis, Minn.). Mouse anti-human ITIH1 polyclonal antibody against full length ITIH1 and rabbit anti-human ITIH2 polyclonal antibody against amino acids 124-321 were from Abcam Inc. (Cambridge, Mass.). HiPerFect Transfection Reagent and RNeasy Mini RNA isolation Kit was from QIAGEN (Valencia, Calif.). Small interfering RNA (siRNA) oligonucleotides for targeting endogenous human PTX3 (ACACUUGAGACUAAUGAAAGAGAGA) and non-targeting siRNA control oligonucleotides (scrambled RNA) siRNA were from OriGene Technologies, Inc (Rockville, Md.). Western Lighting™ Chemiluminesence Reagent was from PerkinElmer, Inc. (Waltham, Mass.). The ultracentrifuge (LM8 model, SW41 rotor) was from Beckman Coulter, Inc. (Fullerton, Calif.).

2. Cell Cultures and Agarose Overlay

Human tissue was handled according to the Declaration of Helsinki. The fresh human placenta was obtained from healthy mothers after elective cesarean deliveries in the Baptist Hospital (Miami, Fla.) via an approval (Protocol Number 03-028) by the Baptist Health South Florida Institutional Review Board. Primary human AM epithelial and stromal cells (designated as AMEC and AMSC, respectively) were isolated from fresh placenta as previously described (Chen et al. (2007) *Stem Cells.* 25: 1995-2005; Li et al. (2008) *J. Cell. Physiol.* 215:657-664) and cultured in supplemental hormonal epithelial medium (SHEM, which consisted of DMEM/F12 (1:1, v/v), 5% (v/v) FBS, 0.5% (v/v) dimethyl sulfoxide, 2 ng/ml EGF, 5 µg/ml insulin, 5 µg/ml transferrin, 5 ng/ml sodium selenite, 0.5 µg/ml hydrocortisone, 0.1 nM cholera toxin, 50 µg/ml gentamicin, 1.25 µg/ml amphotericin B) (Chen et al. (2007) *Stem Cells* 25:1995-2005; Chen et al. (2011) *Tissue Eng Part C Methods* 17:537-548) under a humidified atmosphere of 5% $CO_2$ at 37° C. The culture medium was changed every 2 days. Cells at 80% confluence were switched to DMEM/F12 containing 0.5% FBS for 48 h to let the cells become quiescent and then treated with 20 ng/ml TNF or 20 ng/ml IL-1β for 4 h or 24 before subject to RT-PCR and Western blot analysis. For agarose overlay culture, AMEC, AMSC and HSF are seed in 12-well ($1\times10^5$ cells/well) and 6-well ($2\times10^5$ cells/well) plate at a density of $2\times10^4/cm^2$ in SHEM. The medium are changed at day 1 to serum-free SHEM containing 5% KnockOut serum replacement and 1 mM 2-phospho-L-ascorbic acid and incubated for another 2 days. After removal of the medium, 3% agarose (low melting-type, Type VII, Sigma, A9045) in DMEM/F12 with 1 mM 2-phospho-L-ascorbic acid was over-layered at 1 ml or 0.5 ml to achieve a 1 mm thick gel layer at room temperature for 5-10 min before adding 3 ml or 1.5 ml of serum-free SHEM media with or without 5 ng/ml TNF per 6 or 12 well plate, respectively. Cells were harvested without intervening media changes on Days 5.

3. siRNA Transfection

AMEC and AMSC were cultured in SHEM in six-well plates till 80% confluence. Cells were switched to DMEM/F12 with 0.5% FBS for 48 h and were transfected with PepMute™ siRNA Transfection Reagent with 100 nM of PTX3 siRNA or scrambled (sc) RNA. After 48 h, cells were harvested and subjected to RT-PCR and Western blot analysis.

4. Purification of HC-HA Complex from AM and Serum-Free Cultures by Ultracentrifugation HC-HA complex was purified from AM and cell cultures as previously described (He et al. (2009) *J. Biol. Chem.* 284: 20136-20146; Yoneda et al. (1990) *J. Biol. Chem.* 265:5247-5257; He et al. (2008) *Invest. Ophthalmol. Vis. Sci.* 49:4468-447532). In brief, cryopreserved human AM, obtained from Bio-tissue, Inc. (Miami, Fla.), was sliced into small pieces, frozen in liquid nitrogen, and ground to fine powder by a BioPulverizer. The powder was mixed with cold phosphate-buffered saline (PBS) buffer at 1:1 (g/ml). The mixture was kept at 4° C. for 1 h with gentle stirring and then centrifuged at 48,000 g for 30 min at 4° C. The supernatant (designated as AM extract) was then mixed with a 8 M guanidine HC1/PBS solution (at 1:1 ratio of v/v) containing 10 mM EDTA, 10 mM aminocaproic acid, 10 mM N-ethylmaleimide, and 2 mM PMSF and adjusted to a density of 1.35 g/ml (AM extract) or 1.40 g/ml (cell extract) with cesium chloride, respectively, and subjected to isopycnic centrifugation at 35,000 rpm, 15° C., for 48 h. The resultant density gradients were fractioned into 12 tubes (1 ml/tube), in which the contents of HA and proteins were measured using HA Quantitative Test Kit and BCA Protein Assay Kit, respectively. Fractions from the first ultracentrifugation, which contained most HA were pooled, brought to a density of 1.40 g/ml by addition of CsCl, ultracentrifuged, and fractionated in the same manner as described above. Fractions from the second ultracentrifugation, which contained HA but no detectable proteins, were pooled and continue to the third and the forth ultracentrifugation in a density of 1.42 g/ml by addition of CsCl. Fractions from the second and the forth ultracentrifugation were dialyzed in distill water and then precipitated twice with 3 volumes of 95% (v/v) ethanol containing 1.3% (w/v) potassium acetate at 0° C. for 1 h. After centrifugation at 15,000 g, the pellet was briefly dried by air, stored at −80° C. and designated as AM $2^{nd}$ HC-HA and $4^{th}$ HC-HA, respectively.

5. Immunostaining

Human fetal membrane containing AM and chorion section as well as cell cultures with or without an agarose overlay were fixed with 4% paraformaldehyde at room temperature for 15 min, permeabilized with 0.2% (v/v) Triton X-100 in PBS for 20 min. After blocking with 0.2% (w/v) bovine serum albumin in PBS for 1 h, sections were incubated with biotinylated HABP (for HA, 5 µg/ml), anti-PTX3, anti-HC1 or anti-HC2 antibodies (all diluted 1:200 in blocking solution) overnight in a humidity chamber at 4° C. After washing with PBS, they were incubated with Alexa Fluor 488 Streptavidin (for HA, diluted 1:100), or respective secondary antibodies (i.e., Alexa Fluor 488 anti-mouse IgG, or Alexa Fluor 555-conjugated anti-rat IgG,) for 1 h at room temperature. Isotype-matched nonspecific IgG antibodies were used as a control. Alternatively, sections were treated with 50 U/mL *Streptomyces* HAase at 37° C. for 4 h before fixation. Nuclei were stained by Hoechst 33342, and images were obtained using a Zeiss LSM700 confocal laser scanning microscope (Zeiss, Germany).

6. Real-Time PCR

Total RNA was extracted from cell cultures using RNeasy Mini RNA isolation Kit. The cDNA was reverse-transcribed from 1 µg of total RNA using a Cloned AMW First-Strand cDNA synthesis kit with oligo(dT) primer. First-strand cDNAs were amplified by qPCR using AmpliTaq Gold Fast PCR Master Mix and the specific PTX3 primers (46-48). Glyceraldehyde-3-phosphate dehydrogenase (GAPDH) gene expression was used to normalize the amounts of the amplified products.

7. Western Blot

Culture supernatants were collected, and cell lysates were obtained by washing cells six times with cold PBS followed by incubating in RIPA buffer at 4° C. for 1 h with gentle stirring and centrifugation at 14,000 g for 30 min at 4° C. Protein concentrations in culture supernatants and cell lysates were quantified with a BCA Protein Assay Kit. Samples were incubated in 50 mM NaOH for 1 h at 25° C. or dissolved in 0.1 M sodium acetate buffer (pH 6.0) and incubated at 60° C. for 1 h with or without 20 units/ml of *Streptomyces* HAase. They then were resolved by SDS-PAGE on 4-15% (w/v) gradient acrylamide ready gels under denaturing and reducing conditions and transferred to a nitrocellulose membrane. The membrane was then blocked with 5% (w/v) fat-free milk in 50 mM Tris-HCl, pH 7.5, buffer containing 150 mM NaCl and 0.05% (v/v) Tween-20 followed by sequential incubation with different primary antibodies followed by their respective HRP-conjugated secondary antibodies. Immunoreactive proteins were visualized by Western Lighting™ Chemiluminesence Reagent.

Results

Positive PTX3 Staining in AM Epithelium and the Compact Stroma

Figure 33:
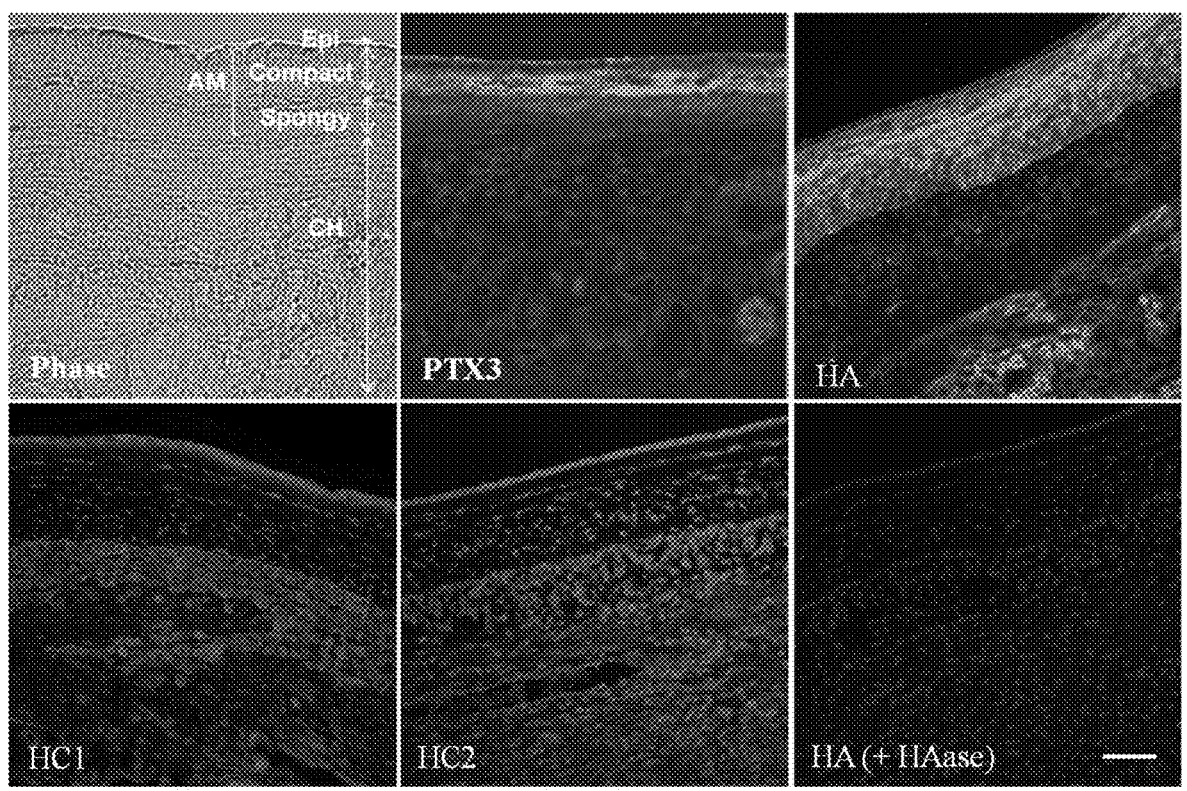
FIG. 33 exemplifies immunolocalization of PTX3 in human AM. Frozen sections of human fetal membrane were probed with anti-PTX3, biotinylated HABP with or without HAase digestion and with chain-specific antibodies against IαI components. Nuclei were counter-stained with Hoechst 33342 (blue). AM, amniotic membrane; Epi, Epithelium; CH, chorion. Bar, represents 100 µm.

Immunofluorescence staining using anti-human PTX3 antibody was performed on cross-sections of fresh human fetal membrane, which consisted of a layer of epithelium and an avascular stroma, which can be further subdivided into a compact layer and a spongy layer, and the subjacent cell-rich chorion (FIG. 33, phase). Positive PTX3 staining was found in the apical surface of the epithelium and the compact stroma. In contrast, PTX3 staining was markedly attenuated in the spongy stroma and the chorion (FIG. 33, PTX3). HAase digestion did not enhance PTX3 staining in the latter, suggesting that the weak PTX3 staining in these two areas was not due to the masking effect. Strong positive HA immunostaining was found in AM stroma and relatively weak staining in AM epithelium using a biotinylated HABP (FIG. 33, HA), while a weak staining of HA was noted in the upper layer of the chorion subjacent to the AM stroma but strong staining in the lower layer of the chorion. This staining disappeared when the tissue section was pre-digested by HAase (FIG. 33, HA (+HAase)) suggesting that HA staining was specific. Immunostaining of individual HC, also revealed a positive staining in AM epithelium, stromal cells and matrix, and chorion (FIG. 33, HC1 and HC2). These results suggested the presence of PTX3 in AM predominantly in the compact stroma and the epithelium.

Presence of PTX3 in AM Soluble Extract and Purified HC-HA Complex

Figure 34A:
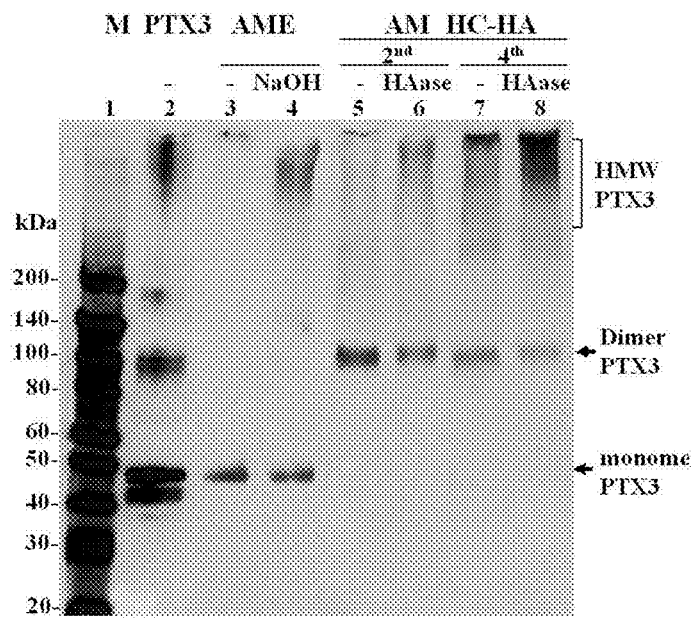
FIG. 34A-C exemplifies presence of PTX3 in AM soluble extract and purified HC-HA complex. Purified PTX3, AM extract (AME) and AM HC-HA complex were treated with or without 50 mM NaOH at 25° C. for 1 h or hyaluronidase (HAase) at 37° C. for 1 h before Western blotting using anti-PTX3 (A) and anti-HC1 (B) antibodies and analysis on 0.5% agarose gel electrophoresis before staining with Stains-all dye (C). PTX3 species and its multimeric form were found in AM soluble extract and purified HC-HA complex. M, protein ladder markers.
Figure 34B:
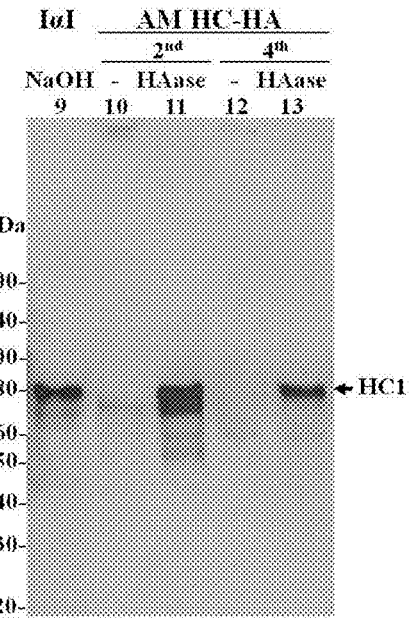
Figure 34C:
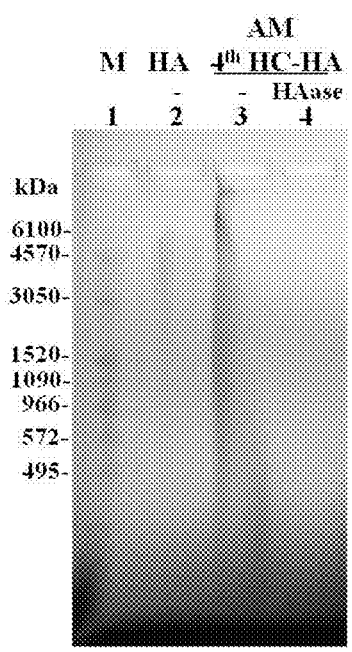

To investigate further the presence of PTX3 in AM, we first performed Western blotting analyses of AM extract obtained by an isotonic salt buffer before and after 50 mM NaOH treatment to cleave ester bonds. Recombinant PTX3 appeared as 45 kDa, 90 kDa, 180 kDa and HMW species (FIG. 34, lane 2). Soluble AM extract revealed 45 kDa and a HMW species at the bottom of the loading well (mostly not entering the gel) (FIG. 34, lane 3). NaOH treatment did not affect the 45 kDa species, but completely eliminated the HMW species, resulting in a HMW smear of PTX3 (FIG. 34, lane 4). These results suggested that PTX3 was present as a monomer and a HMW complex in the AME. Because the latter could be dissociated into a HMW smear by NaOH that can cleave off the ester covalent linkage between HC-HA, the HMW PTX3-containing species in the loading well might be associated with HC-HA.

To further confirm whether PTX3 was associated with AM HC-HA complex, we purified HC-HA complex by two and four successive ultracentrifugations from the AM soluble extract as previous reported (He et al. (2009) *J. Biol. Chem.* 284:20136-20146.; Zhang et al. (2012) *J. Biol. Chem.* 287:12433-12444) and performed Western blotting analyses with or without HAase digestion. Contrasted to the monomer found in soluble AME, a 90 kDa species corresponding to the size of the native PTX3 dimer was shown in AM 2nd and $4^{th}$ HC-HA complex besides a HMW band at the bottom of the loading well (FIG. 34, lanes 5 and 7). In addition, a HMW smear was also seen weak in $2^{nd}$ HC-HA and strong in $4^{th}$ HC-HA complex. After HAase treatment, the 90 kDa dimer remained in both HC-HA complexes, but the HMW smear was intensified in $4^{th}$ HC-HA and increased in $2^{nd}$ HC-HA with the disappearance of HMW band in gel top (FIG. 34, lanes 6 and 8) similar to the results seen in AME. The existence of 90 kDa PTX3 dimer in HC-HA complex with or without HAase was found to be caused by dissociation from HC-HA caused by 2-ME as elimination of 2-ME resulted in the absence of this 90 kDa species (not shown). These results suggested that HC-HA complex contained PTX3 that was bind to HC-HA to form the HC-HA/PTX3 complex despite four times of ultracentrifugation.

Western blot analysis with anti-HC1 antibody showed the presence of HC-HA complex as a HMW species at the bottom of the loading well that disappeared upon HAase digestion (FIG. 34, lanes 10-13), and the presence of HC1 in the HC-HA complex that was released from HC-HA complex after HAase digestion (FIG. 34, lanes 11 and 13). We did not detect HC2 nor TSG-6 (not shown). These results collectively confirmed that HC-HA purified from AM only contained HC1. We also noted a prime difference between $2^{nd}$ and $4^{th}$ HC-HA complexes, that is, a free 80 kDa HC1 band was detected only in the 2nd HC-HA complex (FIG. 34, lane 11), but not 4th HC-HA complex, suggesting that the latter did not contain free HC1. The presence of HA in 4th HC-HA were verified by agarose gel electrophoresis to display as a continuous HA smear from the top loading well to the bottom of the gel, and that such a smearing was resolved by HAase digestion.

Expression of PTX3 mRNA and Protein by AMEC and AMSC

Figure 35A:
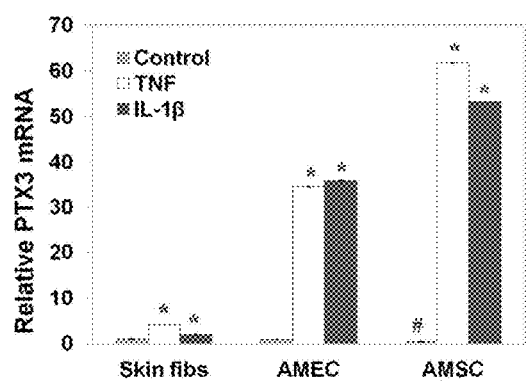
FIG. 35A-C exemplifies expression of PTX3 mRNA and protein by AMECs and AMSCs. RNA and protein were extracted from human skin fibroblasts (Skin Fib.), and both AMECs and AMSCs. Expression of PTX3 mRNA (A) and protein in supernatants and cell lysates (B) was compared. PTX3 siRNA transfection was performed to verify the expression of PTX3 in AMECs and AMSCs (C).
Figure 35B:
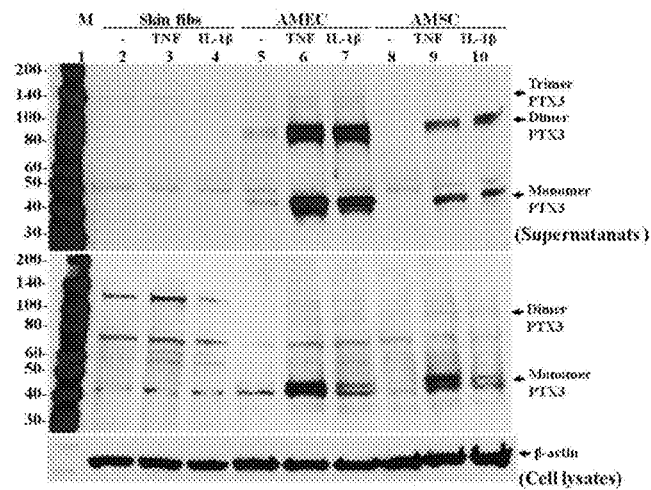
Figure 35C:
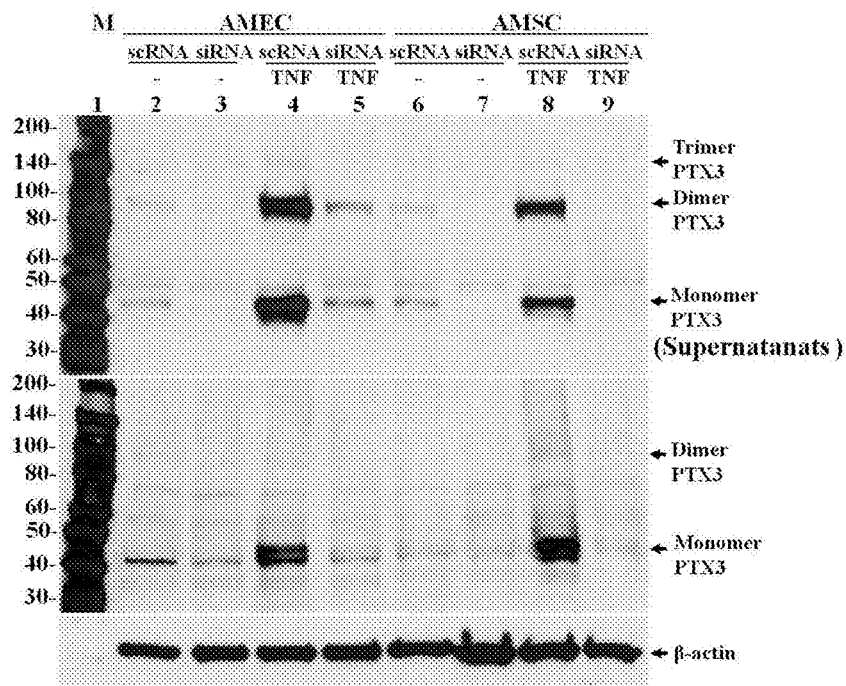

We then determined that PTX3 was synthesized by AM epithelial and stromal cell cultures. We cultured these cells as reported (Chen et al. (2007) *Stem Cells* 25(8):1995-2005; Li et al. (2008) *J Cell Physiol.* 215(3):657-64; Zhang et al. (2012) *J. Biol. Chem.* 287:12433-12444) and extracted total RNA for RT-PCR and proteins for Western blot analysis, and compared them to human skin fibroblasts (HCF), which were reported to express PTX3 mRNA and protein only under the stimulation of pro-inflammatory cytokine such as TNF and IL-1. As expected, qRT-PCR results showed that expression of PTX3 transcript was low in resting HSF, but upregulated by TNF and IL-10 (FIG. 35A). Although expression of PTX3 transcript in resting AMEC and AMSC was also low, it was dramatically elevated by TNF or IL-1β (FIG. 35A). Western blotting analysis confirmed that PTX3 protein was low in lysates (45 kDa) and undetectable in media in resting HSF (FIG. 35B, lane 2) but was detected in lysates but not media after addition of TNF or IL-1β for 24 h. In contrast, PTX3 protein was detectable in resting AMEC and notably increased by TNF or IL-1b in both lysates (45 kDa) and media (45 kDa and 90 kDa) (FIG. 35B, lanes 5, 6 and 7), with TNF being more effective than IL-1b. The same finding was noted in AMSC (FIG. 34B, lanes 8, 9 and 10). To verify that the 75 kDa and 135 kDa bands in lysates and the 50 kDa band in media from all cells were nonspecific because these bands did not changes under TNF or IL-1b, PTX3 siRNA transfection was performed and indeed downregulated the 45 kDa species in lysis and both 45 kDa and 90 kDa species but not these non-specific bands. (FIG. 35C). These results collectively suggested that PTX3 was indeed synthesized and secreted by resting AM cells and was further upregulated by proinflammatory stimuli.

Production of HC-HA/PTX3 Complex by AM Stromal Cells

Figure 36:
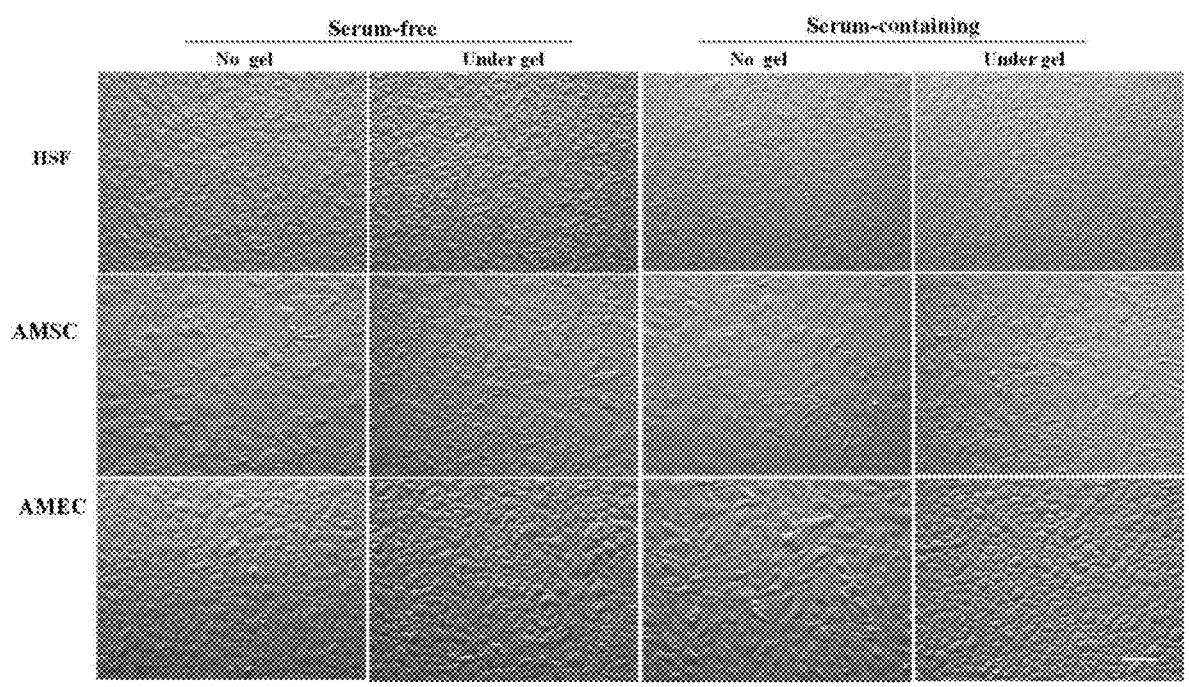
FIG. 36 exemplifies morphological changes of human skin fibroblasts (HSF, A), AMSC (B) and AMEC (C) after agarose overlay. HSF, AMSC and AMEC were cultured in both serum-free and serum-containing conditions with or without a 3% agarose overlay for five days and the cell morphology were photographed. Scale bar, 50 μm.

Previous studies have shown that HC-HA (i.e. SHAP-HA) complex can be isolated from the cell layer of cultured mouse dermal fibroblasts in a medium supplemented with FBS, and that the isolated HC-HA contains both HC1 and HC2 of IαI derived from FBS (Yoneda et al. (1990) *J. Biol. Chem.* 265:5247-5257; Huang et al. (1993) *J. Biol. Chem.* 268:26725-26730). However, we reported that AM cells produce HC-HA by using their endogenously generated IαI (Zhang et al. (2012) *J. Biol. Chem.* 287:12433-12444). Because AM cells synthesized PTX3 protein which was further increased by TNF and IL-1, we aimed to determine whether they produced HC-HA that also contained PTX3. We used HSF as a control, which expressed PTX3 only under pro-inflammatory stimuli, e.g. TNF and IL-1, in a serum-containing condition (Yoneda et al. (1990) *J. Biol. Chem.* 265:5247-5257; Huang et al. (1993) *J. Biol. Chem.* 268:26725-26730) (FIG. 35) and compared to AMECs and AMSCs cultured in both serum-free and serum-containing condition with or without TNF. We also overlayed 3% agarose over cell monolayers because this method has been found to entrap secreted procollagen at or near the cell surface, rather than into the media on keratocyte cultures (Hassell et al. (2008) *Experimental Eye Resarch.* 87:604-611; Etheredge et al. (2010) Matrix Boil. 29:519-524). After 5 days of overlay, HSF, AMSC and AMEC became more compact especially in the serum-containing condition (FIG. 36). The epithelial morphology became more distinct in AMEC.

Figure 37:
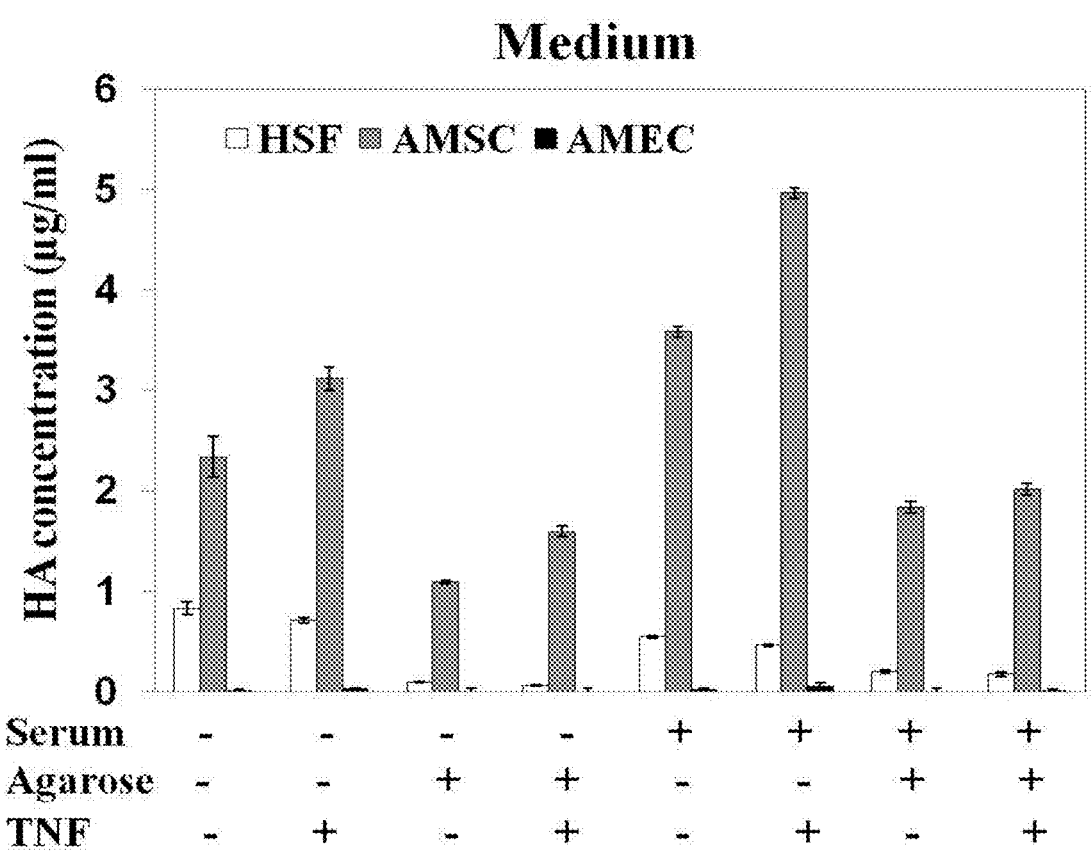
FIG. 37 exemplifies that agarose overlay decreased the release of HA into culture media by HSF, AMSC and AMEC cultures. The HA concentration were measured by ELISA assay in culture media from HSF, AMSC and AMEC with or without agarose overlay in both serum-free and serum-containing conditions.

We then determined whether 3% agarose overlay was also effective in entrapping secreted HA by measuring the HA concentration in culture media by HA ELISA assay. Without agarose overlay, the HA level was readily detectable in the serum-free medium of both AMSC and AMEC but not in that of HSF. TNF significantly increased the HA level of all three cell cultures (FIG. 37). The above pattern was further promoted in the serum-containing medium. Agarose overlay reduce the HA level more than 50% in both serum-free and serum-containing conditions among all three cultures. These results suggested that agarose overlay indeed reduced the HA level into culture medium.

Figure 38:
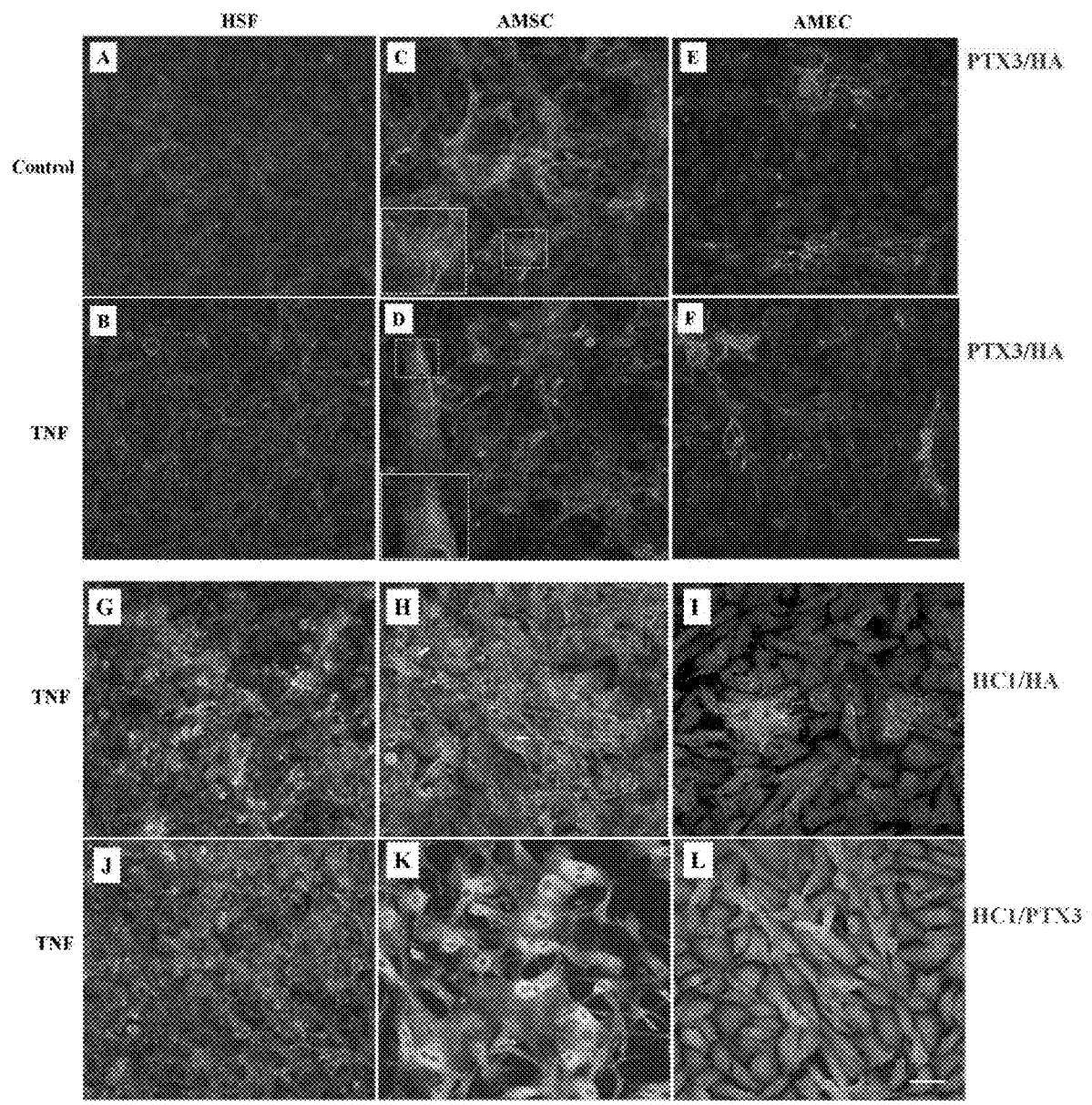
FIG. 38 exemplifies immunolocalization of PTX3, HA and HC1 in cell cultures with an agarose overlay. HSF, AMSC and AMEC were cultured with an agarose overlay with or without TNF treatment and probed for hyaluronan (red), PTX3 (green, A-F; red, J-L) and HC1 (green) (nuclei are blue). Colocalization of HC1 with HA were found in all cultures, but colocalization of PTX3 with HA or HC1 were only found in AMSC and AMEC. Scale bar, 50 μm.

To determine when secreted HA was indeed entrapped in the extracellular matrix after agarose overlay, we performed double immunostaining for PTX3/HA, HC1/HA, and HC1/PTX3 with biotin-labeled HABP, specific antibody to HC1 and HC2, and two different anti-PTX3 antibodies, i.e. MNB4 and biotin-labeled pAb, respectively. In the serum-free condition, positive HA staining was noted in the pericellular region in HSF, while PTX3 staining was negative (FIG. 38A). With TNF stimulation, positive PTX3 staining was observed in the cytoplasm (FIG. 38B), confirming inducible expression of PTX3 by TNF in HSF. TNF did not greatly increase the HA staining intensity but induced a cable-like structure (FIG. 38G) similar to what has been reported in cultured renal proximal tubular epithelial cells (Selbi et al. (2006) *Kidney International.* 70: 1287-1295). No colocalization of PTX3 with HA was observed, suggesting that PTX3 was not associate with HA in HSF after TNF stimulation. In contrast, positive HA staining was detected in resting AMSC as a fibrillar network on the cell surface and extracellular matrix as was colocalized with HA in the extracellular matrix (FIGS. 38C and 6K). TNF further increased PTX3 staining intensity and the amount of HA fibrils (FIGS. 38D and 38K).

In resting AMEC, positive HA staining was also found in extracellular spaces with some fibrillar appearance but only in sporadic areas where cells were not as compact (FIGS. 38E and 38L). PTX3 and HA colocalization was also observed in AMEC. TNF treatment further increased PTX3 staining intensity and the amount of HA fibrils (FIG. 38F). These results further confirmed that PTX3 was constitutively expressed by AMSC and AMEC, and its expression can by further increased by TNF. Weak positive HC1 staining was observed only in some HSF with (FIGS. 38G and 38J) or without (not shown) TNF treatment, and was colocalized with HA especially in HA cable-like structure (FIG. 38G). However, we did not note colocalization between HC1 and PTX3 (FIG. 38J). In contrast, strong positive HC1 staining was noted in AMSC and colocalized with HA on the cell membrane (FIG. 38H) and colocalized with PTX3 in the cytoplasm (FIG. 38K). AMEC also showed the strong positive HC1 staining and colocalization with HA in the cell membrane (FIG. 38I) and with PTX3 in the cytoplasm and the cell membrane (FIG. 38L). Collectively, these results suggested that HA-rich matrix was effectively trapped by agarose overlay in AMSC, AMEC and HSF, and contained both HC1 and PTX3 only in AMSC and AMEC in the serum-free condition, further confirming that such HC-HA/PTX3 complex was synthesized by endogenous IαI.

Figure 39:
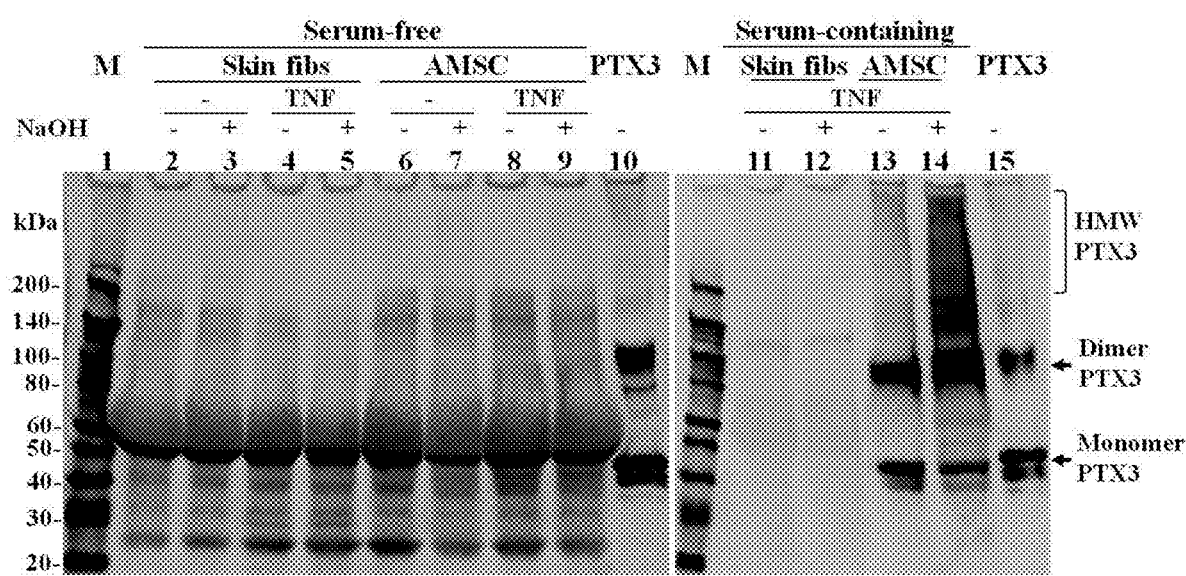
FIG. 39 exemplifies HC-HA/PTX3 complex in AMSC but not HSF under agarose overlay. GnHC1 extracts of cell layers from agarose overlayed HSF and AMSC cultures were subjected to Western blot for PTX3 with or with NaOH treatment. M, protein ladder markers.

To further confirm the formation of HC-HA/PTX3 complex under agarose overlay, we extracted cell layer with 6M GnHC1 and performed Western blot analysis in AMSC and HSF cultures under both serum-free and serum-containing condition with or without NaOH treatment. Serum-free HSF showed a 170 kDa and a 140 kDa species but not 45 kDa species corresponding to the control PTX3 with or without TNF stimulation and NaOH treatment, suggesting that these two bands were not specific (FIG. 38D, lane 2-5). Serum-containing HSF with TNF showed a faint 140 kDa species and some small MW species similar to those seen in serum-free HSF (FIG. 39, lanes 11 and 12). In contrast, serum-free AMSC showed a weak HMW PTX3 smear, a 90 kDa and a 45 kDa species (FIG. 39, lane 6), of which the later two corresponded to PTX3 dimmer and monomer, respectively (FIG. 39, lane 2). These results were similar to those seen in AME (FIG. 34). The same non-specific 170 kDa species and some small molecular species as seen in serum-free HSF were also observed. NaOH treatment increased the HMW PTX3 smear but did not affect the PTX3 monomer and dimmer (FIG. 39, lane 7) and other species. TNF increased the HMW PTX3 smear, PTX3 dimmer and monomer as well as other species (FIG. 39, lane 8 and 9). Serum-containing AMSC with TNF showed strong HMW PTX3 smear, 90 kDa PTX3 dimmer and 45 kDa PTX3 monomer (FIG. 39, lane 13). NaOH treatment greatly increased the HMW PTX3 smear and two species at 60 kDa and 50 kDa (FIG. 39, lane 14). Because NaOH break the ester bound between HC and HA leading to dissolution of HC-HA, these results suggested that HMW PTX3 was released from HC-HA complex. Collectively, above results suggested that AMSC but not HSF produced HC-HA complex containing PTX3.

In Vitro Reconstitution of HC-HA/PTX3 Complex (rcHC-HA/PTX3)

Figure 40A:
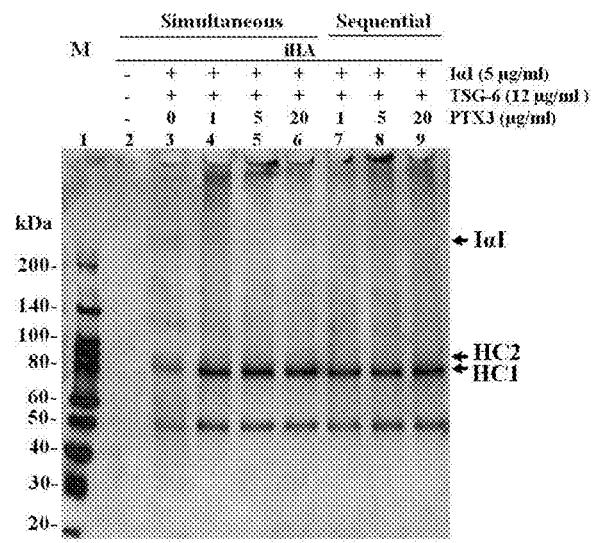
FIG. 40A-C exemplifies reconstitution of HC-HA/PTX3 complex on immobilized HA in vitro. iHA (~14 μg/ml), IαI (5 μg/ml), and TSG-6 (12 μg/ml) were incubated simultaneously without or with PTX3 (1, 5, or 20 μg/ml) for 2 h at 37° C. For sequentially, iHA (~14 μg/ml), IαI (12 μg/ml), and TSG-6 (12 μg/ml) were incubated in the reaction buffer for 2 h at 37° C., then PTX3 (1, 5, or 20 μg/ml) were added and incubated for another 2 h at 37° C. After washes with 8 M GnHC1 and PBS, iHA with bound components were digested with 1 unit/ml of hyaluronidase for 2 h at 60° C. The samples were analyzed by Western blot with antibodies against IαI (A), TSG-6 (B) and PTX3 (C).
Figure 40B:
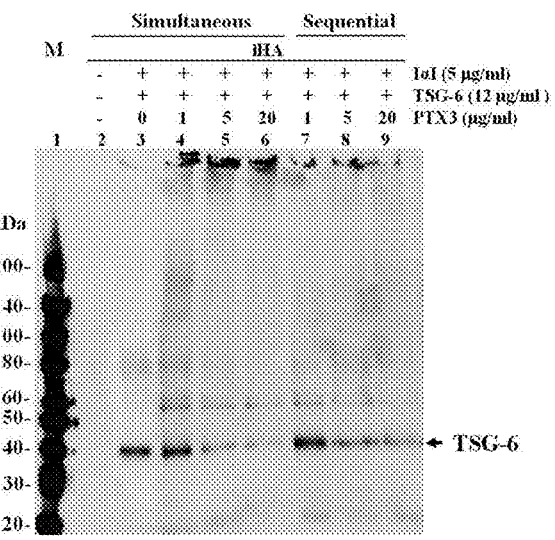
Figure 40C:
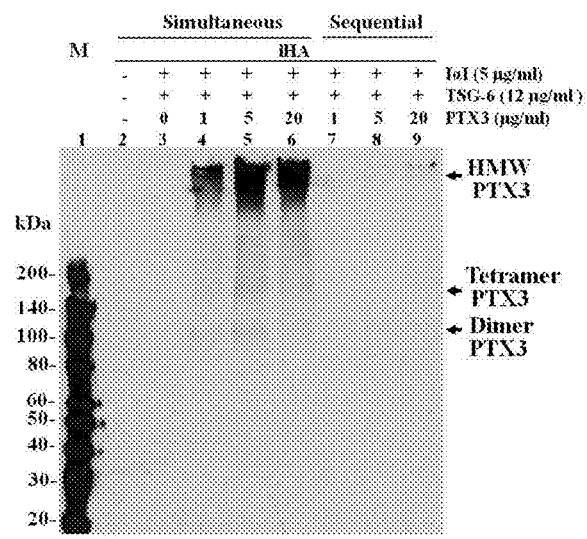

To further confirm how HC-HA/PTX3 complex could be generated, we would like to reconstitute HC-HA/PTX3 complex in vitro with HA, TSG-6, IαI and PTX3. We first immobilized HA on plastic, and successfully added recombinant TSG-6, purified IαI or serum as a source of IαI. It has been reported that TSG-6 can form stable TSG-6/HA complex by binding to HA that is immobilized on a solid surface (Wisniewski et al. (2005) *J Biol Chem.* 280:14476-84), and that both free and HA-bound TSG-6 can transfer HCs from IαI to immobilized HA to form HC-HA (Colon (2009) *J Biol Chem.* 284:2320-31). Western blot using an anti-IαI antibody did not detect any species in control iHA alone as expected (FIG. 40A, lane 2). When IαI and TSG-6 were simultaneously added to iHA, a weak 220 kDa IαI, 85 kDa HC2, a strong ~80 kDa HC1 and a 50 kDa species were detected (FIG. 40A, lane 3), suggesting that both HC1 and HC2 were transfer to iHA in the presence of TSG-6 to form HC-HA. Comparison of the band intensity of HC1 to that of HC2 suggested that more HC1 were transferred to iHA than HC2 by TSG-6, resulting in a truncated 50 kDa species. When PTX3 were simultaneously with IαI and TSG-6 to iHA, the intensity of IαI species decreased but the HC1 intensity increased in a PTX3 dose-dependent manner (FIG. 40A, lanes 4-6), meanwhile HC2 was not detectable, suggesting that PTX3 preferentially promoted transfer of HC1 but not HC2 to immobilized HA catalyzed by TSG-6. When PTX3 were added after simultaneous addition of IαI and TSG-6, HC1 but not IαI or HC2 was detected, and the HC1 intensity was also increased in a PTX3 dose-dependent manner (FIG. 40A, lanes 7-9), confirming that PTX3 promoted transfer of HC1 but not HC2 to immobilized HA. These results suggested that PTX3 uniquely promoted transfer of predominately HC1 to immobilized HA to form HC1-HA complex regardless whether it was simultaneously or sequentially. Western blot using the anti-TSG-6 antibody showed that both 35 kDa TSG-6 monomer and 75 kDa dimer were detected in rcHC-HA formed by simultaneous or sequential addition of PTX3 in midst of IαI and TSG-6 on iHA. Because the intensity of the TSG-6 band decreased in a PTX3 dose-dependent, suggesting that TSG-6 bound to immobilized HA could be competed out by PTX3 (FIG. 40B). The Western blot using the anti-PTX3 antibody showed a prominent HMW PTX3 smear in the loading well with faint tetramer and dimer bands when PTX3 was added simultaneously with IαI and TSG-6, and that their intensity increased in a PTX3 dose-dependent manner (FIG. 40C, lanes 4-6). This finding suggested that PTX3 was preferentially and strongly bound to rcHC-HA complex in which the binding was resistant to 8 M GnHC1 wash. In contrast, when PTX3 was added sequentially after addition of IαI and TSG-6, we did not detect HMW PTX3 and tetramer and dimer species (FIG. 40C, lanes 7-9), suggesting that the binding between PTX3 and preformed rcHC-HA PTX3 was not strong to withstand 8 M GnHC1 wash. Hence, these in vitro reconstitution experiments suggested that PTX3 must have been produced simultaneously with HA, IαI and TSG-6 in vivo to allow formation of HC-HA/PTX3. This interpretation was supported by immunocolocalization of HA, HC, and PTX3 in in vivo tissue sections as well as extracellular matrix formed by AMSCs.

Example 33. Effects of HC-HA Complexes on TGFβ1 Signaling

Immobilized HC-HA inhibits TGFβ1 signaling by downregulating expression of TGF-β1 but upregulating TGF-β3 signaling. Such inhibition of TGFβ1 signaling can withstand the challenge by addition of serum or exogenous TGF-β1 because of further suppression of TGFβRII and TGFβRIII. Consequently, immobilized HC-HA prevents corneal fibroblasts from myofibroblast differentiation by inhibiting SMAD2/3 signaling and expression of alpha smooth muscle formation. This action is also potent enough to revert corneal fibroblasts to keratocytes. HC-HA(Insoluble (I)) differs from HC-HA(Soluble (S)) in consisting of additional small leucine rich proteins (SLRPs), and activates expression of TGFβ1 and BMP signaling by upregulating expression of BMPs and their receptors, thus activating pSMAD1/5/8, which together further promotes formation of aggregation. These actions can further de-differentiate corneal fibroblasts to neural crest progenitors.

In this example the effect of immobilized soluble and insoluble HC-HA on TGF-β signaling in human corneal fibroblasts with or without exogenous TGFβ1 challenge was examined. In addition the effect of HC-HA complexes on SMAD2/3 signaling and suppression of αSMA expression was tested.

Experimental and clinical studies support an anti-scarring therapeutic action by cryopreserved amniotic membrane (AM). Our studies demonstrated that heavy chain-hyaluronan complex (HC-HA) is uniquely produced by and can be purified from AM and suppresses the TGF-β1 promoter activity in human corneal fibroblasts. It is unclear whether HC-HA suppresses TGF-β1 mRNA and protein expression and promotes TGF-β3 mRNA and protein expression known to counteract TGF-β1 signaling, and if so, whether such inhibition of TGFβ signaling by HC-HA is translated in to suppression of nuclear translocation of pSMAD2/3.

Mouse keratocytes can maintain an undifferentiated state (expressing keratocan) in serum-free DMEM/ITS on plastic or in DMEM/10% FBS if cultured on AM. Treatment of keratocytes in serum-free DMEM/ITS with 10% serum or 10 ng/ml TGF-β1 induces Smad2/3 phosphorylation and nuclear localization (3 h) and α-SMA expression (5 days). The activation of Smad2/3 and α-SMA in keratocytes on AM with either serum or TGF-β1 treatment is suppressed (Kawakita et al. (2005) *J Biol Chem.* 280(29):27085-92). Our studies demonstrated HC-HA suppresses the TGF-β1 promoter activity in human corneal fibroblasts. It was expected that pSmad2/3 signaling and α-SMA formation will be suppressed by HC-HA.

Human corneal fibroblasts (or Limbal niche cells, p3) were seeded on plastic dishes with or without immobilized HA, soluble HC-HA (PBS) (2× or 4×) or insoluble HC-HA (GnHC1) (2× or 4×) for 48 h as described above. The cells were then treated with or without TGFβ1 for 24 h before being harvested for mRNA quantitation and determination of SMAD2/3 signaling. For determination of protein of TGFβ receptors, the cells were treated with or without TGF-β1 for 48 h before collection of protein samples to allow time for protein expression from the expressed mRNA. For TGF-β1 ELISA, the cells were treated with or without TGF-β1 for 24 h, and then cultured in the fresh medium for 24 (and 48) h. The supernatants were collected for TGF-β1 ELISA. For TGF-β2 and TGF-β3 ELISA, the cells were treated with or without TGF-β1 for 48 h. The supernatants were collected for TGF-β2 and TGF-β3 ELISA. Phase contrast images were taken up to 72 h for various cultures.

The following experiments were performed:

1. mRNA semiquantitation for TGF-β1, TGF-β2, TGF-β3 and their receptors by real-time PCR: used for estimation of mRNA transcript expression of TGF-β family and their receptors. Real-time RT-PCR profile consisted of 10 minutes of initial activation at 95° C., followed by 40 cycles of 15 seconds denaturation at 95° C., and 1 minute annealing and extension at 60° C.

2. Determination of α-smooth muscle formation and SMAD2/3 signaling by immunostaining: performed to monitor α-smooth muscle formation and SMAD2/3 signaling using standard immunostaining procedure.

The experimental groups for experiments 1 and 2 were:

PBS
PBS + TGF-β1
HA
HA + TGF-β1
2X HC-HA PBS
2X HC-HA PBS + TGF-β1
4X HC-HA PBS
4X HC-HA PBS + TGF-β1
2X HC-HA Gn
2X HC-HA Gn + TGF-β1
4X HC-HA Gn
4X HC-HA Gn + TGF-β1

3. Quantitation of TGFβRs by Western blotting: used to quantitate protein concentration of TGFβRI, TGFβRII, and TGFβRIII using their corresponding antibodies (R&D Systems). The loading sequence was as follows:

| MW marker | Plastic | HA | 4X HC-HA PBS | 4X HC-HA Gn | Plastic + TGF-β1 | HA + TGF-β1 | 4X HC-HA PBS + TGF-β1 | 4X HC-HA Gn + TGF-β1 |
|---|---|---|---|---|---|---|---|---|

4. ELISA for Quantitation of TGFβs in the Medium: The Quantikine Human TGF-β1 and TGF-β2 ELISA Kits from R&D Systems and TGF-β3 ELISA Kit from Norvus Biologicals are solid phase ELISAs designed to measure TGF-β1, TGF-β2 and TGF-β13 in acid activated cell culture supernatants, serum, plasma, and urine. They contain recombinant human TGF-β1, TGF-β2 and TGF-β3 and have been shown to quantitate the recombinant factors accurately. Results obtained using natural TGF-β1, TGF-β2 TGF-β3 showed linear curves that were parallel to the standard curves obtained using the recombinant kit standards. These kits were used to determine TGF-β1, TGF-β2 and TGF-β3 in the medium. The experimental groups for experiment 4 were:

PBS
PBS + TGF-β1
HA
HA + TGF-β1
4X HC-HA PBS
4X HC-HA PBS + TGF-β1
4X HC-HA Gn
4X HC-HA Gn + TGF-β1

Results

Figure 41A:
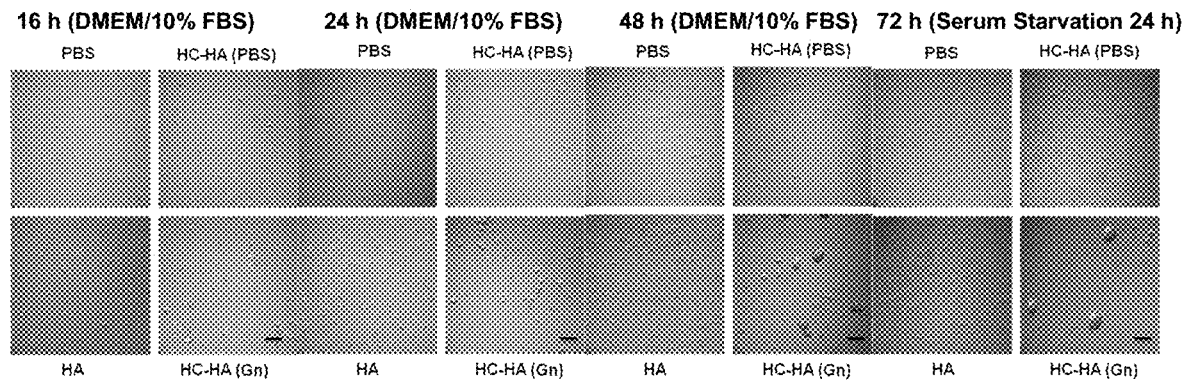
FIG. 41A-B exemplifies cell morphology of human corneal fibroblasts up to D3 cultured on DMEM/10% FBS for 2 Days (A) or DMEM/10% FBS for 2 Days±TGF-β1 for 3 Days (B).
Figure 41B:
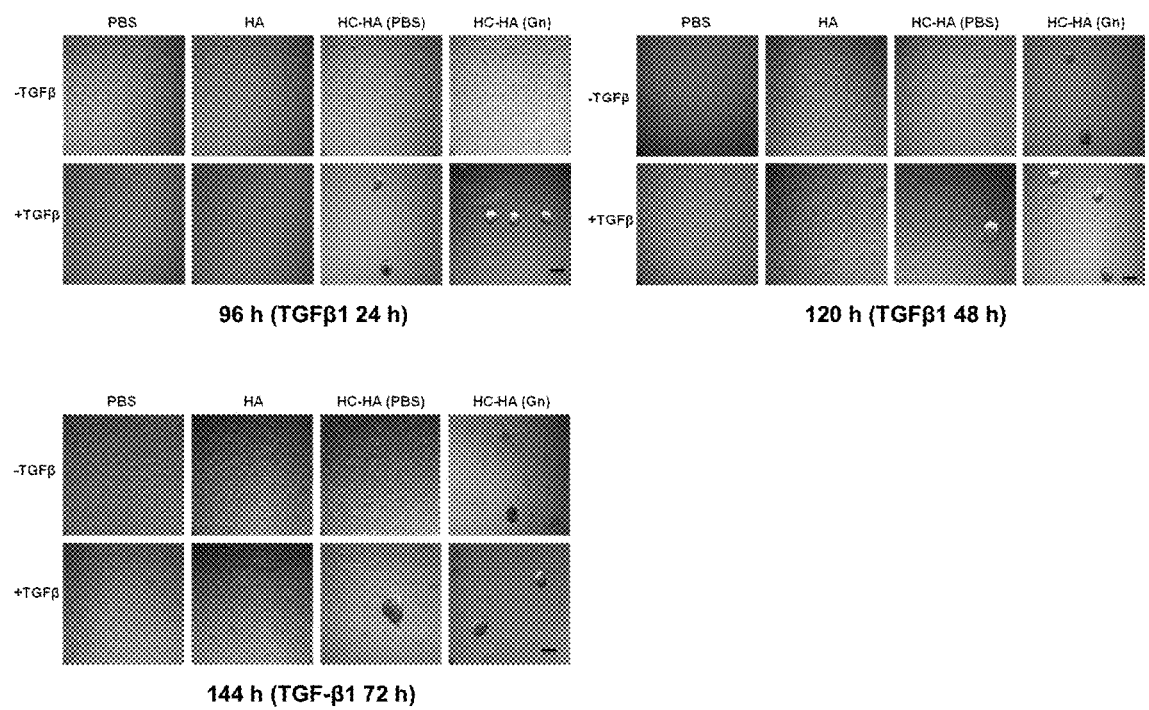

HCF seeded in DMEM/10% FBS formed aggregates by 72 h only on insoluble HC-HA (FIG. 41). Such aggregation persisted after 24 h serum starvation in DMEM/ITS (insulin/transferrin/selenium) medium. The cells were then cultivated into three different culture media: A—DMEM/ITS for 48 h; B—24 h DMEM/ITS, 24 h DMEM/10% FBS; C—24 DMEM/ITS, 24 h DMEM/ITS with 10 ng/ml TGF-β1. The cells cultured in HC-HA form small aggregates on 4× HC-HA (Gn), but not in other culture conditions (FIG. 41). However, after seeding for 2 hours in DMEM/10% FBS on immobilized substrates, only HCF on the control attached well. Cells on HA, HC-HA [HC-HA (4×, PBS) and 4×, GnHC1] were all rounded, suggesting they were not well attached. After incubation for 72 hours, all cells were attached well, however, there were much less cells on immobilized HC-HAs. The number of cells on these substrates was greater on HC-HA (4×, PBS) than on HC-HA (4×, GnHC1). HCF started to form aggregates on HC-HA (Gn) after 24 h of culture and condensed to bigger aggregates after 72 h of culture. After stimulation of TGFβ1, we observed aggregation of HCF cultured on HC-HA (4×, PBS; 4×, Gn).

In summary, HC-HA (Gn) promotes aggregation of HCF with/without challenge of TGFβ1 while HC-HA (PBS) promotes aggregation of HCF under challenge of TGFβ31. The significance of aggregation is unknown.

Figure 42:
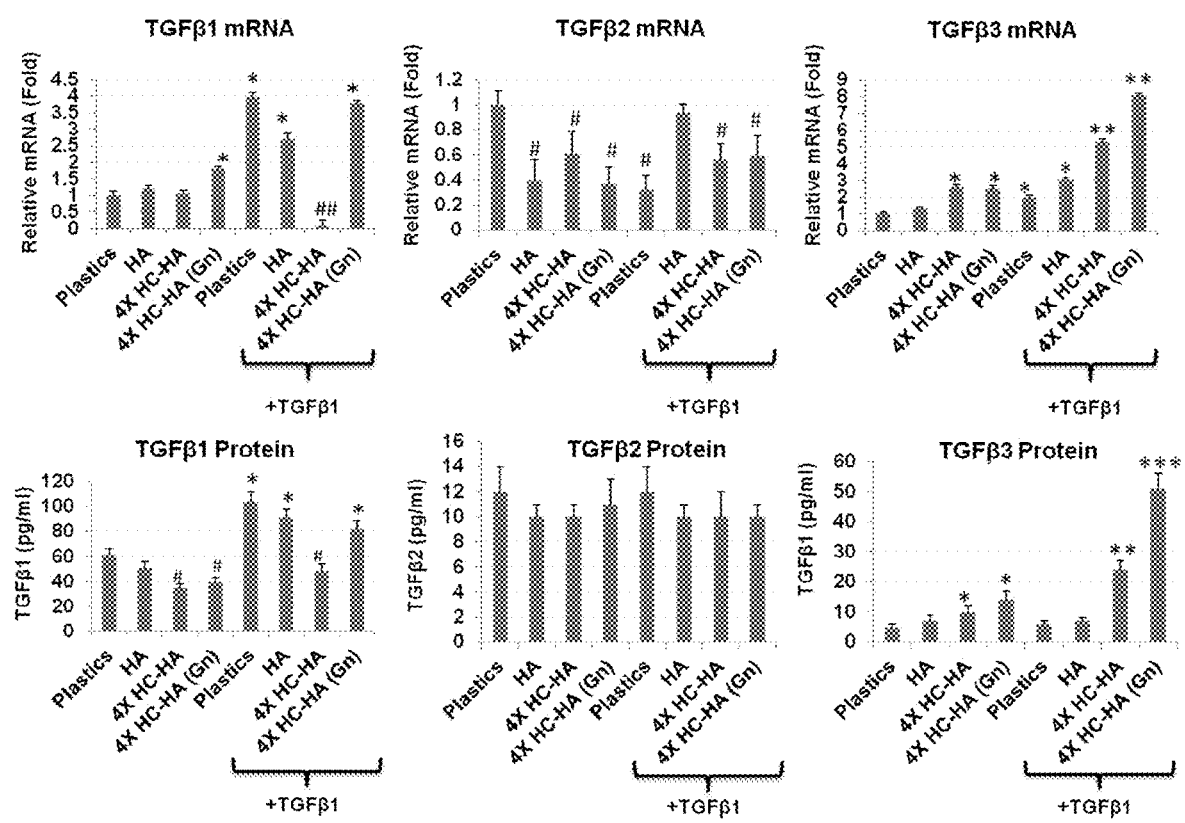
FIG. 42 exemplifies soluble HC-HA (PBS) inhibits TGFβ1 but activates TGFβ3 signaling while insoluble HC-HA (GnHC1) activates both TGFβ1 and TGFβ3 signaling under serum-free conditions and is further enhanced with TGFβ1 stimulation.

In DMEM/ITS, expression of, TGFβ1 and TGFβ3 transcripts were elevated by HC-HA (Gn), but TGFβ3 transcript was elevated by HC-HA (PBS) (FIG. 42). As expected in auto-induction, TGFβ1 and TGFβ3 mRNA were increased by 4- and 2-fold, respectively, in HCF cultured on plastic by TGFβ1 challenge, with corresponding increase of TGFβ1 protein from 60 pg/ml to 105 pg/ml (TGFβ3 protein was not detected in the experiment due experimental error). Under serum-free conditions, soluble 4× HC-HA reduced TGFβ1 protein expression. Insoluble HC-HA also decreased secreted TGFβ1 despite its promotion of TGFβ1 mRNA expression although still higher than the control cultured in DMEM/ITS. In addition, notable suppression of TGFβRII and TGFβRIII by both soluble and insoluble HC-HA was observed. Consequently, autocrine TGFβ signaling was suppressed in HCF cultured on either soluble or insoluble HC-HA but paracrine TGFβ signaling is preserved in HCF cultured on insoluble HC-HA. Furthermore, both soluble and insoluble 4× HC-HA upregulated TGFβ3 mRNA expression by 3-fold under serum-free conditions without TGFβ1 stimulation, which is known to counteract TGF-β1 signaling. Under stimulation by TGFβ1, TGFβ3 mRNA expression is increased by 5- and 8-fold when HCF were cultured on soluble and insoluble HC-HA respectively, indicating that soluble and insoluble HC-HA strongly promotes TGFβ3 transcript expression. These results also indicate that HC-HA purified from AM promotes AM's anti-scarring action by not only suppressing TGFβ1 signaling but also by marked upregulation of TGFβ3 expression. From our results, it appears that HC-HA (PBS and Gn) does not affect TGFβ2 expression at both mRNA and protein levels. In summary, HC-HA (PBS) inhibits TGFβ1, but activates TGFβ3 signaling in HCF challenged with TGFβ1 while HC-HA (Gn) activates both TGFβ1 and TGFβ3 signaling.

Figure 43:
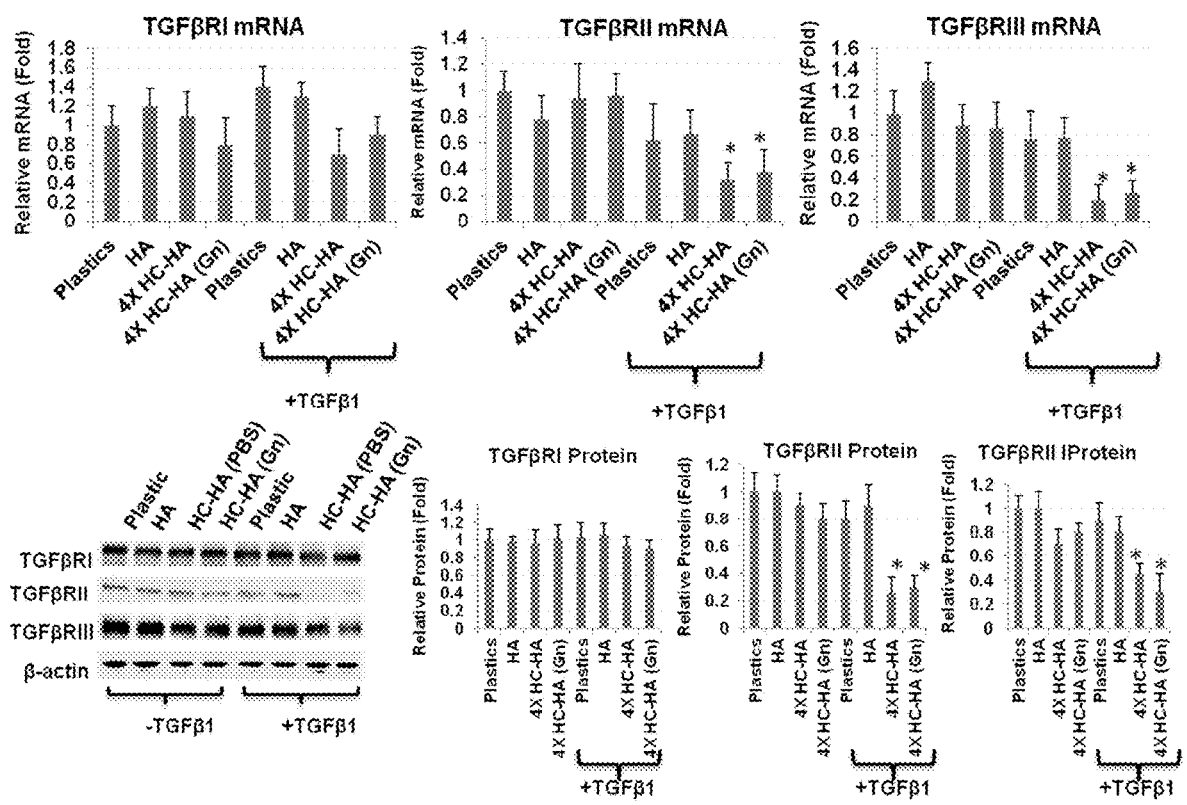
FIG. 43 exemplifies both soluble HC-HA (PBS) and insoluble HC-HA (GnHC1) inhibit TGFβR2 and TGFβR3 expression under challenge of TGFβ1. A, TGFβR mRNA expression. B, TGFβR protein expression.

In the plastic control, TGFβII mRNA was upregulated by 8-fold under TGFβ challenge (FIG. 43). TGFβII and TGFβIII receptor mRNA was upregulated by HC-HA (PBS and Gn) by 2- to 8-fold respectively in serum-free condition, but completely inhibited under TGFβ1 challenge. The same result is noted for HA as well. Corresponding protein expression of TGFβII and TGFβIII was downregulated by 3- and 3-, and 2- and 3-fold respectively when HCF cultured on HC-HA (PBS and Gn respectively) were challenged by TGFβ. Under this situation, these protein expression was not changed by HA. Such downregulation may partially explain the mechanism of the anti-inflammatory and anti-scaring effect by AM. In summary, mRNA expression of TGFβR2 and TGFβR3 was increased when HCF were cultured on HA and HC-HA (PBS and Gn).

Figure 44:
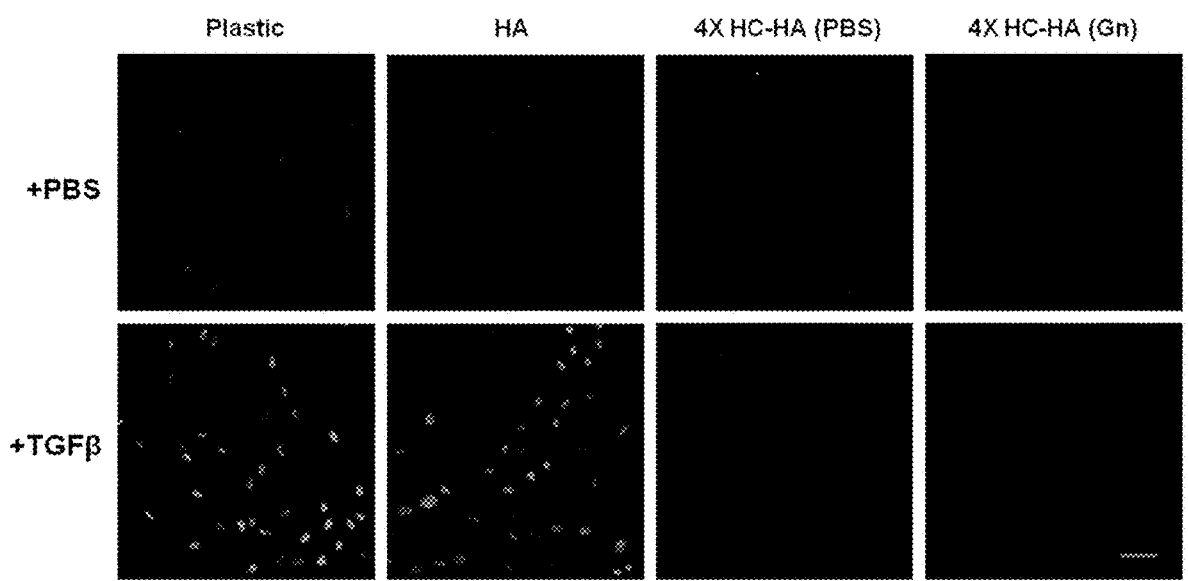
FIG. 44 exemplifies inhibition of nuclear translocation of pSMAD2/3 signaling by HC-HA inhibition of TGFβ1 signaling.

Immunostaining indicated that HC-HA (PBS and Gn) inhibited pSMAD2/3 nuclear translocation in both DMEM/ITS with and without TGFβ1 challenge (FIG. 44). Such an effect was more apparent with TGFβ. This finding further confirmed that suppression of TGFβ1, TGFβII and TGFβRIII was translated into suppression of SMAD-mediated signaling.

Figure 45:
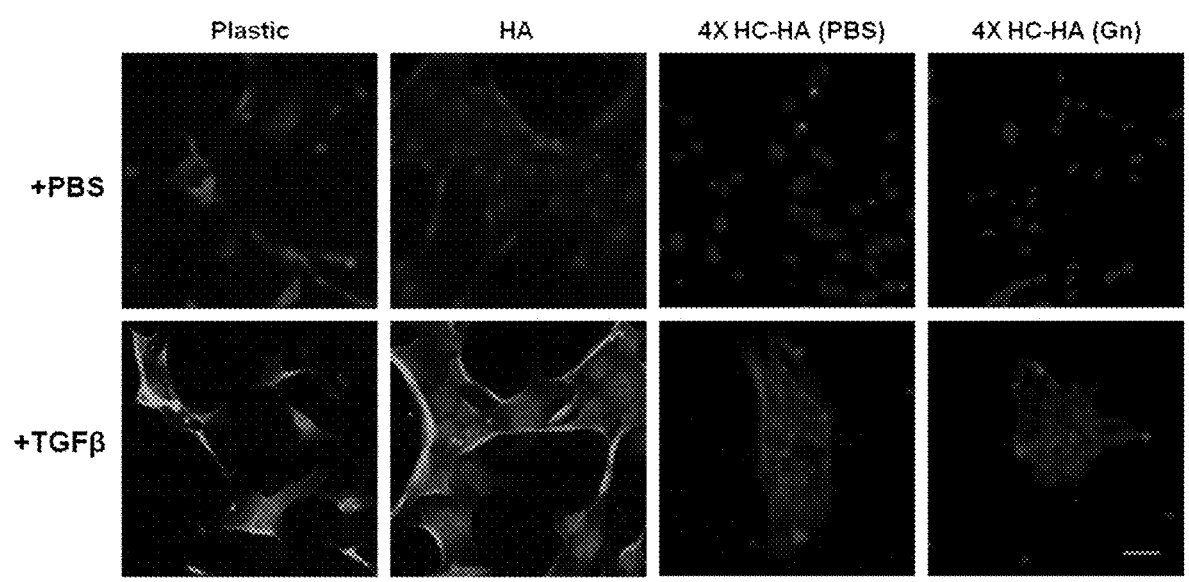
FIG. 45 exemplifies HC-HA inhibition of alpha smooth muscle actin formation.

In addition, immunostaining results indicate that both soluble and insoluble HC-HAs inhibited α-SMA formation after challenge of TGFβ1, further supporting that such inhibition of TGF-β1 signaling by soluble and insoluble HC-HA inhibits differentiation of HCF into myofibroblast with or without addition of TGFβ1 (FIG. 45).

In summary, soluble HC-HA downregulates TGF-β1 but upregulates TGF-β3 expression, while insoluble HC-HA upregulates both TGF-β1 and TGF-β3 expression in HCF under serum-free and TGFβ1 challenging conditions. Because both soluble and insoluble HC-HA downregulated expression of both TGFβII and TGFβRIII, these changes resulted in inhibition of TGFβ signaling as evidenced by the lack of nuclear translocation of pSMAD2/3 and suppression of alpha smooth muscle formation.

Example 34. Effects of HC-HA Complexes on BMP Signaling

In this example, the effect of immobilized HC-HA with additional TGF-β1 on BMP signaling was examined. The activation of BMP signaling via activation of pSMAD1/5/8 also was determined.

BMPs constitute a subgroup of TGFβ superfamily including BMP1-3, BMP3b, BMP4-7, BMP8a, BMP8b, BMP9-15. BMP binds type II receptors (ALK2, ALK3, or ALK6), which activates type I receptor to phosphorylates Smad1, Smad5, and Smad8, resulting in nuclear translocation of pSmad1/5/8 (reviewed in Massague 2000; Herpin, 2007). It was not clear which specific BMPs and BMP receptors are present in HCF, and if so, whether BMP signaling can be activated by HC-HA (PBS and Gn) and additional TGFβ1 when the TGFβ signaling is suppression, and if so, which forms of BMPs and BMP receptors play a major role in controlling BMP signaling and whether such an activation of BMP signaling is via pSMAD1/5/8.

Human corneal fibroblasts were seeded on plastic with or without immobilized HA or HC-HA PBS (4×) or HC-HA Gn (4×) for 48 h, and then treated with or without TGFβ1 for 24 h for mRNA quantitation and determination of pSMAD1/5/8 as described above. For determination of protein of BMP receptors, the cells were treated with or without TGF-β1 for 48 h before collection of protein samples to allow for protein expression. For BMP ELISA, the cells were treated with or without TGF-β1 for 48 h. The supernatants were collected for BMP ELISA. Phase contrast images were taken up to 72 h for various cultures.

The following experiments were performed on the cultures:

1. mRNA semiquantitation for BMPs and their receptors by real-time PCR: used for estimation of mRNA transcript expression of BMP family and their receptors.

2. Determination of α-smooth muscle formation and SMAD1/5/8 signaling by immunostaining: performed to monitor α-smooth muscle formation and SMAD2/3 signaling by immunostaining.

The experimental groups for experiment 1 and 2 are:

---

PBS
PBS + TGF-β1
HA
HA + TGF-β1
4X HC-HA PBS
4X HC-HA PBS + TGF-β1
4X HC-HA Gn
4X HC-HA Gn + TGF-β1

---

3. Quantitation of BMPRs by Western blotting using BMPR1A, BMPR1B and BMPR2 antibodies: used to quantitate protein concentration of BMPR1A, BMPR1B and BMPR2, respectively. The loading sequence was as follows:

| MW marker | Plastic | HA | 4X HC-HA PBS | 4X HC-HA Gn | Plastic + TGF-β1 | HA + TGF-β1 | 4X HC-HA PBS + TGF-β1 | 4X HC-HA Gn + TGF-β1 |
|---|---|---|---|---|---|---|---|---|

4. ELISA for Quantitation of BMPs in the Medium: We used BMP ELISA kits (R&D Systems) to determine BMPs in the medium. The experimental groups for experiment 4 are:

PBS
PBS + TGF-β1
HA
HA + TGF-β1
4X HC-HA PBS
4X HC-HA PBS + TGF-β1
4X HC-HA Gn
4X HC-HAGn + TGF-β1

Results

Figure 46:
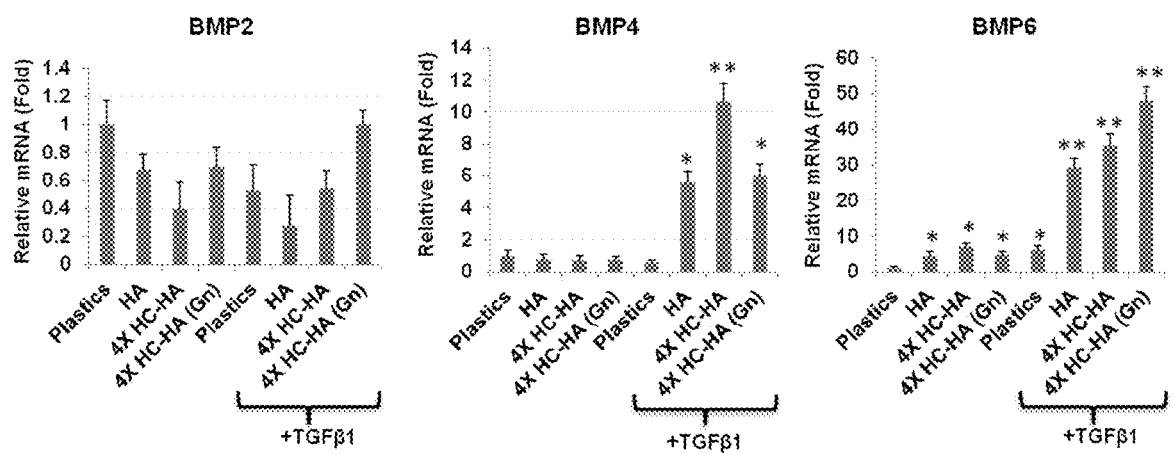
FIG. 46 exemplifies BMP6 transcript was activated by HA and soluble/insoluble HC-HA. Addition of TGFβ1 activates transcript expression of BMP6 on plastic but dramatically activates mRNA expression of BMP4/6 in HCF on HA and both soluble and insoluble HC-HA.

Under the resting state, HA and both HC-HA (PBS) and HC-HA (Gn) activate transcript expression of BMP6 by 7- and 4-fold, respectively (FIG. 46). In the presence of TGFβ1, HA and both HC-HA (PBS) and HC-HA (Gn) activate transcript expression of BMP4 by 6-, 11- and 6-fold, and mRNA expression of BMP6 by 30-, 37- and 46-fold respectively in HCF, indicating that HA and both soluble and insoluble HC-HA can upregulate BMP4/6 expression, while additional TGFβ1 further dramatically upregulated BMP4 and BMP6 signaling. BMP7 and BMP9 were not detected.

Figure 47:
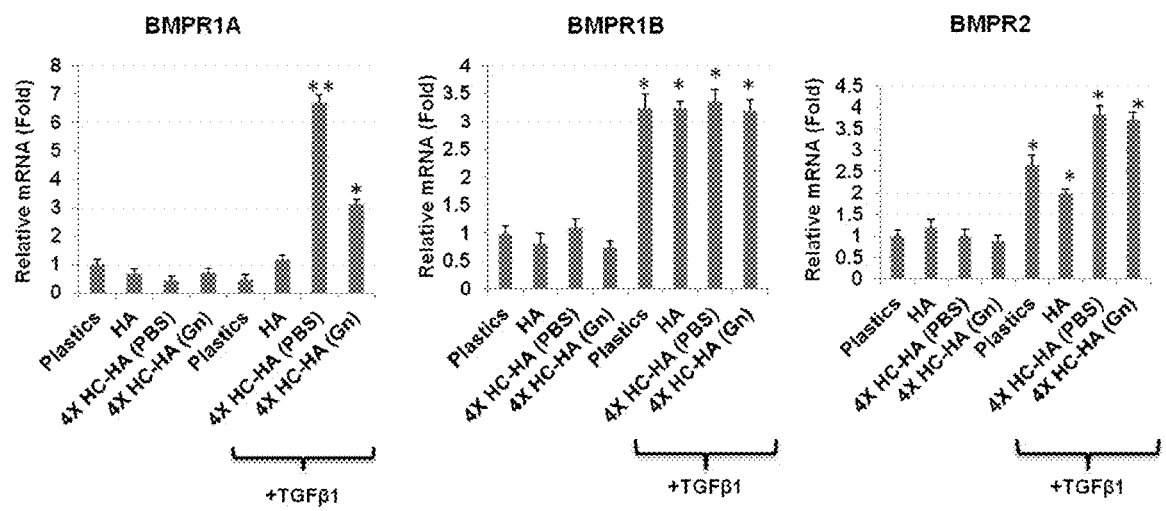
FIG. 47 exemplifies HC-HA but not HA activates transcript expression of BMPR1A in HCF challenged with TGFβ1, while additional TGFβ1 non-specifically activates mRNA expression of BMPR1B and BMPR2 in HCF.

While TGFβ1 itself did not activated transcript expression of BMPR1A, both HC-HA (PBS) and HC-HA (Gn), but not HA activate transcript expression of BMPR1A by 7- and 3-fold respectively in the presence of TGFβ1, indicating that BMPR1A may play a major role in HC-HA+TGFβ1 activated BMP signaling (FIG. 47). In addition, TGFβ1 activates BMPR1B by 3-fold, and BMPR2 by 3-fold, but by 4-fold on plastic with or without HA and both HC-HA (PBS) and HC-HA (Gn), indicating that TGFβ1 itself non-specifically activates mRNA expression of BMPR1B and BMPR2. HC-HA (PBS) or HC-HA (Gn) enhances transcript expression of BMPR2 to 4-fold. BMP-BMPR1A is expected to activate SMAD1/5/8 signaling while BMP-BMPRII activates non-SMAD signaling.

Figure 48:
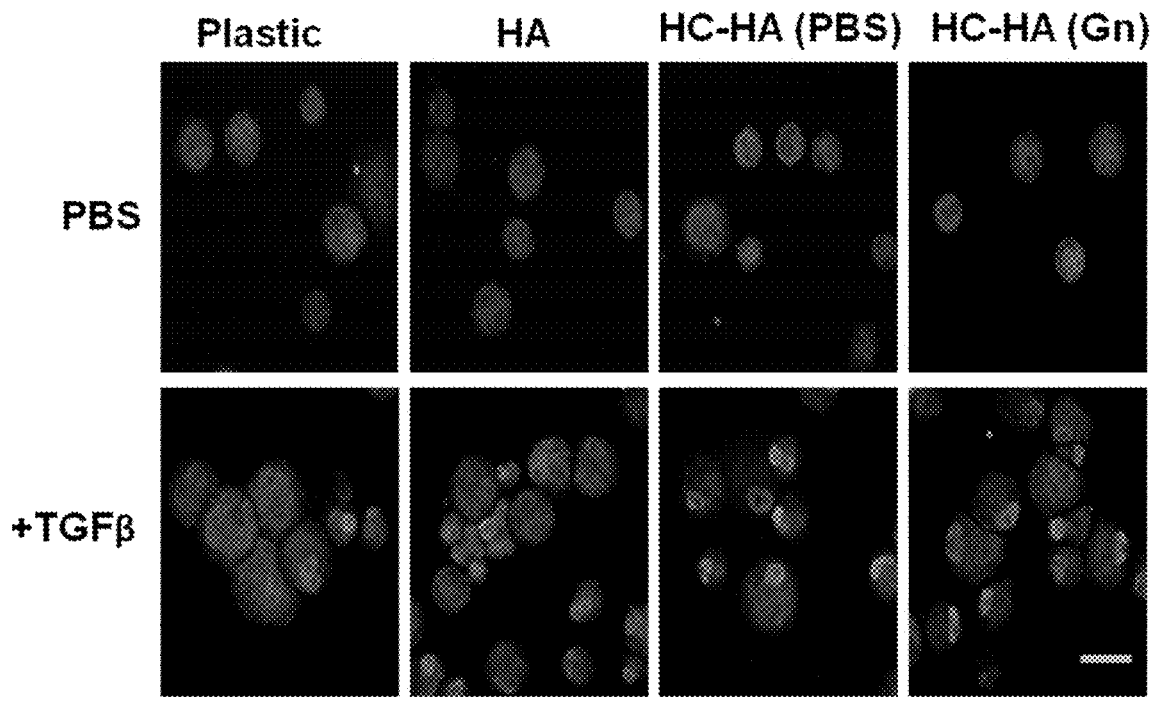
FIG. 48 exemplifies both soluble HC-HA (PBS) and insoluble HC-HA (GnHC1) activates BMP4/6 signaling via pSMAD1/5/8.
Figure 48:
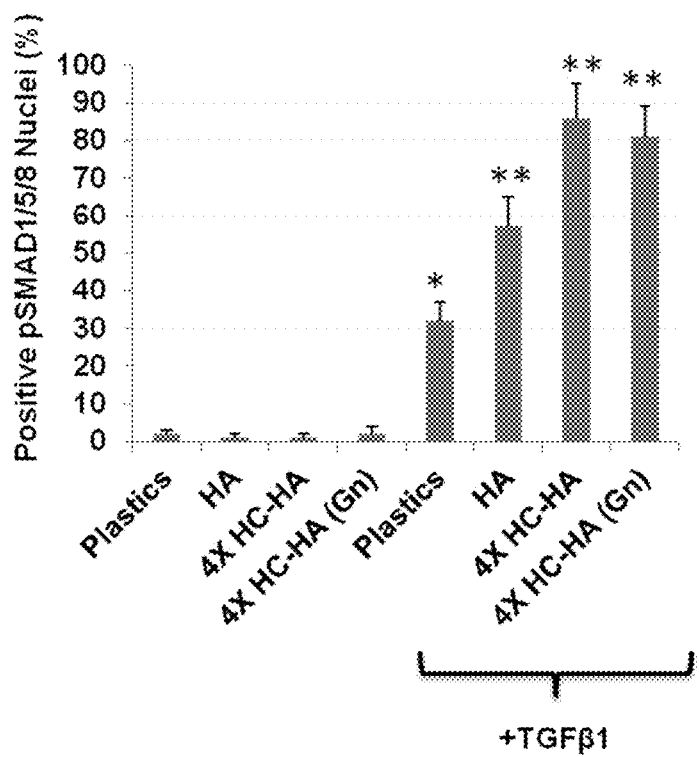

Immunofluorescence results indicate that TGFβ1 itself moderately activates nuclear translocation of pSMAD1/5/8 in HCF despite the substrate used (FIG. 48). HC-HA (PBS and Gn) strongly facilitates activation of BMP4/6 signaling via nuclear translocation of pSMAD1/5/8, as evidenced by more nuclei having pSMAD1/5/8 and a much stronger nuclear staining of pSMAD1/5/8.

Figure 49:
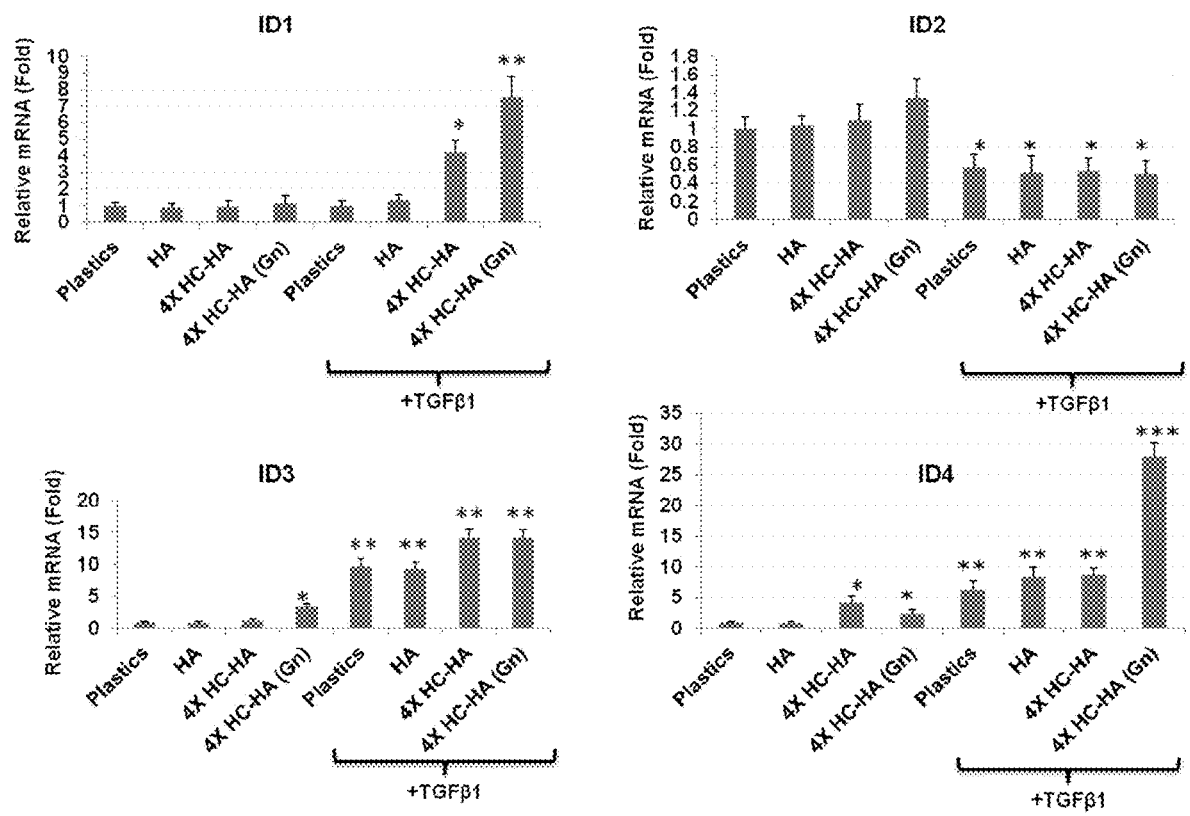
FIG. 49 exemplifies activation of SMAD/1/5/8 resulted in upregulation of its downstream gene, inhibitor of DNA binding 1, 3 and 4 (ID1, ID3 and ID4), downstream targets of BMP signaling.

ID1 is a helix-loop-helix (HLH) protein that can form heterodimers with members of the basic HLH family of transcription factors, a known downstream gene regulated by SMAD1/5/8 signaling. Our results demonstrated that activation of SMAD1/5/8 resulted in 4- and 8-fold upregulation of ID1 mRNA when HCF were cultured on HC-HA (PBS) and HC-HA (Gn) respectively, indicating that SMAD1/5/8 signaling in HCF is indeed activated by HC-HA+TGFβ (FIG. 49). Since ID1 has no DNA binding activity and therefore can inhibit the DNA binding and transcriptional activation ability of basic HLH proteins with which it interacts, we expect that ID1 plays an important role in cell growth, senescence, and differentiation.

Example 35. Effects of HC-HA Complexes on Myofibroblast Differentiation and Reversion of Human Corneal Fibroblasts to Keratocytes or Younger Progenitors Keratocytes, a unique population of neural crest-derived cells embedded in the corneal stroma, express keratan sulfate-containing proteoglycans including cornea-specific keratocan. Keratocan (Kera) is a cornea-specific keratan sulfate proteoglycan (KSPG) in the adult vertebrate eye. It belongs to the small leucine-rich proteoglycan (SLRP) gene family and is one of the major components of extracellular KSPG in the vertebrate corneal stroma. Corneal KSPGs play a pivotal role in matrix assembly, which is accountable for corneal transparency. Lumican constitutes about half of corneal KSPG. Most of the remaining corneal keratan sulfate modifies keratocan. In adult tissues, keratocan is limited to corneal stroma, and keratocan expression is considered a phenotypic marker for keratocytes (Liu et al. (2003) J. Biol Chem. 278(24):21672-7; Carlson et al. (2005) J Biol Chem. 280(27):25541-7). On plastic dishes, human, bovine and rabbit keratocytes lose their characteristic dendritic morphology and keratocan expression when cultured in serum-containing media (Espana et al. (2003) Invest Ophthalmol Vis Sci. 44 (12): 5136-41; Espana et al. (2004) Invest Ophthalmol Vis Sci. 45(9):2985-91). These exposed cells downregulate the expression of keratan sulfate-containing proteoglycans, keratocan and CD34, and upregulate that of chondroitin-dermatan sulfate-containing proteoglycans and α-SMA, indicating that those cells become more differentiated.

Previous studies have shown that human (Espana et al. (2003) Invest Ophthalmol Vis Sci. 44 (12): 5136-41; Espana et al. (2004) Invest Ophthalmol Vis Sci. 45(9):2985-91) and murine (Kawakita et al. (2005) J Biol Chem. 280(29):27085-92) keratocyte can maintain their phenotype without differentiation into α-SMA-expressing myofibroblasts when cultured on the AM stromal surface even when TGF-β is added in a serum-containing medium due to downregulation of the Smad signaling pathway. The amniotic membrane stroma can maintain keratocan expressing in cultures and prevent keratocytes from differentiating into myofibroblasts (Kawakita et al. (2005) J Biol Chem. 280(29):27085-92). The keratocyte maintained a dendritic morphology, continued to express corneal stroma-specific keratocan for at least 5 passages (at 1:2 split), and did not express α-SMA under serum containing conditions or addition of TGFβ1 (Espana et al. (2004) Invest Ophthalmol Vis Sci. 45(9):2985-91). Murine keratocytes can also be expanded on AM for at least 8 passages without losing their normal phenotype and that suppression of Smad-mediated TGFβ signaling pathway is pivotal in maintaining keratocan-expressing phenotype (Kawakita et al. (2005) J Biol Chem. 280(29):27085-92). In this example, it was examined whether immobilized HC-HA can do the same, and if so, whether additional TGFβ1 can affect their outcome.

Results

Figure 50:
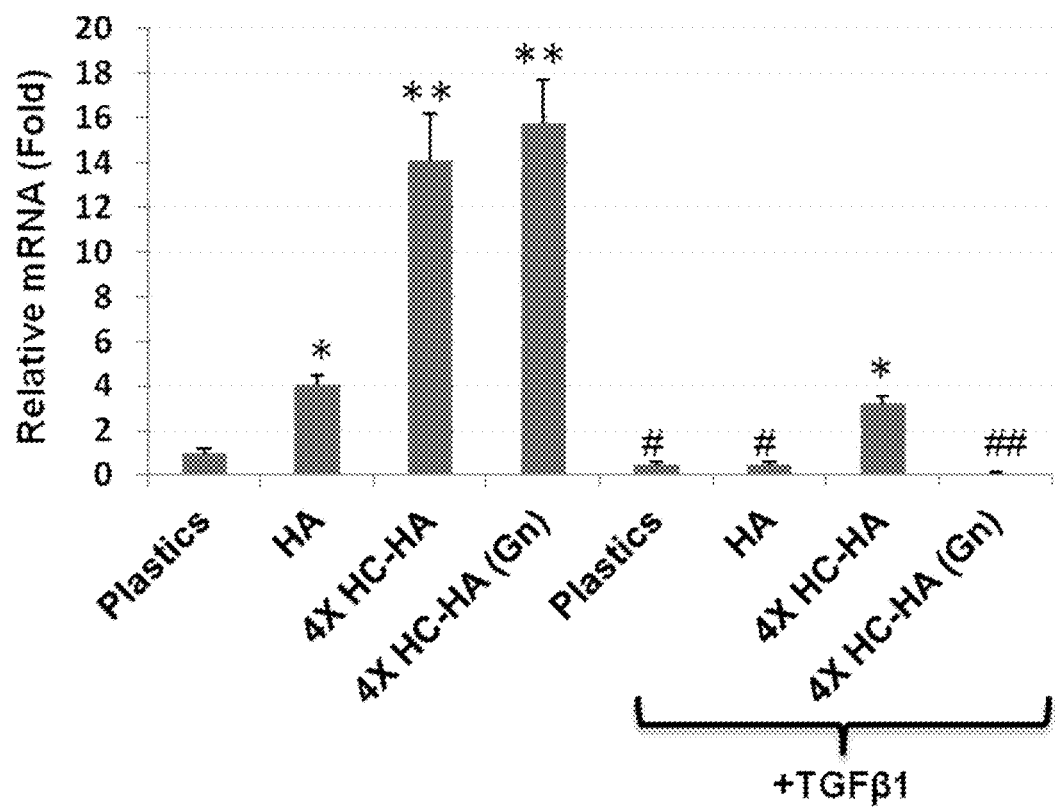
FIG. 50 exemplifies HC-HA (PBS) and HC-HA (GnHC1) promote Keratocan mRNA expression by 14- and 16-fold respectively, which was significantly downregulated by additional TGFβ1.

HA unregulated Keratocan mRNA expression by 4-fold (FIG. 50). Human corneal fibroblasts were seeded on plastics with or without immobilized HA for 48 h, starved without serum for 24 h, and then treated with or without TGFβ1 for 24 h before being harvested for mRNA quantitation and determination of SMAD2/3 signaling. For determination of protein of TGFβ receptors, the cells were treated with or without TGFβ1 for 48 h before collection of protein samples because the protein expression lags behind of mRNA expression. For TGFβ1 ELISA, the cells were treated with or without TGFβ1 for 24 h, and then cultured in the fresh medium for 24 (and 48) h. The supernatants were collected for TGFβ1 ELISA. For TGFβ2 and TGFβ3 ELISA, the cells were treated with or without TGFβ1 for 48 h. The supernatants were collected for TGF-β2 and TGFβ3 ELISA. As expected, immobilized HC-HA promoted mRNA expression of Keratocan by 14- and 16-fold, indicating those HCF are much younger when they were cultured on HC-HA without TGFβ1. After TGFβ1 challenge, the mRNA expression of Keratocan was downregulated dramatically on plastic and HA. However, keratocan expression was still maintained at 3-fold on HC-HA(Soluble, PBS). Expression of keratocan was absent on HC-HA(Insoluble, Gn). We expect that the resultant phenotype on HC-HA (I) should be even more younger than keratocytes.

Figure 51:
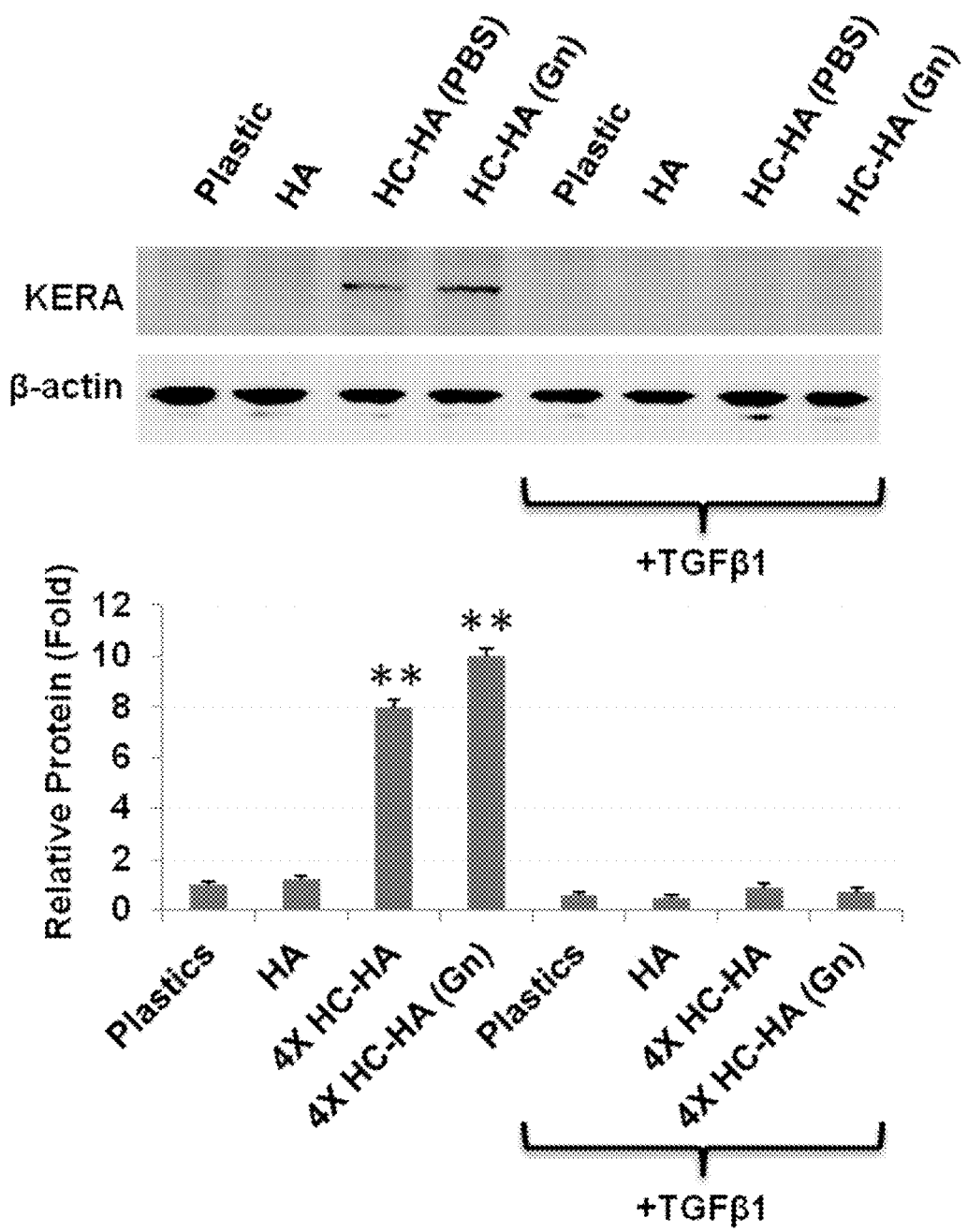
FIG. 51 exemplifies HC-HA (PBS) and HC-HA (GnHC1) promote keratocan protein expression.

Correspondingly, immobilized HC-HA(I/S) promoted protein levels of Keratocan by 8- and 10-fold, indicating those HCF are indeed reverted to keratocytes when they were cultured on HC-HA(S/I) (FIG. 51). We did not see any corresponding keratocan protein expression by other treatments tested, including HA (4-fold increase of keratocan mRNA) and 4× HC-HA (PBS) (3-fold increase of keratocan mRNA), indicating such a moderate increase of keratocan mRNA was not enough to promote corresponding protein expression of keratocan.

Example 36. Effects of HC-HA Complexes on ESC Marker Expression in HCF

Example 35 showed a strong evidence that HCF was not only prevented from undergoing myofibroblast differentiation under the challenge by exogenous TGFβ1 but also reverted back to keratocytes with expression of keratocan with or without exogenous TGFβ 1. We thus examined whether HCF could be further reprogrammed into younger progenitors, especially when seeded on immobilized HC-HA(insoluble, GnHC1) with exogenous TGFβ1, which has been shown to suppress TGF-β signaling, promote BMP signaling, but turning off keratocan expression. We examine the expression of a number of markers found in ESC and endothelial progenitors and pericytes, which as we have recently reported to be found in angiogenesis progenitors. To further look into the potential reprogramming of HCF under these conditions modulated by HC-HA, we also examined expression of the four key transcription factors, i.e., Sox2, Oct4, c-Myc, and KLF4, which have been reported to play a key role of reprogramming adult differentiated fibroblasts into iPSCs.

Results

Figure 52:
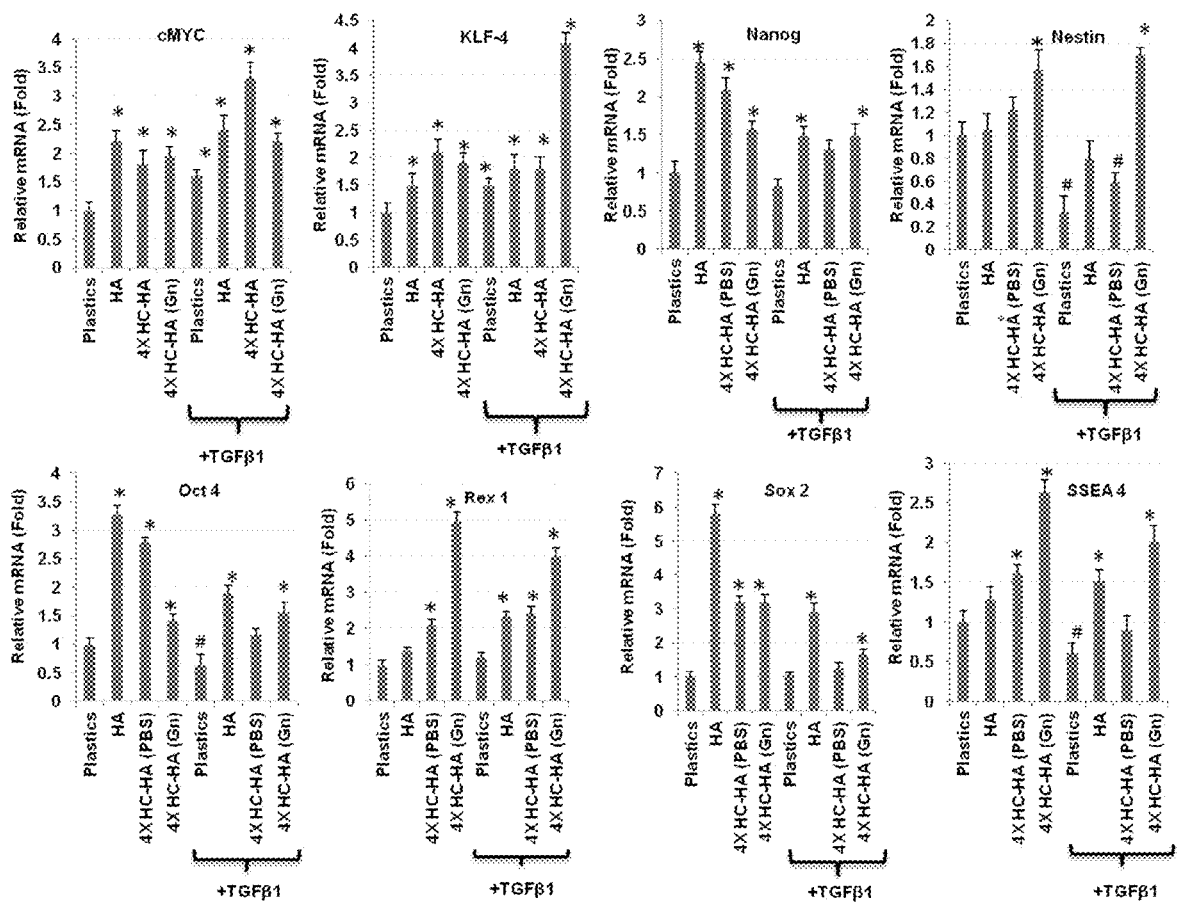
FIG. 52 exemplifies HCF express more ESC markers on 4× HC-HA (PBS and insoluble HC-HA (GnHC1) than on plastic and when the cells were challenged with addition of TGFβ1.

Examination of gene expression was performed on the HCF cultures described above in Example 35. The results indicated that HCF expressed more (2- to 6-fold) ESC markers such as cMYC, KLF-4, Nanog, nestin, Oct4, Rex-1, SOX-2 and SSEA-4 on 4× HC-HA, and 2- to 4-fold more ESC markers even when HCF were challenged by exogenous TGF-β1 when compared to the plastic control (p<0.05, n=3) (FIG. 52). These results suggest that HC-HA, especially HC-HA (insoluble), can reprogram HCF into younger progenitors.

Example 37. HC-HA In Solution Inhibits Osteogenesis by Affecting MC3T3-E1 Cell Viability and Differentiation In this example, we assessed the effect of HC-HA (soluble fraction) and HA in solution on the viability and differentiation of undifferentiated MC3T3-E1 cells. MC3T3-E1 is an osteoblastic cell line established from C57BL/6 mouse. MC3T3-E1 cells have the capacity to differentiate into osteoblasts and osteocytes and have been demonstrated to form calcified bone tissue in vitro.

Figure 53:
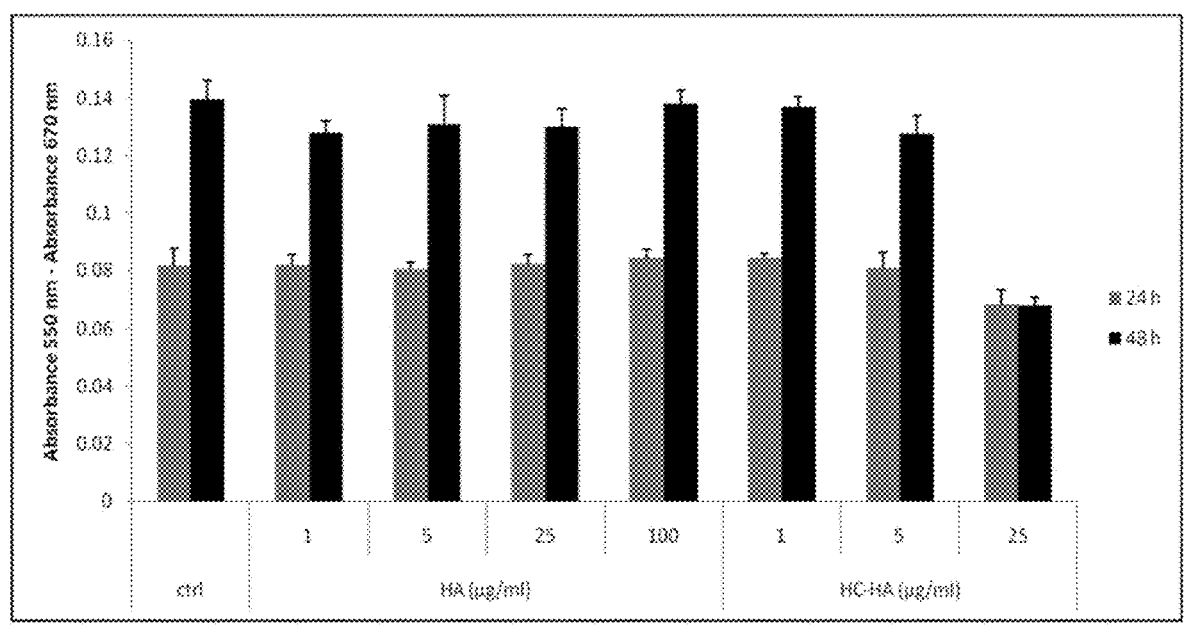
FIG. 53 exemplifies cell viability of MC3T3-E1 cells as measured by MTT.

MC3T3-E1 cells were cultured in the complete medium (α-MEM, 10% FBS, 100 units/ml Penicillin, and 100 µg/ml streptomycin) with various concentrations of HA (1, 5, 25, 100 µg/ml) or HC-HA (1, 5, 25 µg/ml), with PBS as a vehicle control, and seeded in plastic cell culture treated 96 wells at $1.6 \times 10^4$ cells/ml. Cell viability was measured by MTT assays. The result showed that absorbance at 550 nm increased from 24 to 48 h for all conditions except for 25 µg/ml HC-HA, suggesting that cell proliferation proceeds normally in the control, HA from 1 to 100 µg/ml, and HC-HA from 1 to 5 µg/ml (FIG. 53).

Figure 54:
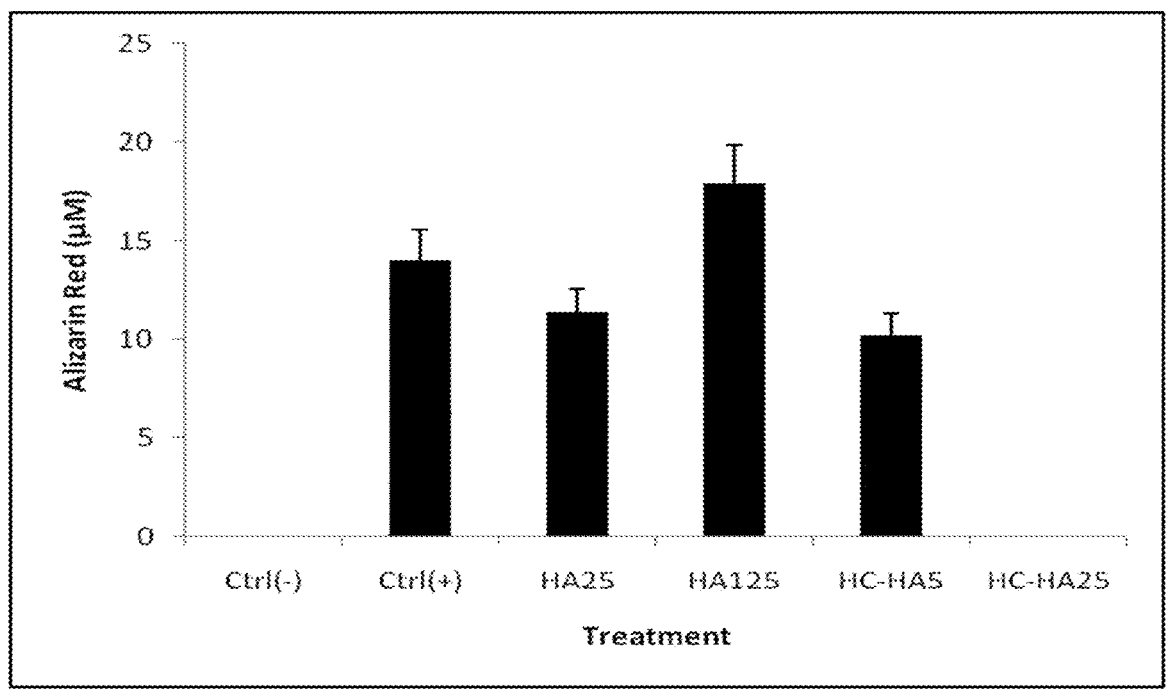
FIG. 54 exemplifies mineralization of MC3T3-E1 cells as measured by Alizarin Red Staining.

Next, the effect of HC-HA or HA on MC3T3-E1 differentiation into osteoblasts was examined. MC3T3-E1 cells were re-suspended in non-induction medium ($1.6 \times 10^5$/ml) and seeded in 96 wells and incubated until confluence. The non-induction medium was removed and induction medium 1 (complete medium with 0.2 mM ascorbic acid 2-phosphate and 10 mM glycerol 2-phospahte, manufacturer's instruction for in vitro osteogenesis assay kit, cat # ECM810, Millipore) was added. After 12 days of differentiation, Alizarin Red staining was used to measure and quantify osteoblast mineralization. The result showed that AR was indeed promoted by the induction medium in the control. Consistent with a prior report (Kawano (2011) *Biochemical and Biophysical Research Communications.* 405: 575-580), 100 µg/ml HA but not 25 µg/ml HA further promoted AR staining when compared to the control. In contrast, AR staining was not reduced by 5 µg/ml HC-HA (p=0.11), but significantly reduced by 25 µg/ml HC-HA (p=0.00002) (FIG. 54). These results suggested that increasing HC-HA concentrations during induction also reduced bone formation.

Example 38. Dose Dependent Response for HC-HA and AMP on Osteoblast Differentiation Using MC3T3-E1 Model System Previous findings showed that HC-HA and AMP dose-dependently inhibit osteoclast differentiation from RAW264.7 cells induced by RANKL (see International PCT Publication No. WO 2012/149486). AMP (Amniotic Membrane Powder) is a lyophilized and then pulverized form of the amniotic membrane. In this example, IC50 of HC-HA and AMP for osteogenesis was determined and compares to that for osteoclastogenesis.

Alkaline phosphatase (ALP) assay and Alizarin Red Staining (AR-S) are two assays used to measure differentiation of MC3T3-E1 cells. ALP is excreted by osteoblasts and has long been a widely recognized biochemical marker for osteoblast activity (Sabokbar (1994) *Bone Miner.* 27(1): 57-67), and hence serves as an early marker for osteogenesis. Alizarin Red (AR) dye forms a chelate with calcium and hence AR-S is used to visualize mineralization. Because ARS dye can be easily extracted, it can also be converted into quantitation of mineralization (Gregory et al. (2005) *Analytical Biochemistry* 329: 77-84).

Part A
Experimental Design:
MC3T3-E1 Culture

The model system of MC3T3-E1 cells from Millipore In Vitro Osteogenesis Kit which consists of the base medium of α-MEM (Invitrogen, Cat. # ICM810) containing 10% FBS, 100 units/ml Penicillin, and 100 µg/ml streptomycin, was employed. Cells were seeded at 50,000 cells/cm$^2$ and cultured in 95% air and 5% $CO_2$ at 37.0° C. in a 100 mL cell culture dish and passaged before confluence. Once sufficient cell numbers were obtained then cells were seeded at $1.6 \times 10^5$ cells/ml in 96-well culture dish with 100 µL volume of the base medium per well (52 wells). Each concentration was done in 4 wells with 2 wells for ALP assay and 2 wells for AR-S staining. Cells were cultured at 37° C. in 5% $CO_2$ humidified air and the medium was changed every 48-72 hrs until confluence.

The dosing range to be investigated was derived from the preliminary data performed in osteoblast differentiation (see above) as well as the dose-response curves for HC-HA and AMP against osteoclast differentiation. Because HC-HA at 25 µg/ml significantly inhibited MC3T3-E1 cell proliferation and differentiation into osteoblasts and completely inhibited osteoclast differentiation from RAW264.7 cells (see International PCT Publication No. WO 2012/149486), it was selected as the highest concentration. Because 5 µg/ml HC-HA showed less than 50% inhibition, suggesting that the IC50 of HC-HA for osteoblast differentiation might be higher than the IC50 in P-214, HC-HA concentrations in the range of 0.1, 0.5, 1, 5, 10, and 25 µg/ml were selected. Based on preliminary data on HC-HA, AMP at the following concentrations: 1, 5, 25, 125, 250 µg/ml was selected. Because the ALP activity peaks at Day 12 of differentiation in MC3T3-E1 cells (Maeda (2004) *Journal of Cellular Biochemistry* 92:458-471; Wang, (2008) *J Dent Res.* 87(7): 650-654), we chose to study osteogenesis at Day 12 after induction.

Upon confluence, the medium from each well was replaced with 100 µL of Osteogenesis Induction Medium #1. Osteogenesis Induction Medium contains 0.2 mM ascorbic acid 2-phosphate and 10 mM β-glycerolphosphate (in vitro osteogenesis assay kit, cat # ECM810, Millipore). 10 µL of working solutions of AMP and HC-HA were added into the Induction Medium #1. (Stock solutions of AMP (AMP-4; Lot # CB102971, see International PCT Publication No. WO 2012/149486) (5 mg/ml) and HC-HA (He et al. (2009) *J. Biol. Chem.* 284(30): 20136-20146) (250 µg/ml) in PBS were made and diluted accordingly with appropriate culture medium (Osteogenesis Induction Medium #1) for each experimental concentration (0.1, 0.5, 1, 5, 10, and 25 µg/ml for HC-HA and 1, 5, 25, 125, 250 µg/ml for AMP)). The medium was changed every 3 days.

On Differentiation Day 6, replace medium with 100 µL fresh Osteogenesis Induction Medium #2 containing ascorbic acid, β-glycerolphosphate, and melatonin. 10 µL of working solutions of AMP and HC-HA were added into the 100 µL the Osteogenesis Induction Medium #2(0.2 mM ascorbic acid 2-phosphate, 10 mM glycerol 2-phosphate and 50 nM Melatonin Solution, manufacturer's instruction for in vitro osteogenesis assay kit, cat # ECM810, Millipore) to make the final experimental concentrations in culture wells. The medium was changed every 2-3 days. Samples were then assayed with ALP assay (H-156) and ARS Staining Assay following the manufacturer's instructions (In Vitro Osteogenesis Assay Kit, (Catalog # ECM810)).

Alizarin Red S Staining

The culture medium from each well was aspirated without disturbing the cells. The cells were washed 1× with 200 µL PBS. The cells were fixed by adding 100 µL 70% ethanol and incubating at R.T. for 15 min. Fixative was then removed and the cells were rinsed 3× (5 min each) with an excess of distilled water without disturbing the cell monolayer. Water was removed and 100 µL/well Alizarin Red Stain Solution was added. The wells were incubated at R.T. for 1 h. Excess dye was removed, and the cells were washed 4× with deionized water (gentle rocking for 5 min with each wash). 0.1-0.15 mL water was added to each well to prevent cells from drying. The stained cells were photographed under microscope.

Excess water was then removed from each well. 100 µL 10% acetic acid was added to each well and incubated with shaking for 30 min. The loosely attached monolayer was carefully removed with cell scraper and the cells and acetic acid were transferred to a 1.5 mL microcentrifuge tube and vortexed vigorously for 30 min. The samples were heated to 85° C. for 10 min, then transfer to ice for 5 min to cool the tubes. The slurry in the tubes was centrifuged at 20,000×g for 15 min. 400 µL of supernatant was removed and transferred to a new 1.5 mL microcentrifuge tube. The pH was neutralized with 150 µL 10% ammonium hydroxide to within range of 4.1-4.5. 150 µL of each sample was added to a transparent bottom 96-well plate and read at OD405. A plot of Alizarin Red concentration vs. OD405 was made.

ALP Assay (BioAssay Systems: QuantiChrom ALP Assay Kit, Cat #: DALP-250)

Cells in each well (96-well plate) were washed with PBS and lysed in 100 µL 0.2% Triton X-100 in distilled water by shaking for 20 min at R.T. 200 µL distilled water and 200 µL Calibrator solution (supplied by kit) were transferred into separate wells for controls. 50 µL samples were transferred into separate wells. 150 µL Working solution (200 µL Assay Buffer, 5 µL Mg Acetate (5 mM), 2 µL pNPP liquid substrate (10 mM)) was added to the sample wells (final reaction volume was 200 µL). The plate was tapped briefly to mix. $OD_{405}$ was read at 0 min and 4 min on plate reader.

Results
Phase Contrast Microscopy

The negative control maintained a hexagonal shape through 13 days of induction (FIG. 55). The monolayer was smoother than the positive control, suggesting that more cells or more pile up of cells occurred in the latter. Cells in the positive control became fusiform in shape after beginning of induction. With more time, a spindle-like ring developed along the edge (~2-3 mm away) of the plastic culture around the 4$^{th}$ day of induction.

Figure 55A:
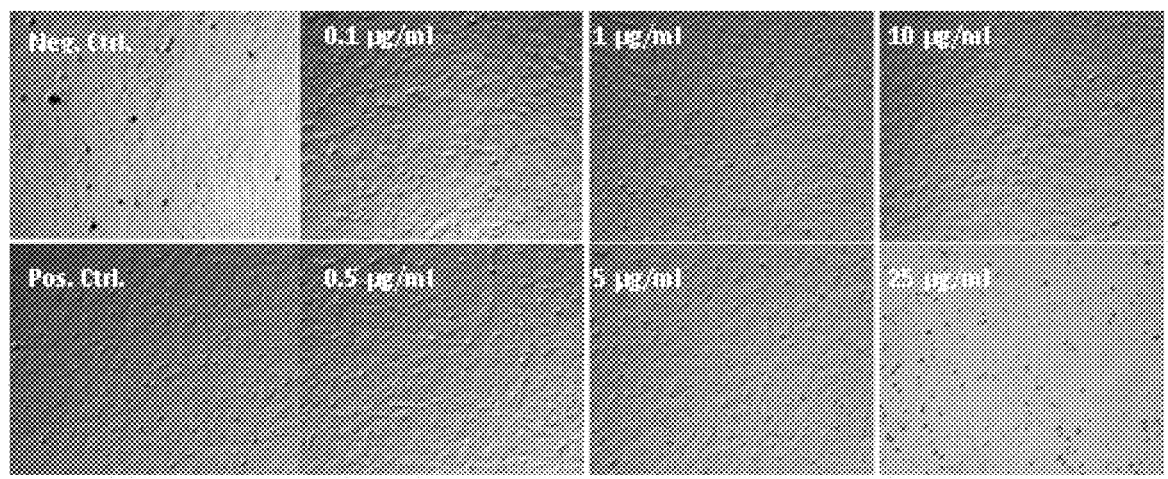
FIG. 55A-B exemplifies morphology of MC3T3-E1 cells treated with HC-HA (A) or AMP (B) on Day 13 of induction.

From 0.1 µg/ml to 10 µg/ml of HC-HA, the cell monolayer did not differ from that of the positive control, suggesting that HC-HA at these concentrations did not negatively affect the induction (FIG. 55A). Like the positive control, cells also developed a fusiform shape and the monolayer developed a spindle-like ring. However, at 25 µg/ml, a dramatic decrease in cell density and change in cell morphology was observed on D13 of induction.

Figure 55B:
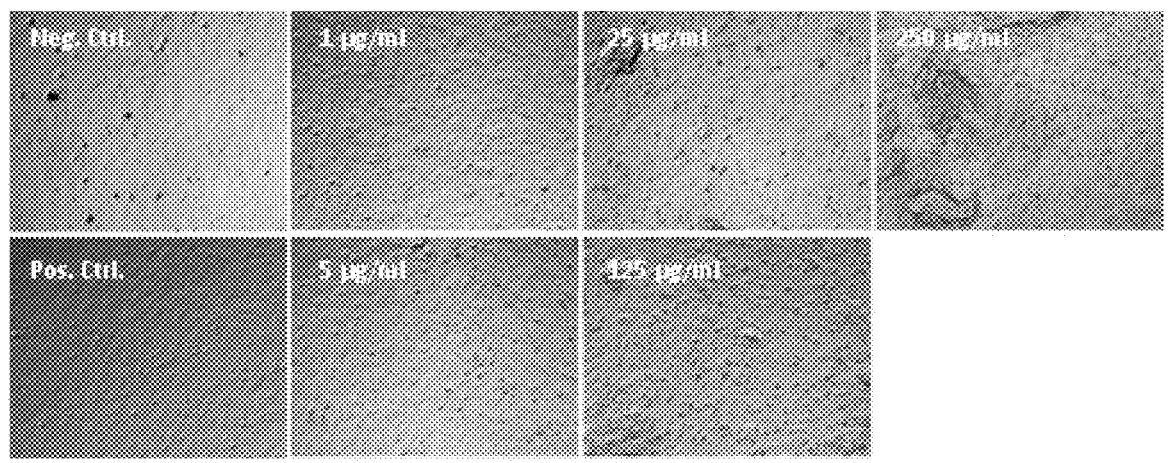

At concentrations above 25 µg/ml, AMP deposited particles that settled on the monolayer (FIG. 55B). Because AMP concentration was replenished after each medium change, AMP deposit on top the monolayer increased through induction period. Treatment with AMP below 125 µg/ml did not affect cell morphology as cells also developed fusiform shapes with spindle rings, suggesting that AMP did not negatively influence induction. At concentrations above 125 µg/ml, AMP particle density increased to the extent that obscured visual observation of spindle ring formation. However, cell density and morphology remained unchanged from that of the positive controls, also confirming that AMP did not negatively affect induction.

Alizarin Red Staining

The negative control yielded a blue-gray background color with parts of the monolayer showing a light pink. In contrast, the positive control yielded a rose pink background (FIG. 56).

Figure 56A:
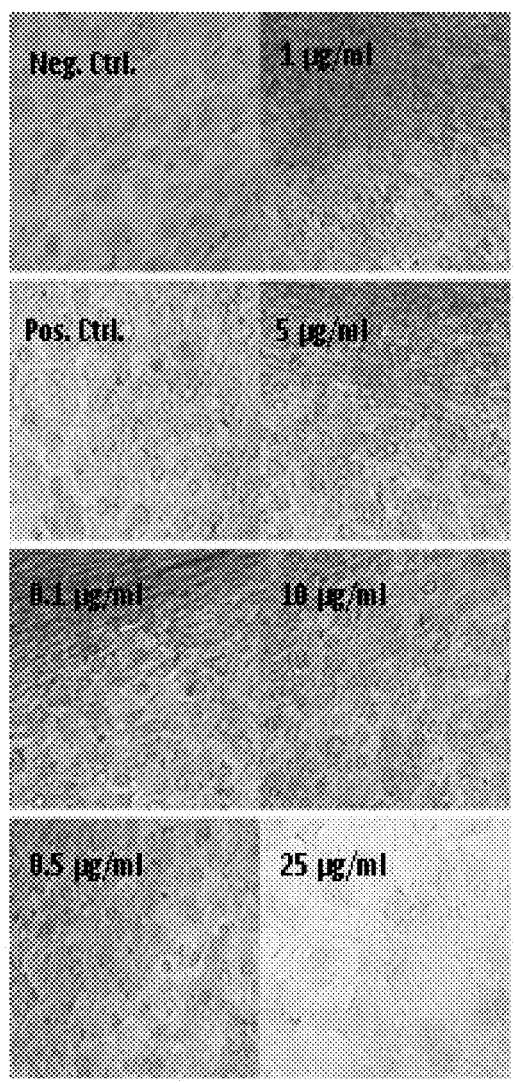
FIG. 56A-B exemplifies Alizarin Red staining of MC3T3-E1 cells treated with HC-HA (A) or AMP (B) on day 13 of induction.

0.1 µg/ml HC-HA yielded a rust red color with the visible spindle ring staining red-brown, which was dramatically different from that of the positive control (FIG. 56A). This trend continued from 0.5 µg/ml to 1 µg/ml with a slight lightening of color at 10 µg/ml, suggesting that the mineralization was maintained from 0.1 to 5 ug/ml and that there might be a dose-dependent relationship between 0 and 0.1 ug/ml. At 25 µg/ml HC-HA, the rust red background disappeared and returned to a light purple-pink with noticeable white gaps in between the cell junction.

Figure 56B:
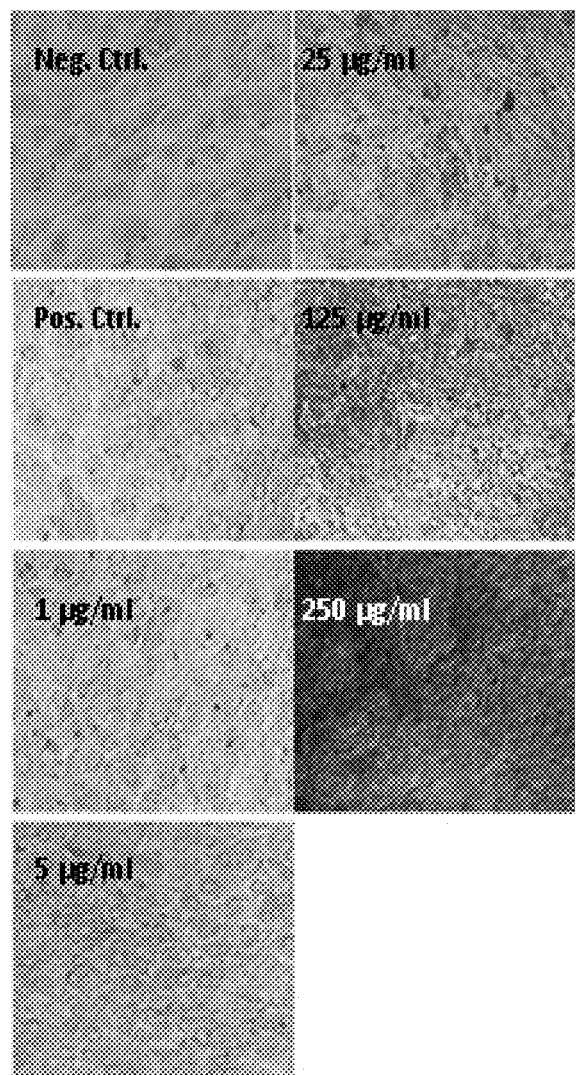

AMP at 1 µg/ml to 125 µg/ml, yielded a dose dependent change of color from a lighter rust brown (1 µg/ml), which appeared to be lighter than 0.1 ug/ml HC-HA, suggesting that the dosing response was more gradual, to a rust red background (5 µg/ml & 25 µg/ml), red-brown (125 µg/ml), and dramatically increased to dark red-brown at 250 µg/ml (FIG. 56B). It is noted that AMP particles found on the top of cell monolayers treated with more than 5 µg/ml of AMP, and the particle size was smaller than the cell itself, and appeared to match the color of the stained background.

Figure 57A:
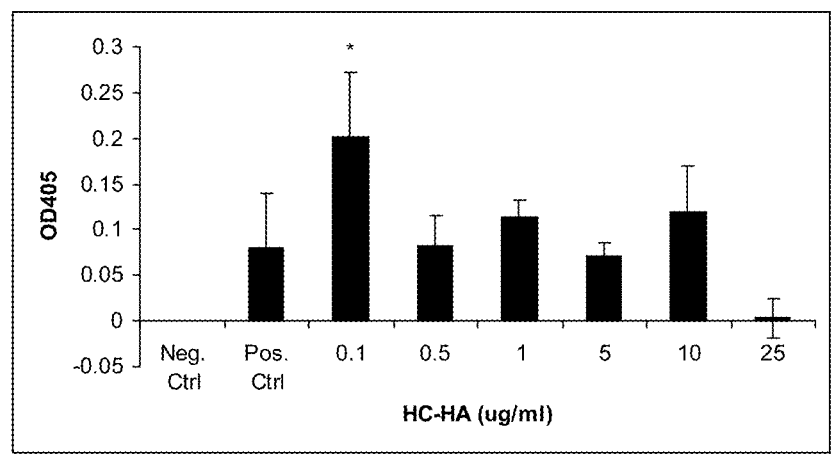
FIG. 57A-B exemplifies quantitative analysis of ARS staining of MC3T3-E1 cells treated with HC-HA (A) or AMP (B) on day 13 of induction.
Figure 57B:
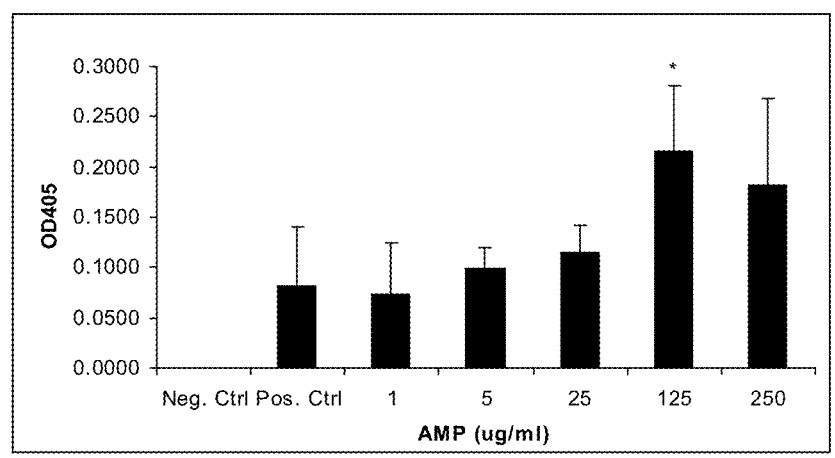

By quantitative analysis of OD value, ARS staining with 0.1 µg/ml HC-HA treatment increased 3× from positive control with statistical significance ($p<0.05$) (FIG. 57A). Some variation in concentrations 0.1 µg/ml to 10 µg/ml was observed, which may be attributed to small sample size (N=2). A dramatic decrease OD value at 25 µg/ml HC-HA treatment was observed. For AMP, treatment with 125 µg/ml of AMP more than doubled the amount of mineralization from positive control and was statistically significant ($p<0.05$) (FIG. 57B). A small decrease in OD value from the positive control was seen in 1 µg/ml AMP, and from 1 µg/ml to 25 µg/ml, there was a small dose dependent increase in OD values. $OD_{405}$ decreased in 250 µg/ml AMP compared to 125 µg/ml. Some variation in may be attributed to small sample size (N=2).

ALP Staining

In both AM derivatives group, the negative control showed 5-fold more ALP activity than the positive control, which could have occurred from loss of sample in the negative control, which decreased the sample size (FIG. 58). The smaller sample size contributed to the standard deviation value being 8× higher for the negative control than the positive control, and this much larger variation could contribute to the increase.

Figure 58A:
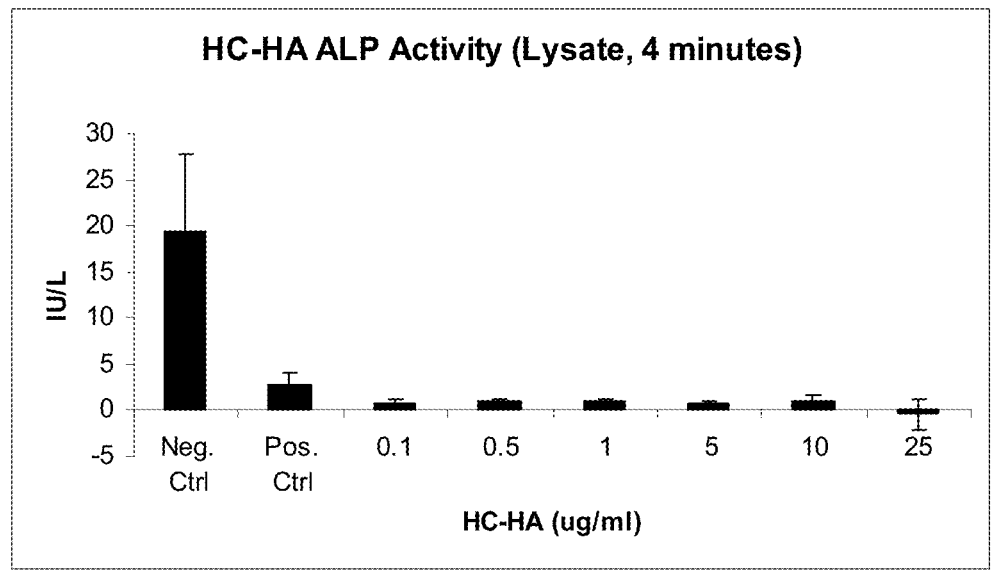
FIG. 58A-B exemplifies ALP activity (IU/L) of HC-HA (A) and AMP (B) treated cells on day 13 of induction.

Treatment of induced MC3T3-E1 with any amount of HC-HA decreased ALP activity compared to the positive and negative control (FIG. 58A). ALP activity varied between the different concentration groups until 25 µg/ml where ALP activity significantly dropped. It is worthwhile to note that there was very little variation from the mean in each of the experimental groups and the positive control.

Figure 58B:
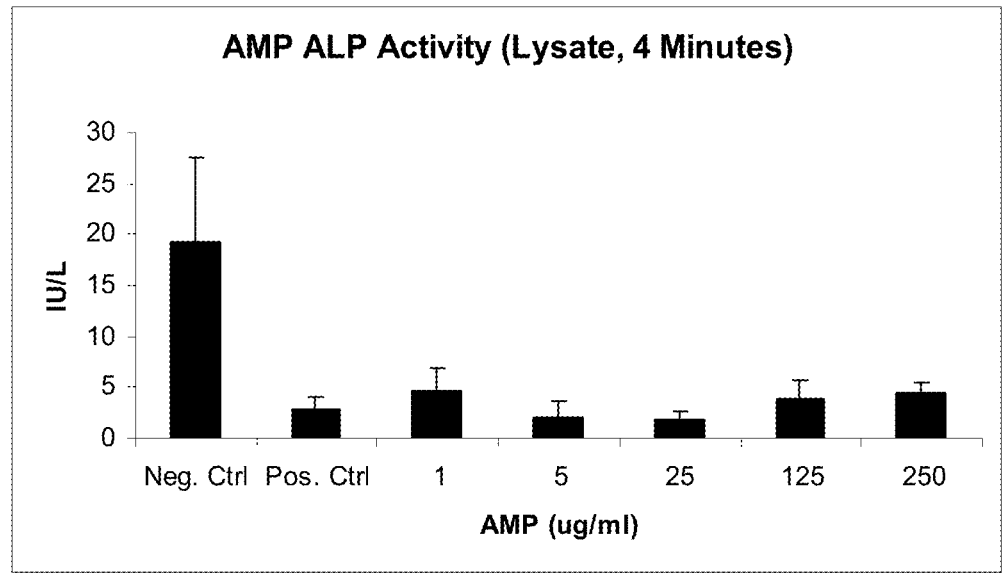

At 1 µg/ml, ALP activity was almost 4-fold higher than the positive control (FIG. 58B). This phenomenon was blocked at 5 µg/ml and 25 µg/ml with ALP activity decreased almost 3× from the positive control. Increasing the concentration to 125 µg/ml to 250 µg/ml restored ALP activity to levels close to 1 µg/ml. It thus appeared that ALP activity was not congruent with the amount of mineralization.

Results Summary

Compared to the negative control, the positive control exhibited more fusiform cells and formed "ring" around the edge of the plastic well (FIG. 55A), a change of color by alizarin staining (FIG. 56A), and a detectable but not significant change of $OD_{405}$ (FIG. 57A). Previously, MC3T3-E1 cells seeded at $5\times10^4$ cells/35 mm plastic dish also revealed formation of layered collagen fibrils after day 4, layered fibrils by day 18, and formation of nodular regions by day 21 of induction. (Sudo (1983) *J. Cell. Biol.* 96: 191-198). This prior study did not note the same ring formation as we observed. [Alternatively, they may interpret the ring as layered collagen fibril. If this were the case, the ring area should be prone for mineralization.]

Alizarin red staining has been described as a crimson red color in the literature to signify mineralization. Mineralization and osteoblastic nodules were described to be stained a deep red and the intensity of color increased with mineralization (Wang, (2006) *Biotechnol. Prog.* 22(6):1697-701; Zhao, 2007). ARS staining is read at 405 nm, which corresponds to a violet color in the visible spectrum. Unlike our results, color photographs of ARS staining of MC3T3-E1 mineralization from published data did not show a rust-red or red-brown color in the monolayer. The darker color in our results indicates more ARS staining and thus more osteogenesis compared with published results. The amount of OD change in ARS staining and quantitation varied depending on the culture conditions and cell type. Human mesenchymal stem cells (hMSCs) cultured in 6-well (10 cm²/well) for 30 days attained an increase from $OD_{405}$ of 0.5 to 4 (Gregory et al. (2005) *Analytical Biochemistry* 329: 77-84). MC3T3-E1 cells cultured for 28 days (α-MEM, ascorbic acid, (3-glycerolphosphate) in 24-well plates attained an OD of 0.6. However, Day 16 and Day 26 OD were much lower than Day 28 at below 0.05 and 0.2, respectively (Burkhardt (2006) University of Basel, Master Thesis). The lack of dramatic color change in the positive control might be due to the time of D13, which was too short for ARS although it is optimal for ALP.

0.1 µg/ml HC-HA also induced "ring change" (FIG. 55A), a clear increase of color (FIG. 56A), and 3× higher OD value than the positive control ($p<0.05$) (FIG. 57A), suggesting that HC-HA at the lower dose promotes mineralization and that a dose-response curve exists between 0 and 0.1 ug/ml. HC-HA from 0.5 to 10 µg/ml also showed "rings" (FIG. 55A), maintained the same color as 0.1 ug/ml (FIG. 56A), and yielded $OD_{405}$ without a statistical significance. HC-HA at 25 µg/ml decreased cell density, changed the cell morphology, lost "ring" (FIG. 55A), did not yield any color change (resembling the negative control) (FIG. 56A), and generated negligible $OD_{405}$ (like the negative control).

AMP from 25 µg/ml left particles (FIG. 55B), from 1 µg/ml increased the color with a positive dose-responsive relationship (FIG. 56B), but $OD_{405}$ showed an increase that was not statistically significant until 125 µg/ml AMP ($p<0.05$), and then declined at 250 µg/ml, which was not consistent with the color change. Unlike HC-HA, AMP at the higher dose did not cause any ill effects on cell morphology.

Part B

The Alizarin Red Staining method was then improved by increasing the sample size and incorporating the methodology with Gregory et al. ((2005) *Analytical Biochemistry* 329: 77-84) used for Alizarin staining of human MSC and other methods known in the art. A comparison of the method of Gregory et al, our previous method described above, and the new method outlined in this example is provided in the table below. Previous studies showed that MC3T3-E1 differentiation under induction can be subdivided into three stages, i.e., proliferation (day 1 to 9), ECM formation (day 9 to day 16), and mineralization (deposit minerals in formed ECM) (day 16+). (Quarles et al. (1992) *Bone Miner Res.* 7(6):683-92; Hong et al. (2010) *Exp Cell Res.* 316(14):2291-300). To compare studies from different groups, it was thus important to time the event starting from confluence as Day 0.

TABLE 5

| | Gregory et al. 2005 | Previous Method | New Extraction Method |
|---|---|---|---|
| Cell Type | Human MSC | MC3T3-E1 | MC3T3-E1 |
| Culturing conditions | 5000 cells per cm$^2$ (6-well) αMEM, 20% FCS, streptomycin, penicillin, glutamine; induction: sodium glycerolphosphate, ascorbic acid, dexamethasone | $3.1 \times 10^4$ cells/cm$^2$ (96-well) αMEM, 10% FBS, streptomycin, penicillin, glutamine; induction: β-glycerophosphate, ascorbic acid, melatonin | $3.1 \times 10^4$ cells/cm$^2$ (96-well) αMEM, 10% FBS, streptomycin, penicillin, glutamine; induction: β-glycerophosphate, ascorbic acid, melatonin |
| ARS Time | Day 0-Day 30 | Day 18 | Day 18 |
| ARS Staining & Quant. Steps | | | |
| 1. | Wash with PBS | ← Same | ← Same |
| 2. | Fix in 10% formaldehyde RT, 15 min. | Fix in 4% Paraformaldehyde RT, 15 min. | Fix 4% Paraformaldehyde RT, 15 min |
| 3. | Wash 2x with dH2O | ← | ← |
| 4. | 1 mL/well 40 mM ARS RT, gentle shaking, 20 min. | 100 μL/well 40 mM ARS per well RT gentle shaking for 1 h. | ← |
| 5. | Wash 4X with dH2O, shaking (5 min). Remove excess water (tip plate) | ← | ← |
| 6. | View by phase microscopy. | ← | ← |
| 7. * | Add 800 μL/well 10% acetic acid RT, shaking (30 min) | Add 300 μL/well 10% acetic acid RT, shaking (30 min) | Incubate samples with 350 μL/well 4M guanidine HCl @ 37° C. O/N |
| 8. | Scrape monolayers w/cell scraper Transfer → 1.5-mL tube | ← | Transfer 150 μL solution in duplicate to read |
| 9. | Vortex for 30 s | ← | |
| 10. | Overlay the slurry with 500 μL mineral oil, heat to 85° C. for 10 min | Heat to 85° C. for 10 min (with the cap on). | |
| 11. | Transfer to ice → open when cooled. | ← | |
| 12. | Centrifuged at 20,000 g for 15 min | ← | |
| 13. * | Remove 500 μL of 800 μL supernatant to a new 1.5-mL tube. | Remove 255 μL of 300 uL supernatant to a new 1.5-mL tube. | |
| 14. | Neutralize pH with 200 μL of 10% ammonium hydroxide (pH 4.1-4.5) | Neutralize pH with 95 μL 10% ammonium hydroxide (pH 4.1-4.5) | |
| 15. * | Add 150 μL in triplicates in opaque-walled, transparent-bottomed 96-well plates. Read at 405 nm. | Add 150 μL of standard/sample in doubles to opaque-walled, transparent bottom 96-well plate. Read at 405 nm. | Read at 490 nm in opaque-walled, transparent bottom 96-well plate. |

* Steps with differences between the 3 methods for ARS staining and quantitation.

Experimental Design:

Cells were cultured and stimulated in differentiation medium as described in Part A and Table 5. Differentiation medium was changed every 3 days for 18 days. 0.1 µg/ml HC-HA and 125 µg/ml AMP were employed for the assay. The ARS assay was performed as described in Part A with the changes as noted in Table 5.

Results

Cell Morphology and Ring Formation

Figure 59A:
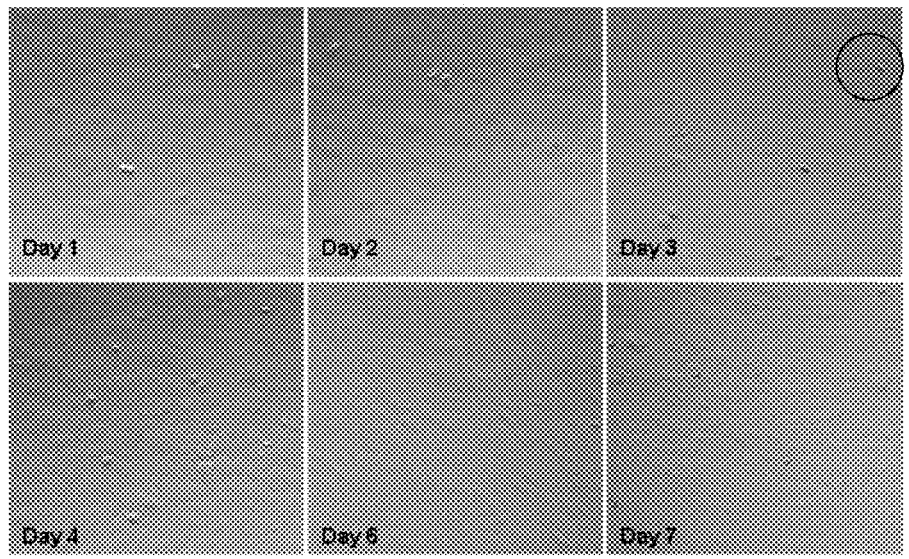

Uninduced cells attained a flat cuboidal shape after seeding (FIG. 59A). Cell border became more defined on Day 4 with raised edges, and some cells developed fusiform shapes on Day 6. No spindle cells or multiple layers developed.

From Day 1 to Day 3, cells maintained a cuboid shape and monolayer remained flat (FIG. 59B). By day 3, cell borders became more distinct and cell edges became raised. In addition, small round cell-like structures were visible on the monolayer (indicated by black circle). Cell morphology changed by day 4 with the appearance of fusiform shaped cells and cells organized in multiple layers. The appearance of the small round cell-like structures continued to increase through Day 6 and Day 7.

Figure 60A:
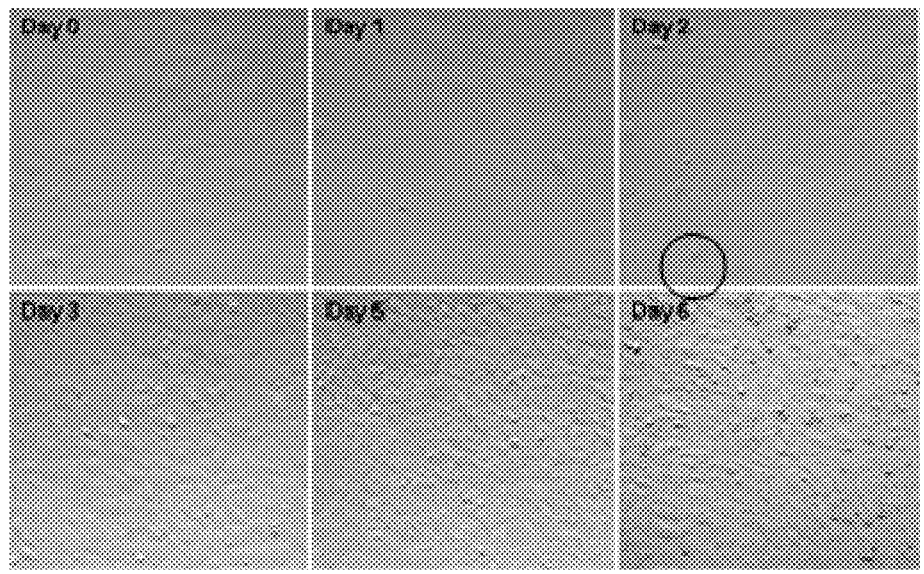
FIG. 60A-B exemplifies phase contrast microscopy of morphological changes in induced MC3T3-E1 cells treated with HC-HA (A) or AMP (B) from Day 1 to Day 7.

Cell morphology change in induced cells treated with HC-HA mirrored the positive control's changes (FIG. 60A). HC-HA did not leave particles on the monolayer like AMP. Like the positive control, small round cell-like structures (shown in black circle) appeared on Day 3 and continued to increase to Day 7.

Figure 60B:
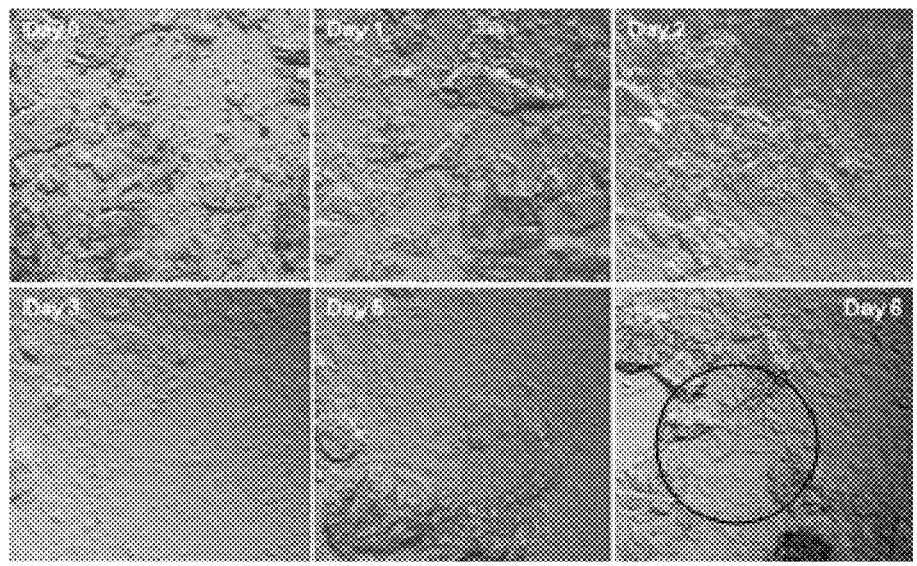

AMP particles (noted with black arrow) settled on top of the monolayer and obstructed observation of the monolayer underneath (FIG. 60B). Areas devoid of AMP particles on Day 0 and Day 1 showed round and cuboidal shapes. On Day 2, some fusiform shaped cells appeared on the monolayer. It was difficult to identify and distinguish the small round cell-like structures from smaller AMP particles and the development of these structures remains unknown. On Day 5, fusiform shapes elongated to form spindle-like cells. On Day 6, long spindle cells formed web-like interactions with AMP particles (shown in black circle).

Figure 61A:
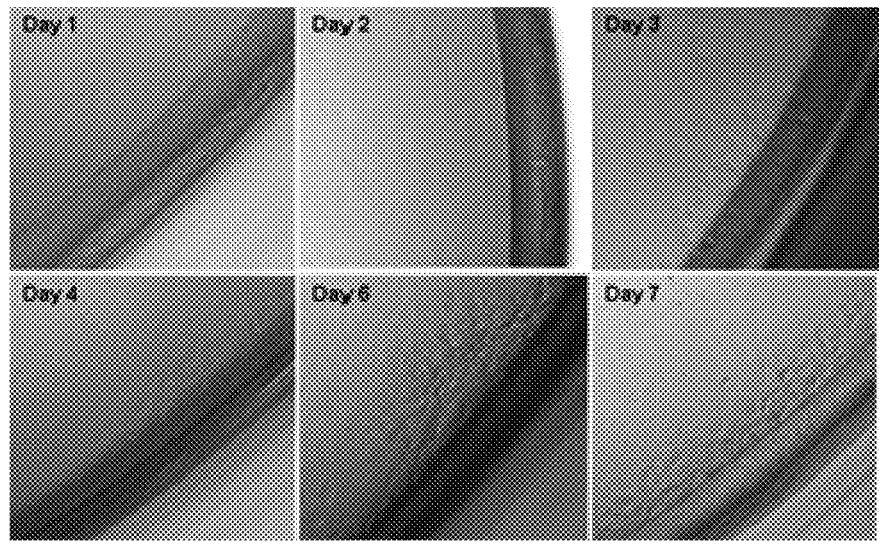
FIG. 61A-B exemplifies phase contrast microscopy of spindle ring formation in induced MC3T3-E1 cells from Day 3 of induction.
Figure 61B:
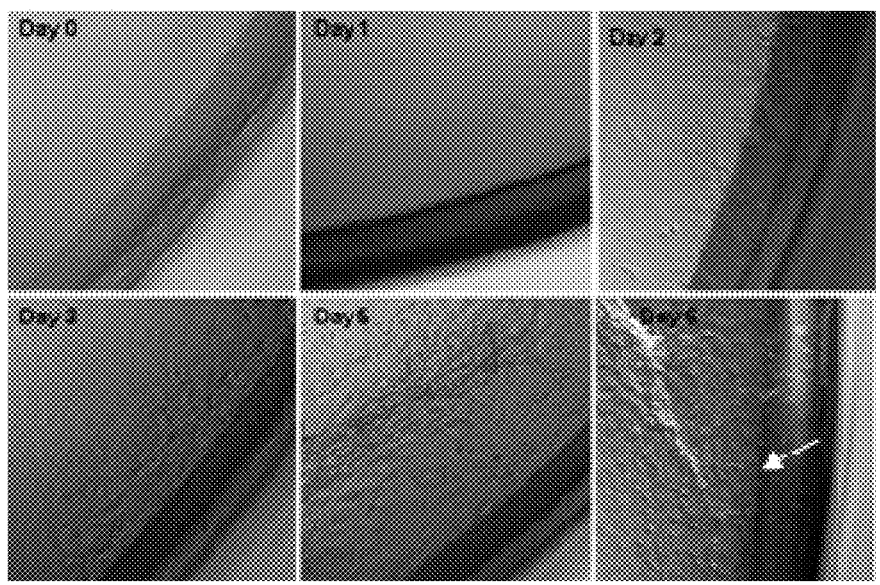

On Day 3, fusiform shaped cells developed near the edge of the well (1-2 mm from the edge) (FIG. 61A). Spindle cells and ring formation did not develop from Day 4 onwards. Cells appeared to overlap each other at the edge and grow into fusiform shapes. From Day 0 to Day 2, there are no spindle-like cells along the well edge (FIG. 61B). On Day 3, similar fusiform cells piled up in a ring configuration were noted in the edge. From Day 5, these cells were concentrated as a prominent ring about 2 mm from the edge. On Day 6, monolayers show detachment from the plastic surface along certain areas near the edge (indicated by white 4).

Figure 62A:
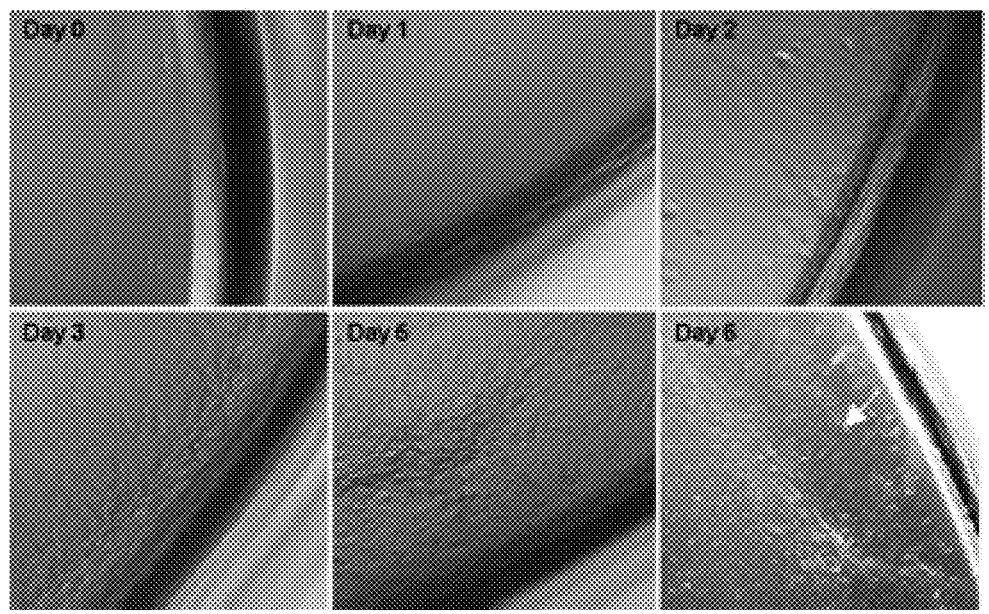
FIG. 62A-B exemplifies phase contrast microscopy of spindle ring formation in induced MC3T3-E1 cells treated with HC-HA (A) and AMP (B) (Day 0 to Day 6).
Figure 62B:
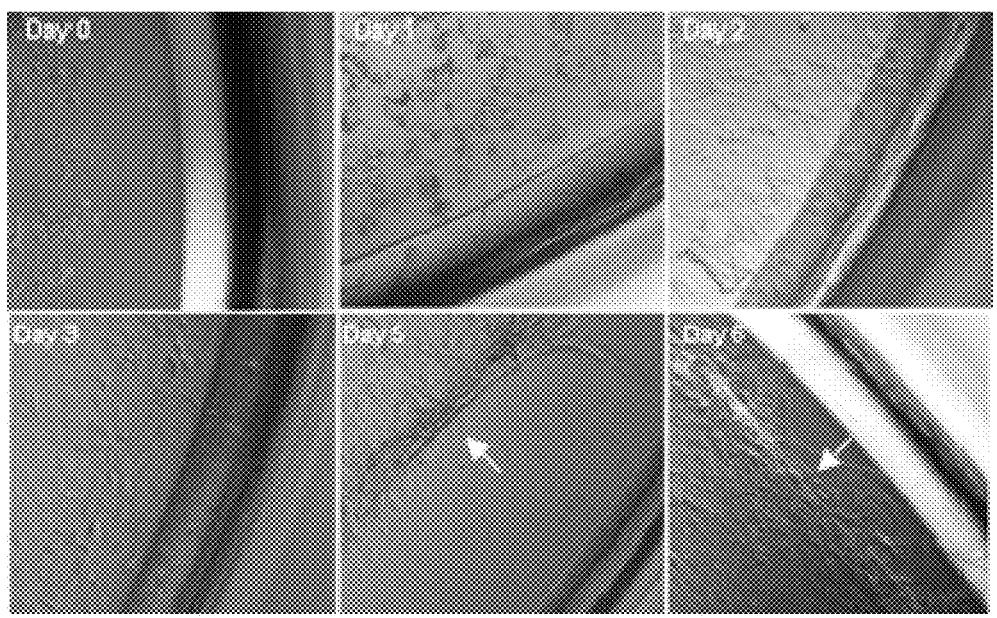

Cells remained smooth and cuboidal along the edge until Day 2 (FIG. 62A). Fusiform shaped cells developed near the edge on Day 2. Some small round cell-like structures were also visible near the edge at the time. Spindle-like cells developed on Day 3 and continued to thicken in a ring around the well edge to Day 5. Monolayer detachment from the plastic well was observed on Day 6 in areas near the edge (noted with white arrow). Fusiform shaped cells appeared near the well edge on Day 2 (FIG. 62B). Spindle-like cells developed from the edge on Day 3 (about 1 to 2 mm away) and a ring of spindle-like cells formed by Day 5. Monolayer detachment from the plastic well was observed on Day 5 in some areas near the edge. Detachment continued on Day 6, but the monolayers did not detach as much as the HC-HA treated cells and the positive control cells.

ARS Staining and Quantitation

Figure 63:
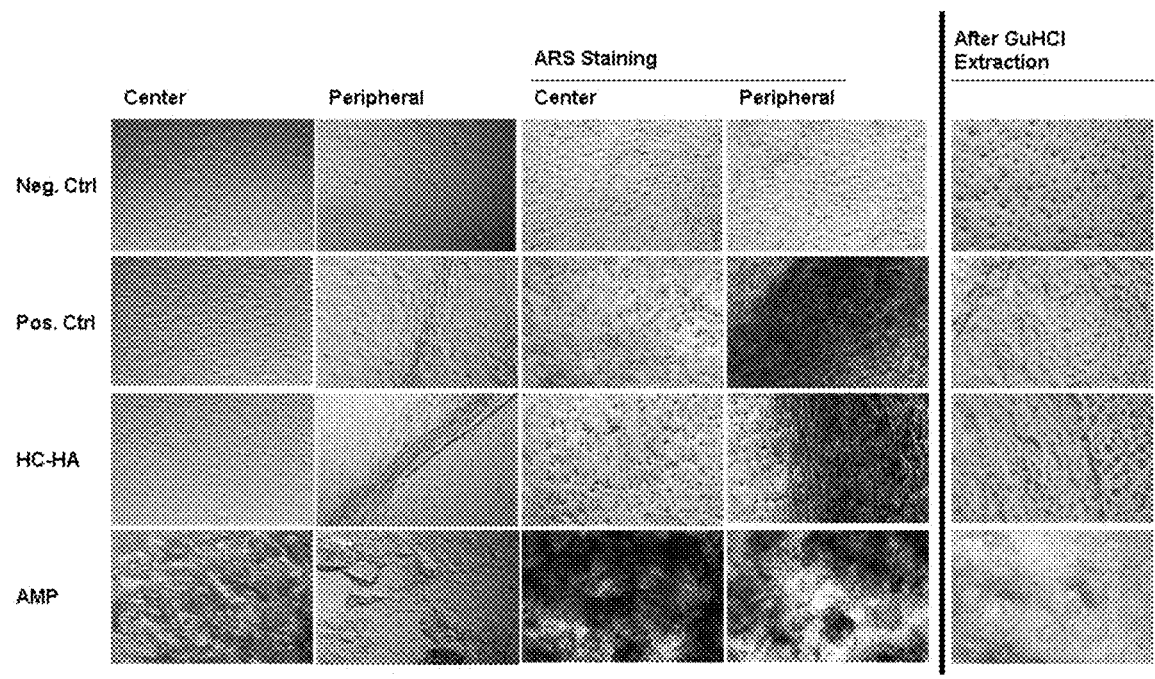
FIG. 63 exemplifies ARS staining of induced MC3T3-E1 cells treated with HC-HA and AMP and Extraction with GnHC1.

The negative controls monolayer stained a light pink color in some areas (FIG. 63). The positive control stained a light pink in the center but showed a bright crimson red color in the spindle ring area, indicating MC3T3-E1 cells deposit mineralization heavily in ring rather than the rest of the monolayer. Both intensity and color of staining in the center monolayer and the spindle ring between 0.1 µg/ml HC-HA and positive control was the same. AMP particles on top of the cells stained a red-brown color. Visual observation of cells underneath was obstructed by the stained particles, but openings showed lack of prominent cell monolayer with some sparse cells staining a light pink color similar to the negative control. Since AMP treated cells did not show a visible spindle ring, and the ARS did not stain a crimson red around the edge similar to the positive control.

GnHC1 treatment solubilized the cell matrix and removed crimson red ARS dye while leaving the monolayer intact in both the positive control and HC-HA treated cells. GnHC1 digested and denatured the cell protein, leaving the extracellular matrix behind. In the AMP experimental group, AMP particle density decreased but most particles still remained on the bottom of the well. With the long culture time, AMP particles may form tight interactions with the ECM matrix that was not dissolved by the GnHC1. The particles that once stained a bright red-brown now showed a light brown like the color AMP naturally exhibits. A distinct monolayer structure, however, was not observed; this supported the observation of a monolayer of cells in the gaps between the AMP. The cells may have migrated from the monolayer into the AMP particles and used it as a scaffold for differentiation and mineralization.

Figure 64A:
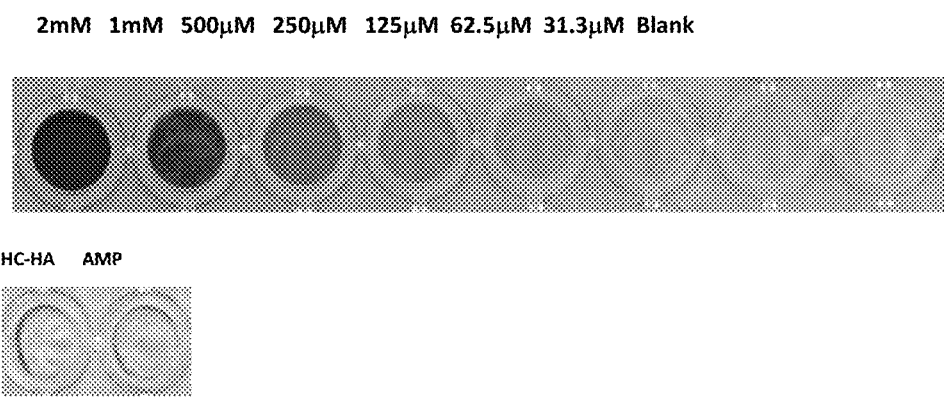
FIG. 64A-B exemplifies ARS Extraction and Quantitation of MC3T3-E1 cells with Acetic Acid and 10% Ammonium Hydroxide. ARS extracts through acetic acid treatment were neutralized with 10% ammonium hydroxide then added to 96-well clear bottom assay plates (A) for reading on a spectrophotometer (B). * denotes statistical significance.
Figure 64B:
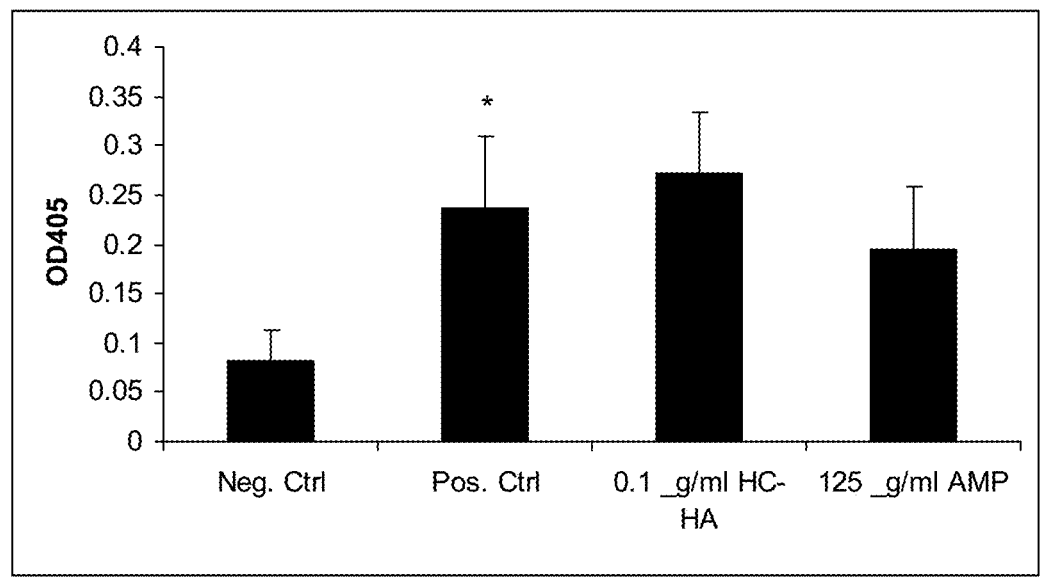

ARS standard showed a progression from crimson red to a cream pink color through serial dilution from 2 mM to 31.3 µM (FIG. 64A). There was a noticeable color change between HC-HA and AMP treated samples. HC-HA treated cell extracts showed a clear cream color while AMP treated cell extracts showed a light cream pink color. The positive control also showed the same color and level of intensity of color as the HC-HA treated cells, while the negative control showed lighter color and resembled the blank (not shown). The $OD_{405}$ values stayed in the same range as the values from in the previous example (FIG. 64B). Compared to the negative control, the positive control showed a statically significant 2-fold decrease in OD. HC-HA-treated (0.1 µg/ml) cells showed slight increase in OD than the positive control, but the difference is not statistically significant. AMP (125 µg/ml) treatment slightly decreased OD values when compared to the positive control, but this decrease was not statistically significant.

Figure 65A:
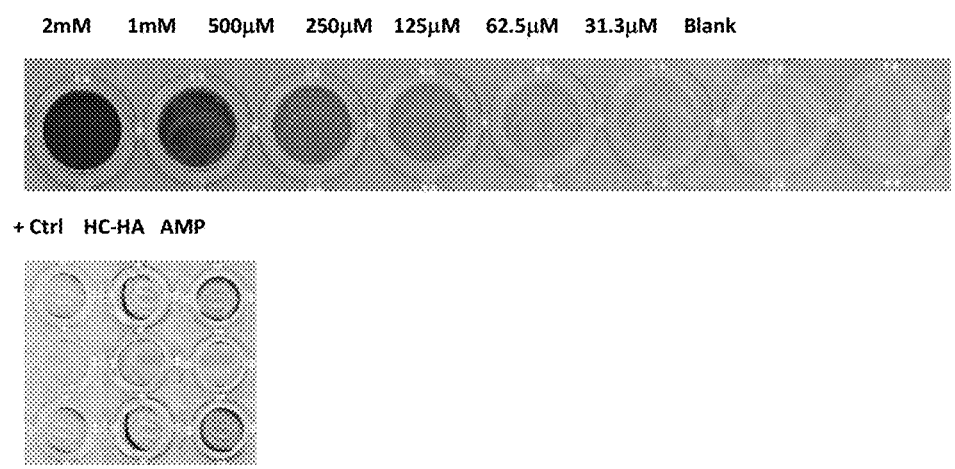
FIG. 65A-B exemplifies ARS Extraction and Quantitation of MC3T3-E1 cells with GnHC1. ARS extracts through GnHC1 treatment were added to 96-well clear bottom assay plates (A) for reading on a spectrophotometer (B). * denotes statistical significance.
Figure 65B:
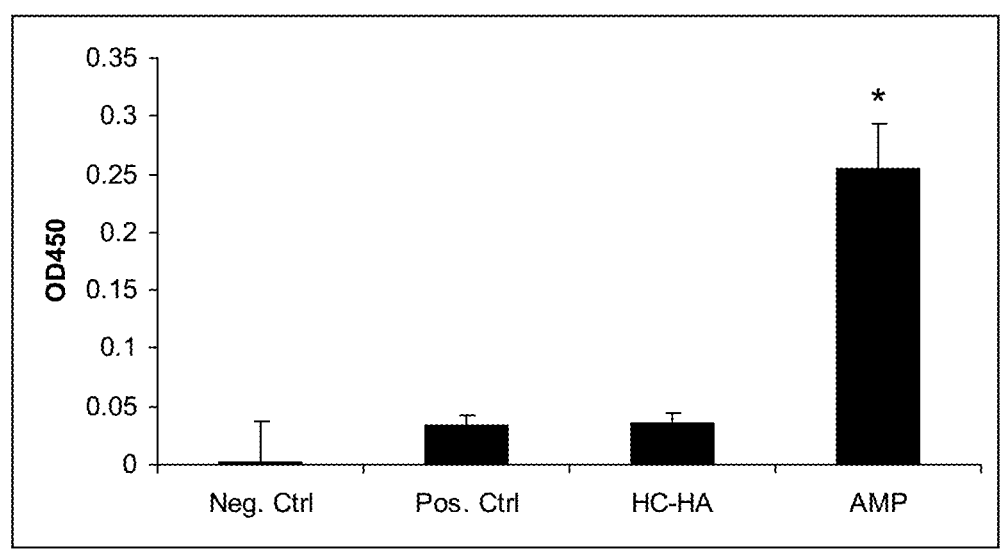

ARS standard showed a progression from crimson red to a cream pink color through serial dilution from 2 mM to 31.3 µM (FIG. 65A). The negative control extract showed a light cream color slightly darker than the blank (not shown). The positive control showed a light golden color and the color was visibly darker than the negative control. HC-HA also showed a light golden color at the same intensity as the positive control. AMP treated extracts showed an orange-golden color that was darker than both the positive and HC-HA extract groups. $OD_{405}$ values stayed in the same range with the highest at around 0.25 (FIG. 65B). Negative controls showed a negligible OD value close to 0. The positive controls and HC-HA (0.1 µg/ml) treated extracts showed an average OD value close to 0.05. AMP-treated (125 µg/ml) extracts showed a statically significant 5-fold increase in OD (P=0.039) from both the positive and HC-HA treated groups.

Summary

Cell Morphology

Figure 59A:
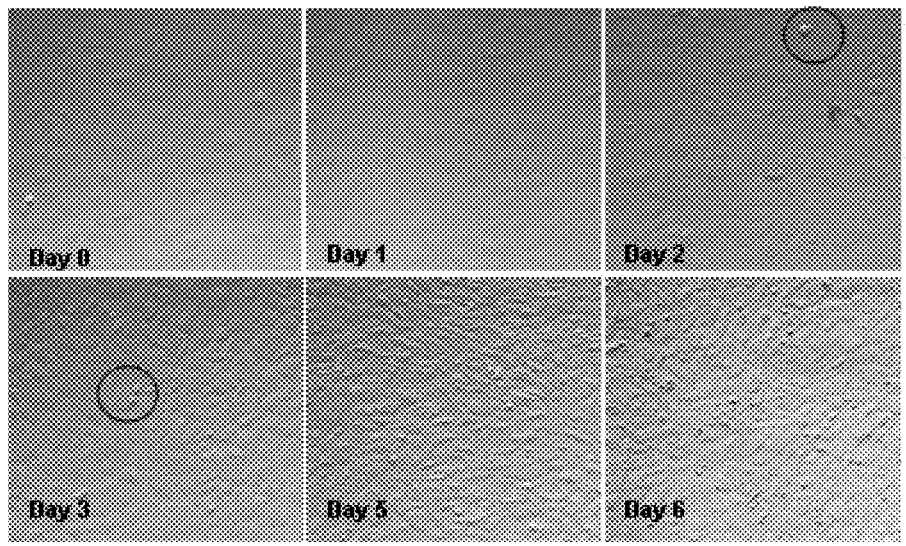

MC3T3-E1 cells cultured in αMEM w/10% FBS grew to confluence and developed cuboidal shape. Like findings in Aim #1 and #2, cells did not differentiate without the addition of ascorbic acid, β-glycerolphosphate, and melatonin. Without induction medium, spindle cells and spindle rings did not form (FIG. 59). MC3T3-E1 cells were induced into differentiation with ascorbic acid, β-glycerolphosphate and melatonin. After seeding, a smooth monolayer formed with cuboidal shaped cells. After 3 days of induction, cells attained a fusiform shape. By day 5, cells elongated and became spindle-like.

In this example, spindle rings developed on Day 3 of induction, with spindle like cells forming 1 to 2 mm from the well wall. On Day 6, detachment of the monolayer from the well edge and plastic bottom was observed (FIG. 60). Small round cell-like structures developed on the monolayer beginning on day 2 and increased in number to day 6 (FIG. 59). They did not float in the culture medium and were firmly attached in the monolayer, resting mostly in between the cell borders. These structures may represent matrix vesicles (MVs) are extracellular, membrane-invested particles located at sites of initial calcification in cartilage and bone. Matrix vesicle synthesis occurs through budding and pinching-off of vesicles from specific regions of the outer plasma membranes of differentiating growth plate chondrocytes and osteoblasts (Anderson et al. (2003) *Curr Rheumatol Rep* 5(3):222-6).

Treatment with HC-HA did not alter MC3T3-E1 cell morphological change through differentiation (FIG. 60). Formation of fusiform shaped cells, spindle-like cells and spindle ring (FIG. 61) followed the reported time course of the positive control. AMP particles settled on top of the cell monolayer similar to pervious findings (FIG. 60). This impeded full observation of the cell monolayer and cell morphology change through induction. However, some observations were noted through openings where AMP particles did not settle. Unlike HC-HA, AMP treatment sped up cell morphological change and some fusiform cells were visible a day earlier on induction Day 2. AMP treated cells formed a spindle ring similar to HC-HA treated cells and the positive control (FIG. 62). However, the monolayer detached earlier (FIG. 62) then the other two experimental groups (on Day 5 instead of Day 6).

ARS Staining and Quantitation

ARS staining showed drastically different color than previous reported (FIG. 66). ARS stained a light pink instead of blue-grey color in the negative control cell monolayers. ARS staining also showed a bright crimson red concentrated in the spindle ring instead of a rust-brown color from previous results in the positive controls and HC-HA treated cells. AMP particles stained a red-brown instead of a dark brown, and the cells underneath was stained light pink instead of a rust-brown. Degradation of ARS Solution may have contributed to the color change.

After Acetic Acid extraction, the monolayer still appeared to have significant amount of stained color left. Acetic Acid is not effective in completely removing ARS stain from the monolayer. With Acetic Acid extraction, there was a statistically significant difference between the OD values of the positive and negative control (FIG. 68) that matched the visual observation of more ARS staining in the positive control (FIG. 66). However, acetic acid extraction was not effective in showing a statistically significant increase in AMP's OD compared to the positive and HC-HA groups (FIG. 66) despite visual observation of AMP groups having more color in the assay extracts than the other two groups (FIG. 67). AMP particle deposits may have made it more difficult to remove ARS from the AMP groups. Mineralized matrix and cells could also may have interactions with the AMP particles that hinder acetic acid extraction of ARS.

GnHC1 removed ARS from cell monolayer more completely than Acetic Acid treatment (FIG. 69). Additionally, color was solubilized in GnHC1 solution without the use of a cell scraper to remove the monolayer. Both methods seem to have left particles invisible to the naked eye and unaffected by centrifuge. For GnHC1, this could be calcium and dissolved matrix that forms fine particles. This caused variations between the duplicates in each sample. Reading at 670 nm to remove the particles solved this problem for the GnHC1 extraction method.

Figure 70:
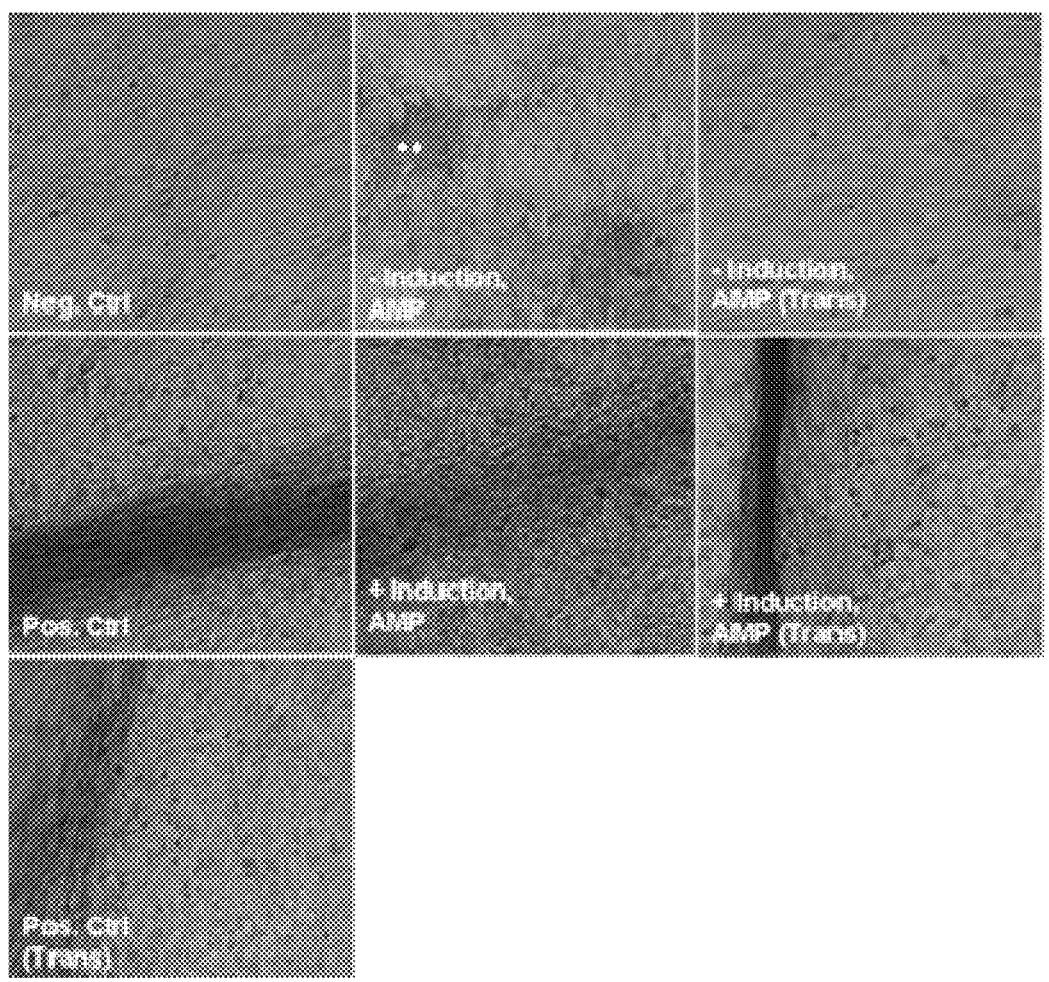
FIG. 70 exemplifies ARS Staining of induced MC3T3-E1 cells at D14 of induction.

GnHC1 extraction could not establish a quantifiable statistical significance between the negative and positive control (FIG. 71) to match the visual observation of the ARS staining. GnHC1 extraction also showed that 0.1 µg/ml HC-HA did not promote more mineralization in differentiating MC3T3-E1 cells (FIG. 71), and this matched the results of the Acetic Acid extraction. From looking at the assay extract colors in 96-wells, the positive control and HC-HA wells showed no difference in color or intensity (FIG. 70).

Figure 71:
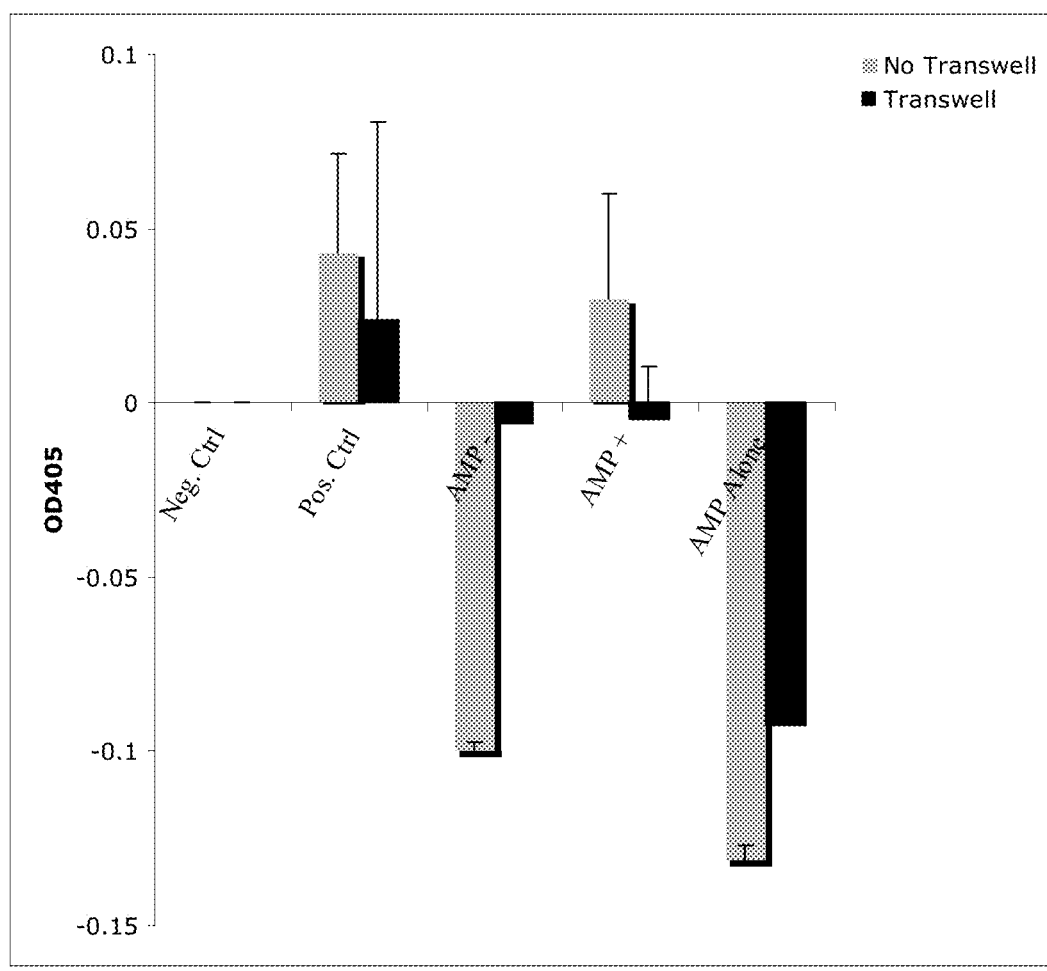
FIG. 71 exemplifies quantitation of ARS Staining of induced MC3T3-E1 cells at D14 of induction.

GnHC1 extraction showed that 125 µg/ml AMP promoted more mineralization in differentiating MC3T3-E1 cells than the positive control (FIG. 71). This matched both the ARS staining of the monolayer (FIG. 66) and the visual observation of the extracts in 96-well assay plates (FIG. 70), where AMP showed a much deeper golden-yellow color than the HC-HA or positive control.

From these results, GnHC1 is the better extraction method because it removes ARS stain more completely from the monolayer and leaving it intact; there is less technical error because the monolayer does not need to be scraped from the well. The extract color can be quantified through spectrophotometer reading.

Part C

The preliminary study above did not exhibit statistically significant results on the dose-response curves for HC-HA and AMP on osteoblast differentiation due to the small sample size and incomplete development of the ARS assay. This suggested that 0.1 µg/ml HC-HA may enhance mineralization. Furthermore, HC-HA at 10 µg/ml to 25 µg/ml might affect cell viability and reduce mineralization. The dose curve for HC-HA should include a lower concentration below 0.1 µg/ml as well as concentrations above 10 µg/ml. Unlike HC-HA, AMP at 5 µg/ml to 125 µg/ml may promote mineralization. In this experiment, the dose response of HC-HA and AMP was retested using the method of Part B. In this experiment, ARS stain was used to assay at Day 15, and the revised protocol using 10% acetic acid to stain and quantitate was employed.

Experimental Design

The same model system as shown in Part B based on 3T3-E1 cells was used by seeding $3 \times 10^4$ cells/cm$^2$/well in 96 well plates in αMEM medium w/10% FBS. Upon confluence, cells were induced to differentiation by adding ascorbic acid, β-glycerolphosphate, melatonin induction medium. For each condition, N=3 was tested. After confluence (Day 0=seeding), HC-HA was added at 0.02 µg/ml, 0.1 µg/ml, 1 µg/ml, 5 µg/ml, and 25 µg/ml while AMP was added at 1 µg/ml, 5 µg/ml, 25 µg/ml, and 125 µg/ml. For ARS staining, the modified method of Part B was employed.

Results

Figure 66A:
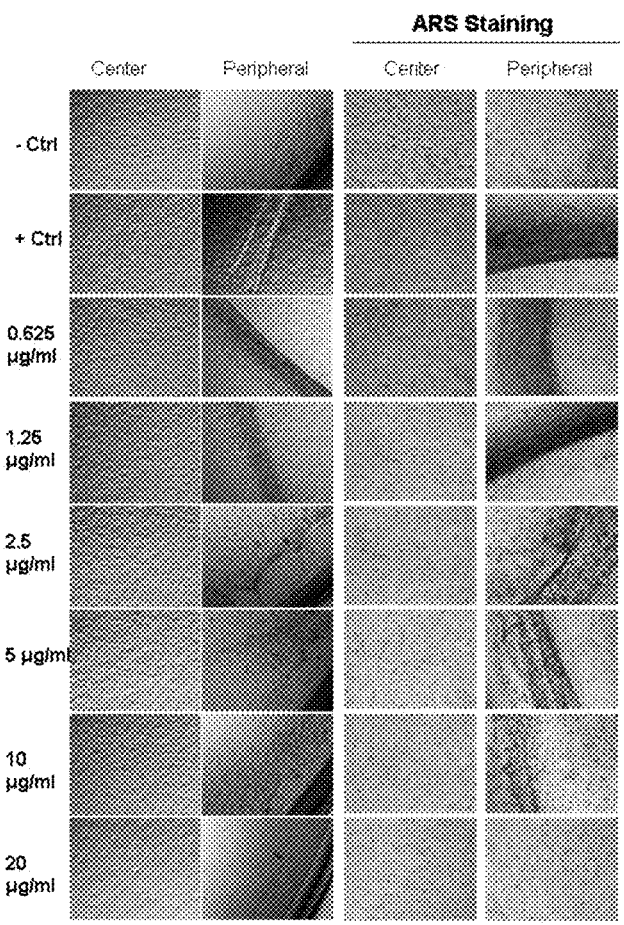
FIG. 66A-B exemplifies ARS staining (A) and quantitation (B) of MC3T3-E1 cells treated with HC-HA on D19 (D18 of Induction). ARS staining was conducted on D19 of culturing (D18 Induction).
Figure 66B:
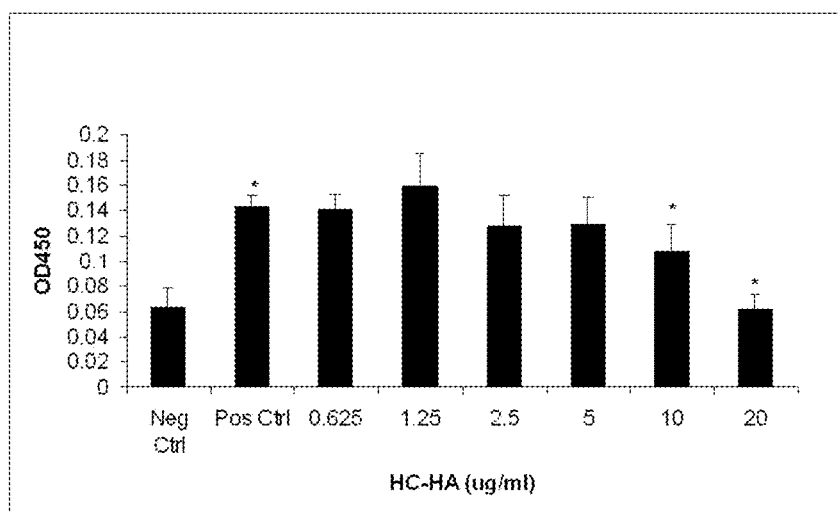

Negative control MC3T3-E1 cells did not develop spindle-like shapes or spindle rings throughout culturing (FIG. 66A). The monlayer center and peripheral stained a beige color. The positive control cells developed fusiform and spindle-like cells, with the appearance of spindle rings around D5 of culturing (D4 of induction). ARS staining showed a light maroon color in the center and was mostly concentrated in the spindle rings with a dark crimson color. Increasing HC-HA concentration to 1.25 µg/ml had no effect on cell morphology or ARS staining intensity and pattern. At 2.5 µg/ml, MC3T3-E1 cells' spindle ring started to degrade and the ARS color changed from crimson to a red-brown color. By 20 µg/ml, cells lost their fusifrom and spindle shapes; cell edges were also less defined and raised. Cells density decreased and the monolayer did not appear raised like before. GnHC1 successfully extracted the ARS dye and the coefficient of variation in $OD_{450}$ values ranged from 5% to 19%. The positive control showed statistically significant increased OD values (FIG. 66B).

Figure 67A:
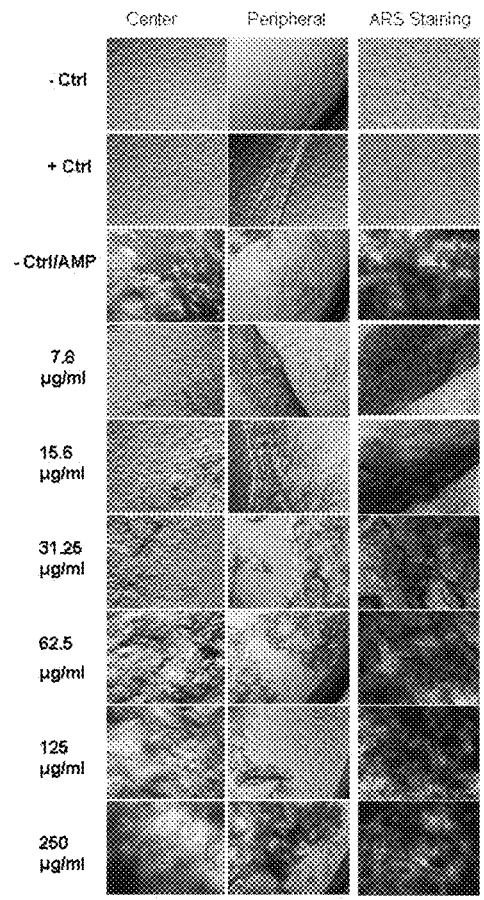
FIG. 67A-B exemplifies ARS staining (A) and quantitation (B) of MC3T3-E1 cells treated with AMP. ARS staining was conducted on D19 of culturing (D18 Induction).
Figure 67B:
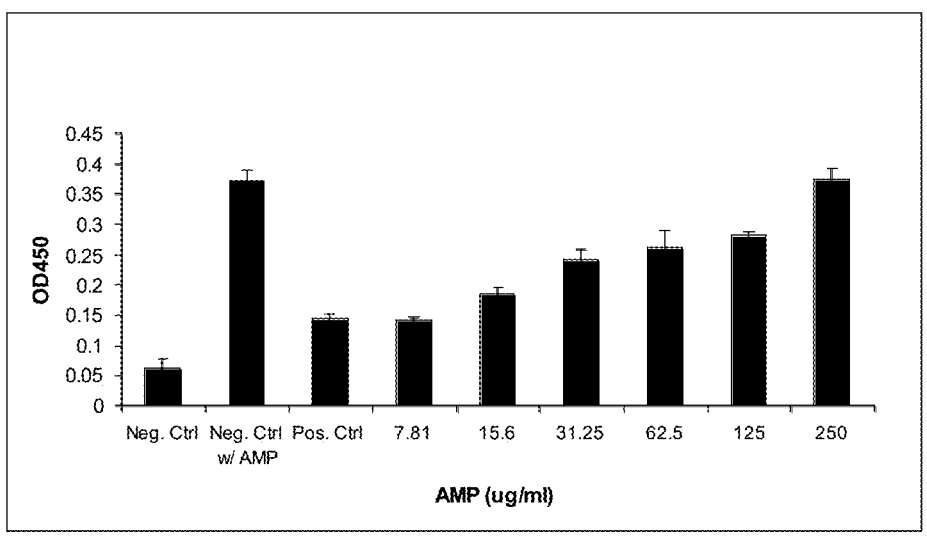

Negative control MC3T3-E1 cells did not develop spindle-like shapes or spindle rings throughout culturing (FIG. 67A). The monlayer center and peripheral stained a beige color. The positive control cells developed fusiform and spindle-like cells, with the appearance of spindle rings around D5 of culturing (D4 of induction). ARS staining showed a light maroon color in the center of the monolayer. AMP treatment left AMP particles that settled on top of the cell monolayer and obscured observation of the monolayer from concentration 62.5 µg/ml upwards. MC3T3-E1 cells treated with only AMP and no induction showed no spindle rings along the edge and ARS staining showed a dark crimson with a light pink background. From 7.8 µg/ml to 31.25 µg/ml, the AMP particles did not completely cover the monolayer and cells showed fusiform and spindle shapes. Along the edge, spindle rings could be seen. ARS staining showed the center monolayer staining a light maroon and the dye concentrated along the spindle ring to a dark crimson color like the positive control. GnHC1 successfully extracted the ARS dye and the coefficient of variation in $OD_{450}$ values ranged from 3% to 10% (FIG. 67B).

Results Summary

Cell Morphology/ARS Staining

Similar to previous results, MC3T3-E1 differentiation progresses from cells changing from cuboidal shape to fusiform and spindle shapes. With increasing induction time, spindle rings form along the well edge (2 mm away) and contracts the monolayer with time. Unlike the positive control, the negative control never developed spindle-like cells or spindle ring. While the negative control monolayer stained a uniform beige color, the positive control showed a light maroon/pink in the center and concentrated dark crimson in the spindle rings.

At 10 µg/ml HC-HA, cell morphology changed from lower concentrations, with less cells showing the fusiform and spindle shapes. Cell density decreased and the monolayer looked less raised. At 20 µg/ml HC-HA, cell density decreased dramatically and few cells were spindle shaped. The monolayer looked smooth like the negative control. For both concentrations, these changes were noticed starting on D5 of culturing and induction. In both concentrations, the spindle rings were either poorly formed or non-existent. Increasing HC-HA concentration caused the disintegration of the spindle ring at a concentration of 2.5 µg/ml and upwards.

In all AMP treated cells, areas around where AMP particles settled stained dark crimson. Around the edge of the well, no monolayer could be seen through the openings of AMP particles. Uninduced MC3T3-E1 treated with 125 µg/ml AMP showed staining similar to induced MC3T3-E1 treated with 125 µg/ml AMP. The cells with settled AMP stained dark crimson in patches, with no observation of a stained monolayer underneath. From 7.8 µg/ml to 15.6 µg/ml AMP, cell morphology was visible. Cells showed fusiform and spindle shapes with spindle rings formed along the edge of the well. ARS staining resembled the positive control with light maroon color in the center and dark crimson in the spindle ring areas.

GnHC1 treatment was successful in extracting ARS dye from the stained monolayer. The extraction showed a statistically significant ($p<0.01$) 2-fold increase in $OD_{450}$ from negative control to positive control. HC-HA treated cells showed a trend of decreasing mineralization with increasing HC-HA concentration. At 10 µg/ml and 20 µg/ml HC-HA, there was a statistically significant ($p<0.05$) decrease in mineralization from the positive control. AMP dose-dependently increased mineralization of differentiating MC3T3-E1 cells.

Uninduced cells treated with AMP also showed mineralization, and it would appear AMP induced and promoted mineralization more than positive control ($p<0.01$). Also, at 125 µg/ml AMP, treatment to uninduced cells showed more mineralization than cells cultured in induction medium ($p<0.05$).

Example 39. Effect of AMP on Osteoblast Differentiation

Although ARS staining showed a clear dose-dependent increase of staining by AMP, and exhibited a statistically significant increase in mineralization at 125 µg/ml, it was unclear whether such a change is caused by non-specific binding of ARS to AMP. Because AMP acted differently from HC-HA especially at the high dose, i.e., promoting mineralization but not inhibiting it, it was important to rule out whether AMP's action depends on cell direct contact with AMP. This question was addressed by the use of transwells with a 3 µm pore size, which is sufficient for HC-HA to pass through but small enough to preclude AMP particles. Because the available transwell plate with this pore size fits in a 24-well plate, the culture conditions of the assay were altered accordingly. A concentration of 125 µg/ml AMP was employed for the assay.

Experimental Design:

MC3T3-E1 cells (Cells at P2; ATCC, catalog number: CRL-2593™) were seeded onto 12-well flat, transparent bottomed wells at a density of $1\times10^5$ cells/ml. The same AMP stock solution (AMP-4; Lot # CB102971) as used above was prepared as 5 mg/ml in PBS. For wells without Transwells, 17.5 µL of AMP stock was added in 0.7 ml of the culture medium (base or induction medium) to achieve 125 µg/ml AMP concentration in either α-MEM w/10% FBS (without induction) or induction medium #1 followed by #2 (with induction). For wells with Transwells, 17.5 µL of AMP stock was added to directly into center of Transwell membrane in the same manner as described above. Culture mediums (α-MEM with 10% FBS; Induction Medium #1 and #2 as described above) were changed every 3 days after D0 of induction. ARS staining and quantitation procedures were performed as described above except that cell monolayers were fixed with 4% paraformaldehyde instead of 70% ethanol, and stained for 2 h instead of 1 h.

Results

Figure 68:
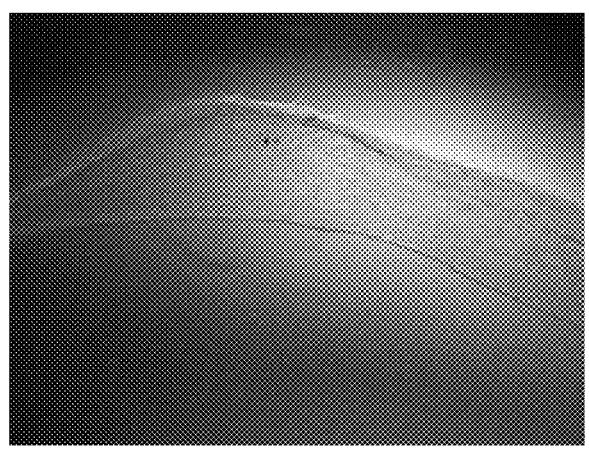
FIG. 68 exemplifies a spindle like ring observed in induced MC3T3-E1 cells on Day 14 of induction.

All induced cells developed ring formation on D4 of induction (FIG. 68). Rings were composed of layers of cells around the edge of the plastic wells, about 2-3 mm away. They grew in layers, curled up, and then the monolayer detached in many wells from the plastic. Without induction, cells maintained mostly hexagonal shapes with some fusiform shapes with increasing culture period, and the monolayer remained smooth compared to induced cells (FIG. 69). Induction rendered the cells with a fusiform shape and the monolayer became raised and borders between cells became more distinct. With induction, by day 4, a spindle-like ring was observed developing along the edge of the culture plate. Treatment with AMP did not affect cell viability; nor did it affect the ring formation, suggesting that AMP did not negatively affect induction. The addition of transwells did not affect cell growth or morphology.

Figure 69A:
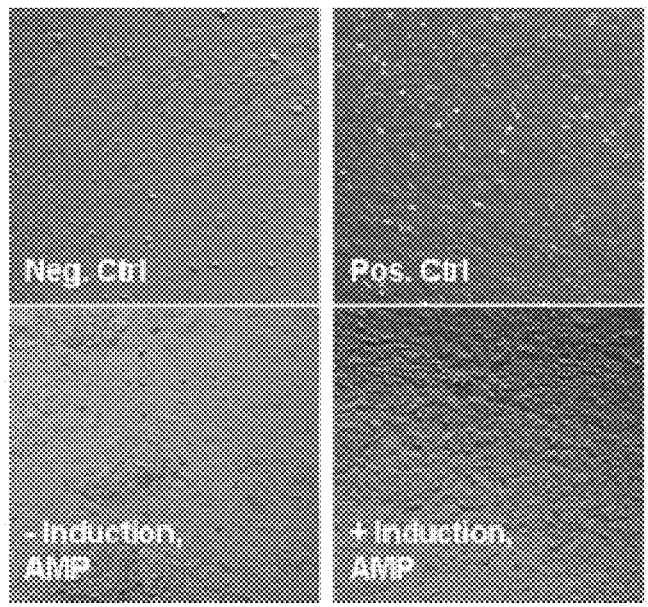
FIG. 69A-B exemplifies phase contrast microscopy of cell morphology of induced MC3T3-E1 cells treated with AMP after 14 days of induction cultured (A) without a transwell or (B) with a transwell.
Figure 69B:
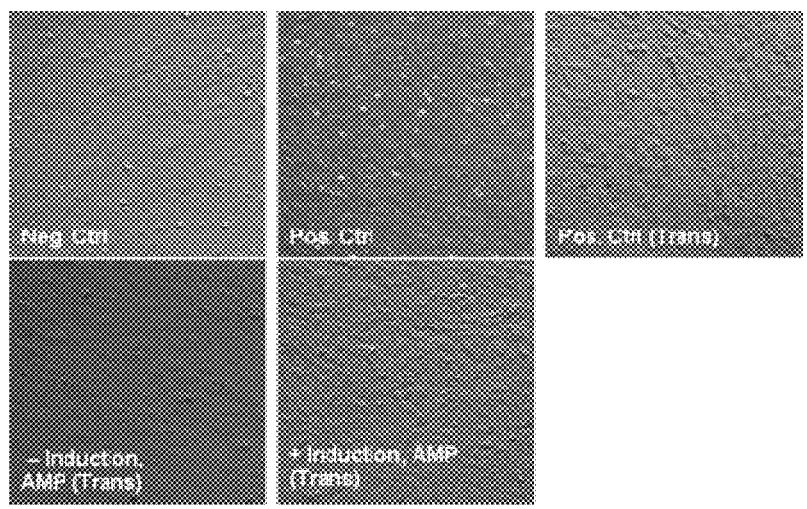

Without transwells, AMP at 125 µg/ml left particles settled on the cell monolayer (FIG. 69A). Without induction, AMP, by itself, did not cause cells to develop spindle shape and did not generate ring, thus suggesting that AMP alone was not sufficient to cause induction, similar to the negative control. With induction, 125 µg/ml of AMP did cause the cell morphology change like the positive control, suggesting that AMP itself did not negatively affect induction. Through transwells, 125 µg/ml AMP left negligible particles on the cell monolayer (FIG. 69B). Without induction, AMP was not sufficient in inducing cells to differentiate and cells resembled the negative control. With induction and 125 µg/ml of AMP, cells developed fusiform and spindle-like shapes and by D14 resembled the positive control, again suggesting that AMP did not negatively affect induction.

The negative control yielded a taupe background color with patches of light pink in the monolayer, which differed from the blue-gray color of the negative control in the previous experiment (FIG. 70). Without induction but with transwell, monolayers stained a taupe background similar to the negative control even when treated with AMP, suggesting that AMP itself did not cause induction. Without transwell, compared to the negative control, there were zones exhibiting a notable decrease of background color, suggesting that AMP particles settled on monolayer might have blocked the color (marked by **), and AMP itself did not generate positive color suggesting mineralization.

The positive control yielded rose pink with the ring stained rust red, which was darker than rose-red color from the positive control in the previous experiment. The addition of a transwell did not affect color of the positive control, confirming that transwell itself did not affect induction. With AMP but without transwell, monolayers yielded a stronger rust red color than the positive control, with the ring stained darker, suggesting that AMP exerted additional positive induction. In contrast, with the transwell, the intensity of the background color decreased to the level of the positive control while the ring maintaining the same color, suggesting that transwell exerted a negative influence on AMP's effect on induction.

Quantitation results were not adequate in providing statistical significance, and did not match visual analysis of ARS staining (FIG. 71). However, the overall trend suggested that the positive control showed more mineralization than the negative control. Furthermore, there was a trend suggesting the less $OD_{405}$ when transwell was included in the presence of AMP and induction.

Results Summary

The ring formation (FIG. 69A) was easy to observe presumably because the size of dish was bigger. However, probably due to the change of fixative, the background color for the negative control was different from the prior experiment. Furthermore, there was a more dramatic color change between negative and positive controls, especially in the ring area (FIG. 70). The introduction of a transwell in the positive control did not affect cell morphology (FIG. 69B) or ARS staining color (FIG. 70).

Without induction, AMP without transwell clearly blocked the positive ARS staining (FIG. 70), and AMP with transwell showed the same color as the negative control. AMP itself does not cause non-specific ARS and does not cause any induction. With induction, AMP without transwell caused more color than the positive control. In contrast, AMP with transwell seemed to yield the same color as the positive control.

Previous ARS quantitation results showed 125 µg/ml AMP promoting 3× more mineralization than positive control (p<0.05) (FIG. 67), but not so in FIG. 71.

There was no difference in cell morphology between cells directly treated with AMP and cells treated with AMP through transwells (FIG. 69A, 69B). Both cell groups developed ring formation and visual observation showed no perceivable difference between the ring structures. ARS staining showed negligible difference in background color between the two experimental groups. However, cells directly treated with AMP showed a more diffuse ring formation, which could be a scattering effect from the AMP particles (FIG. 70).

AMP does not need direct contact with MC3T3-E1 cells to affect mineralization. While it was unclear from this experiment AMP promotes mineralization, AMP has been shown to not affect cell morphology or cell viability (FIG. 69).

Part B

Our results showed that 125 µg/mL AMP significantly increased mineralization of MC3T3-E1 cells (FIG. 65) when compared to the positive control on Day 15 of growth and differentiation. AMP was delivered directly in culture medium and AMP particles settled on top of the cell monolayer; therefore, AMP's effect in Aim 1B necessitated direct contact.

In Part A, we sought to investigate whether AMP's effect is through acting as a scaffold for the differentiating MC3T3-E1 cells or if factors are released from the particles to promote mineralization. However, the small sample size and technical errors in ARS stain extraction with 10% acetic acid affected the data and no statistical significance was found. The experiment was repeated using the improved technical methods of ARS staining and extraction developed in Example 38 with 4M guanidine HCl.

Experimental Design:

MC3T3-E1 cells were seeded at $3\times10^4$ cells/cm$^2$/well in 24-well with αMEM medium plus 10% FBS as described above. Upon confluence, cells were induced to differentiation by adding ascorbic acid, β-glycerolphosphate, melatonin. For each condition, N=3 was tested. Day 0 counted as the day of cell seeding, and induction followed after cell confluence. Total induction time=15 Days. There were two experimental groups: AMP directly added to induction medium and AMP delivered through transwell. AMP concentration was kept the same as before at 125 µg/ml. A negative control (without induction) was added with or without AMP but without insert. ARS staining and quantitation on Day 15 of induction were performed as described above.

Results

Figure 72A:
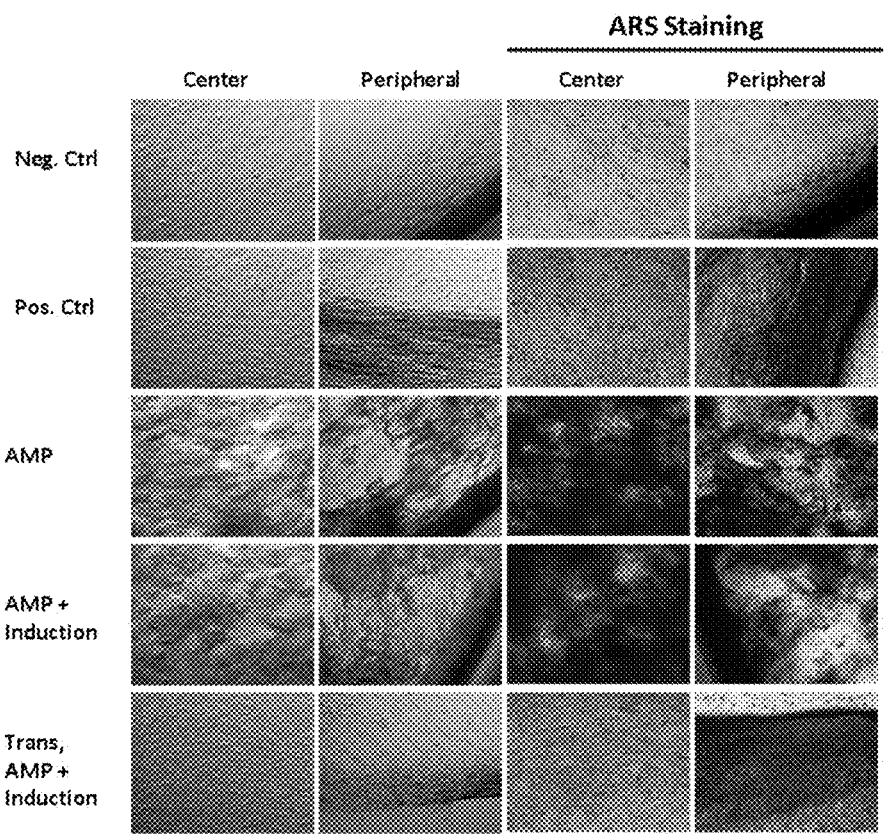
FIG. 72A-B exemplifies ARS staining and quantitation of MC3T3-E1 cells treated with AMP (A) Phase contrast picture and ARS staining picture MC3T3-E1 cells taken on Day 21 culturing (Day 20 of induction). (B) ARS staining was quantified on Day 21 of culture (Day 20 of induction). The * symbol denotes statistical significance of $p<0.05$.
Figure 72B:
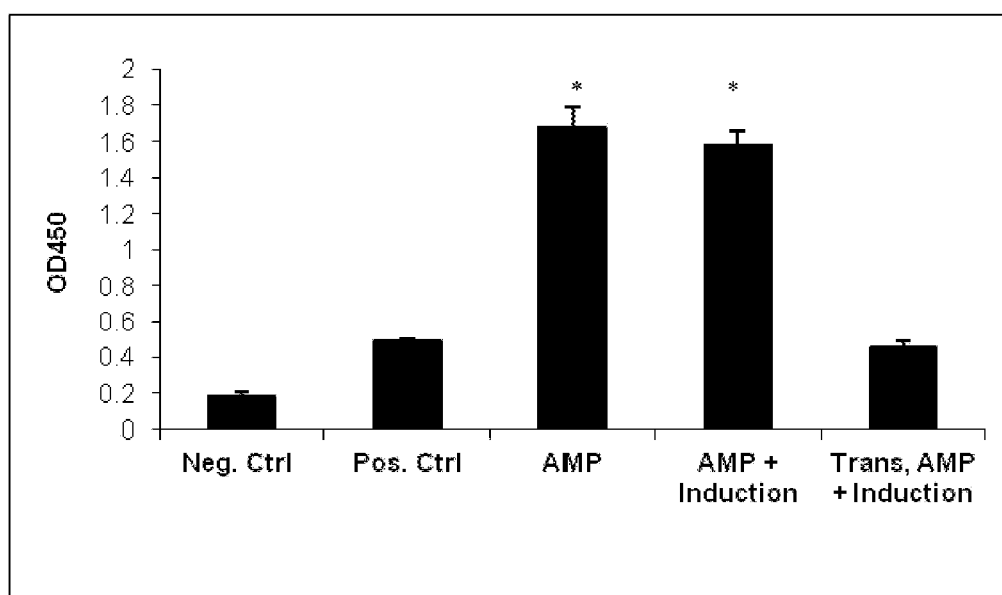
Figure 73:
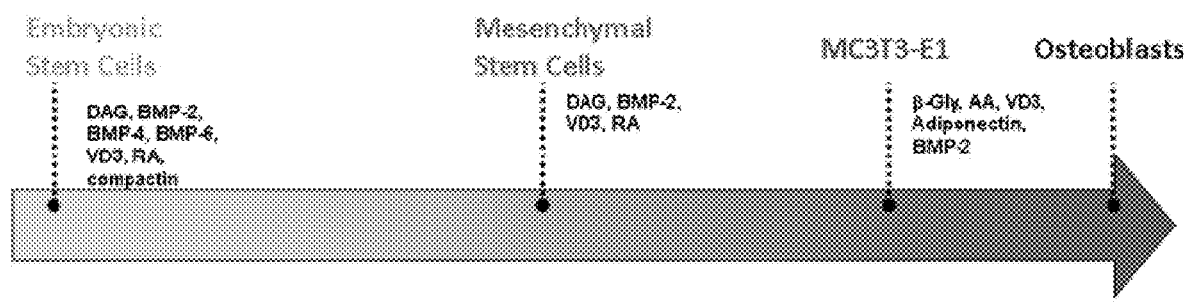
FIG. 73 illustrates a map of different progenitor differentiation to osteoblast, with common factors added to culture medium shown.

Without induction medium, negative control cells maintained hexagonal shapes with some fusiform shapes (FIG. 72A). Spindle-like shapes were not observed, and no spindle ring formed along the periphery. ARS stained the monolayer a light pink. With induction, positive control cells attained spindle like shapes. Cell borders were more prominent and raised; a spindle ring formed along the periphery near the well edge. The monolayer center stained a maroon color, and the ARS stain concentrated in the spindle ring with an intense crimson red color. Treatment with AMP directly caused AMP particles to settle on the monolayer and obscured the morphology of the cells. However, near the culture well edge, gaps between the AMP particles showed lack of a prominent monolayer underneath in both groups. There was no difference in cell morphology between AMP treatment alone and AMP treatment with induction. The cells that were visible were spindle like in shape. No spindle ring like the positive control was observed. ARS staining showed a crimson red staining in the center with reddish-brown staining along the periphery. Staining color and patterns were indistinguishable between the induction and no-induction groups. Treatment with AMP through a transwell did not produce AMP particle settlement on the monolayer. Cells were elongated and spindle-like, with spindle ring formation along the well edge. Like the positive control, the monolayer center stained a maroon color, and ARS dye concentrated in the spindle ring with an intense crimson red color. GnHC1 successfully extracted the ARS dye and the coefficient of variation in $OD_{450}$ values ranged from 2% to 15% (FIG. 72B).

Results Summary

Morphology/ARS Staining

The negative control cultured in α-MEM w/10% FBS for 21 days did not develop spindle-like cells or a spindle ring along the edge. The positive control, after 20 days of induction with AA, β-glycerophosphate, and melatonin, MC3T3-E1 cells developed spindle-like cells and a spindle ring around the edge of the well (FIG. 72). ARS color and stain pattern of the cell monolayer were different between the negative and positive controls. The negative control monolayer failed to collect as much dye as the positive control and showed a uniform light pink color. The positive control monolayer center stained a maroon color and the ARS dye concentrated in the spindle ring into an intense crimson color (FIG. 72).

Treatment with AMP directly in culture medium obscured observation of cell monolayer in AMP and AMP with induction groups due to settlement of AMP particles. However, there was no observation of spindle rings along the well edge, and some cells along the edge showed spindle-like morphology. Openings through the AMP particles showed lack of monolayer underneath. ARS staining showed no difference in color or pattern between the AMP only group and the AMP with induction group.

Treatment with AMP through transwells did not produce AMP particles on top of the monolayer. Cell morphology was similar to the positive control, with spindle-like cells and spindle rings forming. The ARS staining color and pattern also resembled the positive control, with the background monolayer staining maroon and the ARS stain concentrating in the spindle rings in a crimson red color.

ARS Quantitation

GnHC1 was necessary and sufficient in extracting ARS staining from monolayer. Comparing the controls, there was a statistically significant 2-fold increase in $OD_{450}$ from the negative control to the positive control ($p<0.01$). Also, there was about a 6-fold increase in OD from the negative/positive control and AMP+ induction. There is a 6.5× increase in surface area from 96-well to 24-well, and this could account for the increase in OD. We also conducted ARS staining and quantitation on D20 of culturing, which increased the culturing period by 2 days and could have also increased mineralization.

AMP alone induced statistically significant 10-fold ($p<0.01$) and 3-fold ($p<0.01$) increase in $OD_{450}$ values from the negative and positive controls, respectively. Thus, AMP alone was sufficient in inducing and promoting differentiation. AMP with induction slightly decreased the $OD_{450}$ from AMP alone ($p<0.05$), but showed a 3-fold increase in OD from the positive control ($p<0.01$). The induction medium hindered differentiation and mineralization.

AMP delivered through transwells with induction showed an OD that was 3-times lower than AMP delivered directly with induction ($p<0.01$), and it showed a slightly lower OD than the positive control ($p<0.05$). AMP requires direct contact to promote differentiation. Without direct contact, AMP inhibits MC3T3-E1 mineralization.

Example 40. Effect of AMP on Induction of Osteogenesis in MSCs

Our results have shown that AMP promotes MC3T3-E1 differentiation when in contact with the pre-osteoblasts. However, it was unclear how AMP affects the growth and differentiation of less differentiated and less committed cell lines to the osteoblastic lineage, such as Mesenchymal stem cells (MSCs).

MC3T3-E1 cells are pre-osteoblasts, unipotent, and therefore require only supplements to push along their differentiation towards osteoblasts. Other progenitor cell lines such as embryonic stem cells (ESCs) or mesenchymal stem cells (MSCs) are less differentiated and are oligopotent and pluripotent, respectively. Thus, by studying the effect of AMP on MSCs derived from different areas of the human body, we can better understand the role of AMP in osteoblast differentiation programming and the factors involved. This investigation would allow us to narrow down which cell types AMP can affect and what effects it has on inducing osteogenesis in different progenitor cells.

Experimental Design

The following cell lines were used: MC3T3-E1 (ATCC, Manassas, Va.), Mesenchymal stem cells derived from human bone marrow cells (Lonza, Walkerfield, Md.), Limbal Niche cells (Tissue Tech, Miami, Fla.), human Amniotic Membrane (hAM) stromal cells (Tissue Tech, Miami, Fla.), and human umbilical cord vein endothelial cells (HUVEC) (ATCC, Manassas, Va.).

Cells were seeded at $3 \times 10^4$ cells/cm²/well in αMEM medium plus 10% FBS in 96-well plastic culture plates. Upon confluence, cells were induced to osteoblast differentiation by adding ascorbic acid, β-glycerolphosphate, and melatonin (AGM). For each condition, N=5 was tested. Total induction time=20 Days. Day 0 counted as the day of cell seeding, and induction followed after cell confluence. Each cell type had 3 experimental groups: negative control, positive control, and AMP treatment only. For AMP treatment, an AMP Concentration of 125 μg/ml was used. The medium (100 L) was changed every 3 days for culture time of 20 days. A negative control with AMP (without induction or cells) was added. ARS staining and quantitation were performed as described above on D20. Extracts were then read at 450 nm.

Results

Figure 74A:
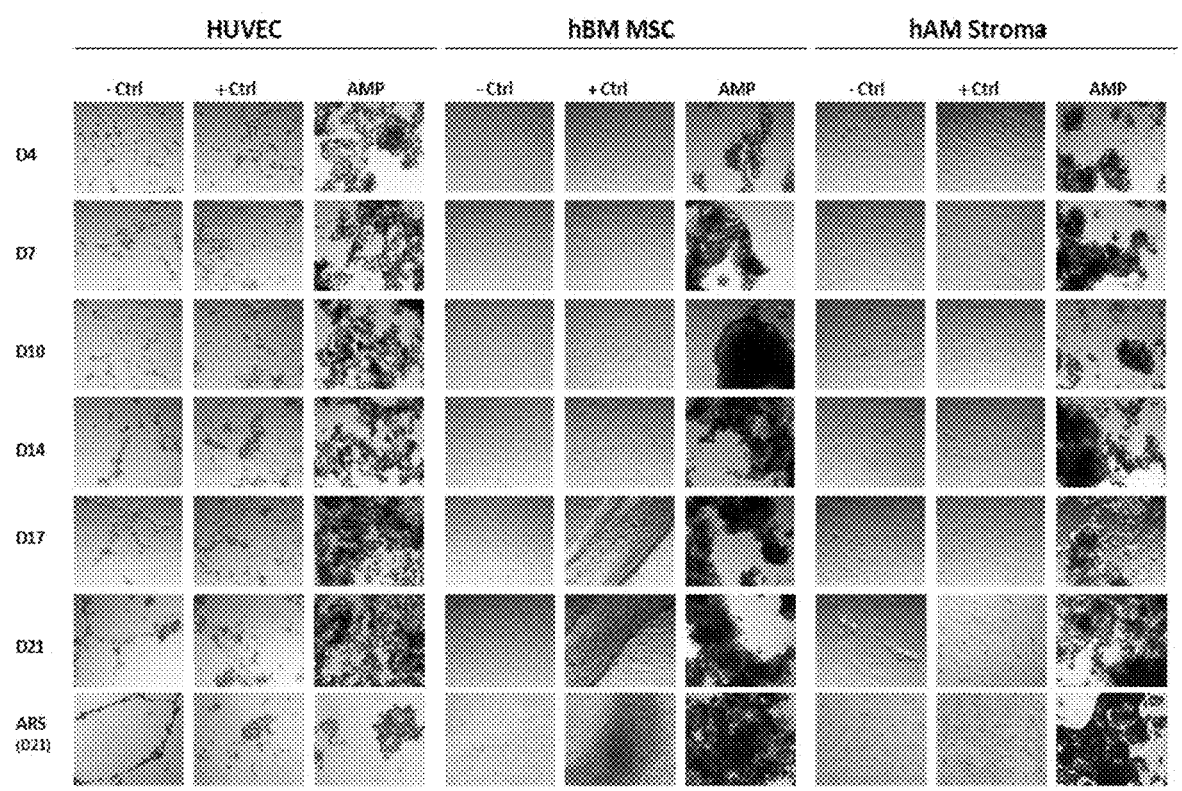
FIG. 74A-B exemplifies ARS staining and quantitation in MC3T3-E1 cells. (A) Phase contrast micrographs with or without ARS staining of HUVEC, hBMMSCs, and hAM stromal stem cells from Day 4 to Day 21. (B) Quantitation of ARS staining. The * symbol denotes statistical significance of $p<0.05$ when compared to the negative control.

HUVEC cells formed a net-like pattern of cell growth by Day 4 (FIG. 74A). However, there was significant cell death with dead cells settled on top of the network of cells until Day 21. Most of the HUVEC cells could not be fixed with 10% Paraformaldehyde and the few cells stained with ARS showed a dark brown color. Although AMP settled on top of the HUVEC cells and covered the network of cells, the AMP particles detached from the plastic well with the cells upon ARS staining; the few remaining AMP particles also stained a dark brown.

hBM MSCs, without induction, maintained a long fibroblastic shape (FIG. 74A). With induction, MSCs became elongated with more raised cell edges by Day 4. By Day 10, induced MSCs developed spindle-like cells, and cells grew overlapping layers with each other on the monolayer. On Day 17, the overlapping spindle cells formed a dense ring about 5 mm from the center of well. ARS staining showed that the un-induced MSCs monolayer stained a cream color, and the spindle ring stained a red-orange color. AMP-treated MSCs contained AMP particles that covered the monolayer. With time, the monolayer retracted around concentrated areas of AMP particles. ARS staining showed a deep red-brown color.

hAM stromal stem cells, without induction, maintained a rectangular shape (FIG. 74A). By Day 4, with induction, cell morphology changed and cells elongated with some developing fusiform shapes. AMP particles settled and covered some of the monolayer by Day 4 in AMP-treated stroma cells. The cells not covered by AMP particles in Day 4 were rectangular in shape. By Day 17, cells not covered by AMP particles were elongated similar to induced cells in the positive control. By Day 21, AMP particles covered the well and cell morphology could not be observed. ARS staining showed the un-induced cells staining a cream color, while the induced cells stained a light pink color. The AMP-treated cells stained a deep red-brown color similar to the AMP-treated hBM MSCs.

Figure 74B:
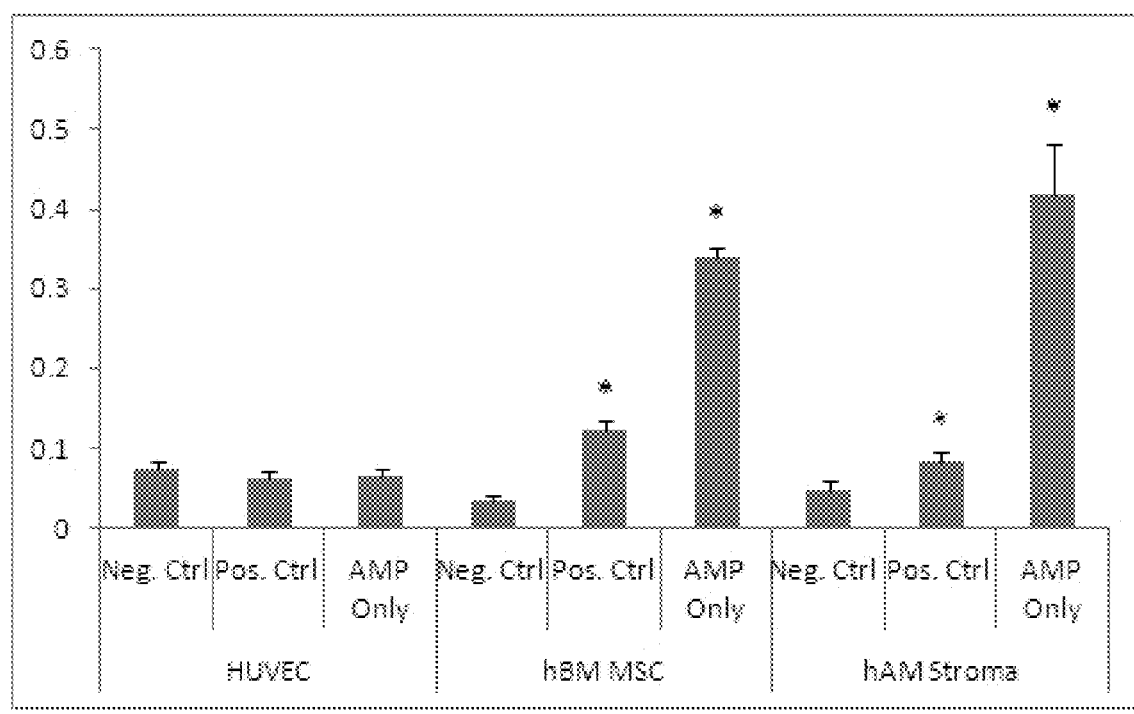

The extract with 4M GnHCl yielded the coefficient of variation in $OD_{450}$ values ranged from 2% to 15% (FIG. 74B).

Results Summary

The results indicated that no mineralization was noted in the negative control of HUVEC with either inductive agent or AMP. For both hBM MSC and hAM stromal stem cells, mineralization was promoted by the inductive agent, which was less than that promoted by AMP.

Figure 75:
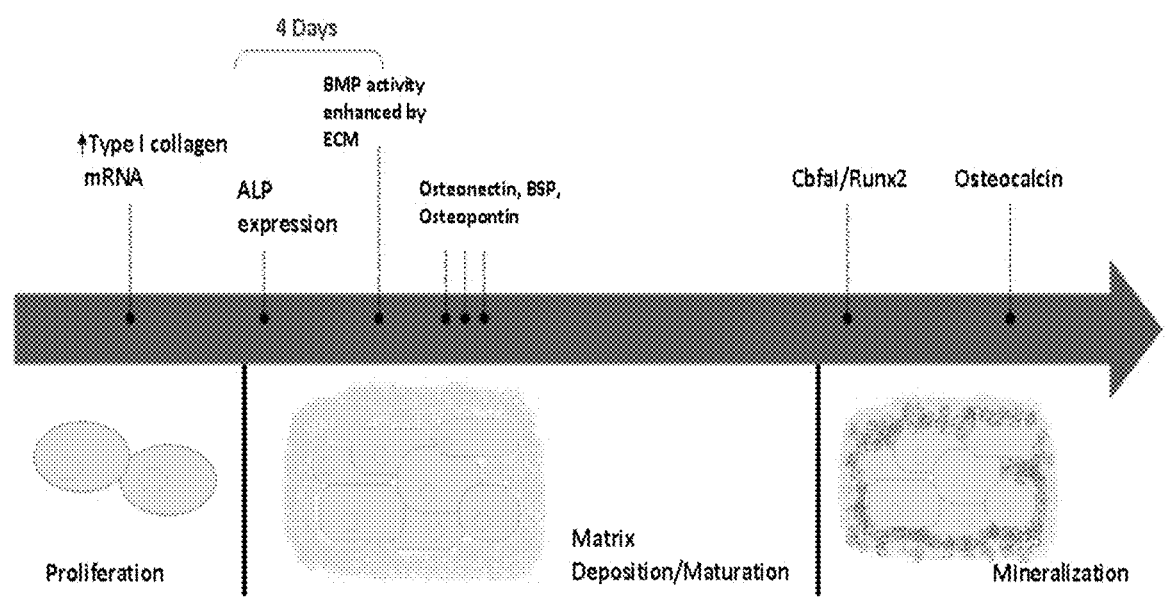
FIG. 75 illustrates a timeline of osteogenesis in MC3T3-E1 cells.

Example 41. Effect of AMP on Mineralization and Cell Proliferation During MC3T3-E1 Differentiation MC3T3-E1 cells undergo three main stages before becoming a mature osteoblast: proliferation, matrix deposition/maturation, and mineralization (FIG. 75). Our results have shown that AMP promotes mineralization in MC3T3-E1 cells. In viewing the ARS staining, it shows that cells treated with AMP stained a darker and denser (FIG. 72) than the positive and negative controls. Additionally, there was a lack of monolayer underneath the AMP particles (FIG. 77) when the AMP particles covered the monolayer. One possibility was that AMP is acting as a scaffold for MC3T3-E1 cells and this interaction in the 3D matrix allowed cells to grow and mineralize. Thus, AMP may be promoting mineralization by increasing proliferation of MC3T3-E1 cells.

Experimental Design

MC3T3-E1 cells were seeded at $3\times10^4$ cells/cm$^2$/well in 24-well with αMEM medium plus 10% FBS as described above. Upon confluence, cells were induced to differentiation by adding ascorbic acid, β-glycerolphosphate, melatonin. For each condition, N=3 was tested. Day 1 counted as the day of cell seeding, and induction followed after cell confluence. Total induction time=20 Days. Four time-points were sampled: D1, D2, D7, D10, D13, D20. Each time-point had four groups: negative control, positive control, AMP treatment only, AMP+(w/induction). The AMP concentration employed was 125 µg/ml.

For the proliferation assay measured by MTT assay, the culture period was 9 days for proliferation. 4 timepoints were sampled: D1, D2, D4, and D9. Each time-point had 3 groups: cells only, AMP only, AMP+cells. The AMP concentration employed was 125 µg/ml.

Results

Mineralization

On Day 1, cells were seeded for 24 hours and were not treated with induction medium or AMP (FIG. 76). Cells were round and appear more raised on the monolayer. ARS staining showed a light beige color with little to no mineralization. On Day 2, without induction, negative control cells became hexagonal. ARS stained the monolayer a light peach color. With induction, positive control cells looked identical to negative control with little mineralization and ARS staining a light peach color. Treatment with AMP caused MC3T3-E1 cell morphology to change, and fusiform shaped cells and spindle cells were observed. ARS staining showed increase in mineralization from Day 1 and the monolayer stained a light pink color. The area where AMP particles settled, however, stained a reddish-brown color. AMP treatment with induction also changed some cell morphology. Fusiform shaped cells were present and the monolayer also stained a light pink color with areas around AMP particles staining reddish-brown. On Day 7, negative control cells appeared more hexagonal and the cell boundaries are more defined. There is an increase in mineralization and the monolayer stained a light beige color. The positive control, with induction, developed spindle shaped cells and spindle rings. ARS also stained a deep pink color with more mineralization. Treatment with AMP and AMP with induction caused AMP particles to settle and cell morphology could not be viewed. A cell monolayer with individual cells could not be seen. ARS showed areas around AMP particles staining a red-brown color and the monolayer staining a light pink. GnHCl successfully extracted the ARS dye and the coefficient of variation in $OD_{450}$ values ranged from 6% to 16%.

Results Summary

Figure 76A:
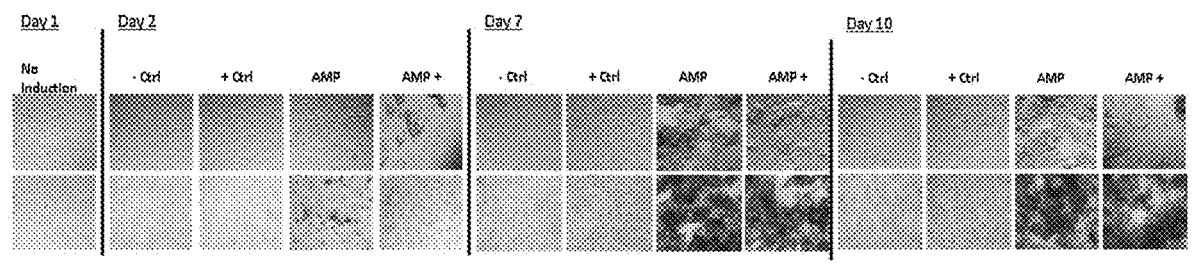
FIG. 76A-B exemplifies ARS staining and quantitation in MC3T3-E1 cells. (A) Cell morphology and ARS staining of MC3T3-E1 cells treated with AMP (Day 1, 2, 7, 10). (B) ARS Quantitation of MC3T3-E1 cells treated with AMP (Day 1, 2, 7, 10) The * symbol denotes statistical significance of $p<0.05$.

Negative control MC3T3-E1 cells show increase in ARS staining and therefore mineralization with increasing cell culturing after Day 2 (FIG. 76). Similar to previous results, positive control MC3T3-E1 cells cultured with induction medium underwent cell morphology change and developed fusiform shaped cells and spindle rings by Day 7 (FIG. 76). After 1 Day of AMP treatment (D2), with or without induction, a change in cell morphology could be seen. Cells become spindle and even fibroblast shaped (FIG. 76A). This change was not observed in the negative or positive control. Additionally, this change was observed in induced MC3T3-E1 cells after at least 4 days of culturing (FIG. 76A).

Figure 76B:
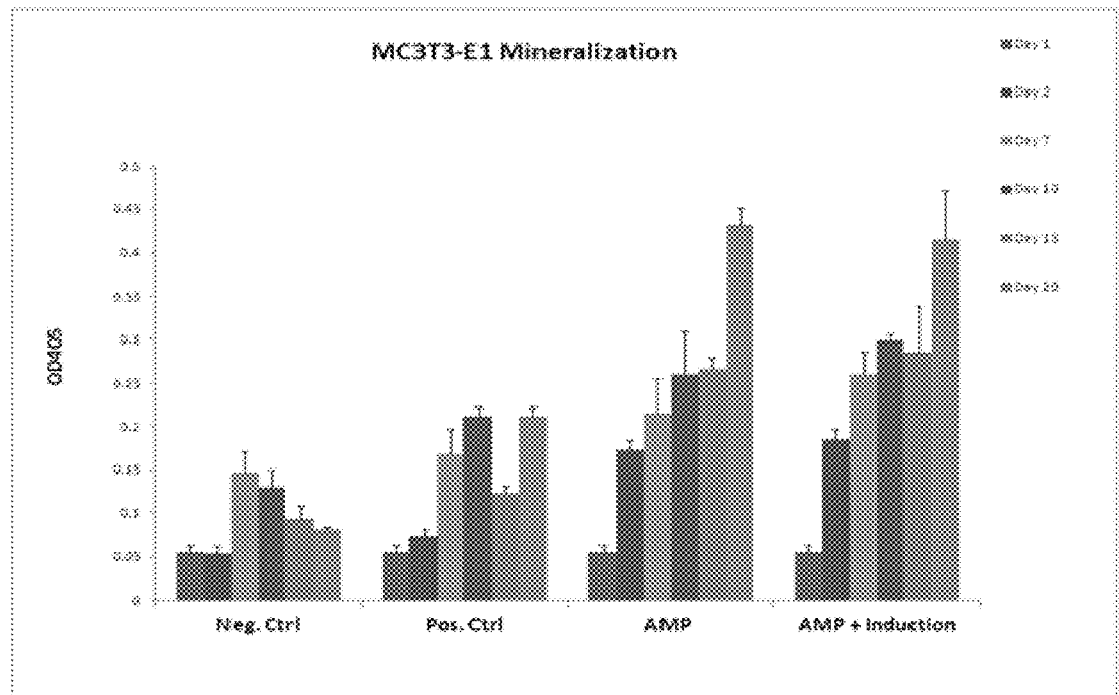

AMP treated and AMP with induction treated cells showed statistically significant increase in mineralization from the positive control by Day 2, as shown through ARS quantitation (FIG. 76B). The monolayer stained a light pink color, but small areas where AMP particles settled showed increased mineralization and stained a deep red-brown color (FIG. 76A). This increase in mineralization continued throughout the culturing period.

There was no increase in promoting mineralization with AMP only when compared to AMP with induction treatment.

Proliferation

To determine whether AMP promoted mineralization via promoting cell proliferation, MC3T3-E1 cells were seeded at $3 \times 10^4$ cells/cm$^2$/well in 96-well with αMEM medium plus 10% FBS. Upon confluence, the AMP group was treated with fresh 125 μg/ml AMP added every 3 days in the culture medium. The MTT assay was conducted on Day 1, 2 and 4, while the BrdU assay was conducted on Day 1, 2, and 16.

Figure 77A:
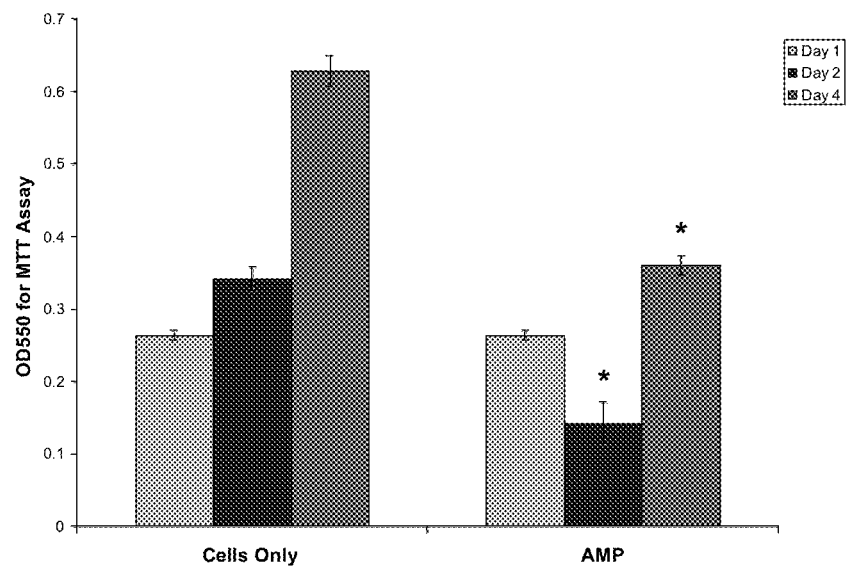
FIG. 77A-B exemplifies a timeline of cell viability and proliferation through MTT assay. (A) MTT Assay of MC3T3-E1 cell viability and metabolic activity on Day 1, 2, and 4. The * symbol denotes statistical significance of $p<0.05$ from Day 1. (B) BrdU Assay of MC3T3-E1 cell proliferation on Day 1, 2, and 16. The * symbol denotes statistical significance of $p<0.05$ from Day 1.
Figure 77B:
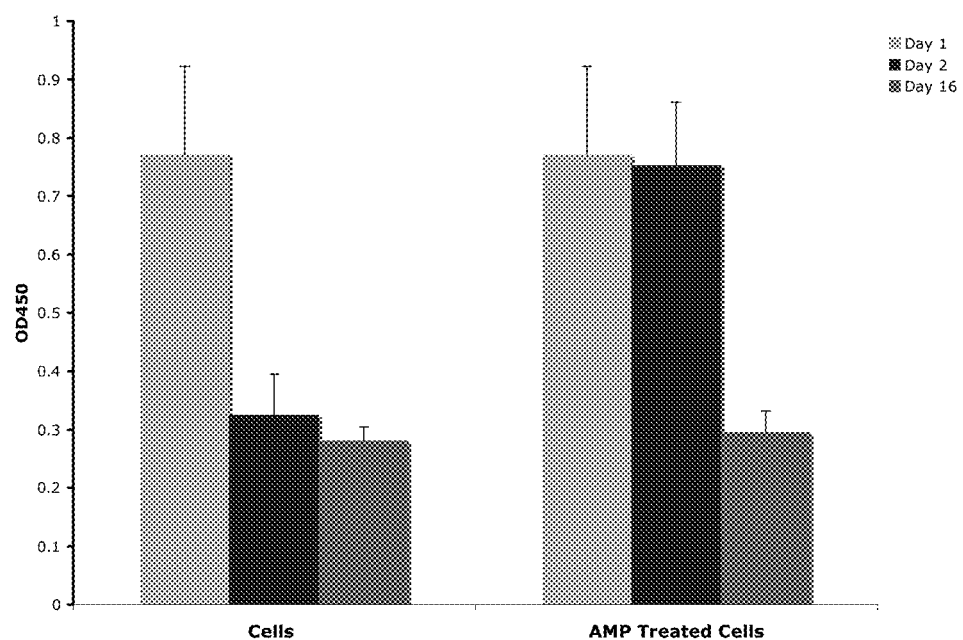

In untreated MC3T3-E1 cells, cell viability increases from Day 1 to Day 4 (FIG. 77A). In AMP-treated cells, cell viability decreased on Day 2 and then more than doubled on Day 4, following the trend of the cells only group. BrdU assay showed decrease in cell proliferation following Day 1 in both the cells only group and AMP-treated cell group (FIG. 77B). Cell proliferation in the cells only group decreased by more than half by Day 2 and continued to decrease on Day 16. In AMP-treated cells, cell proliferation showed a statistically significant decrease only by Day 16. These findings suggest that AMP did not promote proliferation during the culturing period of 16 days.

Results Summary

Cell viability increased in MC3T3-E1 cells from Day 1 until Day 4 as shown through MTT assay. AMP treated MC3T3-E1 cells showed a decrease in cell viability from Day 1 to Day 2 but followed an upwards trend like the untreated cells. However, cell viability on day 4 in the AMP-treated cells were around half of the untreated MC3T3-E1 cells. Cell proliferation, as measured through BrdU, decreased from Day 1 all the way to Day 16. Unlike the AMP-treated cells, cell proliferation decreased by more than half by Day 2 in the untreated MC3T3-E1 cells. By Day 16, AMP-treated and untreated MC3T3-E1 cells exhibited the same levels of cell proliferation.

Example 42. Identification of Genes Expressed During the Early Stages of Osteogenesis in AMP-Treated MC3T3-E1 and hBM MSCs Human bone marrow mesenchymal stem cells (hBMMSCs) are multipotent and can differentiation into multiple tissue types such as osteoblasts, chondrocytes, and adipocytes (Born, 2012 *J Cell Biochem.* 113(1):313-21.). When transplanted in vivo, they are capable of forming new bone, and in vitro, hBM MSCs can be directed towards Osteogenesis by cultivating in β-glycerophosphate, ascorbic acid, vitamin $D_3$, and low doses of dexamethasone. Osteogenesis for hBMMSCs is regulated by the expression of osteoblast-associated genes, including specific transcription factors, adhesion molecules and proteins of the ECM (Born (2012) *J Cell Biochem.* 113(1):313-21; Vater (2011) *Acta Biomater.* 7(2):463-77.). The progression to mature osteoblast mirrors that of MC3T3-E1 and occurs with the loss of cellular expansion capacity, the increase of osteogenic markers expression, and the mineralization of the ECM (Born (2012) *J Cell Biochem.* 113(1):313-21). First, cells initiate the synthesis of the ECM with expression of collagen I (Col I). Simultaneously, bone-specific alkaline phosphatase (bALP) expression increases and by Day 4, significant increase in ALP levels in the induced cells ($6 \times 10^4$ cells/60 mm culture dish) from the control could be observed (Born (2012) *J Cell Biochem.* 113(1):313-21; Jaiswal (1997) *J Cell Biochem.* 64:295-312). As differentiation continues, cells produce proteins such as bone sialo protein (BSP), Osteopontin, Osteonectin and osteocalcin. Finally, mineralization of the ECM, much like osteogenesis in MC3T3-E1 cells, indicates a mature osteoblast.

In this example, genes and transcription factors expressed in the early stages of Osteogenesis in three cell lines: MC3T3-E1 cells and hBM MSC cells were determined. Our results have shown that a statistically significant increase in mineralization could be seen in AMP-treated MC3T3-E1 cells compared to the positive control by Day 2 (Day 1 of treatment). Therefore, the experiment focused on the early stages of Osteogenesis to identify AMP's effect on specific genes after treatment.

Experimental Design

MC3T3-E1 or human Bone Marrow MSC cells were seeded at $3 \times 10^4$ cells/cm$^2$/well in 24-well plates with αMEM medium plus 10% FBS as described above. Upon confluence, cells were induced to differentiation by adding ascorbic acid and β-glycerolphosphate. For each assay at each timepoint, N=2 was tested. There were 4 time-points sampled: D0 (after confluence but before induction/treatment), D1, D2, D4, and D6. Each time-point had three groups: negative control, positive control, AMP treatment only. AMP concentration used was 125 μg/ml.

Results hMSC Expression

Figure 78A:
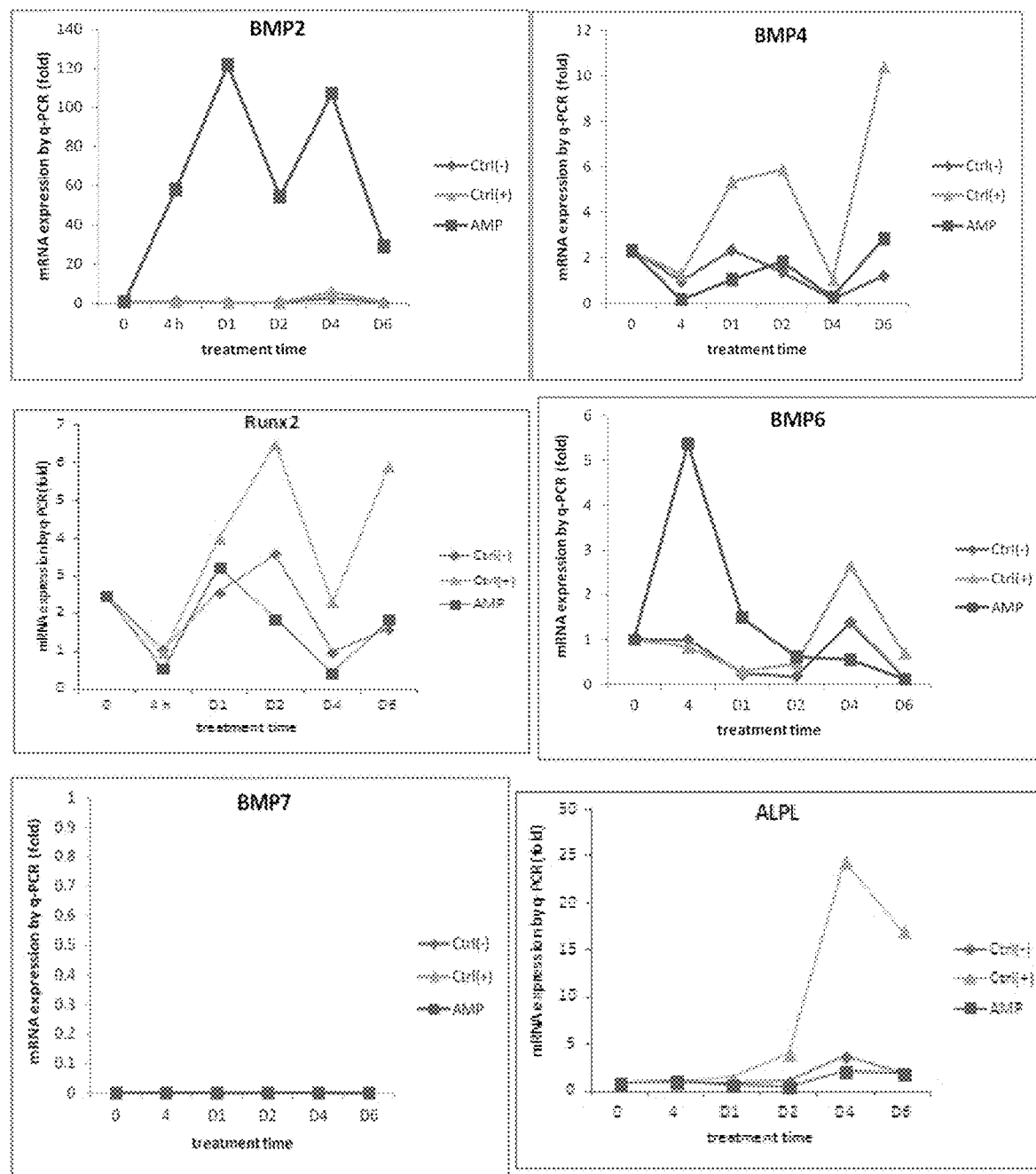
FIG. 78A-B exemplifies mRNA expression by QPCR for various genes tested following differentiation induction with or without AMP treatment. (A) hMSC and (B) MC3T3-E1 cell expression.
Figure 78A:
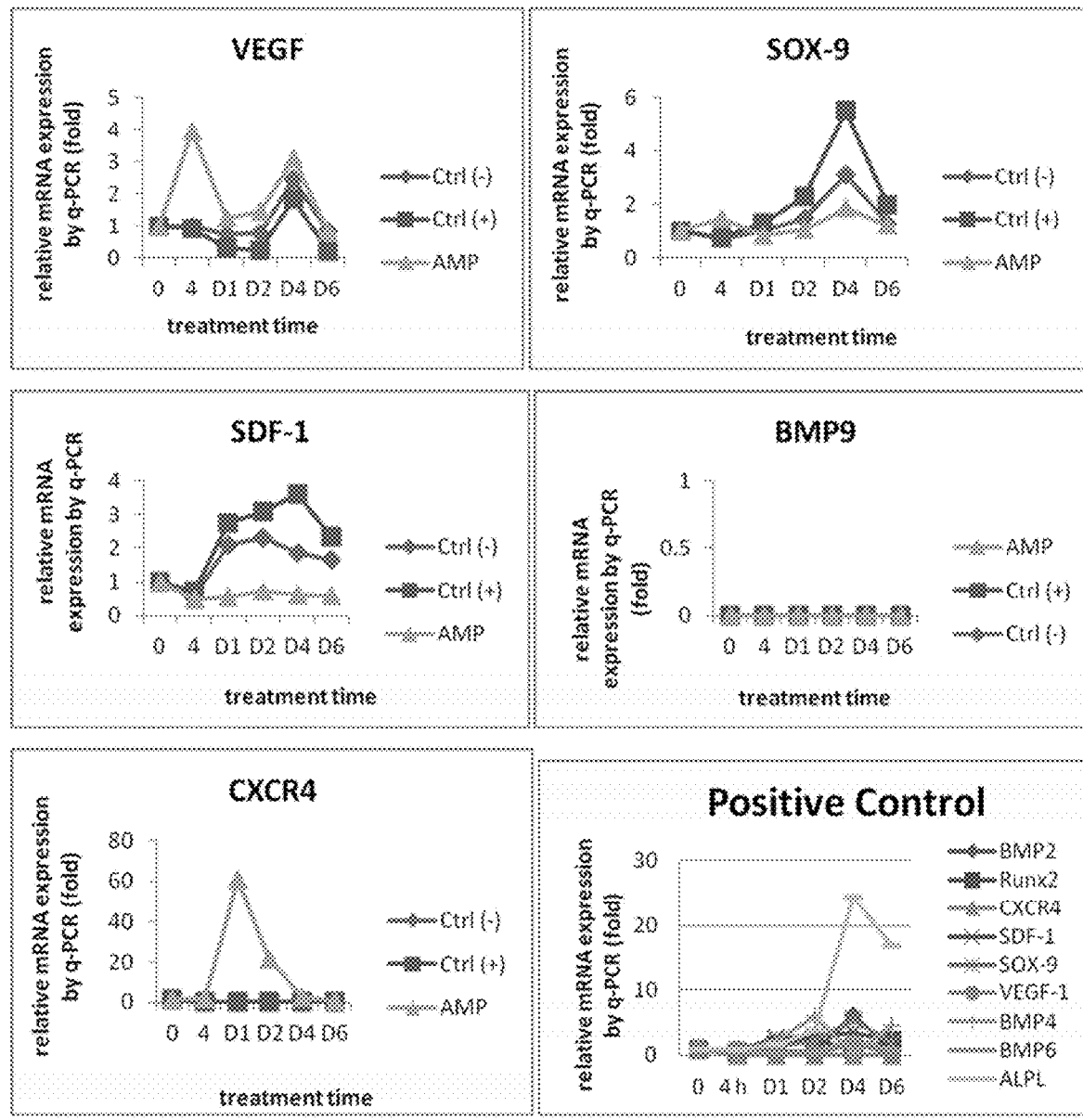
Figure 78B:
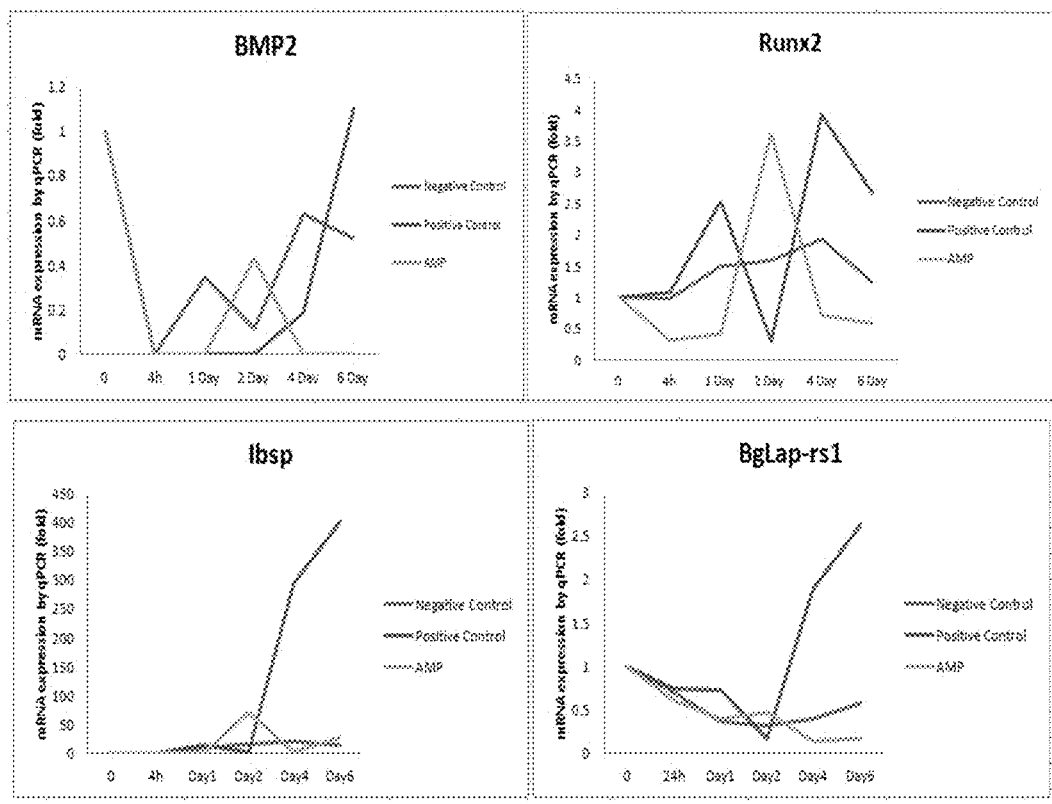

AMP induces robust endogenous expression of BMP2 and BMP6 transcripts within 24 hrs of culturing (60 and 5 folds, respectively) (FIG. 78A). BMP2 reached its peak at D1 (120 folds) and maintained a high level (between 60 to 10 folds) until D4 before showing a decline. In contrast, BMP6 peaked at 4 h and then showed a gradual decline from D1 on. As a comparison, AMP did not change expression level of BMP4, BMP7 and BMP9. Nonetheless, AG induced a mild upregulation of BMP2 and BMP6 (1-2 fold) only at D4 and notable upregulation of BMP4 (4-10 folds) after D1. As a comparison, AGM did not change expression of BMP7 and BMP9 either.

Runx2 peaked at D1 for AMP but D2 for AGM (FIG. 78A). Both groups then had a gradual decline followed by another peak at Day 6. Runx2 induces the differentiation of multipotent mesenchymal cells into immature osteoblasts, directing the formation of immature bone. Furthermore, Runx2 triggers the expression of major bone matrix genes during the early stages of osteoblast differentiation, but Runx2 is not essential for the maintenance of these gene expressions in mature osteoblasts (Komori (2010) *Adv Exp Med Biol.* 658:43-9).

Both ALP and Sox9 peaked at D4, with the level upregulated by AMP being less than AGM (FIG. 78A). This trend is consistent with the view that ALP and Sox9 are downstream of Runx2. ALP is expressed in the early phase of osteogenesis and creates an alkaline environment which causes calcium to come out of solution and crystallize.

AMP upregulated VEGF which peaked at 4 h and D4 but AGM upregulated VEGF only at D4 (FIG. 78A). AMP upregulated CXCR4 while AGM upregulated SDF1 at D1, with a rapid decline for the former but a slower one for the latter. Kortesidis et al. ((2005) *Blood.* 105(10):3793-801) suggest that SDF-1 may act to localize primitive uncommitted BMSSC populations within their perivascular niche until required to proliferate and differentiate in response to environmental cues that may act to disrupt SDF-1/CXCR4 interactions. In 7 preconditioning experiments of MSCs, expression of CXCR4 is normally around 2 to 4 fold increase Cencioni et al. ((2012) *Cardiovasc Res.* 94(3):400-7) however our results with AMP showed a 60 fold increase after Day 1.

SDF-1 expression was very high in all groups of the MSCs, although it does not appear so in FIG. 78A. SDF-1 was seen around Cycle 20 whereas GAPDH was seen around Cycle 17. From the literature it is known stromal cell-derived factor-1 activates adhesion molecules on progenitor cells, and mAb against SDF-1 inhibits transendothelial migration of hematopoietic progenitor cells (Imai et al. (1999) *Blood* 93(1):149-56). SDF-1 activates CXCR4+/CD34+ cells and leads to their adhesion and transendothelial migration (Bhakta et al. (2006) *Cardiovasc Revasc Med.* 7:19-24.). GAPDH expression did increase in the AMP group from Day 2 to Day 6, therefore one would assume proliferation. This trend was not seen in the other samples. Furthermore, BMP9 was not detectable (after Cycle 40), CXCR4 was detected around Cycle 33, VEGF was detected around Cycle 19, and SOX-9 was detected around Cycle 27. BMP4 was detected around Cycle 28, BMP7 was not detected (after Cycle 40), BMP2 was detected around Cycle 20, Runx2 was around Cycle 25, BMP6 was detected around Cycle 27, and ALPL was detected around Cycle 24.

MC3T3-E1 Expression

It is known that MSC are multipotent as where osteoprogenitors are already pushed farther down the lineage pathway and should only produce bone formation. Contrary from what was expected, BMP2 expression was barely expressed in Mouse cells especially compared to human MSC (FIG. 79). BMPs have been shown to be inefficient in promoting osteogenesis in human, yet are more than capable in Mouse cells (Osyzka et al. (2004) *Cells Tissues Organs.* 176(1-3):109-19., Skarzynska et al. (2011) *Connect Tissue Res.* 52(5):408-14). Expression of BMP-2 is not prominent in MC3T3 cells as indicated by gene array (Beck et al. (2001) *Cell Growth & Differentiation* 12: 61-83). The differences seen between human and rodent cells may indicate that, unlike Smad1 in human cells, rodent Smad1 does not undergo ERK linker phosphorylation during osteogenesis. Alternatively, Smad1 activity in rodent cells may not be suppressed by ERK-mediated linker phosphorylation (Skarzynska et al. (2011) *Connect Tissue Res.* 52(5):408-14). BMP-induced osteogenesis in poorly responsive human MSC requires modulation (inhibiting) of ERK and phosphatidylinositol 3-kinase (PI3-K) pathways; inhibiting the insulin/IGF-I-activated PI3-K/AKT pathway decreases BMP-induced alkaline phosphatase and osteopontin expression in serum-free cultures of human MSC, but increases BMP activation of Smads (Osyzka et al. (2005) *Endocrinology.* 2005 (8):3428-37).

Runx2 also was shown to be different in the MC3T3 cells compared to hMSCs. There is clearly an incident on Day 2 that causes an upregulation of genes in MC3T3 cells. The AGM groups appeared to have opposite effects of the AMP group, which may be related to Pi3K, MAPK pathways. Ibsp, also known as Bone Sialprotein (BSP), is upregulated on Day 2 in AMP but not expressed other times. In the positive group, BSP is highly expressed after Day 2.

Bglap-rsl, also known as Osteocalcin (OCN), is also upregulated on Day 2 in AMP but not expressed elsewhere. Consistent with BSP, OC is highly expressed after Day 2 in positive group. Through analysis of these results one would think BSP and OCN need to be upregulated since they are known to be expressed by mature osteoblasts. Runx2 regulates the expression of ColI, BSP and OCN in MC3T3, which is consistent with our results. Runx2 increases on Day 2, as does BSP and OCN, and is not expressed elsewhere. In summary, AMP downregulates osteogenic gene expression but promotes mineralization.

Example 43. Effect of nHC-HA/PTX3 Purified from AM on Mineralization Using MC3T3-E1 Model System Previous experiments have clearly demonstrated AMP's unique properties to promote mineralization independent of inducing agents such as ascorbic acid, β-glycerol phosphate, and melatonin (AGM). In these experiments, AMP was added to the murine osteoblast progenitor cell line (MC3T3) in the presence or absence of AGM to determine the potency of the AMP. Alizarin Red Staining with the GnHC1 extraction method was also used at multiple time points for further quantification. It was concluded AMP not only enhanced mineralization independent of AGM, but also enhanced mineralization at a faster rate. Further investigation of AMP showed that the osteoinductive effect exhibited by AMP requires direct cell contact. That is, under direct contact with AMP, cells will have accelerated and enhanced mineralization without the introduction of AGM.

Previous studies showed that MC3T3-E1 differentiation under induction can be subdivided into three stages, i.e., proliferation (day 1 to 9), ECM formation (day 9 to day 16), and mineralization (deposit minerals in formed ECM) (day 16+) (Quarles et al. (1992) *J Bone Miner Res.* 7(6):683-92.; Hong et al. (2010) *Exp Cell Res.* 316(14):2291-300). However our previous Aim 4 has shown mineralization can be easily detected within 7 to 10 days using AMP. Therefore we will perform our ARS assay at day 8 in order to determine if nHC-HA/PTXS purified from AM is responsible for promoting mineralization. Day 8 was picked because results should be noticeable as seen in Aim 4 and the media will only have to replaced on day 0, day 3 and day 6.

It is already known that nHC-HA/PTX3 is responsible for amniotic membrane's known anti-inflammatory, anti-angiogenic and anti-scarring therapeutic actions. It is our hypothesis that immobilized HC-HC/PTX3 is responsible for AMP's effect on promoting mineralization. Because it also contains HA, we will also compare nHC-HA/PTX3 to HA to see the putative effect is uniquely present in nHC-HA/PTX3 but not in HA. Hyaluronan (HA) is an unsulfated glycosaminoglycan consisting of a single repeating disaccharide unit. It is an important component in connective tissue promoting matrix assembly and tissue hydration. Luben et al speculated HA acts as a calcium binding agent to act as a barrier to the diffusion of enzymes away from the resoprtion site or to regulate the mobility of osteoclasts. Stern and Raisz stated "hyaluronic acid seems to be the most appropriate to study because it has been clearly linked to bone resorption. By the nature of its hygroscopic properties HA can occupy 10,000 times its own volume. Thus, HA allows proliferating cells to avoid inhibitory contacts. Hyaluronic acid synthesis precedes mitosis and dissociates the dividing cell from its substratum, permitting cell movement (Balazs (2001) *Am J Physiol Regulatory Integrative Comp Physiol* 280: R466-R472).

Experimental Design:

Murine MC3T3-E1 cells (C-136) were taken from liquid nitrogen freezer and grown on 100 mm dish (five dishes) in αMEM medium (10 ml per 100 mm dish) plus 10% FBS changed every 3 days till 80% confluence ~1.5×10$^6$ cells [4*(3.1×10$^4$)*9=1,116,000 cells]. Cells were then seeded at 3.1×10$^4$ cells/cm$^2$/96 plastic well. Medium (100 ul per 96 well) was replaced every 2-3 days, i.e., at Day 0 (Wed), 2

(Fri), and 5 (Mon) and cultures will be terminated at Day 8. N=4 was tested per condition.

A summary of the Groups was as follows:
Control Groups:
Negative Control: Nothing on conventional 96 well plate
Positive Control 1: AGM on conventional 96 well plate
Positive Control 2: 125 µg/ml of AMP added every 3 days on conventional 96 well plate
Experimental Groups:
Negative Control: Covalink-NH 96 Well Plate
Experimental Group 1: AGM added every 3 days added to Covalink-NH 96 Well Plate
Experimental Group 2: 20 µg/ml of HA immobilized on Covalink-NH 96 Well Plate
Experimental Group 3: 20 µg/ml of HA immobilized on Covalink-NH 96 Well Plate with AGM added every 3 days (H-124)
Experimental Group 4: 20 µg/ml of nHC-HC/PTX3 immobilized on Covalink-NH 96 Well
Experimental Group 5: 20 µg/ml of nHC-HC/PTX3 immobilized on Covalink-NH 96 Well Plate with AGM added every 3 days For the AGM groups: On Days 0 and 3, Osteogenesis induction media #1 (ascorbic acid, β-glycerolphosphate) was replaced. On Day 6, Osteogenesis induction media #2 (ascorbic acid, β-glycerolphosphate, melatonin) was replaced. On Day 0, only 0.2 ml of 10× Induction media was made. On Days 3 and 6, 10 ml of the Osteogenesis induction media was prepared fresh. Instructions for Induction Medias obtained from In Vitro Osteogenesis Assay Kit (Millipore).

Induction media #1: 9.88 ml of αMEM medium plus 10%, 20 µl Ascorbic Acid 2-Phosphate 500× (Millipore, Part. 2004011), 100 µl Glycerol 2-Phosphate 100× (Millipore, Part. 2004011).

Induction media #2: 9.87 ml of αMEM medium plus 10%, 20 µl Ascorbic Acid 2-Phosphate 500× (Millipore, Part. 2004011), 100 µl Glycerol 2-Phosphate 100× (Millipore, Part. 2004011), 10 µl Melatonin 50 uM (Millipore, Part. 2004011). Add 500 ul dH20 to 6 ug of melantonin supplied.

ARS Staining and Quantification was performed as described above. Pictures were taken at 10× using Nikon Eclipse CFI60.

Results

Figure 79A:
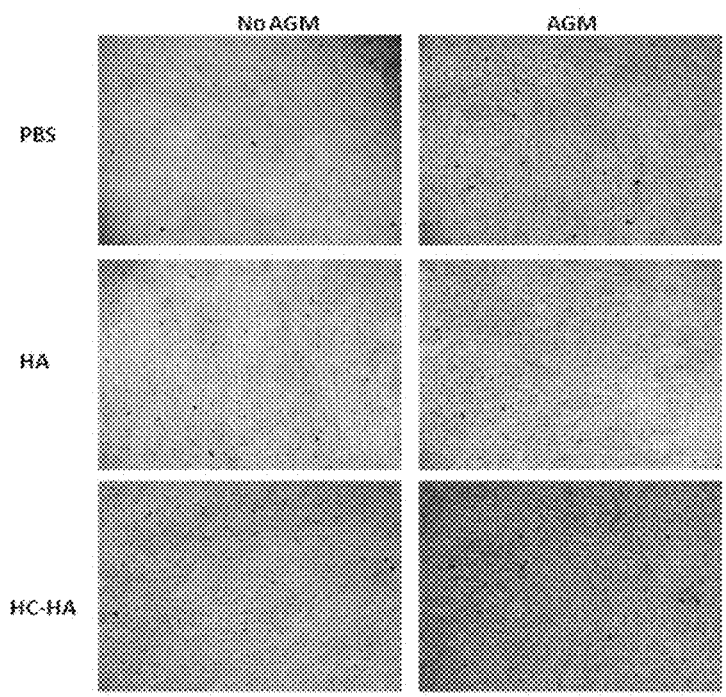
FIG. 79A-C exemplifies phase microscopy and quantitation of ARS Assay. MC3T3-E1 cells deposited mineralization for the duration of the experiment, 8 days. ARS was then used for qualitative analysis. (A) CovaLink-NH 96-well plate in which the PBS, HA, and HC-HA were immobilized. (B) Conventional 96-well plate with the negative control and AGM (inductive agents) and AMP as positive controls. (C) Quantitation of ARS assay. The * symbol denotes statistical significance of $p<0.05$ from Day 1.
Figure 79B:
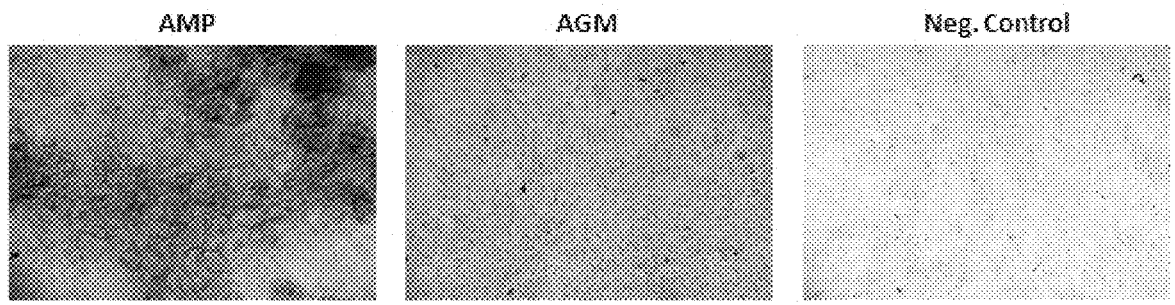
Figure 79C:
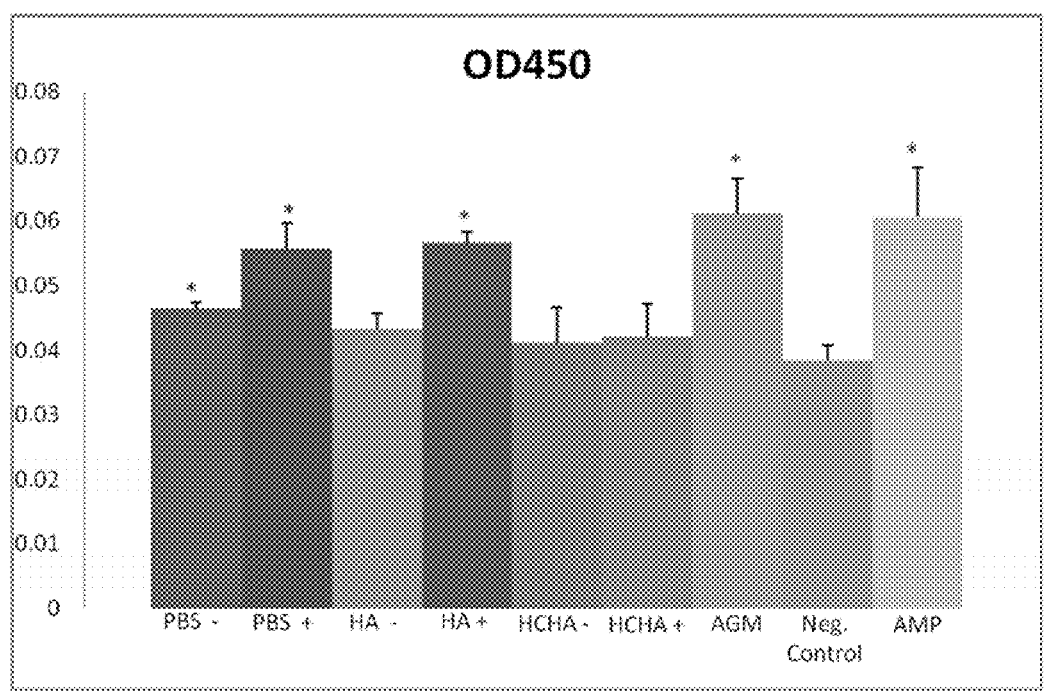

The MC3T3-E1 cells were cultured on the different well plates for 8 days. On Day 8, phase contrast pictures were taken of the wells and can be seen below (FIG. 79A, 79B). Negative control wells showed round cells and the ARS stained a very light pink. Wells with induction media showed much brighter red color and spindle cells were seen on the periphery of the wells. The ARS staining was seen more in abundance in the outer periphery ring. Treatment with AMP showed a crimson red after ARS treatment and the cells were rather hard to see because the AMP settled on top of them. No aggregation was seen during the experiment (even though aggregation has been seen with other cell types on immobilized HC-HA.) Microscopy pictures were taken on Days 6, 7 and 8.

Guanidine hydrochloride extraction method was used on Day 8 and the well plates were incubated overnight. GnHCl was able to extract the ARS dye although it was hard to tell by the naked eye; all the wells seemed to have the same light pink/red color. The ARS extraction was quantified at 450 nm because the plate reader did not have the capabilities of reading at 490 nm or closer. Results can be seen in FIG. 79C. The * symbol denotes statistical significance of $p<0.05$. (+ denotes with AGM, − denotes without AGM)

In agreement with previous results, AMP was able to successfully promote mineralization without the need of induction agents. This experiment only lasted 8 days so the results aren't as noticeable as in Aim 4 which lasted 20 days. All conditions that were treated with AGM showed an increase in mineralization from their negative control counterpart. Our results also show that immobilized nHC-HA/PTX3 is not responsible for promoting mineralization in AMP. Therefore there must be another active component of AMP that is promoting mineralization.

Example 44. Effect of HC-HA/PTX3 (PBS) and HC-HA/PTX3 (Gn) on Endochondral Ossification Master transcription factors for osteogenesis and chondrogenesis (Runx2 and Sox9, respectively) were expressed by cells in both HC-HA conditions through the 14 day culture period. HC-HA/PTX3, both soluble and insoluble, were able to promote the expression of BMP2 and to an extent BMP6 without osteoinductive agents AGM (i.e., ascorbic acid, glycerolphosphate, melatonin) commercially provided (see below).

Chondrogenic marker Collagen 2 was highly expressed by HC-HA/PTX3 (PBS) without the need for AGM. HC-HA/PTX3 (Gn) with the addition of AGM also was able to upregulate Collagen 2. Osteogenic markers (BSP, ALPL, Osx) were upregulated by the HC-HA conditions on Day 14 thus confirming a transition from a cartilage to bone genotype.

Experimental Design:

Culture conditions: Human bone marrow-derived mesenchymal stem cells purchased from Lonza (Basel, Switzerland) were taken from liquid nitrogen freezer and grown on 100 mm dish in the same medium changed every 3 days till 80% confluence. Cell culture medium was αMEM containing 10% fetal bovine serum and antibiotics. Culture medium (10 ml per 100 mm dish) was changed every 3 days, and cells subpassaged at 80% confluence until they reach the above desirable cell numbers. For the experiment the cells were seeded at $3.1\times10^4$ cells/96 plastic well on immobilized HA, HC-HA (PBS) or HC-HA (Gn) with or without osteoinductive agents Ascorbic Acid 2-Phosphate, Glycerol 2-Phosphate and Melatonin (AGM). The final concentration of AGM added was 0.2 mM, 10 mM and 50 nM, respectively. AGM was added simultaneously when cells were seeded (D0) and mRNA was extracted at Days 1, 7 and 14. In order to quantify gene expression, qPCR was performed. Culture medium (100 ul per 96 well) was replaced every 3 days.

A summary of the experimental Groups was as follows:
Negative Control: Covalink-NH 96 Well Plate
Experimental Group 1: AGM added every 3 days added to Covalink-NH 96 Well Plate
Experimental Group 2: 20 µg/ml of HA immobilized on Covalink-NH 96 Well Plate
Experimental Group 3: 20 µg/ml of HA immobilized on Covalink-NH 96 Well Plate with AGM added every 3 days
Experimental Group 4: 20 µg/ml of 4× nHC-HC/PTX3 immobilized on Covalink-NH 96 Well Plate
Experimental Group 5: 20 µg/ml of 4× nHC-HC/PTX3 immobilized on Covalink-NH 96 Well Plate with AGM added every 3 days
Experimental Group 6: 20 µg/ml of 4× nHC-HC/PTX3 (GuHCl extraction) immobilized on Covalink-NH 96 Well Plate
Experimental Group 7: 20 µg/ml of 4× nHC-HC/PTX3 (GuHCl extraction) immobilized on Covalink-NH 96 Well Plate with AGM added every 3 days For the AGM induction groups: On Days 0 and 3, Osteogenesis induction media #1 (ascorbic acid, glycerol-phosphate) replaced the media. On Day 6, Osteogenesis induction media #2 (ascorbic acid, glycerolphosphate, melatonin) will replace the media. On Day 0, 10× Induction media was made. On Days 3 and 6, 10 ml of the Osteogenesis induction media was prepared fresh. Instructions for preparation of Induction Media obtained from In Vitro Osteogenesis Assay Kit (Millipore).

Induction media #1: 9.88 ml of αMEM medium plus 10%, 20 µl Ascorbic Acid 2-Phosphate 500× (Millipore, Part. 2004011), 100 µl Glycerol 2-Phosphate 100× (Millipore, Part. 2004011)

Induction media #2: 9.87 ml of αMEM medium plus 10%, 20 µl Ascorbic Acid 2-Phosphate 500× (Millipore, Part. 2004011), 100 µl Glycerol 2-Phosphate 100× (Millipore, Part. 2004011), 10 µl Melatonin 50 uM (Millipore, Part. 2004011). Add 500 ul dH20 to 6 ug of melantonin supplied.

mRNA was extracted from cells on Days 1, 7, and 14 and gene expression was determined by QPCR (FIG. 80A-E). The following genes were assayed: Osteogenesis markers Runx2, alkaline phosphatase (ALPL), markers Collagen 1 (COL1), Osterix (OSX) and Bone Sialoprotein (BSP) and chondrogenesis markers Sox9 and Collagen 2 (COL2), hypertrophic markers Collagen 10 (COL10) and MMP13. ARS staining and quantification was performed on Day 14 cultures as described above (FIG. 81A, 81B).

Figure 80A:
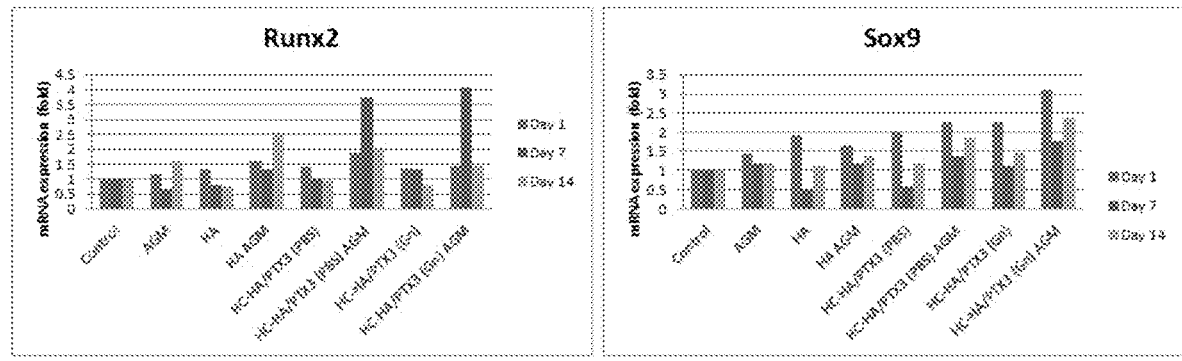
FIG. 80A-E exemplifies mRNA expression by QPCR for various genes tested following differentiation induction with or without HC-HA/PTX3 treatment. (A) Master transcription factors Runx2 and Sox9 for osteogenesis and chondrogenesis, Day2 1, 7, and 14. (B) Bone morphogenic proteins (BMPs) expression on Day 14. (C) Chondrogenic marker Collagen 2 (COL2) and osteogenic marker alkaline phosphatase (ALPL), expressed on Days 7 and 14. (D) Hypertrophic markers Collagen 10 (COL10) and MMP13 expressed on Day 14. (E) Osteogenic markers Collagen 1 (COL1), Osterix (OSX) and Bone Sialoprotein (BSP) on Day 14.
Figure 80B:
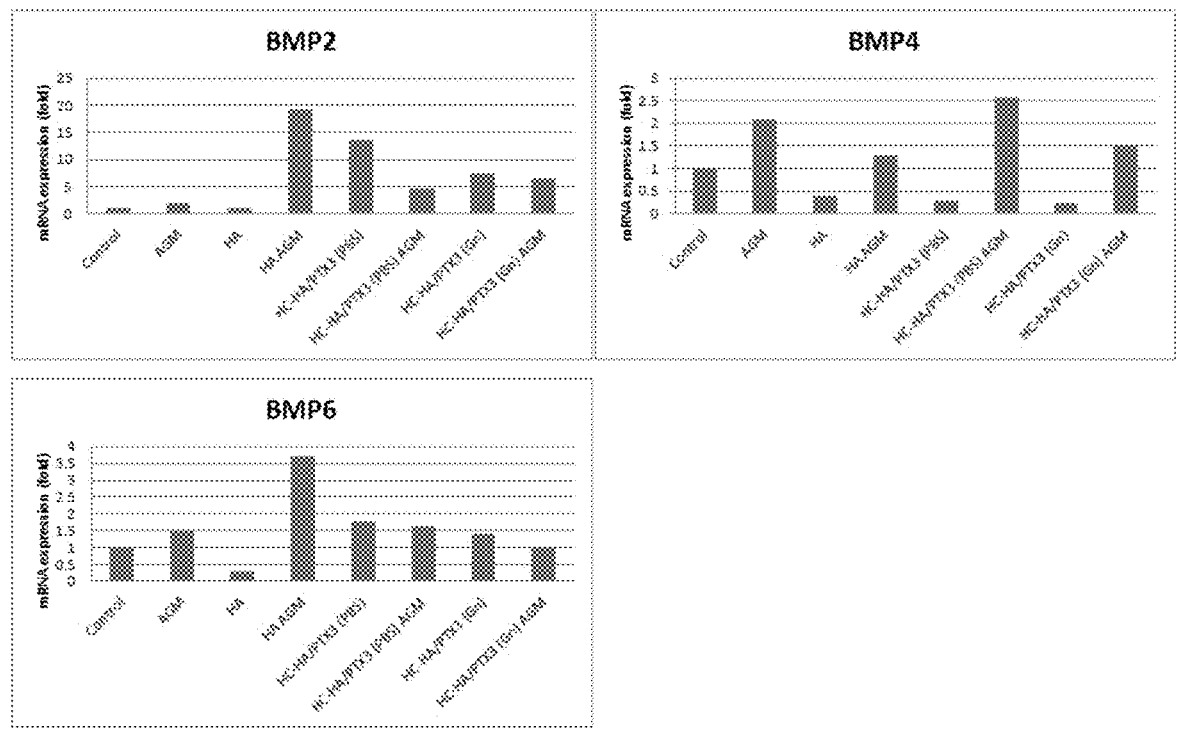
Figure 80C:
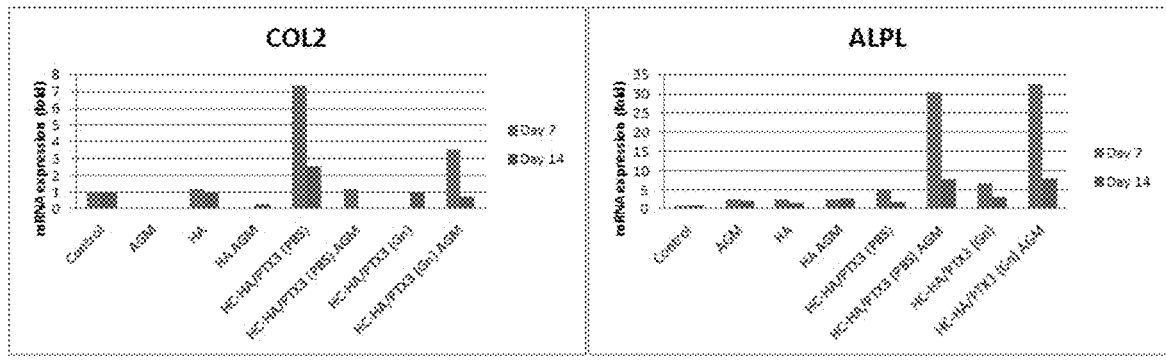
Figure 80D:
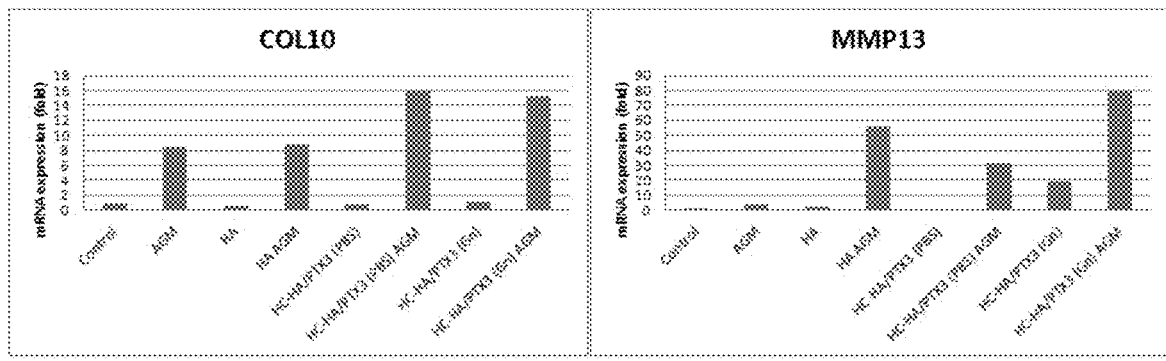
Figure 80E:
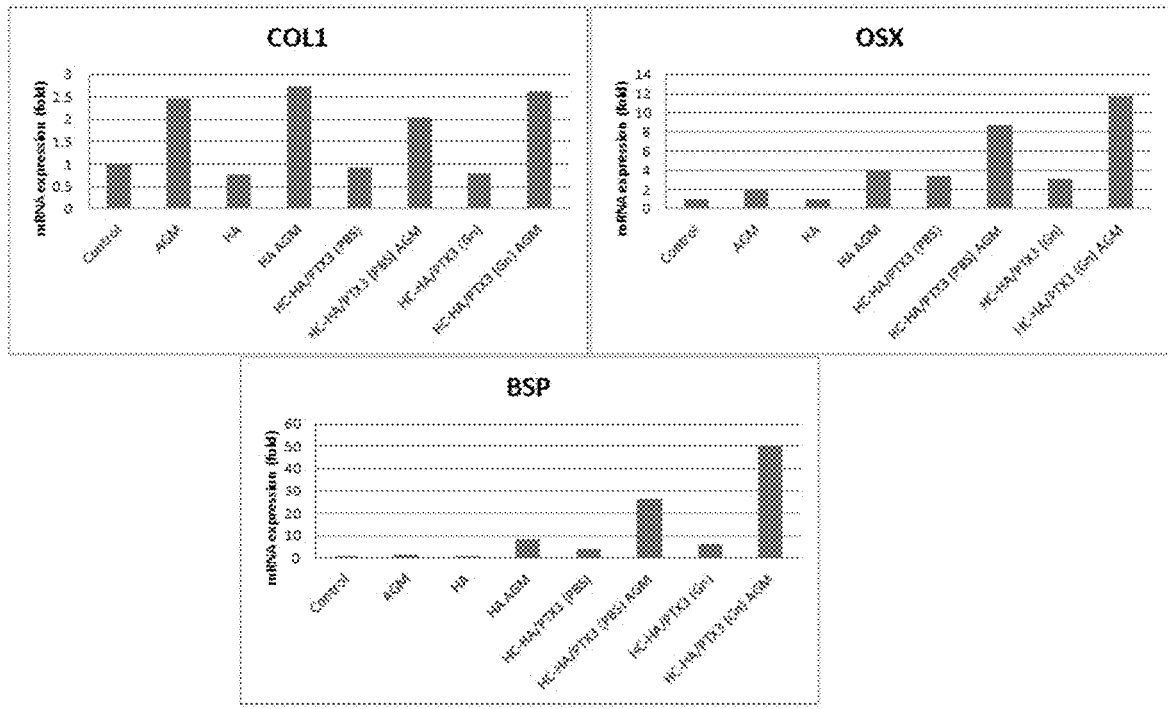
Figure 81A:
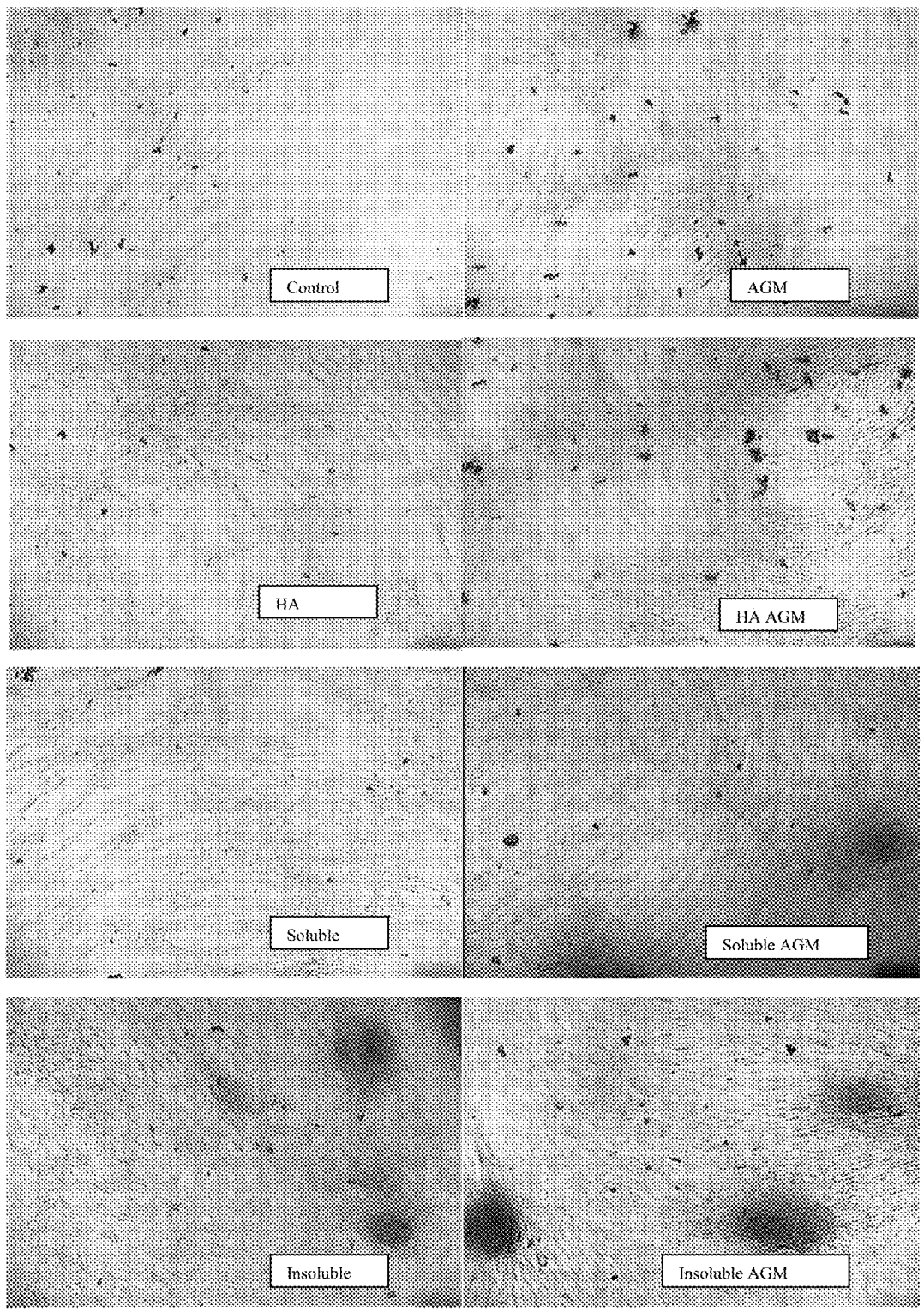
FIG. 81A-B exemplifies phase microscopy (A) and quantitation (B) of ARS Assay following differentiation induction with or without HC-HA/PTX3 (soluble or insoluble) treatment on Day 14.
Figure 81B:
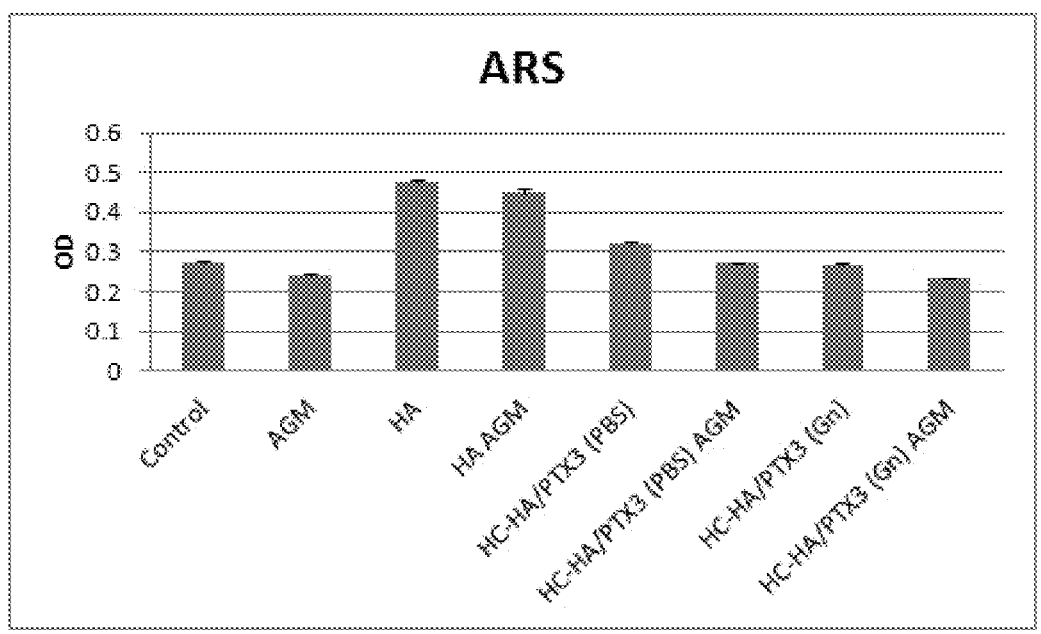

AGM upregulated BMP4 on plastic. HA upregulated BMP4 (early) but downregulated (late) BMP6 and did not affect BMP2 (FIG. 80B). No literature data suggests HA itself upregulates BMP. However, addition of AGM upregulated BMP2 and BMP6.

4× Soluble HC-HA initially upregulated BMP4 but downregulated BMP4 late (like HA) and markedly upregulated BMP2 (like AMP, but without transient BMP6) (FIG. 80B). In contrast, addition of AGM did not change the expression pattern of BMPs.

4× Insoluble HC-HA initially upregulated BMP4 but downregulated BMP4 (late) (like HA) and markedly upregulation of BMP2 (like Soluble HCHA) (FIG. 80B). [Identical to Soluble] Similarly, addition of AGM did not change the expression pattern.

Our results show soluble HC-HA and insoluble HC-HA were able to form bone differentiation and mineralization through an endochondral mechanism. Expression of bone markers (Coll, Osx, ALP, and BSP) were apparent as were expression of chondrocyte markers (Col2) and hypertrophy markers (Col10, MMP13) (FIG. 80A-E). The difference between these HC-HA conditions is that insoluble HC-HA was able to promote greater amplitude of gene expressions and more noticeable bone nodules (even without AGM) while soluble HC-HA requires AGM (data not shown). Thus, HC-HA/PTX3, both soluble and insoluble, were able to promote the expression of BMP2 without osteoinductive agents AGM.

HA without AGM also showed chondrogenic markers (COL2) but also showed signs of bone formation with ARS defined mineralization and a slight increase in ALP and OC. However, HC-HA/PTX3 (PBS) had greater chondrogenic expression and higher expression of bone markers ALP, Osx and BSP than HA. Yet neither of these conditions expressed significant hypertrophic markers. HC-HA/PTX3 (Gn) expressed much greater expression of ALP, OSX and BSP than the two aforementioned conditions. Hypertrophic marker MMP13 was also expressed as was slight expression of chondrogenic marker COL2.

HA plus AGM promotes osteogenesis with increased BMP2, ALP, Osx, BSP and OC expression and exhibits hypertrophic markers COL10 and MMP13. However, HA produced less bone specific mRNA expression and bone nodule formation than HC-HA groups. Another key difference was HA downregulated SOX9 but increased BMP6 expression late.

All prior data indicates insoluble HCHA is the strongest inducer of bone and, more importantly, induces an endochondral mechanism.

Example 45. nHC-HA/PTX3 Suppresses Inflammatory and Immune Responses and Improves Murine Corneal Allograft Survival Experimental and clinical studies have shown that amniotic membrane (AM), AM extract, and nHC-HA/PTX3 [a covalent complex formed by heavy chain (HC) of inter-α-trypsin inhibitor (IαI) and hyaluronan (HA)] suppress pro-inflammatory responses. This example demonstrates that nHC-HA/PTX3/PTX3 can regulate T cell responses and reduce murine corneal allograft rejection.

Figure 82:
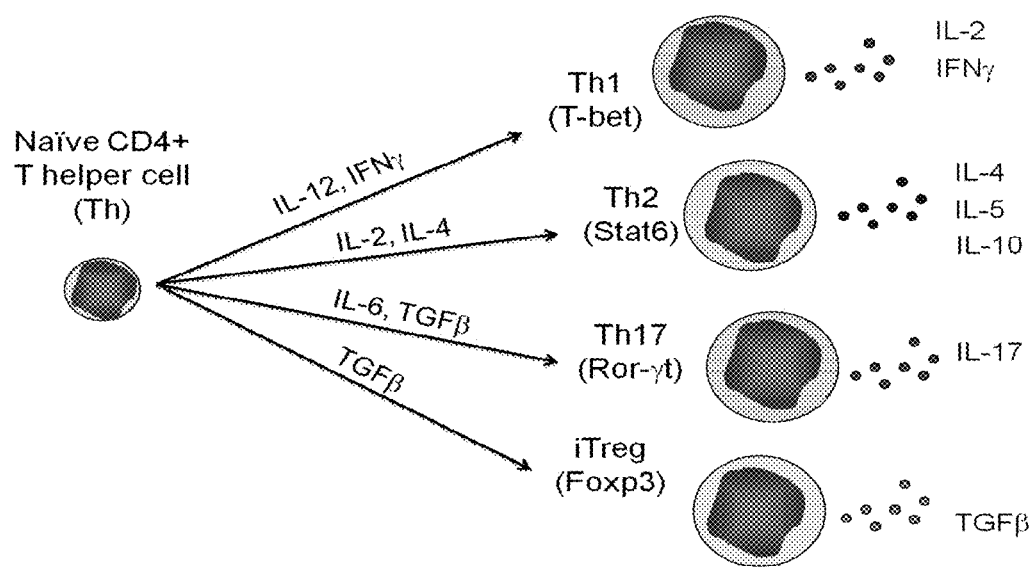
FIG. 82 exemplifies CD4$^+$ T cell activation and differentiation. Under different stimuli, Naïve CD4$^+$ T helper cell (Th) is differentiated into Th1, Th2, Th17, or Treg and secreted different cytokines. Th1-type cytokines (e.g., IFN-γ and IL-2) tend to produce the pro-inflammatory responses.
Figure 83:
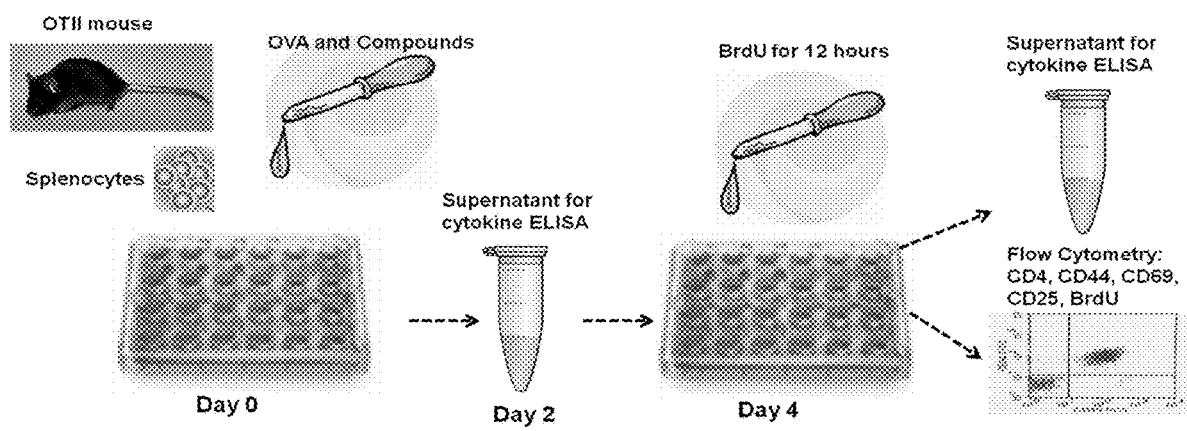
FIG. 83 exemplifies the procedure to measure cell proliferation and cytokine production. Splenocytes were isolated from OT-II mice that express a transgenic TCR specific for ovalbumin (OVA), and stimulated with OVA up to 4 days. Cell proliferation was measured by BrdU labeling and expression of cytokines (IFN-γ and IL-2) was measured by the respective ELISA.
Figure 84:
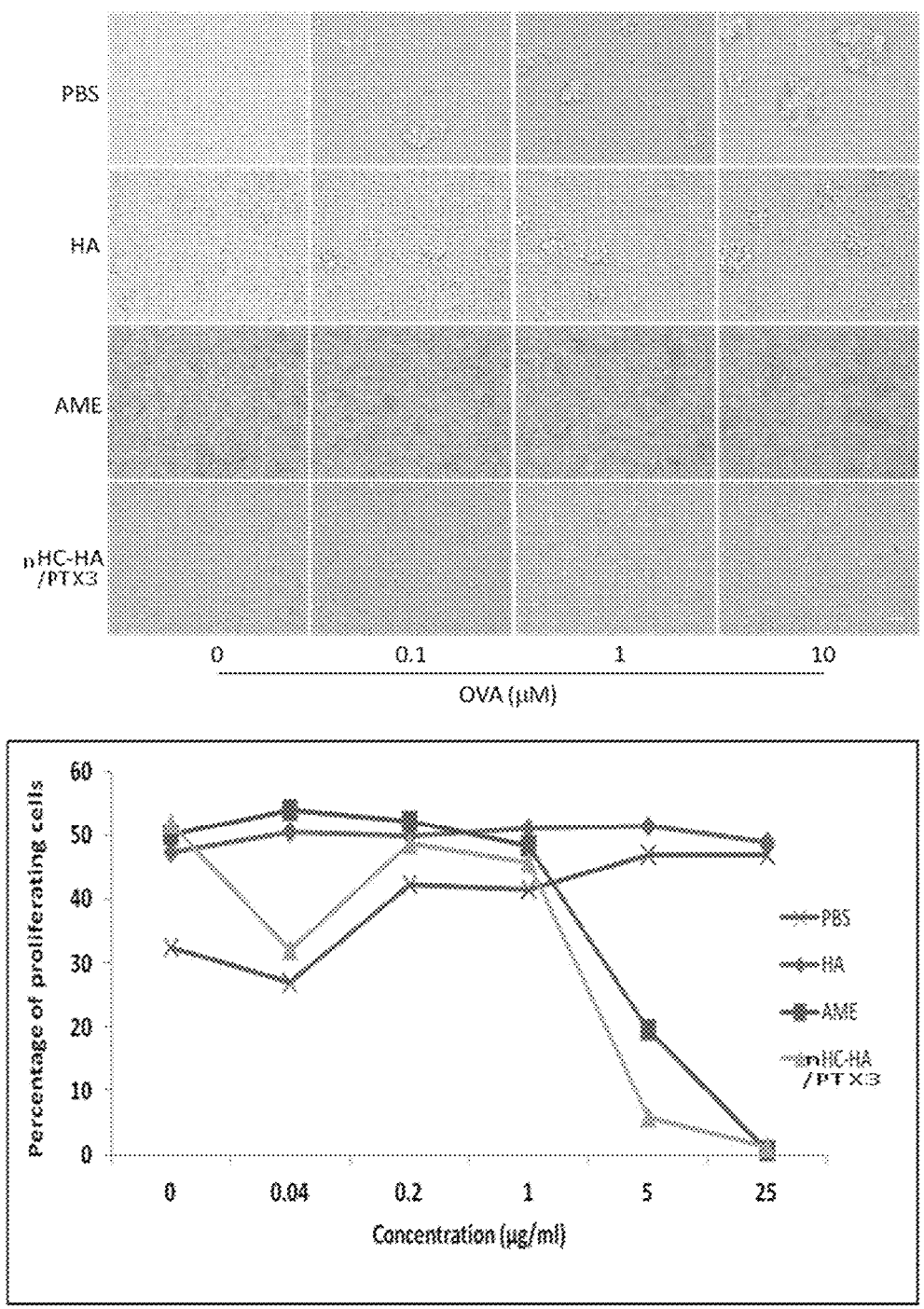
FIG. 84 exemplifies nHC-HA/PTX3 inhibition of CD4$^+$ T cell proliferation. Splenocytes isolated from Ova T cell receptor transgenic mice were stimulated with OVA (0-10 μM) for 4 days. AM extract (AME, 25 μg/ml) and nHC-HA/PTX3 (25 μg/ml) inhibited the clone growth of activated T cells induced by increasing OVA concentrations (top). Proliferation of splenocytes treated with HA, AME, or nHC-HA/PTX3 and labeled with CFSE for 4 days was measured by flow cytometry. Both AME and nHC-HA/PTX3 dose-dependently inhibited the cell proliferation (middle). 25 μg/ml nHC-HA/PTX3 inhibited the proliferation of CD4$^+$ T cell labeled with BrdU (bottom) (*, $p<0.05$ compared to the control).
Figure 84:
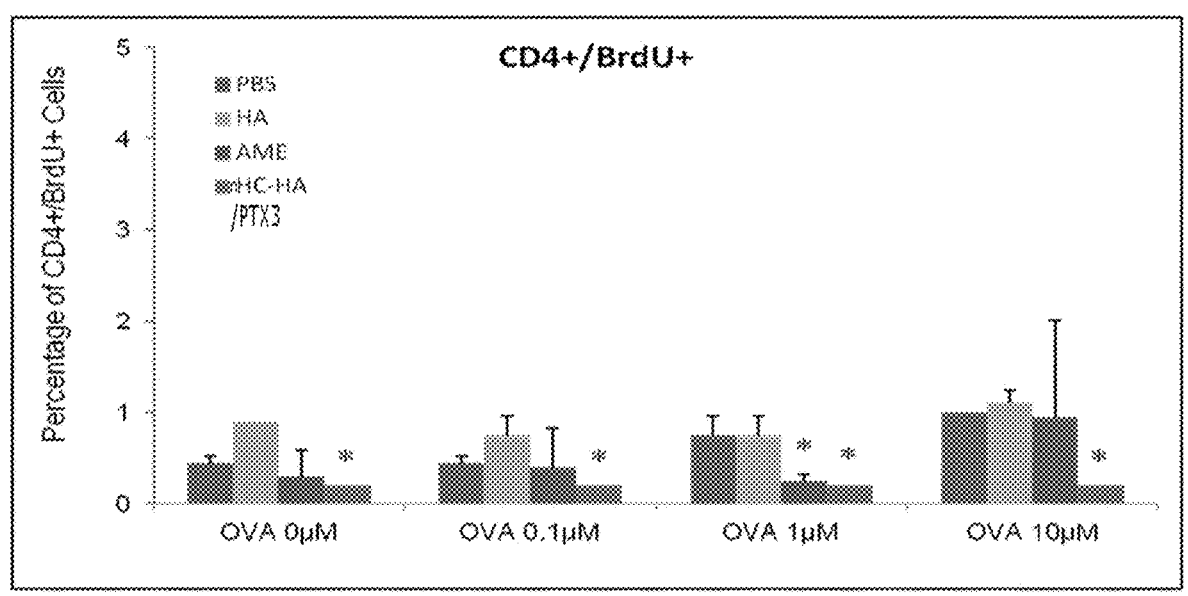
Figure 85:
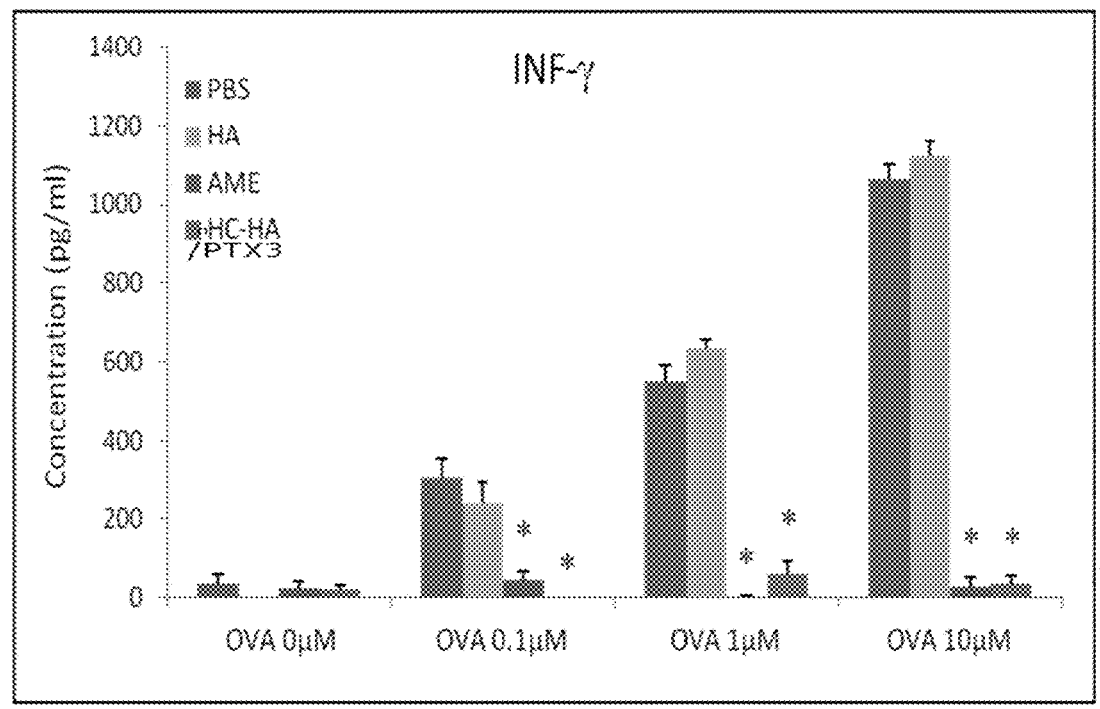
FIG. 85 exemplifies nHC-HA/PTX3 suppression of Th1-type cytokines IFN-γ and IL-2. Splenocytes treated with PBS, 25 μg/ml HA, 25 μg/ml AME, or 25 μg/ml nHC-HA/PTX3 were stimulated with 10 μM OVA for 4 days. IFN-γ and IL-2 in culture supernatants were measured by the respective ELISA. Both AME and nHC-HA/PTX3 suppressed the production of IFN-γ and IL-2 (* $p<0.05$ compared to the control).
Figure 85:
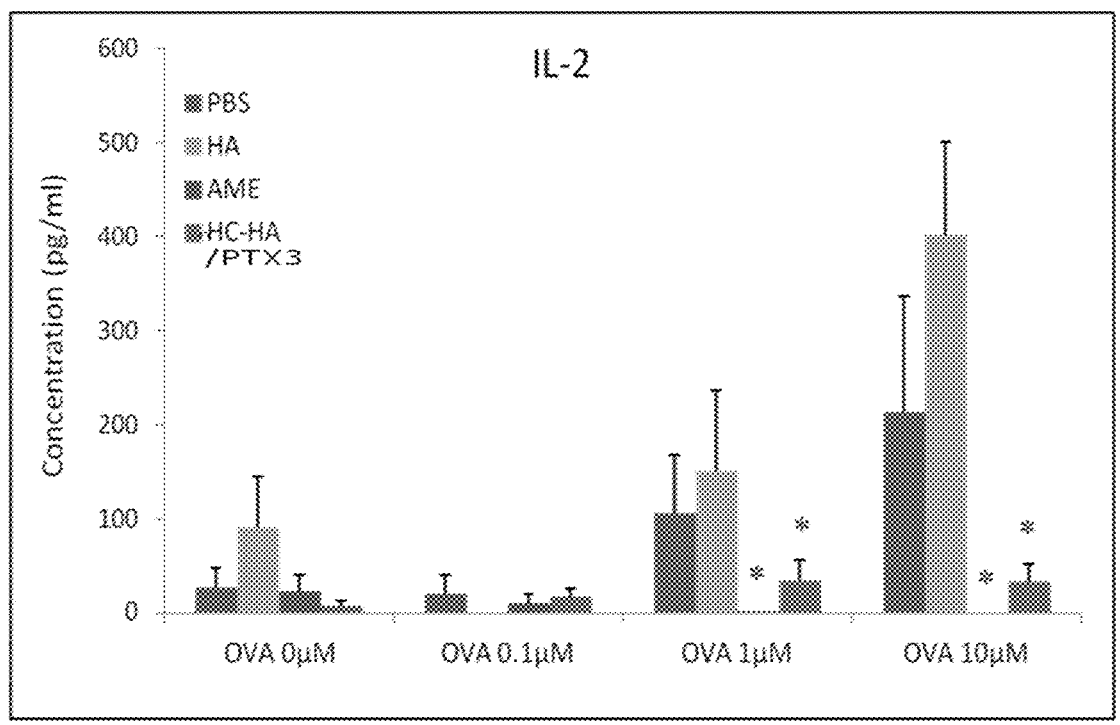

T cell activation may be assessed by proliferation and production of various cytokines (FIG. 82). In this instance, splenocytes were isolated from OT-II mice that express a transgenic TCR specific for ovalbumin (OVA), and stimulated with OVA up to 4 days (FIG. 83). Cell proliferation was measured by BrdU labeling and expression of cytokines (IFN-γ and IL-2) was measured by the respective ELISA. nHC-HA/PTX3 but not HA at 1 mg/ml significantly suppressed the proliferation (FIG. 84) and production of IFN-γ and IL-2 (FIG. 85) in splenocytes with OVA peptide at day 2 and day 4 (all p<0.05). Furthermore, corneal T cells were activated in vivo by LPS injection.

Figure 86:
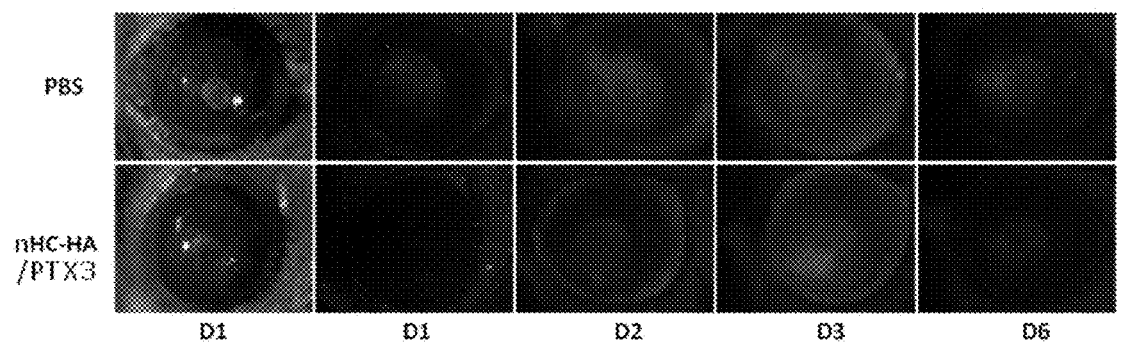
FIG. 86 exemplifies nHC-HA/PTX3 reduction of macrophage (labeled with enhanced green fluorescent protein, or EGFP) influx. LPS (2 μl of 2 μg/ml) was injected into the corneal stroma of Mafia mouse. Immediately, 5 μl of PBS or nHC-HA/PTX3 (1 mg/ml) was injected into each quadrant of one cornea from the same mouse through the subjunctival tissue. The influx of EGFP$^+$ macrophages is monitored using in vivo intravital microscopy at day 1, 2, 3, and 6 after LPS treatment (top). Alternatively, mouse corneas were treated with PBS or nHC-HA/PTX3 simultaneously with LPS (pre-treatment (−) or three days before LPS treatment (pretreatment (+)). At day 4 after LPS treatment, cells in corneas were isolated by collagenase digestion and sorted into EGFP$^-$ or EGFP$^+$ (macrophages) by FACS (* and **, $p<0.05$ and $p<0.01$ compared to the control, respectively).
Figure 86:
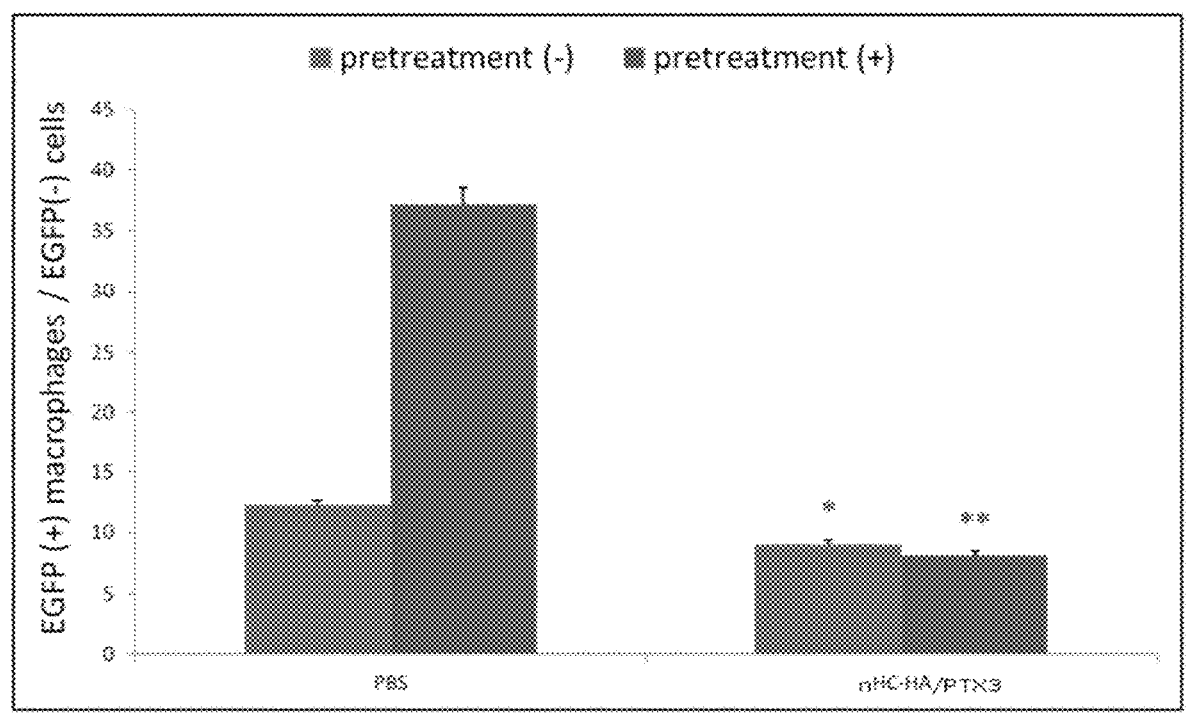
Figure 87:
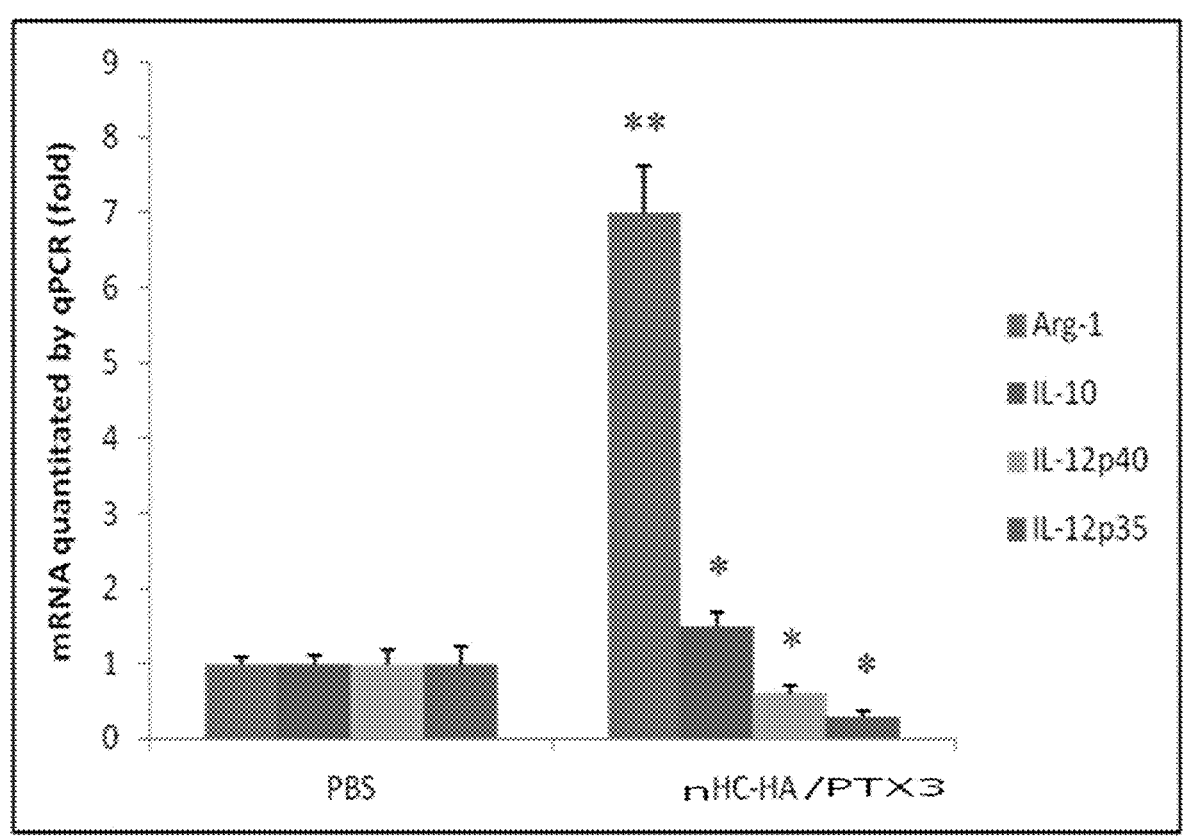
FIG. 87 exemplifies nHC-HA/PTX3 polarization of macrophages toward a M2 phenotype. mRNA expression of M2 markers (Arg-1 and IL-10) and M1 markers (IL-12p40 and IL-12p35) in macrophages (EGFP$^+$) infiltrated to LPS-elicited murine corneas was quantitated by qPCR (* and **, $p<0.05$ and $p<0.01$ compared to the control, respectively).
Figure 88:
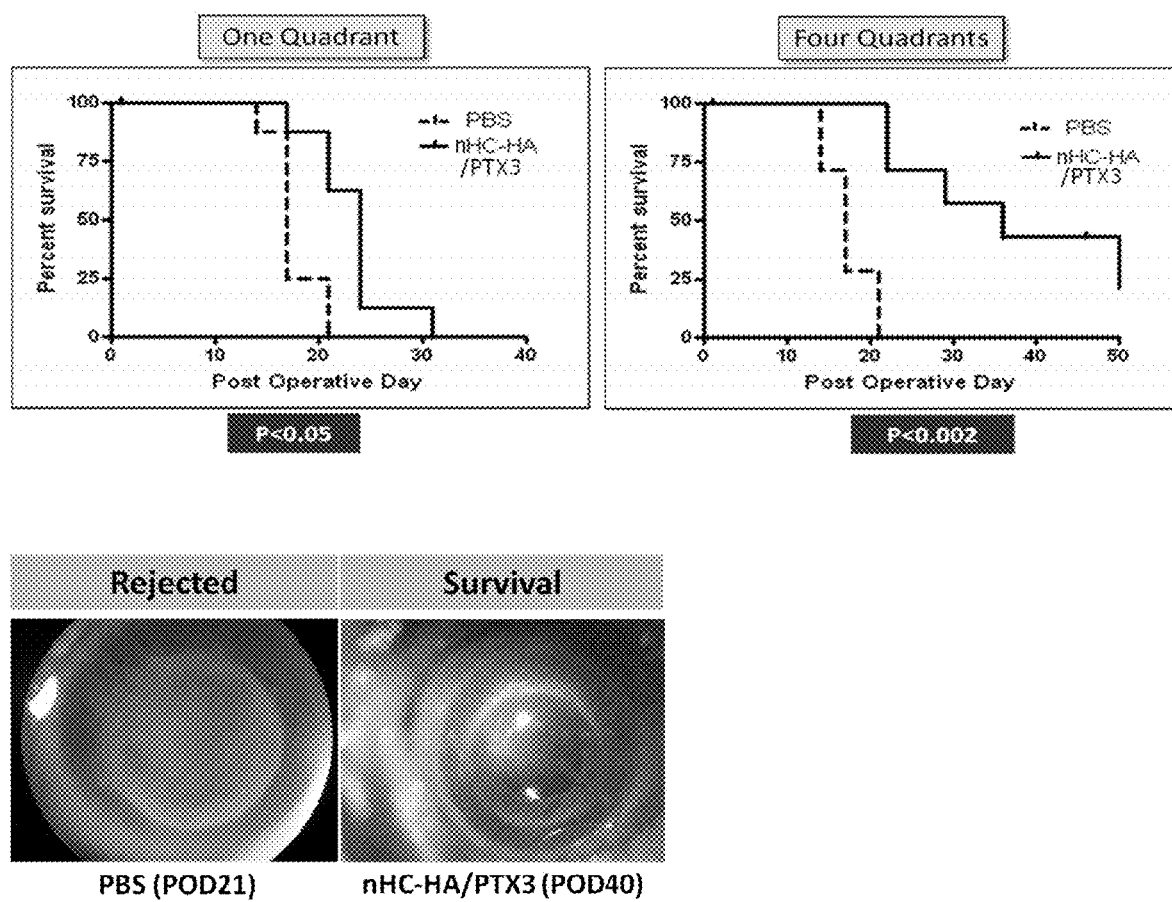
FIG. 88 exemplifies nHC-HA/PTX3 improvement of corneal allograft survival. The survival of murine corneal allograft was significantly improved by injection of nHC-HA/PTX3 at one quadrant subconjunctival site (10 μg/time, two times/a week, top left), but even dramatically better by injection of nHC-HA/PTX3 at four quadrant subconjunctival sites (20 μg/time, two times/a week, top right). Bottom, photographs of PBS (post operative day 21, left) or nHC-HA/PTX3 treatment (post operative day 40, right) in corneal allografts.

Optimization of injection sites, volume, and frequency with nHC-HA/PTX3 before or during intracorneal injection of LPS was determined by influx of EGFP-positive macrophages into corneas of Mafia mice. The injection regimen was further optimized by giving 5 µl at each injection between subconjunctiva and fornix to all four quadrants. At day 4 after nHC-HA/PTX3 treatment, corneas were digested with 820 units/ml of collagenase at 37° C. for 1 h. EGFP− and EGFP+ cells were isolated by FACS. Pretreatment of nHC-HA/PTX3 3 days prior to LPS injection significantly suppressed the influx of EGFP+ macrophages to LPS-insulted corneas (9.1±0.3 vs. 12.3±0.4, nHC-HA/PTX3 vs PBS, p=0.02) (FIG. 86). Importantly, even though EGFP+ macrophages did migrate into corneas, some of them were polarized into M2 phenotype as suggested by significant up-regulation of Arg-1 and IL-10 but down-regulation of IL-12 (p<0.05) (FIG. 87). mRNA expression of Arg-1, IL-10, and IL-12 were measured by qPCR. Finally, allogenic corneal transplantation was performed using wild-type BALB/c mice as recipients and C57BL/6 mice as donors, and its outcome scored by graft clarity measured twice a week using slit lamp biomicroscopy. Grafts that received two consecutive scores 3 without resolution were considered rejected. Compared to PBS control, allograft rejection was significantly suppressed by injection of 10 µl nHC-HA/PTX3 at one quadrant twice a week (p<0.05), and further reduced by injection with 5 µl at 4 quadrants twice a week (p<0.002) (FIG. 88).

These experiments demonstrate that nHC-HA/PTX3 significantly suppresses murine corneal allograft rejection. The mechanism of this action may be contributed by nHC-HA/

PTX3's ability to down-regulate pro-inflammatory macrophages and to suppress T cell immune response.

Example 46. Treatment of Mouse Dry Eye Caused by Desiccating Stress by nHC-HA/PTX3 and AMP Dry eye, also known as dysfunctional tear syndrome, is a common ocular surface disease with high prevalence and significant morbidity worldwide. It is an autoimmune-based inflammatory disease characterized by chronic auto-reactive T cell-mediated inflammation and dysfunction of the lacrimal function unit (LFU; cornea, conjunctiva, lacrimal glands, and meibomian glands). Sjögren's syndrome (SS) is a prevalent chronic autoimmune disorder characterized by infiltration of salivary and lacrimal glands by mononuclear cells, causing secondary destruction of the parenchymal tissue.

Figure 89:
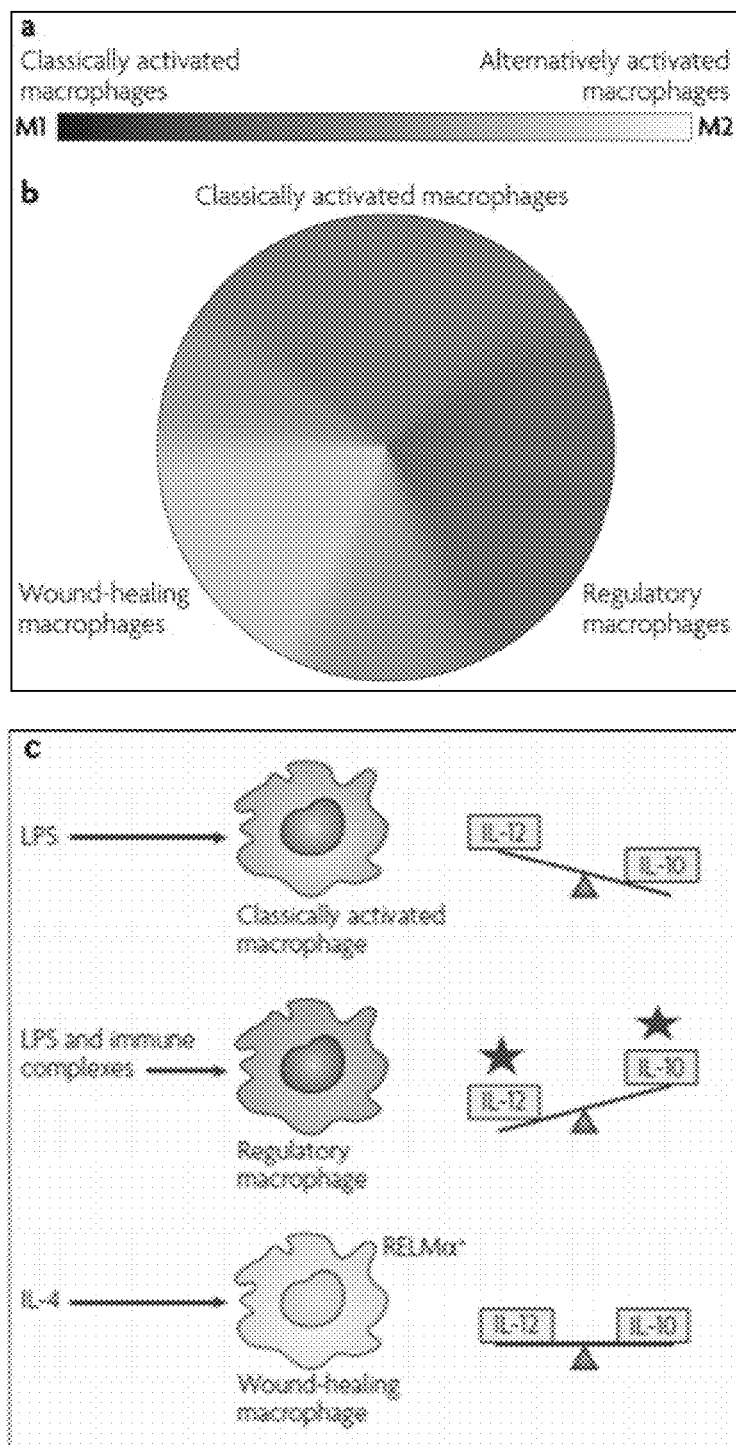
FIG. 89 exemplifies macrophage classical M1 activation (e.g., induced by IFN-γ and/or TLR ligands such as LPS) to express high levels of proinflammatory cytokines (such as TNF-α, IL-12, and IL23), which activate Th1 and Th17 lymphocytes leading to many chronic inflammatory diseases.
Figure 89:
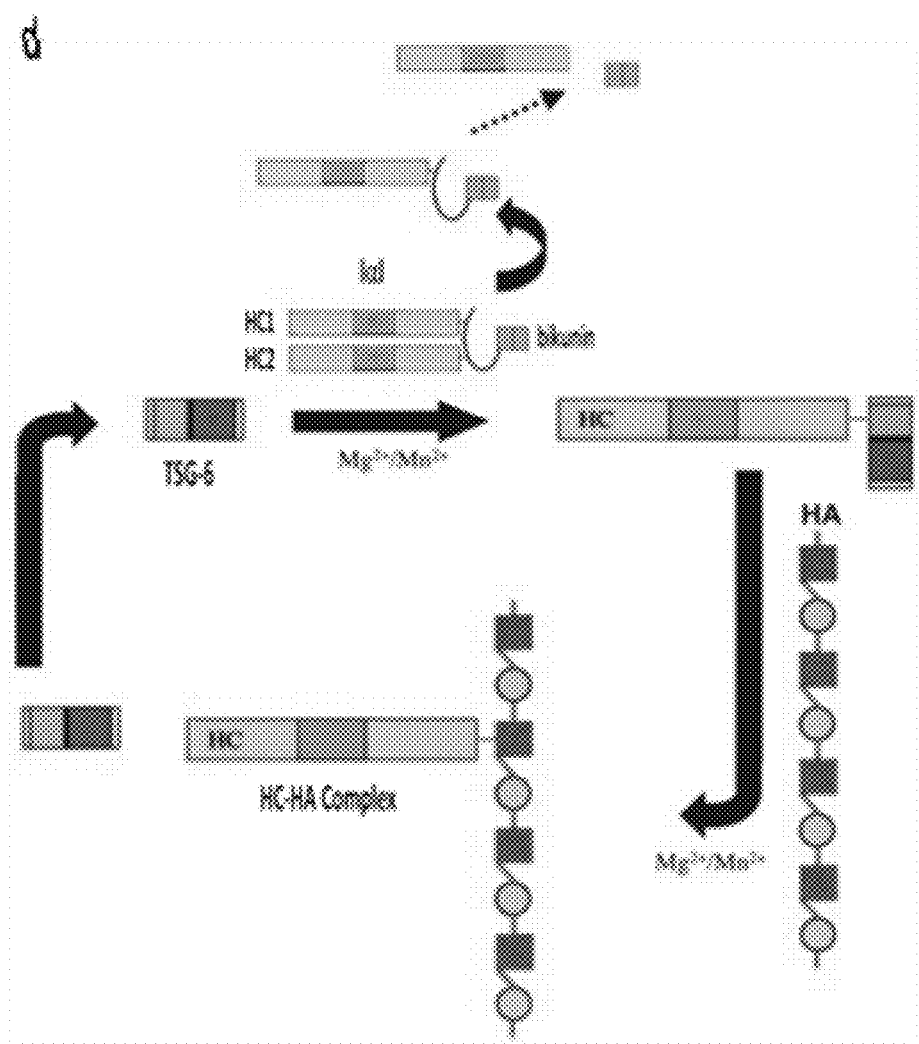
Figure 90A:
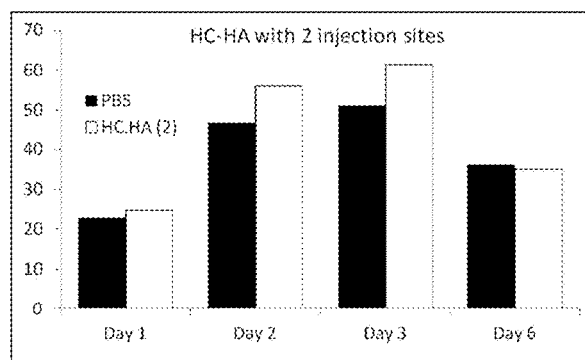
FIG. 90A-D exemplifies LPS-elicited macrophage infiltration to murine corneas with treatment of PBS (control), HC-HA/PTX3, or AMP. Mafia mice (macrophages are EGFP+) with LPS intrastromal injection (5 μg) for both eye. OS was treated with PBS, OD was treated with either HC-HA (2 injection sites) (A), HC-HA (4 injection sites) (B), AMP (2 injection sites) (C), AMP (4 injection sites) (D), each injection was 5 μl. Treatment was one time right after LPS injection. Images were taken on day 1, day 2, day 3 and day 6. Cells were counted based on the intensity of green fluorescence.
Figure 90B:
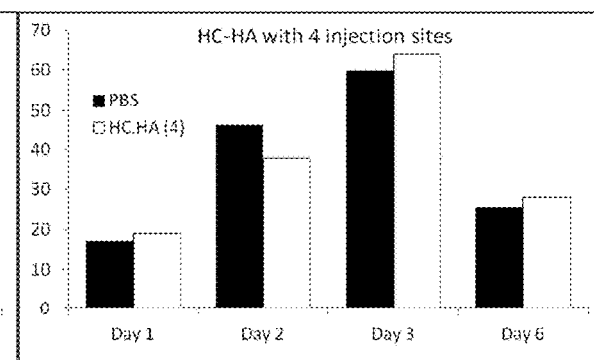
Figure 90C:
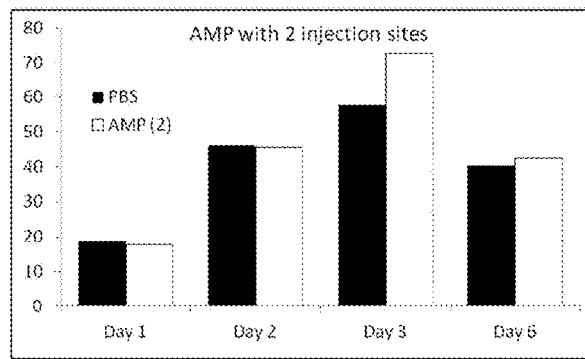
Figure 90D:
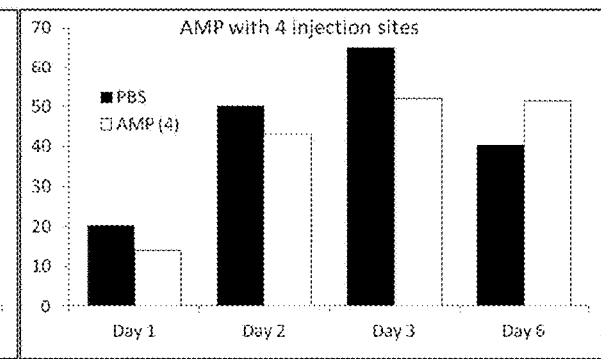

Keratoconjunctivitis sicca (KCS) in SS is a severe and potentially sight-threatening ocular surface epithelial disease characterized by infiltrating CD4+ T cells producing IL-17 and interferon (IFN)-γ. Compounds that inhibit T cell activation (e.g., cyclosporine A) attenuate dry eye disease in both animals and humans. Macrophages may undergo classical M1 activation (e.g., by IFN-γ and/or TLR ligands such as LPS) to express high levels of proinflammatory cytokines (such as TNF-α, IL-12, and IL23), which activate Th1 and Th17 lymphocytes (FIG. 89) leading to many chronic inflammatory diseases. This example demonstrates that nHC-HA/PTX3 and AMP administration may be useful in the treatment of such conditions.

Infiltration of Macrophages into Corneas is Inhibited with Four Injection Sites for Each Eye MAFIA mice permit in vivo tracking of macrophage influx as they are labeled with EGFP. These mice were used to determine if nHC-HA/PTX3 or AMP prevents LPS-induced macrophage influx to the cornea, a model for keratitis. LPS was injected between subconjunctiva and fornix at a suitable volume of 5 μl or less at each injection site. Eyes of MAFIA mice (macrophages are EGFP+) were intrastromally injected with LPS (5 μg per eye). In each eye, OS was treated with PBS (2 or 4 injection sites) while OD was treated one time with either nHC-HA/PTX3 (2 or 4 injection sites; 5 μl of 1 mg/ml HA in nHC-HA/PTX3 per injection site) or AMP (2 or 4 injection sites; 5 μl of 10 mg/ml protein in AMP per injection site). The treatment was immediately after LPS injection. Images of whole corneas were taken with in vivo intravital microscopy on day 1, day 2, day 3 and day 6. EGFP-positive cells were counted based on the intensity of green fluorescence.

At Day 1, EGFP-positive macrophages are detected in the most corneal peripheral area after LPS injection with PBS treatment. Treatment with either nHC-HA/PTX3 or AMP did not significantly increase or decrease macrophages in corneas.

At Day 2, the macrophages in corneas with PBS treatment increased significantly ($p<0.05$) from Day 1, so did with treatment of nHC-HA/PTX3 (2 and 4 injection sites, $p<0.05$) and of AMP (2 and 4 injection sites, $p<0.05$). Specifically, more macrophages were infiltrated in corneas treated with 2 injections of nHC-HA/PTX3 than those with PBS treatment ($p>0.05$), but less are in corneas with 4 injections of nHC-HA/PTX3 ($p>0.05$). For AMP treatment, 2 injections had no significant effect but 4 injections slightly decreased the infiltration of macrophages, suggesting 4 injections of either nHC-HA/PTX3 or AMP for each eye is necessary to have an effect on reducing the infiltration of macrophages.

At Day 3, the infiltration of macrophages continued with treatment of PBS, nHC-HA/PTX3, and AMP.

There was no inhibition of the infiltration with treatment of either 2 injections, 4 injections of nHC-HA/PTX3, or 2 injections of AMP. The only treatment shows the inhibition is the 4 injection of AMP ($p<0.05$).

At Day 6, the infiltration of macrophages decreased. However, no treatment of HC-HA/PTX3 or AMP had a significant inhibitory effect compared to control.

These data showed EGFP-positive macrophages continue to infiltrate into LPS-injected corneas from Day 1 to Day 3 and peaks at Day 4 or Day 5, then decline at Day 6. This is consistent with the previous reported data (FIG. 90). The infiltration of macrophages was slightly inhibited by treatment with 4 injections of nHC-HA/PTX3 per eye at Day 2 or with 4 injection of AMP at Day 2 and Day 3. This suggests AMP has a better potency than nHC-HA/PTX3 in blocking the influx of macrophages elicited by LPS.

Pretreatment with AMP Significantly Inhibits the Macrophage Infiltration Incited by Injuries Due to Additional Injections if Followed by Subsequent Injections of Either nHC-HA/PTX3 or AMP The left eye (OS) of each MAFIA mouse was pretreated with PBS (5 μl) or AMP (5 μl of 10 mg/ml protein) at 4 sites of subconjunctival/fornix as defined above. The right eye (OD) of each mouse was left untreated. Three days later, each eye was injected with LPS (5 μg) to the cornea and immediately followed by treatment with PBS (5 μl), HC-HA/PTX3 (5 μl of 1 mg/ml HA), or AMP (5 μl of 10 mg/ml protein) at 4 sites. The infiltration of EGFP$^+$ macrophages was counted using in vivo intravital microscopy, which did not disclose any significance ($P>0.05$) in reducing macrophage influx to mouse corneas (data not shown). We then investigated the accuracy of this quantitative method by in vivo fluorescence microscopy.

Figure 91A:
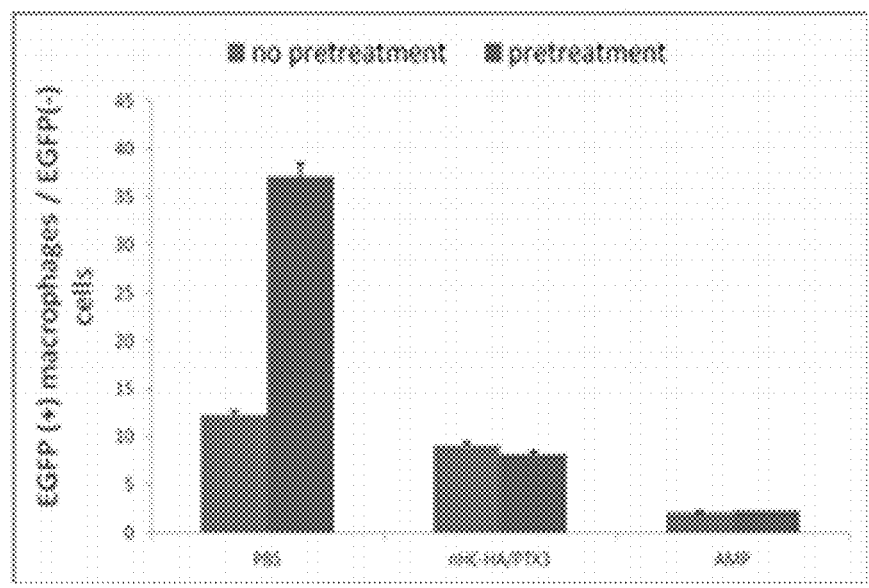
FIG. 91A-B exemplifies LPS-elicited macrophage infiltration to murine corneas and their subtypes (M1 and M2) with treatment or pretreatment of PBS (control), nHC-HA/PTX3, or AMP. Pretreatment and treatment of Mafia mice are the same as described in FIG. 86. On Day 4, cornea buttons are cut and digested with collagenase at 37° C. for 2 h. EGFP-positive/negative cells are sorted out by FACS. The ratio of EGFP-positive macrophages to EGFP-negative cells is calculated and used as an arbitrary unit to determine the extent of macrophage infiltration (A). Total RNA was extracted from sorted EGFP-positive macrophages and converted to cDNAs. The expression of Arg-1, IL-10, IL-12p40, and IL-12p35 is measured by quantitative PCR (B).
Figure 91B:
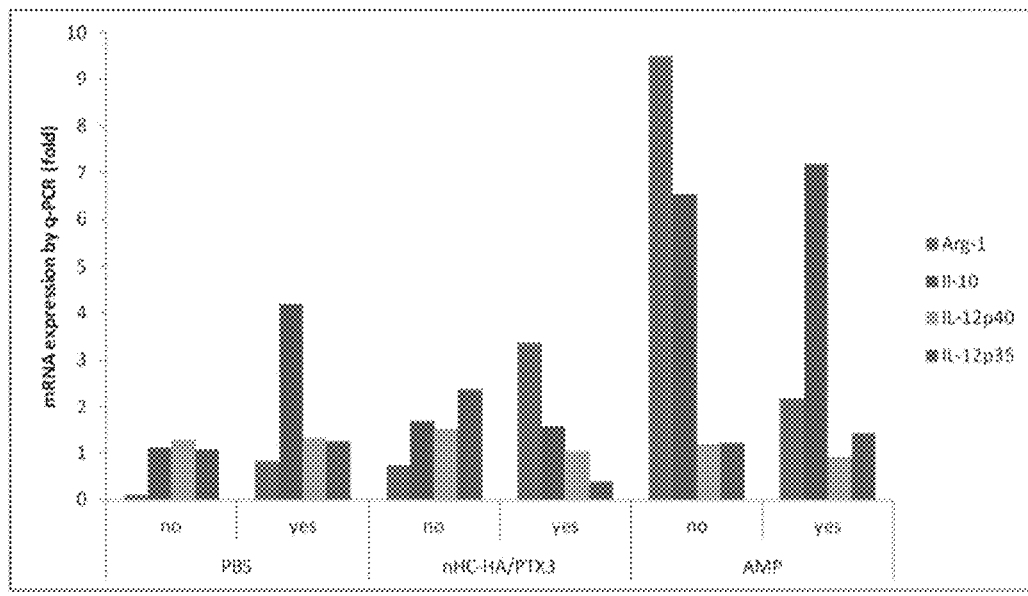

To measure more accurately the infiltrated macrophages and examine the resultant macrophage phenotype (e.g., M1 vs. M2), we decided to quantitate EGFP-positive macrophages by subjecting the corneas removed at Day 4 to collagenase digestion and FACS. EGFP-positive macrophages were then normalized by EGFP-negative cells as a ratio to assess the extent of macrophage infiltration. In groups with no pretreatment, LPS injection caused macrophage infiltration in the PBS control group (FIG. 91, A, the blue bar). This infiltration was significantly inhibited by nHC-HA/PTX3 (9.1±0.3 vs. 12.3±0.4, $p=0.02$) or AMP (2.1±0.1 vs. 12.3±0.4, $p=0.02$). AMP treatment was better than nHC-HA/PTX3 treatment in inhibition of the macrophage infiltration ($p=0.02$).

In groups with pretreatment, LPS injection caused significant macrophage infiltration in PBS control group compared with no pretreatment (37.2±1.3 vs. 12.3±0.4, $p=0.01$) (FIG. 91, A, the red bar). This difference was expected as 4 subconjunctival injections made during pretreatment caused injury that elicited inflammation, which augmented macrophage influx to the cornea which was later on treated by LPS. Nonetheless, this dramatic increased infiltration was completely inhibited by AMP pretreatment followed with either nHC-HA/PTX3 (8.2±0.3 vs. 37.2±1.3, $p=0.02$) or AMP treatment (2.3±0.1 vs. 37.2±1.3, $p=0.02$). Again, AMP pretreatment followed by AMP treatment was better than AMP pretreatment followed by nHC-HA/PTX3 treatment in inhibiting macrophage infiltration (2.3±0.1 vs. 8.2±0.3, $p=0.02$). However, there was no significant difference in inhibition between the group with no pretreatment and the group with pretreatment of AMP for either nHC-HA/PTX3 or AMP ($p>0.05$). qPCR data (FIG. 91, B) show pretreatment of nHC-HA/PTX3 decreases M1 markers if IL-12p40 and IL-12p35 while increases M2 markers of Arg-1. AMP treatment and pretreatment significantly decreases IL-12p40 and IL-12p35 but greatly increases Arg-1 and IL-10. In all, AMP pretreatment can completely eliminate the macrophage infiltration incited by additional injuries during the pretreatment. Such an effect is sustained by subsequent injection of either nHC-HA/PTX3 or AMP simultaneously with LPS injection. This benefit is noted 4 days later, and AMP is more potent than nHC-HA/PTX3.

nHC-HA/PTX3 or AMP Can Reduce DS-Induced ALKC in a Murine Experimental Dry Eye Model.

Design

Species: C57BL/6 mice

Endpoints: corneal epithelial barrier function (OGD staining)

Sample Size: 15 mice per group

Groups: 2 controls and 3 treatment groups (PBS, nHC-HA/PTX3, and AMP): 1) Non-dry eye, untreated control (UT)—kept in a separate vivarium room; 2) Experimental dry eye, untreated control (EDE); 3) PBS; 4) nHA-HC/PTX; 5)AMP.

Desiccating Stress (DS)

The desiccating stress model is created by pharmacological cholinergic blockade of tear secretion and exposure to an air draft and low humidity in an environmentally controlled room for 5 days (Monday-Friday). Mice are placed in specially designed perforated cages which consist of regular mouse cages that have their sides replaced by a wire mesh to allow air flow through the cage. Each cage is placed in front a constant air flow (electrical fan). Lacrimal gland secretion is inhibited by subcutaneous administration of scopolamine (0.5 mg in 0.2 mL, Sigma-Aldrich) 4 times per day for 5 days (8:30 am, 11:30 am, 1:30 pm, 4:30 pm). Humidity in the environmentally controlled room is maintained at ~25-30% relative humidity, which is achieved by 4 portable dehumidifiers and a dehumidifier unit in the ceiling.

Treatment Procedure (5-Day Protocol)

During each experiment, 3 controls are included:

Untreated control, consists of a group of mice that are kept in the vivarium, under relative humidity of 40~70%. These mice are never exposed to DS nor receive any topical treatment.

Dry eye control, which consists of a group of mice that are placed in the environmental dry eye chamber but receive no treatment.

Vehicle control, consists of a group of mice that are subjected to DS but receive PBS.

In addition, two experimental groups are included: nHA-HC/PTX3 and AMP

Figure 92:
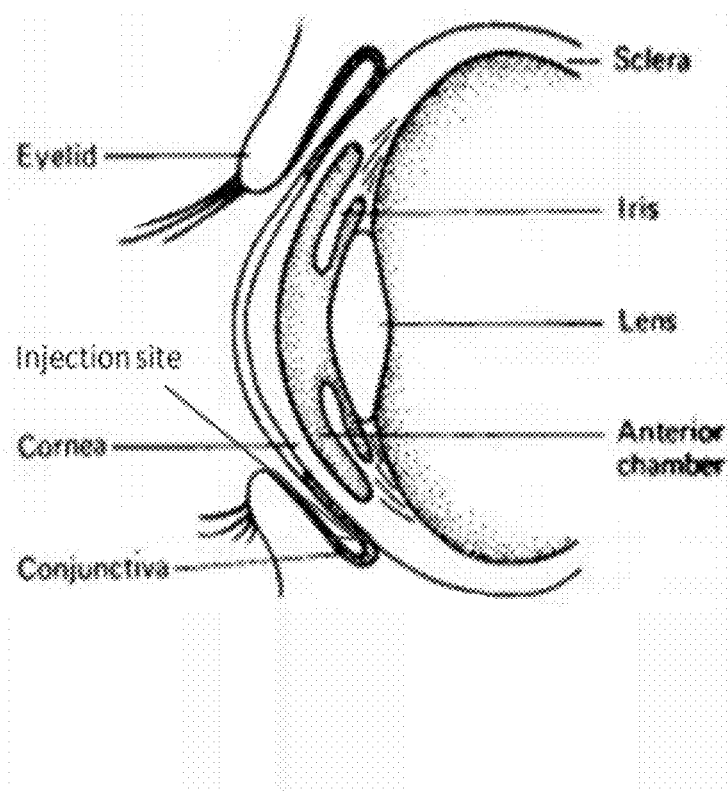
FIG. 92 Diagram of injection site. The injection locations will be subconjunctiva close to fornix nHC-HA/PTX3 or AMP can reduce DS-induced ALKC in murine experimental dry eye model.
Figure 93:
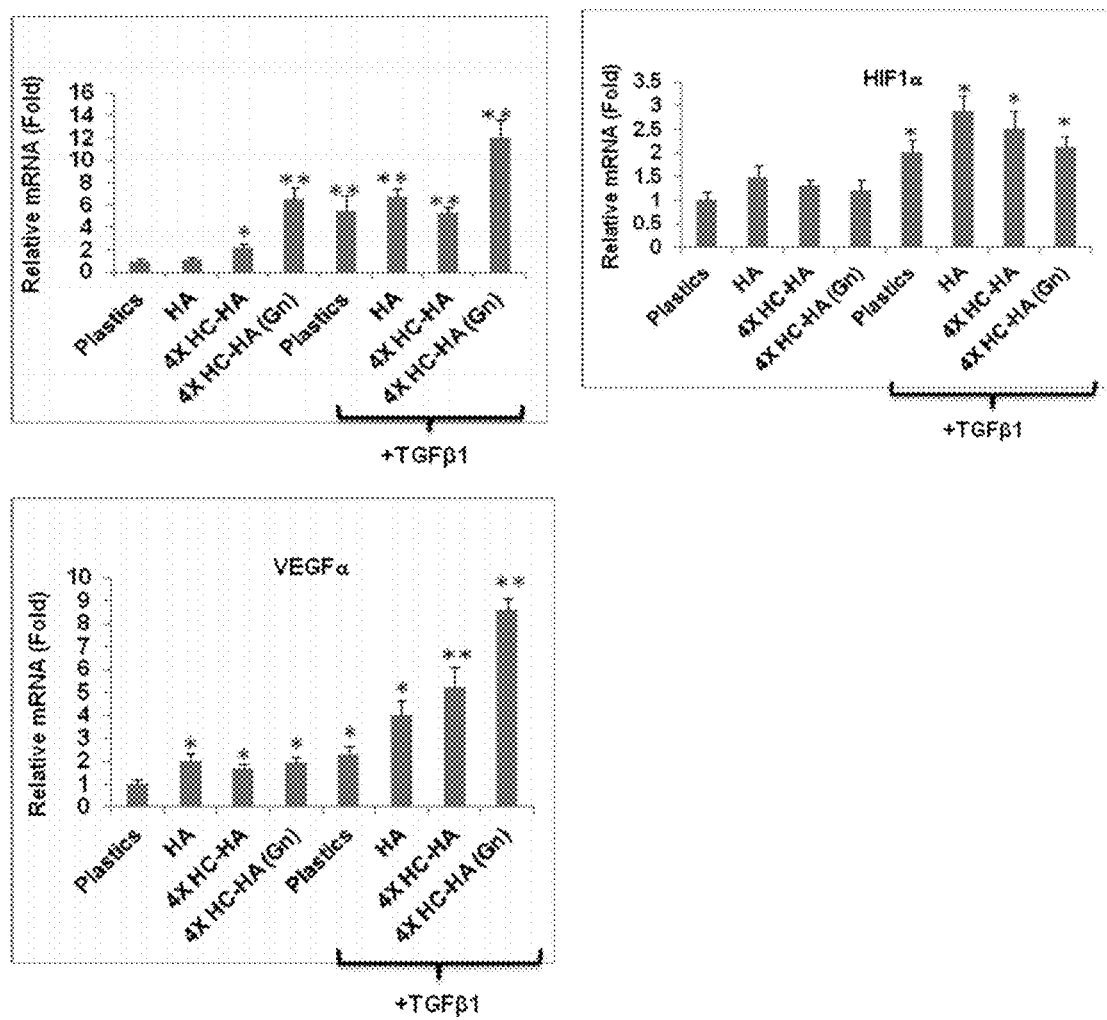
FIG. 93 exemplifies HC-HA activation of IGF1-HIF1α-VEGF signaling to promote angiogenesis. HC-HA induces 2- to 6-fold increase of IGF1 mRNA and 2-fold increase of VEGF mRNA when the cells are in rest condition. HC-HA induces 5- to 12-fold increase of IGF1 mRNA and 5- to 9-fold increase of VEGF mRNA when the cells are challenged by TGFβ (10 ng/ml). n=4, *p<0.05, **p<0.01. IGF1, Insulin-like growth factor 1; HIF1α, Hypoxia-inducible factor 1-alpha; VEGF, Vascular endothelial growth factor.

For injection, we used nHC-HA/PTX3 (containing 1 mg/ml HMW HA) and AMP (containing 10 mg/ml total protein) with PBS as the vehicle control. All solutions (PBS, nHC-HA/PTX3, and AMP) were drawn into a tuberculin syringe with 30 G. The injection locations are subconjunctiva close to fornix (FIG. 92). Four (4) injections at 3, 6, 9, and 12 o'clock with 5 µl per injection sites were administrated. The diffused solution completely covered the whole peripheral of conjunctiva and caused a minimum conjunctival or globe congestion/swelling (If any, it should disappear in 15 min) which impeded eye closure and corneal surface breakdown or inflammation. The injection was administrated at Day 1 and Day 3 (for all reagents), making a total of 2 times. This injection protocol is summarized in Table 6.

TABLE 6

Experimental groups and required reagents for nHC-HA/PTX3 or AMP reduction of DS-induced ALKC in murine experimental dry eye model.

| Group | Treatment | # Mice | Injection sites × volume × days × eyes × mice |
|---|---|---|---|
| 1 | UT | 15 | NA |
| 2 | EDE | 15 | NA |
| 3 | EDE + PBS | 15 | 4 × 5 µl × 5 × 2 × 15 = 3.0 ml |
| 4 | EDE + nHC-HA/PTX3 (1 mg/ml) | 15 | 4 × 5 µl × 5 × 2 × 15 = 3.0 ml |
| 5 | EDE + AMP (10 mg/ml) | 15 | 4 × 5 µl × 5 × 2 × 15 = 3.0 ml |

Measurement of Corneal Staining

On the morning of $5^{th}$ day, mice received one s.c. dose of scopolamine after measurement of tear volume. 2 hours after that scopolamine dose corneal staining was performed using Oregon Green Dextran (OGD-488), which is a conjugated fluorescent dye of a 70 kDa molecular size (Molecular Probes). The procedure consisted of instillation of 0.5 µl of OGD on the cornea using a glass capillary pipette, 1 minute before euthanasia. Mice were euthanized by inhalation of isoflurane anesthesic gas followed by cervical dislocation. Eyes were then rinsed with 2 ml of BSS. Excess liquid was carefully blotted from the ocular surface with filter papers without touching the cornea. Digital images of both eyes were captured under 470 nm excitation and 488 nm emission wave lengths using a Nikon SMZ-1500 stereo microscope with CoolSnap $HQ_2$ cooled CCD camera, with an exposure time of 1 second. Both eyes from each animal were evaluated. The fluorescence intensity in a fixed region of interest (a 1-mm diameter circle) in the central cornea was measured in 3 digital images using Nikon Elements software and data is stored in a database (Excel, Microsoft). Results were presented as mean±standard deviation of gray levels. Results from 3 separate experiments were averaged for statistical comparisons of groups.

The effects of nHC-HA/PTX3 and lyophilized amniotic membrane powder (AMP) on levels of T helper cell pathway mediators were compared in an experimental dry eye (EDE) model created in C57BL/6 mice for 5 days. Expression of Th1 (IL-12, IFN-γ and T-Bet), Th-17 (IL-23, IL-17, ROR-γt, IL-6, TGF-β1, MMP-3 and MMP-9) and Th2 (IL-4, IL-13 and GATA3) related factors were measured in the corneal epithelium and conjunctiva in the following groups by real-time PCR.

Statistical Analysis

Statistical analysis was performed using GraphPad Prism 5.0 software (GraphPad Inc). One-way analysis of variance (ANOVA) was used to determine overall differences among groups, followed by a post-hoc test (Tukey's post hoc). An unpaired t-test is used to evaluate statistical differences between 2 experimental groups.

Example 47. HC-HA Activates IGF1-HIF1α-VEGF Signaling to Promote Angiogenesis, which is Further Promoted by Addition of TGFβ1 in Human Corneal Fibroblasts In this example, the effect of HC-HA complexes on the induction of angiogenic markers in human corneal fibroblasts was examined.

Human corneal fibroblasts (3000 cells/well in a 96-well plate) were seeded on plastic dishes with or without immobilized HA, soluble HC-HA (PBS) (4×) or insoluble HC-HA (GnHC1) (4×) for 48 h as described above. The cells were then treated with or without TGFβ1 for 24 h before being harvested for mRNA quantitation of IGF1, HIF1α and VEGF. The experimental groups were:

```
PBS
PBS + TGF-β1
HA
HA + TGF-β1
4X HC-HA PBS
4X HC-HA PBS + TGF-β1
4X HC-HA Gn
4X HC-HA Gn + TGF-β1
```

Total RNAs were extracted using RNeasy Mini Kit (Qiagen) and were reverse transcribed using High Capacity Reverse Transcription Kit (Applied Biosystems). cDNA of each cell component was amplified by real-time RT-PCR using specific primer-probe mixtures and DNA polymerase in 7000 Real-time PCR System (Applied Biosystems). Real-time RT-PCR profile consisted of 10 minutes of initial activation at 95° C., followed by 40 cycles of 15 seconds denaturation at 95° C., and 1 minute annealing and extension at 60° C. The identity of each PCR product (IGF1, HIF1α and VEGF) was confirmed size determination using 2% agarose gels followed by ethidium bromide staining together with PCR marker according to EC3 Imaging System (BioImaging System).

HC-HA induced a 2- to 6-fold increase of IGF1 mRNA and 2-fold increase of VEGF mRNA when the cells were in resting conditions (FIG. 92). In contrast, HC-HA induced 5- to 12-fold increase of IGF1 mRNA and 5- to 9-fold increase of VEGF mRNA when the cells were challenged by TGFβ (10 ng/ml). VEGF has been demonstrated to be a major contributor to angiogenesis, increasing the number of capillaries in a given network. VEGF activation is controlled by upstream regulators such as IGF1 and HIF1α. Our results demonstrate that HC-HA activates IGF1-HIF1α-VEGF network to promote angiogenesis, which is further promoted by addition of TGFβ1 in human corneal fibroblasts.

While preferred embodiments have been shown and described herein, it will be obvious to those skilled in the art that such embodiments are provided by way of example only. Numerous variations, changes, and substitutions may now occur. It should be understood that various alternatives to the embodiments described herein can be employed in practicing the described methods. It is intended that the following claims define the scope of the embodiments and that methods and structures within the scope of these claims and their equivalents be covered thereby.

What is claimed is:

1. A method of reducing pain in an individual in need thereof, comprising administering to an individual having a chemical burn, severe bacterial keratitis, Stevens-Johnson syndrome, toxic epidermal necrolysis, irradiation of ocular tumors, arthritis, or bone spurs, a therapeutically effective amount of a composition comprising (i) a reconstituted HC-HA/PTX3 (rcHC-HA/PTX3) (heavy chain-hyaluronic acid/pentraxin3) complex; and (ii) a natural polymer, adjuvant, excipient, preservative, agent for delaying absorption, filler, binder, adsorbent, buffer, or combination thereof, thereby reducing pain associated with chemical burns, severe bacterial keratitis, Stevens-Johnson syndrome, toxic epidermal necrolysis, irradiation of ocular tumors, arthritis, or bone spurs.

2. The method of claim 1, wherein the rcHC-HA/PTX3 complex comprises hyaluronic acid (HA), heavy chain 1 (HC1) and heavy chain 2 (HC2) of inter-α-inhibitor (IαI) protein, and pentraxin 3 (PTX3).

3. The method of claim 1, wherein the administering is to an epidermis, dermis, hypodermis, sclera, cornea, retina, choroid, vitreous, optic nerve, nerve, tendon, tissue surrounding tendon, joint, or spine.

4. The method of claim 1, wherein the administering is by topical administration, injection, infusion, inhalation, or implantation.

5. The method of claim 4, wherein the injection is a subconjunctival injection, intracorneal injection, intravitreal injection, intrastromal injection, intraarterial injection, intracardiac injection, intraduodenal injection, intramedullary injection, intraosseous injection, intraperitoneal injection, intrathecal injection, intravascular injection, epidural injection, parenteral injection, enteral injection, subcutaneous injection, percutaneous injection, transdermal injection, intradermal injection, or injection into a joint.

6. The method of claim 1, wherein the composition is a solution, suspension, gel, powder, ointment, tablet, capsule, cream, lotion, paste, stick, syrup, granule, pill, aerosol, injectable depot preparation, or combinations thereof.

7. The method of claim 1, wherein the complex further comprises a small leucine rich proteoglycan (SLRP).

8. The method of claim 1, wherein the natural polymer comprises hyaluronic acid, collagen, fibrin, fibronectin, laminin, keratin, fibrinogen, heparan sulfate, chondroitin sulfate, or combinations thereof.

9. The method of claim 1, wherein the excipient is a tonicity agent.

10. The method of claim 9, wherein the tonicity agent is sodium chloride, potassium chloride, sodium thiosulfate, sodium bisulfate, or ammonium sulfate.

11. The method of claim 1, wherein the excipient is a clarifying agent.

12. The method of claim 11, wherein the clarifying agent is polysorbate 20, polysorbate 80, or combinations thereof.

13. The method of claim 1, wherein the excipient is a viscosity enhancer.

14. The method of claim 13, wherein the viscosity enhancer is carboxymethylcellulose, carbomer (acrylic acid polymer), poly(methylmethacrylate), polyacrylamide, polycarbophil, acrylic acid/butyl acrylate copolymer, sodium alginate, or dextran.

15. The method of claim 1, wherein the excipient is a solubilizing agent.

16. The method of claim 15, wherein the solubilizing agent is glucan sulfate, cyclodextrin, derivatives thereof, or a combination thereof.

17. The method of claim 1, further comprising administering to the individual an additional therapeutic agent.

18. The method of claim 1, wherein the composition comprises liposomes, niosomes, pharmacosomes, microspheres, microparticles, or nanoparticles.

19. The method of claim 1, wherein the rcHC-HA/PTX3 complex consists of HMW HA, HC1, HC2, and PTX3.

20. The method of claim 1, wherein the rcHC-HA/PTX3 complex consists of HMW HA, HC1, HC2, PTX3, and TSG-6.

* * * * *

SEQUENCE LISTING

<160> NUMBER OF SEQ ID NOS: 99

<210> SEQ ID NO 1
<211> LENGTH: 277
<212> TYPE: PRT
<213> ORGANISM: Homo sapiens

<400> SEQUENCE: 1

```
Met Ile Ile Leu Ile Tyr Leu Phe Leu Leu Leu Trp Glu Asp Thr Gln
1               5                   10                  15

Gly Trp Gly Phe Lys Asp Gly Ile Phe His Asn Ser Ile Trp Leu Glu
            20                  25                  30

Arg Ala Ala Gly Val Tyr His Arg Glu Ala Arg Ser Gly Lys Tyr Lys
        35                  40                  45

Leu Thr Tyr Ala Glu Ala Lys Ala Val Cys Glu Phe Glu Gly Gly His
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr
        115                 120                 125

Asn Pro His Ala Lys Glu Cys Gly Gly Val Phe Thr Asp Pro Lys Gln
    130                 135                 140

Ile Phe Lys Ser Pro Gly Phe Pro Asn Glu Tyr Glu Asp Asn Gln Ile
145                 150                 155                 160

Cys Tyr Trp His Ile Arg Leu Lys Tyr Gly Gln Arg Ile His Leu Ser
                165                 170                 175

Phe Leu Asp Phe Asp Leu Glu Asp Asp Pro Gly Cys Leu Ala Asp Tyr
            180                 185                 190
```

```
Val Glu Ile Tyr Asp Ser Tyr Asp Val His Gly Phe Val Gly Arg
            195                 200                 205

Tyr Cys Gly Asp Glu Leu Pro Asp Asp Ile Ile Ser Thr Gly Asn Val
210                 215                 220

Met Thr Leu Lys Phe Leu Ser Asp Ala Ser Val Thr Ala Gly Gly Phe
225                 230                 235                 240

Gln Ile Lys Tyr Val Ala Met Asp Pro Val Ser Lys Ser Ser Gln Gly
                245                 250                 255

Lys Asn Thr Ser Thr Thr Ser Thr Gly Asn Lys Asn Phe Leu Ala Gly
            260                 265                 270

Arg Phe Ser His Leu
            275

<210> SEQ ID NO 2
<211> LENGTH: 260
<212> TYPE: PRT
<213> ORGANISM: Homo sapiens

<400> SEQUENCE: 2

Trp Gly Phe Lys Asp Gly Ile Phe His Asn Ser Ile Trp Leu Glu Arg
1               5                   10                  15

Ala Ala Gly Val Tyr His Arg Glu Ala Arg Ser Gly Lys Tyr Lys Leu
                20                  25                  30

Thr Tyr Ala Glu Ala Lys Ala Val Cys Glu Phe Glu Gly Gly His Leu
            35                  40                  45

Ala Thr Tyr Lys Gln Leu Glu Ala Ala Arg Lys Ile Gly Phe His Val
        50                  55                  60

Cys Ala Ala Gly Trp Met Ala Lys Gly Arg Val Gly Tyr Pro Ile Val
65                  70                  75                  80

Lys Pro Gly Pro Asn Cys Gly Phe Gly Lys Thr Gly Ile Ile Asp Tyr
                85                  90                  95

Gly Ile Arg Leu Asn Arg Ser Glu Arg Trp Asp Ala Tyr Cys Tyr Asn
            100                 105                 110

Pro His Ala Lys Glu Cys Gly Gly Val Phe Thr Asp Pro Lys Gln Ile
        115                 120                 125

Phe Lys Ser Pro Gly Phe Pro Asn Glu Tyr Glu Asp Asn Gln Ile Cys
    130                 135                 140

Tyr Trp His Ile Arg Leu Lys Tyr Gly Gln Arg Ile His Leu Ser Phe
145                 150                 155                 160

Leu Asp Phe Asp Leu Glu Asp Asp Pro Gly Cys Leu Ala Asp Tyr Val
                165                 170                 175

Glu Ile Tyr Asp Ser Tyr Asp Val His Gly Phe Val Gly Arg Tyr
            180                 185                 190

Cys Gly Asp Glu Leu Pro Asp Asp Ile Ile Ser Thr Gly Asn Val Met
        195                 200                 205

Thr Leu Lys Phe Leu Ser Asp Ala Ser Val Thr Ala Gly Gly Phe Gln
    210                 215                 220

Ile Lys Tyr Val Ala Met Asp Pro Val Ser Lys Ser Ser Gln Gly Lys
225                 230                 235                 240

Asn Thr Ser Thr Thr Ser Thr Gly Asn Lys Asn Phe Leu Ala Gly Arg
                245                 250                 255

Phe Ser His Leu
            260

<210> SEQ ID NO 3
```

```
<211> LENGTH: 94
<212> TYPE: PRT
<213> ORGANISM: Homo sapiens

<400> SEQUENCE: 3

Gly Val Tyr His Arg Glu Ala Arg Ser Gly Lys Tyr Lys Leu Thr Tyr
1               5                   10                  15

Ala Glu Ala Lys Ala Val Cys Glu Phe Glu Gly Gly His Leu Ala Thr
            20                  25                  30

Tyr Lys Gln Leu Glu Ala Ala Arg Lys Ile Gly Phe His Val Cys Ala
        35                  40                  45

Ala Gly Trp Met Ala Lys Gly Arg Val Gly Tyr Pro Ile Val Lys Pro
    50                  55                  60

Gly Pro Asn Cys Gly Phe Gly Lys Thr Gly Ile Ile Asp Tyr Gly Ile
65                  70                  75                  80

Arg Leu Asn Arg Ser Glu Arg Trp Asp Ala Tyr Cys Tyr Asn
                85                  90

<210> SEQ ID NO 4
<211> LENGTH: 275
<212> TYPE: PRT
<213> ORGANISM: Mus musculus

<400> SEQUENCE: 4

Met Val Val Leu Leu Cys Leu Cys Val Leu Leu Trp Glu Glu Ala His
1               5                   10                  15

Gly Trp Gly Phe Lys Asn Gly Ile Phe His Asn Ser Ile Trp Leu Glu
            20                  25                  30

Gln Ala Ala Gly Val Tyr His Arg Glu Ala Arg Ala Gly Arg Tyr Lys
        35                  40                  45

Leu Thr Tyr Ala Glu Ala Lys Ala Val Cys Glu Phe Glu Gly Gly Arg
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr
        115                 120                 125

Asn Pro His Ala Lys Glu Cys Gly Gly Val Phe Thr Asp Pro Lys Arg
    130                 135                 140

Ile Phe Lys Ser Pro Gly Phe Pro Asn Glu Tyr Asp Asp Asn Gln Val
145                 150                 155                 160

Cys Tyr Trp His Ile Arg Leu Lys Tyr Gly Gln Arg Ile His Leu Ser
                165                 170                 175

Phe Leu Asp Phe Asp Leu Glu His Asp Pro Gly Cys Leu Ala Asp Tyr
            180                 185                 190

Val Glu Ile Tyr Asp Ser Tyr Asp Asp Val His Gly Phe Val Gly Arg
        195                 200                 205

Tyr Cys Gly Asp Glu Leu Pro Glu Asp Ile Ile Ser Thr Gly Asn Val
    210                 215                 220

Met Thr Leu Lys Phe Leu Ser Asp Ala Ser Val Thr Ala Gly Gly Phe
225                 230                 235                 240

Gln Ile Lys Tyr Val Thr Val Asp Pro Ala Ser Lys Ser Ser Gln Ala
                245                 250                 255
```

Lys Asn Thr Ser Thr Thr Gly Asn Lys Lys Phe Leu Pro Gly Arg Phe
                260                 265                 270

Ser His Leu
        275

<210> SEQ ID NO 5
<211> LENGTH: 258
<212> TYPE: PRT
<213> ORGANISM: Mus musculus

<400> SEQUENCE: 5

Trp Gly Phe Lys Asn Gly Ile Phe His Asn Ser Ile Trp Leu Glu Gln
1               5                   10                  15

Ala Ala Gly Val Tyr His Arg Glu Ala Arg Ala Gly Arg Tyr Lys Leu
            20                  25                  30

Thr Tyr Ala Glu Ala Lys Ala Val Cys Glu Phe Glu Gly Gly Arg Leu
        35                  40                  45

Ala Thr Tyr Lys Gln Leu Glu Ala Arg Lys Ile Gly Phe His Val
    50                  55                  60

Cys Ala Ala Gly Trp Met Ala Lys Gly Arg Val Gly Tyr Pro Ile Val
65                  70                  75                  80

Lys Pro Gly Pro Asn Cys Gly Phe Gly Lys Thr Gly Ile Ile Asp Tyr
                85                  90                  95

Gly Ile Arg Leu Asn Arg Ser Glu Arg Trp Asp Ala Tyr Cys Tyr Asn
            100                 105                 110

Pro His Ala Lys Glu Cys Gly Gly Val Phe Thr Asp Pro Lys Arg Ile
        115                 120                 125

Phe Lys Ser Pro Gly Phe Pro Asn Glu Tyr Asp Asp Asn Gln Val Cys
    130                 135                 140

Tyr Trp His Ile Arg Leu Lys Tyr Gly Gln Arg Ile His Leu Ser Phe
145                 150                 155                 160

Leu Asp Phe Asp Leu Glu His Asp Pro Gly Cys Leu Ala Asp Tyr Val
                165                 170                 175

Glu Ile Tyr Asp Ser Tyr Asp Asp Val His Gly Phe Val Gly Arg Tyr
            180                 185                 190

Cys Gly Asp Glu Leu Pro Glu Asp Ile Ile Ser Thr Gly Asn Val Met
        195                 200                 205

Thr Leu Lys Phe Leu Ser Asp Ala Ser Val Thr Ala Gly Gly Phe Gln
    210                 215                 220

Ile Lys Tyr Val Thr Val Asp Pro Ala Ser Lys Ser Ser Gln Ala Lys
225                 230                 235                 240

Asn Thr Ser Thr Thr Gly Asn Lys Lys Phe Leu Pro Gly Arg Phe Ser
                245                 250                 255

His Leu

<210> SEQ ID NO 6
<211> LENGTH: 94
<212> TYPE: PRT
<213> ORGANISM: Mus musculus

<400> SEQUENCE: 6

Gly Val Tyr His Arg Glu Ala Arg Ala Gly Arg Tyr Lys Leu Thr Tyr
1               5                   10                  15

Ala Glu Ala Lys Ala Val Cys Glu Phe Glu Gly Gly Arg Leu Ala Thr
            20                  25                  30

Tyr Lys Gln Leu Glu Ala Ala Arg Lys Ile Gly Phe His Val Cys Ala
    35                  40                  45

Ala Gly Trp Met Ala Lys Gly Arg Val Gly Tyr Pro Ile Val Lys Pro
50                  55                  60

Gly Pro Asn Cys Gly Phe Gly Lys Thr Gly Ile Ile Asp Tyr Gly Ile
65                  70                  75                  80

Arg Leu Asn Arg Ser Glu Arg Trp Asp Ala Tyr Cys Tyr Asn
                85                  90

<210> SEQ ID NO 7
<211> LENGTH: 276
<212> TYPE: PRT
<213> ORGANISM: Oryctolagus cuniculus

<400> SEQUENCE: 7

Met Ile Ile Leu Ile Tyr Leu Phe Val Leu Val Trp Glu Glu Ala Gln
1               5                   10                  15

Gly Trp Gly Phe Lys Asn Gly Ile Phe His Asn Ser Ile Trp Leu Glu
                20                  25                  30

Gln Ala Ala Gly Val Tyr His Arg Glu Ala Arg Ser Gly Lys Tyr Lys
            35                  40                  45

Leu Thr Tyr Ala Glu Ala Lys Ala Val Cys Glu Phe Glu Gly Gly Arg
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Ser Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr
        115                 120                 125

Asn Pro His Ala Lys Glu Cys Gly Gly Val Phe Thr Asp Pro Lys Arg
    130                 135                 140

Ile Phe Lys Ser Pro Gly Phe Pro Asn Glu Tyr Asp Asp Asn Gln Ile
145                 150                 155                 160

Cys Tyr Trp His Ile Arg Leu Lys Tyr Gly Gln Arg Ile His Leu Ser
                165                 170                 175

Phe Leu Asn Phe Asp Leu Glu Tyr Asp Pro Gly Cys Leu Ala Asp Tyr
            180                 185                 190

Val Glu Ile Tyr Asp Ser Tyr Asp Asp Val His Gly Phe Val Gly Arg
        195                 200                 205

Tyr Cys Gly Asp Glu Leu Pro Glu Asp Ile Ile Ser Thr Gly Asn Val
    210                 215                 220

Met Thr Leu Lys Phe Leu Ser Asp Ala Ser Val Thr Ala Gly Gly Phe
225                 230                 235                 240

Gln Ile Lys Tyr Val Thr Val Asp Pro Ala Ser Lys Ser Ser Gln Gly
                245                 250                 255

Lys Asn Thr Ser Thr Val Ser Gly Asn Lys Asn Phe Leu Ala Gly Arg
            260                 265                 270

Phe Ser His Leu
        275

<210> SEQ ID NO 8
<211> LENGTH: 259
<212> TYPE: PRT
<213> ORGANISM: Oryctolagus cuniculus

<400> SEQUENCE: 8

```
Trp Gly Phe Lys Asn Gly Ile Phe His Asn Ser Ile Trp Leu Glu Gln
1               5                   10                  15
Ala Ala Gly Val Tyr His Arg Glu Ala Arg Ser Gly Lys Tyr Lys Leu
            20                  25                  30
Thr Tyr Ala Glu Ala Lys Ala Val Cys Glu Phe Glu Gly Gly Arg Leu
        35                  40                  45
Ala Thr Tyr Lys Gln Leu Glu Ala Ala Arg Lys Ile Gly Phe His Val
    50                  55                  60
Cys Ala Ala Gly Trp Met Ala Lys Gly Arg Val Gly Tyr Pro Ile Val
65                  70                  75                  80
Lys Pro Gly Ser Asn Cys Gly Phe Gly Lys Thr Gly Ile Ile Asp Tyr
                85                  90                  95
Gly Ile Arg Leu Asn Arg Ser Glu Arg Trp Asp Ala Tyr Cys Tyr Asn
            100                 105                 110
Pro His Ala Lys Glu Cys Gly Gly Val Phe Thr Asp Pro Lys Arg Ile
        115                 120                 125
Phe Lys Ser Pro Gly Phe Pro Asn Glu Tyr Asp Asp Asn Gln Ile Cys
    130                 135                 140
Tyr Trp His Ile Arg Leu Lys Tyr Gly Gln Arg Ile His Leu Ser Phe
145                 150                 155                 160
Leu Asn Phe Asp Leu Glu Tyr Asp Pro Gly Cys Leu Ala Asp Tyr Val
                165                 170                 175
Glu Ile Tyr Asp Ser Tyr Asp Asp Val His Gly Phe Val Gly Arg Tyr
            180                 185                 190
Cys Gly Asp Glu Leu Pro Glu Asp Ile Ile Ser Thr Gly Asn Val Met
        195                 200                 205
Thr Leu Lys Phe Leu Ser Asp Ala Ser Val Thr Ala Gly Gly Phe Gln
    210                 215                 220
Ile Lys Tyr Val Thr Val Asp Pro Ala Ser Lys Ser Gln Gly Lys
225                 230                 235                 240
Asn Thr Ser Thr Val Ser Gly Asn Lys Asn Phe Leu Ala Gly Arg Phe
                245                 250                 255
Ser His Leu
```

<210> SEQ ID NO 9
<211> LENGTH: 94
<212> TYPE: PRT
<213> ORGANISM: Oryctolagus cuniculus

<400> SEQUENCE: 9

```
Gly Val Tyr His Arg Glu Ala Arg Ser Gly Lys Tyr Lys Leu Thr Tyr
1               5                   10                  15
Ala Glu Ala Lys Ala Val Cys Glu Phe Glu Gly Gly Arg Leu Ala Thr
            20                  25                  30
Tyr Lys Gln Leu Glu Ala Ala Arg Lys Ile Gly Phe His Val Cys Ala
        35                  40                  45
Ala Gly Trp Met Ala Lys Gly Arg Val Gly Tyr Pro Ile Val Lys Pro
    50                  55                  60
Gly Ser Asn Cys Gly Phe Gly Lys Thr Gly Ile Ile Asp Tyr Gly Ile
65                  70                  75                  80
Arg Leu Asn Arg Ser Glu Arg Trp Asp Ala Tyr Cys Tyr Asn
                85                  90
```

<210> SEQ ID NO 10
<211> LENGTH: 280
<212> TYPE: PRT
<213> ORGANISM: Bos taurus

<400> SEQUENCE: 10

Met Ile Ile Leu Ile Tyr Leu Phe Val Leu Trp Glu Glu Ala His
1               5                   10                  15

Gly Trp Gly Phe Lys Asn Gly Ile Phe His Asn Ser Ile Trp Leu Glu
            20                  25                  30

Gln Ala Ala Gly Val Tyr His Arg Glu Ala Arg Ser Gly Lys Tyr Lys
        35                  40                  45

Leu Thr Tyr Ala Glu Ala Lys Ala Val Cys Glu Tyr Glu Gly Gly His
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr
        115                 120                 125

Asn Pro His Ala Lys Glu Cys Gly Gly Val Phe Thr Asp Pro Lys Arg
    130                 135                 140

Ile Phe Lys Ser Pro Gly Phe Pro Asn Glu Tyr Asp Asp Asn Gln Ile
145                 150                 155                 160

Cys Tyr Trp His Ile Arg Leu Lys Tyr Gly Gln Arg Ile His Leu Ser
                165                 170                 175

Phe Leu Asp Phe Asp Leu Glu Asp Asp Pro Ala Cys Leu Ala Asp Tyr
            180                 185                 190

Val Glu Val Tyr Asp Ser Tyr Asp Asp Val His Gly Phe Val Gly Arg
        195                 200                 205

Tyr Cys Gly Asp Glu Leu Pro Glu Asp Ile Ile Ser Thr Gly Asn Val
    210                 215                 220

Met Thr Leu Lys Phe Leu Ser Asp Ala Ser Val Thr Ala Gly Gly Phe
225                 230                 235                 240

Gln Ile Lys Tyr Val Ala Val Asp Pro Val Ser Lys Ser Ser Gln Gly
                245                 250                 255

Lys Asn Ala Ser Thr Thr Ser Thr Thr Ser Thr Gly Asn Lys Asn Phe
            260                 265                 270

Leu Ala Gly Arg Phe Ser His Leu
        275                 280

<210> SEQ ID NO 11
<211> LENGTH: 263
<212> TYPE: PRT
<213> ORGANISM: Bos Taurus

<400> SEQUENCE: 11

Trp Gly Phe Lys Asn Gly Ile Phe His Asn Ser Ile Trp Leu Glu Gln
1               5                   10                  15

Ala Ala Gly Val Tyr His Arg Glu Ala Arg Ser Gly Lys Tyr Lys Leu
            20                  25                  30

Thr Tyr Ala Glu Ala Lys Ala Val Cys Glu Tyr Glu Gly Gly His Leu
        35                  40                  45

```
Ala Thr Tyr Lys Gln Leu Glu Ala Ala Arg Lys Ile Gly Phe His Val
 50                  55                  60
Cys Ala Ala Gly Trp Met Ala Lys Gly Arg Val Gly Tyr Pro Ile Val
 65                  70                  75                  80
Lys Pro Gly Pro Asn Cys Gly Phe Gly Lys Thr Gly Ile Ile Asp Tyr
                 85                  90                  95
Gly Ile Arg Leu Asn Arg Ser Glu Arg Trp Asp Ala Tyr Cys Tyr Asn
                100                 105                 110
Pro His Ala Lys Glu Cys Gly Gly Val Phe Thr Asp Pro Lys Arg Ile
            115                 120                 125
Phe Lys Ser Pro Gly Phe Pro Asn Glu Tyr Asp Asn Gln Ile Cys
130                 135                 140
Tyr Trp His Ile Arg Leu Lys Tyr Gly Gln Arg Ile His Leu Ser Phe
145                 150                 155                 160
Leu Asp Phe Asp Leu Glu Asp Pro Ala Cys Leu Ala Asp Tyr Val
                165                 170                 175
Glu Val Tyr Asp Ser Tyr Asp Val His Gly Phe Val Gly Arg Tyr
                180                 185                 190
Cys Gly Asp Glu Leu Pro Glu Asp Ile Ile Ser Thr Gly Asn Val Met
            195                 200                 205
Thr Leu Lys Phe Leu Ser Asp Ala Ser Val Thr Ala Gly Phe Gln
210                 215                 220
Ile Lys Tyr Val Ala Val Asp Pro Val Ser Lys Ser Gln Gly Lys
225                 230                 235                 240
Asn Ala Ser Thr Thr Ser Thr Thr Ser Thr Gly Asn Lys Asn Phe Leu
                245                 250                 255
Ala Gly Arg Phe Ser His Leu
            260

<210> SEQ ID NO 12
<211> LENGTH: 275
<212> TYPE: PRT
<213> ORGANISM: Gallus gallus

<400> SEQUENCE: 12

Met Ile Ala Leu Ile Phe Phe Ser Ala Leu Leu Trp Asp Glu Ala Gln
  1               5                  10                  15
Ala Trp Gly Phe Lys Asp Gly Val Leu His Asn Ser Ile Trp Leu Glu
                 20                  25                  30
Arg Ala Ala Gly Val Tyr His Arg Glu Ser Arg Ser Gly Lys Tyr Gln
             35                  40                  45
Leu Thr Tyr Ala Glu Ala Lys Ala Val Cys Glu Tyr Glu Gly Gly His
 50                  55                  60
Leu Ala Thr Tyr Gln Gln Leu Glu Ala Ala Arg Lys Ile Gly Phe His
 65                  70                  75                  80
Val Cys Ala Ala Gly Trp Met Ala Lys Gly Arg Val Gly Tyr Pro Ile
                 85                  90                  95
Val Lys Ala Gly Ala Asn Cys Gly Phe Gly Arg Thr Gly Ile Val Asp
            100                 105                 110
Tyr Gly Ile Arg Leu Asn Arg Ser Glu Arg Trp Asp Ala Tyr Cys Tyr
            115                 120                 125
Asn Pro Asn Gly Lys Glu Cys Gly Gly Val Phe Thr Asp Ser Lys His
130                 135                 140
Val Phe Lys Ser Pro Gly Tyr Pro Asn Glu Tyr Glu Asn Asp Gln Ile
145                 150                 155                 160
```

```
Cys Tyr Trp His Ile Arg Val Lys Tyr Gly Gln Arg Ile His Leu Gln
                165                 170                 175

Phe Leu Glu Phe Asp Val Glu Asp Thr Ala Cys Met Ala Asp Tyr
            180                 185                 190

Leu Glu Ile Tyr Asp Ser Tyr Asp Asp Ile Asn Gly Phe Val Gly Arg
            195                 200                 205

Phe Cys Gly Asp Glu Leu Pro Asp Asp Ile Ile Ser Thr Gly Asn Val
        210                 215                 220

Met Thr Leu Lys Phe Leu Ser Asp Ala Ser Val Thr Ala Gly Gly Phe
225                 230                 235                 240

Gln Ile Arg Tyr Val Thr Ile Asp Val Pro Ser Lys Ala Gly Asp Gly
                245                 250                 255

Lys Asn Thr Thr Ser Gln Gly Lys Ala Asn Phe Leu Ser Gly Lys Phe
                260                 265                 270

Gly Ile Met
        275

<210> SEQ ID NO 13
<211> LENGTH: 258
<212> TYPE: PRT
<213> ORGANISM: Gallus gallus

<400> SEQUENCE: 13

Trp Gly Phe Lys Asp Gly Val Leu His Asn Ser Ile Trp Leu Glu Arg
1               5                   10                  15

Ala Ala Gly Val Tyr His Arg Glu Ser Arg Ser Gly Lys Tyr Gln Leu
            20                  25                  30

Thr Tyr Ala Glu Ala Lys Ala Val Cys Glu Tyr Glu Gly Gly His Leu
        35                  40                  45

Ala Thr Tyr Gln Gln Leu Glu Ala Ala Arg Lys Ile Gly Phe His Val
    50                  55                  60

Cys Ala Ala Gly Trp Met Ala Lys Gly Arg Val Gly Tyr Pro Ile Val
65                  70                  75                  80

Lys Ala Gly Ala Asn Cys Gly Phe Gly Arg Thr Gly Ile Val Asp Tyr
                85                  90                  95

Gly Ile Arg Leu Asn Arg Ser Glu Arg Trp Asp Ala Tyr Cys Tyr Asn
                100                 105                 110

Pro Asn Gly Lys Glu Cys Gly Gly Val Phe Thr Asp Ser Lys His Val
            115                 120                 125

Phe Lys Ser Pro Gly Tyr Pro Asn Glu Tyr Glu Asn Asp Gln Ile Cys
        130                 135                 140

Tyr Trp His Ile Arg Val Lys Tyr Gly Gln Arg Ile His Leu Gln Phe
145                 150                 155                 160

Leu Glu Phe Asp Val Glu Asp Thr Ala Cys Met Ala Asp Tyr Leu
                165                 170                 175

Glu Ile Tyr Asp Ser Tyr Asp Asp Ile Asn Gly Phe Val Gly Arg Phe
            180                 185                 190

Cys Gly Asp Glu Leu Pro Asp Asp Ile Ile Ser Thr Gly Asn Val Met
        195                 200                 205

Thr Leu Lys Phe Leu Ser Asp Ala Ser Val Thr Ala Gly Gly Phe Gln
    210                 215                 220

Ile Arg Tyr Val Thr Ile Asp Val Pro Ser Lys Ala Gly Asp Gly Lys
225                 230                 235                 240

Asn Thr Thr Ser Gln Gly Lys Ala Asn Phe Leu Ser Gly Lys Phe Gly
```

```
                        245                 250                 255

Ile Met

<210> SEQ ID NO 14
<211> LENGTH: 277
<212> TYPE: PRT
<213> ORGANISM: Macaca mulatta

<400> SEQUENCE: 14

Met Ile Ile Leu Ile Tyr Leu Phe Leu Leu Trp Glu Glu Ala Gln
1               5                   10                  15

Gly Trp Gly Phe Lys Asp Gly Ile Phe His Asn Ser Ile Trp Leu Glu
            20                  25                  30

Arg Ala Ala Gly Val Tyr His Arg Glu Ser Arg Ser Gly Lys Tyr Lys
        35                  40                  45

Leu Thr Tyr Ala Glu Ala Lys Ala Val Cys Glu Phe Glu Gly Gly His
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Val Arg Leu Asn Arg Ser Glu Arg Trp Asp Ala Tyr Cys Tyr
        115                 120                 125

Asn Pro His Ala Lys Glu Cys Gly Gly Val Phe Thr Asp Ser Lys Gly
    130                 135                 140

Ile Phe Lys Ser Pro Gly Phe Pro Asn Glu Tyr Glu Asp Asn Gln Ile
145                 150                 155                 160

Cys Tyr Trp His Ile Arg Leu Lys Tyr Gly Gln His Ile His Leu Ser
                165                 170                 175

Phe Leu Asp Phe Asp Leu Glu Asp Asp Pro Gly Cys Leu Ala Asp Tyr
            180                 185                 190

Val Glu Ile Tyr Asp Ser Tyr Asp Asp Val His Gly Phe Val Gly Arg
        195                 200                 205

Tyr Cys Gly Asp Glu Leu Pro Asp Asp Ile Ile Ser Thr Gly Asn Val
    210                 215                 220

Met Thr Leu Lys Phe Leu Ser Asp Ala Ser Val Thr Ala Gly Gly Phe
225                 230                 235                 240

Gln Ile Lys Tyr Val Ala Val Asp Pro Val Ser Lys Ser Ser Gln Gly
                245                 250                 255

Lys Asn Thr Ser Thr Thr Ser Thr Gly Asn Lys Asn Phe Leu Ala Gly
            260                 265                 270

Arg Phe Ser His Leu
        275

<210> SEQ ID NO 15
<211> LENGTH: 260
<212> TYPE: PRT
<213> ORGANISM: Macaca mulatta

<400> SEQUENCE: 15

Trp Gly Phe Lys Asp Gly Ile Phe His Asn Ser Ile Trp Leu Glu Arg
1               5                   10                  15

Ala Ala Gly Val Tyr His Arg Glu Ser Arg Ser Gly Lys Tyr Lys Leu
            20                  25                  30
```

```
Thr Tyr Ala Glu Ala Lys Ala Val Cys Glu Phe Glu Gly Gly His Leu
        35                  40                  45

Ala Thr Tyr Lys Gln Leu Glu Ala Ala Arg Lys Ile Gly Phe His Val
 50                  55                  60

Cys Ala Ala Gly Trp Met Ala Lys Gly Arg Val Gly Tyr Pro Ile Val
 65                  70                  75                  80

Lys Pro Gly Pro Asn Cys Gly Phe Gly Lys Thr Gly Ile Ile Asp Tyr
                 85                  90                  95

Gly Val Arg Leu Asn Arg Ser Glu Arg Trp Asp Ala Tyr Cys Tyr Asn
            100                 105                 110

Pro His Ala Lys Glu Cys Gly Gly Val Phe Thr Asp Ser Lys Gly Ile
        115                 120                 125

Phe Lys Ser Pro Gly Phe Pro Asn Glu Tyr Glu Asp Asn Gln Ile Cys
    130                 135                 140

Tyr Trp His Ile Arg Leu Lys Tyr Gly Gln His Ile His Leu Ser Phe
145                 150                 155                 160

Leu Asp Phe Asp Leu Glu Asp Pro Gly Cys Leu Ala Asp Tyr Val
                165                 170                 175

Glu Ile Tyr Asp Ser Tyr Asp Asp Val His Gly Phe Val Gly Arg Tyr
            180                 185                 190

Cys Gly Asp Glu Leu Pro Asp Asp Ile Ile Ser Thr Gly Asn Val Met
        195                 200                 205

Thr Leu Lys Phe Leu Ser Asp Ala Ser Val Thr Ala Gly Gly Phe Gln
    210                 215                 220

Ile Lys Tyr Val Ala Val Asp Pro Val Ser Lys Ser Ser Gln Gly Lys
225                 230                 235                 240

Asn Thr Ser Thr Thr Ser Thr Gly Asn Lys Asn Phe Leu Ala Gly Arg
                245                 250                 255

Phe Ser His Leu
            260

<210> SEQ ID NO 16
<211> LENGTH: 277
<212> TYPE: PRT
<213> ORGANISM: Sus scrofa

<400> SEQUENCE: 16

Met Ile Ile Leu Ile Tyr Leu Phe Val Phe Leu Trp Glu Glu Ala His
 1               5                  10                  15

Gly Trp Gly Phe Lys Asn Gly Ile Phe His Asn Ser Ile Trp Leu Glu
            20                  25                  30

Gln Ala Ala Gly Val Tyr Leu Arg Glu Ala Arg Ser Gly Lys Tyr Lys
        35                  40                  45

Leu Thr Tyr Ala Glu Ala Lys Ala Val Cys Glu Tyr Glu Gly Gly Arg
 50                  55                  60

Leu Ala Thr Tyr Lys Gln Leu Glu Ala Ala Arg Lys Ile Gly Phe His
 65                  70                  75                  80

Val Cys Ala Ala Gly Trp Met Ala Lys Gly Arg Val Gly Tyr Pro Ile
                 85                  90                  95

Val Lys Pro Gly Pro Asn Cys Gly Phe Gly Lys Thr Gly Ile Ile Asp
            100                 105                 110

Tyr Gly Val Arg Leu Asn Arg Ser Glu Arg Trp Asp Ala Tyr Cys Tyr
        115                 120                 125

Asn Pro His Ala Lys Glu Cys Gly Gly Val Phe Thr Asp Pro Lys Arg
```

```
                130                 135                 140
Ile Phe Lys Ser Pro Gly Phe Pro Asn Glu Tyr Asp Asp Asn Gln Ile
145                 150                 155                 160

Cys Tyr Trp His Ile Arg Leu Lys Tyr Gly Gln Arg Ile His Val Ser
                165                 170                 175

Phe Leu Asp Phe Asp Leu Glu Asp Asp Pro Ala Cys Leu Ala Asp Tyr
                180                 185                 190

Val Glu Ile Tyr Asp Ser Tyr Asp Asp Val His Gly Phe Val Gly Arg
                195                 200                 205

Tyr Cys Gly Ala Glu Leu Pro Glu Asp Ile Ile Ser Thr Gly Asn Val
                210                 215                 220

Met Thr Leu Lys Phe Leu Ser Asp Ala Ser Val Thr Ala Gly Gly Phe
225                 230                 235                 240

Gln Ile Lys Tyr Val Ala Val Asp Pro Leu Ser Lys Thr Ser Gln Gly
                245                 250                 255

Lys Asn Thr Thr Thr Thr Ser Thr Gly Asn Lys Ser Phe Leu Ala Gly
                260                 265                 270

Arg Phe Ser His Leu
                275

<210> SEQ ID NO 17
<211> LENGTH: 260
<212> TYPE: PRT
<213> ORGANISM: Sus scrofa

<400> SEQUENCE: 17

Trp Gly Phe Lys Asn Gly Ile Phe His Asn Ser Ile Trp Leu Glu Gln
1               5                   10                  15

Ala Ala Gly Val Tyr Leu Arg Glu Ala Arg Ser Gly Lys Tyr Lys Leu
                20                  25                  30

Thr Tyr Ala Glu Ala Lys Ala Val Cys Glu Tyr Glu Gly Gly Arg Leu
                35                  40                  45

Ala Thr Tyr Lys Gln Leu Glu Ala Ala Arg Lys Ile Gly Phe His Val
        50                  55                  60

Cys Ala Ala Gly Trp Met Ala Lys Gly Arg Val Gly Tyr Pro Ile Val
65                  70                  75                  80

Lys Pro Gly Pro Asn Cys Gly Phe Gly Lys Thr Gly Ile Ile Asp Tyr
                85                  90                  95

Gly Val Arg Leu Asn Arg Ser Glu Arg Trp Asp Ala Tyr Cys Tyr Asn
                100                 105                 110

Pro His Ala Lys Glu Cys Gly Gly Val Phe Thr Asp Pro Lys Arg Ile
        115                 120                 125

Phe Lys Ser Pro Gly Phe Pro Asn Glu Tyr Asp Asp Asn Gln Ile Cys
        130                 135                 140

Tyr Trp His Ile Arg Leu Lys Tyr Gly Gln Arg Ile His Val Ser Phe
145                 150                 155                 160

Leu Asp Phe Asp Leu Glu Asp Asp Pro Ala Cys Leu Ala Asp Tyr Val
                165                 170                 175

Glu Ile Tyr Asp Ser Tyr Asp Asp Val His Gly Phe Val Gly Arg Tyr
                180                 185                 190

Cys Gly Ala Glu Leu Pro Glu Asp Ile Ile Ser Thr Gly Asn Val Met
        195                 200                 205

Thr Leu Lys Phe Leu Ser Asp Ala Ser Val Thr Ala Gly Gly Phe Gln
        210                 215                 220
```

```
Ile Lys Tyr Val Ala Val Asp Pro Leu Ser Lys Thr Ser Gln Gly Lys
225                 230                 235                 240

Asn Thr Thr Thr Thr Ser Thr Gly Asn Lys Ser Phe Leu Ala Gly Arg
                245                 250                 255

Phe Ser His Leu
            260

<210> SEQ ID NO 18
<211> LENGTH: 277
<212> TYPE: PRT
<213> ORGANISM: Canis lupus familiaris

<400> SEQUENCE: 18

Met Ile Ile Phe Ile Ser Leu Phe Val Leu Leu Trp Glu Glu Ala His
1               5                   10                  15

Gly Trp Gly Phe Asn Asn Gly Ile Phe His Asn Ser Ile Trp Leu Glu
            20                  25                  30

Gln Ala Ala Gly Val Tyr His Arg Glu Ala Arg Ser Gly Arg Tyr Arg
        35                  40                  45

Leu Thr Tyr Ala Glu Ala Lys Ala Val Cys Glu Phe Glu Gly Gly Arg
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Val Arg Leu Asn Arg Ser Glu Arg Trp Asp Ala Tyr Cys Tyr
        115                 120                 125

Asn Pro His Ala Lys Glu Cys Gly Gly Val Phe Thr Asp Pro Lys Arg
    130                 135                 140

Ile Phe Lys Ser Pro Gly Phe Pro Asn Glu Tyr Asp Asp Asn Gln Ile
145                 150                 155                 160

Cys Tyr Trp His Ile Arg Val Lys Tyr Gly Gln Arg Val His Leu Ser
                165                 170                 175

Phe Leu Asp Phe Asp Leu Glu Asp Pro Ala Cys Leu Ala Asp Tyr
            180                 185                 190

Val Glu Ile Tyr Asp Ser Tyr Asp Asp Val His Gly Phe Val Gly Arg
        195                 200                 205

Tyr Cys Gly Asp Glu Leu Pro Glu Asp Ile Ile Ser Thr Gly Asn Val
    210                 215                 220

Met Thr Leu Lys Phe Leu Ser Asp Ala Ser Val Thr Ala Gly Gly Phe
225                 230                 235                 240

Gln Ile Lys Tyr Ile Ala Val Asp Pro Leu Ser Lys Ser Ser Gln Gly
                245                 250                 255

Lys Asn Thr Ser Thr Thr Ser Thr Gly Asn Lys Asn Phe Leu Ala Gly
            260                 265                 270

Arg Phe Ser His Leu
        275

<210> SEQ ID NO 19
<211> LENGTH: 260
<212> TYPE: PRT
<213> ORGANISM: Canis lupus familiaris

<400> SEQUENCE: 19
```

```
Trp Gly Phe Asn Asn Gly Ile Phe His Asn Ser Ile Trp Leu Glu Gln
1               5                   10                  15

Ala Ala Gly Val Tyr His Arg Glu Ala Arg Ser Gly Arg Tyr Arg Leu
            20                  25                  30

Thr Tyr Ala Glu Ala Lys Ala Val Cys Glu Phe Glu Gly Gly Arg Leu
        35                  40                  45

Ala Thr Tyr Lys Gln Leu Glu Ala Ala Arg Lys Ile Gly Phe His Val
    50                  55                  60

Cys Ala Ala Gly Trp Met Ala Lys Gly Arg Val Gly Tyr Pro Ile Val
65                  70                  75                  80

Lys Pro Gly Pro Asn Cys Gly Phe Gly Lys Thr Gly Ile Ile Asp Tyr
                85                  90                  95

Gly Val Arg Leu Asn Arg Ser Glu Arg Trp Asp Ala Tyr Cys Tyr Asn
            100                 105                 110

Pro His Ala Lys Glu Cys Gly Gly Val Phe Thr Asp Pro Lys Arg Ile
        115                 120                 125

Phe Lys Ser Pro Gly Phe Pro Asn Glu Tyr Asp Asn Gln Ile Cys
    130                 135                 140

Tyr Trp His Ile Arg Val Lys Tyr Gly Gln Arg Val His Leu Ser Phe
145                 150                 155                 160

Leu Asp Phe Asp Leu Glu Asp Pro Ala Cys Leu Ala Asp Tyr Val
                165                 170                 175

Glu Ile Tyr Asp Ser Tyr Asp Val His Gly Phe Val Gly Arg Tyr
                180                 185                 190

Cys Gly Asp Glu Leu Pro Glu Asp Ile Ile Ser Thr Gly Asn Val Met
    195                 200                 205

Thr Leu Lys Phe Leu Ser Asp Ala Ser Val Thr Ala Gly Gly Phe Gln
    210                 215                 220

Ile Lys Tyr Ile Ala Val Asp Pro Leu Ser Lys Ser Ser Gln Gly Lys
225                 230                 235                 240

Asn Thr Ser Thr Thr Ser Thr Gly Asn Lys Asn Phe Leu Ala Gly Arg
                245                 250                 255

Phe Ser His Leu
            260

<210> SEQ ID NO 20
<211> LENGTH: 275
<212> TYPE: PRT
<213> ORGANISM: Cricetulus griseus

<400> SEQUENCE: 20

Met Val Val Leu Ile Cys Leu Cys Val Leu Leu Trp Glu Glu Val His
1               5                   10                  15

Gly Trp Gly Phe Lys Asn Gly Ile Phe His Asn Ser Ile Trp Leu Glu
            20                  25                  30

Gln Ala Ala Gly Val Tyr His Arg Glu Ala Arg Ala Gly Lys Tyr Lys
        35                  40                  45

Leu Thr Tyr Ala Glu Ala Lys Thr Val Cys Glu Phe Glu Gly Gly Arg
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110
```

Tyr Gly Ile Arg Leu Asn Arg Ser Glu Arg Trp Asp Ala Tyr Cys Tyr
            115                 120                 125

Asn Pro His Ala Lys Glu Cys Gly Val Phe Thr Asp Pro Lys Arg
    130                 135                 140

Ile Phe Lys Ser Pro Gly Phe Pro Asn Glu Tyr Asp Asp Asn Gln Val
145                 150                 155                 160

Cys Tyr Trp His Ile Arg Leu Lys Tyr Gly Gln Arg Ile His Leu Ser
                165                 170                 175

Phe Leu Asp Phe Asp Leu Glu His Asp Pro Gly Cys Leu Ala Asp Tyr
            180                 185                 190

Val Glu Ile Tyr Asp Ser Tyr Asp Asp Val His Gly Phe Val Gly Arg
            195                 200                 205

Tyr Cys Gly Asp Glu Leu Pro Glu Asp Ile Ile Ser Thr Gly Asn Val
        210                 215                 220

Met Thr Leu Lys Phe Leu Ser Asp Ala Ser Val Thr Ala Gly Gly Phe
225                 230                 235                 240

Gln Ile Lys Tyr Val Thr Val Asp Pro Ala Ser Lys Ser Asn Gln Thr
                245                 250                 255

Lys Asn Thr Ile Thr Thr Gly Asn Lys Lys Leu Leu Ala Gly Arg Tyr
            260                 265                 270

Ser His Leu
        275

<210> SEQ ID NO 21
<211> LENGTH: 258
<212> TYPE: PRT
<213> ORGANISM: Cricetulus griseus

<400> SEQUENCE: 21

Trp Gly Phe Lys Asn Gly Ile Phe His Asn Ser Ile Trp Leu Glu Gln
1               5                   10                  15

Ala Ala Gly Val Tyr His Arg Glu Ala Arg Ala Gly Lys Tyr Lys Leu
            20                  25                  30

Thr Tyr Ala Glu Ala Lys Thr Val Cys Glu Phe Glu Gly Gly Arg Leu
        35                  40                  45

Ala Thr Tyr Lys Gln Leu Glu Ala Ala Arg Lys Ile Gly Phe His Val
    50                  55                  60

Cys Ala Ala Gly Trp Met Ala Lys Gly Arg Val Gly Tyr Pro Ile Val
65                  70                  75                  80

Lys Pro Gly Pro Asn Cys Gly Phe Gly Lys Thr Gly Ile Ile Asp Tyr
                85                  90                  95

Gly Ile Arg Leu Asn Arg Ser Glu Arg Trp Asp Ala Tyr Cys Tyr Asn
            100                 105                 110

Pro His Ala Lys Glu Cys Gly Gly Val Phe Thr Asp Pro Lys Arg Ile
        115                 120                 125

Phe Lys Ser Pro Gly Phe Pro Asn Glu Tyr Asp Asp Asn Gln Val Cys
    130                 135                 140

Tyr Trp His Ile Arg Leu Lys Tyr Gly Gln Arg Ile His Leu Ser Phe
145                 150                 155                 160

Leu Asp Phe Asp Leu Glu His Asp Pro Gly Cys Leu Ala Asp Tyr Val
                165                 170                 175

Glu Ile Tyr Asp Ser Tyr Asp Asp Val His Gly Phe Val Gly Arg Tyr
            180                 185                 190

Cys Gly Asp Glu Leu Pro Glu Asp Ile Ile Ser Thr Gly Asn Val Met

```
              195                 200                 205
Thr Leu Lys Phe Leu Ser Asp Ala Ser Val Thr Ala Gly Gly Phe Gln
    210                 215                 220

Ile Lys Tyr Val Thr Val Asp Pro Ala Ser Lys Ser Asn Gln Thr Lys
225                 230                 235                 240

Asn Thr Ile Thr Thr Gly Asn Lys Lys Leu Leu Ala Gly Arg Tyr Ser
                245                 250                 255

His Leu
```

<210> SEQ ID NO 22
<211> LENGTH: 277
<212> TYPE: PRT
<213> ORGANISM: Heterocephalus glaber

<400> SEQUENCE: 22

```
Met Ile Ile Leu Thr Tyr Leu Phe Leu Leu Leu Trp Asp Gln Ala Arg
1               5                   10                  15

Gly Trp Gly Phe Lys Asp Gly Ile Phe His Asn Ser Ile Trp Leu Glu
            20                  25                  30

Gln Ala Ala Gly Val Tyr His Arg Glu Ala Arg Ser Gly Lys Tyr Lys
        35                  40                  45

Leu Thr Tyr Ala Glu Ala Lys Ala Val Cys Glu Phe Glu Gly Gly Arg
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Ile Gly Val Ile Asp
            100                 105                 110

Tyr Gly Val Arg Leu Asn Arg Ser Glu Arg Trp Asp Ala Tyr Cys Tyr
        115                 120                 125

Asn Pro His Ala Lys Glu Cys Gly Gly Val Phe Thr Glu Pro Lys Arg
    130                 135                 140

Ile Phe Lys Ser Pro Gly Phe Pro Asn Glu Tyr Glu Asp Asn Gln Ile
145                 150                 155                 160

Cys Tyr Trp His Ile Arg Leu Lys Tyr Gly Gln Arg Ile His Leu Ser
                165                 170                 175

Phe Leu Asp Phe Asp Leu Glu Asp Asp Pro Gly Cys Leu Ala Asp Tyr
            180                 185                 190

Val Glu Ile Tyr Asp Ser Tyr Asp Asp Val His Gly Phe Val Gly Arg
        195                 200                 205

Tyr Cys Gly Asp Glu Leu Pro Glu Asp Ile Ile Ser Thr Gly Asn Val
    210                 215                 220

Met Thr Leu Lys Phe Leu Ser Asp Ala Ser Ile Thr Ala Gly Gly Phe
225                 230                 235                 240

Gln Ile Lys Tyr Val Val Val Glu Pro Val Ser Lys Ser Ser Gln Gly
                245                 250                 255

Lys Asn Thr Ser Ser Thr Ser Thr Gly Ser Lys Asn Phe Leu Ala Gly
            260                 265                 270

Arg Phe Ser His Ile
        275
```

<210> SEQ ID NO 23
<211> LENGTH: 260
<212> TYPE: PRT

<213> ORGANISM: Heterocephalus glaber

<400> SEQUENCE: 23

```
Trp Gly Phe Lys Asp Gly Ile Phe His Asn Ser Ile Trp Leu Glu Gln
1               5                   10                  15
Ala Ala Gly Val Tyr His Arg Glu Ala Arg Ser Gly Lys Tyr Lys Leu
            20                  25                  30
Thr Tyr Ala Glu Ala Lys Ala Val Cys Glu Phe Glu Gly Gly Arg Leu
        35                  40                  45
Ala Thr Tyr Lys Gln Leu Glu Ala Ala Arg Lys Ile Gly Phe His Val
    50                  55                  60
Cys Ala Ala Gly Trp Met Ala Lys Gly Arg Val Gly Tyr Pro Ile Val
65                  70                  75                  80
Lys Pro Gly Pro Asn Cys Gly Phe Gly Lys Ile Gly Val Ile Asp Tyr
                85                  90                  95
Gly Val Arg Leu Asn Arg Ser Glu Arg Trp Asp Ala Tyr Cys Tyr Asn
            100                 105                 110
Pro His Ala Lys Glu Cys Gly Gly Val Phe Thr Glu Pro Lys Arg Ile
        115                 120                 125
Phe Lys Ser Pro Gly Phe Pro Asn Glu Tyr Glu Asp Asn Gln Ile Cys
    130                 135                 140
Tyr Trp His Ile Arg Leu Lys Tyr Gly Gln Arg Ile His Leu Ser Phe
145                 150                 155                 160
Leu Asp Phe Asp Leu Glu Asp Pro Gly Cys Leu Ala Asp Tyr Val
                165                 170                 175
Glu Ile Tyr Asp Ser Tyr Asp Val His Gly Phe Val Gly Arg Tyr
            180                 185                 190
Cys Gly Asp Glu Leu Pro Glu Asp Ile Ile Ser Thr Gly Asn Val Met
        195                 200                 205
Thr Leu Lys Phe Leu Ser Asp Ala Ser Ile Thr Ala Gly Gly Phe Gln
    210                 215                 220
Ile Lys Tyr Val Val Val Glu Pro Val Ser Lys Ser Ser Gln Gly Lys
225                 230                 235                 240
Asn Thr Ser Ser Thr Ser Thr Gly Ser Lys Asn Phe Leu Ala Gly Arg
                245                 250                 255
Phe Ser His Ile
            260
```

<210> SEQ ID NO 24
<211> LENGTH: 277
<212> TYPE: PRT
<213> ORGANISM: Cavia porcellus

<400> SEQUENCE: 24

```
Met Ile Ile Leu Thr Tyr Leu Phe Leu Leu Leu Trp Glu Glu Ala Gln
1               5                   10                  15
Gly Trp Gly Phe Lys Asp Gly Ile Phe His Asn Ser Ile Trp Leu Glu
            20                  25                  30
Gln Ala Ala Gly Val Tyr His Arg Glu Ala Arg Ser Gly Lys Tyr Lys
        35                  40                  45
Leu Thr Tyr Ala Glu Ala Lys Ala Val Cys Glu Phe Glu Gly Gly Arg
    50                  55                  60
Leu Ala Thr Tyr Lys Gln Leu Glu Ala Ala Arg Lys Ile Gly Phe His
65                  70                  75                  80
Val Cys Ala Ala Gly Trp Met Ala Lys Gly Arg Val Gly Tyr Pro Ile
```

```
            85                  90                  95
Val Lys Pro Gly Pro Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr
            115                 120                 125

Asn Pro His Ala Lys Glu Cys Gly Gly Val Phe Thr Asp Pro Lys Arg
        130                 135                 140

Ile Phe Lys Ser Pro Gly Phe Pro Asn Glu Tyr Glu Asp Asn Gln Ile
145                 150                 155                 160

Cys Tyr Trp His Ile Arg Leu Lys Tyr Gly Gln Arg Ile His Leu Ser
                165                 170                 175

Phe Leu Asp Phe Asp Leu Glu Asp Asp Pro Gly Cys Leu Ala Asp Tyr
            180                 185                 190

Val Glu Val Tyr Asp Ser Tyr Asp Asp Val His Gly Phe Val Gly Arg
            195                 200                 205

Tyr Cys Gly Asp Glu Leu Pro Glu Asp Ile Ile Ser Thr Gly Asn Val
        210                 215                 220

Met Thr Leu Lys Phe Leu Ser Asp Ala Ser Val Thr Ala Gly Gly Phe
225                 230                 235                 240

Gln Ile Lys Tyr Ile Ala Val Asp Pro Val Ser Lys Ser Ser Gln Gly
                245                 250                 255

Lys Asn Thr Thr Thr Arg Ser Thr Gly Ser Lys Asn Phe Leu Gly Gly
            260                 265                 270

Arg Phe Ser Asn Leu
            275

<210> SEQ ID NO 25
<211> LENGTH: 260
<212> TYPE: PRT
<213> ORGANISM: Cavia porcellus

<400> SEQUENCE: 25

Trp Gly Phe Lys Asp Gly Ile Phe His Asn Ser Ile Trp Leu Glu Gln
1               5                   10                  15

Ala Ala Gly Val Tyr His Arg Glu Ala Arg Ser Gly Lys Tyr Lys Leu
            20                  25                  30

Thr Tyr Ala Glu Ala Lys Ala Val Cys Glu Phe Glu Gly Gly Arg Leu
        35                  40                  45

Ala Thr Tyr Lys Gln Leu Glu Ala Ala Arg Lys Ile Gly Phe His Val
    50                  55                  60

Cys Ala Ala Gly Trp Met Ala Lys Gly Arg Val Gly Tyr Pro Ile Val
65                  70                  75                  80

Lys Pro Gly Pro Asn Cys Gly Phe Gly Lys Thr Gly Ile Ile Asp Tyr
                85                  90                  95

Gly Ile Arg Leu Asn Arg Ser Glu Arg Trp Asp Ala Tyr Cys Tyr Asn
            100                 105                 110

Pro His Ala Lys Glu Cys Gly Gly Val Phe Thr Asp Pro Lys Arg Ile
        115                 120                 125

Phe Lys Ser Pro Gly Phe Pro Asn Glu Tyr Glu Asp Asn Gln Ile Cys
    130                 135                 140

Tyr Trp His Ile Arg Leu Lys Tyr Gly Gln Arg Ile His Leu Ser Phe
145                 150                 155                 160

Leu Asp Phe Asp Leu Glu Asp Asp Pro Gly Cys Leu Ala Asp Tyr Val
                165                 170                 175
```

```
Glu Val Tyr Asp Ser Tyr Asp Val His Gly Phe Val Gly Arg Tyr
            180                 185                 190

Cys Gly Asp Glu Leu Pro Glu Asp Ile Ile Ser Thr Gly Asn Val Met
            195                 200                 205

Thr Leu Lys Phe Leu Ser Asp Ala Ser Val Thr Ala Gly Gly Phe Gln
            210                 215                 220

Ile Lys Tyr Ile Ala Val Asp Pro Val Ser Lys Ser Ser Gln Gly Lys
225                 230                 235                 240

Asn Thr Thr Thr Arg Ser Thr Gly Ser Lys Asn Phe Leu Gly Gly Arg
            245                 250                 255

Phe Ser Asn Leu
            260

<210> SEQ ID NO 26
<211> LENGTH: 277
<212> TYPE: PRT
<213> ORGANISM: Ornithorhynchus anatinus

<400> SEQUENCE: 26

Met Ile Ala Leu Ile Tyr Phe Phe Val Leu Leu Trp Asp Glu Thr Arg
1               5                   10                  15

Glu Trp Gly Phe Lys Asp Gly Ile Phe His Asn Ser Ile Trp Leu Glu
            20                  25                  30

Gln Ala Ala Gly Val Tyr His Arg Glu Ala Arg Thr Gly Lys Tyr Lys
            35                  40                  45

Leu Thr Tyr Ala Glu Ala Lys Ala Val Cys Glu Phe Glu Gly Gly His
        50                  55                  60

Leu Ala Thr Tyr Gln Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Ala Gly Pro Asn Cys Gly Phe Gly Lys Thr Gly Ile Ile Asp
            100                 105                 110

Tyr Gly Phe Arg Leu Asn Arg Ser Glu Arg Trp Asp Ala Tyr Cys Phe
            115                 120                 125

Asn Pro His Ala Lys Glu Cys Gly Gly Ile Phe Thr Asp Pro Lys Arg
        130                 135                 140

Ile Ile Lys Ser Pro Gly Phe Pro Asn Glu Tyr Glu Asp Asp Gln Ile
145                 150                 155                 160

Cys Tyr Trp His Ile Arg Leu Lys Tyr Gly Gln Arg Ile Leu Leu Ser
                165                 170                 175

Phe Leu Asp Phe Asp Leu Glu Asp Asp Thr Ser Cys Leu Ala Asp Tyr
            180                 185                 190

Leu Glu Ile Tyr Asp Ser Tyr Asp Val His Gly Phe Met Gly Arg
            195                 200                 205

Phe Cys Gly Asp Ala Leu Pro Glu Asp Ile Val Ser Thr Gly Asn Val
            210                 215                 220

Met Thr Leu Lys Phe Leu Ser Asp Ala Ser Val Thr Ala Gly Gly Phe
225                 230                 235                 240

Gln Leu Lys Tyr Val Ala Val Asp Pro Val Ser Lys Pro Ser Asp Gly
            245                 250                 255

Lys Asn Ser Ser Thr Thr Ser Gln Gly Ser Lys Asn Phe Leu Pro Gly
            260                 265                 270

Lys Phe Gly His Leu
            275
```

<210> SEQ ID NO 27
<211> LENGTH: 260
<212> TYPE: PRT
<213> ORGANISM: Ornithorhynchus anatinus

<400> SEQUENCE: 27

```
Trp Gly Phe Lys Asp Gly Ile Phe His Asn Ser Ile Trp Leu Glu Gln
1               5                   10                  15
Ala Ala Gly Val Tyr His Arg Glu Ala Arg Thr Gly Lys Tyr Lys Leu
            20                  25                  30
Thr Tyr Ala Glu Ala Lys Ala Val Cys Glu Phe Glu Gly Gly His Leu
        35                  40                  45
Ala Thr Tyr Gln Gln Leu Glu Ala Ala Arg Lys Ile Gly Phe His Val
    50                  55                  60
Cys Ala Ala Gly Trp Met Ala Lys Gly Arg Val Gly Tyr Pro Ile Val
65                  70                  75                  80
Lys Ala Gly Pro Asn Cys Gly Phe Gly Lys Thr Gly Ile Ile Asp Tyr
                85                  90                  95
Gly Phe Arg Leu Asn Arg Ser Glu Arg Trp Asp Ala Tyr Cys Phe Asn
            100                 105                 110
Pro His Ala Lys Glu Cys Gly Gly Ile Phe Thr Asp Pro Lys Arg Ile
        115                 120                 125
Ile Lys Ser Pro Gly Phe Pro Asn Glu Tyr Glu Asp Gln Ile Cys
    130                 135                 140
Tyr Trp His Ile Arg Leu Lys Tyr Gly Gln Arg Ile Leu Leu Ser Phe
145                 150                 155                 160
Leu Asp Phe Asp Leu Glu Asp Asp Thr Ser Cys Leu Ala Asp Tyr Leu
                165                 170                 175
Glu Ile Tyr Asp Ser Tyr Asp Val His Gly Phe Met Gly Arg Phe
            180                 185                 190
Cys Gly Asp Ala Leu Pro Glu Asp Ile Val Ser Thr Gly Asn Val Met
        195                 200                 205
Thr Leu Lys Phe Leu Ser Asp Ala Ser Val Thr Ala Gly Gly Phe Gln
    210                 215                 220
Leu Lys Tyr Val Ala Val Asp Pro Val Ser Lys Pro Ser Asp Gly Lys
225                 230                 235                 240
Asn Ser Ser Thr Thr Ser Gln Gly Ser Lys Asn Phe Leu Pro Gly Lys
                245                 250                 255
Phe Gly His Leu
            260
```

<210> SEQ ID NO 28
<211> LENGTH: 269
<212> TYPE: PRT
<213> ORGANISM: Xenopus (Silurana) tropicalis

<400> SEQUENCE: 28

```
Met Lys Thr Val Ile Phe Leu Val Leu Val Phe Leu Glu Glu Thr Phe
1               5                   10                  15
Gly Trp Gly Phe Lys Asn Gly Val Leu His Asn Ser Ile Trp Leu Glu
            20                  25                  30
Gln Ala Ala Gly Val Tyr His Arg Glu Ser Arg Asn Gly Lys Tyr Lys
        35                  40                  45
Leu Thr Tyr Arg Glu Ala Lys Ala Val Cys Glu Tyr Glu Gly Gly Arg
    50                  55                  60
```

```
Leu Ala Thr Tyr Glu Gln Leu Glu Ala Ala Arg Gln Ile Gly Phe His
 65                  70                  75                  80

Val Cys Ala Ala Gly Trp Leu His Lys Gly Arg Val Gly Tyr Pro Ile
                 85                  90                  95

Val Lys Pro Thr Phe Asn Cys Gly Phe Gly Lys Lys Gly Ile Ile Asp
            100                 105                 110

Tyr Gly Phe Arg Leu Asn Lys Ser Glu Arg Trp Asp Thr Tyr Cys Tyr
        115                 120                 125

Asn Pro His Ser Lys Glu Cys Gly Gly Val Leu Thr Glu Pro Glu Arg
    130                 135                 140

Ile Ile Lys Ser Pro Gly Tyr Pro Asn Asn Tyr Glu Asn Asp Gln Ile
145                 150                 155                 160

Cys Tyr Trp His Ile Arg Val Asn Tyr Gly Gln Arg Val Phe Ile Glu
                165                 170                 175

Phe Leu Asp Ile Asp Ile Glu Glu Asp Ile Asp Cys Leu Ser Asp Tyr
            180                 185                 190

Phe Glu Ile Tyr Asp Ser Tyr Asp Asp Ile His Gly Leu Val Gly Arg
        195                 200                 205

Tyr Cys Gly Tyr Glu Leu Pro Asp Ser Ile Ile Ser Thr Gly Asn Val
210                 215                 220

Met Thr Leu Lys Phe Leu Thr Asp Arg Ser Val Ser Gly Gly Phe
225                 230                 235                 240

Gln Ile Lys Tyr Thr Ala Ile Asp Leu Pro Ser Lys Gln Ser Asp Gly
        245                 250                 255

Ala Asn Gly Ser Ser Glu Ala Tyr Asn Glu Phe Glu Tyr
        260                 265

<210> SEQ ID NO 29
<211> LENGTH: 252
<212> TYPE: PRT
<213> ORGANISM: Xenopus (Silurana) tropicalis

<400> SEQUENCE: 29

Trp Gly Phe Lys Asn Gly Val Leu His Asn Ser Ile Trp Leu Glu Gln
  1               5                  10                  15

Ala Ala Gly Val Tyr His Arg Glu Ser Arg Asn Gly Lys Tyr Lys Leu
                 20                  25                  30

Thr Tyr Arg Glu Ala Lys Ala Val Cys Glu Tyr Glu Gly Gly Arg Leu
            35                  40                  45

Ala Thr Tyr Glu Gln Leu Glu Ala Ala Arg Gln Ile Gly Phe His Val
        50                  55                  60

Cys Ala Ala Gly Trp Leu His Lys Gly Arg Val Gly Tyr Pro Ile Val
 65                  70                  75                  80

Lys Pro Thr Phe Asn Cys Gly Phe Gly Lys Lys Gly Ile Ile Asp Tyr
                 85                  90                  95

Gly Phe Arg Leu Asn Lys Ser Glu Arg Trp Asp Thr Tyr Cys Tyr Asn
            100                 105                 110

Pro His Ser Lys Glu Cys Gly Gly Val Leu Thr Glu Pro Glu Arg Ile
        115                 120                 125

Ile Lys Ser Pro Gly Tyr Pro Asn Asn Tyr Glu Asn Asp Gln Ile Cys
    130                 135                 140

Tyr Trp His Ile Arg Val Asn Tyr Gly Gln Arg Val Phe Ile Glu Phe
145                 150                 155                 160

Leu Asp Ile Asp Ile Glu Glu Asp Ile Asp Cys Leu Ser Asp Tyr Phe
```

165                 170                 175

Glu Ile Tyr Asp Ser Tyr Asp Asp Ile His Gly Leu Val Gly Arg Tyr
                180                 185                 190

Cys Gly Tyr Glu Leu Pro Asp Ser Ile Ile Ser Thr Gly Asn Val Met
                195                 200                 205

Thr Leu Lys Phe Leu Thr Asp Arg Ser Val Ser Gly Gly Phe Gln
            210                 215                 220

Ile Lys Tyr Thr Ala Ile Asp Leu Pro Ser Lys Gln Ser Asp Gly Ala
225                 230                 235                 240

Asn Gly Ser Ser Glu Ala Tyr Asn Glu Phe Glu Tyr
                245                 250

<210> SEQ ID NO 30
<211> LENGTH: 277
<212> TYPE: PRT
<213> ORGANISM: Pan troglodytes

<400> SEQUENCE: 30

Met Ile Ile Leu Ile Tyr Leu Phe Leu Leu Trp Glu Asp Thr Gln
1               5                   10                  15

Gly Trp Gly Phe Lys Asp Gly Ile Phe His Asn Ser Ile Trp Leu Glu
                20                  25                  30

Arg Ala Ala Gly Val Tyr His Arg Glu Ala Arg Ser Gly Lys Tyr Lys
            35                  40                  45

Leu Thr Tyr Ala Glu Ala Lys Ala Val Cys Glu Phe Glu Gly Gly His
        50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Val Arg Leu Asn Arg Ser Glu Arg Trp Asp Ala Tyr Cys Tyr
        115                 120                 125

Asn Pro His Ala Lys Glu Cys Gly Gly Val Phe Thr Asp Pro Lys Arg
130                 135                 140

Ile Phe Lys Ser Pro Gly Phe Pro Asn Glu Tyr Glu Asp Asn Gln Ile
145                 150                 155                 160

Cys Tyr Trp His Ile Arg Leu Lys Tyr Gly Gln Arg Ile His Leu Ser
                165                 170                 175

Phe Leu Asp Phe Asp Leu Glu Asp Asp Pro Gly Cys Leu Ala Asp Tyr
            180                 185                 190

Val Glu Ile Tyr Asp Ser Tyr Asp Asp Val His Gly Phe Val Gly Arg
        195                 200                 205

Tyr Cys Gly Asp Glu Leu Pro Asp Asp Ile Ile Ser Thr Gly Asn Val
    210                 215                 220

Met Thr Leu Lys Phe Leu Ser Asp Ala Ser Val Thr Ala Gly Gly Phe
225                 230                 235                 240

Gln Ile Lys Tyr Val Ala Met Asp Pro Val Ser Lys Ser Ser Gln Gly
                245                 250                 255

Lys Asn Thr Ser Thr Thr Ser Thr Gly Asn Lys Asn Phe Leu Ala Gly
            260                 265                 270

Arg Phe Ser His Leu
        275

<210> SEQ ID NO 31
<211> LENGTH: 260
<212> TYPE: PRT
<213> ORGANISM: Pan troglodytes

<400> SEQUENCE: 31

Trp Gly Phe Lys Asp Gly Ile Phe His Asn Ser Ile Trp Leu Glu Arg
1               5                   10                  15

Ala Ala Gly Val Tyr His Arg Glu Ala Arg Ser Gly Lys Tyr Lys Leu
            20                  25                  30

Thr Tyr Ala Glu Ala Lys Ala Val Cys Glu Phe Glu Gly Gly His Leu
        35                  40                  45

Ala Thr Tyr Lys Gln Leu Glu Ala Ala Arg Lys Ile Gly Phe His Val
    50                  55                  60

Cys Ala Ala Gly Trp Met Ala Lys Gly Arg Val Gly Tyr Pro Ile Val
65                  70                  75                  80

Lys Pro Gly Pro Asn Cys Gly Phe Gly Lys Thr Gly Ile Ile Asp Tyr
                85                  90                  95

Gly Val Arg Leu Asn Arg Ser Glu Arg Trp Asp Ala Tyr Cys Tyr Asn
            100                 105                 110

Pro His Ala Lys Glu Cys Gly Gly Val Phe Thr Asp Pro Lys Arg Ile
        115                 120                 125

Phe Lys Ser Pro Gly Phe Pro Asn Glu Tyr Glu Asp Asn Gln Ile Cys
    130                 135                 140

Tyr Trp His Ile Arg Leu Lys Tyr Gly Gln Arg Ile His Leu Ser Phe
145                 150                 155                 160

Leu Asp Phe Asp Leu Glu Asp Pro Gly Cys Leu Ala Asp Tyr Val
                165                 170                 175

Glu Ile Tyr Asp Ser Tyr Asp Asp Val His Gly Phe Val Gly Arg Tyr
            180                 185                 190

Cys Gly Asp Glu Leu Pro Asp Asp Ile Ile Ser Thr Gly Asn Val Met
        195                 200                 205

Thr Leu Lys Phe Leu Ser Asp Ala Ser Val Thr Ala Gly Gly Phe Gln
    210                 215                 220

Ile Lys Tyr Val Ala Met Asp Pro Val Ser Lys Ser Gln Gly Lys
225                 230                 235                 240

Asn Thr Ser Thr Thr Ser Thr Gly Asn Lys Asn Phe Leu Ala Gly Arg
                245                 250                 255

Phe Ser His Leu
        260

<210> SEQ ID NO 32
<211> LENGTH: 381
<212> TYPE: PRT
<213> ORGANISM: Homo sapiens

<400> SEQUENCE: 32

Met His Leu Leu Ala Ile Leu Phe Cys Ala Leu Trp Ser Ala Val Leu
1               5                   10                  15

Ala Glu Asn Ser Asp Asp Tyr Asp Leu Met Tyr Val Asn Leu Asp Asn
            20                  25                  30

Glu Ile Asp Asn Gly Leu His Pro Thr Glu Asp Pro Thr Pro Cys Ala
        35                  40                  45

Cys Gly Gln Glu His Ser Glu Trp Asp Lys Leu Phe Ile Met Leu Glu
    50                  55                  60

Asn Ser Gln Met Arg Glu Arg Met Leu Leu Gln Ala Thr Asp Asp Val
65                  70                  75                  80

Leu Arg Gly Glu Leu Gln Arg Leu Arg Glu Glu Leu Gly Arg Leu Ala
            85                  90                  95

Glu Ser Leu Ala Arg Pro Cys Ala Pro Gly Ala Pro Ala Glu Ala Arg
        100                 105                 110

Leu Thr Ser Ala Leu Asp Glu Leu Leu Gln Ala Thr Arg Asp Ala Gly
        115                 120                 125

Arg Arg Leu Ala Arg Met Glu Gly Ala Glu Ala Gln Arg Pro Glu Glu
130                 135                 140

Ala Gly Arg Ala Leu Ala Ala Val Leu Glu Glu Leu Arg Gln Thr Arg
145                 150                 155                 160

Ala Asp Leu His Ala Val Gln Gly Trp Ala Ala Arg Ser Trp Leu Pro
                165                 170                 175

Ala Gly Cys Glu Thr Ala Ile Leu Phe Pro Met Arg Ser Lys Lys Ile
            180                 185                 190

Phe Gly Ser Val His Pro Val Arg Pro Met Arg Leu Glu Ser Phe Ser
        195                 200                 205

Ala Cys Ile Trp Val Lys Ala Thr Asp Val Leu Asn Lys Thr Ile Leu
210                 215                 220

Phe Ser Tyr Gly Thr Lys Arg Asn Pro Tyr Glu Ile Gln Leu Tyr Leu
225                 230                 235                 240

Ser Tyr Gln Ser Ile Val Phe Val Val Gly Gly Glu Asn Lys Leu
                245                 250                 255

Val Ala Glu Ala Met Val Ser Leu Gly Arg Trp Thr His Leu Cys Gly
        260                 265                 270

Thr Trp Asn Ser Glu Glu Gly Leu Thr Ser Leu Trp Val Asn Gly Glu
        275                 280                 285

Leu Ala Ala Thr Thr Val Glu Met Ala Thr Gly His Ile Val Pro Glu
        290                 295                 300

Gly Gly Ile Leu Gln Ile Gly Gln Glu Lys Asn Gly Cys Cys Val Gly
305                 310                 315                 320

Gly Gly Phe Asp Glu Thr Leu Ala Phe Ser Gly Arg Leu Thr Gly Phe
                325                 330                 335

Asn Ile Trp Asp Ser Val Leu Ser Asn Glu Glu Ile Arg Glu Thr Gly
            340                 345                 350

Gly Ala Glu Ser Cys His Ile Arg Gly Asn Ile Val Gly Trp Gly Val
        355                 360                 365

Thr Glu Ile Gln Pro His Gly Gly Ala Gln Tyr Val Ser
370                 375                 380

<210> SEQ ID NO 33
<211> LENGTH: 364
<212> TYPE: PRT
<213> ORGANISM: Homo sapiens

<400> SEQUENCE: 33

Glu Asn Ser Asp Asp Tyr Asp Leu Met Tyr Val Asn Leu Asp Asn Glu
1               5                   10                  15

Ile Asp Asn Gly Leu His Pro Thr Glu Asp Pro Thr Pro Cys Ala Cys
            20                  25                  30

Gly Gln Glu His Ser Glu Trp Asp Lys Leu Phe Ile Met Leu Glu Asn
        35                  40                  45

Ser Gln Met Arg Glu Arg Met Leu Leu Gln Ala Thr Asp Asp Val Leu
        50                  55                  60

```
Arg Gly Glu Leu Gln Arg Leu Arg Glu Glu Leu Gly Arg Leu Ala Glu
 65                  70                  75                  80

Ser Leu Ala Arg Pro Cys Ala Pro Gly Ala Pro Ala Glu Ala Arg Leu
                 85                  90                  95

Thr Ser Ala Leu Asp Glu Leu Leu Gln Ala Thr Arg Asp Ala Gly Arg
            100                 105                 110

Arg Leu Ala Arg Met Glu Gly Ala Glu Ala Gln Arg Pro Glu Glu Ala
        115                 120                 125

Gly Arg Ala Leu Ala Ala Val Leu Glu Glu Leu Arg Gln Thr Arg Ala
130                 135                 140

Asp Leu His Ala Val Gln Gly Trp Ala Ala Arg Ser Trp Leu Pro Ala
145                 150                 155                 160

Gly Cys Glu Thr Ala Ile Leu Phe Pro Met Arg Ser Lys Lys Ile Phe
                165                 170                 175

Gly Ser Val His Pro Val Arg Pro Met Arg Leu Glu Ser Phe Ser Ala
            180                 185                 190

Cys Ile Trp Val Lys Ala Thr Asp Val Leu Asn Lys Thr Ile Leu Phe
        195                 200                 205

Ser Tyr Gly Thr Lys Arg Asn Pro Tyr Glu Ile Gln Leu Tyr Leu Ser
210                 215                 220

Tyr Gln Ser Ile Val Phe Val Val Gly Gly Glu Glu Asn Lys Leu Val
225                 230                 235                 240

Ala Glu Ala Met Val Ser Leu Gly Arg Trp Thr His Leu Cys Gly Thr
                245                 250                 255

Trp Asn Ser Glu Gly Leu Thr Ser Leu Trp Val Asn Gly Glu Leu
            260                 265                 270

Ala Ala Thr Thr Val Glu Met Ala Thr Gly His Ile Val Pro Glu Gly
        275                 280                 285

Gly Ile Leu Gln Ile Gly Gln Glu Lys Asn Gly Cys Cys Val Gly Gly
290                 295                 300

Gly Phe Asp Glu Thr Leu Ala Phe Ser Gly Arg Leu Thr Gly Phe Asn
305                 310                 315                 320

Ile Trp Asp Ser Val Leu Ser Asn Glu Glu Ile Arg Glu Thr Gly Gly
                325                 330                 335

Ala Glu Ser Cys His Ile Arg Gly Asn Ile Val Gly Trp Gly Val Thr
            340                 345                 350

Glu Ile Gln Pro His Gly Gly Ala Gln Tyr Val Ser
        355                 360

<210> SEQ ID NO 34
<211> LENGTH: 381
<212> TYPE: PRT
<213> ORGANISM: Rattus norvegicus

<400> SEQUENCE: 34

Met His Leu Pro Val Ile Leu Leu Cys Ala Leu Trp Ser Ala Val Leu
 1               5                  10                  15

Ala Glu Thr Ser Tyr Asp Tyr Glu Leu Met His Val Asn Leu Asp Asn
             20                  25                  30

Glu Ile Asp Asn Gly Leu His Pro Thr Glu Asp Pro Thr Pro Cys Asp
         35                  40                  45

Cys Arg Gln Glu His Ser Glu Trp Asp Lys Leu Phe Ile Met Leu Glu
     50                  55                  60

Asn Ser Gln Met Arg Glu Ala Met Leu Leu Gln Ala Thr Asp Asp Val
```

```
            65                  70                  75                  80
Leu Arg Gly Glu Leu Gln Arg Leu Arg Ala Glu Leu Gly Arg Leu Ala
                85                  90                  95

Gly Gly Met Ala Arg Pro Cys Ser Ala Ser Gly Pro Ala Asp Ala Arg
            100                 105                 110

Leu Ala Gln Ala Leu Glu Pro Leu Leu Gln Glu Ser Arg Asp Ala Asn
        115                 120                 125

Arg Arg Leu Ala Arg Leu Glu Asp Ala Glu Ala Arg Arg His Glu Ala
    130                 135                 140

Thr Val Pro Ser Leu Gly Ala Val Leu Glu Glu Leu Gln Arg Thr Arg
145                 150                 155                 160

Ala Asp Leu Ser Ala Met Gln Ser Trp Val Ala Arg His Trp Leu Pro
                165                 170                 175

Ala Gly Cys Glu Thr Ala Ile Phe Phe Pro Met Arg Ser Lys Lys Ile
            180                 185                 190

Phe Gly Ser Val His Pro Val Arg Pro Met Lys Leu Glu Ser Phe Ser
        195                 200                 205

Ala Cys Ile Trp Val Lys Ala Thr Asp Val Leu Asn Lys Thr Ile Leu
    210                 215                 220

Phe Ser Tyr Gly Thr Lys Trp Asn Pro Tyr Glu Ile Gln Leu Tyr Leu
225                 230                 235                 240

Ser Ser Gln Ser Leu Val Phe Val Val Gly Lys Glu Asn Lys Leu
                245                 250                 255

Ala Ala Asp Thr Val Val Ser Leu Gly Arg Trp Ser His Leu Cys Gly
            260                 265                 270

Thr Trp Ser Ser Glu Gln Gly Ser Met Ser Leu Trp Ala Asn Gly Glu
        275                 280                 285

Leu Val Ala Thr Thr Leu Glu Met Ala Lys Ser His Pro Val Pro Glu
    290                 295                 300

Gly Gly Leu Leu Gln Ile Gly Gln Glu Lys Asn Gly Cys Cys Val Gly
305                 310                 315                 320

Gly Gly Phe Asp Glu Thr Leu Ala Phe Ser Gly Arg Ile Thr Gly Phe
                325                 330                 335

Asn Ile Trp Asp Arg Val Leu Ser Lys Glu Ile Arg Ala Ser Gly
            340                 345                 350

Gly Ala Glu Ser Cys His Ile Arg Gly Asn Ile Val Gly Trp Gly Val
        355                 360                 365

Thr Glu Ile Gln Ala His Gly Gly Ala Gln Tyr Val Ser
    370                 375                 380

<210> SEQ ID NO 35
<211> LENGTH: 364
<212> TYPE: PRT
<213> ORGANISM: Rattus norvegicus

<400> SEQUENCE: 35

Glu Thr Ser Tyr Asp Tyr Glu Leu Met His Val Asn Leu Asp Asn Glu
1               5                   10                  15

Ile Asp Asn Gly Leu His Pro Thr Glu Asp Pro Thr Pro Cys Asp Cys
            20                  25                  30

Arg Gln Glu His Ser Glu Trp Asp Lys Leu Phe Ile Met Leu Glu Asn
        35                  40                  45

Ser Gln Met Arg Glu Ala Met Leu Leu Gln Ala Thr Asp Asp Val Leu
    50                  55                  60
```

Arg Gly Glu Leu Gln Arg Leu Arg Ala Glu Leu Gly Arg Leu Ala Gly
65                  70                  75                  80

Gly Met Ala Arg Pro Cys Ser Ala Ser Gly Pro Ala Asp Ala Arg Leu
                85                  90                  95

Ala Gln Ala Leu Glu Pro Leu Leu Gln Glu Ser Arg Asp Ala Asn Arg
            100                 105                 110

Arg Leu Ala Arg Leu Glu Asp Ala Glu Ala Arg Arg His Glu Ala Thr
        115                 120                 125

Val Pro Ser Leu Gly Ala Val Leu Glu Glu Leu Gln Arg Thr Arg Ala
    130                 135                 140

Asp Leu Ser Ala Met Gln Ser Trp Val Ala Arg His Trp Leu Pro Ala
145                 150                 155                 160

Gly Cys Glu Thr Ala Ile Phe Phe Pro Met Arg Ser Lys Lys Ile Phe
                165                 170                 175

Gly Ser Val His Pro Val Arg Pro Met Lys Leu Glu Ser Phe Ser Ala
            180                 185                 190

Cys Ile Trp Val Lys Ala Thr Asp Val Leu Asn Lys Thr Ile Leu Phe
        195                 200                 205

Ser Tyr Gly Thr Lys Trp Asn Pro Tyr Glu Ile Gln Leu Tyr Leu Ser
    210                 215                 220

Ser Gln Ser Leu Val Phe Val Gly Gly Lys Glu Asn Lys Leu Ala
225                 230                 235                 240

Ala Asp Thr Val Val Ser Leu Gly Arg Trp Ser His Leu Cys Gly Thr
                245                 250                 255

Trp Ser Ser Glu Gln Gly Ser Met Ser Leu Trp Ala Asn Gly Glu Leu
            260                 265                 270

Val Ala Thr Thr Leu Glu Met Ala Lys Ser His Pro Val Pro Glu Gly
        275                 280                 285

Gly Leu Leu Gln Ile Gly Gln Glu Lys Asn Gly Cys Cys Val Gly Gly
    290                 295                 300

Gly Phe Asp Glu Thr Leu Ala Phe Ser Arg Ile Thr Gly Phe Asn
305                 310                 315                 320

Ile Trp Asp Arg Val Leu Ser Lys Glu Glu Ile Arg Ala Ser Gly Gly
                325                 330                 335

Ala Glu Ser Cys His Ile Arg Gly Asn Ile Val Gly Trp Gly Val Thr
            340                 345                 350

Glu Ile Gln Ala His Gly Gly Ala Gln Tyr Val Ser
        355                 360

<210> SEQ ID NO 36
<211> LENGTH: 381
<212> TYPE: PRT
<213> ORGANISM: Mus musculus

<400> SEQUENCE: 36

Met His Leu Pro Ala Ile Leu Leu Cys Ala Leu Trp Ser Ala Val Val
1               5                   10                  15

Ala Glu Thr Ser Asp Asp Tyr Glu Leu Met Tyr Val Asn Leu Asp Asn
                20                  25                  30

Glu Ile Asp Asn Gly Leu His Pro Thr Glu Asp Pro Thr Pro Cys Asp
            35                  40                  45

Cys Arg Gln Glu His Ser Glu Trp Asp Lys Leu Phe Ile Met Leu Glu
        50                  55                  60

Asn Ser Gln Met Arg Glu Gly Met Leu Leu Gln Ala Thr Asp Asp Val
65                  70                  75                  80

Leu Arg Gly Glu Leu Gln Arg Leu Arg Ala Glu Leu Gly Arg Leu Ala
            85                  90                  95

Gly Gly Met Ala Arg Pro Cys Ala Ala Gly Gly Pro Ala Asp Ala Arg
            100                 105                 110

Leu Val Arg Ala Leu Glu Pro Leu Leu Gln Glu Ser Arg Asp Ala Ser
            115                 120                 125

Leu Arg Leu Ala Arg Leu Glu Asp Ala Glu Ala Arg Arg Pro Glu Ala
    130                 135                 140

Thr Val Pro Gly Leu Gly Ala Val Leu Glu Glu Leu Arg Arg Thr Arg
145                 150                 155                 160

Ala Asp Leu Ser Ala Val Gln Ser Trp Val Ala Arg His Trp Leu Pro
            165                 170                 175

Ala Gly Cys Glu Thr Ala Ile Phe Phe Pro Met Arg Ser Lys Lys Ile
            180                 185                 190

Phe Gly Ser Val His Pro Val Arg Pro Met Lys Leu Glu Ser Phe Ser
            195                 200                 205

Thr Cys Ile Trp Val Lys Ala Thr Asp Val Leu Asn Lys Thr Ile Leu
    210                 215                 220

Phe Ser Tyr Gly Thr Lys Trp Asn Pro Tyr Glu Ile Gln Leu Tyr Leu
225                 230                 235                 240

Ser Ser Gln Ser Leu Val Leu Val Val Gly Gly Lys Glu Asn Lys Leu
            245                 250                 255

Ala Ala Asp Thr Val Val Ser Leu Gly Arg Trp Ser His Leu Cys Gly
            260                 265                 270

Thr Trp Ser Ser Glu Gln Gly Ser Met Ser Leu Trp Ala Asn Gly Glu
    275                 280                 285

Leu Val Ala Thr Thr Val Glu Met Ala Lys Ser His Ser Val Pro Glu
290                 295                 300

Gly Gly Leu Leu Gln Ile Gly Gln Glu Lys Asn Gly Cys Cys Val Gly
305                 310                 315                 320

Gly Gly Phe Asp Glu Ser Leu Ala Phe Ser Gly Arg Ile Thr Gly Phe
            325                 330                 335

Asn Ile Trp Asp Arg Val Leu Ser Glu Glu Ile Arg Ala Ser Gly
            340                 345                 350

Gly Val Glu Ser Cys His Ile Arg Gly Asn Val Val Gly Trp Gly Val
            355                 360                 365

Thr Glu Ile Gln Ala His Gly Gly Ala Gln Tyr Val Ser
    370                 375                 380

<210> SEQ ID NO 37
<211> LENGTH: 364
<212> TYPE: PRT
<213> ORGANISM: Mus musculus

<400> SEQUENCE: 37

Glu Thr Ser Asp Asp Tyr Glu Leu Met Tyr Val Asn Leu Asp Asn Glu
1               5                   10                  15

Ile Asp Asn Gly Leu His Pro Thr Glu Asp Pro Thr Pro Cys Asp Cys
            20                  25                  30

Arg Gln Glu His Ser Glu Trp Asp Lys Leu Phe Ile Met Leu Glu Asn
        35                  40                  45

Ser Gln Met Arg Glu Gly Met Leu Leu Gln Ala Thr Asp Asp Val Leu
    50                  55                  60

Arg Gly Glu Leu Gln Arg Leu Arg Ala Glu Leu Gly Arg Leu Ala Gly

```
            65                  70                  75                  80
Gly Met Ala Arg Pro Cys Ala Ala Gly Gly Pro Ala Asp Ala Arg Leu
                    85                  90                  95

Val Arg Ala Leu Glu Pro Leu Leu Gln Glu Ser Arg Asp Ala Ser Leu
                    100                 105                 110

Arg Leu Ala Arg Leu Glu Asp Ala Glu Ala Arg Arg Pro Glu Ala Thr
                    115                 120                 125

Val Pro Gly Leu Gly Ala Val Leu Glu Glu Leu Arg Arg Thr Arg Ala
                    130                 135                 140

Asp Leu Ser Ala Val Gln Ser Trp Val Ala Arg His Trp Leu Pro Ala
145                 150                 155                 160

Gly Cys Glu Thr Ala Ile Phe Phe Pro Met Arg Ser Lys Lys Ile Phe
                    165                 170                 175

Gly Ser Val His Pro Val Arg Pro Met Lys Leu Glu Ser Phe Ser Thr
                    180                 185                 190

Cys Ile Trp Val Lys Ala Thr Asp Val Leu Asn Lys Thr Ile Leu Phe
                    195                 200                 205

Ser Tyr Gly Thr Lys Trp Asn Pro Tyr Glu Ile Gln Leu Tyr Leu Ser
                    210                 215                 220

Ser Gln Ser Leu Val Leu Val Val Gly Gly Lys Glu Asn Lys Leu Ala
225                 230                 235                 240

Ala Asp Thr Val Val Ser Leu Gly Arg Trp Ser His Leu Cys Gly Thr
                    245                 250                 255

Trp Ser Ser Glu Gln Gly Ser Met Ser Leu Trp Ala Asn Gly Glu Leu
                    260                 265                 270

Val Ala Thr Thr Val Glu Met Ala Lys Ser His Ser Val Pro Glu Gly
                    275                 280                 285

Gly Leu Leu Gln Ile Gly Gln Glu Lys Asn Gly Cys Cys Val Gly Gly
                    290                 295                 300

Gly Phe Asp Glu Ser Leu Ala Phe Ser Gly Arg Ile Thr Gly Phe Asn
305                 310                 315                 320

Ile Trp Asp Arg Val Leu Ser Glu Glu Ile Arg Ala Ser Gly Gly
                    325                 330                 335

Val Glu Ser Cys His Ile Arg Gly Asn Val Val Gly Trp Gly Val Thr
                    340                 345                 350

Glu Ile Gln Ala His Gly Gly Ala Gln Tyr Val Ser
                    355                 360

<210> SEQ ID NO 38
<211> LENGTH: 382
<212> TYPE: PRT
<213> ORGANISM: Bos taurus

<400> SEQUENCE: 38

Met His Ile Ser Val Ile Leu Phe Cys Ala Leu Trp Ser Ala Val Ser
1                   5                   10                  15

Ala Glu Asn Ser Asp Asp Tyr Glu Leu Met Tyr Val Asn Leu Asp Asn
                    20                  25                  30

Glu Ile Asp Asn Gly Leu His Pro Thr Glu Asp Pro Thr Pro Cys Asp
                    35                  40                  45

Cys Ser Arg Glu Asn Ser Glu Trp Asp Lys Leu Phe Thr Met Leu Glu
                    50                  55                  60

Asn Ser Gln Met Arg Glu Gly Met Leu Leu Gln Ala Thr Asp Val Met
65                  70                  75                  80
```

```
Leu Arg Gly Glu Leu Gln Lys Leu Gln Ala Glu Leu Gly Arg Leu Glu
                85                  90                  95

Gly Ser Leu Gln Lys Leu Cys Gly Pro Glu Ala Pro Ser Glu Thr Arg
            100                 105                 110

Leu Ala Arg Ala Leu Asp Asp Leu Leu Gln Ala Ser Arg Asp Ala Gly
        115                 120                 125

Arg Arg Leu Ala Arg Leu Glu Asp Ala Gly Ala Leu Arg Pro Gln Glu
    130                 135                 140

Glu Ala Gly Arg Ala Leu Gly Ala Val Leu Glu Leu Arg Arg Thr
145                 150                 155                 160

Arg Ala Asp Leu Arg Ala Val Gln Gly Trp Ala Ala Ser Arg Trp Leu
                165                 170                 175

Pro Ala Gly Cys Glu Thr Ala Ile Leu Phe Pro Met Arg Ser Lys Lys
            180                 185                 190

Ile Phe Ala Ser Val His Pro Val Thr Pro Met Lys Leu Glu Thr Phe
        195                 200                 205

Ser Ala Cys Ile Trp Val Lys Ala Thr Glu Val Leu Asn Lys Thr Val
    210                 215                 220

Leu Phe Ser Tyr Gly Thr Lys Arg Asn Pro Tyr Glu Ile Gln Leu Tyr
225                 230                 235                 240

Leu Ser Tyr Arg Ser Ile Met Leu Val Val Gly Gly Glu Asn Arg
                245                 250                 255

Leu Val Ala Asp Ala Val Ile Ser Leu Gly Thr Trp Thr His Leu Cys
            260                 265                 270

Ser Thr Trp Asp Ser Lys Lys Gly His Met Ala Leu Trp Val Asn Gly
        275                 280                 285

Asp Ser Val Ala Thr Ala Val Asp Met Ala Thr Gly His Val Val Pro
    290                 295                 300

Glu Gly Gly Ile Leu Gln Ile Gly Gln Glu Lys Asn Gly Cys Cys Val
305                 310                 315                 320

Gly Gly Gly Phe Asp Glu Thr Leu Ala Phe Ser Gly Arg Leu Thr Gly
                325                 330                 335

Phe Asn Ile Trp Glu Gly Val Leu Ser Asn Glu Glu Ile Arg Glu Ala
            340                 345                 350

Gly Gly Ala Glu Ser Cys His Ile Arg Gly Asn Val Val Gly Trp Gly
        355                 360                 365

Val Thr Glu Ile Gln Pro His Gly Gly Ala Gln Tyr Val Tyr
    370                 375                 380

<210> SEQ ID NO 39
<211> LENGTH: 365
<212> TYPE: PRT
<213> ORGANISM: Bos taurus

<400> SEQUENCE: 39

Glu Asn Ser Asp Asp Tyr Glu Leu Met Tyr Val Asn Leu Asp Asn Glu
1               5                   10                  15

Ile Asp Asn Gly Leu His Pro Thr Glu Asp Pro Thr Pro Cys Asp Cys
            20                  25                  30

Ser Arg Glu Asn Ser Glu Trp Asp Lys Leu Phe Thr Met Leu Glu Asn
        35                  40                  45

Ser Gln Met Arg Glu Gly Met Leu Leu Gln Ala Thr Asp Val Met Leu
    50                  55                  60

Arg Gly Glu Leu Gln Lys Leu Gln Ala Glu Leu Gly Arg Leu Glu Gly
65                  70                  75                  80
```

```
Ser Leu Gln Lys Leu Cys Gly Pro Glu Ala Pro Ser Glu Thr Arg Leu
                85                  90                  95

Ala Arg Ala Leu Asp Asp Leu Leu Gln Ala Ser Arg Asp Ala Gly Arg
            100                 105                 110

Arg Leu Ala Arg Leu Glu Asp Ala Gly Ala Leu Arg Pro Gln Glu Glu
        115                 120                 125

Ala Gly Arg Ala Leu Gly Ala Val Leu Glu Glu Leu Arg Arg Thr Arg
    130                 135                 140

Ala Asp Leu Arg Ala Val Gln Gly Trp Ala Ala Ser Arg Trp Leu Pro
145                 150                 155                 160

Ala Gly Cys Glu Thr Ala Ile Leu Phe Pro Met Arg Ser Lys Lys Ile
                165                 170                 175

Phe Ala Ser Val His Pro Val Thr Pro Met Lys Leu Glu Thr Phe Ser
            180                 185                 190

Ala Cys Ile Trp Val Lys Ala Thr Glu Val Leu Asn Lys Thr Val Leu
        195                 200                 205

Phe Ser Tyr Gly Thr Lys Arg Asn Pro Tyr Glu Ile Gln Leu Tyr Leu
    210                 215                 220

Ser Tyr Arg Ser Ile Met Leu Val Val Gly Gly Glu Glu Asn Arg Leu
225                 230                 235                 240

Val Ala Asp Ala Val Ile Ser Leu Gly Thr Trp Thr His Leu Cys Ser
                245                 250                 255

Thr Trp Asp Ser Lys Lys Gly His Met Ala Leu Trp Val Asn Gly Asp
            260                 265                 270

Ser Val Ala Thr Ala Val Asp Met Ala Thr Gly His Val Val Pro Glu
        275                 280                 285

Gly Gly Ile Leu Gln Ile Gly Gln Glu Lys Asn Gly Cys Cys Val Gly
    290                 295                 300

Gly Gly Phe Asp Glu Thr Leu Ala Phe Ser Gly Arg Leu Thr Gly Phe
305                 310                 315                 320

Asn Ile Trp Glu Gly Val Leu Ser Asn Glu Glu Ile Arg Glu Ala Gly
                325                 330                 335

Gly Ala Glu Ser Cys His Ile Arg Gly Asn Val Val Gly Trp Gly Val
            340                 345                 350

Thr Glu Ile Gln Pro His Gly Gly Ala Gln Tyr Val Tyr
        355                 360                 365

<210> SEQ ID NO 40
<211> LENGTH: 433
<212> TYPE: PRT
<213> ORGANISM: Gallus gallus

<400> SEQUENCE: 40

Met Leu Pro Gly Gly Val Leu Ser Leu Leu Met Leu Phe Cys Val Phe
1               5                   10                  15

Arg Ala Ser Ala Ser Val Leu Asp Glu Gly Asp Asp Tyr Asp Leu Met
            20                  25                  30

Tyr Val Asn Leu Asp Asn Glu Ile Glu Gly Pro Val Leu Gly Thr Glu
        35                  40                  45

Glu Ser Ala Ser Cys Asp Cys Gln Arg Glu His Thr Glu Trp Asp Lys
    50                  55                  60

Leu Phe Ile Met Leu Glu Asn Ser Gln Met Lys Glu Asn Met Met Leu
65                  70                  75                  80

Gln Ala Leu Glu Asp Gly Leu Lys Ala Asp Val Gln Ala Ile Arg Ala
```

```
                    85                  90                  95
Glu Leu Asn Gln Leu Thr Ala Gly Leu Ala Gly Thr Phe Ser Ser Thr
                100                 105                 110

Val Gln Gln Leu Thr Ser His Ala Leu Ala Gln Leu Glu Gln Ala Leu
                115                 120                 125

Gln Arg Asn Gly Asp Gln Pro Glu Asp Ala Glu Arg Leu Cys Glu Ser
130                 135                 140

Gln Gln Gly Lys Val Leu Glu Gln Val Leu Gln Leu Ser His Asn Val
145                 150                 155                 160

Ser Ala Arg Leu Gly Gln Leu Glu Ser Ser Trp Leu Arg Trp Ala Glu
                165                 170                 175

Arg Glu Ala Gln Glu Thr Ala Phe Gln Leu Gln Gln Asp Lys Leu Gly
                180                 185                 190

His Ser Arg Glu Asp Asn Leu Leu Leu Asn Thr Leu Trp Lys Glu Leu
                195                 200                 205

Gln Gln Thr Arg Ser Glu Leu Lys Ala Ser Gln Lys Trp Ala Ser Gln
                210                 215                 220

His Leu Leu Pro Ala Gly Tyr Glu Thr Ala Ile Leu Phe Pro Met Arg
225                 230                 235                 240

Ser Arg Lys Ile Phe Gly Ser Ile His Pro Thr Ala Ala Met Thr Leu
                245                 250                 255

Ser Ser Phe Thr Val Cys Val Trp Val Lys Ala Thr Glu Ala Leu Asp
                260                 265                 270

Lys Thr Ile Ile Phe Ser Tyr Gly Thr Lys Leu Asn Pro Tyr Glu Ile
                275                 280                 285

Gln Leu Tyr Leu Ser Arg Gln Ser Ala Val Leu Ala Val Gly Ser Ala
                290                 295                 300

Gln His Lys Leu Ala Ala Arg Asp Val Val Pro Gly Lys Trp Ile
305                 310                 315                 320

His Leu Cys Gly Thr Trp Ser Ser Asp Asn Gly Thr Ala Ser Leu Trp
                325                 330                 335

Val Asp Gly Glu Leu Thr Ala Thr Ala Val Gly Ile Ala Asp Thr His
                340                 345                 350

Ile Val Pro Asp Gly Gly Ile Leu Gln Val Gly Gln Glu Lys Asn Gly
                355                 360                 365

Cys Cys Val Gly Gly Phe Asp Glu Ala Leu Ala Phe Ser Gly Lys
                370                 375                 380

Leu Thr Gly Leu Asn Leu Trp Asp Arg Val Leu Ser Thr Glu Glu Ile
385                 390                 395                 400

Ala Ala Gln Gly Gly Glu Asp Ala Cys Ser Ser Arg Gly Asn Ile Val
                405                 410                 415

Gly Trp Gly Val Thr Glu Val Leu Leu Tyr Gly Gly Ala Gln Tyr Val
                420                 425                 430

Ser

<210> SEQ ID NO 41
<211> LENGTH: 413
<212> TYPE: PRT
<213> ORGANISM: Gallus gallus

<400> SEQUENCE: 41

Ser Val Leu Asp Glu Gly Asp Asp Tyr Asp Leu Met Tyr Val Asn Leu
1               5                   10                  15

Asp Asn Glu Ile Glu Gly Pro Val Leu Gly Thr Glu Glu Ser Ala Ser
```

-continued

```
                20                  25                  30
        Cys Asp Cys Gln Arg Glu His Thr Glu Trp Asp Lys Leu Phe Ile Met
                 35                  40                  45
        Leu Glu Asn Ser Gln Met Lys Glu Asn Met Met Leu Gln Ala Leu Glu
         50                  55                  60
        Asp Gly Leu Lys Ala Asp Val Gln Ala Ile Arg Ala Glu Leu Asn Gln
         65                  70                  75                  80
        Leu Thr Ala Gly Leu Ala Gly Thr Phe Ser Ser Thr Val Gln Gln Leu
                         85                  90                  95
        Thr Ser His Ala Leu Ala Gln Leu Glu Gln Ala Leu Gln Arg Asn Gly
                    100                 105                 110
        Asp Gln Pro Glu Asp Ala Glu Arg Leu Cys Glu Ser Gln Gln Gly Lys
                    115                 120                 125
        Val Leu Glu Gln Val Leu Gln Leu Ser His Asn Val Ser Ala Arg Leu
                    130                 135                 140
        Gly Gln Leu Glu Ser Ser Trp Leu Arg Trp Ala Glu Arg Glu Ala Gln
        145                 150                 155                 160
        Glu Thr Ala Phe Gln Leu Gln Gln Asp Lys Leu Gly His Ser Arg Glu
                            165                 170                 175
        Asp Asn Leu Leu Leu Asn Thr Leu Trp Lys Glu Leu Gln Gln Thr Arg
                    180                 185                 190
        Ser Glu Leu Lys Ala Ser Gln Lys Trp Ala Ser Gln His Leu Leu Pro
                    195                 200                 205
        Ala Gly Tyr Glu Thr Ala Ile Leu Phe Pro Met Arg Ser Arg Lys Ile
                    210                 215                 220
        Phe Gly Ser Ile His Pro Thr Ala Ala Met Thr Leu Ser Ser Phe Thr
        225                 230                 235                 240
        Val Cys Val Trp Val Lys Ala Thr Glu Ala Leu Asp Lys Thr Ile Ile
                            245                 250                 255
        Phe Ser Tyr Gly Thr Lys Leu Asn Pro Tyr Glu Ile Gln Leu Tyr Leu
                    260                 265                 270
        Ser Arg Gln Ser Ala Val Leu Ala Val Gly Ser Ala Gln His Lys Leu
                    275                 280                 285
        Ala Ala Arg Asp Val Val Pro Gly Lys Trp Ile His Leu Cys Gly
                    290                 295                 300
        Thr Trp Ser Ser Asp Asn Gly Thr Ala Ser Leu Trp Val Asp Gly Glu
        305                 310                 315                 320
        Leu Thr Ala Thr Ala Val Gly Ile Ala Asp Thr His Ile Val Pro Asp
                            325                 330                 335
        Gly Gly Ile Leu Gln Val Gly Gln Glu Lys Asn Gly Cys Cys Val Gly
                    340                 345                 350
        Gly Gly Phe Asp Glu Ala Leu Ala Phe Ser Gly Lys Leu Thr Gly Leu
                    355                 360                 365
        Asn Leu Trp Asp Arg Val Leu Ser Thr Glu Glu Ile Ala Ala Gln Gly
                    370                 375                 380
        Gly Glu Asp Ala Cys Ser Ser Arg Gly Asn Ile Val Gly Trp Gly Val
        385                 390                 395                 400
        Thr Glu Val Leu Leu Tyr Gly Gly Ala Gln Tyr Val Ser
                            405                 410

<210> SEQ ID NO 42
<211> LENGTH: 382
<212> TYPE: PRT
<213> ORGANISM: Sus scrofa
```

<400> SEQUENCE: 42

```
Met Arg Leu Pro Ala Ile Leu Phe Cys Ala Leu Trp Ser Ala Val Leu
1               5                   10                  15
Ala Glu Asn Ser Asp Asp Tyr Glu Leu Met Tyr Val Asn Leu Asp Asn
            20                  25                  30
Glu Ile Asp Asn Gly Leu His Pro Thr Glu Asp Pro Thr Leu Cys Asp
        35                  40                  45
Cys Ser Pro Glu His Ser Glu Trp Asp Lys Leu Phe Ile Met Leu Glu
    50                  55                  60
Asn Ser Gln Met Arg Glu Ser Met Leu Leu Gln Ala Thr Asp Asp Ile
65                  70                  75                  80
Leu Arg Gly Glu Leu Gln Arg Leu Arg Ala Glu Leu Gly Arg Leu Ala
                85                  90                  95
Gly Ser Leu Ala Arg Pro Cys Ala Pro Thr Ala Pro Ala Glu Val Gln
            100                 105                 110
Leu Ala Arg Ala Leu Asp Glu Leu Leu Gln Ala Ser Arg Asp Ala Gly
        115                 120                 125
Arg Arg Leu Glu Arg Leu Glu Glu Ala Gly Thr Pro Gln Leu Gln Glu
    130                 135                 140
Glu Ala Gly Arg Thr Leu Gly Ala Val Leu Glu Glu Leu Arg Arg Thr
145                 150                 155                 160
Arg Ala Asp Leu Arg Ala Val Gln Gly Trp Ala Ala Gly Arg Trp Leu
                165                 170                 175
Pro Ala Gly Cys Glu Thr Ala Ile Leu Phe Pro Met Arg Ser Lys Lys
            180                 185                 190
Ile Phe Ala Ser Val His Pro Ala Thr Pro Met Lys Leu Glu Ala Phe
        195                 200                 205
Ser Ala Cys Ile Trp Val Lys Ala Thr Asp Val Leu Ser Lys Thr Ile
    210                 215                 220
Leu Phe Ser Tyr Gly Thr Lys Arg Asn Pro Tyr Glu Ile Gln Leu Tyr
225                 230                 235                 240
Leu Ser Tyr Gln Ser Thr Val Leu Val Val Gly Gly Glu Glu Asn Arg
                245                 250                 255
Leu Val Ala Asn Thr Val Ile Ser Pro Gly Thr Trp Thr His Leu Cys
            260                 265                 270
Ser Thr Trp Asn Ser Glu Gln Gly His Val Ala Leu Trp Val Asn Gly
        275                 280                 285
Asp Leu Ile Ala Thr Lys Val Asp Met Ala Thr Gly His Ile Val Pro
    290                 295                 300
Gly Gly Gly Ile Leu Gln Ile Gly Gln Glu Lys Asn Gly Cys Cys Val
305                 310                 315                 320
Gly Gly Gly Phe Asp Glu Ile Leu Ala Phe Ser Gly Arg Leu Thr Gly
                325                 330                 335
Phe Asn Ile Trp Asp Arg Val Leu Ser Thr Glu Glu Ile Lys Lys Thr
            340                 345                 350
Gly Gly Ala Glu Ser Cys His Ile Arg Gly Asn Val Val Gly Trp Gly
        355                 360                 365
Val Thr Glu Ile Gln Pro His Gly Gly Ala Gln Tyr Val Ser
    370                 375                 380
```

<210> SEQ ID NO 43
<211> LENGTH: 365
<212> TYPE: PRT

<213> ORGANISM: Sus scrofa

<400> SEQUENCE: 43

Glu Asn Ser Asp Asp Tyr Glu Leu Met Tyr Val Asn Leu Asp Asn Glu
1               5                   10                  15

Ile Asp Asn Gly Leu His Pro Thr Glu Asp Pro Thr Leu Cys Asp Cys
            20                  25                  30

Ser Pro Glu His Ser Glu Trp Asp Lys Leu Phe Ile Met Leu Glu Asn
        35                  40                  45

Ser Gln Met Arg Glu Ser Met Leu Leu Gln Ala Thr Asp Asp Ile Leu
    50                  55                  60

Arg Gly Glu Leu Gln Arg Leu Arg Ala Glu Leu Gly Arg Leu Ala Gly
65                  70                  75                  80

Ser Leu Ala Arg Pro Cys Ala Pro Thr Ala Pro Ala Glu Val Gln Leu
                85                  90                  95

Ala Arg Ala Leu Asp Glu Leu Leu Gln Ala Ser Arg Asp Ala Gly Arg
            100                 105                 110

Arg Leu Glu Arg Leu Glu Glu Ala Gly Thr Pro Gln Leu Gln Glu Glu
        115                 120                 125

Ala Gly Arg Thr Leu Gly Ala Val Leu Glu Glu Leu Arg Arg Thr Arg
    130                 135                 140

Ala Asp Leu Arg Ala Val Gln Gly Trp Ala Ala Gly Arg Trp Leu Pro
145                 150                 155                 160

Ala Gly Cys Glu Thr Ala Ile Leu Phe Pro Met Arg Ser Lys Lys Ile
                165                 170                 175

Phe Ala Ser Val His Pro Ala Thr Pro Met Lys Leu Glu Ala Phe Ser
            180                 185                 190

Ala Cys Ile Trp Val Lys Ala Thr Asp Val Leu Ser Lys Thr Ile Leu
        195                 200                 205

Phe Ser Tyr Gly Thr Lys Arg Asn Pro Tyr Glu Ile Gln Leu Tyr Leu
    210                 215                 220

Ser Tyr Gln Ser Thr Val Leu Val Val Gly Gly Glu Glu Asn Arg Leu
225                 230                 235                 240

Val Ala Asn Thr Val Ile Ser Pro Gly Thr Trp Thr His Leu Cys Ser
                245                 250                 255

Thr Trp Asn Ser Glu Gln Gly His Val Ala Leu Trp Val Asn Gly Asp
            260                 265                 270

Leu Ile Ala Thr Lys Val Asp Met Ala Thr Gly His Ile Val Pro Gly
        275                 280                 285

Gly Gly Ile Leu Gln Ile Gly Gln Glu Lys Asn Gly Cys Cys Val Gly
    290                 295                 300

Gly Gly Phe Asp Glu Ile Leu Ala Phe Ser Gly Arg Leu Thr Gly Phe
305                 310                 315                 320

Asn Ile Trp Asp Arg Val Leu Ser Thr Glu Glu Ile Lys Lys Thr Gly
                325                 330                 335

Gly Ala Glu Ser Cys His Ile Arg Gly Asn Val Val Gly Trp Gly Val
            340                 345                 350

Thr Glu Ile Gln Pro His Gly Gly Ala Gln Tyr Val Ser
        355                 360                 365

<210> SEQ ID NO 44
<211> LENGTH: 417
<212> TYPE: PRT
<213> ORGANISM: Xenopus laevis

```
<400> SEQUENCE: 44

Met Ile Phe Ser Leu Ile Thr Pro Leu Asn Ile Leu Val Cys Ala Val
1               5                   10                  15

Cys Cys Phe Ser Thr Ala Leu Thr Ile Asp Asp Ile Ile His Val Lys
            20                  25                  30

Leu Asn Asn Asp Leu Glu Asn Gly Ile Leu Glu Asn Glu Glu Val Phe
        35                  40                  45

Ser Asp Cys Gln Val Lys Asp Met Thr Lys Trp Asp Lys Leu Phe Thr
    50                  55                  60

Met Leu Glu Asn Ser Gln Met Arg Glu Asn Met Leu Leu Gln Thr Val
65                  70                  75                  80

Asp Glu Val Val Ser Val Glu Leu Gln Ser Leu Arg Ala Glu Met Leu
                85                  90                  95

Gln Phe Val Ser Asn Phe Ala Gly Ala Cys Ala Ser Asn Ile Glu Lys
            100                 105                 110

Ser Thr Val Lys Ile Thr Thr Glu Leu Asn Arg Ser Leu Ala Ser Lys
        115                 120                 125

Cys Glu Gln Ala Gln Arg Arg Glu Asn Ser Leu Asn Thr Lys Lys Glu
    130                 135                 140

Asn Asp Leu Glu Asn Ala Val Leu Leu Asn Phe Asn Ile Ser Glu Arg
145                 150                 155                 160

Ile Ser Arg Ile Glu Glu Ala Leu Leu Leu Arg Thr Thr Glu Asp Ser
                165                 170                 175

Ser Asn Cys Ala Glu Thr Ser Ser Ala Leu Glu Ala Val Gln Gln Met
            180                 185                 190

Leu Asp Gln Thr Asn Ala Lys Leu Gln Thr Ala Gln Ser Trp Ile Ser
        195                 200                 205

Gln Arg Tyr Leu Pro Gly Gly Cys Glu Leu Ala Ile Leu Phe Pro Met
    210                 215                 220

Arg Ser Pro Lys Ile Tyr Ala Ser Val His Pro Ala Asp Met Thr Leu
225                 230                 235                 240

Gln Ala Phe Ser Phe Cys Val Trp Val Lys Val Thr Glu Ala Leu Asp
                245                 250                 255

Lys Thr Ile Val Phe Ser Tyr Gly Thr Lys Arg Asn Pro Tyr Glu Ile
            260                 265                 270

Gln Leu Tyr Leu Asn His Gln Ser Ser Val Leu Val Ile Gly Gly Asp
        275                 280                 285

Gln Asn Lys Val Ile Ala Asp Asn Val Val Glu Pro Ser Asn Trp Thr
    290                 295                 300

Asn Val Cys Gly Thr Trp Ser Ser Glu Asn Gly Lys Ala Thr Leu Trp
305                 310                 315                 320

Val Asn Gly Asn Asn Arg Val Thr Ser Tyr Asp Ile Ala Lys Gly His
                325                 330                 335

Glu Ile Pro Asn Arg Gly Ile Phe Gln Leu Gly Gln Glu Lys Asn Gly
            340                 345                 350

Cys Cys Val Gly Gly Gly Phe Asp Glu Leu Leu Ser Phe Ser Gly Lys
        355                 360                 365

Ile Thr Gly Phe Asn Leu Trp Asp Lys Glu Leu Ser Asp Glu Glu Ile
    370                 375                 380

Thr Leu Thr Gly Thr Glu Gln Gly Cys Ser Val Arg Gly Asn Val Val
385                 390                 395                 400

Gly Trp Gly Thr Thr Glu Ile Leu Leu His Gly Gly Ala Gln Tyr Ile
                405                 410                 415
```

His

<210> SEQ ID NO 45
<211> LENGTH: 393
<212> TYPE: PRT
<213> ORGANISM: Xenopus laevis

<400> SEQUENCE: 45

Ile Asp Asp Ile Ile His Val Lys Leu Asn Asn Asp Leu Glu Asn Gly
1               5                   10                  15

Ile Leu Glu Asn Glu Glu Val Phe Ser Asp Cys Gln Val Lys Asp Met
            20                  25                  30

Thr Lys Trp Asp Lys Leu Phe Thr Met Leu Glu Asn Ser Gln Met Arg
        35                  40                  45

Glu Asn Met Leu Leu Gln Thr Val Asp Glu Val Ser Val Glu Leu
    50                  55                  60

Gln Ser Leu Arg Ala Glu Met Leu Gln Phe Val Ser Asn Phe Ala Gly
65                  70                  75                  80

Ala Cys Ala Ser Asn Ile Glu Lys Ser Thr Val Lys Ile Thr Thr Glu
                85                  90                  95

Leu Asn Arg Ser Leu Ala Ser Lys Cys Glu Gln Ala Gln Arg Arg Glu
            100                 105                 110

Asn Ser Leu Asn Thr Lys Lys Glu Asn Asp Leu Glu Asn Ala Val Leu
        115                 120                 125

Leu Asn Phe Asn Ile Ser Glu Arg Ile Ser Arg Ile Glu Glu Ala Leu
    130                 135                 140

Leu Leu Arg Thr Thr Glu Asp Ser Ser Asn Cys Ala Glu Thr Ser Ser
145                 150                 155                 160

Ala Leu Glu Ala Val Gln Gln Met Leu Asp Gln Thr Asn Ala Lys Leu
                165                 170                 175

Gln Thr Ala Gln Ser Trp Ile Ser Gln Arg Tyr Leu Pro Gly Gly Cys
            180                 185                 190

Glu Leu Ala Ile Leu Phe Pro Met Arg Ser Pro Lys Ile Tyr Ala Ser
        195                 200                 205

Val His Pro Ala Asp Met Thr Leu Gln Ala Phe Ser Phe Cys Val Trp
    210                 215                 220

Val Lys Val Thr Glu Ala Leu Asp Lys Thr Ile Val Phe Ser Tyr Gly
225                 230                 235                 240

Thr Lys Arg Asn Pro Tyr Glu Ile Gln Leu Tyr Leu Asn His Gln Ser
                245                 250                 255

Ser Val Leu Val Ile Gly Gly Asp Gln Asn Lys Val Ile Ala Asp Asn
            260                 265                 270

Val Val Glu Pro Ser Asn Trp Thr Asn Val Cys Gly Thr Trp Ser Ser
        275                 280                 285

Glu Asn Gly Lys Ala Thr Leu Trp Val Asn Gly Asn Asn Arg Val Thr
    290                 295                 300

Ser Tyr Asp Ile Ala Lys Gly His Glu Ile Pro Asn Arg Gly Ile Phe
305                 310                 315                 320

Gln Leu Gly Gln Glu Lys Asn Gly Cys Cys Val Gly Gly Phe Asp
                325                 330                 335

Glu Leu Leu Ser Phe Ser Gly Lys Ile Thr Gly Phe Asn Leu Trp Asp
            340                 345                 350

Lys Glu Leu Ser Asp Glu Glu Ile Thr Leu Thr Gly Thr Glu Gln Gly
        355                 360                 365

Cys Ser Val Arg Gly Asn Val Gly Trp Gly Thr Thr Glu Ile Leu
    370                 375                 380

Leu His Gly Gly Ala Gln Tyr Ile His
385                 390

<210> SEQ ID NO 46
<211> LENGTH: 911
<212> TYPE: PRT
<213> ORGANISM: Homo sapiens

<400> SEQUENCE: 46

Met Asp Gly Ala Met Gly Pro Arg Gly Leu Leu Leu Cys Met Tyr Leu
1               5                   10                  15

Val Ser Leu Leu Ile Leu Gln Ala Met Pro Ala Leu Gly Ser Ala Thr
            20                  25                  30

Gly Arg Ser Lys Ser Ser Glu Lys Arg Gln Ala Val Asp Thr Ala Val
        35                  40                  45

Asp Gly Val Phe Ile Arg Ser Leu Lys Val Asn Cys Lys Val Thr Ser
    50                  55                  60

Arg Phe Ala His Tyr Val Val Thr Ser Gln Val Val Asn Thr Ala Asn
65                  70                  75                  80

Glu Ala Arg Glu Val Ala Phe Asp Leu Glu Ile Pro Lys Thr Ala Phe
                85                  90                  95

Ile Ser Asp Phe Ala Val Thr Ala Asp Gly Asn Ala Phe Ile Gly Asp
            100                 105                 110

Ile Lys Asp Lys Val Thr Ala Trp Lys Gln Tyr Arg Lys Ala Ala Ile
        115                 120                 125

Ser Gly Glu Asn Ala Gly Leu Val Arg Ala Ser Gly Arg Thr Met Glu
    130                 135                 140

Gln Phe Thr Ile His Leu Thr Val Asn Pro Gln Ser Lys Val Thr Phe
145                 150                 155                 160

Gln Leu Thr Tyr Glu Glu Val Leu Lys Arg Asn His Met Gln Tyr Glu
                165                 170                 175

Ile Val Ile Lys Val Lys Pro Lys Gln Leu Val His His Phe Glu Ile
            180                 185                 190

Asp Val Asp Ile Phe Glu Pro Gln Gly Ile Ser Lys Leu Asp Ala Gln
        195                 200                 205

Ala Ser Phe Leu Pro Lys Glu Leu Ala Ala Gln Thr Ile Lys Lys Ser
    210                 215                 220

Phe Ser Gly Lys Lys Gly His Val Leu Phe Arg Pro Thr Val Ser Gln
225                 230                 235                 240

Gln Gln Ser Cys Pro Thr Cys Ser Thr Ser Leu Leu Asn Gly His Phe
                245                 250                 255

Lys Val Thr Tyr Asp Val Ser Arg Asp Lys Ile Cys Asp Leu Leu Val
            260                 265                 270

Ala Asn Asn His Phe Ala His Phe Phe Ala Pro Gln Asn Leu Thr Asn
        275                 280                 285

Met Asn Lys Asn Val Val Phe Val Ile Asp Ile Ser Gly Ser Met Arg
    290                 295                 300

Gly Gln Lys Val Lys Gln Thr Lys Glu Ala Leu Leu Lys Ile Leu Gly
305                 310                 315                 320

Asp Met Gln Pro Gly Asp Tyr Phe Asp Leu Val Leu Phe Gly Thr Arg
                325                 330                 335

Val Gln Ser Trp Lys Gly Ser Leu Val Gln Ala Ser Glu Ala Asn Leu

```
              340                 345                 350
Gln Ala Ala Gln Asp Phe Val Arg Gly Phe Ser Leu Asp Glu Ala Thr
            355                 360                 365

Asn Leu Asn Gly Gly Leu Leu Arg Gly Ile Glu Ile Leu Asn Gln Val
        370                 375                 380

Gln Glu Ser Leu Pro Glu Leu Ser Asn His Ala Ser Ile Leu Ile Met
385                 390                 395                 400

Leu Thr Asp Gly Asp Pro Thr Glu Gly Val Thr Asp Arg Ser Gln Ile
                405                 410                 415

Leu Lys Asn Val Arg Asn Ala Ile Arg Gly Arg Phe Pro Leu Tyr Asn
            420                 425                 430

Leu Gly Phe Gly His Asn Val Asp Phe Asn Phe Leu Glu Val Met Ser
        435                 440                 445

Met Glu Asn Asn Gly Arg Ala Gln Arg Ile Tyr Glu Asp His Asp Ala
    450                 455                 460

Thr Gln Gln Leu Gln Gly Phe Tyr Ser Gln Val Ala Lys Pro Leu Leu
465                 470                 475                 480

Val Asp Val Asp Leu Gln Tyr Pro Gln Asp Ala Val Leu Ala Leu Thr
                485                 490                 495

Gln Asn His His Lys Gln Tyr Glu Gly Ser Glu Ile Val Val Ala
            500                 505                 510

Gly Arg Ile Ala Asp Asn Lys Gln Ser Ser Phe Lys Ala Asp Val Gln
        515                 520                 525

Ala His Gly Glu Gly Gln Glu Phe Ser Ile Thr Cys Leu Val Asp Glu
    530                 535                 540

Glu Glu Met Lys Lys Leu Leu Arg Glu Arg Gly His Met Leu Glu Asn
545                 550                 555                 560

His Val Glu Arg Leu Trp Ala Tyr Leu Thr Ile Gln Glu Leu Leu Ala
                565                 570                 575

Lys Arg Met Lys Val Asp Arg Glu Glu Arg Ala Asn Leu Ser Ser Gln
            580                 585                 590

Ala Leu Gln Met Ser Leu Asp Tyr Gly Phe Val Thr Pro Leu Thr Ser
        595                 600                 605

Met Ser Ile Arg Gly Met Ala Asp Gln Asp Gly Leu Lys Pro Thr Ile
    610                 615                 620

Asp Lys Pro Ser Glu Asp Ser Pro Leu Glu Met Leu Gly Pro Arg
625                 630                 635                 640

Arg Thr Phe Val Leu Ser Ala Leu Gln Pro Ser Pro Thr His Ser Ser
                645                 650                 655

Ser Asn Thr Gln Arg Leu Pro Asp Arg Val Thr Gly Val Asp Thr Asp
            660                 665                 670

Pro His Phe Ile Ile His Val Pro Gln Lys Glu Asp Thr Leu Cys Phe
        675                 680                 685

Asn Ile Asn Glu Glu Pro Gly Val Ile Leu Ser Leu Val Gln Asp Pro
    690                 695                 700

Asn Thr Gly Phe Ser Val Asn Gly Gln Leu Ile Gly Asn Lys Ala Arg
705                 710                 715                 720

Ser Pro Gly Gln His Asp Gly Thr Tyr Phe Gly Arg Leu Gly Ile Ala
                725                 730                 735

Asn Pro Ala Thr Asp Phe Gln Leu Glu Val Thr Pro Gln Asn Ile Thr
            740                 745                 750

Leu Asn Pro Gly Phe Gly Gly Pro Val Phe Ser Trp Arg Asp Gln Ala
        755                 760                 765
```

Val Leu Arg Gln Asp Gly Val Val Thr Ile Asn Lys Arg Asn
        770             775                 780

Leu Val Val Ser Val Asp Asp Gly Thr Phe Glu Val Val Leu His
785             790             795                 800

Arg Val Trp Lys Gly Ser Ser Val His Gln Asp Phe Leu Gly Phe Tyr
                805             810                 815

Val Leu Asp Ser His Arg Met Ser Ala Arg Thr His Gly Leu Leu Gly
            820             825                 830

Gln Phe Phe His Pro Ile Gly Phe Glu Val Ser Asp Ile His Pro Gly
        835             840                 845

Ser Asp Pro Thr Lys Pro Asp Ala Thr Met Val Val Arg Asn Arg Arg
850             855                 860

Leu Thr Val Thr Arg Gly Leu Gln Lys Asp Tyr Ser Lys Asp Pro Trp
865             870                 875                 880

His Gly Ala Glu Val Ser Cys Trp Phe Ile His Asn Asn Gly Ala Gly
                885             890                 895

Leu Ile Asp Gly Ala Tyr Thr Asp Tyr Ile Val Pro Asp Ile Phe
            900             905                 910

<210> SEQ ID NO 47
<211> LENGTH: 638
<212> TYPE: PRT
<213> ORGANISM: Homo sapiens

<400> SEQUENCE: 47

Ser Lys Ser Ser Glu Lys Arg Gln Ala Val Asp Thr Ala Val Asp Gly
1               5                   10                  15

Val Phe Ile Arg Ser Leu Lys Val Asn Cys Lys Val Thr Ser Arg Phe
            20                  25                  30

Ala His Tyr Val Val Thr Ser Gln Val Val Asn Thr Ala Asn Glu Ala
        35                  40                  45

Arg Glu Val Ala Phe Asp Leu Glu Ile Pro Lys Thr Ala Phe Ile Ser
    50                  55                  60

Asp Phe Ala Val Thr Ala Asp Gly Asn Ala Phe Ile Gly Asp Ile Lys
65                  70                  75                  80

Asp Lys Val Thr Ala Trp Lys Gln Tyr Arg Lys Ala Ala Ile Ser Gly
                85                  90                  95

Glu Asn Ala Gly Leu Val Arg Ala Ser Gly Arg Thr Met Glu Gln Phe
            100                 105                 110

Thr Ile His Leu Thr Val Asn Pro Gln Ser Lys Val Thr Phe Gln Leu
        115                 120                 125

Thr Tyr Glu Glu Val Leu Lys Arg Asn His Met Gln Tyr Glu Ile Val
    130                 135                 140

Ile Lys Val Lys Pro Lys Gln Leu Val His His Phe Glu Ile Asp Val
145                 150                 155                 160

Asp Ile Phe Glu Pro Gln Gly Ile Ser Lys Leu Asp Ala Gln Ala Ser
                165                 170                 175

Phe Leu Pro Lys Glu Leu Ala Ala Gln Thr Ile Lys Lys Ser Phe Ser
            180                 185                 190

Gly Lys Lys Gly His Val Leu Phe Arg Pro Thr Val Ser Gln Gln Gln
        195                 200                 205

Ser Cys Pro Thr Cys Ser Thr Ser Leu Leu Asn Gly His Phe Lys Val
    210                 215                 220

Thr Tyr Asp Val Ser Arg Asp Lys Ile Cys Asp Leu Leu Val Ala Asn

```
            225                 230                 235                 240
Asn His Phe Ala His Phe Phe Ala Pro Gln Asn Leu Thr Asn Met Asn
                245                 250                 255
Lys Asn Val Val Phe Val Ile Asp Ile Ser Gly Ser Met Arg Gly Gln
                260                 265                 270
Lys Val Lys Gln Thr Lys Glu Ala Leu Leu Lys Ile Leu Gly Asp Met
                275                 280                 285
Gln Pro Gly Asp Tyr Phe Asp Leu Val Leu Phe Gly Thr Arg Val Gln
            290                 295                 300
Ser Trp Lys Gly Ser Leu Val Gln Ala Ser Glu Ala Asn Leu Gln Ala
305                 310                 315                 320
Ala Gln Asp Phe Val Arg Gly Phe Ser Leu Asp Glu Ala Thr Asn Leu
                325                 330                 335
Asn Gly Gly Leu Leu Arg Gly Ile Glu Ile Leu Asn Gln Val Gln Glu
                340                 345                 350
Ser Leu Pro Glu Leu Ser Asn His Ala Ser Ile Leu Ile Met Leu Thr
            355                 360                 365
Asp Gly Asp Pro Thr Glu Gly Val Thr Asp Arg Ser Gln Ile Leu Lys
        370                 375                 380
Asn Val Arg Asn Ala Ile Arg Gly Arg Phe Pro Leu Tyr Asn Leu Gly
385                 390                 395                 400
Phe Gly His Asn Val Asp Phe Asn Phe Leu Glu Val Met Ser Met Glu
                405                 410                 415
Asn Asn Gly Arg Ala Gln Arg Ile Tyr Glu Asp His Asp Ala Thr Gln
                420                 425                 430
Gln Leu Gln Gly Phe Tyr Ser Gln Val Ala Lys Pro Leu Leu Val Asp
            435                 440                 445
Val Asp Leu Gln Tyr Pro Gln Asp Ala Val Leu Ala Leu Thr Gln Asn
        450                 455                 460
His His Lys Gln Tyr Tyr Glu Gly Ser Glu Ile Val Val Ala Gly Arg
465                 470                 475                 480
Ile Ala Asp Asn Lys Gln Ser Ser Phe Lys Ala Asp Val Gln Ala His
                485                 490                 495
Gly Glu Gly Gln Glu Phe Ser Ile Thr Cys Leu Val Asp Glu Glu Glu
                500                 505                 510
Met Lys Lys Leu Leu Arg Glu Arg Gly His Met Leu Glu Asn His Val
            515                 520                 525
Glu Arg Leu Trp Ala Tyr Leu Thr Ile Gln Glu Leu Leu Ala Lys Arg
        530                 535                 540
Met Lys Val Asp Arg Glu Arg Ala Asn Leu Ser Ser Gln Ala Leu
545                 550                 555                 560
Gln Met Ser Leu Asp Tyr Gly Phe Val Thr Pro Leu Thr Ser Met Ser
                565                 570                 575
Ile Arg Gly Met Ala Asp Gln Asp Gly Leu Lys Pro Thr Ile Asp Lys
                580                 585                 590
Pro Ser Glu Asp Ser Pro Leu Glu Met Leu Gly Pro Arg Arg Thr
            595                 600                 605
Phe Val Leu Ser Ala Leu Gln Pro Ser Pro Thr His Ser Ser Ser Asn
        610                 615                 620
Thr Gln Arg Leu Pro Asp Arg Val Thr Gly Val Asp Thr Asp
625                 630                 635
```

<210> SEQ ID NO 48

```
<211> LENGTH: 946
<212> TYPE: PRT
<213> ORGANISM: Homo sapiens

<400> SEQUENCE: 48

Met Lys Arg Leu Thr Cys Phe Ile Cys Phe Phe Leu Ser Glu Val
1               5                   10                  15

Ser Gly Phe Glu Ile Pro Ile Asn Gly Leu Ser Glu Phe Val Asp Tyr
            20                  25                  30

Glu Asp Leu Val Glu Leu Ala Pro Gly Lys Phe Gln Leu Val Ala Glu
        35                  40                  45

Asn Arg Arg Tyr Gln Arg Ser Leu Pro Gly Glu Ser Glu Met Met
50                  55                  60

Glu Glu Val Asp Gln Val Thr Leu Tyr Ser Tyr Lys Val Gln Ser Thr
65                  70                  75                  80

Ile Thr Ser Arg Met Ala Thr Thr Met Ile Gln Ser Lys Val Val Asn
                85                  90                  95

Asn Ser Pro Gln Pro Gln Asn Val Val Phe Asp Val Gln Ile Pro Lys
            100                 105                 110

Gly Ala Phe Ile Ser Asn Phe Ser Met Thr Val Asp Gly Lys Thr Phe
        115                 120                 125

Arg Ser Ser Ile Lys Glu Lys Thr Val Gly Arg Ala Leu Tyr Ala Gln
130                 135                 140

Ala Arg Ala Lys Gly Lys Thr Ala Gly Leu Val Arg Ser Ser Ala Leu
145                 150                 155                 160

Asp Met Glu Asn Phe Arg Thr Glu Val Asn Val Leu Pro Gly Ala Lys
                165                 170                 175

Val Gln Phe Glu Leu His Tyr Gln Glu Val Lys Trp Arg Lys Leu Gly
            180                 185                 190

Ser Tyr Glu His Arg Ile Tyr Leu Gln Pro Gly Arg Leu Ala Lys His
        195                 200                 205

Leu Glu Val Asp Val Trp Val Ile Glu Pro Gln Gly Leu Arg Phe Leu
210                 215                 220

His Val Pro Asp Thr Phe Glu Gly His Phe Asp Gly Val Pro Val Ile
225                 230                 235                 240

Ser Lys Gly Gln Gln Lys Ala His Val Ser Phe Lys Pro Thr Val Ala
                245                 250                 255

Gln Gln Arg Ile Cys Pro Asn Cys Arg Glu Thr Ala Val Asp Gly Glu
            260                 265                 270

Leu Val Val Leu Tyr Asp Val Lys Arg Glu Lys Ala Gly Glu Leu
        275                 280                 285

Glu Val Phe Asn Gly Tyr Phe Val His Phe Phe Ala Pro Asp Asn Leu
290                 295                 300

Asp Pro Ile Pro Lys Asn Ile Leu Phe Val Ile Asp Val Ser Gly Ser
305                 310                 315                 320

Met Trp Gly Val Lys Met Lys Gln Thr Val Glu Ala Met Lys Thr Ile
                325                 330                 335

Leu Asp Asp Leu Arg Ala Glu Asp His Phe Ser Val Ile Asp Phe Asn
            340                 345                 350

Gln Asn Ile Arg Thr Trp Arg Asn Asp Leu Ile Ser Ala Thr Lys Thr
        355                 360                 365

Gln Val Ala Asp Ala Lys Arg Tyr Ile Glu Lys Ile Gln Pro Ser Gly
370                 375                 380

Gly Thr Asn Ile Asn Glu Ala Leu Leu Arg Ala Ile Phe Ile Leu Asn
```

```
            385                 390                 395                 400

Glu Ala Asn Asn Leu Gly Leu Leu Asp Pro Asn Ser Val Ser Leu Ile
                405                 410                 415

Ile Leu Val Ser Asp Gly Asp Pro Thr Val Gly Glu Leu Lys Leu Ser
                420                 425                 430

Lys Ile Gln Lys Asn Val Lys Glu Asn Ile Gln Asp Asn Ile Ser Leu
                435                 440                 445

Phe Ser Leu Gly Met Gly Phe Asp Val Asp Tyr Asp Phe Leu Lys Arg
            450                 455                 460

Leu Ser Asn Glu Asn His Gly Ile Ala Gln Arg Ile Tyr Gly Asn Gln
465                 470                 475                 480

Asp Thr Ser Ser Gln Leu Lys Lys Phe Tyr Asn Gln Val Ser Thr Pro
                485                 490                 495

Leu Leu Arg Asn Val Gln Phe Asn Tyr Pro His Thr Ser Val Thr Asp
                500                 505                 510

Val Thr Gln Asn Asn Phe His Asn Tyr Phe Gly Gly Ser Glu Ile Val
                515                 520                 525

Val Ala Gly Lys Phe Asp Pro Ala Lys Leu Asp Gln Ile Glu Ser Val
            530                 535                 540

Ile Thr Ala Thr Ser Ala Asn Thr Gln Leu Val Leu Glu Thr Leu Ala
545                 550                 555                 560

Gln Met Asp Asp Leu Gln Asp Phe Leu Ser Lys Asp Lys His Ala Asp
                565                 570                 575

Pro Asp Phe Thr Arg Lys Leu Trp Ala Tyr Leu Thr Ile Asn Gln Leu
                580                 585                 590

Leu Ala Glu Arg Ser Leu Ala Pro Thr Ala Ala Lys Arg Arg Ile
            595                 600                 605

Thr Arg Ser Ile Leu Gln Met Ser Leu Asp His Ile Val Thr Pro
            610                 615                 620

Leu Thr Ser Leu Val Ile Glu Asn Glu Ala Gly Asp Glu Arg Met Leu
625                 630                 635                 640

Ala Asp Ala Pro Pro Gln Asp Pro Ser Cys Cys Ser Gly Ala Leu Tyr
                645                 650                 655

Tyr Gly Ser Lys Val Val Pro Asp Ser Thr Pro Ser Trp Ala Asn Pro
                660                 665                 670

Ser Pro Thr Pro Val Ile Ser Met Leu Ala Gln Gly Ser Gln Val Leu
                675                 680                 685

Glu Ser Thr Pro Pro His Val Met Arg Val Glu Asn Asp Pro His
            690                 695                 700

Phe Ile Ile Tyr Leu Pro Lys Ser Gln Lys Asn Ile Cys Phe Asn Ile
705                 710                 715                 720

Asp Ser Glu Pro Gly Lys Ile Leu Asn Leu Val Ser Asp Pro Glu Ser
                725                 730                 735

Gly Ile Val Val Asn Gly Gln Leu Val Gly Ala Lys Lys Pro Asn Asn
                740                 745                 750

Gly Lys Leu Ser Thr Tyr Phe Gly Lys Leu Gly Phe Tyr Phe Gln Ser
            755                 760                 765

Glu Asp Ile Lys Ile Glu Ile Ser Thr Glu Thr Ile Thr Leu Ser His
            770                 775                 780

Gly Ser Ser Thr Phe Ser Leu Ser Trp Ser Asp Thr Ala Gln Val Thr
785                 790                 795                 800

Asn Gln Arg Val Gln Ile Ser Val Lys Lys Glu Lys Val Val Thr Ile
                805                 810                 815
```

```
Thr Leu Asp Lys Glu Met Ser Phe Ser Val Leu Leu His Arg Val Trp
                820                 825                 830

Lys Lys His Pro Val Asn Val Asp Phe Leu Gly Ile Tyr Ile Pro Pro
            835                 840                 845

Thr Asn Lys Phe Ser Pro Lys Ala His Gly Leu Ile Gly Gln Phe Met
        850                 855                 860

Gln Glu Pro Lys Ile His Ile Phe Asn Glu Arg Pro Gly Lys Asp Pro
865                 870                 875                 880

Glu Lys Pro Glu Ala Ser Met Glu Val Lys Gly Gln Lys Leu Ile Ile
                885                 890                 895

Thr Arg Gly Leu Gln Lys Asp Tyr Arg Thr Asp Leu Val Phe Gly Thr
            900                 905                 910

Asp Val Thr Cys Trp Phe Val His Asn Ser Gly Lys Gly Phe Ile Asp
        915                 920                 925

Gly His Tyr Lys Asp Tyr Phe Val Pro Gln Leu Tyr Ser Phe Leu Lys
    930                 935                 940

Arg Pro
945

<210> SEQ ID NO 49
<211> LENGTH: 648
<212> TYPE: PRT
<213> ORGANISM: Homo sapiens

<400> SEQUENCE: 49

Ser Leu Pro Gly Glu Ser Glu Glu Met Met Glu Glu Val Asp Gln Val
1               5                   10                  15

Thr Leu Tyr Ser Tyr Lys Val Gln Ser Thr Ile Thr Ser Arg Met Ala
            20                  25                  30

Thr Thr Met Ile Gln Ser Lys Val Val Asn Asn Ser Pro Gln Pro Gln
        35                  40                  45

Asn Val Val Phe Asp Val Gln Ile Pro Lys Gly Ala Phe Ile Ser Asn
    50                  55                  60

Phe Ser Met Thr Val Asp Gly Lys Thr Phe Arg Ser Ser Ile Lys Glu
65                  70                  75                  80

Lys Thr Val Gly Arg Ala Leu Tyr Ala Gln Ala Arg Ala Lys Gly Lys
                85                  90                  95

Thr Ala Gly Leu Val Arg Ser Ser Ala Leu Asp Met Glu Asn Phe Arg
            100                 105                 110

Thr Glu Val Asn Val Leu Pro Gly Ala Lys Val Gln Phe Glu Leu His
        115                 120                 125

Tyr Gln Glu Val Lys Trp Arg Lys Leu Gly Ser Tyr Glu His Arg Ile
    130                 135                 140

Tyr Leu Gln Pro Gly Arg Leu Ala Lys His Leu Glu Val Asp Val Trp
145                 150                 155                 160

Val Ile Glu Pro Gln Gly Leu Arg Phe Leu His Val Pro Asp Thr Phe
                165                 170                 175

Glu Gly His Phe Asp Gly Val Pro Val Ile Ser Lys Gly Gln Gln Lys
            180                 185                 190

Ala His Val Ser Phe Lys Pro Thr Val Ala Gln Gln Arg Ile Cys Pro
        195                 200                 205

Asn Cys Arg Glu Thr Ala Val Asp Gly Glu Leu Val Val Leu Tyr Asp
    210                 215                 220

Val Lys Arg Glu Glu Lys Ala Gly Glu Leu Glu Val Phe Asn Gly Tyr
```

```
              225                 230                 235                 240
        Phe Val His Phe Phe Ala Pro Asp Asn Leu Asp Pro Ile Pro Lys Asn
                            245                 250                 255
        Ile Leu Phe Val Ile Asp Val Ser Gly Ser Met Trp Gly Val Lys Met
                            260                 265                 270
        Lys Gln Thr Val Glu Ala Met Lys Thr Ile Leu Asp Asp Leu Arg Ala
                            275                 280                 285
        Glu Asp His Phe Ser Val Ile Asp Phe Asn Gln Asn Ile Arg Thr Trp
                            290                 295                 300
        Arg Asn Asp Leu Ile Ser Ala Thr Lys Thr Gln Val Ala Asp Ala Lys
        305                 310                 315                 320
        Arg Tyr Ile Glu Lys Ile Gln Pro Ser Gly Gly Thr Asn Ile Asn Glu
                            325                 330                 335
        Ala Leu Leu Arg Ala Ile Phe Ile Leu Asn Glu Ala Asn Asn Leu Gly
                            340                 345                 350
        Leu Leu Asp Pro Asn Ser Val Ser Leu Ile Ile Leu Val Ser Asp Gly
                            355                 360                 365
        Asp Pro Thr Val Gly Glu Leu Lys Leu Ser Lys Ile Gln Lys Asn Val
                            370                 375                 380
        Lys Glu Asn Ile Gln Asp Asn Ile Ser Leu Phe Ser Leu Gly Met Gly
        385                 390                 395                 400
        Phe Asp Val Asp Tyr Asp Phe Leu Lys Arg Leu Ser Asn Glu Asn His
                            405                 410                 415
        Gly Ile Ala Gln Arg Ile Tyr Gly Asn Gln Asp Thr Ser Ser Gln Leu
                            420                 425                 430
        Lys Lys Phe Tyr Asn Gln Val Ser Thr Pro Leu Leu Arg Asn Val Gln
                            435                 440                 445
        Phe Asn Tyr Pro His Thr Ser Val Thr Asp Val Thr Gln Asn Asn Phe
                            450                 455                 460
        His Asn Tyr Phe Gly Gly Ser Glu Ile Val Val Ala Gly Lys Phe Asp
        465                 470                 475                 480
        Pro Ala Lys Leu Asp Gln Ile Glu Ser Val Ile Thr Ala Thr Ser Ala
                            485                 490                 495
        Asn Thr Gln Leu Val Leu Glu Thr Leu Ala Gln Met Asp Asp Leu Gln
                            500                 505                 510
        Asp Phe Leu Ser Lys Asp Lys His Ala Asp Pro Asp Phe Thr Arg Lys
                            515                 520                 525
        Leu Trp Ala Tyr Leu Thr Ile Asn Gln Leu Leu Ala Glu Arg Ser Leu
                            530                 535                 540
        Ala Pro Thr Ala Ala Lys Arg Arg Ile Thr Arg Ser Ile Leu Gln
        545                 550                 555                 560
        Met Ser Leu Asp His His Ile Val Thr Pro Leu Thr Ser Leu Val Ile
                            565                 570                 575
        Glu Asn Glu Ala Gly Asp Glu Arg Met Leu Ala Asp Ala Pro Pro Gln
                            580                 585                 590
        Asp Pro Ser Cys Cys Ser Gly Ala Leu Tyr Tyr Gly Ser Lys Val Val
                            595                 600                 605
        Pro Asp Ser Thr Pro Ser Trp Ala Asn Pro Ser Pro Thr Pro Val Ile
                            610                 615                 620
        Ser Met Leu Ala Gln Gly Ser Gln Val Leu Glu Ser Thr Pro Pro
        625                 630                 635                 640
        His Val Met Arg Val Glu Asn Asp
                            645
```

<210> SEQ ID NO 50
<211> LENGTH: 890
<212> TYPE: PRT
<213> ORGANISM: Homo sapiens

<400> SEQUENCE: 50

```
Met Ala Phe Ala Trp Trp Pro Cys Leu Ile Leu Ala Leu Leu Ser Ser
1               5                   10                  15

Leu Ala Ala Ser Gly Phe Pro Arg Ser Pro Phe Arg Leu Leu Gly Lys
            20                  25                  30

Arg Ser Leu Pro Glu Gly Val Ala Asn Gly Ile Glu Val Tyr Ser Thr
        35                  40                  45

Lys Ile Asn Ser Lys Val Thr Ser Arg Phe Ala His Asn Val Val Thr
    50                  55                  60

Met Arg Ala Val Asn Arg Ala Asp Thr Ala Lys Glu Val Ser Phe Asp
65                  70                  75                  80

Val Glu Leu Pro Lys Thr Ala Phe Ile Thr Asn Phe Thr Leu Thr Ile
                85                  90                  95

Asp Gly Val Thr Tyr Pro Gly Asn Val Lys Glu Lys Glu Val Ala Lys
            100                 105                 110

Lys Gln Tyr Glu Lys Ala Val Ser Gln Gly Lys Thr Ala Gly Leu Val
        115                 120                 125

Lys Ala Ser Gly Arg Lys Leu Glu Lys Phe Thr Val Ser Val Asn Val
    130                 135                 140

Ala Ala Gly Ser Lys Val Thr Phe Glu Leu Thr Tyr Glu Glu Leu Leu
145                 150                 155                 160

Lys Arg His Lys Gly Lys Tyr Glu Met Tyr Leu Lys Val Gln Pro Lys
                165                 170                 175

Gln Leu Val Lys His Phe Glu Ile Glu Val Asp Ile Phe Glu Pro Gln
            180                 185                 190

Gly Ile Ser Met Leu Asp Ala Glu Ala Ser Phe Ile Thr Asn Asp Leu
        195                 200                 205

Leu Gly Ser Ala Leu Thr Lys Ser Phe Ser Gly Lys Lys Gly His Val
    210                 215                 220

Ser Phe Lys Pro Ser Leu Asp Gln Gln Arg Ser Cys Pro Thr Cys Thr
225                 230                 235                 240

Asp Ser Leu Leu Asn Gly Asp Phe Thr Ile Thr Tyr Asp Val Asn Arg
                245                 250                 255

Glu Ser Pro Gly Asn Val Gln Ile Val Asn Gly Tyr Phe Val His Phe
            260                 265                 270

Phe Ala Pro Gln Gly Leu Pro Val Val Pro Lys Asn Val Ala Phe Val
        275                 280                 285

Ile Asp Ile Ser Gly Ser Met Ala Gly Arg Lys Leu Glu Gln Thr Lys
    290                 295                 300

Glu Ala Leu Leu Arg Ile Leu Glu Asp Met Gln Glu Glu Asp Tyr Leu
305                 310                 315                 320

Asn Phe Ile Leu Phe Ser Gly Asp Val Ser Thr Trp Lys Glu His Leu
                325                 330                 335

Val Gln Ala Thr Pro Glu Asn Leu Gln Glu Ala Arg Thr Phe Val Lys
            340                 345                 350

Ser Met Glu Asp Lys Gly Met Thr Asn Ile Asn Asp Gly Leu Leu Arg
        355                 360                 365

Gly Ile Ser Met Leu Asn Lys Ala Arg Glu Glu His Arg Ile Pro Glu
```

```
              370                 375                 380
Arg Ser Thr Ser Ile Val Ile Met Leu Thr Asp Gly Asp Ala Asn Val
385                 390                 395                 400

Gly Glu Ser Arg Pro Glu Lys Ile Gln Glu Asn Val Arg Asn Ala Ile
                405                 410                 415

Gly Gly Lys Phe Pro Leu Tyr Asn Leu Gly Phe Gly Asn Asn Leu Asn
                420                 425                 430

Tyr Asn Phe Leu Glu Asn Met Ala Leu Glu Asn His Gly Phe Ala Arg
            435                 440                 445

Arg Ile Tyr Glu Asp Ser Asp Ala Asp Leu Gln Leu Gln Gly Phe Tyr
            450                 455                 460

Glu Glu Val Ala Asn Pro Leu Leu Thr Gly Val Glu Met Glu Tyr Pro
465                 470                 475                 480

Glu Asn Ala Ile Leu Asp Leu Thr Gln Asn Thr Tyr Gln His Phe Tyr
                485                 490                 495

Asp Gly Ser Glu Ile Val Val Ala Gly Arg Leu Val Asp Glu Asp Met
                500                 505                 510

Asn Ser Phe Lys Ala Asp Val Lys Gly His Gly Ala Thr Asn Asp Leu
            515                 520                 525

Thr Phe Thr Glu Glu Val Asp Met Lys Glu Met Glu Lys Ala Leu Gln
            530                 535                 540

Glu Arg Asp Tyr Ile Phe Gly Asn Tyr Ile Glu Arg Leu Trp Ala Tyr
545                 550                 555                 560

Leu Thr Ile Glu Gln Leu Leu Glu Lys Arg Lys Asn Ala His Gly Glu
                565                 570                 575

Glu Lys Glu Asn Leu Thr Ala Arg Ala Leu Asp Leu Ser Leu Lys Tyr
            580                 585                 590

His Phe Val Thr Pro Leu Thr Ser Met Val Val Thr Lys Pro Glu Asp
            595                 600                 605

Asn Glu Asp Glu Arg Ala Ile Ala Asp Lys Pro Gly Glu Asp Ala Glu
            610                 615                 620

Ala Thr Pro Val Ser Pro Ala Met Ser Tyr Leu Thr Ser Tyr Gln Pro
625                 630                 635                 640

Pro Gln Asn Pro Tyr Tyr Val Asp Gly Asp Pro His Phe Ile Ile
                645                 650                 655

Gln Ile Pro Glu Lys Asp Asp Ala Leu Cys Phe Asn Ile Asp Glu Ala
                660                 665                 670

Pro Gly Thr Val Leu Arg Leu Ile Gln Asp Ala Val Thr Gly Leu Thr
            675                 680                 685

Val Asn Gly Gln Ile Thr Gly Asp Lys Arg Gly Ser Pro Asp Ser Lys
            690                 695                 700

Thr Arg Lys Thr Tyr Phe Gly Lys Leu Gly Ile Ala Asn Ala Gln Met
705                 710                 715                 720

Asp Phe Gln Val Glu Val Thr Thr Glu Lys Ile Thr Leu Trp Asn Arg
                725                 730                 735

Ala Val Pro Ser Thr Phe Ser Trp Leu Asp Thr Val Thr Val Thr Gln
                740                 745                 750

Asp Gly Leu Ser Met Met Ile Asn Arg Lys Asn Met Val Val Ser Phe
            755                 760                 765

Gly Asp Gly Val Thr Phe Val Val Leu His Gln Val Trp Lys Lys
            770                 775                 780

His Pro Val His Arg Asp Phe Leu Gly Phe Tyr Val Val Asp Ser His
785                 790                 795                 800
```

```
Arg Met Ser Ala Gln Thr His Gly Leu Leu Gly Gln Phe Phe Gln Pro
                805                 810                 815

Phe Asp Phe Lys Val Ser Asp Ile Arg Pro Gly Ser Asp Pro Thr Lys
            820                 825                 830

Pro Asp Ala Thr Leu Val Val Lys Asn His Gln Leu Ile Val Thr Arg
        835                 840                 845

Gly Ser Gln Lys Asp Tyr Arg Lys Asp Ala Ser Ile Gly Thr Lys Val
    850                 855                 860

Val Cys Trp Phe Val His Asn Asn Gly Glu Gly Leu Ile Asp Gly Val
865                 870                 875                 880

His Thr Asp Tyr Ile Val Pro Asn Leu Phe
            885                 890

<210> SEQ ID NO 51
<211> LENGTH: 617
<212> TYPE: PRT
<213> ORGANISM: Homo sapiens

<400> SEQUENCE: 51

Leu Pro Glu Gly Val Ala Asn Gly Ile Glu Val Tyr Ser Thr Lys Ile
1               5                   10                  15

Asn Ser Lys Val Thr Ser Arg Phe Ala His Asn Val Val Thr Met Arg
            20                  25                  30

Ala Val Asn Arg Ala Asp Thr Ala Lys Glu Val Ser Phe Asp Val Glu
        35                  40                  45

Leu Pro Lys Thr Ala Phe Ile Thr Asn Phe Thr Leu Thr Ile Asp Gly
    50                  55                  60

Val Thr Tyr Pro Gly Asn Val Lys Glu Lys Glu Val Ala Lys Lys Gln
65                  70                  75                  80

Tyr Glu Lys Ala Val Ser Gln Gly Lys Thr Ala Gly Leu Val Lys Ala
                85                  90                  95

Ser Gly Arg Lys Leu Glu Lys Phe Thr Val Ser Val Asn Val Ala Ala
            100                 105                 110

Gly Ser Lys Val Thr Phe Glu Leu Thr Tyr Glu Glu Leu Leu Lys Arg
        115                 120                 125

His Lys Gly Lys Tyr Glu Met Tyr Leu Lys Val Gln Pro Lys Gln Leu
    130                 135                 140

Val Lys His Phe Glu Ile Glu Val Asp Ile Phe Glu Pro Gln Gly Ile
145                 150                 155                 160

Ser Met Leu Asp Ala Glu Ala Ser Phe Ile Thr Asn Asp Leu Leu Gly
                165                 170                 175

Ser Ala Leu Thr Lys Ser Phe Ser Gly Lys Lys Gly His Val Ser Phe
            180                 185                 190

Lys Pro Ser Leu Asp Gln Gln Arg Ser Cys Pro Thr Cys Thr Asp Ser
        195                 200                 205

Leu Leu Asn Gly Asp Phe Thr Ile Thr Tyr Asp Val Asn Arg Glu Ser
    210                 215                 220

Pro Gly Asn Val Gln Ile Val Asn Gly Tyr Phe Val His Phe Phe Ala
225                 230                 235                 240

Pro Gln Gly Leu Pro Val Val Pro Lys Asn Val Ala Phe Val Ile Asp
                245                 250                 255

Ile Ser Gly Ser Met Ala Gly Arg Lys Leu Glu Gln Thr Lys Glu Ala
            260                 265                 270

Leu Leu Arg Ile Leu Glu Asp Met Gln Glu Glu Asp Tyr Leu Asn Phe
```

275                 280                 285
Ile Leu Phe Ser Gly Asp Val Ser Thr Trp Lys Glu His Leu Val Gln
    290                 295                 300

Ala Thr Pro Glu Asn Leu Gln Glu Ala Arg Thr Phe Val Lys Ser Met
305                 310                 315                 320

Glu Asp Lys Gly Met Thr Asn Ile Asn Asp Gly Leu Leu Arg Gly Ile
                325                 330                 335

Ser Met Leu Asn Lys Ala Arg Glu Glu His Arg Ile Pro Glu Arg Ser
            340                 345                 350

Thr Ser Ile Val Ile Met Leu Thr Asp Gly Asp Ala Asn Val Gly Glu
        355                 360                 365

Ser Arg Pro Glu Lys Ile Gln Glu Asn Val Arg Asn Ala Ile Gly Gly
    370                 375                 380

Lys Phe Pro Leu Tyr Asn Leu Gly Phe Gly Asn Asn Leu Asn Tyr Asn
385                 390                 395                 400

Phe Leu Glu Asn Met Ala Leu Glu Asn His Gly Phe Ala Arg Arg Ile
                405                 410                 415

Tyr Glu Asp Ser Asp Ala Asp Leu Gln Leu Gln Gly Phe Tyr Glu Glu
            420                 425                 430

Val Ala Asn Pro Leu Leu Thr Gly Val Glu Met Glu Tyr Pro Glu Asn
        435                 440                 445

Ala Ile Leu Asp Leu Thr Gln Asn Thr Tyr Gln His Phe Tyr Asp Gly
    450                 455                 460

Ser Glu Ile Val Val Ala Gly Arg Leu Val Asp Glu Asp Met Asn Ser
465                 470                 475                 480

Phe Lys Ala Asp Val Lys Gly His Gly Ala Thr Asn Asp Leu Thr Phe
                485                 490                 495

Thr Glu Glu Val Asp Met Lys Glu Met Glu Lys Ala Leu Gln Glu Arg
            500                 505                 510

Asp Tyr Ile Phe Gly Asn Tyr Ile Glu Arg Leu Trp Ala Tyr Leu Thr
        515                 520                 525

Ile Glu Gln Leu Leu Glu Lys Arg Lys Asn Ala His Gly Glu Glu Lys
    530                 535                 540

Glu Asn Leu Thr Ala Arg Ala Leu Asp Leu Ser Leu Lys Tyr His Phe
545                 550                 555                 560

Val Thr Pro Leu Thr Ser Met Val Val Thr Lys Pro Glu Asp Asn Glu
                565                 570                 575

Asp Glu Arg Ala Ile Ala Asp Lys Pro Gly Glu Asp Ala Glu Ala Thr
            580                 585                 590

Pro Val Ser Pro Ala Met Ser Tyr Leu Thr Ser Tyr Gln Pro Pro Gln
        595                 600                 605

Asn Pro Tyr Tyr Tyr Val Asp Gly Asp
    610                 615

<210> SEQ ID NO 52
<211> LENGTH: 252
<212> TYPE: PRT
<213> ORGANISM: Homo sapiens

<400> SEQUENCE: 52

Met Ala Gln Leu Cys Gly Leu Arg Arg Ser Arg Ala Phe Leu Ala Leu
1               5                   10                  15

Leu Gly Ser Leu Leu Leu Ser Gly Val Leu Ala Ala Asp Arg Glu Arg
            20                  25                  30

```
Ser Ile His Asp Phe Cys Leu Val Ser Lys Val Val Gly Arg Cys Arg
        35                  40                  45

Ala Ser Met Pro Arg Trp Trp Tyr Asn Val Thr Asp Gly Ser Cys Gln
 50                  55                  60

Leu Phe Val Tyr Gly Gly Cys Asp Gly Asn Ser Asn Asn Tyr Leu Thr
 65                  70                  75                  80

Lys Glu Glu Cys Leu Lys Lys Cys Ala Thr Val Thr Glu Asn Ala Thr
                 85                  90                  95

Gly Asp Leu Ala Thr Ser Arg Asn Ala Ala Asp Ser Ser Val Pro Ser
                100                 105                 110

Ala Pro Arg Arg Gln Asp Ser Glu Asp His Ser Ser Asp Met Phe Asn
                115                 120                 125

Tyr Glu Glu Tyr Cys Thr Ala Asn Ala Val Thr Gly Pro Cys Arg Ala
130                 135                 140

Ser Phe Pro Arg Trp Tyr Phe Asp Val Glu Arg Asn Ser Cys Asn Asn
145                 150                 155                 160

Phe Ile Tyr Gly Gly Cys Arg Gly Asn Lys Asn Ser Tyr Arg Ser Glu
                165                 170                 175

Glu Ala Cys Met Leu Arg Cys Phe Arg Gln Gln Glu Asn Pro Pro Leu
                180                 185                 190

Pro Leu Gly Ser Lys Val Val Val Leu Ala Gly Leu Phe Val Met Val
                195                 200                 205

Leu Ile Leu Phe Leu Gly Ala Ser Met Val Tyr Leu Ile Arg Val Ala
                210                 215                 220

Arg Arg Asn Gln Glu Arg Ala Leu Arg Thr Val Trp Ser Ser Gly Asp
225                 230                 235                 240

Asp Lys Glu Gln Leu Val Lys Asn Thr Tyr Val Leu
                245                 250

<210> SEQ ID NO 53
<211> LENGTH: 225
<212> TYPE: PRT
<213> ORGANISM: Homo sapiens

<400> SEQUENCE: 53

Ala Asp Arg Glu Arg Ser Ile His Asp Phe Cys Leu Val Ser Lys Val
 1               5                  10                  15

Val Gly Arg Cys Arg Ala Ser Met Pro Arg Trp Trp Tyr Asn Val Thr
                20                  25                  30

Asp Gly Ser Cys Gln Leu Phe Val Tyr Gly Gly Cys Asp Gly Asn Ser
                35                  40                  45

Asn Asn Tyr Leu Thr Lys Glu Glu Cys Leu Lys Lys Cys Ala Thr Val
 50                  55                  60

Thr Glu Asn Ala Thr Gly Asp Leu Ala Thr Ser Arg Asn Ala Ala Asp
 65                  70                  75                  80

Ser Ser Val Pro Ser Ala Pro Arg Arg Gln Asp Ser Glu Asp His Ser
                 85                  90                  95

Ser Asp Met Phe Asn Tyr Glu Glu Tyr Cys Thr Ala Asn Ala Val Thr
                100                 105                 110

Gly Pro Cys Arg Ala Ser Phe Pro Arg Trp Tyr Phe Asp Val Glu Arg
                115                 120                 125

Asn Ser Cys Asn Asn Phe Ile Tyr Gly Gly Cys Arg Gly Asn Lys Asn
                130                 135                 140

Ser Tyr Arg Ser Glu Glu Ala Cys Met Leu Arg Cys Phe Arg Gln Gln
145                 150                 155                 160
```

Glu Asn Pro Pro Leu Pro Leu Gly Ser Lys Val Val Leu Ala Gly
                165                 170                 175

Leu Phe Val Met Val Leu Ile Leu Phe Leu Gly Ala Ser Met Val Tyr
            180                 185                 190

Leu Ile Arg Val Ala Arg Arg Asn Gln Glu Arg Ala Leu Arg Thr Val
        195                 200                 205

Trp Ser Ser Gly Asp Asp Lys Glu Gln Leu Val Lys Asn Thr Tyr Val
210                 215                 220

Leu
225

<210> SEQ ID NO 54
<211> LENGTH: 354
<212> TYPE: PRT
<213> ORGANISM: Homo sapiens

<400> SEQUENCE: 54

Met Lys Ser Leu Leu Leu Val Leu Ile Ser Ile Cys Trp Ala Asp
1               5                   10                  15

His Leu Ser Asp Asn Tyr Thr Leu Asp His Asp Arg Ala Ile His Ile
            20                  25                  30

Gln Ala Glu Asn Gly Pro His Leu Leu Val Glu Ala Glu Gln Ala Lys
        35                  40                  45

Val Phe Ser His Arg Gly Gly Asn Val Thr Leu Pro Cys Lys Phe Tyr
    50                  55                  60

Arg Asp Pro Thr Ala Phe Gly Ser Gly Ile His Lys Ile Arg Ile Lys
65                  70                  75                  80

Trp Thr Lys Leu Thr Ser Asp Tyr Leu Lys Glu Val Asp Val Phe Val
                85                  90                  95

Ser Met Gly Tyr His Lys Lys Thr Tyr Gly Gly Tyr Gln Gly Arg Val
            100                 105                 110

Phe Leu Lys Gly Gly Ser Asp Ser Asp Ala Ser Leu Val Ile Thr Asp
        115                 120                 125

Leu Thr Leu Glu Asp Tyr Gly Arg Tyr Lys Cys Glu Val Ile Glu Gly
    130                 135                 140

Leu Glu Asp Asp Thr Val Val Val Ala Leu Asp Leu Gln Gly Val Val
145                 150                 155                 160

Phe Pro Tyr Phe Pro Arg Leu Gly Arg Tyr Asn Leu Asn Phe His Glu
                165                 170                 175

Ala Gln Gln Ala Cys Leu Asp Gln Asp Ala Val Ile Ala Ser Phe Asp
            180                 185                 190

Gln Leu Tyr Asp Ala Trp Arg Gly Gly Leu Asp Trp Cys Asn Ala Gly
        195                 200                 205

Trp Leu Ser Asp Gly Ser Val Gln Tyr Pro Ile Thr Lys Pro Arg Glu
    210                 215                 220

Pro Cys Gly Gly Gln Asn Thr Val Pro Gly Val Arg Asn Tyr Gly Phe
225                 230                 235                 240

Trp Asp Lys Asp Lys Ser Arg Tyr Asp Val Phe Cys Phe Thr Ser Asn
                245                 250                 255

Phe Asn Gly Arg Phe Tyr Tyr Leu Ile His Pro Thr Lys Leu Thr Tyr
            260                 265                 270

Asp Glu Ala Val Gln Ala Cys Leu Asn Asp Gly Ala Gln Ile Ala Lys
        275                 280                 285

Val Gly Gln Ile Phe Ala Ala Trp Lys Ile Leu Gly Tyr Asp Arg Cys

```
            290                 295                 300

Asp Ala Gly Trp Leu Ala Asp Gly Ser Val Arg Tyr Pro Ile Ser Arg
305                 310                 315                 320

Pro Arg Arg Arg Cys Ser Pro Thr Glu Ala Ala Val Arg Phe Val Gly
                325                 330                 335

Phe Pro Asp Lys Lys His Lys Leu Tyr Gly Val Tyr Cys Phe Arg Ala
                340                 345                 350

Tyr Asn

<210> SEQ ID NO 55
<211> LENGTH: 339
<212> TYPE: PRT
<213> ORGANISM: Homo sapiens

<400> SEQUENCE: 55

Asp His Leu Ser Asp Asn Tyr Thr Leu Asp His Asp Arg Ala Ile His
1               5                   10                  15

Ile Gln Ala Glu Asn Gly Pro His Leu Leu Val Glu Ala Glu Gln Ala
                20                  25                  30

Lys Val Phe Ser His Arg Gly Gly Asn Val Thr Leu Pro Cys Lys Phe
                35                  40                  45

Tyr Arg Asp Pro Thr Ala Phe Gly Ser Gly Ile His Lys Ile Arg Ile
50                  55                  60

Lys Trp Thr Lys Leu Thr Ser Asp Tyr Leu Lys Glu Val Asp Val Phe
65                  70                  75                  80

Val Ser Met Gly Tyr His Lys Lys Thr Tyr Gly Gly Tyr Gln Gly Arg
                85                  90                  95

Val Phe Leu Lys Gly Gly Ser Asp Ser Asp Ala Ser Leu Val Ile Thr
                100                 105                 110

Asp Leu Thr Leu Glu Asp Tyr Gly Arg Tyr Lys Cys Glu Val Ile Glu
                115                 120                 125

Gly Leu Glu Asp Asp Thr Val Val Val Ala Leu Asp Leu Gln Gly Val
                130                 135                 140

Val Phe Pro Tyr Phe Pro Arg Leu Gly Arg Tyr Asn Leu Asn Phe His
145                 150                 155                 160

Glu Ala Gln Gln Ala Cys Leu Asp Gln Asp Ala Val Ile Ala Ser Phe
                165                 170                 175

Asp Gln Leu Tyr Asp Ala Trp Arg Gly Gly Leu Asp Trp Cys Asn Ala
                180                 185                 190

Gly Trp Leu Ser Asp Gly Ser Val Gln Tyr Pro Ile Thr Lys Pro Arg
                195                 200                 205

Glu Pro Cys Gly Gly Gln Asn Thr Val Pro Gly Val Arg Asn Tyr Gly
                210                 215                 220

Phe Trp Asp Lys Asp Lys Ser Arg Tyr Asp Val Phe Cys Phe Thr Ser
225                 230                 235                 240

Asn Phe Asn Gly Arg Phe Tyr Tyr Leu Ile His Pro Thr Lys Leu Thr
                245                 250                 255

Tyr Asp Glu Ala Val Gln Ala Cys Leu Asn Asp Gly Ala Gln Ile Ala
                260                 265                 270

Lys Val Gly Gln Ile Phe Ala Ala Trp Lys Ile Leu Gly Tyr Asp Arg
                275                 280                 285

Cys Asp Ala Gly Trp Leu Ala Asp Gly Ser Val Arg Tyr Pro Ile Ser
                290                 295                 300

Arg Pro Arg Arg Arg Cys Ser Pro Thr Glu Ala Ala Val Arg Phe Val
```

```
305                 310                 315                 320
Gly Phe Pro Asp Lys Lys His Lys Leu Tyr Gly Val Tyr Cys Phe Arg
                325                 330                 335

Ala Tyr Asn

<210> SEQ ID NO 56
<211> LENGTH: 96
<212> TYPE: PRT
<213> ORGANISM: Homo sapiens

<400> SEQUENCE: 56

Val Val Phe Pro Tyr Phe Pro Arg Leu Gly Arg Tyr Asn Leu Asn Phe
1               5                   10                  15

His Glu Ala Gln Gln Ala Cys Leu Asp Gln Asp Ala Val Ile Ala Ser
            20                  25                  30

Phe Asp Gln Leu Tyr Asp Ala Trp Arg Gly Leu Asp Trp Cys Asn
        35                  40                  45

Ala Gly Trp Leu Ser Asp Gly Ser Val Gln Tyr Pro Ile Thr Lys Pro
    50                  55                  60

Arg Glu Pro Cys Gly Gly Gln Asn Thr Val Pro Gly Val Arg Asn Tyr
65                  70                  75                  80

Gly Phe Trp Asp Lys Asp Lys Ser Arg Tyr Asp Val Phe Cys Phe Thr
                85                  90                  95

<210> SEQ ID NO 57
<211> LENGTH: 93
<212> TYPE: PRT
<213> ORGANISM: Homo sapiens

<400> SEQUENCE: 57

Gly Arg Phe Tyr Tyr Leu Ile His Pro Thr Lys Leu Thr Tyr Asp Glu
1               5                   10                  15

Ala Val Gln Ala Cys Leu Asn Asp Gly Ala Gln Ile Ala Lys Val Gly
            20                  25                  30

Gln Ile Phe Ala Ala Trp Lys Ile Leu Gly Tyr Asp Arg Cys Asp Ala
        35                  40                  45

Gly Trp Leu Ala Asp Gly Ser Val Arg Tyr Pro Ile Ser Arg Pro Arg
    50                  55                  60

Arg Arg Cys Ser Pro Thr Glu Ala Ala Val Arg Phe Val Gly Phe Pro
65                  70                  75                  80

Asp Lys Lys His Lys Leu Tyr Gly Val Tyr Cys Phe Arg
                85                  90

<210> SEQ ID NO 58
<211> LENGTH: 340
<212> TYPE: PRT
<213> ORGANISM: Homo sapiens

<400> SEQUENCE: 58

Met Pro Gly Trp Leu Thr Leu Pro Thr Leu Cys Arg Phe Leu Leu Trp
1               5                   10                  15

Ala Phe Thr Ile Phe His Lys Ala Gln Gly Asp Pro Ala Ser His Pro
            20                  25                  30

Gly Pro His Tyr Leu Leu Pro Ile His Glu Val Ile His Ser His
        35                  40                  45

Arg Gly Ala Thr Ala Thr Leu Pro Cys Val Leu Gly Thr Thr Pro Pro
    50                  55                  60
```

Ser Tyr Lys Val Arg Trp Ser Lys Val Glu Pro Gly Glu Leu Arg Glu
65                  70                  75                  80

Thr Leu Ile Leu Ile Thr Asn Gly Leu His Ala Arg Gly Tyr Gly Pro
                85                  90                  95

Leu Gly Gly Arg Ala Arg Met Arg Arg Gly His Arg Leu Asp Ala Ser
            100                 105                 110

Leu Val Ile Ala Gly Val Arg Leu Glu Asp Glu Gly Arg Tyr Arg Cys
        115                 120                 125

Glu Leu Ile Asn Gly Ile Glu Asp Glu Ser Val Ala Leu Thr Leu Ser
130                 135                 140

Leu Glu Gly Val Val Phe Pro Tyr Gln Pro Ser Arg Gly Arg Tyr Gln
145                 150                 155                 160

Phe Asn Tyr Tyr Glu Ala Lys Gln Ala Cys Glu Glu Gln Asp Gly Arg
                165                 170                 175

Leu Ala Thr Tyr Ser Gln Leu Tyr Gln Ala Trp Thr Glu Gly Leu Asp
            180                 185                 190

Trp Cys Asn Ala Gly Trp Leu Leu Glu Gly Ser Val Arg Tyr Pro Val
        195                 200                 205

Leu Thr Ala Arg Ala Pro Cys Gly Gly Arg Gly Arg Pro Gly Ile Arg
210                 215                 220

Ser Tyr Gly Pro Arg Asp Arg Met Arg Asp Arg Tyr Asp Ala Phe Cys
225                 230                 235                 240

Phe Thr Ser Ala Leu Ala Gly Gln Val Phe Phe Val Pro Gly Arg Leu
                245                 250                 255

Thr Leu Ser Glu Ala His Ala Ala Cys Arg Arg Arg Gly Ala Val Val
            260                 265                 270

Ala Lys Val Gly His Leu Tyr Ala Ala Trp Lys Phe Ser Gly Leu Asp
        275                 280                 285

Gln Cys Asp Gly Gly Trp Leu Ala Asp Gly Ser Val Arg Phe Pro Ile
290                 295                 300

Thr Thr Pro Arg Pro Arg Cys Gly Gly Leu Pro Asp Pro Gly Val Arg
305                 310                 315                 320

Ser Phe Gly Phe Pro Arg Pro Gln Gln Ala Ala Tyr Gly Thr Tyr Cys
                325                 330                 335

Tyr Ala Glu Asn
            340

<210> SEQ ID NO 59
<211> LENGTH: 314
<212> TYPE: PRT
<213> ORGANISM: Homo sapiens

<400> SEQUENCE: 59

Asp Pro Ala Ser His Pro Gly Pro His Tyr Leu Leu Pro Pro Ile His
1               5                   10                  15

Glu Val Ile His Ser His Arg Gly Ala Thr Ala Thr Leu Pro Cys Val
                20                  25                  30

Leu Gly Thr Thr Pro Pro Ser Tyr Lys Val Arg Trp Ser Lys Val Glu
            35                  40                  45

Pro Gly Glu Leu Arg Glu Thr Leu Ile Leu Ile Thr Asn Gly Leu His
        50                  55                  60

Ala Arg Gly Tyr Gly Pro Leu Gly Gly Arg Ala Arg Met Arg Arg Gly
65                  70                  75                  80

His Arg Leu Asp Ala Ser Leu Val Ile Ala Gly Val Arg Leu Glu Asp
                85                  90                  95

```
Glu Gly Arg Tyr Arg Cys Glu Leu Ile Asn Gly Ile Glu Asp Glu Ser
                100                 105                 110

Val Ala Leu Thr Leu Ser Leu Glu Gly Val Val Phe Pro Tyr Gln Pro
        115                 120                 125

Ser Arg Gly Arg Tyr Gln Phe Asn Tyr Tyr Glu Ala Lys Gln Ala Cys
    130                 135                 140

Glu Glu Gln Asp Gly Arg Leu Ala Thr Tyr Ser Gln Leu Tyr Gln Ala
145                 150                 155                 160

Trp Thr Glu Gly Leu Asp Trp Cys Asn Ala Gly Trp Leu Leu Glu Gly
                165                 170                 175

Ser Val Arg Tyr Pro Val Leu Thr Ala Arg Ala Pro Cys Gly Gly Arg
            180                 185                 190

Gly Arg Pro Gly Ile Arg Ser Tyr Gly Pro Arg Asp Arg Met Arg Asp
        195                 200                 205

Arg Tyr Asp Ala Phe Cys Phe Thr Ser Ala Leu Ala Gly Gln Val Phe
210                 215                 220

Phe Val Pro Gly Arg Leu Thr Leu Ser Glu Ala His Ala Ala Cys Arg
225                 230                 235                 240

Arg Arg Gly Ala Val Val Ala Lys Val Gly His Leu Tyr Ala Ala Trp
                245                 250                 255

Lys Phe Ser Gly Leu Asp Gln Cys Asp Gly Gly Trp Leu Ala Asp Gly
            260                 265                 270

Ser Val Arg Phe Pro Ile Thr Thr Pro Arg Pro Arg Cys Gly Gly Leu
        275                 280                 285

Pro Asp Pro Gly Val Arg Ser Phe Gly Phe Pro Arg Pro Gln Gln Ala
    290                 295                 300

Ala Tyr Gly Thr Tyr Cys Tyr Ala Glu Asn
305                 310

<210> SEQ ID NO 60
<211> LENGTH: 95
<212> TYPE: PRT
<213> ORGANISM: Homo sapiens

<400> SEQUENCE: 60

Val Val Phe Pro Tyr Gln Pro Ser Arg Gly Arg Tyr Gln Phe Asn Tyr
1               5                   10                  15

Tyr Glu Ala Lys Gln Ala Cys Glu Glu Gln Asp Gly Arg Leu Ala Thr
                20                  25                  30

Tyr Ser Gln Leu Tyr Gln Ala Trp Thr Glu Gly Leu Asp Trp Cys Asn
            35                  40                  45

Ala Gly Trp Leu Leu Glu Gly Ser Val Arg Tyr Pro Val Leu Thr Ala
        50                  55                  60

Arg Ala Pro Cys Gly Gly Arg Gly Arg Pro Gly Ile Arg Ser Tyr Gly
65                  70                  75                  80

Pro Arg Asp Arg Met Arg Asp Arg Tyr Asp Ala Phe Cys Phe Thr
                85                  90                  95

<210> SEQ ID NO 61
<211> LENGTH: 94
<212> TYPE: PRT
<213> ORGANISM: Homo sapiens

<400> SEQUENCE: 61

Leu Ala Gly Gln Val Phe Phe Val Pro Gly Arg Leu Thr Leu Ser Glu
1               5                   10                  15
```

```
Ala His Ala Ala Cys Arg Arg Gly Ala Val Val Ala Lys Val Gly
        20                  25                  30

His Leu Tyr Ala Ala Trp Lys Phe Ser Gly Leu Asp Gln Cys Asp Gly
            35                  40                  45

Gly Trp Leu Ala Asp Gly Ser Val Arg Phe Pro Ile Thr Thr Pro Arg
 50                  55                  60

Pro Arg Cys Gly Gly Leu Pro Asp Pro Gly Val Arg Ser Phe Gly Phe
 65                  70                  75                  80

Pro Arg Pro Gln Gln Ala Ala Tyr Gly Thr Tyr Cys Tyr Ala
                85                  90

<210> SEQ ID NO 62
<211> LENGTH: 360
<212> TYPE: PRT
<213> ORGANISM: Homo sapiens

<400> SEQUENCE: 62

Met Gly Leu Leu Leu Val Pro Leu Leu Leu Pro Gly Ser Tyr
 1               5                  10                  15

Gly Leu Pro Phe Tyr Asn Gly Phe Tyr Tyr Ser Asn Ser Ala Asn Asp
            20                  25                  30

Gln Asn Leu Gly Asn Gly His Gly Lys Asp Leu Leu Asn Gly Val Lys
        35                  40                  45

Leu Val Val Glu Thr Pro Glu Thr Leu Phe Thr Tyr Gln Gly Ala
 50                  55                  60

Ser Val Ile Leu Pro Cys Arg Tyr Arg Tyr Glu Pro Ala Leu Val Ser
 65                  70                  75                  80

Pro Arg Arg Val Arg Val Lys Trp Trp Lys Leu Ser Glu Asn Gly Ala
                85                  90                  95

Pro Glu Lys Asp Val Leu Val Ala Ile Gly Leu Arg His Arg Ser Phe
            100                 105                 110

Gly Asp Tyr Gln Gly Arg Val His Leu Arg Gln Asp Lys Glu His Asp
        115                 120                 125

Val Ser Leu Glu Ile Gln Asp Leu Arg Leu Glu Asp Tyr Gly Arg Tyr
130                 135                 140

Arg Cys Glu Val Ile Asp Gly Leu Glu Asp Glu Ser Gly Leu Val Glu
145                 150                 155                 160

Leu Glu Leu Arg Gly Val Val Phe Pro Tyr Gln Ser Pro Asn Gly Arg
                165                 170                 175

Tyr Gln Phe Asn Phe His Glu Gly Gln Gln Val Cys Ala Glu Gln Ala
            180                 185                 190

Ala Val Val Ala Ser Phe Glu Gln Leu Phe Arg Ala Trp Glu Glu Gly
        195                 200                 205

Leu Asp Trp Cys Asn Ala Gly Trp Leu Gln Asp Ala Thr Val Gln Tyr
    210                 215                 220

Pro Ile Met Leu Pro Arg Gln Pro Cys Gly Gly Pro Gly Leu Ala Pro
225                 230                 235                 240

Gly Val Arg Ser Tyr Gly Pro Arg His Arg Leu His Arg Tyr Asp
                245                 250                 255

Val Phe Cys Phe Ala Thr Ala Leu Lys Gly Arg Val Tyr Tyr Leu Glu
            260                 265                 270

His Pro Glu Lys Leu Thr Leu Thr Glu Ala Arg Glu Ala Cys Gln Glu
        275                 280                 285

Asp Asp Ala Thr Ile Ala Lys Val Gly Gln Leu Phe Ala Ala Trp Lys
```

```
            290                 295                 300

Phe His Gly Leu Asp Arg Cys Asp Ala Gly Trp Leu Ala Asp Gly Ser
305                 310                 315                 320

Val Arg Tyr Pro Val His Pro His Pro Asn Cys Gly Pro Pro Glu
                        325                 330                 335

Pro Gly Val Arg Ser Phe Gly Phe Pro Asp Pro Gln Ser Arg Leu Tyr
                        340                 345                 350

Gly Val Tyr Cys Tyr Arg Gln His
                355                 360

<210> SEQ ID NO 63
<211> LENGTH: 343
<212> TYPE: PRT
<213> ORGANISM: Homo sapiens

<400> SEQUENCE: 63

Leu Pro Phe Tyr Asn Gly Phe Tyr Tyr Ser Asn Ser Ala Asn Asp Gln
1               5                   10                  15

Asn Leu Gly Asn Gly His Gly Lys Asp Leu Leu Asn Gly Val Lys Leu
                20                  25                  30

Val Val Glu Thr Pro Glu Glu Thr Leu Phe Thr Tyr Gln Gly Ala Ser
            35                  40                  45

Val Ile Leu Pro Cys Arg Tyr Arg Tyr Glu Pro Ala Leu Val Ser Pro
50                  55                  60

Arg Arg Val Arg Val Lys Trp Trp Lys Leu Ser Glu Asn Gly Ala Pro
65                  70                  75                  80

Glu Lys Asp Val Leu Val Ala Ile Gly Leu Arg His Arg Ser Phe Gly
                85                  90                  95

Asp Tyr Gln Gly Arg Val His Leu Arg Gln Asp Lys Glu His Asp Val
            100                 105                 110

Ser Leu Glu Ile Gln Asp Leu Arg Leu Glu Asp Tyr Gly Arg Tyr Arg
        115                 120                 125

Cys Glu Val Ile Asp Gly Leu Glu Asp Glu Ser Gly Leu Val Glu Leu
130                 135                 140

Glu Leu Arg Gly Val Val Phe Pro Tyr Gln Ser Pro Asn Gly Arg Tyr
145                 150                 155                 160

Gln Phe Asn Phe His Glu Gly Gln Gln Val Cys Ala Glu Gln Ala Ala
                165                 170                 175

Val Val Ala Ser Phe Glu Gln Leu Phe Arg Ala Trp Glu Glu Gly Leu
            180                 185                 190

Asp Trp Cys Asn Ala Gly Trp Leu Gln Asp Ala Thr Val Gln Tyr Pro
        195                 200                 205

Ile Met Leu Pro Arg Gln Pro Cys Gly Gly Pro Gly Leu Ala Pro Gly
210                 215                 220

Val Arg Ser Tyr Gly Pro Arg His Arg Leu His Arg Tyr Asp Val
225                 230                 235                 240

Phe Cys Phe Ala Thr Ala Leu Lys Gly Arg Val Tyr Tyr Leu Glu His
                245                 250                 255

Pro Glu Lys Leu Thr Leu Thr Glu Ala Arg Glu Ala Cys Gln Glu Asp
            260                 265                 270

Asp Ala Thr Ile Ala Lys Val Gly Gln Leu Phe Ala Ala Trp Lys Phe
        275                 280                 285

His Gly Leu Asp Arg Cys Asp Ala Gly Trp Leu Ala Asp Gly Ser Val
290                 295                 300
```

Arg Tyr Pro Val Val His Pro His Pro Asn Cys Gly Pro Pro Glu Pro
305                 310                 315                 320

Gly Val Arg Ser Phe Gly Phe Pro Asp Pro Gln Ser Arg Leu Tyr Gly
                325                 330                 335

Val Tyr Cys Tyr Arg Gln His
            340

<210> SEQ ID NO 64
<211> LENGTH: 96
<212> TYPE: PRT
<213> ORGANISM: Homo sapiens

<400> SEQUENCE: 64

Val Val Phe Pro Tyr Gln Ser Pro Asn Gly Arg Tyr Gln Phe Asn Phe
1               5                   10                  15

His Glu Gly Gln Gln Val Cys Ala Glu Gln Ala Ala Val Val Ala Ser
            20                  25                  30

Phe Glu Gln Leu Phe Arg Ala Trp Glu Glu Gly Leu Asp Trp Cys Asn
        35                  40                  45

Ala Gly Trp Leu Gln Asp Ala Thr Val Gln Tyr Pro Ile Met Leu Pro
    50                  55                  60

Arg Gln Pro Cys Gly Gly Pro Gly Leu Ala Pro Gly Val Arg Ser Tyr
65                  70                  75                  80

Gly Pro Arg His Arg Leu His Arg Tyr Asp Val Phe Cys Phe Ala
                85                  90                  95

<210> SEQ ID NO 65
<211> LENGTH: 93
<212> TYPE: PRT
<213> ORGANISM: Homo sapiens

<400> SEQUENCE: 65

Gly Arg Val Tyr Tyr Leu Glu His Pro Glu Lys Leu Thr Leu Thr Glu
1               5                   10                  15

Ala Arg Glu Ala Cys Gln Glu Asp Asp Ala Thr Ile Ala Lys Val Gly
            20                  25                  30

Gln Leu Phe Ala Ala Trp Lys Phe His Gly Leu Asp Arg Cys Asp Ala
        35                  40                  45

Gly Trp Leu Ala Asp Gly Ser Val Arg Tyr Pro Val Val His Pro His
    50                  55                  60

Pro Asn Cys Gly Pro Pro Glu Pro Gly Val Arg Ser Phe Gly Phe Pro
65                  70                  75                  80

Asp Pro Gln Ser Arg Leu Tyr Gly Val Tyr Cys Tyr Arg
                85                  90

<210> SEQ ID NO 66
<211> LENGTH: 402
<212> TYPE: PRT
<213> ORGANISM: Homo sapiens

<400> SEQUENCE: 66

Met Val Cys Ala Arg Ala Ala Leu Gly Pro Gly Ala Leu Trp Ala Ala
1               5                   10                  15

Ala Trp Gly Val Leu Leu Leu Thr Ala Pro Ala Gly Ala Gln Arg Gly
            20                  25                  30

Arg Lys Lys Val Val His Val Leu Glu Gly Glu Ser Gly Ser Val Val
        35                  40                  45

Val Gln Thr Ala Pro Gly Gln Val Val Ser His Arg Gly Gly Thr Ile

```
                50                  55                  60
Val Leu Pro Cys Arg Tyr His Tyr Glu Ala Ala His Gly His Asp
 65                  70                  75                  80

Gly Val Arg Leu Lys Trp Thr Lys Val Val Asp Pro Leu Ala Phe Thr
                 85                  90                  95

Asp Val Phe Val Ala Leu Gly Pro Gln His Arg Ala Phe Gly Ser Tyr
                100                 105                 110

Arg Gly Arg Ala Glu Leu Gln Gly Asp Gly Pro Gly Asp Ala Ser Leu
            115                 120                 125

Val Leu Arg Asn Val Thr Leu Gln Asp Tyr Gly Arg Tyr Glu Cys Glu
            130                 135                 140

Val Thr Asn Glu Leu Glu Asp Asp Ala Gly Met Val Lys Leu Asp Leu
145                 150                 155                 160

Glu Gly Val Val Phe Pro Tyr His Pro Arg Gly Gly Arg Tyr Lys Leu
                165                 170                 175

Thr Phe Ala Glu Ala Gln Arg Ala Cys Ala Glu Gln Asp Gly Ile Leu
            180                 185                 190

Ala Ser Ala Glu Gln Leu His Ala Ala Trp Arg Asp Gly Leu Asp Trp
            195                 200                 205

Cys Asn Ala Gly Trp Leu Arg Asp Gly Ser Val Gln Tyr Pro Val Asn
210                 215                 220

Arg Pro Arg Glu Pro Cys Gly Gly Leu Gly Thr Gly Ser Ala Gly
225                 230                 235                 240

Gly Gly Gly Asp Ala Asn Gly Gly Leu Arg Asn Tyr Gly Tyr Arg His
                245                 250                 255

Asn Ala Glu Glu Arg Tyr Asp Ala Phe Cys Phe Thr Ser Asn Leu Pro
            260                 265                 270

Gly Arg Val Phe Phe Leu Lys Pro Leu Arg Pro Val Pro Phe Ser Gly
            275                 280                 285

Ala Ala Arg Ala Cys Ala Ala Arg Gly Ala Ala Val Ala Lys Val Gly
            290                 295                 300

Gln Leu Phe Ala Ala Trp Lys Leu Gln Leu Leu Asp Arg Cys Thr Ala
305                 310                 315                 320

Gly Trp Leu Ala Asp Gly Ser Ala Arg Tyr Pro Ile Val Asn Pro Arg
                325                 330                 335

Ala Arg Cys Gly Gly Arg Arg Pro Gly Val Arg Ser Leu Gly Phe Pro
            340                 345                 350

Asp Ala Thr Arg Arg Leu Phe Gly Val Tyr Cys Tyr Arg Ala Pro Gly
            355                 360                 365

Ala Pro Asp Pro Ala Pro Gly Gly Trp Gly Trp Gly Trp Ala Gly Gly
            370                 375                 380

Gly Gly Trp Ala Gly Gly Ala Arg Asp Pro Ala Ala Trp Thr Pro Leu
385                 390                 395                 400

His Val

<210> SEQ ID NO 67
<211> LENGTH: 373
<212> TYPE: PRT
<213> ORGANISM: Homo sapiens

<400> SEQUENCE: 67

Gln Arg Gly Arg Lys Lys Val Val His Val Leu Glu Gly Glu Ser Gly
 1               5                  10                  15

Ser Val Val Val Gln Thr Ala Pro Gly Gln Val Val Ser His Arg Gly
```

```
            20                  25                  30
Gly Thr Ile Val Leu Pro Cys Arg Tyr His Tyr Glu Ala Ala His
        35                  40                  45
Gly His Asp Gly Val Arg Leu Lys Trp Thr Lys Val Asp Pro Leu
        50                  55                  60
Ala Phe Thr Asp Val Phe Val Ala Leu Gly Pro Gln His Arg Ala Phe
65                  70                  75                  80
Gly Ser Tyr Arg Gly Arg Ala Glu Leu Gln Gly Asp Gly Pro Gly Asp
                85                  90                  95
Ala Ser Leu Val Leu Arg Asn Val Thr Leu Gln Asp Tyr Gly Arg Tyr
                100                 105                 110
Glu Cys Glu Val Thr Asn Glu Leu Glu Asp Asp Ala Gly Met Val Lys
                115                 120                 125
Leu Asp Leu Glu Gly Val Val Phe Pro Tyr His Pro Arg Gly Gly Arg
        130                 135                 140
Tyr Lys Leu Thr Phe Ala Glu Ala Gln Arg Ala Cys Ala Glu Gln Asp
145                 150                 155                 160
Gly Ile Leu Ala Ser Ala Glu Gln Leu His Ala Ala Trp Arg Asp Gly
                165                 170                 175
Leu Asp Trp Cys Asn Ala Gly Trp Leu Arg Asp Gly Ser Val Gln Tyr
                180                 185                 190
Pro Val Asn Arg Pro Arg Glu Pro Cys Gly Gly Leu Gly Thr Gly
                195                 200                 205
Ser Ala Gly Gly Gly Asp Ala Asn Gly Gly Leu Arg Asn Tyr Gly
        210                 215                 220
Tyr Arg His Asn Ala Glu Glu Arg Tyr Asp Ala Phe Cys Phe Thr Ser
225                 230                 235                 240
Asn Leu Pro Gly Arg Val Phe Phe Leu Lys Pro Leu Arg Pro Val Pro
                245                 250                 255
Phe Ser Gly Ala Ala Arg Ala Cys Ala Ala Arg Gly Ala Ala Val Ala
                260                 265                 270
Lys Val Gly Gln Leu Phe Ala Ala Trp Lys Leu Gln Leu Leu Asp Arg
        275                 280                 285
Cys Thr Ala Gly Trp Leu Ala Asp Gly Ser Ala Arg Tyr Pro Ile Val
        290                 295                 300
Asn Pro Arg Ala Arg Cys Gly Arg Arg Pro Gly Val Arg Ser Leu
305                 310                 315                 320
Gly Phe Pro Asp Ala Thr Arg Arg Leu Phe Gly Val Tyr Cys Tyr Arg
                325                 330                 335
Ala Pro Gly Ala Pro Asp Pro Ala Pro Gly Gly Trp Gly Trp Gly Trp
                340                 345                 350
Ala Gly Gly Gly Gly Trp Ala Gly Ala Arg Asp Pro Ala Ala Trp
        355                 360                 365
Thr Pro Leu His Val
        370

<210> SEQ ID NO 68
<211> LENGTH: 106
<212> TYPE: PRT
<213> ORGANISM: Homo sapiens

<400> SEQUENCE: 68

Val Val Phe Pro Tyr His Pro Arg Gly Gly Arg Tyr Lys Leu Thr Phe
1               5                   10                  15
```

Ala Glu Ala Gln Arg Ala Cys Ala Glu Gln Asp Gly Ile Leu Ala Ser
                20                  25                  30

Ala Glu Gln Leu His Ala Ala Trp Arg Asp Gly Leu Asp Trp Cys Asn
            35                  40                  45

Ala Gly Trp Leu Arg Asp Gly Ser Val Gln Tyr Pro Val Asn Arg Pro
        50                  55                  60

Arg Glu Pro Cys Gly Gly Leu Gly Gly Thr Gly Ser Ala Gly Gly Gly
65                  70                  75                  80

Gly Asp Ala Asn Gly Gly Leu Arg Asn Tyr Gly Tyr Arg His Asn Ala
                85                  90                  95

Glu Glu Arg Tyr Asp Ala Phe Cys Phe Thr
            100                 105

<210> SEQ ID NO 69
<211> LENGTH: 93
<212> TYPE: PRT
<213> ORGANISM: Homo sapiens

<400> SEQUENCE: 69

Gly Arg Val Phe Phe Leu Lys Pro Leu Arg Pro Val Pro Phe Ser Gly
1               5                   10                  15

Ala Ala Arg Ala Cys Ala Ala Arg Gly Ala Ala Val Ala Lys Val Gly
                20                  25                  30

Gln Leu Phe Ala Ala Trp Lys Leu Gln Leu Leu Asp Arg Cys Thr Ala
            35                  40                  45

Gly Trp Leu Ala Asp Gly Ser Ala Arg Tyr Pro Ile Val Asn Pro Arg
        50                  55                  60

Ala Arg Cys Gly Gly Arg Arg Pro Gly Val Arg Ser Leu Gly Phe Pro
65                  70                  75                  80

Asp Ala Thr Arg Arg Leu Phe Gly Val Tyr Cys Tyr Arg
                85                  90

<210> SEQ ID NO 70
<211> LENGTH: 2415
<212> TYPE: PRT
<213> ORGANISM: Homo sapiens

<400> SEQUENCE: 70

Met Thr Thr Leu Leu Trp Val Phe Val Thr Leu Arg Val Ile Thr Ala
1               5                   10                  15

Ala Val Thr Val Glu Thr Ser Asp His Asp Asn Ser Leu Ser Val Ser
                20                  25                  30

Ile Pro Gln Pro Ser Pro Leu Arg Val Leu Leu Gly Thr Ser Leu Thr
            35                  40                  45

Ile Pro Cys Tyr Phe Ile Asp Pro Met His Pro Val Thr Thr Ala Pro
        50                  55                  60

Ser Thr Ala Pro Leu Ala Pro Arg Ile Lys Trp Ser Arg Val Ser Lys
65                  70                  75                  80

Glu Lys Glu Val Val Leu Leu Val Ala Thr Glu Gly Arg Val Arg Val
                85                  90                  95

Asn Ser Ala Tyr Gln Asp Lys Val Ser Leu Pro Asn Tyr Pro Ala Ile
                100                 105                 110

Pro Ser Asp Ala Thr Leu Glu Val Gln Ser Leu Arg Ser Asn Asp Ser
            115                 120                 125

Gly Val Tyr Arg Cys Glu Val Met His Gly Ile Glu Asp Ser Glu Ala
        130                 135                 140

```
Thr Leu Glu Val Val Lys Gly Ile Val Phe His Tyr Arg Ala Ile
145                 150                 155                 160

Ser Thr Arg Tyr Thr Leu Asp Phe Asp Arg Ala Gln Arg Ala Cys Leu
                165                 170                 175

Gln Asn Ser Ala Ile Ile Ala Thr Pro Glu Gln Leu Gln Ala Ala Tyr
            180                 185                 190

Glu Asp Gly Phe His Gln Cys Asp Ala Gly Trp Leu Ala Asp Gln Thr
            195                 200                 205

Val Arg Tyr Pro Ile His Thr Pro Arg Glu Gly Cys Tyr Gly Asp Lys
            210                 215                 220

Asp Glu Phe Pro Gly Val Arg Thr Tyr Gly Ile Arg Asp Thr Asn Glu
225                 230                 235                 240

Thr Tyr Asp Val Tyr Cys Phe Ala Glu Glu Met Glu Gly Glu Val Phe
                245                 250                 255

Tyr Ala Thr Ser Pro Glu Lys Phe Thr Phe Gln Glu Ala Ala Asn Glu
            260                 265                 270

Cys Arg Arg Leu Gly Ala Arg Leu Ala Thr Thr Gly His Val Tyr Leu
            275                 280                 285

Ala Trp Gln Ala Gly Met Asp Met Cys Ser Ala Gly Trp Leu Ala Asp
290                 295                 300

Arg Ser Val Arg Tyr Pro Ile Ser Lys Ala Arg Pro Asn Cys Gly Gly
305                 310                 315                 320

Asn Leu Leu Gly Val Arg Thr Val Tyr Val His Ala Asn Gln Thr Gly
                325                 330                 335

Tyr Pro Asp Pro Ser Ser Arg Tyr Asp Ala Ile Cys Tyr Thr Gly Glu
            340                 345                 350

Asp Phe Val Asp Ile Pro Glu Asn Phe Phe Gly Val Gly Gly Glu Glu
            355                 360                 365

Asp Ile Thr Val Gln Thr Val Thr Trp Pro Asp Met Glu Leu Pro Leu
            370                 375                 380

Pro Arg Asn Ile Thr Glu Gly Glu Ala Arg Gly Ser Val Ile Leu Thr
385                 390                 395                 400

Val Lys Pro Ile Phe Glu Val Ser Pro Ser Pro Leu Glu Pro Glu Glu
                405                 410                 415

Pro Phe Thr Phe Ala Pro Glu Ile Gly Ala Thr Ala Phe Ala Glu Val
            420                 425                 430

Glu Asn Glu Thr Gly Glu Ala Thr Arg Pro Trp Gly Phe Pro Thr Pro
            435                 440                 445

Gly Leu Gly Pro Ala Thr Ala Phe Thr Ser Glu Asp Leu Val Val Gln
            450                 455                 460

Val Thr Ala Val Pro Gly Gln Pro His Leu Pro Gly Gly Val Val Phe
465                 470                 475                 480

His Tyr Arg Pro Gly Pro Thr Arg Tyr Ser Leu Thr Phe Glu Glu Ala
                485                 490                 495

Gln Gln Ala Cys Pro Gly Thr Gly Ala Val Ile Ala Ser Pro Glu Gln
            500                 505                 510

Leu Gln Ala Ala Tyr Glu Ala Gly Tyr Glu Gln Cys Asp Ala Gly Trp
            515                 520                 525

Leu Arg Asp Gln Thr Val Arg Tyr Pro Ile Val Ser Pro Arg Thr Pro
            530                 535                 540

Cys Val Gly Asp Lys Asp Ser Ser Pro Gly Val Arg Thr Tyr Gly Val
545                 550                 555                 560

Arg Pro Ser Thr Glu Thr Tyr Asp Val Tyr Cys Phe Val Asp Arg Leu
```

```
                    565                 570                 575
Glu Gly Glu Val Phe Ala Thr Arg Leu Glu Gln Phe Thr Phe Gln
                580                 585                 590
Glu Ala Leu Glu Phe Cys Glu Ser His Asn Ala Thr Ala Thr Gly
                595                 600                 605
Gln Leu Tyr Ala Ala Trp Ser Arg Gly Leu Asp Lys Cys Tyr Ala Gly
    610                 615                 620
Trp Leu Ala Asp Gly Ser Leu Arg Tyr Pro Ile Val Thr Pro Arg Pro
625                 630                 635                 640
Ala Cys Gly Gly Asp Lys Pro Gly Val Arg Thr Val Tyr Leu Tyr Pro
                645                 650                 655
Asn Gln Thr Gly Leu Pro Asp Pro Leu Ser Arg His His Ala Phe Cys
                660                 665                 670
Phe Arg Gly Ile Ser Ala Val Pro Ser Pro Gly Glu Glu Gly Gly
                675                 680                 685
Thr Pro Thr Ser Pro Ser Gly Val Glu Glu Trp Ile Val Thr Gln Val
                690                 695                 700
Val Pro Gly Val Ala Ala Val Pro Val Glu Glu Thr Thr Ala Val
705                 710                 715                 720
Pro Ser Gly Glu Thr Thr Ala Ile Leu Glu Phe Thr Glu Pro Glu
                725                 730                 735
Asn Gln Thr Glu Trp Glu Pro Ala Tyr Thr Pro Val Gly Thr Ser Pro
                740                 745                 750
Leu Pro Gly Ile Leu Pro Thr Trp Pro Pro Thr Gly Ala Glu Thr Glu
                755                 760                 765
Glu Ser Thr Glu Gly Pro Ser Ala Thr Glu Val Pro Ser Ala Ser Glu
                770                 775                 780
Glu Pro Ser Pro Ser Glu Val Pro Phe Pro Glu Glu Pro Ser Pro
785                 790                 795                 800
Ser Glu Glu Pro Phe Pro Ser Val Arg Pro Phe Pro Ser Val Glu Leu
                805                 810                 815
Phe Pro Ser Glu Glu Pro Phe Pro Ser Lys Glu Pro Ser Pro Ser Glu
                820                 825                 830
Glu Pro Ser Ala Ser Glu Glu Pro Tyr Thr Pro Ser Pro Pro Glu Pro
                835                 840                 845
Ser Trp Thr Glu Leu Pro Ser Ser Gly Glu Ser Gly Ala Pro Asp
                850                 855                 860
Val Ser Gly Asp Phe Thr Gly Ser Gly Asp Val Ser Gly His Leu Asp
865                 870                 875                 880
Phe Ser Gly Gln Leu Ser Gly Asp Arg Ala Ser Gly Leu Pro Ser Gly
                885                 890                 895
Asp Leu Asp Ser Ser Gly Leu Thr Ser Thr Val Gly Ser Gly Leu Thr
                900                 905                 910
Val Glu Ser Gly Leu Pro Ser Gly Asp Glu Arg Ile Glu Trp Pro
                915                 920                 925
Ser Thr Pro Thr Val Gly Glu Leu Pro Ser Gly Ala Glu Ile Leu Glu
                930                 935                 940
Gly Ser Ala Ser Gly Val Gly Asp Leu Ser Gly Leu Pro Ser Gly Glu
945                 950                 955                 960
Val Leu Glu Thr Ser Ala Ser Gly Val Gly Asp Leu Ser Gly Leu Pro
                965                 970                 975
Ser Gly Glu Val Leu Glu Thr Thr Ala Pro Gly Val Glu Asp Ile Ser
                980                 985                 990
```

```
Gly Leu Pro Ser Gly Glu Val Leu Glu Thr Thr Ala Pro Gly Val Glu
        995                 1000                1005

Asp Ile Ser Gly Leu Pro Ser Gly Glu Val Leu Glu Thr Thr Ala
    1010                1015                1020

Pro Gly Val Glu Asp Ile Ser Gly Leu Pro Ser Gly Glu Val Leu
    1025                1030                1035

Glu Thr Thr Ala Pro Gly Val Glu Asp Ile Ser Gly Leu Pro Ser
    1040                1045                1050

Gly Glu Val Leu Glu Thr Thr Ala Pro Gly Val Glu Asp Ile Ser
    1055                1060                1065

Gly Leu Pro Ser Gly Glu Val Leu Glu Thr Ala Ala Pro Gly Val
    1070                1075                1080

Glu Asp Ile Ser Gly Leu Pro Ser Gly Glu Val Leu Glu Thr Ala
    1085                1090                1095

Ala Pro Gly Val Glu Asp Ile Ser Gly Leu Pro Ser Gly Glu Val
    1100                1105                1110

Leu Glu Thr Ala Ala Pro Gly Val Glu Asp Ile Ser Gly Leu Pro
    1115                1120                1125

Ser Gly Glu Val Leu Glu Thr Ala Ala Pro Gly Val Glu Asp Ile
    1130                1135                1140

Ser Gly Leu Pro Ser Gly Glu Val Leu Glu Thr Ala Ala Pro Gly
    1145                1150                1155

Val Glu Asp Ile Ser Gly Leu Pro Ser Gly Glu Val Leu Glu Thr
    1160                1165                1170

Ala Ala Pro Gly Val Glu Asp Ile Ser Gly Leu Pro Ser Gly Glu
    1175                1180                1185

Val Leu Glu Thr Ala Ala Pro Gly Val Glu Asp Ile Ser Gly Leu
    1190                1195                1200

Pro Ser Gly Glu Val Leu Glu Thr Ala Ala Pro Gly Val Glu Asp
    1205                1210                1215

Ile Ser Gly Leu Pro Ser Gly Glu Val Leu Glu Thr Ala Ala Pro
    1220                1225                1230

Gly Val Glu Asp Ile Ser Gly Leu Pro Ser Gly Glu Val Leu Glu
    1235                1240                1245

Thr Ala Ala Pro Gly Val Glu Asp Ile Ser Gly Leu Pro Ser Gly
    1250                1255                1260

Glu Val Leu Glu Thr Ala Ala Pro Gly Val Glu Asp Ile Ser Gly
    1265                1270                1275

Leu Pro Ser Gly Glu Val Leu Glu Thr Thr Ala Pro Gly Val Glu
    1280                1285                1290

Glu Ile Ser Gly Leu Pro Ser Gly Glu Val Leu Glu Thr Thr Ala
    1295                1300                1305

Pro Gly Val Asp Glu Ile Ser Gly Leu Pro Ser Gly Glu Val Leu
    1310                1315                1320

Glu Thr Thr Ala Pro Gly Val Glu Glu Ile Ser Gly Leu Pro Ser
    1325                1330                1335

Gly Glu Val Leu Glu Thr Ser Thr Ser Ala Val Gly Asp Leu Ser
    1340                1345                1350

Gly Leu Pro Ser Gly Gly Glu Val Leu Glu Ile Ser Val Ser Gly
    1355                1360                1365

Val Glu Asp Ile Ser Gly Leu Pro Ser Gly Glu Val Val Glu Thr
    1370                1375                1380
```

Ser Ala Ser Gly Ile Glu Asp Val Ser Glu Leu Pro Ser Gly Glu
1385                1390                1395

Gly Leu Glu Thr Ser Ala Ser Gly Val Glu Asp Leu Ser Arg Leu
1400                1405                1410

Pro Ser Gly Glu Glu Val Leu Glu Ile Ser Ala Ser Gly Phe Gly
1415                1420                1425

Asp Leu Ser Gly Val Pro Ser Gly Glu Gly Leu Glu Thr Ser
1430                1435                1440

Ala Ser Glu Val Gly Thr Asp Leu Ser Gly Leu Pro Ser Gly Arg
1445                1450                1455

Glu Gly Leu Glu Thr Ser Ala Ser Gly Ala Glu Asp Leu Ser Gly
1460                1465                1470

Leu Pro Ser Gly Lys Glu Asp Leu Val Gly Ser Ala Ser Gly Asp
1475                1480                1485

Leu Asp Leu Gly Lys Leu Pro Ser Gly Thr Leu Gly Ser Gly Gln
1490                1495                1500

Ala Pro Glu Thr Ser Gly Leu Pro Ser Gly Phe Ser Gly Glu Tyr
1505                1510                1515

Ser Gly Val Asp Leu Gly Ser Gly Pro Pro Ser Gly Leu Pro Asp
1520                1525                1530

Phe Ser Gly Leu Pro Ser Gly Phe Pro Thr Val Ser Leu Val Asp
1535                1540                1545

Ser Thr Leu Val Glu Val Val Thr Ala Ser Thr Ala Ser Glu Leu
1550                1555                1560

Glu Gly Arg Gly Thr Ile Gly Ile Ser Gly Ala Gly Glu Ile Ser
1565                1570                1575

Gly Leu Pro Ser Ser Glu Leu Asp Ile Ser Gly Arg Ala Ser Gly
1580                1585                1590

Leu Pro Ser Gly Thr Glu Leu Ser Gly Gln Ala Ser Gly Ser Pro
1595                1600                1605

Asp Val Ser Gly Glu Ile Pro Gly Leu Phe Gly Val Ser Gly Gln
1610                1615                1620

Pro Ser Gly Phe Pro Asp Thr Ser Gly Glu Thr Ser Gly Val Thr
1625                1630                1635

Glu Leu Ser Gly Leu Ser Ser Gly Gln Pro Gly Val Ser Gly Glu
1640                1645                1650

Ala Ser Gly Val Leu Tyr Gly Thr Ser Gln Pro Phe Gly Ile Thr
1655                1660                1665

Asp Leu Ser Gly Glu Thr Ser Gly Val Pro Asp Leu Ser Gly Gln
1670                1675                1680

Pro Ser Gly Leu Pro Gly Phe Ser Gly Ala Thr Ser Gly Val Pro
1685                1690                1695

Asp Leu Val Ser Gly Thr Thr Ser Gly Ser Gly Glu Ser Ser Gly
1700                1705                1710

Ile Thr Phe Val Asp Thr Ser Leu Val Glu Val Ala Pro Thr Thr
1715                1720                1725

Phe Lys Glu Glu Glu Gly Leu Gly Ser Val Glu Leu Ser Gly Leu
1730                1735                1740

Pro Ser Gly Glu Ala Asp Leu Ser Gly Lys Ser Gly Met Val Asp
1745                1750                1755

Val Ser Gly Gln Phe Ser Gly Thr Val Asp Ser Ser Gly Phe Thr
1760                1765                1770

Ser Gln Thr Pro Glu Phe Ser Gly Leu Pro Ser Gly Ile Ala Glu

-continued

```
                1775                1780                1785

Val Ser Gly Glu Ser Ser Arg Ala Glu Ile Gly Ser Ser Leu Pro
    1790                1795                1800

Ser Gly Ala Tyr Tyr Gly Ser Gly Thr Pro Ser Ser Phe Pro Thr
    1805                1810                1815

Val Ser Leu Val Asp Arg Thr Leu Val Glu Ser Val Thr Gln Ala
    1820                1825                1830

Pro Thr Ala Gln Glu Ala Gly Glu Gly Pro Ser Gly Ile Leu Glu
    1835                1840                1845

Leu Ser Gly Ala His Ser Gly Ala Pro Asp Met Ser Gly Glu His
    1850                1855                1860

Ser Gly Phe Leu Asp Leu Ser Gly Leu Gln Ser Gly Leu Ile Glu
    1865                1870                1875

Pro Ser Gly Glu Pro Pro Gly Thr Pro Tyr Phe Ser Gly Asp Phe
    1880                1885                1890

Ala Ser Thr Thr Asn Val Ser Gly Glu Ser Ser Val Ala Met Gly
    1895                1900                1905

Thr Ser Gly Glu Ala Ser Gly Leu Pro Glu Val Thr Leu Ile Thr
    1910                1915                1920

Ser Glu Phe Val Glu Gly Val Thr Glu Pro Thr Ile Ser Gln Glu
    1925                1930                1935

Leu Gly Gln Arg Pro Pro Val Thr His Thr Pro Gln Leu Phe Glu
    1940                1945                1950

Ser Ser Gly Lys Val Ser Thr Ala Gly Asp Ile Ser Gly Ala Thr
    1955                1960                1965

Pro Val Leu Pro Gly Ser Gly Val Glu Val Ser Ser Val Pro Glu
    1970                1975                1980

Ser Ser Ser Glu Thr Ser Ala Tyr Pro Glu Ala Gly Phe Gly Ala
    1985                1990                1995

Ser Ala Ala Pro Glu Ala Ser Arg Glu Asp Ser Gly Ser Pro Asp
    2000                2005                2010

Leu Ser Glu Thr Thr Ser Ala Phe His Glu Ala Asn Leu Glu Arg
    2015                2020                2025

Ser Ser Gly Leu Gly Val Ser Gly Ser Thr Leu Thr Phe Gln Glu
    2030                2035                2040

Gly Glu Ala Ser Ala Ala Pro Glu Val Ser Gly Glu Ser Thr Thr
    2045                2050                2055

Thr Ser Asp Val Gly Thr Glu Ala Pro Gly Leu Pro Ser Ala Thr
    2060                2065                2070

Pro Thr Ala Ser Gly Asp Arg Thr Glu Ile Ser Gly Asp Leu Ser
    2075                2080                2085

Gly His Thr Ser Gln Leu Gly Val Val Ile Ser Thr Ser Ile Pro
    2090                2095                2100

Glu Ser Glu Trp Thr Gln Gln Thr Gln Arg Pro Ala Glu Thr His
    2105                2110                2115

Leu Glu Ile Glu Ser Ser Ser Leu Leu Tyr Ser Gly Glu Glu Thr
    2120                2125                2130

His Thr Val Glu Thr Ala Thr Ser Pro Thr Asp Ala Ser Ile Pro
    2135                2140                2145

Ala Ser Pro Glu Trp Lys Arg Glu Ser Glu Ser Thr Ala Ala Ala
    2150                2155                2160

Pro Ala Arg Ser Cys Ala Glu Glu Pro Cys Gly Ala Gly Thr Cys
    2165                2170                2175
```

| Lys | Glu | Thr | Glu | Gly | His | Val | Ile | Cys | Leu | Cys | Pro | Pro | Gly | Tyr |
|---|---|---|---|---|---|---|---|---|---|---|---|---|---|---|
| | 2180 | | | | 2185 | | | | 2190 | | | | | |

```
Lys Glu Thr Glu Gly His Val Ile Cys Leu Cys Pro Pro Gly Tyr
    2180                2185                2190

Thr Gly Glu His Cys Asn Ile Asp Gln Glu Val Cys Glu Glu Gly
    2195                2200                2205

Trp Asn Lys Tyr Gln Gly His Cys Tyr Arg His Phe Pro Asp Arg
    2210                2215                2220

Glu Thr Trp Val Asp Ala Glu Arg Arg Cys Arg Glu Gln Gln Ser
    2225                2230                2235

His Leu Ser Ser Ile Val Thr Pro Glu Gln Glu Phe Val Asn
    2240                2245                2250

Asn Asn Ala Gln Asp Tyr Gln Trp Ile Gly Leu Asn Asp Arg Thr
    2255                2260                2265

Ile Glu Gly Asp Phe Arg Trp Ser Asp Gly His Pro Met Gln Phe
    2270                2275                2280

Glu Asn Trp Arg Pro Asn Gln Pro Asp Asn Phe Phe Ala Ala Gly
    2285                2290                2295

Glu Asp Cys Val Val Met Ile Trp His Glu Lys Gly Glu Trp Asn
    2300                2305                2310

Asp Val Pro Cys Asn Tyr His Leu Pro Phe Thr Cys Lys Lys Gly
    2315                2320                2325

Thr Val Ala Cys Gly Glu Pro Pro Val Val Glu His Ala Arg Thr
    2330                2335                2340

Phe Gly Gln Lys Lys Asp Arg Tyr Glu Ile Asn Ser Leu Val Arg
    2345                2350                2355

Tyr Gln Cys Thr Glu Gly Phe Val Gln Arg His Met Pro Thr Ile
    2360                2365                2370

Arg Cys Gln Pro Ser Gly His Trp Glu Glu Pro Arg Ile Thr Cys
    2375                2380                2385

Thr Asp Ala Thr Thr Tyr Lys Arg Arg Leu Gln Lys Arg Ser Ser
    2390                2395                2400

Arg His Pro Arg Arg Ser Arg Pro Ser Thr Ala His
    2405                2410                2415

<210> SEQ ID NO 71
<211> LENGTH: 2399
<212> TYPE: PRT
<213> ORGANISM: Homo sapiens

<400> SEQUENCE: 71

Ala Val Thr Val Glu Thr Ser Asp His Asp Asn Ser Leu Ser Val Ser
1               5                   10                  15

Ile Pro Gln Pro Ser Pro Leu Arg Val Leu Leu Gly Thr Ser Leu Thr
                20                  25                  30

Ile Pro Cys Tyr Phe Ile Asp Pro Met His Pro Val Thr Thr Ala Pro
            35                  40                  45

Ser Thr Ala Pro Leu Ala Pro Arg Ile Lys Trp Ser Arg Val Ser Lys
        50                  55                  60

Glu Lys Glu Val Val Leu Leu Val Ala Thr Glu Gly Arg Val Arg Val
65                  70                  75                  80

Asn Ser Ala Tyr Gln Asp Lys Val Ser Leu Pro Asn Tyr Pro Ala Ile
                85                  90                  95

Pro Ser Asp Ala Thr Leu Glu Val Gln Ser Leu Arg Ser Asn Asp Ser
                100                 105                 110

Gly Val Tyr Arg Cys Glu Val Met His Gly Ile Glu Asp Ser Glu Ala
```

```
            115                 120                 125
Thr Leu Glu Val Val Lys Gly Ile Val Phe His Tyr Arg Ala Ile
    130                 135                 140

Ser Thr Arg Tyr Thr Leu Asp Phe Asp Arg Ala Gln Arg Ala Cys Leu
145                 150                 155                 160

Gln Asn Ser Ala Ile Ile Ala Thr Pro Glu Gln Leu Gln Ala Ala Tyr
                165                 170                 175

Glu Asp Gly Phe His Gln Cys Asp Ala Gly Trp Leu Ala Asp Gln Thr
            180                 185                 190

Val Arg Tyr Pro Ile His Thr Pro Arg Glu Gly Cys Tyr Gly Asp Lys
        195                 200                 205

Asp Glu Phe Pro Gly Val Arg Thr Tyr Gly Ile Arg Asp Thr Asn Glu
    210                 215                 220

Thr Tyr Asp Val Tyr Cys Phe Ala Glu Glu Met Glu Gly Glu Val Phe
225                 230                 235                 240

Tyr Ala Thr Ser Pro Glu Lys Phe Thr Phe Gln Glu Ala Ala Asn Glu
                245                 250                 255

Cys Arg Arg Leu Gly Ala Arg Leu Ala Thr Thr Gly His Val Tyr Leu
            260                 265                 270

Ala Trp Gln Ala Gly Met Asp Met Cys Ser Ala Gly Trp Leu Ala Asp
        275                 280                 285

Arg Ser Val Arg Tyr Pro Ile Ser Lys Ala Arg Pro Asn Cys Gly Gly
    290                 295                 300

Asn Leu Leu Gly Val Arg Thr Val Tyr Val His Ala Asn Gln Thr Gly
305                 310                 315                 320

Tyr Pro Asp Pro Ser Ser Arg Tyr Asp Ala Ile Cys Tyr Thr Gly Glu
                325                 330                 335

Asp Phe Val Asp Ile Pro Glu Asn Phe Phe Gly Val Gly Gly Glu Glu
            340                 345                 350

Asp Ile Thr Val Gln Thr Val Thr Trp Pro Asp Met Glu Leu Pro Leu
        355                 360                 365

Pro Arg Asn Ile Thr Glu Gly Glu Ala Arg Gly Ser Val Ile Leu Thr
    370                 375                 380

Val Lys Pro Ile Phe Glu Val Ser Pro Ser Pro Leu Glu Pro Glu Glu
385                 390                 395                 400

Pro Phe Thr Phe Ala Pro Glu Ile Gly Ala Thr Ala Phe Ala Glu Val
                405                 410                 415

Glu Asn Glu Thr Gly Glu Ala Thr Arg Pro Trp Gly Phe Pro Thr Pro
            420                 425                 430

Gly Leu Gly Pro Ala Thr Ala Phe Thr Ser Glu Asp Leu Val Val Gln
        435                 440                 445

Val Thr Ala Val Pro Gly Gln Pro His Leu Pro Gly Gly Val Val Phe
    450                 455                 460

His Tyr Arg Pro Gly Pro Thr Arg Tyr Ser Leu Thr Phe Glu Glu Ala
465                 470                 475                 480

Gln Gln Ala Cys Pro Gly Thr Gly Ala Val Ile Ala Ser Pro Glu Gln
                485                 490                 495

Leu Gln Ala Ala Tyr Glu Ala Gly Tyr Glu Gln Cys Asp Ala Gly Trp
            500                 505                 510

Leu Arg Asp Gln Thr Val Arg Tyr Pro Ile Val Ser Pro Arg Thr Pro
        515                 520                 525

Cys Val Gly Asp Lys Asp Ser Ser Pro Gly Val Arg Thr Tyr Gly Val
    530                 535                 540
```

```
Arg Pro Ser Thr Glu Thr Tyr Asp Val Tyr Cys Phe Val Asp Arg Leu
545                 550                 555                 560

Glu Gly Glu Val Phe Phe Ala Thr Arg Leu Glu Gln Phe Thr Phe Gln
                565                 570                 575

Glu Ala Leu Glu Phe Cys Glu Ser His Asn Ala Thr Ala Thr Thr Gly
                580                 585                 590

Gln Leu Tyr Ala Ala Trp Ser Arg Gly Leu Asp Lys Cys Tyr Ala Gly
            595                 600                 605

Trp Leu Ala Asp Gly Ser Leu Arg Tyr Pro Ile Val Thr Pro Arg Pro
            610                 615                 620

Ala Cys Gly Gly Asp Lys Pro Gly Val Arg Thr Val Tyr Leu Tyr Pro
625                 630                 635                 640

Asn Gln Thr Gly Leu Pro Asp Pro Leu Ser Arg His His Ala Phe Cys
                645                 650                 655

Phe Arg Gly Ile Ser Ala Val Pro Ser Pro Gly Glu Glu Gly Gly
                660                 665                 670

Thr Pro Thr Ser Pro Ser Gly Val Glu Glu Trp Ile Val Thr Gln Val
            675                 680                 685

Val Pro Gly Val Ala Ala Val Pro Val Glu Glu Thr Thr Ala Val
690                 695                 700

Pro Ser Gly Glu Thr Thr Ala Ile Leu Glu Phe Thr Thr Glu Pro Glu
705                 710                 715                 720

Asn Gln Thr Glu Trp Glu Pro Ala Tyr Thr Pro Val Gly Thr Ser Pro
                725                 730                 735

Leu Pro Gly Ile Leu Pro Thr Trp Pro Pro Thr Gly Ala Glu Thr Glu
                740                 745                 750

Glu Ser Thr Glu Gly Pro Ser Ala Thr Glu Val Pro Ser Ala Ser Glu
            755                 760                 765

Glu Pro Ser Pro Ser Glu Val Pro Phe Pro Ser Glu Glu Pro Ser Pro
            770                 775                 780

Ser Glu Glu Pro Phe Pro Ser Val Arg Pro Phe Pro Ser Val Glu Leu
785                 790                 795                 800

Phe Pro Ser Glu Glu Pro Phe Pro Ser Lys Glu Pro Ser Pro Ser Glu
                805                 810                 815

Glu Pro Ser Ala Ser Glu Glu Pro Tyr Thr Pro Ser Pro Pro Glu Pro
                820                 825                 830

Ser Trp Thr Glu Leu Pro Ser Ser Gly Glu Glu Ser Gly Ala Pro Asp
            835                 840                 845

Val Ser Gly Asp Phe Thr Gly Ser Gly Asp Val Ser Gly His Leu Asp
            850                 855                 860

Phe Ser Gly Gln Leu Ser Gly Asp Arg Ala Ser Gly Leu Pro Ser Gly
865                 870                 875                 880

Asp Leu Asp Ser Ser Gly Leu Thr Ser Thr Val Gly Ser Gly Leu Thr
                885                 890                 895

Val Glu Ser Gly Leu Pro Ser Gly Asp Glu Glu Arg Ile Glu Trp Pro
            900                 905                 910

Ser Thr Pro Thr Val Gly Glu Leu Pro Ser Gly Ala Glu Ile Leu Glu
            915                 920                 925

Gly Ser Ala Ser Gly Val Gly Asp Leu Ser Gly Leu Pro Ser Gly Glu
            930                 935                 940

Val Leu Glu Thr Ser Ala Ser Gly Val Gly Asp Leu Ser Gly Leu Pro
945                 950                 955                 960
```

```
Ser Gly Glu Val Leu Glu Thr Thr Ala Pro Gly Val Glu Asp Ile Ser
            965                 970                 975

Gly Leu Pro Ser Gly Glu Val Leu Glu Thr Thr Ala Pro Gly Val Glu
            980                 985                 990

Asp Ile Ser Gly Leu Pro Ser Gly  Glu Val Leu Glu Thr  Thr Ala Pro
            995                 1000                 1005

Gly Val  Glu Asp Ile Ser Gly  Leu Pro Ser Gly Glu  Val Leu Glu
           1010                 1015                 1020

Thr Thr  Ala Pro Gly Val Glu  Asp Ile Ser Gly Leu  Pro Ser Gly
           1025                 1030                 1035

Glu Val  Leu Glu Thr Thr Ala  Pro Gly Val Glu Asp  Ile Ser Gly
           1040                 1045                 1050

Leu Pro  Ser Gly Glu Val Leu  Glu Thr Ala Ala Pro  Gly Val Glu
           1055                 1060                 1065

Asp Ile  Ser Gly Leu Pro Ser  Gly Val Leu Glu  Thr Ala Ala
           1070                 1075                 1080

Pro Gly  Val Glu Asp Ile Ser  Gly Leu Pro Ser Gly  Glu Val Leu
           1085                 1090                 1095

Glu Thr  Ala Ala Pro Gly Val  Glu Asp Ile Ser Gly  Leu Pro Ser
           1100                 1105                 1110

Gly Glu  Val Leu Glu Thr Ala  Ala Pro Gly Val Glu  Asp Ile Ser
           1115                 1120                 1125

Gly Leu  Pro Ser Gly Glu Val  Leu Glu Thr Ala Ala  Pro Gly Val
           1130                 1135                 1140

Glu Asp  Ile Ser Gly Leu Pro  Ser Gly Glu Val Leu  Glu Thr Ala
           1145                 1150                 1155

Ala Pro  Gly Val Glu Asp Ile  Ser Gly Leu Pro Ser  Gly Glu Val
           1160                 1165                 1170

Leu Glu  Thr Ala Ala Pro Gly  Val Glu Asp Ile Ser  Gly Leu Pro
           1175                 1180                 1185

Ser Gly  Glu Val Leu Glu Thr  Ala Ala Pro Gly Val  Glu Asp Ile
           1190                 1195                 1200

Ser Gly  Leu Pro Ser Gly Glu  Val Leu Glu Thr Ala  Ala Pro Gly
           1205                 1210                 1215

Val Glu  Asp Ile Ser Gly Leu  Pro Ser Gly Glu Val  Leu Glu Thr
           1220                 1225                 1230

Ala Ala  Pro Gly Val Glu Asp  Ile Ser Gly Leu Pro  Ser Gly Glu
           1235                 1240                 1245

Val Leu  Glu Thr Ala Ala Pro  Gly Val Glu Asp Ile  Ser Gly Leu
           1250                 1255                 1260

Pro Ser  Gly Glu Val Leu Glu  Thr Thr Ala Pro Gly  Val Glu Glu
           1265                 1270                 1275

Ile Ser  Gly Leu Pro Ser Gly  Glu Val Leu Glu Thr  Thr Ala Pro
           1280                 1285                 1290

Gly Val  Asp Glu Ile Ser Gly  Leu Pro Ser Gly Glu  Val Leu Glu
           1295                 1300                 1305

Thr Thr  Ala Pro Gly Val Glu  Glu Ile Ser Gly Leu  Pro Ser Gly
           1310                 1315                 1320

Glu Val  Leu Glu Thr Ser Thr  Ser Ala Val Gly Asp  Leu Ser Gly
           1325                 1330                 1335

Leu Pro  Ser Gly Gly Glu Val  Leu Glu Ile Ser Val  Ser Gly Val
           1340                 1345                 1350

Glu Asp  Ile Ser Gly Leu Pro  Ser Gly Glu Val Val  Glu Thr Ser
```

-continued

```
              1355                1360                1365

Ala Ser  Gly Ile Glu Asp Val  Ser Glu Leu Pro  Ser Gly Glu Gly
    1370                1375                1380

Leu Glu  Thr Ser Ala Ser Gly  Val Glu Asp Leu  Ser Arg Leu Pro
    1385                1390                1395

Ser Gly  Glu Glu Val Leu Glu  Ile Ser Ala Ser  Gly Phe Gly Asp
    1400                1405                1410

Leu Ser  Gly Val Pro Ser Gly  Gly Glu Gly Leu  Glu Thr Ser Ala
    1415                1420                1425

Ser Glu  Val Gly Thr Asp Leu  Ser Gly Leu Pro  Ser Gly Arg Glu
    1430                1435                1440

Gly Leu  Glu Thr Ser Ala Ser  Gly Ala Glu Asp  Leu Ser Gly Leu
    1445                1450                1455

Pro Ser  Gly Lys Glu Asp Leu  Val Gly Ser Ala  Ser Gly Asp Leu
    1460                1465                1470

Asp Leu  Gly Lys Leu Pro Ser  Gly Thr Leu Gly  Ser Gly Gln Ala
    1475                1480                1485

Pro Glu  Thr Ser Gly Leu Pro  Ser Gly Phe Ser  Gly Glu Tyr Ser
    1490                1495                1500

Gly Val  Asp Leu Gly Ser Gly  Pro Pro Ser Gly  Leu Pro Asp Phe
    1505                1510                1515

Ser Gly  Leu Pro Ser Gly Phe  Pro Thr Val Ser  Leu Val Asp Ser
    1520                1525                1530

Thr Leu  Val Glu Val Val Thr  Ala Ser Thr Ala  Ser Glu Leu Glu
    1535                1540                1545

Gly Arg  Gly Thr Ile Gly Ile  Ser Gly Ala Gly  Glu Ile Ser Gly
    1550                1555                1560

Leu Pro  Ser Ser Glu Leu Asp  Ile Ser Gly Arg  Ala Ser Gly Leu
    1565                1570                1575

Pro Ser  Gly Thr Glu Leu Ser  Gly Gln Ala Ser  Gly Ser Pro Asp
    1580                1585                1590

Val Ser  Gly Glu Ile Pro Gly  Leu Phe Gly Val  Ser Gly Gln Pro
    1595                1600                1605

Ser Gly  Phe Pro Asp Thr Ser  Gly Glu Thr Ser  Gly Val Thr Glu
    1610                1615                1620

Leu Ser  Gly Leu Ser Ser Gly  Gln Pro Gly Val  Ser Gly Glu Ala
    1625                1630                1635

Ser Gly  Val Leu Tyr Gly Thr  Ser Gln Pro Phe  Gly Ile Thr Asp
    1640                1645                1650

Leu Ser  Gly Glu Thr Ser Gly  Val Pro Asp Leu  Ser Gly Gln Pro
    1655                1660                1665

Ser Gly  Leu Pro Gly Phe Ser  Gly Ala Thr Ser  Gly Val Pro Asp
    1670                1675                1680

Leu Val  Ser Gly Thr Thr Ser  Gly Ser Gly Glu  Ser Ser Gly Ile
    1685                1690                1695

Thr Phe  Val Asp Thr Ser Leu  Val Glu Val Ala  Pro Thr Thr Phe
    1700                1705                1710

Lys Glu  Glu Glu Gly Leu Gly  Ser Val Glu Leu  Ser Gly Leu Pro
    1715                1720                1725

Ser Gly  Glu Ala Asp Leu Ser  Gly Lys Ser Gly  Met Val Asp Val
    1730                1735                1740

Ser Gly  Gln Phe Ser Gly Thr  Val Asp Ser Ser  Gly Phe Thr Ser
    1745                1750                1755
```

```
Gln Thr Pro Glu Phe Ser Gly Leu Pro Ser Gly Ile Ala Glu Val
1760                1765                1770

Ser Gly Glu Ser Ser Arg Ala Glu Ile Gly Ser Ser Leu Pro Ser
1775                1780                1785

Gly Ala Tyr Tyr Gly Ser Gly Thr Pro Ser Ser Phe Pro Thr Val
1790                1795                1800

Ser Leu Val Asp Arg Thr Leu Val Glu Ser Val Thr Gln Ala Pro
1805                1810                1815

Thr Ala Gln Glu Ala Gly Glu Gly Pro Ser Gly Ile Leu Glu Leu
1820                1825                1830

Ser Gly Ala His Ser Gly Ala Pro Asp Met Ser Gly Glu His Ser
1835                1840                1845

Gly Phe Leu Asp Leu Ser Gly Leu Gln Ser Gly Leu Ile Glu Pro
1850                1855                1860

Ser Gly Glu Pro Pro Gly Thr Pro Tyr Phe Ser Gly Asp Phe Ala
1865                1870                1875

Ser Thr Thr Asn Val Ser Gly Glu Ser Ser Val Ala Met Gly Thr
1880                1885                1890

Ser Gly Glu Ala Ser Gly Leu Pro Glu Val Thr Leu Ile Thr Ser
1895                1900                1905

Glu Phe Val Glu Gly Val Thr Glu Pro Thr Ile Ser Gln Glu Leu
1910                1915                1920

Gly Gln Arg Pro Pro Val Thr His Thr Pro Gln Leu Phe Glu Ser
1925                1930                1935

Ser Gly Lys Val Ser Thr Ala Gly Asp Ile Ser Gly Ala Thr Pro
1940                1945                1950

Val Leu Pro Gly Ser Gly Val Glu Val Ser Ser Val Pro Glu Ser
1955                1960                1965

Ser Ser Glu Thr Ser Ala Tyr Pro Glu Ala Gly Phe Gly Ala Ser
1970                1975                1980

Ala Ala Pro Glu Ala Ser Arg Glu Asp Ser Gly Ser Pro Asp Leu
1985                1990                1995

Ser Glu Thr Thr Ser Ala Phe His Glu Ala Asn Leu Glu Arg Ser
2000                2005                2010

Ser Gly Leu Gly Val Ser Gly Ser Thr Leu Thr Phe Gln Glu Gly
2015                2020                2025

Glu Ala Ser Ala Ala Pro Glu Val Ser Gly Glu Ser Thr Thr Thr
2030                2035                2040

Ser Asp Val Gly Thr Glu Ala Pro Gly Leu Pro Ser Ala Thr Pro
2045                2050                2055

Thr Ala Ser Gly Asp Arg Thr Glu Ile Ser Gly Asp Leu Ser Gly
2060                2065                2070

His Thr Ser Gln Leu Gly Val Val Ile Ser Thr Ser Ile Pro Glu
2075                2080                2085

Ser Glu Trp Thr Gln Gln Thr Gln Arg Pro Ala Glu Thr His Leu
2090                2095                2100

Glu Ile Glu Ser Ser Ser Leu Leu Tyr Ser Gly Glu Glu Thr His
2105                2110                2115

Thr Val Glu Thr Ala Thr Ser Pro Thr Asp Ala Ser Ile Pro Ala
2120                2125                2130

Ser Pro Glu Trp Lys Arg Glu Ser Glu Ser Thr Ala Ala Ala Pro
2135                2140                2145
```

Ala Arg Ser Cys Ala Glu Glu Pro Cys Gly Ala Gly Thr Cys Lys
2150                2155                2160

Glu Thr Glu Gly His Val Ile Cys Leu Cys Pro Gly Tyr Thr
2165                2170                2175

Gly Glu His Cys Asn Ile Asp Gln Glu Val Cys Glu Glu Gly Trp
2180                2185                2190

Asn Lys Tyr Gln Gly His Cys Tyr Arg His Phe Pro Asp Arg Glu
2195                2200                2205

Thr Trp Val Asp Ala Glu Arg Arg Cys Arg Glu Gln Gln Ser His
2210                2215                2220

Leu Ser Ser Ile Val Thr Pro Glu Glu Gln Glu Phe Val Asn Asn
2225                2230                2235

Asn Ala Gln Asp Tyr Gln Trp Ile Gly Leu Asn Asp Arg Thr Ile
2240                2245                2250

Glu Gly Asp Phe Arg Trp Ser Asp Gly His Pro Met Gln Phe Glu
2255                2260                2265

Asn Trp Arg Pro Asn Gln Pro Asp Asn Phe Phe Ala Ala Gly Glu
2270                2275                2280

Asp Cys Val Val Met Ile Trp His Glu Lys Gly Glu Trp Asn Asp
2285                2290                2295

Val Pro Cys Asn Tyr His Leu Pro Phe Thr Cys Lys Lys Gly Thr
2300                2305                2310

Val Ala Cys Gly Glu Pro Pro Val Val Glu His Ala Arg Thr Phe
2315                2320                2325

Gly Gln Lys Lys Asp Arg Tyr Glu Ile Asn Ser Leu Val Arg Tyr
2330                2335                2340

Gln Cys Thr Glu Gly Phe Val Gln Arg His Met Pro Thr Ile Arg
2345                2350                2355

Cys Gln Pro Ser Gly His Trp Glu Glu Pro Arg Ile Thr Cys Thr
2360                2365                2370

Asp Ala Thr Thr Tyr Lys Arg Arg Leu Gln Lys Arg Ser Ser Arg
2375                2380                2385

His Pro Arg Arg Ser Arg Pro Ser Thr Ala His
2390                2395

<210> SEQ ID NO 72
<211> LENGTH: 2023
<212> TYPE: PRT
<213> ORGANISM: Homo sapiens

<400> SEQUENCE: 72

Ala Arg Gly Ser Val Ile Leu Thr Val Lys Pro Ile Phe Glu Val Ser
1               5                   10                  15

Pro Ser Pro Leu Glu Pro Glu Pro Phe Thr Phe Ala Pro Glu Ile
            20                  25                  30

Gly Ala Thr Ala Phe Ala Glu Val Glu Asn Glu Thr Gly Glu Ala Thr
                35                  40                  45

Arg Pro Trp Gly Phe Pro Thr Pro Gly Leu Gly Pro Ala Thr Ala Phe
50                  55                  60

Thr Ser Glu Asp Leu Val Val Gln Val Thr Ala Val Pro Gly Gln Pro
65                  70                  75                  80

His Leu Pro Gly Gly Val Val Phe His Tyr Arg Pro Gly Pro Thr Arg
                85                  90                  95

Tyr Ser Leu Thr Phe Glu Glu Ala Gln Gln Ala Cys Pro Gly Thr Gly
            100                 105                 110

```
Ala Val Ile Ala Ser Pro Glu Gln Leu Gln Ala Ala Tyr Glu Ala Gly
            115                 120                 125

Tyr Glu Gln Cys Asp Ala Gly Trp Leu Arg Asp Gln Thr Val Arg Tyr
            130                 135                 140

Pro Ile Val Ser Pro Arg Thr Pro Cys Val Gly Asp Lys Asp Ser Ser
145                 150                 155                 160

Pro Gly Val Arg Thr Tyr Gly Val Arg Pro Ser Thr Glu Thr Tyr Asp
                165                 170                 175

Val Tyr Cys Phe Val Asp Arg Leu Glu Gly Glu Val Phe Phe Ala Thr
                180                 185                 190

Arg Leu Glu Gln Phe Thr Phe Gln Glu Ala Leu Glu Phe Cys Glu Ser
            195                 200                 205

His Asn Ala Thr Ala Thr Thr Gly Gln Leu Tyr Ala Ala Trp Ser Arg
            210                 215                 220

Gly Leu Asp Lys Cys Tyr Ala Gly Trp Leu Ala Asp Gly Ser Leu Arg
225                 230                 235                 240

Tyr Pro Ile Val Thr Pro Arg Pro Ala Cys Gly Gly Asp Lys Pro Gly
                245                 250                 255

Val Arg Thr Val Tyr Leu Tyr Pro Asn Gln Thr Gly Leu Pro Asp Pro
                260                 265                 270

Leu Ser Arg His His Ala Phe Cys Phe Arg Gly Ile Ser Ala Val Pro
            275                 280                 285

Ser Pro Gly Glu Glu Glu Gly Gly Thr Pro Thr Ser Pro Ser Gly Val
            290                 295                 300

Glu Glu Trp Ile Val Thr Gln Val Val Pro Gly Val Ala Ala Val Pro
305                 310                 315                 320

Val Glu Glu Glu Thr Thr Ala Val Pro Ser Gly Glu Thr Thr Ala Ile
                325                 330                 335

Leu Glu Phe Thr Thr Glu Pro Glu Asn Gln Thr Glu Trp Glu Pro Ala
            340                 345                 350

Tyr Thr Pro Val Gly Thr Ser Pro Leu Pro Gly Ile Leu Pro Thr Trp
            355                 360                 365

Pro Pro Thr Gly Ala Glu Thr Glu Glu Ser Thr Glu Gly Pro Ser Ala
            370                 375                 380

Thr Glu Val Pro Ser Ala Ser Glu Glu Pro Ser Pro Ser Glu Val Pro
385                 390                 395                 400

Phe Pro Ser Glu Glu Pro Ser Pro Ser Glu Glu Pro Phe Pro Ser Val
                405                 410                 415

Arg Pro Phe Pro Ser Val Glu Leu Phe Pro Ser Glu Glu Pro Phe Pro
                420                 425                 430

Ser Lys Glu Pro Ser Pro Ser Glu Glu Pro Ser Ala Ser Glu Glu Pro
            435                 440                 445

Tyr Thr Pro Ser Pro Pro Glu Pro Ser Trp Thr Glu Leu Pro Ser Ser
            450                 455                 460

Gly Glu Glu Ser Gly Ala Pro Asp Val Ser Gly Asp Phe Thr Gly Ser
465                 470                 475                 480

Gly Asp Val Ser Gly His Leu Asp Phe Ser Gly Gln Leu Ser Gly Asp
                485                 490                 495

Arg Ala Ser Gly Leu Pro Ser Gly Asp Leu Asp Ser Ser Gly Leu Thr
            500                 505                 510

Ser Thr Val Gly Ser Gly Leu Thr Val Glu Ser Gly Leu Pro Ser Gly
            515                 520                 525
```

```
Asp Glu Glu Arg Ile Glu Trp Pro Ser Thr Pro Thr Val Gly Glu Leu
530                 535                 540

Pro Ser Gly Ala Glu Ile Leu Glu Gly Ser Ala Ser Gly Val Gly Asp
545                 550                 555                 560

Leu Ser Gly Leu Pro Ser Gly Glu Val Leu Glu Thr Ser Ala Ser Gly
                565                 570                 575

Val Gly Asp Leu Ser Gly Leu Pro Ser Gly Glu Val Leu Glu Thr Thr
            580                 585                 590

Ala Pro Gly Val Glu Asp Ile Ser Gly Leu Pro Ser Gly Glu Val Leu
        595                 600                 605

Glu Thr Thr Ala Pro Gly Val Glu Asp Ile Ser Gly Leu Pro Ser Gly
    610                 615                 620

Glu Val Leu Glu Thr Thr Ala Pro Gly Val Glu Asp Ile Ser Gly Leu
625                 630                 635                 640

Pro Ser Gly Glu Val Leu Glu Thr Thr Ala Pro Gly Val Glu Asp Ile
                645                 650                 655

Ser Gly Leu Pro Ser Gly Glu Val Leu Glu Thr Thr Ala Pro Gly Val
            660                 665                 670

Glu Asp Ile Ser Gly Leu Pro Ser Gly Glu Val Leu Glu Thr Ala Ala
        675                 680                 685

Pro Gly Val Glu Asp Ile Ser Gly Leu Pro Ser Gly Glu Val Leu Glu
    690                 695                 700

Thr Ala Ala Pro Gly Val Glu Asp Ile Ser Gly Leu Pro Ser Gly Glu
705                 710                 715                 720

Val Leu Glu Thr Ala Ala Pro Gly Val Glu Asp Ile Ser Gly Leu Pro
                725                 730                 735

Ser Gly Glu Val Leu Glu Thr Ala Ala Pro Gly Val Glu Asp Ile Ser
            740                 745                 750

Gly Leu Pro Ser Gly Glu Val Leu Glu Thr Ala Ala Pro Gly Val Glu
        755                 760                 765

Asp Ile Ser Gly Leu Pro Ser Gly Glu Val Leu Glu Thr Ala Ala Pro
    770                 775                 780

Gly Val Glu Asp Ile Ser Gly Leu Pro Ser Gly Glu Val Leu Glu Thr
785                 790                 795                 800

Ala Ala Pro Gly Val Glu Asp Ile Ser Gly Leu Pro Ser Gly Glu Val
                805                 810                 815

Leu Glu Thr Ala Ala Pro Gly Val Glu Asp Ile Ser Gly Leu Pro Ser
            820                 825                 830

Gly Glu Val Leu Glu Thr Ala Ala Pro Gly Val Glu Asp Ile Ser Gly
        835                 840                 845

Leu Pro Ser Gly Glu Val Leu Glu Thr Ala Ala Pro Gly Val Glu Asp
    850                 855                 860

Ile Ser Gly Leu Pro Ser Gly Glu Val Leu Glu Thr Ala Ala Pro Gly
865                 870                 875                 880

Val Glu Asp Ile Ser Gly Leu Pro Ser Gly Glu Val Leu Glu Thr Thr
                885                 890                 895

Ala Pro Gly Val Glu Glu Ile Ser Gly Leu Pro Ser Gly Glu Val Leu
            900                 905                 910

Glu Thr Thr Ala Pro Gly Val Asp Glu Ile Ser Gly Leu Pro Ser Gly
        915                 920                 925

Glu Val Leu Glu Thr Thr Ala Pro Gly Val Glu Glu Ile Ser Gly Leu
    930                 935                 940

Pro Ser Gly Glu Val Leu Glu Thr Ser Thr Ser Ala Val Gly Asp Leu
```

-continued

```
                945                 950                 955                 960
Ser Gly Leu Pro Ser Gly Gly Glu Val Leu Glu Ile Ser Val Ser Gly
                    965                 970                 975
Val Glu Asp Ile Ser Gly Leu Pro Ser Gly Glu Val Val Glu Thr Ser
                980                 985                 990
Ala Ser Gly Ile Glu Asp Val Ser  Glu Leu Pro Ser Gly  Glu Gly Leu
            995                 1000                1005
Glu Thr  Ser Ala Ser Gly Val  Glu Asp Leu Ser Arg  Leu Pro Ser
    1010                1015                1020
Gly Glu  Glu Val Leu Glu Ile  Ser Ala Ser Gly Phe  Gly Asp Leu
    1025                1030                1035
Ser Gly  Val Pro Ser Gly Gly  Glu Gly Leu Glu Thr  Ser Ala Ser
    1040                1045                1050
Glu Val  Gly Thr Asp Leu Ser  Gly Leu Pro Ser Gly  Arg Glu Gly
    1055                1060                1065
Leu Glu  Thr Ser Ala Ser Gly  Ala Glu Asp Leu Ser  Gly Leu Pro
    1070                1075                1080
Ser Gly  Lys Glu Asp Leu Val  Gly Ser Ala Ser Gly  Asp Leu Asp
    1085                1090                1095
Leu Gly  Lys Leu Pro Ser Gly  Thr Leu Gly Ser Gly  Gln Ala Pro
    1100                1105                1110
Glu Thr  Ser Gly Leu Pro Ser  Gly Phe Ser Gly Glu  Tyr Ser Gly
    1115                1120                1125
Val Asp  Leu Gly Ser Gly Pro  Pro Ser Gly Leu Pro  Asp Phe Ser
    1130                1135                1140
Gly Leu  Pro Ser Gly Phe Pro  Thr Val Ser Leu Val  Asp Ser Thr
    1145                1150                1155
Leu Val  Glu Val Val Thr Ala  Ser Thr Ala Ser Glu  Leu Glu Gly
    1160                1165                1170
Arg Gly  Thr Ile Gly Ile Ser  Gly Ala Gly Glu Ile  Ser Gly Leu
    1175                1180                1185
Pro Ser  Ser Glu Leu Asp Ile  Ser Gly Arg Ala Ser  Gly Leu Pro
    1190                1195                1200
Ser Gly  Thr Glu Leu Ser Gly  Gln Ala Ser Gly Ser  Pro Asp Val
    1205                1210                1215
Ser Gly  Glu Ile Pro Gly Leu  Phe Gly Val Ser Gly  Gln Pro Ser
    1220                1225                1230
Gly Phe  Pro Asp Thr Ser Gly  Glu Thr Ser Gly Val  Thr Glu Leu
    1235                1240                1245
Ser Gly  Leu Ser Ser Gly Gln  Pro Gly Val Ser Gly  Glu Ala Ser
    1250                1255                1260
Gly Val  Leu Tyr Gly Thr Ser  Gln Pro Phe Gly Ile  Thr Asp Leu
    1265                1270                1275
Ser Gly  Glu Thr Ser Gly Val  Pro Asp Leu Ser Gly  Gln Pro Ser
    1280                1285                1290
Gly Leu  Pro Gly Phe Ser Gly  Ala Thr Ser Gly Val  Pro Asp Leu
    1295                1300                1305
Val Ser  Gly Thr Thr Ser Gly  Ser Gly Glu Ser Ser  Gly Ile Thr
    1310                1315                1320
Phe Val  Asp Thr Ser Leu Val  Glu Val Ala Pro Thr  Thr Phe Lys
    1325                1330                1335
Glu Glu  Glu Gly Leu Gly Ser  Val Glu Leu Ser Gly  Leu Pro Ser
    1340                1345                1350
```

```
Gly Glu Ala Asp Leu Ser Gly Lys Ser Gly Met Val Asp Val Ser
    1355                1360                1365

Gly Gln Phe Ser Gly Thr Val Asp Ser Ser Gly Phe Thr Ser Gln
    1370                1375                1380

Thr Pro Glu Phe Ser Gly Leu Pro Ser Gly Ile Ala Glu Val Ser
    1385                1390                1395

Gly Glu Ser Ser Arg Ala Glu Ile Gly Ser Ser Leu Pro Ser Gly
    1400                1405                1410

Ala Tyr Tyr Gly Ser Gly Thr Pro Ser Ser Phe Pro Thr Val Ser
    1415                1420                1425

Leu Val Asp Arg Thr Leu Val Glu Ser Val Thr Gln Ala Pro Thr
    1430                1435                1440

Ala Gln Glu Ala Gly Glu Gly Pro Ser Gly Ile Leu Glu Leu Ser
    1445                1450                1455

Gly Ala His Ser Gly Ala Pro Asp Met Ser Gly Glu His Ser Gly
    1460                1465                1470

Phe Leu Asp Leu Ser Gly Leu Gln Ser Gly Leu Ile Glu Pro Ser
    1475                1480                1485

Gly Glu Pro Pro Gly Thr Pro Tyr Phe Ser Gly Asp Phe Ala Ser
    1490                1495                1500

Thr Thr Asn Val Ser Gly Glu Ser Ser Val Ala Met Gly Thr Ser
    1505                1510                1515

Gly Glu Ala Ser Gly Leu Pro Glu Val Thr Leu Ile Thr Ser Glu
    1520                1525                1530

Phe Val Glu Gly Val Thr Glu Pro Thr Ile Ser Gln Glu Leu Gly
    1535                1540                1545

Gln Arg Pro Pro Val Thr His Thr Pro Gln Leu Phe Glu Ser Ser
    1550                1555                1560

Gly Lys Val Ser Thr Ala Gly Asp Ile Ser Gly Ala Thr Pro Val
    1565                1570                1575

Leu Pro Gly Ser Gly Val Glu Val Ser Ser Val Pro Glu Ser Ser
    1580                1585                1590

Ser Glu Thr Ser Ala Tyr Pro Glu Ala Gly Phe Gly Ala Ser Ala
    1595                1600                1605

Ala Pro Glu Ala Ser Arg Glu Asp Ser Gly Ser Pro Asp Leu Ser
    1610                1615                1620

Glu Thr Thr Ser Ala Phe His Glu Ala Asn Leu Glu Arg Ser Ser
    1625                1630                1635

Gly Leu Gly Val Ser Gly Ser Thr Leu Thr Phe Gln Glu Gly Glu
    1640                1645                1650

Ala Ser Ala Ala Pro Glu Val Ser Gly Glu Ser Thr Thr Thr Ser
    1655                1660                1665

Asp Val Gly Thr Glu Ala Pro Gly Leu Pro Ser Ala Thr Pro Thr
    1670                1675                1680

Ala Ser Gly Asp Arg Thr Glu Ile Ser Gly Asp Leu Ser Gly His
    1685                1690                1695

Thr Ser Gln Leu Gly Val Val Ile Ser Thr Ser Ile Pro Glu Ser
    1700                1705                1710

Glu Trp Thr Gln Gln Thr Gln Arg Pro Ala Glu Thr His Leu Glu
    1715                1720                1725

Ile Glu Ser Ser Ser Leu Leu Tyr Ser Gly Glu Glu Thr His Thr
    1730                1735                1740
```

-continued

Val Glu Thr Ala Thr Ser Pro Thr Asp Ala Ser Ile Pro Ala Ser
   1745                1750                1755

Pro Glu Trp Lys Arg Glu Ser Glu Ser Thr Ala Ala Ala Pro Ala
   1760                1765                1770

Arg Ser Cys Ala Glu Glu Pro Cys Gly Ala Gly Thr Cys Lys Glu
   1775                1780                1785

Thr Glu Gly His Val Ile Cys Leu Cys Pro Pro Gly Tyr Thr Gly
   1790                1795                1800

Glu His Cys Asn Ile Asp Gln Glu Val Cys Glu Glu Gly Trp Asn
   1805                1810                1815

Lys Tyr Gln Gly His Cys Tyr Arg His Phe Pro Asp Arg Glu Thr
   1820                1825                1830

Trp Val Asp Ala Glu Arg Arg Cys Arg Glu Gln Gln Ser His Leu
   1835                1840                1845

Ser Ser Ile Val Thr Pro Glu Glu Gln Glu Phe Val Asn Asn Asn
   1850                1855                1860

Ala Gln Asp Tyr Gln Trp Ile Gly Leu Asn Asp Arg Thr Ile Glu
   1865                1870                1875

Gly Asp Phe Arg Trp Ser Asp Gly His Pro Met Gln Phe Glu Asn
   1880                1885                1890

Trp Arg Pro Asn Gln Pro Asp Asn Phe Phe Ala Ala Gly Glu Asp
   1895                1900                1905

Cys Val Val Met Ile Trp His Glu Lys Gly Glu Trp Asn Asp Val
   1910                1915                1920

Pro Cys Asn Tyr His Leu Pro Phe Thr Cys Lys Lys Gly Thr Val
   1925                1930                1935

Ala Cys Gly Glu Pro Pro Val Val Glu His Ala Arg Thr Phe Gly
   1940                1945                1950

Gln Lys Lys Asp Arg Tyr Glu Ile Asn Ser Leu Val Arg Tyr Gln
   1955                1960                1965

Cys Thr Glu Gly Phe Val Gln Arg His Met Pro Thr Ile Arg Cys
   1970                1975                1980

Gln Pro Ser Gly His Trp Glu Pro Arg Ile Thr Cys Thr Asp
   1985                1990                1995

Ala Thr Thr Tyr Lys Arg Arg Leu Gln Lys Arg Ser Ser Arg His
   2000                2005                2010

Pro Arg Arg Ser Arg Pro Ser Thr Ala His
   2015                2020

<210> SEQ ID NO 73
<211> LENGTH: 96
<212> TYPE: PRT
<213> ORGANISM: Homo sapiens

<400> SEQUENCE: 73

Ile Val Phe His Tyr Arg Ala Ile Ser Thr Arg Tyr Thr Leu Asp Phe
 1               5                   10                  15

Asp Arg Ala Gln Arg Ala Cys Leu Gln Asn Ser Ala Ile Ile Ala Thr
                20                  25                  30

Pro Glu Gln Leu Gln Ala Ala Tyr Glu Asp Gly Phe His Gln Cys Asp
            35                  40                  45

Ala Gly Trp Leu Ala Asp Gln Thr Val Arg Tyr Pro Ile His Thr Pro
        50                  55                  60

Arg Glu Gly Cys Tyr Gly Asp Lys Asp Glu Phe Pro Gly Val Arg Thr
65                  70                  75                  80

Tyr Gly Ile Arg Asp Thr Asn Glu Thr Tyr Asp Val Tyr Cys Phe Ala
            85                  90                  95

<210> SEQ ID NO 74
<211> LENGTH: 97
<212> TYPE: PRT
<213> ORGANISM: Homo sapiens

<400> SEQUENCE: 74

Glu Val Phe Tyr Ala Thr Ser Pro Glu Lys Phe Thr Phe Gln Glu Ala
1               5                   10                  15

Ala Asn Glu Cys Arg Arg Leu Gly Ala Arg Leu Ala Thr Thr Gly His
            20                  25                  30

Val Tyr Leu Ala Trp Gln Ala Gly Met Asp Met Cys Ser Ala Gly Trp
        35                  40                  45

Leu Ala Asp Arg Ser Val Arg Tyr Pro Ile Ser Lys Ala Arg Pro Asn
    50                  55                  60

Cys Gly Gly Asn Leu Leu Gly Val Arg Thr Val Tyr Val His Ala Asn
65                  70                  75                  80

Gln Thr Gly Tyr Pro Asp Pro Ser Ser Arg Tyr Asp Ala Ile Cys Tyr
                85                  90                  95

Thr

<210> SEQ ID NO 75
<211> LENGTH: 96
<212> TYPE: PRT
<213> ORGANISM: Homo sapiens

<400> SEQUENCE: 75

Val Val Phe His Tyr Arg Pro Gly Pro Thr Arg Tyr Ser Leu Thr Phe
1               5                   10                  15

Glu Glu Ala Gln Gln Ala Cys Pro Gly Thr Gly Ala Val Ile Ala Ser
            20                  25                  30

Pro Glu Gln Leu Gln Ala Ala Tyr Glu Ala Gly Tyr Glu Gln Cys Asp
        35                  40                  45

Ala Gly Trp Leu Arg Asp Gln Thr Val Arg Tyr Pro Ile Val Ser Pro
    50                  55                  60

Arg Thr Pro Cys Val Gly Asp Lys Asp Ser Ser Pro Gly Val Arg Thr
65                  70                  75                  80

Tyr Gly Val Arg Pro Ser Thr Glu Thr Tyr Asp Val Tyr Cys Phe Val
                85                  90                  95

<210> SEQ ID NO 76
<211> LENGTH: 96
<212> TYPE: PRT
<213> ORGANISM: Homo sapiens

<400> SEQUENCE: 76

Glu Val Phe Phe Ala Thr Arg Leu Glu Gln Phe Thr Phe Gln Glu Ala
1               5                   10                  15

Leu Glu Phe Cys Glu Ser His Asn Ala Thr Ala Thr Thr Gly Gln Leu
            20                  25                  30

Tyr Ala Ala Trp Ser Arg Gly Leu Asp Lys Cys Tyr Ala Gly Trp Leu
        35                  40                  45

Ala Asp Gly Ser Leu Arg Tyr Pro Ile Val Thr Pro Arg Pro Ala Cys
    50                  55                  60

Gly Gly Asp Lys Pro Gly Val Arg Thr Val Tyr Leu Tyr Pro Asn Gln

```
                65                  70                  75                  80
Thr Gly Leu Pro Asp Pro Leu Ser Arg His His Ala Phe Cys Phe Arg
                85                  90                  95
```

<210> SEQ ID NO 77
<211> LENGTH: 3396
<212> TYPE: PRT
<213> ORGANISM: Homo sapiens

<400> SEQUENCE: 77

```
Met Phe Ile Asn Ile Lys Ser Ile Leu Trp Met Cys Ser Thr Leu Ile
1               5                   10                  15

Val Thr His Ala Leu His Lys Val Lys Val Gly Lys Ser Pro Pro Val
                20                  25                  30

Arg Gly Ser Leu Ser Gly Lys Val Ser Leu Pro Cys His Phe Ser Thr
                35                  40                  45

Met Pro Thr Leu Pro Pro Ser Tyr Asn Thr Ser Glu Phe Leu Arg Ile
            50                  55                  60

Lys Trp Ser Lys Ile Glu Val Asp Lys Asn Gly Lys Asp Leu Lys Glu
65                  70                  75                  80

Thr Thr Val Leu Val Ala Gln Asn Gly Asn Ile Lys Ile Gly Gln Asp
                85                  90                  95

Tyr Lys Gly Arg Val Ser Val Pro Thr His Pro Glu Ala Val Gly Asp
                100                 105                 110

Ala Ser Leu Thr Val Val Lys Leu Leu Ala Ser Asp Ala Gly Leu Tyr
                115                 120                 125

Arg Cys Asp Val Met Tyr Gly Ile Glu Asp Thr Gln Asp Thr Val Ser
            130                 135                 140

Leu Thr Val Asp Gly Val Val Phe His Tyr Arg Ala Ala Thr Ser Arg
145                 150                 155                 160

Tyr Thr Leu Asn Phe Glu Ala Ala Gln Lys Ala Cys Leu Asp Val Gly
                165                 170                 175

Ala Val Ile Ala Thr Pro Glu Gln Leu Phe Ala Ala Tyr Glu Asp Gly
                180                 185                 190

Phe Glu Gln Cys Asp Ala Gly Trp Leu Ala Asp Gln Thr Val Arg Tyr
            195                 200                 205

Pro Ile Arg Ala Pro Arg Val Gly Cys Tyr Gly Asp Lys Met Gly Lys
        210                 215                 220

Ala Gly Val Arg Thr Tyr Gly Phe Arg Ser Pro Gln Glu Thr Tyr Asp
225                 230                 235                 240

Val Tyr Cys Tyr Val Asp His Leu Asp Gly Asp Val Phe His Leu Thr
                245                 250                 255

Val Pro Ser Lys Phe Thr Phe Glu Glu Ala Lys Gly Cys Glu Asn
                260                 265                 270

Gln Asp Ala Arg Leu Ala Thr Val Gly Glu Leu Gln Ala Ala Trp Arg
            275                 280                 285

Asn Gly Phe Asp Gln Cys Asp Tyr Gly Trp Leu Ser Asp Ala Ser Val
        290                 295                 300

Arg His Pro Val Thr Val Ala Arg Ala Gln Cys Gly Gly Gly Leu Leu
305                 310                 315                 320

Gly Val Arg Thr Leu Tyr Arg Phe Glu Asn Gln Thr Gly Phe Pro Pro
                325                 330                 335

Pro Asp Ser Arg Phe Asp Ala Tyr Cys Phe Lys Pro Lys Glu Ala Thr
            340                 345                 350
```

-continued

```
Thr Ile Asp Leu Ser Ile Leu Ala Glu Thr Ala Ser Pro Ser Leu Ser
        355                 360                 365
Lys Glu Pro Gln Met Val Ser Asp Arg Thr Thr Pro Ile Ile Pro Leu
370                 375                 380
Val Asp Glu Leu Pro Val Ile Pro Thr Glu Phe Pro Pro Val Gly Asn
385                 390                 395                 400
Ile Val Ser Phe Glu Gln Lys Ala Thr Val Gln Pro Gln Ala Ile Thr
                405                 410                 415
Asp Ser Leu Ala Thr Lys Leu Pro Thr Pro Thr Gly Ser Thr Lys Lys
                420                 425                 430
Pro Trp Asp Met Asp Asp Tyr Ser Pro Ser Ala Ser Gly Pro Leu Gly
            435                 440                 445
Lys Leu Asp Ile Ser Glu Ile Lys Glu Glu Val Leu Gln Ser Thr Thr
        450                 455                 460
Gly Val Ser His Tyr Ala Thr Asp Ser Trp Asp Gly Val Val Glu Asp
465                 470                 475                 480
Lys Gln Thr Gln Glu Ser Val Thr Gln Ile Glu Gln Ile Glu Val Gly
                485                 490                 495
Pro Leu Val Thr Ser Met Glu Ile Leu Lys His Ile Pro Ser Lys Glu
                500                 505                 510
Phe Pro Val Thr Glu Thr Pro Leu Val Thr Ala Arg Met Ile Leu Glu
            515                 520                 525
Ser Lys Thr Glu Lys Lys Met Val Ser Thr Val Ser Glu Leu Val Thr
        530                 535                 540
Thr Gly His Tyr Gly Phe Thr Leu Gly Glu Glu Asp Asp Glu Asp Arg
545                 550                 555                 560
Thr Leu Thr Val Gly Ser Asp Glu Ser Thr Leu Ile Phe Asp Gln Ile
                565                 570                 575
Pro Glu Val Ile Thr Val Ser Lys Thr Ser Glu Asp Thr Ile His Thr
                580                 585                 590
His Leu Glu Asp Leu Glu Ser Val Ser Ala Ser Thr Thr Val Ser Pro
            595                 600                 605
Leu Ile Met Pro Asp Asn Asn Gly Ser Ser Met Asp Asp Trp Glu Glu
        610                 615                 620
Arg Gln Thr Ser Gly Arg Ile Thr Glu Glu Phe Leu Gly Lys Tyr Leu
625                 630                 635                 640
Ser Thr Thr Pro Phe Pro Ser Gln His Arg Thr Glu Ile Glu Leu Phe
                645                 650                 655
Pro Tyr Ser Gly Asp Lys Ile Leu Val Glu Gly Ile Ser Thr Val Ile
                660                 665                 670
Tyr Pro Ser Leu Gln Thr Glu Met Thr His Arg Arg Glu Arg Thr Glu
            675                 680                 685
Thr Leu Ile Pro Glu Met Arg Thr Asp Thr Tyr Thr Asp Glu Ile Gln
        690                 695                 700
Glu Glu Ile Thr Lys Ser Pro Phe Met Gly Lys Thr Glu Glu Val
705                 710                 715                 720
Phe Ser Gly Met Lys Leu Ser Thr Ser Leu Ser Glu Pro Ile His Val
                725                 730                 735
Thr Glu Ser Ser Val Glu Met Thr Lys Ser Phe Asp Phe Pro Thr Leu
                740                 745                 750
Ile Thr Lys Leu Ser Ala Glu Pro Thr Glu Val Arg Asp Met Glu Glu
        755                 760                 765
Asp Phe Thr Ala Thr Pro Gly Thr Thr Lys Tyr Asp Glu Asn Ile Thr
```

```
                770             775             780
Thr Val Leu Leu Ala His Gly Thr Leu Ser Val Glu Ala Ala Thr Val
785                 790             795                 800

Ser Lys Trp Ser Trp Asp Glu Asp Asn Thr Thr Ser Lys Pro Leu Glu
                    805             810              815

Ser Thr Glu Pro Ser Ala Ser Ser Lys Leu Pro Pro Ala Leu Leu Thr
                820             825             830

Thr Val Gly Met Asn Gly Lys Asp Lys Asp Ile Pro Ser Phe Thr Glu
                835             840             845

Asp Gly Ala Asp Glu Phe Thr Leu Ile Pro Asp Ser Thr Gln Lys Gln
850                 855             860

Leu Glu Glu Val Thr Asp Glu Asp Ile Ala Ala His Gly Lys Phe Thr
865                 870             875             880

Ile Arg Phe Gln Pro Thr Thr Ser Thr Gly Ile Ala Glu Lys Ser Thr
                    885             890             895

Leu Arg Asp Ser Thr Thr Glu Glu Lys Val Pro Pro Ile Thr Ser Thr
                900             905             910

Glu Gly Gln Val Tyr Ala Thr Met Glu Gly Ser Ala Leu Gly Glu Val
                915             920             925

Glu Asp Val Asp Leu Ser Lys Pro Val Ser Thr Val Pro Gln Phe Ala
930                 935             940

His Thr Ser Glu Val Glu Gly Leu Ala Phe Val Ser Tyr Ser Ser Thr
945                 950             955             960

Gln Glu Pro Thr Thr Tyr Val Asp Ser Ser His Thr Ile Pro Leu Ser
                    965             970             975

Val Ile Pro Lys Thr Asp Trp Gly Val Leu Val Pro Ser Val Pro Ser
                980             985             990

Glu Asp Glu Val Leu Gly Glu Pro Ser Gln Asp Ile Leu Val Ile Asp
                995             1000            1005

Gln Thr Arg Leu Glu Ala Thr Ile Ser Pro Glu Thr Met Arg Thr
        1010            1015            1020

Thr Lys Ile Thr Glu Gly Thr Gln Glu Glu Phe Pro Trp Lys
        1025            1030            1035

Glu Gln Thr Ala Glu Lys Pro Val Pro Ala Leu Ser Ser Thr Ala
        1040            1045            1050

Trp Thr Pro Lys Glu Ala Val Thr Pro Leu Asp Glu Gln Glu Gly
        1055            1060            1065

Asp Gly Ser Ala Tyr Thr Val Ser Glu Asp Glu Leu Leu Thr Gly
        1070            1075            1080

Ser Glu Arg Val Pro Val Leu Glu Thr Thr Pro Val Gly Lys Ile
        1085            1090            1095

Asp His Ser Val Ser Tyr Pro Pro Gly Ala Val Thr Glu His Lys
        1100            1105            1110

Val Lys Thr Asp Glu Val Val Thr Leu Thr Pro Arg Ile Gly Pro
        1115            1120            1125

Lys Val Ser Leu Ser Pro Gly Pro Glu Gln Lys Tyr Glu Thr Glu
        1130            1135            1140

Gly Ser Ser Thr Thr Gly Phe Thr Ser Ser Leu Ser Pro Phe Ser
        1145            1150            1155

Thr His Ile Thr Gln Leu Met Glu Glu Thr Thr Thr Glu Lys Thr
        1160            1165            1170

Ser Leu Glu Asp Ile Asp Leu Gly Ser Gly Leu Phe Glu Lys Pro
        1175            1180            1185
```

```
Lys Ala Thr Glu Leu Ile Glu Phe Ser Thr Ile Lys Val Thr Val
    1190                1195                1200

Pro Ser Asp Ile Thr Thr Ala Phe Ser Ser Val Asp Arg Leu His
    1205                1210                1215

Thr Thr Ser Ala Phe Lys Pro Ser Ser Ala Ile Thr Lys Lys Pro
    1220                1225                1230

Pro Leu Ile Asp Arg Glu Pro Gly Glu Thr Thr Ser Asp Met
    1235                1240                1245

Val Ile Ile Gly Glu Ser Thr Ser His Val Pro Pro Thr Thr Leu
    1250                1255                1260

Glu Asp Ile Val Ala Lys Glu Thr Glu Thr Asp Ile Asp Arg Glu
    1265                1270                1275

Tyr Phe Thr Thr Ser Ser Pro Pro Ala Thr Gln Pro Thr Arg Pro
    1280                1285                1290

Pro Thr Val Glu Asp Lys Glu Ala Phe Gly Pro Gln Ala Leu Ser
    1295                1300                1305

Thr Pro Gln Pro Pro Ala Ser Thr Lys Phe His Pro Asp Ile Asn
    1310                1315                1320

Val Tyr Ile Ile Glu Val Arg Glu Asn Lys Thr Gly Arg Met Ser
    1325                1330                1335

Asp Leu Ser Val Ile Gly His Pro Ile Asp Ser Glu Ser Lys Glu
    1340                1345                1350

Asp Glu Pro Cys Ser Glu Glu Thr Asp Pro Val His Asp Leu Met
    1355                1360                1365

Ala Glu Ile Leu Pro Glu Phe Pro Asp Ile Ile Glu Ile Asp Leu
    1370                1375                1380

Tyr His Ser Glu Glu Asn Glu Glu Glu Glu Glu Cys Ala Asn
    1385                1390                1395

Ala Thr Asp Val Thr Thr Thr Pro Ser Val Gln Tyr Ile Asn Gly
    1400                1405                1410

Lys His Leu Val Thr Thr Val Pro Lys Asp Pro Glu Ala Ala Glu
    1415                1420                1425

Ala Arg Arg Gly Gln Phe Glu Ser Val Ala Pro Ser Gln Asn Phe
    1430                1435                1440

Ser Asp Ser Ser Glu Ser Asp Thr His Pro Phe Val Ile Ala Lys
    1445                1450                1455

Thr Glu Leu Ser Thr Ala Val Gln Pro Asn Glu Ser Thr Glu Thr
    1460                1465                1470

Thr Glu Ser Leu Glu Val Thr Trp Lys Pro Glu Thr Tyr Pro Glu
    1475                1480                1485

Thr Ser Glu His Phe Ser Gly Gly Glu Pro Asp Val Phe Pro Thr
    1490                1495                1500

Val Pro Phe His Glu Glu Phe Glu Ser Gly Thr Ala Lys Lys Gly
    1505                1510                1515

Ala Glu Ser Val Thr Glu Arg Asp Thr Glu Val Gly His Gln Ala
    1520                1525                1530

His Glu His Thr Glu Pro Val Ser Leu Phe Pro Glu Glu Ser Ser
    1535                1540                1545

Gly Glu Ile Ala Ile Asp Gln Glu Ser Gln Lys Ile Ala Phe Ala
    1550                1555                1560

Arg Ala Thr Glu Val Thr Phe Gly Glu Glu Val Glu Lys Ser Thr
    1565                1570                1575
```

```
Ser Val Thr Tyr Thr Pro Thr Ile Val Pro Ser Ser Ala Ser Ala
    1580            1585            1590

Tyr Val Ser Glu Glu Glu Ala Val Thr Leu Ile Gly Asn Pro Trp
    1595            1600            1605

Pro Asp Asp Leu Leu Ser Thr Lys Glu Ser Trp Val Glu Ala Thr
    1610            1615            1620

Pro Arg Gln Val Val Glu Leu Ser Gly Ser Ser Ile Pro Ile
    1625            1630            1635

Thr Glu Gly Ser Gly Glu Ala Glu Glu Asp Glu Asp Thr Met Phe
    1640            1645            1650

Thr Met Val Thr Asp Leu Ser Gln Arg Asn Thr Thr Asp Thr Leu
    1655            1660            1665

Ile Thr Leu Asp Thr Ser Arg Ile Ile Thr Glu Ser Phe Phe Glu
    1670            1675            1680

Val Pro Ala Thr Thr Ile Tyr Pro Val Ser Glu Gln Pro Ser Ala
    1685            1690            1695

Lys Val Val Pro Thr Lys Phe Val Ser Glu Thr Asp Thr Ser Glu
    1700            1705            1710

Trp Ile Ser Ser Thr Thr Val Glu Glu Lys Lys Arg Lys Glu Glu
    1715            1720            1725

Glu Gly Thr Thr Gly Thr Ala Ser Thr Phe Glu Val Tyr Ser Ser
    1730            1735            1740

Thr Gln Arg Ser Asp Gln Leu Ile Leu Pro Phe Glu Leu Glu Ser
    1745            1750            1755

Pro Asn Val Ala Thr Ser Ser Asp Ser Gly Thr Arg Lys Ser Phe
    1760            1765            1770

Met Ser Leu Thr Thr Pro Thr Gln Ser Glu Arg Glu Met Thr Asp
    1775            1780            1785

Ser Thr Pro Val Phe Thr Glu Thr Asn Thr Leu Glu Asn Leu Gly
    1790            1795            1800

Ala Gln Thr Thr Glu His Ser Ser Ile His Gln Pro Gly Val Gln
    1805            1810            1815

Glu Gly Leu Thr Thr Leu Pro Arg Ser Pro Ala Ser Val Phe Met
    1820            1825            1830

Glu Gln Gly Ser Gly Glu Ala Ala Ala Asp Pro Glu Thr Thr Thr
    1835            1840            1845

Val Ser Ser Phe Ser Leu Asn Val Glu Tyr Ala Ile Gln Ala Glu
    1850            1855            1860

Lys Glu Val Ala Gly Thr Leu Ser Pro His Val Glu Thr Thr Phe
    1865            1870            1875

Ser Thr Glu Pro Thr Gly Leu Val Leu Ser Thr Val Met Asp Arg
    1880            1885            1890

Val Val Ala Glu Asn Ile Thr Gln Thr Ser Arg Glu Ile Val Ile
    1895            1900            1905

Ser Glu Arg Leu Gly Glu Pro Asn Tyr Gly Ala Glu Ile Arg Gly
    1910            1915            1920

Phe Ser Thr Gly Phe Pro Leu Glu Glu Asp Phe Ser Gly Asp Phe
    1925            1930            1935

Arg Glu Tyr Ser Thr Val Ser His Pro Ile Ala Lys Glu Glu Thr
    1940            1945            1950

Val Met Met Glu Gly Ser Gly Asp Ala Ala Phe Arg Asp Thr Gln
    1955            1960            1965

Thr Ser Pro Ser Thr Val Pro Thr Ser Val His Ile Ser His Ile
```

```
            1970                1975                1980
Ser Asp Ser Glu Gly Pro Ser Ser Thr Met Val Ser Thr Ser Ala
            1985                1990                1995

Phe Pro Trp Glu Glu Phe Thr Ser Ser Ala Glu Gly Ser Gly Glu
            2000                2005                2010

Gln Leu Val Thr Val Ser Ser Ser Val Val Pro Val Leu Pro Ser
            2015                2020                2025

Ala Val Gln Lys Phe Ser Gly Thr Ala Ser Ser Ile Ile Asp Glu
            2030                2035                2040

Gly Leu Gly Glu Val Gly Thr Val Asn Glu Ile Asp Arg Arg Ser
            2045                2050                2055

Thr Ile Leu Pro Thr Ala Glu Val Glu Gly Thr Lys Ala Pro Val
            2060                2065                2070

Glu Lys Glu Glu Val Lys Val Ser Gly Thr Val Ser Thr Asn Phe
            2075                2080                2085

Pro Gln Thr Ile Glu Pro Ala Lys Leu Trp Ser Arg Gln Glu Val
            2090                2095                2100

Asn Pro Val Arg Gln Glu Ile Glu Ser Glu Thr Ser Glu Glu
            2105                2110                2115

Gln Ile Gln Glu Glu Lys Ser Phe Glu Ser Pro Gln Asn Ser Pro
            2120                2125                2130

Ala Thr Glu Gln Thr Ile Phe Asp Ser Gln Thr Phe Thr Glu Thr
            2135                2140                2145

Glu Leu Lys Thr Thr Asp Tyr Ser Val Leu Thr Thr Lys Lys Thr
            2150                2155                2160

Tyr Ser Asp Asp Lys Glu Met Lys Glu Glu Asp Thr Ser Leu Val
            2165                2170                2175

Asn Met Ser Thr Pro Asp Pro Asp Ala Asn Gly Leu Glu Ser Tyr
            2180                2185                2190

Thr Thr Leu Pro Glu Ala Thr Glu Lys Ser His Phe Phe Leu Ala
            2195                2200                2205

Thr Ala Leu Val Thr Glu Ser Ile Pro Ala Glu His Val Val Thr
            2210                2215                2220

Asp Ser Pro Ile Lys Lys Glu Glu Ser Thr Lys His Phe Pro Lys
            2225                2230                2235

Gly Met Arg Pro Thr Ile Gln Glu Ser Asp Thr Glu Leu Leu Phe
            2240                2245                2250

Ser Gly Leu Gly Ser Gly Glu Glu Val Leu Pro Thr Leu Pro Thr
            2255                2260                2265

Glu Ser Val Asn Phe Thr Glu Val Glu Gln Ile Asn Asn Thr Leu
            2270                2275                2280

Tyr Pro His Thr Ser Gln Val Glu Ser Thr Ser Ser Asp Lys Ile
            2285                2290                2295

Glu Asp Phe Asn Arg Met Glu Asn Val Ala Lys Glu Val Gly Pro
            2300                2305                2310

Leu Val Ser Gln Thr Asp Ile Phe Glu Gly Ser Gly Ser Val Thr
            2315                2320                2325

Ser Thr Thr Leu Ile Glu Ile Leu Ser Asp Thr Gly Ala Glu Gly
            2330                2335                2340

Pro Thr Val Ala Pro Leu Pro Phe Ser Thr Asp Ile Gly His Pro
            2345                2350                2355

Gln Asn Gln Thr Val Arg Trp Ala Glu Glu Ile Gln Thr Ser Arg
            2360                2365                2370
```

-continued

```
Pro Gln Thr Ile Thr Glu Gln Asp Ser Asn Lys Asn  Ser Ser Thr
    2375            2380                2385

Ala Glu Ile Asn Glu Thr Thr  Thr Ser Ser Thr Asp  Phe Leu Ala
    2390            2395                2400

Arg Ala Tyr Gly Phe Glu Met  Ala Lys Glu Phe Val  Thr Ser Ala
    2405            2410                2415

Pro Lys Pro Ser Asp Leu Tyr  Tyr Glu Pro Ser Gly  Glu Gly Ser
    2420            2425                2430

Gly Glu Val Asp Ile Val Asp  Ser Phe His Thr Ser  Ala Thr Thr
    2435            2440                2445

Gln Ala Thr Arg Gln Glu Ser  Ser Thr Thr Phe Val  Ser Asp Gly
    2450            2455                2460

Ser Leu Glu Lys His Pro Glu  Val Pro Ser Ala Lys  Ala Val Thr
    2465            2470                2475

Ala Asp Gly Phe Pro Thr Val  Ser Val Met Leu Pro  Leu His Ser
    2480            2485                2490

Glu Gln Asn Lys Ser Ser Pro  Asp Pro Thr Ser Thr  Leu Ser Asn
    2495            2500                2505

Thr Val Ser Tyr Glu Arg Ser  Thr Asp Gly Ser Phe  Gln Asp Arg
    2510            2515                2520

Phe Arg Glu Phe Glu Asp Ser  Thr Leu Lys Pro Asn  Arg Lys Lys
    2525            2530                2535

Pro Thr Glu Asn Ile Ile Ile  Asp Leu Asp Lys Glu  Asp Lys Asp
    2540            2545                2550

Leu Ile Leu Thr Ile Thr Glu  Ser Thr Ile Leu Glu  Ile Leu Pro
    2555            2560                2565

Glu Leu Thr Ser Asp Lys Asn  Thr Ile Ile Asp Ile  Asp His Thr
    2570            2575                2580

Lys Pro Val Tyr Glu Asp Ile  Leu Gly Met Gln Thr  Asp Ile Asp
    2585            2590                2595

Thr Glu Val Pro Ser Glu Pro  His Asp Ser Asn Asp  Glu Ser Asn
    2600            2605                2610

Asp Asp Ser Thr Gln Val Gln  Glu Ile Tyr Glu Ala  Ala Val Asn
    2615            2620                2625

Leu Ser Leu Thr Glu Glu Thr  Phe Glu Gly Ser Ala  Asp Val Leu
    2630            2635                2640

Ala Ser Tyr Thr Gln Ala Thr  His Asp Glu Ser Met  Thr Tyr Glu
    2645            2650                2655

Asp Arg Ser Gln Leu Asp His  Met Gly Phe His Phe  Thr Thr Gly
    2660            2665                2670

Ile Pro Ala Pro Ser Thr Glu  Thr Glu Leu Asp Val  Leu Leu Pro
    2675            2680                2685

Thr Ala Thr Ser Leu Pro Ile  Pro Arg Lys Ser Ala  Thr Val Ile
    2690            2695                2700

Pro Glu Ile Glu Gly Ile Lys  Ala Glu Ala Lys Ala  Leu Asp Asp
    2705            2710                2715

Met Phe Glu Ser Ser Thr Leu  Ser Asp Gly Gln Ala  Ile Ala Asp
    2720            2725                2730

Gln Ser Glu Ile Ile Pro Thr  Leu Gly Gln Phe Glu  Arg Thr Gln
    2735            2740                2745

Glu Glu Tyr Glu Asp Lys Lys  His Ala Gly Pro Ser  Phe Gln Pro
    2750            2755                2760
```

-continued

| | | | | | | | | | | | |
|---|---|---|---|---|---|---|---|---|---|---|---|
|Glu|Phe|Ser|Ser|Gly|Ala|Glu|Glu|Ala|Leu|Val|Asp|His|Thr|Pro|
|2765| | | | |2770| | | |2775| | | | | |

Glu Phe Ser Ser Gly Ala Glu Glu Ala Leu Val Asp His Thr Pro
2765                2770               2775

Tyr Leu Ser Ile Ala Thr Thr His Leu Met Asp Gln Ser Val Thr
2780                2785               2790

Glu Val Pro Asp Val Met Glu Gly Ser Asn Pro Tyr Tyr Thr
2795                2800               2805

Asp Thr Thr Leu Ala Val Ser Thr Phe Ala Lys Leu Ser Ser Gln
2810                2815               2820

Thr Pro Ser Ser Pro Leu Thr Ile Tyr Ser Gly Ser Glu Ala Ser
2825                2830               2835

Gly His Thr Glu Ile Pro Gln Pro Ser Ala Leu Pro Gly Ile Asp
2840                2845               2850

Val Gly Ser Ser Val Met Ser Pro Gln Asp Ser Phe Lys Glu Ile
2855                2860               2865

His Val Asn Ile Glu Ala Thr Phe Lys Pro Ser Ser Glu Glu Tyr
2870                2875               2880

Leu His Ile Thr Glu Pro Pro Ser Leu Ser Pro Asp Thr Lys Leu
2885                2890               2895

Glu Pro Ser Glu Asp Asp Gly Lys Pro Glu Leu Leu Glu Glu Met
2900                2905               2910

Glu Ala Ser Pro Thr Glu Leu Ile Ala Val Glu Gly Thr Glu Ile
2915                2920               2925

Leu Gln Asp Phe Gln Asn Lys Thr Asp Gly Gln Val Ser Gly Glu
2930                2935               2940

Ala Ile Lys Met Phe Pro Thr Ile Lys Thr Pro Glu Ala Gly Thr
2945                2950               2955

Val Ile Thr Thr Ala Asp Glu Ile Glu Leu Glu Gly Ala Thr Gln
2960                2965               2970

Trp Pro His Ser Thr Ser Ala Ser Ala Thr Tyr Gly Val Glu Ala
2975                2980               2985

Gly Val Val Pro Trp Leu Ser Pro Gln Thr Ser Glu Arg Pro Thr
2990                2995               3000

Leu Ser Ser Ser Pro Glu Ile Asn Pro Glu Thr Gln Ala Ala Leu
3005                3010               3015

Ile Arg Gly Gln Asp Ser Thr Ile Ala Ala Ser Glu Gln Gln Val
3020                3025               3030

Ala Ala Arg Ile Leu Asp Ser Asn Asp Gln Ala Thr Val Asn Pro
3035                3040               3045

Val Glu Phe Asn Thr Glu Val Ala Thr Pro Pro Phe Ser Leu Leu
3050                3055               3060

Glu Thr Ser Asn Glu Thr Asp Phe Leu Ile Gly Ile Asn Glu Glu
3065                3070               3075

Ser Val Glu Gly Thr Ala Ile Tyr Leu Pro Gly Pro Asp Arg Cys
3080                3085               3090

Lys Met Asn Pro Cys Leu Asn Gly Gly Thr Cys Tyr Pro Thr Glu
3095                3100               3105

Thr Ser Tyr Val Cys Thr Cys Val Pro Gly Tyr Ser Gly Asp Gln
3110                3115               3120

Cys Glu Leu Asp Phe Asp Glu Cys His Ser Asn Pro Cys Arg Asn
3125                3130               3135

Gly Ala Thr Cys Val Asp Gly Phe Asn Thr Phe Arg Cys Leu Cys
3140                3145               3150

Leu Pro Ser Tyr Val Gly Ala Leu Cys Glu Gln Asp Thr Glu Thr

-continued

```
            3155                3160                3165

Cys Asp Tyr Gly Trp His Lys Phe Gln Gly Gln Cys Tyr Lys Tyr
    3170                3175                3180

Phe Ala His Arg Arg Thr Trp Asp Ala Ala Glu Arg Glu Cys Arg
    3185                3190                3195

Leu Gln Gly Ala His Leu Thr Ser Ile Leu Ser His Glu Glu Gln
    3200                3205                3210

Met Phe Val Asn Arg Val Gly His Asp Tyr Gln Trp Ile Gly Leu
    3215                3220                3225

Asn Asp Lys Met Phe Glu His Asp Phe Arg Trp Thr Asp Gly Ser
    3230                3235                3240

Thr Leu Gln Tyr Glu Asn Trp Arg Pro Asn Gln Pro Asp Ser Phe
    3245                3250                3255

Phe Ser Ala Gly Glu Asp Cys Val Val Ile Ile Trp His Glu Asn
    3260                3265                3270

Gly Gln Trp Asn Asp Val Pro Cys Asn Tyr His Leu Thr Tyr Thr
    3275                3280                3285

Cys Lys Lys Gly Thr Val Ala Cys Gly Gln Pro Pro Val Val Glu
    3290                3295                3300

Asn Ala Lys Thr Phe Gly Lys Met Lys Pro Arg Tyr Glu Ile Asn
    3305                3310                3315

Ser Leu Ile Arg Tyr His Cys Lys Asp Gly Phe Ile Gln Arg His
    3320                3325                3330

Leu Pro Thr Ile Arg Cys Leu Gly Asn Gly Arg Trp Ala Ile Pro
    3335                3340                3345

Lys Ile Thr Cys Met Asn Pro Ser Ala Tyr Gln Arg Thr Tyr Ser
    3350                3355                3360

Met Lys Tyr Phe Lys Asn Ser Ser Ala Lys Asp Asn Ser Ile
    3365                3370                3375

Asn Thr Ser Lys His Asp His Arg Trp Ser Arg Arg Trp Gln Glu
    3380                3385                3390

Ser Arg Arg
    3395

<210> SEQ ID NO 78
<211> LENGTH: 3376
<212> TYPE: PRT
<213> ORGANISM: Homo sapiens

<400> SEQUENCE: 78

Leu His Lys Val Lys Val Gly Lys Ser Pro Pro Val Arg Gly Ser Leu
1               5                   10                  15

Ser Gly Lys Val Ser Leu Pro Cys His Phe Ser Thr Met Pro Thr Leu
                20                  25                  30

Pro Pro Ser Tyr Asn Thr Ser Glu Phe Leu Arg Ile Lys Trp Ser Lys
            35                  40                  45

Ile Glu Val Asp Lys Asn Gly Lys Asp Leu Lys Glu Thr Thr Val Leu
        50                  55                  60

Val Ala Gln Asn Gly Asn Ile Lys Ile Gly Gln Asp Tyr Lys Gly Arg
65                  70                  75                  80

Val Ser Val Pro Thr His Pro Glu Ala Val Gly Asp Ala Ser Leu Thr
                85                  90                  95

Val Val Lys Leu Leu Ala Ser Asp Ala Gly Leu Tyr Arg Cys Asp Val
            100                 105                 110
```

```
Met Tyr Gly Ile Glu Asp Thr Gln Asp Thr Val Ser Leu Thr Val Asp
            115                 120                 125
Gly Val Val Phe His Tyr Arg Ala Ala Thr Ser Arg Tyr Thr Leu Asn
130                 135                 140
Phe Glu Ala Ala Gln Lys Ala Cys Leu Asp Val Gly Ala Val Ile Ala
145                 150                 155                 160
Thr Pro Glu Gln Leu Phe Ala Ala Tyr Glu Asp Gly Phe Glu Gln Cys
                165                 170                 175
Asp Ala Gly Trp Leu Ala Asp Gln Thr Val Arg Tyr Pro Ile Arg Ala
            180                 185                 190
Pro Arg Val Gly Cys Tyr Gly Asp Lys Met Gly Lys Ala Gly Val Arg
            195                 200                 205
Thr Tyr Gly Phe Arg Ser Pro Gln Glu Thr Tyr Asp Val Tyr Cys Tyr
210                 215                 220
Val Asp His Leu Asp Gly Asp Val Phe His Leu Thr Val Pro Ser Lys
225                 230                 235                 240
Phe Thr Phe Glu Glu Ala Ala Lys Glu Cys Glu Asn Gln Asp Ala Arg
                245                 250                 255
Leu Ala Thr Val Gly Glu Leu Gln Ala Ala Trp Arg Asn Gly Phe Asp
            260                 265                 270
Gln Cys Asp Tyr Gly Trp Leu Ser Asp Ala Ser Val Arg His Pro Val
            275                 280                 285
Thr Val Ala Arg Ala Gln Cys Gly Gly Gly Leu Leu Gly Val Arg Thr
            290                 295                 300
Leu Tyr Arg Phe Glu Asn Gln Thr Gly Phe Pro Pro Pro Asp Ser Arg
305                 310                 315                 320
Phe Asp Ala Tyr Cys Phe Lys Pro Lys Glu Ala Thr Thr Ile Asp Leu
                325                 330                 335
Ser Ile Leu Ala Glu Thr Ala Ser Pro Ser Leu Ser Lys Glu Pro Gln
            340                 345                 350
Met Val Ser Asp Arg Thr Thr Pro Ile Ile Pro Leu Val Asp Glu Leu
            355                 360                 365
Pro Val Ile Pro Thr Glu Phe Pro Pro Val Gly Asn Ile Val Ser Phe
370                 375                 380
Glu Gln Lys Ala Thr Val Gln Pro Gln Ala Ile Thr Asp Ser Leu Ala
385                 390                 395                 400
Thr Lys Leu Pro Thr Pro Thr Gly Ser Thr Lys Lys Pro Trp Asp Met
                405                 410                 415
Asp Asp Tyr Ser Pro Ser Ala Ser Gly Pro Leu Gly Lys Leu Asp Ile
            420                 425                 430
Ser Glu Ile Lys Glu Glu Val Leu Gln Ser Thr Thr Gly Val Ser His
            435                 440                 445
Tyr Ala Thr Asp Ser Trp Asp Gly Val Val Glu Asp Lys Gln Thr Gln
450                 455                 460
Glu Ser Val Thr Gln Ile Glu Gln Ile Glu Val Gly Pro Leu Val Thr
465                 470                 475                 480
Ser Met Glu Ile Leu Lys His Ile Pro Ser Lys Glu Phe Pro Val Thr
                485                 490                 495
Glu Thr Pro Leu Val Thr Ala Arg Met Ile Leu Glu Ser Lys Thr Glu
            500                 505                 510
Lys Lys Met Val Ser Thr Val Ser Glu Leu Val Thr Thr Gly His Tyr
            515                 520                 525
Gly Phe Thr Leu Gly Glu Glu Asp Asp Glu Asp Arg Thr Leu Thr Val
```

```
                530             535             540
Gly Ser Asp Glu Ser Thr Leu Ile Phe Asp Gln Ile Pro Glu Val Ile
545                 550                 555                 560

Thr Val Ser Lys Thr Ser Glu Asp Thr Ile His Thr His Leu Glu Asp
                565                 570                 575

Leu Glu Ser Val Ser Ala Ser Thr Thr Val Ser Pro Leu Ile Met Pro
                580                 585                 590

Asp Asn Asn Gly Ser Ser Met Asp Asp Trp Glu Glu Arg Gln Thr Ser
                595                 600                 605

Gly Arg Ile Thr Glu Glu Phe Leu Gly Lys Tyr Leu Ser Thr Thr Pro
                610                 615                 620

Phe Pro Ser Gln His Arg Thr Glu Ile Glu Leu Phe Pro Tyr Ser Gly
625                 630                 635                 640

Asp Lys Ile Leu Val Glu Gly Ile Ser Thr Val Ile Tyr Pro Ser Leu
                645                 650                 655

Gln Thr Glu Met Thr His Arg Arg Glu Arg Thr Glu Thr Leu Ile Pro
                660                 665                 670

Glu Met Arg Thr Asp Thr Tyr Thr Asp Glu Ile Gln Glu Glu Ile Thr
                675                 680                 685

Lys Ser Pro Phe Met Gly Lys Thr Glu Glu Glu Val Phe Ser Gly Met
                690                 695                 700

Lys Leu Ser Thr Ser Leu Ser Glu Pro Ile His Val Thr Glu Ser Ser
705                 710                 715                 720

Val Glu Met Thr Lys Ser Phe Asp Phe Pro Thr Leu Ile Thr Lys Leu
                725                 730                 735

Ser Ala Glu Pro Thr Glu Val Arg Asp Met Glu Glu Asp Phe Thr Ala
                740                 745                 750

Thr Pro Gly Thr Thr Lys Tyr Asp Glu Asn Ile Thr Thr Val Leu Leu
                755                 760                 765

Ala His Gly Thr Leu Ser Val Glu Ala Ala Thr Val Ser Lys Trp Ser
                770                 775                 780

Trp Asp Glu Asp Asn Thr Thr Ser Lys Pro Leu Glu Ser Thr Glu Pro
785                 790                 795                 800

Ser Ala Ser Ser Lys Leu Pro Pro Ala Leu Leu Thr Thr Val Gly Met
                805                 810                 815

Asn Gly Lys Asp Lys Asp Ile Pro Ser Phe Thr Glu Asp Gly Ala Asp
                820                 825                 830

Glu Phe Thr Leu Ile Pro Asp Ser Thr Gln Lys Gln Leu Glu Glu Val
                835                 840                 845

Thr Asp Glu Asp Ile Ala Ala His Gly Lys Phe Thr Ile Arg Phe Gln
850                 855                 860

Pro Thr Thr Ser Thr Gly Ile Ala Glu Lys Thr Leu Arg Asp Ser
865                 870                 875                 880

Thr Thr Glu Glu Lys Val Pro Pro Ile Thr Ser Thr Glu Gly Gln Val
                885                 890                 895

Tyr Ala Thr Met Glu Gly Ser Ala Leu Gly Glu Val Glu Asp Val Asp
                900                 905                 910

Leu Ser Lys Pro Val Ser Thr Val Pro Gln Phe Ala His Thr Ser Glu
                915                 920                 925

Val Glu Gly Leu Ala Phe Val Ser Tyr Ser Ser Thr Gln Glu Pro Thr
                930                 935                 940

Thr Tyr Val Asp Ser Ser His Thr Ile Pro Leu Ser Val Ile Pro Lys
945                 950                 955                 960
```

```
Thr Asp Trp Gly Val Leu Val Pro Ser Val Pro Ser Glu Asp Glu Val
                965                 970                 975

Leu Gly Glu Pro Ser Gln Asp Ile Leu Val Ile Asp Gln Thr Arg Leu
            980                 985                 990

Glu Ala Thr Ile Ser Pro Glu Thr Met Arg Thr Thr Lys Ile Thr Glu
        995                 1000                1005

Gly Thr Thr Gln Glu Glu Phe Pro Trp Lys Gln Thr Ala Glu
    1010                1015                1020

Lys Pro Val Pro Ala Leu Ser Ser Thr Ala Trp Thr Pro Lys Glu
    1025                1030                1035

Ala Val Thr Pro Leu Asp Glu Gln Glu Gly Asp Gly Ser Ala Tyr
    1040                1045                1050

Thr Val Ser Glu Asp Glu Leu Leu Thr Gly Ser Glu Arg Val Pro
    1055                1060                1065

Val Leu Glu Thr Thr Pro Val Gly Lys Ile Asp His Ser Val Ser
    1070                1075                1080

Tyr Pro Pro Gly Ala Val Thr Glu His Lys Val Lys Thr Asp Glu
    1085                1090                1095

Val Val Thr Leu Thr Pro Arg Ile Gly Pro Lys Val Ser Leu Ser
    1100                1105                1110

Pro Gly Pro Glu Gln Lys Tyr Glu Thr Glu Gly Ser Ser Thr Thr
    1115                1120                1125

Gly Phe Thr Ser Ser Leu Ser Pro Phe Ser Thr His Ile Thr Gln
    1130                1135                1140

Leu Met Glu Glu Thr Thr Thr Glu Lys Thr Ser Leu Glu Asp Ile
    1145                1150                1155

Asp Leu Gly Ser Gly Leu Phe Glu Lys Pro Lys Ala Thr Glu Leu
    1160                1165                1170

Ile Glu Phe Ser Thr Ile Lys Val Thr Val Pro Ser Asp Ile Thr
    1175                1180                1185

Thr Ala Phe Ser Ser Val Asp Arg Leu His Thr Thr Ser Ala Phe
    1190                1195                1200

Lys Pro Ser Ser Ala Ile Thr Lys Lys Pro Pro Leu Ile Asp Arg
    1205                1210                1215

Glu Pro Gly Glu Glu Thr Thr Ser Asp Met Val Ile Ile Gly Glu
    1220                1225                1230

Ser Thr Ser His Val Pro Pro Thr Thr Leu Glu Asp Ile Val Ala
    1235                1240                1245

Lys Glu Thr Glu Thr Asp Ile Asp Arg Glu Tyr Phe Thr Thr Ser
    1250                1255                1260

Ser Pro Pro Ala Thr Gln Pro Thr Arg Pro Pro Thr Val Glu Asp
    1265                1270                1275

Lys Glu Ala Phe Gly Pro Gln Ala Leu Ser Thr Pro Gln Pro Pro
    1280                1285                1290

Ala Ser Thr Lys Phe His Pro Asp Ile Asn Val Tyr Ile Ile Glu
    1295                1300                1305

Val Arg Glu Asn Lys Thr Gly Arg Met Ser Asp Leu Ser Val Ile
    1310                1315                1320

Gly His Pro Ile Asp Ser Glu Ser Lys Glu Asp Glu Pro Cys Ser
    1325                1330                1335

Glu Glu Thr Asp Pro Val His Asp Leu Met Ala Glu Ile Leu Pro
    1340                1345                1350
```

```
Glu Phe Pro Asp Ile Ile Glu Ile Asp Leu Tyr His Ser Glu Glu
1355                1360                1365

Asn Glu Glu Glu Glu Glu Cys Ala Asn Ala Thr Asp Val Thr
    1370                1375                1380

Thr Thr Pro Ser Val Gln Tyr Ile Asn Gly Lys His Leu Val Thr
    1385                1390                1395

Thr Val Pro Lys Asp Pro Glu Ala Ala Glu Ala Arg Arg Gly Gln
    1400                1405                1410

Phe Glu Ser Val Ala Pro Ser Gln Asn Phe Ser Asp Ser Ser Glu
    1415                1420                1425

Ser Asp Thr His Pro Phe Val Ile Ala Lys Thr Glu Leu Ser Thr
    1430                1435                1440

Ala Val Gln Pro Asn Glu Ser Thr Glu Thr Thr Glu Ser Leu Glu
    1445                1450                1455

Val Thr Trp Lys Pro Glu Thr Tyr Pro Glu Thr Ser Glu His Phe
    1460                1465                1470

Ser Gly Gly Glu Pro Asp Val Phe Pro Thr Val Pro Phe His Glu
    1475                1480                1485

Glu Phe Glu Ser Gly Thr Ala Lys Lys Gly Ala Glu Ser Val Thr
    1490                1495                1500

Glu Arg Asp Thr Glu Val Gly His Gln Ala His Glu His Thr Glu
    1505                1510                1515

Pro Val Ser Leu Phe Pro Glu Glu Ser Ser Gly Glu Ile Ala Ile
    1520                1525                1530

Asp Gln Glu Ser Gln Lys Ile Ala Phe Ala Arg Ala Thr Glu Val
    1535                1540                1545

Thr Phe Gly Glu Glu Val Glu Lys Ser Thr Ser Val Thr Tyr Thr
    1550                1555                1560

Pro Thr Ile Val Pro Ser Ser Ala Ser Ala Tyr Val Ser Glu Glu
    1565                1570                1575

Glu Ala Val Thr Leu Ile Gly Asn Pro Trp Pro Asp Asp Leu Leu
    1580                1585                1590

Ser Thr Lys Glu Ser Trp Val Glu Ala Thr Pro Arg Gln Val Val
    1595                1600                1605

Glu Leu Ser Gly Ser Ser Ser Ile Pro Ile Thr Glu Gly Ser Gly
    1610                1615                1620

Glu Ala Glu Glu Asp Glu Asp Thr Met Phe Thr Met Val Thr Asp
    1625                1630                1635

Leu Ser Gln Arg Asn Thr Thr Asp Thr Leu Ile Thr Leu Asp Thr
    1640                1645                1650

Ser Arg Ile Ile Thr Glu Ser Phe Phe Glu Val Pro Ala Thr Thr
    1655                1660                1665

Ile Tyr Pro Val Ser Glu Gln Pro Ser Ala Lys Val Val Pro Thr
    1670                1675                1680

Lys Phe Val Ser Glu Thr Asp Thr Ser Glu Trp Ile Ser Ser Thr
    1685                1690                1695

Thr Val Glu Glu Lys Lys Arg Lys Glu Glu Glu Gly Thr Thr Gly
    1700                1705                1710

Thr Ala Ser Thr Phe Glu Val Tyr Ser Ser Thr Gln Arg Ser Asp
    1715                1720                1725

Gln Leu Ile Leu Pro Phe Glu Leu Glu Ser Pro Asn Val Ala Thr
    1730                1735                1740

Ser Ser Asp Ser Gly Thr Arg Lys Ser Phe Met Ser Leu Thr Thr
```

-continued

```
                1745                1750                1755

Pro Thr Gln Ser Glu Arg Glu Met Thr Asp Ser Thr Pro Val Phe
        1760                1765                1770

Thr Glu Thr Asn Thr Leu Glu Asn Leu Gly Ala Gln Thr Thr Glu
        1775                1780                1785

His Ser Ser Ile His Gln Pro Gly Val Gln Glu Gly Leu Thr Thr
        1790                1795                1800

Leu Pro Arg Ser Pro Ala Ser Val Phe Met Glu Gln Gly Ser Gly
        1805                1810                1815

Glu Ala Ala Ala Asp Pro Glu Thr Thr Thr Val Ser Ser Phe Ser
        1820                1825                1830

Leu Asn Val Glu Tyr Ala Ile Gln Ala Glu Lys Glu Val Ala Gly
        1835                1840                1845

Thr Leu Ser Pro His Val Glu Thr Thr Phe Ser Thr Glu Pro Thr
        1850                1855                1860

Gly Leu Val Leu Ser Thr Val Met Asp Arg Val Val Ala Glu Asn
        1865                1870                1875

Ile Thr Gln Thr Ser Arg Glu Ile Val Ile Ser Glu Arg Leu Gly
        1880                1885                1890

Glu Pro Asn Tyr Gly Ala Glu Ile Arg Gly Phe Ser Thr Gly Phe
        1895                1900                1905

Pro Leu Glu Glu Asp Phe Ser Gly Asp Phe Arg Glu Tyr Ser Thr
        1910                1915                1920

Val Ser His Pro Ile Ala Lys Glu Glu Thr Val Met Met Glu Gly
        1925                1930                1935

Ser Gly Asp Ala Ala Phe Arg Asp Thr Gln Thr Ser Pro Ser Thr
        1940                1945                1950

Val Pro Thr Ser Val His Ile Ser His Ile Ser Asp Ser Glu Gly
        1955                1960                1965

Pro Ser Ser Thr Met Val Ser Thr Ser Ala Phe Pro Trp Glu Glu
        1970                1975                1980

Phe Thr Ser Ser Ala Glu Gly Ser Gly Glu Gln Leu Val Thr Val
        1985                1990                1995

Ser Ser Ser Val Val Pro Val Leu Pro Ser Ala Val Gln Lys Phe
        2000                2005                2010

Ser Gly Thr Ala Ser Ser Ile Ile Asp Glu Gly Leu Gly Glu Val
        2015                2020                2025

Gly Thr Val Asn Glu Ile Asp Arg Arg Ser Thr Ile Leu Pro Thr
        2030                2035                2040

Ala Glu Val Glu Gly Thr Lys Ala Pro Val Glu Lys Glu Glu Val
        2045                2050                2055

Lys Val Ser Gly Thr Val Ser Thr Asn Phe Pro Gln Thr Ile Glu
        2060                2065                2070

Pro Ala Lys Leu Trp Ser Arg Gln Glu Val Asn Pro Val Arg Gln
        2075                2080                2085

Glu Ile Glu Ser Glu Thr Thr Ser Glu Glu Gln Ile Gln Glu Glu
        2090                2095                2100

Lys Ser Phe Glu Ser Pro Gln Asn Ser Pro Ala Thr Glu Gln Thr
        2105                2110                2115

Ile Phe Asp Ser Gln Thr Phe Thr Glu Thr Glu Leu Lys Thr Thr
        2120                2125                2130

Asp Tyr Ser Val Leu Thr Thr Lys Lys Thr Tyr Ser Asp Asp Lys
        2135                2140                2145
```

-continued

```
Glu Met Lys Glu Glu Asp Thr Ser Leu Val Asn Met Ser Thr Pro
    2150                2155                2160

Asp Pro Asp Ala Asn Gly Leu Glu Ser Tyr Thr Thr Leu Pro Glu
    2165                2170                2175

Ala Thr Glu Lys Ser His Phe Phe Leu Ala Thr Ala Leu Val Thr
    2180                2185                2190

Glu Ser Ile Pro Ala Glu His Val Val Thr Asp Ser Pro Ile Lys
    2195                2200                2205

Lys Glu Glu Ser Thr Lys His Phe Pro Lys Gly Met Arg Pro Thr
    2210                2215                2220

Ile Gln Glu Ser Asp Thr Glu Leu Leu Phe Ser Gly Leu Gly Ser
    2225                2230                2235

Gly Glu Glu Val Leu Pro Thr Leu Pro Thr Glu Ser Val Asn Phe
    2240                2245                2250

Thr Glu Val Glu Gln Ile Asn Asn Thr Leu Tyr Pro His Thr Ser
    2255                2260                2265

Gln Val Glu Ser Thr Ser Ser Asp Lys Ile Glu Asp Phe Asn Arg
    2270                2275                2280

Met Glu Asn Val Ala Lys Glu Val Gly Pro Leu Val Ser Gln Thr
    2285                2290                2295

Asp Ile Phe Glu Gly Ser Gly Ser Val Thr Ser Thr Thr Leu Ile
    2300                2305                2310

Glu Ile Leu Ser Asp Thr Gly Ala Glu Gly Pro Thr Val Ala Pro
    2315                2320                2325

Leu Pro Phe Ser Thr Asp Ile Gly His Pro Gln Asn Gln Thr Val
    2330                2335                2340

Arg Trp Ala Glu Glu Ile Gln Thr Ser Arg Pro Gln Thr Ile Thr
    2345                2350                2355

Glu Gln Asp Ser Asn Lys Asn Ser Ser Thr Ala Glu Ile Asn Glu
    2360                2365                2370

Thr Thr Thr Ser Ser Thr Asp Phe Leu Ala Arg Ala Tyr Gly Phe
    2375                2380                2385

Glu Met Ala Lys Glu Phe Val Thr Ser Ala Pro Lys Pro Ser Asp
    2390                2395                2400

Leu Tyr Tyr Glu Pro Ser Gly Glu Gly Ser Gly Glu Val Asp Ile
    2405                2410                2415

Val Asp Ser Phe His Thr Ser Ala Thr Thr Gln Ala Thr Arg Gln
    2420                2425                2430

Glu Ser Ser Thr Thr Phe Val Ser Asp Gly Ser Leu Glu Lys His
    2435                2440                2445

Pro Glu Val Pro Ser Ala Lys Ala Val Thr Ala Asp Gly Phe Pro
    2450                2455                2460

Thr Val Ser Val Met Leu Pro Leu His Ser Glu Gln Asn Lys Ser
    2465                2470                2475

Ser Pro Asp Pro Thr Ser Thr Leu Ser Asn Thr Val Ser Tyr Glu
    2480                2485                2490

Arg Ser Thr Asp Gly Ser Phe Gln Asp Arg Phe Arg Glu Phe Glu
    2495                2500                2505

Asp Ser Thr Leu Lys Pro Asn Arg Lys Lys Pro Thr Glu Asn Ile
    2510                2515                2520

Ile Ile Asp Leu Asp Lys Glu Asp Lys Asp Leu Ile Leu Thr Ile
    2525                2530                2535
```

```
Thr Glu Ser Thr Ile Leu Glu Ile Leu Pro Glu Leu Thr Ser Asp
    2540                2545                2550

Lys Asn Thr Ile Ile Asp Ile Asp His Thr Lys Pro Val Tyr Glu
    2555                2560                2565

Asp Ile Leu Gly Met Gln Thr Asp Ile Asp Thr Glu Val Pro Ser
    2570                2575                2580

Glu Pro His Asp Ser Asn Asp Glu Ser Asn Asp Asp Ser Thr Gln
    2585                2590                2595

Val Gln Glu Ile Tyr Glu Ala Ala Val Asn Leu Ser Leu Thr Glu
    2600                2605                2610

Glu Thr Phe Glu Gly Ser Ala Asp Val Leu Ala Ser Tyr Thr Gln
    2615                2620                2625

Ala Thr His Asp Glu Ser Met Thr Tyr Glu Asp Arg Ser Gln Leu
    2630                2635                2640

Asp His Met Gly Phe His Phe Thr Thr Gly Ile Pro Ala Pro Ser
    2645                2650                2655

Thr Glu Thr Glu Leu Asp Val Leu Leu Pro Thr Ala Thr Ser Leu
    2660                2665                2670

Pro Ile Pro Arg Lys Ser Ala Thr Val Ile Pro Glu Ile Glu Gly
    2675                2680                2685

Ile Lys Ala Glu Ala Lys Ala Leu Asp Asp Met Phe Glu Ser Ser
    2690                2695                2700

Thr Leu Ser Asp Gly Gln Ala Ile Ala Asp Gln Ser Glu Ile Ile
    2705                2710                2715

Pro Thr Leu Gly Gln Phe Glu Arg Thr Gln Glu Glu Tyr Glu Asp
    2720                2725                2730

Lys Lys His Ala Gly Pro Ser Phe Gln Pro Glu Phe Ser Ser Gly
    2735                2740                2745

Ala Glu Glu Ala Leu Val Asp His Thr Pro Tyr Leu Ser Ile Ala
    2750                2755                2760

Thr Thr His Leu Met Asp Gln Ser Val Thr Glu Val Pro Asp Val
    2765                2770                2775

Met Glu Gly Ser Asn Pro Pro Tyr Tyr Thr Asp Thr Thr Leu Ala
    2780                2785                2790

Val Ser Thr Phe Ala Lys Leu Ser Ser Gln Thr Pro Ser Ser Pro
    2795                2800                2805

Leu Thr Ile Tyr Ser Gly Ser Glu Ala Ser Gly His Thr Glu Ile
    2810                2815                2820

Pro Gln Pro Ser Ala Leu Pro Gly Ile Asp Val Gly Ser Ser Val
    2825                2830                2835

Met Ser Pro Gln Asp Ser Phe Lys Glu Ile His Val Asn Ile Glu
    2840                2845                2850

Ala Thr Phe Lys Pro Ser Ser Glu Glu Tyr Leu His Ile Thr Glu
    2855                2860                2865

Pro Pro Ser Leu Ser Pro Asp Thr Lys Leu Glu Pro Ser Glu Asp
    2870                2875                2880

Asp Gly Lys Pro Glu Leu Leu Glu Glu Met Glu Ala Ser Pro Thr
    2885                2890                2895

Glu Leu Ile Ala Val Glu Gly Thr Glu Ile Leu Gln Asp Phe Gln
    2900                2905                2910

Asn Lys Thr Asp Gly Gln Val Ser Gly Glu Ala Ile Lys Met Phe
    2915                2920                2925

Pro Thr Ile Lys Thr Pro Glu Ala Gly Thr Val Ile Thr Thr Ala
```

```
              2930                2935                2940

Asp Glu Ile Glu Leu Glu Gly Ala Thr Gln Trp Pro His Ser Thr
         2945                2950                2955

Ser Ala Ser Ala Thr Tyr Gly Val Glu Ala Gly Val Val Pro Trp
         2960                2965                2970

Leu Ser Pro Gln Thr Ser Glu Arg Pro Thr Leu Ser Ser Ser Pro
         2975                2980                2985

Glu Ile Asn Pro Glu Thr Gln Ala Ala Leu Ile Arg Gly Gln Asp
         2990                2995                3000

Ser Thr Ile Ala Ala Ser Glu Gln Gln Val Ala Ala Arg Ile Leu
         3005                3010                3015

Asp Ser Asn Asp Gln Ala Thr Val Asn Pro Val Glu Phe Asn Thr
         3020                3025                3030

Glu Val Ala Thr Pro Pro Phe Ser Leu Leu Glu Thr Ser Asn Glu
         3035                3040                3045

Thr Asp Phe Leu Ile Gly Ile Asn Glu Glu Ser Val Glu Gly Thr
         3050                3055                3060

Ala Ile Tyr Leu Pro Gly Pro Asp Arg Cys Lys Met Asn Pro Cys
         3065                3070                3075

Leu Asn Gly Gly Thr Cys Tyr Pro Thr Glu Thr Ser Tyr Val Cys
         3080                3085                3090

Thr Cys Val Pro Gly Tyr Ser Gly Asp Gln Cys Glu Leu Asp Phe
         3095                3100                3105

Asp Glu Cys His Ser Asn Pro Cys Arg Asn Gly Ala Thr Cys Val
         3110                3115                3120

Asp Gly Phe Asn Thr Phe Arg Cys Leu Cys Leu Pro Ser Tyr Val
         3125                3130                3135

Gly Ala Leu Cys Glu Gln Asp Thr Glu Thr Cys Asp Tyr Gly Trp
         3140                3145                3150

His Lys Phe Gln Gly Gln Cys Tyr Lys Tyr Phe Ala His Arg Arg
         3155                3160                3165

Thr Trp Asp Ala Ala Glu Arg Glu Cys Arg Leu Gln Gly Ala His
         3170                3175                3180

Leu Thr Ser Ile Leu Ser His Glu Glu Gln Met Phe Val Asn Arg
         3185                3190                3195

Val Gly His Asp Tyr Gln Trp Ile Gly Leu Asn Asp Lys Met Phe
         3200                3205                3210

Glu His Asp Phe Arg Trp Thr Asp Gly Ser Thr Leu Gln Tyr Glu
         3215                3220                3225

Asn Trp Arg Pro Asn Gln Pro Asp Ser Phe Phe Ser Ala Gly Glu
         3230                3235                3240

Asp Cys Val Val Ile Ile Trp His Glu Asn Gly Gln Trp Asn Asp
         3245                3250                3255

Val Pro Cys Asn Tyr His Leu Thr Tyr Thr Cys Lys Lys Gly Thr
         3260                3265                3270

Val Ala Cys Gly Gln Pro Pro Val Val Glu Asn Ala Lys Thr Phe
         3275                3280                3285

Gly Lys Met Lys Pro Arg Tyr Glu Ile Asn Ser Leu Ile Arg Tyr
         3290                3295                3300

His Cys Lys Asp Gly Phe Ile Gln Arg His Leu Pro Thr Ile Arg
         3305                3310                3315

Cys Leu Gly Asn Gly Arg Trp Ala Ile Pro Lys Ile Thr Cys Met
         3320                3325                3330
```

Asn Pro Ser Ala Tyr Gln Arg Thr Tyr Ser Met Lys Tyr Phe Lys
    3335                3340                3345

Asn Ser Ser Ala Lys Asp Asn Ser Ile Asn Thr Ser Lys His
    3350                3355                3360

Asp His Arg Trp Ser Arg Arg Trp Gln Glu Ser Arg Arg
    3365                3370                3375

<210> SEQ ID NO 79
<211> LENGTH: 96
<212> TYPE: PRT
<213> ORGANISM: Homo sapiens

<400> SEQUENCE: 79

Val Val Phe His Tyr Arg Ala Ala Thr Ser Arg Tyr Thr Leu Asn Phe
1               5                   10                  15

Glu Ala Ala Gln Lys Ala Cys Leu Asp Val Gly Ala Val Ile Ala Thr
            20                  25                  30

Pro Glu Gln Leu Phe Ala Ala Tyr Glu Asp Gly Phe Glu Gln Cys Asp
        35                  40                  45

Ala Gly Trp Leu Ala Asp Gln Thr Val Arg Tyr Pro Ile Arg Ala Pro
    50                  55                  60

Arg Val Gly Cys Tyr Gly Asp Lys Met Gly Lys Ala Gly Val Arg Thr
65                  70                  75                  80

Tyr Gly Phe Arg Ser Pro Gln Glu Thr Tyr Asp Val Tyr Cys Tyr Val
                85                  90                  95

<210> SEQ ID NO 80
<211> LENGTH: 97
<212> TYPE: PRT
<213> ORGANISM: Homo sapiens

<400> SEQUENCE: 80

Asp Val Phe His Leu Thr Val Pro Ser Lys Phe Thr Phe Glu Glu Ala
1               5                   10                  15

Ala Lys Glu Cys Glu Asn Gln Asp Ala Arg Leu Ala Thr Val Gly Glu
            20                  25                  30

Leu Gln Ala Ala Trp Arg Asn Gly Phe Asp Gln Cys Asp Tyr Gly Trp
        35                  40                  45

Leu Ser Asp Ala Ser Val Arg His Pro Val Thr Val Ala Arg Ala Gln
    50                  55                  60

Cys Gly Gly Gly Leu Leu Gly Val Arg Thr Leu Tyr Arg Phe Glu Asn
65                  70                  75                  80

Gln Thr Gly Phe Pro Pro Pro Asp Ser Arg Phe Asp Ala Tyr Cys Phe
                85                  90                  95

Lys

<210> SEQ ID NO 81
<211> LENGTH: 1321
<212> TYPE: PRT
<213> ORGANISM: Homo sapiens

<400> SEQUENCE: 81

Met Gly Ala Pro Phe Val Trp Ala Leu Gly Leu Leu Met Leu Gln Met
1               5                   10                  15

Leu Leu Phe Val Ala Gly Glu Gln Gly Thr Gln Asp Ile Thr Asp Ala
            20                  25                  30

Ser Glu Arg Gly Leu His Met Gln Lys Leu Gly Ser Gly Ser Val Gln

```
                35                  40                  45
Ala Ala Leu Ala Glu Leu Val Ala Leu Pro Cys Leu Phe Thr Leu Gln
 50                  55                  60

Pro Arg Pro Ser Ala Ala Arg Asp Ala Pro Arg Ile Lys Trp Thr Lys
 65                  70                  75                  80

Val Arg Thr Ala Ser Gly Gln Arg Gln Asp Leu Pro Ile Leu Val Ala
                 85                  90                  95

Lys Asp Asn Val Val Arg Val Ala Lys Ser Trp Gln Gly Arg Val Ser
                100                 105                 110

Leu Pro Ser Tyr Pro Arg Arg Ala Asn Ala Thr Leu Leu Leu Gly
            115                 120                 125

Pro Leu Arg Ala Ser Asp Ser Gly Leu Tyr Arg Cys Gln Val Val Arg
130                 135                 140

Gly Ile Glu Asp Glu Gln Asp Leu Val Pro Leu Glu Val Thr Gly Val
145                 150                 155                 160

Val Phe His Tyr Arg Ser Ala Arg Asp Arg Tyr Ala Leu Thr Phe Ala
                165                 170                 175

Glu Ala Gln Glu Ala Cys Arg Leu Ser Ser Ala Ile Ile Ala Ala Pro
                180                 185                 190

Arg His Leu Gln Ala Ala Phe Glu Asp Gly Phe Asp Asn Cys Asp Ala
            195                 200                 205

Gly Trp Leu Ser Asp Arg Thr Val Arg Tyr Pro Ile Thr Gln Ser Arg
210                 215                 220

Pro Gly Cys Tyr Gly Asp Arg Ser Ser Leu Pro Gly Val Arg Ser Tyr
225                 230                 235                 240

Gly Arg Arg Asn Pro Gln Glu Leu Tyr Asp Val Tyr Cys Phe Ala Arg
                245                 250                 255

Glu Leu Gly Gly Glu Val Phe Tyr Val Gly Pro Ala Arg Arg Leu Thr
                260                 265                 270

Leu Ala Gly Ala Arg Ala Gln Cys Arg Arg Gln Gly Ala Ala Leu Ala
            275                 280                 285

Ser Val Gly Gln Leu His Leu Ala Trp His Glu Gly Leu Asp Gln Cys
290                 295                 300

Asp Pro Gly Trp Leu Ala Asp Gly Ser Val Arg Tyr Pro Ile Gln Thr
305                 310                 315                 320

Pro Arg Arg Arg Cys Gly Gly Pro Ala Pro Gly Val Arg Thr Val Tyr
                325                 330                 335

Arg Phe Ala Asn Arg Thr Gly Phe Pro Ser Pro Ala Glu Arg Phe Asp
                340                 345                 350

Ala Tyr Cys Phe Arg Ala His His Pro Thr Ser Gln His Gly Asp Leu
            355                 360                 365

Glu Thr Pro Ser Ser Gly Asp Glu Gly Glu Ile Leu Ser Ala Glu Gly
        370                 375                 380

Pro Pro Val Arg Glu Leu Glu Pro Thr Leu Glu Glu Glu Val Val
385                 390                 395                 400

Thr Pro Asp Phe Gln Glu Pro Leu Val Ser Ser Gly Glu Glu Thr
                405                 410                 415

Leu Ile Leu Glu Glu Lys Gln Glu Ser Gln Gln Thr Leu Ser Pro Thr
                420                 425                 430

Pro Gly Asp Pro Met Leu Ala Ser Trp Pro Thr Gly Glu Val Trp Leu
            435                 440                 445

Ser Thr Val Ala Pro Ser Pro Ser Asp Met Gly Ala Gly Thr Ala Ala
450                 455                 460
```

```
Ser Ser His Thr Glu Val Ala Pro Thr Asp Pro Met Pro Arg Arg
465                 470                 475                 480

Gly Arg Phe Lys Gly Leu Asn Gly Arg Tyr Phe Gln Gln Gln Glu Pro
                485                 490                 495

Glu Pro Gly Leu Gln Gly Gly Met Glu Ala Ser Ala Gln Pro Pro Thr
            500                 505                 510

Ser Glu Ala Ala Val Asn Gln Met Glu Pro Pro Leu Ala Met Ala Val
        515                 520                 525

Thr Glu Met Leu Gly Ser Gly Gln Ser Arg Ser Pro Trp Ala Asp Leu
    530                 535                 540

Thr Asn Glu Val Asp Met Pro Gly Ala Gly Ser Ala Gly Gly Lys Ser
545                 550                 555                 560

Ser Pro Glu Pro Trp Leu Trp Pro Pro Thr Met Val Pro Pro Ser Ile
                565                 570                 575

Ser Gly His Ser Arg Ala Pro Val Leu Glu Leu Glu Lys Ala Glu Gly
            580                 585                 590

Pro Ser Ala Arg Pro Ala Thr Pro Asp Leu Phe Trp Ser Pro Leu Glu
        595                 600                 605

Ala Thr Val Ser Ala Pro Ser Pro Ala Pro Trp Glu Ala Phe Pro Val
    610                 615                 620

Ala Thr Ser Pro Asp Leu Pro Met Met Ala Met Leu Arg Gly Pro Lys
625                 630                 635                 640

Glu Trp Met Leu Pro His Pro Thr Pro Ile Ser Thr Glu Ala Asn Arg
                645                 650                 655

Val Glu Ala His Gly Glu Ala Thr Ala Thr Ala Pro Pro Ser Pro Ala
            660                 665                 670

Ala Glu Thr Lys Val Tyr Ser Leu Pro Leu Ser Leu Thr Pro Thr Gly
        675                 680                 685

Gln Gly Gly Glu Ala Met Pro Thr Thr Pro Glu Ser Pro Arg Ala Asp
    690                 695                 700

Phe Arg Glu Thr Gly Glu Thr Ser Pro Ala Gln Val Asn Lys Ala Glu
705                 710                 715                 720

His Ser Ser Ser Ser Pro Trp Pro Ser Val Asn Arg Asn Val Ala Val
                725                 730                 735

Gly Phe Val Pro Thr Glu Thr Ala Thr Glu Pro Thr Gly Leu Arg Gly
            740                 745                 750

Ile Pro Gly Ser Glu Ser Gly Val Phe Asp Thr Ala Glu Ser Pro Thr
        755                 760                 765

Ser Gly Leu Gln Ala Thr Val Asp Glu Val Gln Asp Pro Trp Pro Ser
    770                 775                 780

Val Tyr Ser Lys Gly Leu Asp Ala Ser Ser Pro Ser Ala Pro Leu Gly
785                 790                 795                 800

Ser Pro Gly Val Phe Leu Val Pro Lys Val Thr Pro Asn Leu Glu Pro
                805                 810                 815

Trp Val Ala Thr Asp Glu Gly Pro Thr Val Asn Pro Met Asp Ser Thr
            820                 825                 830

Val Thr Pro Ala Pro Ser Asp Ala Ser Gly Ile Trp Glu Pro Gly Ser
        835                 840                 845

Gln Val Phe Glu Glu Ala Glu Ser Thr Thr Leu Ser Pro Gln Val Ala
    850                 855                 860

Leu Asp Thr Ser Ile Val Thr Pro Leu Thr Thr Leu Glu Gln Gly Asp
865                 870                 875                 880
```

```
Lys Val Gly Val Pro Ala Met Ser Thr Leu Gly Ser Ser Ser Gln
                885                 890                 895

Pro His Pro Glu Pro Glu Asp Gln Val Glu Thr Gln Gly Thr Ser Gly
        900                 905                 910

Ala Ser Val Pro Pro His Gln Ser Ser Pro Leu Gly Lys Pro Ala Val
            915                 920                 925

Pro Pro Gly Thr Pro Thr Ala Ala Ser Val Gly Glu Ser Ala Ser Val
        930                 935                 940

Ser Ser Gly Glu Pro Thr Val Pro Trp Asp Pro Ser Ser Thr Leu Leu
945                 950                 955                 960

Pro Val Thr Leu Gly Ile Glu Asp Phe Glu Leu Glu Val Leu Ala Gly
                965                 970                 975

Ser Pro Gly Val Glu Ser Phe Trp Glu Glu Val Ala Ser Gly Glu Glu
                980                 985                 990

Pro Ala Leu Pro Gly Thr Pro Met Asn Ala Gly Ala Glu Glu Val His
            995                 1000                1005

Ser Asp Pro Cys Glu Asn Asn Pro Cys Leu His Gly Gly Thr Cys
    1010                1015                1020

Asn Ala Asn Gly Thr Met Tyr Gly Cys Ser Cys Asp Gln Gly Phe
    1025                1030                1035

Ala Gly Glu Asn Cys Glu Ile Asp Ile Asp Asp Cys Leu Cys Ser
    1040                1045                1050

Pro Cys Glu Asn Gly Gly Thr Cys Ile Asp Glu Val Asn Gly Phe
    1055                1060                1065

Val Cys Leu Cys Leu Pro Ser Tyr Gly Gly Ser Phe Cys Glu Lys
    1070                1075                1080

Asp Thr Glu Gly Cys Asp Arg Gly Trp His Lys Phe Gln Gly His
    1085                1090                1095

Cys Tyr Arg Tyr Phe Ala His Arg Arg Ala Trp Glu Asp Ala Glu
    1100                1105                1110

Lys Asp Cys Arg Arg Arg Ser Gly His Leu Thr Ser Val His Ser
    1115                1120                1125

Pro Glu Glu His Ser Phe Ile Asn Ser Phe Gly His Glu Asn Thr
    1130                1135                1140

Trp Ile Gly Leu Asn Asp Arg Ile Val Glu Arg Asp Phe Gln Trp
    1145                1150                1155

Thr Asp Asn Thr Gly Leu Gln Phe Glu Asn Trp Arg Glu Asn Gln
    1160                1165                1170

Pro Asp Asn Phe Phe Ala Gly Gly Glu Asp Cys Val Val Met Val
    1175                1180                1185

Ala His Glu Ser Gly Arg Trp Asn Asp Val Pro Cys Asn Tyr Asn
    1190                1195                1200

Leu Pro Tyr Val Cys Lys Lys Gly Thr Val Leu Cys Gly Pro Pro
    1205                1210                1215

Pro Ala Val Glu Asn Ala Ser Leu Ile Gly Ala Arg Lys Ala Lys
    1220                1225                1230

Tyr Asn Val His Ala Thr Val Arg Tyr Gln Cys Asn Glu Gly Phe
    1235                1240                1245

Ala Gln His His Val Ala Thr Ile Arg Cys Arg Ser Asn Gly Lys
    1250                1255                1260

Trp Asp Arg Pro Gln Ile Val Cys Thr Lys Pro Arg Arg Ser His
    1265                1270                1275

Arg Met Arg Arg His His His His His Gln His His Gln His
```

```
                      1280                1285                1290
His His His Lys Ser Arg Lys Glu Arg Arg Lys His Lys Lys His
              1295                1300                1305

Pro Thr Glu Asp Trp Glu Lys Asp Glu Gly Asn Phe Cys
    1310                1315                1320

<210> SEQ ID NO 82
<211> LENGTH: 1299
<212> TYPE: PRT
<213> ORGANISM: Homo sapiens

<400> SEQUENCE: 82

Glu Gln Gly Thr Gln Asp Ile Thr Asp Ala Ser Glu Arg Gly Leu His
1               5                   10                  15

Met Gln Lys Leu Gly Ser Gly Ser Val Gln Ala Ala Leu Ala Glu Leu
            20                  25                  30

Val Ala Leu Pro Cys Leu Phe Thr Leu Gln Pro Arg Pro Ser Ala Ala
        35                  40                  45

Arg Asp Ala Pro Arg Ile Lys Trp Thr Lys Val Arg Thr Ala Ser Gly
    50                  55                  60

Gln Arg Gln Asp Leu Pro Ile Leu Val Ala Lys Asp Asn Val Val Arg
65                  70                  75                  80

Val Ala Lys Ser Trp Gln Gly Arg Val Ser Leu Pro Ser Tyr Pro Arg
                85                  90                  95

Arg Arg Ala Asn Ala Thr Leu Leu Leu Gly Pro Leu Arg Ala Ser Asp
            100                 105                 110

Ser Gly Leu Tyr Arg Cys Gln Val Val Arg Gly Ile Glu Asp Glu Gln
        115                 120                 125

Asp Leu Val Pro Leu Glu Val Thr Gly Val Val Phe His Tyr Arg Ser
    130                 135                 140

Ala Arg Asp Arg Tyr Ala Leu Thr Phe Ala Glu Ala Gln Glu Ala Cys
145                 150                 155                 160

Arg Leu Ser Ser Ala Ile Ile Ala Ala Pro Arg His Leu Gln Ala Ala
                165                 170                 175

Phe Glu Asp Gly Phe Asp Asn Cys Asp Ala Gly Trp Leu Ser Asp Arg
            180                 185                 190

Thr Val Arg Tyr Pro Ile Thr Gln Ser Arg Pro Gly Cys Tyr Gly Asp
        195                 200                 205

Arg Ser Ser Leu Pro Gly Val Arg Ser Tyr Gly Arg Arg Asn Pro Gln
    210                 215                 220

Glu Leu Tyr Asp Val Tyr Cys Phe Ala Arg Glu Leu Gly Gly Glu Val
225                 230                 235                 240

Phe Tyr Val Gly Pro Ala Arg Arg Leu Thr Leu Ala Gly Ala Arg Ala
                245                 250                 255

Gln Cys Arg Arg Gln Gly Ala Ala Leu Ala Ser Val Gly Gln Leu His
            260                 265                 270

Leu Ala Trp His Glu Gly Leu Asp Gln Cys Asp Pro Gly Trp Leu Ala
        275                 280                 285

Asp Gly Ser Val Arg Tyr Pro Ile Gln Thr Pro Arg Arg Arg Cys Gly
    290                 295                 300

Gly Pro Ala Pro Gly Val Arg Thr Val Tyr Arg Phe Ala Asn Arg Thr
305                 310                 315                 320

Gly Phe Pro Ser Pro Ala Glu Arg Phe Asp Ala Tyr Cys Phe Arg Ala
                325                 330                 335
```

His His Pro Thr Ser Gln His Gly Asp Leu Glu Thr Pro Ser Ser Gly
                340                 345                 350

Asp Glu Gly Glu Ile Leu Ser Ala Gly Pro Pro Val Arg Glu Leu
            355                 360                 365

Glu Pro Thr Leu Glu Glu Glu Val Val Thr Pro Asp Phe Gln Glu
        370                 375                 380

Pro Leu Val Ser Ser Gly Glu Glu Thr Leu Ile Leu Glu Glu Lys
385                 390                 395                 400

Gln Glu Ser Gln Gln Thr Leu Ser Pro Thr Pro Gly Asp Pro Met Leu
                405                 410                 415

Ala Ser Trp Pro Thr Gly Glu Val Trp Leu Ser Thr Val Ala Pro Ser
                420                 425                 430

Pro Ser Asp Met Gly Ala Gly Thr Ala Ala Ser Ser His Thr Glu Val
            435                 440                 445

Ala Pro Thr Asp Pro Met Pro Arg Arg Gly Arg Phe Lys Gly Leu
        450                 455                 460

Asn Gly Arg Tyr Phe Gln Gln Glu Pro Glu Pro Gly Leu Gln Gly
465                 470                 475                 480

Gly Met Glu Ala Ser Ala Gln Pro Pro Thr Ser Glu Ala Ala Val Asn
                485                 490                 495

Gln Met Glu Pro Pro Leu Ala Met Ala Val Thr Glu Met Leu Gly Ser
            500                 505                 510

Gly Gln Ser Arg Ser Pro Trp Ala Asp Leu Thr Asn Glu Val Asp Met
        515                 520                 525

Pro Gly Ala Gly Ser Ala Gly Gly Lys Ser Ser Pro Glu Pro Trp Leu
    530                 535                 540

Trp Pro Pro Thr Met Val Pro Pro Ser Ile Ser Gly His Ser Arg Ala
545                 550                 555                 560

Pro Val Leu Glu Leu Glu Lys Ala Glu Gly Pro Ser Ala Arg Pro Ala
                565                 570                 575

Thr Pro Asp Leu Phe Trp Ser Pro Leu Glu Ala Thr Val Ser Ala Pro
            580                 585                 590

Ser Pro Ala Pro Trp Glu Ala Phe Pro Val Ala Thr Ser Pro Asp Leu
        595                 600                 605

Pro Met Met Ala Met Leu Arg Gly Pro Lys Glu Trp Met Leu Pro His
    610                 615                 620

Pro Thr Pro Ile Ser Thr Glu Ala Asn Arg Val Glu Ala His Gly Glu
625                 630                 635                 640

Ala Thr Ala Thr Ala Pro Pro Ser Pro Ala Ala Glu Thr Lys Val Tyr
                645                 650                 655

Ser Leu Pro Leu Ser Leu Thr Pro Thr Gly Gln Gly Gly Glu Ala Met
            660                 665                 670

Pro Thr Thr Pro Glu Ser Pro Arg Ala Asp Phe Arg Glu Thr Gly Glu
        675                 680                 685

Thr Ser Pro Ala Gln Val Asn Lys Ala Glu His Ser Ser Ser Ser Pro
    690                 695                 700

Trp Pro Ser Val Asn Arg Asn Val Ala Val Gly Phe Val Pro Thr Glu
705                 710                 715                 720

Thr Ala Thr Glu Pro Thr Gly Leu Arg Gly Ile Pro Gly Ser Glu Ser
                725                 730                 735

Gly Val Phe Asp Thr Ala Glu Ser Pro Thr Ser Gly Leu Gln Ala Thr
            740                 745                 750

Val Asp Glu Val Gln Asp Pro Trp Pro Ser Val Tyr Ser Lys Gly Leu

```
              755                 760                 765
Asp Ala Ser Ser Pro Ser Ala Pro Leu Gly Ser Pro Gly Val Phe Leu
            770                 775                 780
Val Pro Lys Val Thr Pro Asn Leu Glu Pro Trp Val Ala Thr Asp Glu
785                 790                 795                 800
Gly Pro Thr Val Asn Pro Met Asp Ser Thr Val Thr Pro Ala Pro Ser
            805                 810                 815
Asp Ala Ser Gly Ile Trp Glu Pro Gly Ser Gln Val Phe Glu Glu Ala
            820                 825                 830
Glu Ser Thr Thr Leu Ser Pro Gln Val Ala Leu Asp Thr Ser Ile Val
            835                 840                 845
Thr Pro Leu Thr Thr Leu Glu Gln Gly Asp Lys Val Gly Val Pro Ala
850                 855                 860
Met Ser Thr Leu Gly Ser Ser Ser Gln Pro His Pro Glu Pro Glu
865                 870                 875                 880
Asp Gln Val Glu Thr Gln Gly Thr Ser Gly Ala Ser Val Pro Pro His
            885                 890                 895
Gln Ser Ser Pro Leu Gly Lys Pro Ala Val Pro Pro Gly Thr Pro Thr
            900                 905                 910
Ala Ala Ser Val Gly Glu Ser Ala Val Ser Ser Gly Glu Pro Thr
            915                 920                 925
Val Pro Trp Asp Pro Ser Ser Thr Leu Leu Pro Val Thr Leu Gly Ile
930                 935                 940
Glu Asp Phe Glu Leu Glu Val Leu Ala Gly Ser Pro Gly Val Glu Ser
945                 950                 955                 960
Phe Trp Glu Glu Val Ala Ser Gly Glu Pro Ala Leu Pro Gly Thr
            965                 970                 975
Pro Met Asn Ala Gly Ala Glu Glu Val His Ser Asp Pro Cys Glu Asn
            980                 985                 990
Asn Pro Cys Leu His Gly Gly Thr Cys Asn Ala Asn Gly Thr Met Tyr
            995                 1000                1005
Gly Cys Ser Cys Asp Gln Gly Phe Ala Gly Glu Asn Cys Glu Ile
            1010                1015                1020
Asp Ile Asp Asp Cys Leu Cys Ser Pro Cys Glu Asn Gly Gly Thr
            1025                1030                1035
Cys Ile Asp Glu Val Asn Gly Phe Val Cys Leu Cys Leu Pro Ser
            1040                1045                1050
Tyr Gly Gly Ser Phe Cys Glu Lys Asp Thr Glu Gly Cys Asp Arg
            1055                1060                1065
Gly Trp His Lys Phe Gln Gly His Cys Tyr Arg Tyr Phe Ala His
            1070                1075                1080
Arg Arg Ala Trp Glu Asp Ala Glu Lys Asp Cys Arg Arg Arg Ser
            1085                1090                1095
Gly His Leu Thr Ser Val His Ser Pro Glu Glu His Ser Phe Ile
            1100                1105                1110
Asn Ser Phe Gly His Glu Asn Thr Trp Ile Gly Leu Asn Asp Arg
            1115                1120                1125
Ile Val Glu Arg Asp Phe Gln Trp Thr Asp Asn Thr Gly Leu Gln
            1130                1135                1140
Phe Glu Asn Trp Arg Glu Asn Gln Pro Asp Asn Phe Phe Ala Gly
            1145                1150                1155
Gly Glu Asp Cys Val Val Met Val Ala His Glu Ser Gly Arg Trp
            1160                1165                1170
```

-continued

Asn Asp Val Pro Cys Asn Tyr Asn Leu Pro Tyr Val Cys Lys Lys
1175                 1180                1185

Gly Thr Val Leu Cys Gly Pro Pro Ala Val Glu Asn Ala Ser
    1190            1195             1200

Leu Ile Gly Ala Arg Lys Ala Lys Tyr Asn Val His Ala Thr Val
    1205                1210                1215

Arg Tyr Gln Cys Asn Glu Gly Phe Ala Gln His His Val Ala Thr
    1220                1225                1230

Ile Arg Cys Arg Ser Asn Gly Lys Trp Asp Arg Pro Gln Ile Val
1235                 1240                1245

Cys Thr Lys Pro Arg Arg Ser His Arg Met Arg Arg His His His
    1250                1255                1260

His His Gln His His His Gln His His His His Lys Ser Arg Lys
1265                 1270                1275

Glu Arg Arg Lys His Lys Lys His Pro Thr Glu Asp Trp Glu Lys
    1280                1285                1290

Asp Glu Gly Asn Phe Cys
    1295

<210> SEQ ID NO 83
<211> LENGTH: 96
<212> TYPE: PRT
<213> ORGANISM: Homo sapiens

<400> SEQUENCE: 83

Val Val Phe His Tyr Arg Ser Ala Arg Asp Tyr Ala Leu Thr Phe
1               5                   10                  15

Ala Glu Ala Gln Glu Ala Cys Arg Leu Ser Ser Ala Ile Ile Ala Ala
                20                  25                  30

Pro Arg His Leu Gln Ala Ala Phe Glu Asp Gly Phe Asp Asn Cys Asp
            35                  40                  45

Ala Gly Trp Leu Ser Asp Arg Thr Val Arg Tyr Pro Ile Thr Gln Ser
        50                  55                  60

Arg Pro Gly Cys Tyr Gly Asp Arg Ser Ser Leu Pro Gly Val Arg Ser
65                  70                  75                  80

Tyr Gly Arg Arg Asn Pro Gln Glu Leu Tyr Asp Val Tyr Cys Phe Ala
                85                  90                  95

<210> SEQ ID NO 84
<211> LENGTH: 99
<212> TYPE: PRT
<213> ORGANISM: Homo sapiens

<400> SEQUENCE: 84

Gly Gly Glu Val Phe Tyr Val Gly Pro Ala Arg Arg Leu Thr Leu Ala
1               5                   10                  15

Gly Ala Arg Ala Gln Cys Arg Arg Gln Gly Ala Ala Leu Ala Ser Val
                20                  25                  30

Gly Gln Leu His Leu Ala Trp His Glu Gly Leu Asp Gln Cys Asp Pro
            35                  40                  45

Gly Trp Leu Ala Asp Gly Ser Val Arg Tyr Pro Ile Gln Thr Pro Arg
        50                  55                  60

Arg Arg Cys Gly Gly Pro Ala Pro Gly Val Arg Thr Val Tyr Arg Phe
65                  70                  75                  80

Ala Asn Arg Thr Gly Phe Pro Ser Pro Ala Glu Arg Phe Asp Ala Tyr
                85                  90                  95

Cys Phe Arg

<210> SEQ ID NO 85
<211> LENGTH: 911
<212> TYPE: PRT
<213> ORGANISM: Homo sapiens

<400> SEQUENCE: 85

| Met | Ala | Gln | Leu | Phe | Pro | Leu | Leu | Ala | Leu | Val | Leu | Ala | Gln |
| 1 | | | | 5 | | | | | 10 | | | | 15 |

| Ala | Pro | Ala | Ala | Leu | Ala | Asp | Val | Leu | Glu | Gly | Asp | Ser | Ser | Glu | Asp |
| | | | 20 | | | | | 25 | | | | | 30 | | |

| Arg | Ala | Phe | Arg | Val | Arg | Ile | Ala | Gly | Asp | Ala | Pro | Leu | Gln | Gly | Val |
| | | | 35 | | | | | 40 | | | | | 45 | | |

| Leu | Gly | Gly | Ala | Leu | Thr | Ile | Pro | Cys | His | Val | His | Tyr | Leu | Arg | Pro |
| | 50 | | | | | 55 | | | | | 60 | | | | |

| Pro | Pro | Ser | Arg | Arg | Ala | Val | Leu | Gly | Ser | Pro | Arg | Val | Lys | Trp | Thr |
| 65 | | | | | 70 | | | | | 75 | | | | | 80 |

| Phe | Leu | Ser | Arg | Gly | Arg | Glu | Ala | Glu | Val | Leu | Val | Ala | Arg | Gly | Val |
| | | | | 85 | | | | | 90 | | | | | 95 | |

| Arg | Val | Lys | Val | Asn | Glu | Ala | Tyr | Arg | Phe | Arg | Val | Ala | Leu | Pro | Ala |
| | | | 100 | | | | | 105 | | | | | 110 | | |

| Tyr | Pro | Ala | Ser | Leu | Thr | Asp | Val | Ser | Leu | Ala | Leu | Ser | Glu | Leu | Arg |
| | | | 115 | | | | | 120 | | | | | 125 | | |

| Pro | Asn | Asp | Ser | Gly | Ile | Tyr | Arg | Cys | Glu | Val | Gln | His | Gly | Ile | Asp |
| | | 130 | | | | | 135 | | | | | 140 | | | |

| Asp | Ser | Ser | Asp | Ala | Val | Glu | Val | Lys | Val | Lys | Gly | Val | Val | Phe | Leu |
| 145 | | | | | 150 | | | | | 155 | | | | | 160 |

| Tyr | Arg | Glu | Gly | Ser | Ala | Arg | Tyr | Ala | Phe | Ser | Phe | Ser | Gly | Ala | Gln |
| | | | | 165 | | | | | 170 | | | | | 175 | |

| Glu | Ala | Cys | Ala | Arg | Ile | Gly | Ala | His | Ile | Ala | Thr | Pro | Glu | Gln | Leu |
| | | | 180 | | | | | 185 | | | | | 190 | | |

| Tyr | Ala | Ala | Tyr | Leu | Gly | Gly | Tyr | Glu | Gln | Cys | Asp | Ala | Gly | Trp | Leu |
| | | | 195 | | | | | 200 | | | | | 205 | | |

| Ser | Asp | Gln | Thr | Val | Arg | Tyr | Pro | Ile | Gln | Thr | Pro | Arg | Glu | Ala | Cys |
| | | 210 | | | | | 215 | | | | | 220 | | | |

| Tyr | Gly | Asp | Met | Asp | Gly | Phe | Pro | Gly | Val | Arg | Asn | Tyr | Gly | Val | Val |
| 225 | | | | | 230 | | | | | 235 | | | | | 240 |

| Asp | Pro | Asp | Asp | Leu | Tyr | Asp | Val | Tyr | Cys | Tyr | Ala | Glu | Asp | Leu | Asn |
| | | | | 245 | | | | | 250 | | | | | 255 | |

| Gly | Glu | Leu | Phe | Leu | Gly | Asp | Pro | Pro | Glu | Lys | Leu | Thr | Leu | Glu | Glu |
| | | | 260 | | | | | 265 | | | | | 270 | | |

| Ala | Arg | Ala | Tyr | Cys | Gln | Glu | Arg | Gly | Ala | Glu | Ile | Ala | Thr | Thr | Gly |
| | | | 275 | | | | | 280 | | | | | 285 | | |

| Gln | Leu | Tyr | Ala | Ala | Trp | Asp | Gly | Gly | Leu | Asp | His | Cys | Ser | Pro | Gly |
| | | 290 | | | | | 295 | | | | | 300 | | | |

| Trp | Leu | Ala | Asp | Gly | Ser | Val | Arg | Tyr | Pro | Ile | Val | Thr | Pro | Ser | Gln |
| 305 | | | | | 310 | | | | | 315 | | | | | 320 |

| Arg | Cys | Gly | Gly | Gly | Leu | Pro | Gly | Val | Lys | Thr | Leu | Phe | Leu | Phe | Pro |
| | | | | 325 | | | | | 330 | | | | | 335 | |

| Asn | Gln | Thr | Gly | Phe | Pro | Asn | Lys | His | Ser | Arg | Phe | Asn | Val | Tyr | Cys |
| | | | 340 | | | | | 345 | | | | | 350 | | |

| Phe | Arg | Asp | Ser | Ala | Gln | Pro | Ser | Ala | Ile | Pro | Glu | Ala | Ser | Asn | Pro |
| | | | 355 | | | | | 360 | | | | | 365 | | |

```
Ala Ser Asn Pro Ala Ser Asp Gly Leu Glu Ala Ile Val Thr Val Thr
    370                 375                 380
Glu Thr Leu Glu Glu Leu Gln Leu Pro Gln Glu Ala Thr Glu Ser Glu
385                 390                 395                 400
Ser Arg Gly Ala Ile Tyr Ser Ile Pro Ile Met Glu Asp Gly Gly Gly
                405                 410                 415
Gly Ser Ser Thr Pro Glu Asp Pro Ala Glu Ala Pro Arg Thr Leu Leu
            420                 425                 430
Glu Phe Glu Thr Gln Ser Met Val Pro Pro Thr Gly Phe Ser Glu Glu
        435                 440                 445
Glu Gly Lys Ala Leu Glu Glu Glu Lys Tyr Glu Asp Glu Glu Glu
    450                 455                 460
Lys Glu Glu Glu Glu Glu Glu Val Glu Asp Glu Ala Leu Trp
465                 470                 475                 480
Ala Trp Pro Ser Glu Leu Ser Ser Pro Gly Pro Glu Ala Ser Leu Pro
                485                 490                 495
Thr Glu Pro Ala Ala Gln Glu Glu Ser Leu Ser Gln Ala Pro Ala Arg
            500                 505                 510
Ala Val Leu Gln Pro Gly Ala Ser Pro Leu Pro Asp Gly Glu Ser Glu
        515                 520                 525
Ala Ser Arg Pro Pro Arg Val His Gly Pro Pro Thr Glu Thr Leu Pro
    530                 535                 540
Thr Pro Arg Glu Arg Asn Leu Ala Ser Pro Ser Pro Ser Thr Leu Val
545                 550                 555                 560
Glu Ala Arg Glu Val Gly Glu Ala Thr Gly Pro Glu Leu Ser Gly
                565                 570                 575
Val Pro Arg Gly Glu Ser Glu Glu Thr Gly Ser Ser Glu Gly Ala Pro
            580                 585                 590
Ser Leu Leu Pro Ala Thr Arg Ala Pro Glu Gly Thr Arg Glu Leu Glu
        595                 600                 605
Ala Pro Ser Glu Asp Asn Ser Gly Arg Thr Ala Pro Ala Gly Thr Ser
    610                 615                 620
Val Gln Ala Gln Pro Val Leu Pro Thr Asp Ser Ala Ser Arg Gly Gly
625                 630                 635                 640
Val Ala Val Pro Ala Ser Gly Asp Cys Val Pro Ser Pro Cys His
                645                 650                 655
Asn Gly Gly Thr Cys Leu Glu Glu Glu Gly Val Arg Cys Leu Cys
            660                 665                 670
Leu Pro Gly Tyr Gly Gly Asp Leu Cys Asp Val Gly Leu Arg Phe Cys
        675                 680                 685
Asn Pro Gly Trp Asp Ala Phe Gln Gly Ala Cys Tyr Lys His Phe Ser
    690                 695                 700
Thr Arg Arg Ser Trp Glu Glu Ala Glu Thr Gln Cys Arg Met Tyr Gly
705                 710                 715                 720
Ala His Leu Ala Ser Ile Ser Thr Pro Glu Glu Gln Asp Phe Ile Asn
                725                 730                 735
Asn Arg Tyr Arg Glu Tyr Gln Trp Ile Gly Leu Asn Asp Arg Thr Ile
            740                 745                 750
Glu Gly Asp Phe Leu Trp Ser Asp Gly Val Pro Leu Leu Tyr Glu Asn
        755                 760                 765
Trp Asn Pro Gly Gln Pro Asp Ser Tyr Phe Leu Ser Gly Glu Asn Cys
    770                 775                 780
```

```
Val Val Met Val Trp His Asp Gln Gly Gln Trp Ser Asp Val Pro Cys
785                 790                 795                 800

Asn Tyr His Leu Ser Tyr Thr Cys Lys Met Gly Leu Val Ser Cys Gly
            805                 810                 815

Pro Pro Pro Glu Leu Pro Leu Ala Gln Val Phe Gly Arg Pro Arg Leu
        820                 825                 830

Arg Tyr Glu Val Asp Thr Val Leu Arg Tyr Arg Cys Arg Glu Gly Leu
        835                 840                 845

Ala Gln Arg Asn Leu Pro Leu Ile Arg Cys Gln Glu Asn Gly Arg Trp
    850                 855                 860

Glu Ala Pro Gln Ile Ser Cys Val Pro Arg Arg Pro Ala Arg Ala Leu
865                 870                 875                 880

His Pro Glu Glu Asp Pro Glu Gly Arg Gln Gly Arg Leu Leu Gly Arg
                885                 890                 895

Trp Lys Ala Leu Leu Ile Pro Pro Ser Ser Pro Met Pro Gly Pro
                900                 905                 910

<210> SEQ ID NO 86
<211> LENGTH: 889
<212> TYPE: PRT
<213> ORGANISM: Homo sapiens

<400> SEQUENCE: 86

Asp Val Leu Glu Gly Asp Ser Glu Asp Arg Ala Phe Arg Val Arg
1               5                   10                  15

Ile Ala Gly Asp Ala Pro Leu Gln Gly Val Leu Gly Gly Ala Leu Thr
            20                  25                  30

Ile Pro Cys His Val His Tyr Leu Arg Pro Pro Ser Arg Arg Ala
            35                  40                  45

Val Leu Gly Ser Pro Arg Val Lys Trp Thr Phe Leu Ser Arg Gly Arg
    50                  55                  60

Glu Ala Glu Val Leu Val Ala Arg Gly Val Arg Val Lys Val Asn Glu
65                  70                  75                  80

Ala Tyr Arg Phe Arg Val Ala Leu Pro Ala Tyr Pro Ala Ser Leu Thr
                85                  90                  95

Asp Val Ser Leu Ala Leu Ser Glu Leu Arg Pro Asn Asp Ser Gly Ile
            100                 105                 110

Tyr Arg Cys Glu Val Gln His Gly Ile Asp Asp Ser Ser Asp Ala Val
        115                 120                 125

Glu Val Lys Val Lys Gly Val Val Phe Leu Tyr Arg Glu Gly Ser Ala
    130                 135                 140

Arg Tyr Ala Phe Ser Phe Ser Gly Ala Gln Glu Ala Cys Ala Arg Ile
145                 150                 155                 160

Gly Ala His Ile Ala Thr Pro Glu Gln Leu Tyr Ala Ala Tyr Leu Gly
                165                 170                 175

Gly Tyr Glu Gln Cys Asp Ala Gly Trp Leu Ser Asp Gln Thr Val Arg
            180                 185                 190

Tyr Pro Ile Gln Thr Pro Arg Glu Ala Cys Tyr Gly Asp Met Asp Gly
        195                 200                 205

Phe Pro Gly Val Arg Asn Tyr Gly Val Val Asp Pro Asp Leu Tyr
    210                 215                 220

Asp Val Tyr Cys Tyr Ala Glu Asp Leu Asn Gly Glu Leu Phe Leu Gly
225                 230                 235                 240

Asp Pro Pro Glu Lys Leu Thr Leu Glu Glu Ala Arg Ala Tyr Cys Gln
                245                 250                 255
```

-continued

Glu Arg Gly Ala Glu Ile Ala Thr Thr Gly Gln Leu Tyr Ala Ala Trp
            260                 265                 270

Asp Gly Gly Leu Asp His Cys Ser Pro Gly Trp Leu Ala Asp Gly Ser
            275                 280                 285

Val Arg Tyr Pro Ile Val Thr Pro Ser Gln Arg Cys Gly Gly Gly Leu
            290                 295                 300

Pro Gly Val Lys Thr Leu Phe Leu Phe Pro Asn Gln Thr Gly Phe Pro
305                 310                 315                 320

Asn Lys His Ser Arg Phe Asn Val Tyr Cys Phe Arg Asp Ser Ala Gln
            325                 330                 335

Pro Ser Ala Ile Pro Glu Ala Ser Asn Pro Ala Ser Asn Pro Ala Ser
            340                 345                 350

Asp Gly Leu Glu Ala Ile Val Thr Val Thr Glu Thr Leu Glu Glu Leu
            355                 360                 365

Gln Leu Pro Gln Glu Ala Thr Glu Ser Glu Ser Arg Gly Ala Ile Tyr
            370                 375                 380

Ser Ile Pro Ile Met Glu Asp Gly Gly Gly Ser Ser Thr Pro Glu
385                 390                 395                 400

Asp Pro Ala Glu Ala Pro Arg Thr Leu Leu Glu Phe Glu Thr Gln Ser
            405                 410                 415

Met Val Pro Pro Thr Gly Phe Ser Glu Glu Glu Gly Lys Ala Leu Glu
            420                 425                 430

Glu Glu Glu Lys Tyr Glu Asp Glu Glu Lys Glu Glu Glu Glu Glu
            435                 440                 445

Glu Glu Glu Val Glu Asp Glu Ala Leu Trp Ala Trp Pro Ser Glu Leu
            450                 455                 460

Ser Ser Pro Gly Pro Glu Ala Ser Leu Pro Thr Glu Pro Ala Ala Gln
465                 470                 475                 480

Glu Glu Ser Leu Ser Gln Ala Pro Ala Arg Ala Val Leu Gln Pro Gly
            485                 490                 495

Ala Ser Pro Leu Pro Asp Gly Glu Ser Glu Ala Ser Arg Pro Pro Arg
            500                 505                 510

Val His Gly Pro Pro Thr Glu Thr Leu Pro Thr Pro Arg Glu Arg Asn
            515                 520                 525

Leu Ala Ser Pro Ser Pro Ser Thr Leu Val Glu Ala Arg Glu Val Gly
            530                 535                 540

Glu Ala Thr Gly Gly Pro Glu Leu Ser Gly Val Pro Arg Gly Glu Ser
545                 550                 555                 560

Glu Glu Thr Gly Ser Ser Glu Gly Ala Pro Ser Leu Leu Pro Ala Thr
            565                 570                 575

Arg Ala Pro Glu Gly Thr Arg Glu Leu Glu Ala Pro Ser Glu Asp Asn
            580                 585                 590

Ser Gly Arg Thr Ala Pro Ala Gly Thr Ser Val Gln Ala Gln Pro Val
            595                 600                 605

Leu Pro Thr Asp Ser Ala Ser Arg Gly Gly Val Ala Val Val Pro Ala
            610                 615                 620

Ser Gly Asp Cys Val Pro Ser Pro Cys His Asn Gly Gly Thr Cys Leu
625                 630                 635                 640

Glu Glu Glu Glu Gly Val Arg Cys Leu Cys Leu Pro Gly Tyr Gly Gly
            645                 650                 655

Asp Leu Cys Asp Val Gly Leu Arg Phe Cys Asn Pro Gly Trp Asp Ala
            660                 665                 670

Phe Gln Gly Ala Cys Tyr Lys His Phe Ser Thr Arg Arg Ser Trp Glu
            675                 680                 685

Glu Ala Glu Thr Gln Cys Arg Met Tyr Gly Ala His Leu Ala Ser Ile
690                 695                 700

Ser Thr Pro Glu Glu Gln Asp Phe Ile Asn Asn Arg Tyr Arg Glu Tyr
705                 710                 715                 720

Gln Trp Ile Gly Leu Asn Asp Arg Thr Ile Glu Gly Asp Phe Leu Trp
            725                 730                 735

Ser Asp Gly Val Pro Leu Leu Tyr Glu Asn Trp Asn Pro Gly Gln Pro
            740                 745                 750

Asp Ser Tyr Phe Leu Ser Gly Glu Asn Cys Val Val Met Val Trp His
            755                 760                 765

Asp Gln Gly Gln Trp Ser Asp Val Pro Cys Asn Tyr His Leu Ser Tyr
770                 775                 780

Thr Cys Lys Met Gly Leu Val Ser Cys Gly Pro Pro Glu Leu Pro
785                 790                 795                 800

Leu Ala Gln Val Phe Gly Arg Pro Arg Leu Arg Tyr Glu Val Asp Thr
            805                 810                 815

Val Leu Arg Tyr Arg Cys Arg Glu Gly Leu Ala Gln Arg Asn Leu Pro
            820                 825                 830

Leu Ile Arg Cys Gln Glu Asn Gly Arg Trp Glu Ala Pro Gln Ile Ser
            835                 840                 845

Cys Val Pro Arg Arg Pro Ala Arg Ala Leu His Pro Glu Glu Asp Pro
            850                 855                 860

Glu Gly Arg Gln Gly Arg Leu Leu Gly Arg Trp Lys Ala Leu Leu Ile
865                 870                 875                 880

Pro Pro Ser Ser Pro Met Pro Gly Pro
                885

<210> SEQ ID NO 87
<211> LENGTH: 96
<212> TYPE: PRT
<213> ORGANISM: Homo sapiens

<400> SEQUENCE: 87

Val Val Phe Leu Tyr Arg Glu Gly Ser Ala Arg Tyr Ala Phe Ser Phe
1               5                   10                  15

Ser Gly Ala Gln Glu Ala Cys Ala Arg Ile Gly Ala His Ile Ala Thr
            20                  25                  30

Pro Glu Gln Leu Tyr Ala Ala Tyr Leu Gly Gly Tyr Glu Gln Cys Asp
        35                  40                  45

Ala Gly Trp Leu Ser Asp Gln Thr Val Arg Tyr Pro Ile Gln Thr Pro
    50                  55                  60

Arg Glu Ala Cys Tyr Gly Asp Met Asp Gly Phe Pro Gly Val Arg Asn
65                  70                  75                  80

Tyr Gly Val Val Asp Pro Asp Asp Leu Tyr Asp Val Tyr Cys Tyr Ala
                85                  90                  95

<210> SEQ ID NO 88
<211> LENGTH: 98
<212> TYPE: PRT
<213> ORGANISM: Homo sapiens

<400> SEQUENCE: 88

Gly Glu Leu Phe Leu Gly Asp Pro Pro Glu Lys Leu Thr Leu Glu Glu
1               5                   10                  15

Ala Arg Ala Tyr Cys Gln Glu Arg Gly Ala Glu Ile Ala Thr Thr Gly
            20                  25                  30

Gln Leu Tyr Ala Ala Trp Asp Gly Gly Leu Asp His Cys Ser Pro Gly
            35                  40                  45

Trp Leu Ala Asp Gly Ser Val Arg Tyr Pro Ile Val Thr Pro Ser Gln
 50                  55                  60

Arg Cys Gly Gly Gly Leu Pro Gly Val Lys Thr Leu Phe Leu Phe Pro
 65                  70                  75                  80

Asn Gln Thr Gly Phe Pro Asn Lys His Ser Arg Phe Asn Val Tyr Cys
                85                  90                  95

Phe Arg

<210> SEQ ID NO 89
<211> LENGTH: 597
<212> TYPE: PRT
<213> ORGANISM: Mus musculus

<400> SEQUENCE: 89

Met Arg Ile Leu Gln Ser Phe Leu Ala Cys Val Gln Leu Leu Cys Leu
 1               5                  10                  15

Cys Arg Leu Asp Trp Ala Tyr Gly Tyr Tyr Arg Gln Gln Arg Lys Leu
            20                  25                  30

Val Glu Glu Ile Gly Trp Ser Tyr Thr Gly Ala Leu Asn Gln Lys Asn
            35                  40                  45

Trp Gly Lys Lys Tyr Pro Met Cys Asn Ser Pro Lys Gln Ser Pro Ile
 50                  55                  60

Asn Ile Asp Glu Asp Leu Thr Gln Val Asn Val Asn Leu Lys Lys Leu
 65                  70                  75                  80

Lys Phe Gln Gly Trp Glu Lys Ala Ser Leu Glu Asn Thr Phe Ile His
            85                  90                  95

Ser Thr Gly Lys Thr Val Glu Ile Asn Leu Thr Asn Asp Tyr Tyr Leu
            100                 105                 110

Ser Gly Gly Leu Ser Glu Lys Val Phe Lys Ala Ser Lys Ile Thr Phe
            115                 120                 125

His Arg Gly Lys Cys Asn Val Ser Ser Glu Gly Ser Glu His Ser Leu
130                 135                 140

Glu Gly Gln Lys Phe Pro Leu Glu Met Gln Val Tyr Cys Phe Asp Ala
145                 150                 155                 160

Asp Arg Phe Ser Ser Phe Glu Glu Ala Val Lys Gly Lys Gly Arg Leu
                165                 170                 175

Arg Ala Leu Ser Ile Leu Phe Glu Val Gly Val Glu Glu Asn Leu Asp
            180                 185                 190

Tyr Lys Ala Ile Ile Asp Gly Thr Glu Ser Val Ser Arg Phe Gly Lys
            195                 200                 205

Gln Ala Ala Leu Asp Pro Phe Val Leu Gln Asn Leu Leu Gln Asn Ser
210                 215                 220

Thr Asp Lys Tyr Tyr Ile Tyr Asn Gly Ser Leu Thr Ser Pro Pro Cys
225                 230                 235                 240

Thr Asp Thr Val Glu Trp Ile Val Phe Lys Asp Thr Val Ser Ile Ser
                245                 250                 255

Glu Ser Gln Leu Ala Val Phe Cys Glu Val Leu Thr Met Gln Gln Ser
            260                 265                 270

Gly Tyr Val Met Leu Met Asp Tyr Leu Gln Asn Asn Phe Arg Glu Gln
            275                 280                 285

```
Gln Tyr Lys Phe Ser Arg Gln Val Phe Ser Ser Tyr Thr Gly Lys Glu
    290                 295                 300

Glu Ile His Glu Val Val Cys Ser Ser Glu Pro Glu Asn Val Gln Ala
305                 310                 315                 320

Asp Pro Glu Asn Tyr Thr Ser Leu Leu Val Thr Trp Glu Arg Pro Arg
                325                 330                 335

Val Val Tyr Asp Ala Met Ile Glu Lys Phe Ala Val Leu Tyr Gln Pro
            340                 345                 350

Leu Ala Gly Asn Asp Gln Ala Lys His Glu Phe Leu Thr Asp Gly Tyr
        355                 360                 365

Gln Asp Leu Gly Ala Ile Leu Asn Asn Leu Leu Pro Asn Met Ser Tyr
370                 375                 380

Val Leu Gln Ile Val Ala Val Cys Ser Asn Gly Leu Tyr Gly Lys Tyr
385                 390                 395                 400

Ser Asp Gln Leu Ile Val Asp Met Pro Thr Glu Asp Ala Glu Leu Asp
                405                 410                 415

Leu Phe Pro Glu Leu Ile Gly Thr Glu Glu Ile Ile Lys Glu Glu
            420                 425                 430

Tyr Gly Lys Asp Asn Glu Glu Asp Thr Gly Leu Asn Pro Gly Arg Asp
        435                 440                 445

Ser Val Thr Asn Gln Ile Arg Lys Lys Glu Pro Gln Val Ser Thr Thr
    450                 455                 460

Thr His Tyr Asn His Met Gly Thr Lys Tyr Asn Glu Ala Lys Thr Asn
465                 470                 475                 480

Arg Ser Pro Thr Arg Gly Ser Glu Phe Ser Gly Lys Ser Asp Val Pro
                485                 490                 495

Asn Thr Ser Pro Asn Ser Thr Ser Gln His Val Ala Glu Phe Glu Thr
            500                 505                 510

Glu Arg Gly Ile Ser Leu Pro Ser Gln Thr Gly Thr Asn Leu Pro Pro
        515                 520                 525

His Asn Val Glu Gly Thr Ser Ala Ser Leu Asn Ser Gly Ser Lys Thr
    530                 535                 540

Leu Phe Ile Phe Pro Gln Met Asn Leu Ser Gly Thr Ala Glu Ser Leu
545                 550                 555                 560

Asn Thr Val Pro Ile Thr Glu Tyr Lys Glu Val Ser Ala Asp Val Ser
                565                 570                 575

Glu Glu Glu Asn Phe Leu Thr Asp Phe Lys Leu Asp Thr Gly Ala Asp
            580                 585                 590

Asp Ser Ser Ala Gly
        595

<210> SEQ ID NO 90
<211> LENGTH: 574
<212> TYPE: PRT
<213> ORGANISM: Homo sapiens

<400> SEQUENCE: 90

Gly Tyr Tyr Arg Gln Gln Arg Lys Leu Val Glu Glu Ile Gly Trp Ser
1               5                   10                  15

Tyr Thr Gly Ala Leu Asn Gln Lys Asn Trp Gly Lys Lys Tyr Pro Met
            20                  25                  30

Cys Asn Ser Pro Lys Gln Ser Pro Ile Asn Ile Asp Glu Asp Leu Thr
        35                  40                  45

Gln Val Asn Val Asn Leu Lys Lys Leu Lys Phe Gln Gly Trp Glu Lys
    50                  55                  60
```

```
Ala Ser Leu Glu Asn Thr Phe Ile His Ser Thr Gly Lys Thr Val Glu
 65                  70                  75                  80

Ile Asn Leu Thr Asn Asp Tyr Tyr Leu Ser Gly Gly Leu Ser Glu Lys
                 85                  90                  95

Val Phe Lys Ala Ser Lys Ile Thr Phe His Arg Gly Lys Cys Asn Val
            100                 105                 110

Ser Ser Glu Gly Ser Glu His Ser Leu Glu Gly Gln Lys Phe Pro Leu
            115                 120                 125

Glu Met Gln Val Tyr Cys Phe Asp Ala Asp Arg Phe Ser Ser Phe Glu
        130                 135                 140

Glu Ala Val Lys Gly Lys Gly Arg Leu Arg Ala Leu Ser Ile Leu Phe
145                 150                 155                 160

Glu Val Gly Val Glu Glu Asn Leu Asp Tyr Lys Ala Ile Ile Asp Gly
                165                 170                 175

Thr Glu Ser Val Ser Arg Phe Gly Lys Gln Ala Ala Leu Asp Pro Phe
            180                 185                 190

Val Leu Gln Asn Leu Leu Gln Asn Ser Thr Asp Lys Tyr Tyr Ile Tyr
                195                 200                 205

Asn Gly Ser Leu Thr Ser Pro Pro Cys Thr Asp Thr Val Glu Trp Ile
210                 215                 220

Val Phe Lys Asp Thr Val Ser Ile Ser Glu Ser Gln Leu Ala Val Phe
225                 230                 235                 240

Cys Glu Val Leu Thr Met Gln Gln Ser Gly Tyr Val Met Leu Met Asp
                245                 250                 255

Tyr Leu Gln Asn Asn Phe Arg Glu Gln Tyr Lys Phe Ser Arg Gln
                260                 265                 270

Val Phe Ser Ser Tyr Thr Gly Lys Glu Glu Ile His Glu Val Val Cys
            275                 280                 285

Ser Ser Glu Pro Glu Asn Val Gln Ala Asp Pro Glu Asn Tyr Thr Ser
290                 295                 300

Leu Leu Val Thr Trp Glu Arg Pro Arg Val Val Tyr Asp Ala Met Ile
305                 310                 315                 320

Glu Lys Phe Ala Val Leu Tyr Gln Pro Leu Ala Gly Asn Asp Gln Ala
            325                 330                 335

Lys His Glu Phe Leu Thr Asp Gly Tyr Gln Asp Leu Gly Ala Ile Leu
            340                 345                 350

Asn Asn Leu Leu Pro Asn Met Ser Tyr Val Leu Gln Ile Val Ala Val
            355                 360                 365

Cys Ser Asn Gly Leu Tyr Gly Lys Tyr Ser Asp Gln Leu Ile Val Asp
            370                 375                 380

Met Pro Thr Glu Asp Ala Glu Leu Asp Leu Phe Pro Glu Leu Ile Gly
385                 390                 395                 400

Thr Glu Glu Ile Ile Lys Glu Glu Tyr Gly Lys Asp Asn Glu Glu
                405                 410                 415

Asp Thr Gly Leu Asn Pro Gly Arg Asp Ser Val Thr Asn Gln Ile Arg
            420                 425                 430

Lys Lys Glu Pro Gln Val Ser Thr Thr Thr His Tyr Asn His Met Gly
            435                 440                 445

Thr Lys Tyr Asn Glu Ala Lys Thr Asn Arg Ser Pro Thr Arg Gly Ser
            450                 455                 460

Glu Phe Ser Gly Lys Ser Asp Val Pro Asn Thr Ser Pro Asn Ser Thr
465                 470                 475                 480
```

-continued

```
Ser Gln His Val Ala Glu Phe Glu Thr Glu Arg Gly Ile Ser Leu Pro
                485                 490                 495
Ser Gln Thr Gly Thr Asn Leu Pro Pro His Asn Val Glu Gly Thr Ser
            500                 505                 510
Ala Ser Leu Asn Ser Gly Ser Lys Thr Leu Phe Ile Phe Pro Gln Met
            515                 520                 525
Asn Leu Ser Gly Thr Ala Glu Ser Leu Asn Thr Val Pro Ile Thr Glu
    530                 535                 540
Tyr Lys Glu Val Ser Ala Asp Val Ser Glu Glu Asn Phe Leu Thr
545                 550                 555                 560
Asp Phe Lys Leu Asp Thr Gly Ala Asp Ser Ser Ala Gly
                565                 570

<210> SEQ ID NO 91
<211> LENGTH: 742
<212> TYPE: PRT
<213> ORGANISM: Homo sapiens

<400> SEQUENCE: 91

Met Asp Lys Phe Trp Trp His Ala Ala Trp Gly Leu Cys Leu Val Pro
1               5                   10                  15
Leu Ser Leu Ala Gln Ile Asp Leu Asn Ile Thr Cys Arg Phe Ala Gly
            20                  25                  30
Val Phe His Val Glu Lys Asn Gly Arg Tyr Ser Ile Ser Arg Thr Glu
        35                  40                  45
Ala Ala Asp Leu Cys Lys Ala Phe Asn Ser Thr Leu Pro Thr Met Ala
    50                  55                  60
Gln Met Glu Lys Ala Leu Ser Ile Gly Phe Glu Thr Cys Arg Tyr Gly
65                  70                  75                  80
Phe Ile Glu Gly His Val Val Ile Pro Arg Ile His Pro Asn Ser Ile
                85                  90                  95
Cys Ala Ala Asn Asn Thr Gly Val Tyr Ile Leu Thr Ser Asn Thr Ser
            100                 105                 110
Gln Tyr Asp Thr Tyr Cys Phe Asn Ala Ser Ala Pro Pro Glu Glu Asp
        115                 120                 125
Cys Thr Ser Val Thr Asp Leu Pro Asn Ala Phe Asp Gly Pro Ile Thr
    130                 135                 140
Ile Thr Ile Val Asn Arg Asp Gly Thr Arg Tyr Val Gln Lys Gly Glu
145                 150                 155                 160
Tyr Arg Thr Asn Pro Glu Asp Ile Tyr Pro Ser Asn Pro Thr Asp Asp
                165                 170                 175
Asp Val Ser Ser Gly Ser Ser Ser Glu Arg Ser Ser Thr Ser Gly Gly
            180                 185                 190
Tyr Ile Phe Tyr Thr Phe Ser Thr Val His Pro Ile Pro Asp Glu Asp
        195                 200                 205
Ser Pro Trp Ile Thr Asp Ser Thr Asp Arg Ile Pro Ala Thr Thr Leu
    210                 215                 220
Met Ser Thr Ser Ala Thr Ala Thr Glu Thr Ala Thr Lys Arg Gln Glu
225                 230                 235                 240
Thr Trp Asp Trp Phe Ser Trp Leu Phe Leu Pro Ser Glu Ser Lys Asn
                245                 250                 255
His Leu His Thr Thr Thr Gln Met Ala Gly Thr Ser Ser Asn Thr Ile
            260                 265                 270
Ser Ala Gly Trp Glu Pro Asn Glu Glu Asn Glu Asp Glu Arg Asp Arg
        275                 280                 285
```

```
His Leu Ser Phe Ser Gly Ser Gly Ile Asp Asp Glu Asp Phe Ile
    290                 295                 300

Ser Ser Thr Ile Ser Thr Thr Pro Arg Ala Phe Asp His Thr Lys Gln
305                 310                 315                 320

Asn Gln Asp Trp Thr Gln Trp Asn Pro Ser His Ser Asn Pro Glu Val
                325                 330                 335

Leu Leu Gln Thr Thr Thr Arg Met Thr Asp Val Asp Arg Asn Gly Thr
                340                 345                 350

Thr Ala Tyr Glu Gly Asn Trp Asn Pro Glu Ala His Pro Pro Leu Ile
            355                 360                 365

His His Glu His His Glu Glu Glu Thr Pro His Ser Thr Ser Thr
    370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro
                405                 410                 415

Lys Glu Asp Ser His Ser Thr Thr Gly Thr Ala Ala Ala Ser Ala His
                420                 425                 430

Thr Ser His Pro Met Gln Gly Arg Thr Thr Pro Ser Pro Glu Asp Ser
        435                 440                 445

Ser Trp Thr Asp Phe Phe Asn Pro Ile Ser His Pro Met Gly Arg Gly
    450                 455                 460

His Gln Ala Gly Arg Arg Met Asp Met Asp Ser Ser His Ser Ile Thr
465                 470                 475                 480

Leu Gln Pro Thr Ala Asn Pro Asn Thr Gly Leu Val Glu Asp Leu Asp
                485                 490                 495

Arg Thr Gly Pro Leu Ser Met Thr Thr Gln Gln Ser Asn Ser Gln Ser
                500                 505                 510

Phe Ser Thr Ser His Glu Gly Leu Glu Glu Asp Lys Asp His Pro Thr
            515                 520                 525

Thr Ser Thr Leu Thr Ser Ser Asn Arg Asn Asp Val Thr Gly Gly Arg
    530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
                565                 570                 575

Thr Ser Ala Lys Thr Gly Ser Phe Gly Val Thr Ala Val Thr Val Gly
                580                 585                 590

Asp Ser Asn Ser Asn Val Asn Arg Ser Leu Ser Gly Asp Gln Asp Thr
            595                 600                 605

Phe His Pro Ser Gly Gly Ser His Thr Thr His Gly Ser Glu Ser Asp
    610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn Ser
                660                 665                 670

Arg Arg Arg Cys Gly Gln Lys Lys Lys Leu Val Ile Asn Ser Gly Asn
            675                 680                 685

Gly Ala Val Glu Asp Arg Lys Pro Ser Gly Leu Asn Gly Glu Ala Ser
    690                 695                 700
```

```
Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
            725                 730                 735

Asp Met Lys Ile Gly Val
            740

<210> SEQ ID NO 92
<211> LENGTH: 722
<212> TYPE: PRT
<213> ORGANISM: Homo sapiens

<400> SEQUENCE: 92

Gln Ile Asp Leu Asn Ile Thr Cys Arg Phe Ala Gly Val Phe His Val
1               5                   10                  15

Glu Lys Asn Gly Arg Tyr Ser Ile Ser Arg Thr Glu Ala Ala Asp Leu
            20                  25                  30

Cys Lys Ala Phe Asn Ser Thr Leu Pro Thr Met Ala Gln Met Glu Lys
        35                  40                  45

Ala Leu Ser Ile Gly Phe Glu Thr Cys Arg Tyr Gly Phe Ile Glu Gly
    50                  55                  60

His Val Val Ile Pro Arg Ile His Pro Asn Ser Ile Cys Ala Ala Asn
65                  70                  75                  80

Asn Thr Gly Val Tyr Ile Leu Thr Ser Asn Thr Ser Gln Tyr Asp Thr
                85                  90                  95

Tyr Cys Phe Asn Ala Ser Ala Pro Pro Glu Glu Asp Cys Thr Ser Val
            100                 105                 110

Thr Asp Leu Pro Asn Ala Phe Asp Gly Pro Ile Thr Ile Thr Ile Val
        115                 120                 125

Asn Arg Asp Gly Thr Arg Tyr Val Gln Lys Gly Glu Tyr Arg Thr Asn
    130                 135                 140

Pro Glu Asp Ile Tyr Pro Ser Asn Pro Thr Asp Asp Asp Val Ser Ser
145                 150                 155                 160

Gly Ser Ser Ser Glu Arg Ser Ser Thr Ser Gly Gly Tyr Ile Phe Tyr
                165                 170                 175

Thr Phe Ser Thr Val His Pro Ile Pro Asp Glu Asp Ser Pro Trp Ile
            180                 185                 190

Thr Asp Ser Thr Asp Arg Ile Pro Ala Thr Thr Leu Met Ser Thr Ser
        195                 200                 205

Ala Thr Ala Thr Glu Thr Ala Thr Lys Arg Gln Glu Thr Trp Asp Trp
    210                 215                 220

Phe Ser Trp Leu Phe Leu Pro Ser Glu Ser Lys Asn His Leu His Thr
225                 230                 235                 240

Thr Thr Gln Met Ala Gly Thr Ser Ser Asn Thr Ile Ser Ala Gly Trp
                245                 250                 255

Glu Pro Asn Glu Glu Asn Glu Asp Glu Arg Asp Arg His Leu Ser Phe
            260                 265                 270

Ser Gly Ser Gly Ile Asp Asp Asp Glu Asp Phe Ile Ser Ser Thr Ile
        275                 280                 285

Ser Thr Thr Pro Arg Ala Phe Asp His Thr Lys Gln Asn Gln Asp Trp
    290                 295                 300

Thr Gln Trp Asn Pro Ser His Ser Asn Pro Glu Val Leu Leu Gln Thr
305                 310                 315                 320

Thr Thr Arg Met Thr Asp Val Asp Arg Asn Gly Thr Thr Ala Tyr Glu
                325                 330                 335
```

Gly Asn Trp Asn Pro Glu Ala His Pro Leu Ile His His Glu His
                340                 345                 350

His Glu Glu Glu Glu Thr Pro His Ser Thr Ser Thr Ile Gln Ala Thr
            355                 360                 365

Pro Ser Ser Thr Thr Glu Glu Thr Ala Thr Gln Lys Glu Gln Trp Phe
370                 375                 380

Gly Asn Arg Trp His Glu Gly Tyr Arg Gln Thr Pro Lys Glu Asp Ser
385                 390                 395                 400

His Ser Thr Thr Gly Thr Ala Ala Ser Ala His Thr Ser His Pro
                405                 410                 415

Met Gln Gly Arg Thr Thr Pro Ser Pro Glu Asp Ser Ser Trp Thr Asp
            420                 425                 430

Phe Phe Asn Pro Ile Ser His Pro Met Gly Arg Gly His Gln Ala Gly
                435                 440                 445

Arg Arg Met Asp Met Asp Ser Ser His Ser Ile Thr Leu Gln Pro Thr
450                 455                 460

Ala Asn Pro Asn Thr Gly Leu Val Glu Asp Leu Asp Arg Thr Gly Pro
465                 470                 475                 480

Leu Ser Met Thr Thr Gln Gln Ser Asn Ser Gln Ser Phe Ser Thr Ser
                485                 490                 495

His Glu Gly Leu Glu Glu Asp Lys Asp His Pro Thr Thr Ser Thr Leu
            500                 505                 510

Thr Ser Ser Asn Arg Asn Asp Val Thr Gly Gly Arg Arg Asp Pro Asn
        515                 520                 525

His Ser Glu Gly Ser Thr Thr Leu Leu Glu Gly Tyr Thr Ser His Tyr
    530                 535                 540

Pro His Thr Lys Glu Ser Arg Thr Phe Ile Pro Val Thr Ser Ala Lys
545                 550                 555                 560

Thr Gly Ser Phe Gly Val Thr Ala Val Thr Val Gly Asp Ser Asn Ser
                565                 570                 575

Asn Val Asn Arg Ser Leu Ser Gly Asp Gln Asp Thr Phe His Pro Ser
            580                 585                 590

Gly Gly Ser His Thr Thr His Gly Ser Glu Ser Asp Gly His Ser His
        595                 600                 605

Gly Ser Gln Glu Gly Gly Ala Asn Thr Thr Ser Gly Pro Ile Arg Thr
    610                 615                 620

Pro Gln Ile Pro Glu Trp Leu Ile Ile Leu Ala Ser Leu Leu Ala Leu
625                 630                 635                 640

Ala Leu Ile Leu Ala Val Cys Ile Ala Val Asn Ser Arg Arg Arg Cys
                645                 650                 655

Gly Gln Lys Lys Lys Leu Val Ile Asn Ser Gly Asn Gly Ala Val Glu
            660                 665                 670

Asp Arg Lys Pro Ser Gly Leu Asn Gly Glu Ala Ser Lys Ser Gln Glu
        675                 680                 685

Met Val His Leu Val Asn Lys Glu Ser Ser Glu Thr Pro Asp Gln Phe
    690                 695                 700

Met Thr Ala Asp Glu Thr Arg Asn Leu Gln Asn Val Asp Met Lys Ile
705                 710                 715                 720

Gly Val

<210> SEQ ID NO 93
<211> LENGTH: 89
<212> TYPE: PRT

<213> ORGANISM: Homo sapiens

<400> SEQUENCE: 93

```
Gly Val Phe His Val Glu Lys Asn Gly Arg Tyr Ser Ile Ser Arg Thr
1               5                   10                  15

Glu Ala Ala Asp Leu Cys Lys Ala Phe Asn Ser Thr Leu Pro Thr Met
            20                  25                  30

Ala Gln Met Glu Lys Ala Leu Ser Ile Gly Phe Glu Thr Cys Arg Tyr
        35                  40                  45

Gly Phe Ile Glu Gly His Val Val Ile Pro Arg Ile His Pro Asn Ser
    50                  55                  60

Ile Cys Ala Ala Asn Asn Thr Gly Val Tyr Ile Leu Thr Ser Asn Thr
65                  70                  75                  80

Ser Gln Tyr Asp Thr Tyr Cys Phe Asn
                85
```

<210> SEQ ID NO 94
<211> LENGTH: 2570
<212> TYPE: PRT
<213> ORGANISM: Homo sapiens

<400> SEQUENCE: 94

```
Met Ala Gly Pro Arg Gly Leu Leu Pro Leu Cys Leu Leu Ala Phe Cys
1               5                   10                  15

Leu Ala Gly Phe Ser Phe Val Arg Gly Gln Val Leu Phe Lys Gly Cys
            20                  25                  30

Asp Val Lys Thr Thr Phe Val Thr His Val Pro Cys Thr Ser Cys Ala
        35                  40                  45

Ala Ile Lys Lys Gln Thr Cys Pro Ser Gly Trp Leu Arg Glu Leu Pro
    50                  55                  60

Asp Gln Ile Thr Gln Asp Cys Arg Tyr Glu Val Gln Leu Gly Gly Ser
65                  70                  75                  80

Met Val Ser Met Ser Gly Cys Arg Arg Lys Cys Arg Lys Gln Val Val
                85                  90                  95

Gln Lys Ala Cys Cys Pro Gly Tyr Trp Gly Ser Arg Cys His Glu Cys
            100                 105                 110

Pro Gly Gly Ala Glu Thr Pro Cys Asn Gly His Gly Thr Cys Leu Asp
        115                 120                 125

Gly Met Asp Arg Asn Gly Thr Cys Val Cys Gln Glu Asn Phe Arg Gly
    130                 135                 140

Ser Ala Cys Gln Glu Cys Gln Asp Pro Asn Arg Phe Gly Pro Asp Cys
145                 150                 155                 160

Gln Ser Val Cys Ser Cys Val His Gly Val Cys Asn His Gly Pro Arg
                165                 170                 175

Gly Asp Gly Ser Cys Leu Cys Phe Ala Gly Tyr Thr Gly Pro His Cys
            180                 185                 190

Asp Gln Glu Leu Pro Val Cys Gln Glu Leu Arg Cys Pro Gln Asn Thr
        195                 200                 205

Gln Cys Ser Ala Glu Ala Pro Ser Cys Arg Cys Leu Pro Gly Tyr Thr
    210                 215                 220

Gln Gln Gly Ser Glu Cys Arg Ala Pro Asn Pro Cys Trp Pro Ser Pro
225                 230                 235                 240

Cys Ser Leu Leu Ala Gln Cys Ser Val Ser Pro Lys Gly Gln Ala Gln
                245                 250                 255

Cys His Cys Pro Glu Asn Tyr His Gly Asp Gly Met Val Cys Leu Pro
```

```
                260                 265                 270
Lys Asp Pro Cys Thr Asp Asn Leu Gly Gly Cys Pro Ser Asn Ser Thr
            275                 280                 285
Leu Cys Val Tyr Gln Lys Pro Gly Gln Ala Phe Cys Thr Cys Arg Pro
            290                 295                 300
Gly Leu Val Ser Ile Asn Ser Asn Ala Ser Ala Gly Cys Phe Ala Phe
305                 310                 315                 320
Cys Ser Pro Phe Ser Cys Asp Arg Ser Ala Thr Cys Gln Val Thr Ala
                325                 330                 335
Asp Gly Lys Thr Ser Cys Val Cys Arg Glu Ser Glu Val Gly Asp Gly
                340                 345                 350
Arg Ala Cys Tyr Gly His Leu Leu His Glu Val Gln Lys Ala Thr Gln
                355                 360                 365
Thr Gly Arg Val Phe Leu Gln Leu Arg Val Ala Val Ala Met Met Asp
                370                 375                 380
Gln Gly Cys Arg Glu Ile Leu Thr Thr Ala Gly Pro Phe Thr Val Leu
385                 390                 395                 400
Val Pro Ser Val Ser Ser Phe Ser Ser Arg Thr Met Asn Ala Ser Leu
                405                 410                 415
Ala Gln Gln Leu Cys Arg Gln His Ile Ile Ala Gly Gln His Ile Leu
                420                 425                 430
Glu Asp Thr Arg Thr Gln Gln Thr Arg Arg Trp Trp Thr Leu Ala Gly
                435                 440                 445
Gln Glu Ile Thr Val Thr Phe Asn Gln Phe Thr Lys Tyr Ser Tyr Lys
                450                 455                 460
Tyr Lys Asp Gln Pro Gln Gln Thr Phe Asn Ile Tyr Lys Ala Asn Asn
465                 470                 475                 480
Ile Ala Ala Asn Gly Val Phe His Val Val Thr Gly Leu Arg Trp Gln
                485                 490                 495
Ala Pro Ser Gly Thr Pro Gly Asp Pro Lys Arg Thr Ile Gly Gln Ile
                500                 505                 510
Leu Ala Ser Thr Glu Ala Phe Ser Arg Phe Glu Thr Ile Leu Glu Asn
                515                 520                 525
Cys Gly Leu Pro Ser Ile Leu Asp Gly Pro Gly Pro Phe Thr Val Phe
                530                 535                 540
Ala Pro Ser Asn Glu Ala Val Asp Ser Leu Arg Asp Gly Arg Leu Ile
545                 550                 555                 560
Tyr Leu Phe Thr Ala Gly Leu Ser Lys Leu Gln Glu Leu Val Arg Tyr
                565                 570                 575
His Ile Tyr Asn His Gly Gln Leu Thr Val Glu Lys Leu Ile Ser Lys
                580                 585                 590
Gly Arg Ile Leu Thr Met Ala Asn Gln Val Leu Ala Val Asn Ile Ser
                595                 600                 605
Glu Glu Gly Arg Ile Leu Leu Gly Pro Glu Gly Val Pro Leu Gln Arg
                610                 615                 620
Val Asp Val Met Ala Ala Asn Gly Val Ile His Met Leu Asp Gly Ile
625                 630                 635                 640
Leu Leu Pro Pro Thr Ile Leu Pro Ile Leu Pro Lys His Cys Ser Glu
                645                 650                 655
Glu Gln His Lys Ile Val Ala Gly Ser Cys Val Asp Cys Gln Ala Leu
                660                 665                 670
Asn Thr Ser Thr Cys Pro Pro Asn Ser Val Lys Leu Asp Ile Phe Pro
                675                 680                 685
```

```
Lys Glu Cys Val Tyr Ile His Asp Pro Thr Gly Leu Asn Val Leu Lys
    690             695             700

Lys Gly Cys Ala Ser Tyr Cys Asn Gln Thr Ile Met Glu Gln Gly Cys
705             710             715             720

Cys Lys Gly Phe Phe Gly Pro Asp Cys Thr Gln Cys Pro Gly Gly Phe
            725             730             735

Ser Asn Pro Cys Tyr Gly Lys Gly Asn Cys Ser Asp Gly Ile Gln Gly
            740             745             750

Asn Gly Ala Cys Leu Cys Phe Pro Asp Tyr Lys Gly Ile Ala Cys His
        755             760             765

Ile Cys Ser Asn Pro Asn Lys His Gly Glu Gln Cys Gln Glu Asp Cys
770             775             780

Gly Cys Val His Gly Leu Cys Asp Asn Arg Pro Gly Ser Gly Gly Val
785             790             795             800

Cys Gln Gln Gly Thr Cys Ala Pro Gly Phe Ser Gly Arg Phe Cys Asn
            805             810             815

Glu Ser Met Gly Asp Cys Gly Pro Thr Gly Leu Ala Gln His Cys His
            820             825             830

Leu His Ala Arg Cys Val Ser Gln Glu Gly Val Ala Arg Cys Arg Cys
        835             840             845

Leu Asp Gly Phe Glu Gly Asp Gly Phe Ser Cys Thr Pro Ser Asn Pro
850             855             860

Cys Ser His Pro Asp Arg Gly Gly Cys Ser Glu Asn Ala Glu Cys Val
865             870             875             880

Pro Gly Ser Leu Gly Thr His Cys Thr Cys His Lys Gly Trp Ser
            885             890             895

Gly Asp Gly Arg Val Cys Val Ala Ile Asp Glu Cys Glu Leu Asp Met
            900             905             910

Arg Gly Gly Cys His Thr Asp Ala Leu Cys Ser Tyr Val Gly Pro Gly
        915             920             925

Gln Ser Arg Cys Thr Cys Lys Leu Gly Phe Ala Gly Asp Gly Tyr Gln
        930             935             940

Cys Ser Pro Ile Asp Pro Cys Arg Ala Gly Asn Gly Gly Cys His Gly
945             950             955             960

Leu Ala Thr Cys Arg Ala Val Gly Gly Gly Gln Arg Val Cys Thr Cys
            965             970             975

Pro Pro Gly Phe Gly Gly Asp Gly Phe Ser Cys Tyr Gly Asp Ile Phe
            980             985             990

Arg Glu Leu Glu Ala Asn Ala His Phe Ser Ile Phe Tyr Gln Trp Leu
        995             1000            1005

Lys Ser Ala Gly Ile Thr Leu Pro Ala Asp Arg Arg Val Thr Ala
    1010            1015            1020

Leu Val Pro Ser Glu Ala Ala Val Arg Gln Leu Ser Pro Glu Asp
    1025            1030            1035

Arg Ala Phe Trp Leu Gln Pro Arg Thr Leu Pro Asn Leu Val Arg
    1040            1045            1050

Ala His Phe Leu Gln Gly Ala Leu Phe Glu Glu Leu Ala Arg
    1055            1060            1065

Leu Gly Gly Gln Glu Val Ala Thr Leu Asn Pro Thr Thr Arg Trp
    1070            1075            1080

Glu Ile Arg Asn Ile Ser Gly Arg Val Trp Val Gln Asn Ala Ser
    1085            1090            1095
```

-continued

```
Val Asp Val Ala Asp Leu Leu Ala Thr Asn Gly Val Leu His Ile
1100                1105                1110

Leu Ser Gln Val Leu Leu Pro Pro Arg Gly Asp Val Pro Gly Gly
1115                1120                1125

Gln Gly Leu Leu Gln Gln Leu Asp Leu Val Pro Ala Phe Ser Leu
1130                1135                1140

Phe Arg Glu Leu Leu Gln His His Gly Leu Val Pro Gln Ile Glu
1145                1150                1155

Ala Ala Thr Ala Tyr Thr Ile Phe Val Pro Thr Asn Arg Ser Leu
1160                1165                1170

Glu Ala Gln Gly Asn Ser Ser His Leu Asp Ala Asp Thr Val Arg
1175                1180                1185

His His Val Val Leu Gly Glu Ala Leu Ser Met Glu Thr Leu Arg
1190                1195                1200

Lys Gly Gly His Arg Asn Ser Leu Leu Gly Pro Ala His Trp Ile
1205                1210                1215

Val Phe Tyr Asn His Ser Gly Gln Pro Glu Val Asn His Val Pro
1220                1225                1230

Leu Glu Gly Pro Met Leu Glu Ala Pro Gly Arg Ser Leu Ile Gly
1235                1240                1245

Leu Ser Gly Val Leu Thr Val Gly Ser Ser Arg Cys Leu His Ser
1250                1255                1260

His Ala Glu Ala Leu Arg Glu Lys Cys Val Asn Cys Thr Arg Arg
1265                1270                1275

Phe Arg Cys Thr Gln Gly Phe Gln Leu Gln Asp Thr Pro Arg Lys
1280                1285                1290

Ser Cys Val Tyr Arg Ser Gly Phe Ser Phe Ser Arg Gly Cys Ser
1295                1300                1305

Tyr Thr Cys Ala Lys Lys Ile Gln Val Pro Asp Cys Cys Pro Gly
1310                1315                1320

Phe Phe Gly Thr Leu Cys Glu Pro Cys Pro Gly Gly Leu Gly Gly
1325                1330                1335

Val Cys Ser Gly His Gly Gln Cys Gln Asp Arg Phe Leu Gly Ser
1340                1345                1350

Gly Glu Cys His Cys His Glu Gly Phe His Gly Thr Ala Cys Glu
1355                1360                1365

Val Cys Glu Leu Gly Arg Tyr Gly Pro Asn Cys Thr Gly Val Cys
1370                1375                1380

Asp Cys Ala His Gly Leu Cys Gln Glu Gly Leu Gln Gly Asp Gly
1385                1390                1395

Ser Cys Val Cys Asn Val Gly Trp Gln Gly Leu Arg Cys Asp Gln
1400                1405                1410

Lys Ile Thr Ser Pro Gln Cys Pro Arg Lys Cys Asp Pro Asn Ala
1415                1420                1425

Asn Cys Val Gln Asp Ser Ala Gly Ala Ser Thr Cys Ala Cys Ala
1430                1435                1440

Ala Gly Tyr Ser Gly Asn Gly Ile Phe Cys Ser Glu Val Asp Pro
1445                1450                1455

Cys Ala His Gly His Gly Gly Cys Ser Pro His Ala Asn Cys Thr
1460                1465                1470

Lys Val Ala Pro Gly Gln Arg Thr Cys Thr Cys Gln Asp Gly Tyr
1475                1480                1485

Met Gly Asp Gly Glu Leu Cys Gln Glu Ile Asn Ser Cys Leu Ile
```

-continued

```
           1490               1495               1500

His His Gly Gly Cys His Ile His Ala Glu Cys Ile Pro Thr Gly
       1505               1510               1515

Pro Gln Gln Val Ser Cys Ser Cys Arg Glu Gly Tyr Ser Gly Asp
       1520               1525               1530

Gly Ile Arg Thr Cys Glu Leu Leu Asp Pro Cys Ser Lys Asn Asn
       1535               1540               1545

Gly Gly Cys Ser Pro Tyr Ala Thr Cys Lys Ser Thr Gly Asp Gly
       1550               1555               1560

Gln Arg Thr Cys Thr Cys Asp Thr Ala His Thr Val Gly Asp Gly
       1565               1570               1575

Leu Thr Cys Arg Ala Arg Val Gly Leu Glu Leu Leu Arg Asp Lys
       1580               1585               1590

His Ala Ser Phe Phe Ser Leu Arg Leu Leu Glu Tyr Lys Glu Leu
       1595               1600               1605

Lys Gly Asp Gly Pro Phe Thr Ile Phe Val Pro His Ala Asp Leu
       1610               1615               1620

Met Ser Asn Leu Ser Gln Asp Glu Leu Ala Arg Ile Arg Ala His
       1625               1630               1635

Arg Gln Leu Val Phe Arg Tyr His Val Val Gly Cys Arg Arg Leu
       1640               1645               1650

Arg Ser Glu Asp Leu Leu Glu Gln Gly Tyr Ala Thr Ala Leu Ser
       1655               1660               1665

Gly His Pro Leu Arg Phe Ser Glu Arg Glu Gly Ser Ile Tyr Leu
       1670               1675               1680

Asn Asp Phe Ala Arg Val Val Ser Ser Asp His Glu Ala Val Asn
       1685               1690               1695

Gly Ile Leu His Phe Ile Asp Arg Val Leu Leu Pro Pro Glu Ala
       1700               1705               1710

Leu His Trp Glu Pro Asp Asp Ala Pro Ile Pro Arg Arg Asn Val
       1715               1720               1725

Thr Ala Ala Ala Gln Gly Phe Gly Tyr Lys Ile Phe Ser Gly Leu
       1730               1735               1740

Leu Lys Val Ala Gly Leu Leu Pro Leu Leu Arg Glu Ala Ser His
       1745               1750               1755

Arg Pro Phe Thr Met Leu Trp Pro Thr Asp Ala Ala Phe Arg Ala
       1760               1765               1770

Leu Pro Pro Asp Arg Gln Ala Trp Leu Tyr His Glu Asp His Arg
       1775               1780               1785

Asp Lys Leu Ala Ala Ile Leu Arg Gly His Met Ile Arg Asn Val
       1790               1795               1800

Glu Ala Leu Ala Ser Asp Leu Pro Asn Leu Gly Pro Leu Arg Thr
       1805               1810               1815

Met His Gly Thr Pro Ile Ser Phe Ser Cys Ser Arg Thr Arg Ala
       1820               1825               1830

Gly Glu Leu Met Val Gly Glu Asp Asp Ala Arg Ile Val Gln Arg
       1835               1840               1845

His Leu Pro Phe Glu Gly Gly Leu Ala Tyr Gly Ile Asp Gln Leu
       1850               1855               1860

Leu Glu Pro Pro Gly Leu Gly Ala Arg Cys Asp His Phe Glu Thr
       1865               1870               1875

Arg Pro Leu Arg Leu Asn Thr Cys Ser Ile Cys Gly Leu Glu Pro
       1880               1885               1890
```

-continued

```
Pro Cys Pro Glu Gly Ser Gln Gln Gly Ser Pro Glu Ala Cys
    1895            1900            1905

Trp Arg Phe Tyr Pro Lys Phe Trp Thr Ser Pro Leu His Ser
    1910            1915            1920

Leu Gly Leu Arg Ser Val Trp Val His Pro Ser Leu Trp Gly Arg
    1925            1930            1935

Pro Gln Gly Leu Gly Arg Gly Cys His Arg Asn Cys Val Thr Thr
    1940            1945            1950

Thr Trp Lys Pro Ser Cys Cys Pro Gly His Tyr Gly Ser Glu Cys
    1955            1960            1965

Gln Ala Cys Pro Gly Gly Pro Ser Ser Pro Cys Ser Asp Arg Gly
    1970            1975            1980

Val Cys Met Asp Gly Met Ser Gly Ser Gly Gln Cys Leu Cys Arg
    1985            1990            1995

Ser Gly Phe Ala Gly Thr Ala Cys Glu Leu Cys Ala Pro Gly Ala
    2000            2005            2010

Phe Gly Pro His Cys Gln Ala Cys Arg Cys Thr Val His Gly Arg
    2015            2020            2025

Cys Asp Glu Gly Leu Gly Gly Ser Gly Ser Cys Phe Cys Asp Glu
    2030            2035            2040

Gly Trp Thr Gly Pro Arg Cys Glu Val Gln Leu Glu Leu Gln Pro
    2045            2050            2055

Val Cys Thr Pro Pro Cys Ala Pro Glu Ala Val Cys Arg Ala Gly
    2060            2065            2070

Asn Ser Cys Glu Cys Ser Leu Gly Tyr Glu Gly Asp Gly Arg Val
    2075            2080            2085

Cys Thr Val Ala Asp Leu Cys Gln Asp Gly His Gly Gly Cys Ser
    2090            2095            2100

Glu His Ala Asn Cys Ser Gln Val Gly Thr Met Val Thr Cys Thr
    2105            2110            2115

Cys Leu Pro Asp Tyr Glu Gly Asp Gly Trp Ser Cys Arg Ala Arg
    2120            2125            2130

Asn Pro Cys Thr Asp Gly His Arg Gly Gly Cys Ser Glu His Ala
    2135            2140            2145

Asn Cys Leu Ser Thr Gly Leu Asn Thr Arg Arg Cys Glu Cys His
    2150            2155            2160

Ala Gly Tyr Val Gly Asp Gly Leu Gln Cys Leu Glu Glu Ser Glu
    2165            2170            2175

Pro Pro Val Asp Arg Cys Leu Gly Gln Pro Pro Cys His Ser
    2180            2185            2190

Asp Ala Met Cys Thr Asp Leu His Phe Gln Glu Lys Arg Ala Gly
    2195            2200            2205

Val Phe His Leu Gln Ala Thr Ser Gly Pro Tyr Gly Leu Asn Phe
    2210            2215            2220

Ser Glu Ala Glu Ala Ala Cys Glu Ala Gln Gly Ala Val Leu Ala
    2225            2230            2235

Ser Phe Pro Gln Leu Ser Ala Ala Gln Gln Leu Gly Phe His Leu
    2240            2245            2250

Cys Leu Met Gly Trp Leu Ala Asn Gly Ser Thr Ala His Pro Val
    2255            2260            2265

Val Phe Pro Val Ala Asp Cys Gly Asn Gly Arg Val Gly Ile Val
    2270            2275            2280
```

Ser Leu Gly Ala Arg Lys Asn Leu Ser Glu Arg Trp Asp Ala Tyr
    2285                2290                2295

Cys Phe Arg Val Gln Asp Val Ala Cys Arg Cys Arg Asn Gly Phe
    2300                2305                2310

Val Gly Asp Gly Ile Ser Thr Cys Asn Gly Lys Leu Leu Asp Val
    2315                2320                2325

Leu Ala Ala Thr Ala Asn Phe Ser Thr Phe Tyr Gly Met Leu Leu
    2330                2335                2340

Gly Tyr Ala Asn Ala Thr Gln Arg Gly Leu Asp Phe Leu Asp Phe
    2345                2350                2355

Leu Asp Asp Glu Leu Thr Tyr Lys Thr Leu Phe Val Pro Val Asn
    2360                2365                2370

Glu Gly Phe Val Asp Asn Met Thr Leu Ser Gly Pro Asp Leu Glu
    2375                2380                2385

Leu His Ala Ser Asn Ala Thr Leu Leu Ser Ala Asn Ala Ser Gln
    2390                2395                2400

Gly Lys Leu Leu Pro Ala His Ser Gly Leu Ser Leu Ile Ile Ser
    2405                2410                2415

Asp Ala Gly Pro Asp Asn Ser Ser Trp Ala Pro Val Ala Pro Gly
    2420                2425                2430

Thr Val Val Val Ser Arg Ile Ile Val Trp Asp Ile Met Ala Phe
    2435                2440                2445

Asn Gly Ile Ile His Ala Leu Ala Ser Pro Leu Leu Ala Pro Pro
    2450                2455                2460

Gln Pro Gln Ala Val Leu Ala Pro Glu Ala Pro Val Ala Ala
    2465                2470                2475

Gly Val Gly Ala Val Leu Ala Ala Gly Ala Leu Leu Gly Leu Val
    2480                2485                2490

Ala Gly Ala Leu Tyr Leu Arg Ala Arg Gly Lys Pro Met Gly Phe
    2495                2500                2505

Gly Phe Ser Ala Phe Gln Ala Glu Asp Asp Ala Asp Asp Asp Phe
    2510                2515                2520

Ser Pro Trp Gln Glu Gly Thr Asn Pro Thr Leu Val Ser Val Pro
    2525                2530                2535

Asn Pro Val Phe Gly Ser Asp Thr Phe Cys Glu Pro Phe Asp Asp
    2540                2545                2550

Ser Leu Leu Glu Glu Asp Phe Pro Asp Thr Gln Arg Ile Leu Thr
    2555                2560                2565

Val Lys
    2570

<210> SEQ ID NO 95
<211> LENGTH: 2545
<212> TYPE: PRT
<213> ORGANISM: Homo sapiens

<400> SEQUENCE: 95

Gln Val Leu Phe Lys Gly Cys Asp Val Lys Thr Thr Phe Val Thr His
1               5                   10                  15

Val Pro Cys Thr Ser Cys Ala Ala Ile Lys Lys Gln Thr Cys Pro Ser
                20                  25                  30

Gly Trp Leu Arg Glu Leu Pro Asp Gln Ile Thr Gln Asp Cys Arg Tyr
            35                  40                  45

Glu Val Gln Leu Gly Gly Ser Met Val Ser Met Ser Gly Cys Arg Arg
        50                  55                  60

-continued

```
Lys Cys Arg Lys Gln Val Gln Lys Ala Cys Cys Pro Gly Tyr Trp
 65                  70                  75                  80

Gly Ser Arg Cys His Glu Cys Pro Gly Gly Ala Glu Thr Pro Cys Asn
                 85                  90                  95

Gly His Gly Thr Cys Leu Asp Gly Met Asp Arg Asn Gly Thr Cys Val
            100                 105                 110

Cys Gln Glu Asn Phe Arg Gly Ser Ala Cys Gln Glu Cys Gln Asp Pro
        115                 120                 125

Asn Arg Phe Gly Pro Asp Cys Gln Ser Val Cys Ser Cys Val His Gly
130                 135                 140

Val Cys Asn His Gly Pro Arg Gly Asp Gly Ser Cys Leu Cys Phe Ala
145                 150                 155                 160

Gly Tyr Thr Gly Pro His Cys Asp Gln Glu Leu Pro Val Cys Gln Glu
                165                 170                 175

Leu Arg Cys Pro Gln Asn Thr Gln Cys Ser Ala Glu Ala Pro Ser Cys
            180                 185                 190

Arg Cys Leu Pro Gly Tyr Thr Gln Gln Gly Ser Glu Cys Arg Ala Pro
        195                 200                 205

Asn Pro Cys Trp Pro Ser Pro Cys Ser Leu Leu Ala Gln Cys Ser Val
210                 215                 220

Ser Pro Lys Gly Gln Ala Gln Cys His Cys Pro Glu Asn Tyr His Gly
225                 230                 235                 240

Asp Gly Met Val Cys Leu Pro Lys Asp Pro Cys Thr Asp Asn Leu Gly
                245                 250                 255

Gly Cys Pro Ser Asn Ser Thr Leu Cys Val Tyr Gln Lys Pro Gly Gln
            260                 265                 270

Ala Phe Cys Thr Cys Arg Pro Gly Leu Val Ser Ile Asn Ser Asn Ala
        275                 280                 285

Ser Ala Gly Cys Phe Ala Phe Cys Ser Pro Phe Ser Cys Asp Arg Ser
290                 295                 300

Ala Thr Cys Gln Val Thr Ala Asp Gly Lys Thr Ser Cys Val Cys Arg
305                 310                 315                 320

Glu Ser Glu Val Gly Asp Gly Arg Ala Cys Tyr Gly His Leu Leu His
                325                 330                 335

Glu Val Gln Lys Ala Thr Gln Thr Gly Arg Val Phe Leu Gln Leu Arg
            340                 345                 350

Val Ala Val Ala Met Met Asp Gln Gly Cys Arg Glu Ile Leu Thr Thr
        355                 360                 365

Ala Gly Pro Phe Thr Val Leu Val Pro Ser Val Ser Ser Phe Ser Ser
370                 375                 380

Arg Thr Met Asn Ala Ser Leu Ala Gln Gln Leu Cys Arg Gln His Ile
385                 390                 395                 400

Ile Ala Gly Gln His Ile Leu Glu Asp Thr Arg Thr Gln Gln Thr Arg
                405                 410                 415

Arg Trp Trp Thr Leu Ala Gly Gln Glu Ile Thr Val Thr Phe Asn Gln
            420                 425                 430

Phe Thr Lys Tyr Ser Tyr Lys Tyr Lys Asp Gln Pro Gln Gln Thr Phe
        435                 440                 445

Asn Ile Tyr Lys Ala Asn Asn Ile Ala Ala Asn Gly Val Phe His Val
450                 455                 460

Val Thr Gly Leu Arg Trp Gln Ala Pro Ser Gly Thr Pro Gly Asp Pro
465                 470                 475                 480
```

-continued

```
Lys Arg Thr Ile Gly Gln Ile Leu Ala Ser Thr Glu Ala Phe Ser Arg
                485                 490                 495

Phe Glu Thr Ile Leu Glu Asn Cys Gly Leu Pro Ser Ile Leu Asp Gly
            500                 505                 510

Pro Gly Pro Phe Thr Val Phe Ala Pro Ser Asn Glu Ala Val Asp Ser
        515                 520                 525

Leu Arg Asp Gly Arg Leu Ile Tyr Leu Phe Thr Ala Gly Leu Ser Lys
    530                 535                 540

Leu Gln Glu Leu Val Arg Tyr His Ile Tyr Asn His Gly Gln Leu Thr
545                 550                 555                 560

Val Glu Lys Leu Ile Ser Lys Gly Arg Ile Leu Thr Met Ala Asn Gln
                565                 570                 575

Val Leu Ala Val Asn Ile Ser Glu Glu Gly Arg Ile Leu Leu Gly Pro
            580                 585                 590

Glu Gly Val Pro Leu Gln Arg Val Asp Val Met Ala Ala Asn Gly Val
        595                 600                 605

Ile His Met Leu Asp Gly Ile Leu Leu Pro Pro Thr Ile Leu Pro Ile
    610                 615                 620

Leu Pro Lys His Cys Ser Glu Glu Gln His Lys Ile Val Ala Gly Ser
625                 630                 635                 640

Cys Val Asp Cys Gln Ala Leu Asn Thr Ser Thr Cys Pro Pro Asn Ser
                645                 650                 655

Val Lys Leu Asp Ile Phe Pro Lys Glu Cys Val Tyr Ile His Asp Pro
            660                 665                 670

Thr Gly Leu Asn Val Leu Lys Lys Gly Cys Ala Ser Tyr Cys Asn Gln
        675                 680                 685

Thr Ile Met Glu Gln Gly Cys Cys Lys Gly Phe Phe Gly Pro Asp Cys
    690                 695                 700

Thr Gln Cys Pro Gly Gly Phe Ser Asn Pro Cys Tyr Gly Lys Gly Asn
705                 710                 715                 720

Cys Ser Asp Gly Ile Gln Gly Asn Gly Ala Cys Leu Cys Phe Pro Asp
                725                 730                 735

Tyr Lys Gly Ile Ala Cys His Ile Cys Ser Asn Pro Asn Lys His Gly
            740                 745                 750

Glu Gln Cys Gln Glu Asp Cys Gly Cys Val His Gly Leu Cys Asp Asn
        755                 760                 765

Arg Pro Gly Ser Gly Gly Val Cys Gln Gln Gly Thr Cys Ala Pro Gly
    770                 775                 780

Phe Ser Gly Arg Phe Cys Asn Glu Ser Met Gly Asp Cys Gly Pro Thr
785                 790                 795                 800

Gly Leu Ala Gln His Cys His Leu His Ala Arg Cys Val Ser Gln Glu
                805                 810                 815

Gly Val Ala Arg Cys Arg Cys Leu Asp Gly Phe Glu Gly Asp Gly Phe
            820                 825                 830

Ser Cys Thr Pro Ser Asn Pro Cys Ser His Pro Asp Arg Gly Gly Cys
        835                 840                 845

Ser Glu Asn Ala Glu Cys Val Pro Gly Ser Leu Gly Thr His His Cys
    850                 855                 860

Thr Cys His Lys Gly Trp Ser Gly Asp Gly Arg Val Cys Val Ala Ile
865                 870                 875                 880

Asp Glu Cys Glu Leu Asp Met Arg Gly Gly Cys His Thr Asp Ala Leu
                885                 890                 895

Cys Ser Tyr Val Gly Pro Gly Gln Ser Arg Cys Thr Cys Lys Leu Gly
```

```
                900             905             910
Phe Ala Gly Asp Gly Tyr Gln Cys Ser Pro Ile Asp Pro Cys Arg Ala
        915             920             925
Gly Asn Gly Gly Cys His Gly Leu Ala Thr Cys Arg Ala Val Gly Gly
        930             935             940
Gly Gln Arg Val Cys Thr Cys Pro Pro Gly Phe Gly Gly Asp Gly Phe
945             950             955             960
Ser Cys Tyr Gly Asp Ile Phe Arg Glu Leu Glu Ala Asn Ala His Phe
                965             970             975
Ser Ile Phe Tyr Gln Trp Leu Lys Ser Ala Gly Ile Thr Leu Pro Ala
                980             985             990
Asp Arg Arg Val Thr Ala Leu Val Pro Ser Glu Ala Ala Val Arg Gln
                995             1000            1005
Leu Ser Pro Glu Asp Arg Ala Phe Trp Leu Gln Pro Arg Thr Leu
        1010            1015            1020
Pro Asn Leu Val Arg Ala His Phe Leu Gln Gly Ala Leu Phe Glu
        1025            1030            1035
Glu Glu Leu Ala Arg Leu Gly Gly Gln Glu Val Ala Thr Leu Asn
        1040            1045            1050
Pro Thr Thr Arg Trp Glu Ile Arg Asn Ile Ser Gly Arg Val Trp
        1055            1060            1065
Val Gln Asn Ala Ser Val Asp Val Ala Asp Leu Leu Ala Thr Asn
        1070            1075            1080
Gly Val Leu His Ile Leu Ser Gln Val Leu Leu Pro Pro Arg Gly
        1085            1090            1095
Asp Val Pro Gly Gly Gln Gly Leu Leu Gln Gln Leu Asp Leu Val
        1100            1105            1110
Pro Ala Phe Ser Leu Phe Arg Glu Leu Leu Gln His His Gly Leu
        1115            1120            1125
Val Pro Gln Ile Glu Ala Ala Thr Ala Tyr Thr Ile Phe Val Pro
        1130            1135            1140
Thr Asn Arg Ser Leu Glu Ala Gln Gly Asn Ser Ser His Leu Asp
        1145            1150            1155
Ala Asp Thr Val Arg His His Val Val Leu Gly Glu Ala Leu Ser
        1160            1165            1170
Met Glu Thr Leu Arg Lys Gly Gly His Arg Asn Ser Leu Leu Gly
        1175            1180            1185
Pro Ala His Trp Ile Val Phe Tyr Asn His Ser Gly Gln Pro Glu
        1190            1195            1200
Val Asn His Val Pro Leu Glu Gly Pro Met Leu Glu Ala Pro Gly
        1205            1210            1215
Arg Ser Leu Ile Gly Leu Ser Gly Val Leu Thr Val Gly Ser Ser
        1220            1225            1230
Arg Cys Leu His Ser His Ala Glu Ala Leu Arg Glu Lys Cys Val
        1235            1240            1245
Asn Cys Thr Arg Arg Phe Arg Cys Thr Gln Gly Phe Gln Leu Gln
        1250            1255            1260
Asp Thr Pro Arg Lys Ser Cys Val Tyr Arg Ser Gly Phe Ser Phe
        1265            1270            1275
Ser Arg Gly Cys Ser Tyr Thr Cys Ala Lys Lys Ile Gln Val Pro
        1280            1285            1290
Asp Cys Cys Pro Gly Phe Phe Gly Thr Leu Cys Glu Pro Cys Pro
        1295            1300            1305
```

```
Gly Gly Leu Gly Gly Val Cys Ser Gly His Gly Gln Cys Gln Asp
            1310                1315                1320

Arg Phe Leu Gly Ser Gly Glu Cys His Cys His Glu Gly Phe His
    1325                1330                1335

Gly Thr Ala Cys Glu Val Cys Glu Leu Gly Arg Tyr Gly Pro Asn
    1340                1345                1350

Cys Thr Gly Val Cys Asp Cys Ala His Gly Leu Cys Gln Glu Gly
    1355                1360                1365

Leu Gln Gly Asp Gly Ser Cys Val Cys Asn Val Gly Trp Gln Gly
    1370                1375                1380

Leu Arg Cys Asp Gln Lys Ile Thr Ser Pro Gln Cys Pro Arg Lys
    1385                1390                1395

Cys Asp Pro Asn Ala Asn Cys Val Gln Asp Ser Ala Gly Ala Ser
    1400                1405                1410

Thr Cys Ala Cys Ala Ala Gly Tyr Ser Gly Asn Gly Ile Phe Cys
    1415                1420                1425

Ser Glu Val Asp Pro Cys Ala His Gly His Gly Gly Cys Ser Pro
    1430                1435                1440

His Ala Asn Cys Thr Lys Val Ala Pro Gly Gln Arg Thr Cys Thr
    1445                1450                1455

Cys Gln Asp Gly Tyr Met Gly Asp Gly Glu Leu Cys Gln Glu Ile
    1460                1465                1470

Asn Ser Cys Leu Ile His His Gly Gly Cys His Ile His Ala Glu
    1475                1480                1485

Cys Ile Pro Thr Gly Pro Gln Gln Val Ser Cys Ser Cys Arg Glu
    1490                1495                1500

Gly Tyr Ser Gly Asp Gly Ile Arg Thr Cys Glu Leu Leu Asp Pro
    1505                1510                1515

Cys Ser Lys Asn Asn Gly Gly Cys Ser Pro Tyr Ala Thr Cys Lys
    1520                1525                1530

Ser Thr Gly Asp Gly Gln Arg Thr Cys Thr Cys Asp Thr Ala His
    1535                1540                1545

Thr Val Gly Asp Gly Leu Thr Cys Arg Ala Arg Val Gly Leu Glu
    1550                1555                1560

Leu Leu Arg Asp Lys His Ala Ser Phe Phe Ser Leu Arg Leu Leu
    1565                1570                1575

Glu Tyr Lys Glu Leu Lys Gly Asp Gly Pro Phe Thr Ile Phe Val
    1580                1585                1590

Pro His Ala Asp Leu Met Ser Asn Leu Ser Gln Asp Glu Leu Ala
    1595                1600                1605

Arg Ile Arg Ala His Arg Gln Leu Val Phe Arg Tyr His Val Val
    1610                1615                1620

Gly Cys Arg Arg Leu Arg Ser Glu Asp Leu Leu Glu Gln Gly Tyr
    1625                1630                1635

Ala Thr Ala Leu Ser Gly His Pro Leu Arg Phe Ser Glu Arg Glu
    1640                1645                1650

Gly Ser Ile Tyr Leu Asn Asp Phe Ala Arg Val Val Ser Ser Asp
    1655                1660                1665

His Glu Ala Val Asn Gly Ile Leu His Phe Ile Asp Arg Val Leu
    1670                1675                1680

Leu Pro Pro Glu Ala Leu His Trp Glu Pro Asp Asp Ala Pro Ile
    1685                1690                1695
```

-continued

```
Pro Arg Arg Asn Val Thr Ala Ala Gln Gly Phe Gly Tyr Lys
1700                1705                1710

Ile Phe Ser Gly Leu Leu Lys Val Ala Gly Leu Leu Pro Leu Leu
    1715                1720                1725

Arg Glu Ala Ser His Arg Pro Phe Thr Met Leu Trp Pro Thr Asp
1730                1735                1740

Ala Ala Phe Arg Ala Leu Pro Pro Asp Arg Gln Ala Trp Leu Tyr
1745                1750                1755

His Glu Asp His Arg Asp Lys Leu Ala Ala Ile Leu Arg Gly His
1760                1765                1770

Met Ile Arg Asn Val Glu Ala Leu Ala Ser Asp Leu Pro Asn Leu
1775                1780                1785

Gly Pro Leu Arg Thr Met His Gly Thr Pro Ile Ser Phe Ser Cys
1790                1795                1800

Ser Arg Thr Arg Ala Gly Glu Leu Met Val Gly Glu Asp Asp Ala
1805                1810                1815

Arg Ile Val Gln Arg His Leu Pro Phe Glu Gly Gly Leu Ala Tyr
1820                1825                1830

Gly Ile Asp Gln Leu Leu Glu Pro Pro Gly Leu Gly Ala Arg Cys
1835                1840                1845

Asp His Phe Glu Thr Arg Pro Leu Arg Leu Asn Thr Cys Ser Ile
1850                1855                1860

Cys Gly Leu Glu Pro Pro Cys Pro Glu Gly Ser Gln Glu Gln Gly
1865                1870                1875

Ser Pro Glu Ala Cys Trp Arg Phe Tyr Pro Lys Phe Trp Thr Ser
1880                1885                1890

Pro Pro Leu His Ser Leu Gly Leu Arg Ser Val Trp Val His Pro
1895                1900                1905

Ser Leu Trp Gly Arg Pro Gln Gly Leu Gly Arg Gly Cys His Arg
1910                1915                1920

Asn Cys Val Thr Thr Thr Trp Lys Pro Ser Cys Cys Pro Gly His
1925                1930                1935

Tyr Gly Ser Glu Cys Gln Ala Cys Pro Gly Gly Pro Ser Ser Pro
1940                1945                1950

Cys Ser Asp Arg Gly Val Cys Met Asp Gly Met Ser Gly Ser Gly
1955                1960                1965

Gln Cys Leu Cys Arg Ser Gly Phe Ala Gly Thr Ala Cys Glu Leu
1970                1975                1980

Cys Ala Pro Gly Ala Phe Gly Pro His Cys Gln Ala Cys Arg Cys
1985                1990                1995

Thr Val His Gly Arg Cys Asp Glu Gly Leu Gly Gly Ser Gly Ser
2000                2005                2010

Cys Phe Cys Asp Glu Gly Trp Thr Gly Pro Arg Cys Glu Val Gln
2015                2020                2025

Leu Glu Leu Gln Pro Val Cys Thr Pro Pro Cys Ala Pro Glu Ala
2030                2035                2040

Val Cys Arg Ala Gly Asn Ser Cys Glu Cys Ser Leu Gly Tyr Glu
2045                2050                2055

Gly Asp Gly Arg Val Cys Thr Val Ala Asp Leu Cys Gln Asp Gly
2060                2065                2070

His Gly Gly Cys Ser Glu His Ala Asn Cys Ser Gln Val Gly Thr
2075                2080                2085

Met Val Thr Cys Thr Cys Leu Pro Asp Tyr Glu Gly Asp Gly Trp
```

-continued

```
              2090                2095                2100
Ser Cys Arg Ala Arg Asn Pro Cys Thr Asp Gly His Arg Gly Gly
    2105                2110                2115
Cys Ser Glu His Ala Asn Cys Leu Ser Thr Gly Leu Asn Thr Arg
    2120                2125                2130
Arg Cys Glu Cys His Ala Gly Tyr Val Gly Asp Gly Leu Gln Cys
    2135                2140                2145
Leu Glu Glu Ser Glu Pro Pro Val Asp Arg Cys Leu Gly Gln Pro
    2150                2155                2160
Pro Pro Cys His Ser Asp Ala Met Cys Thr Asp Leu His Phe Gln
    2165                2170                2175
Glu Lys Arg Ala Gly Val Phe His Leu Gln Ala Thr Ser Gly Pro
    2180                2185                2190
Tyr Gly Leu Asn Phe Ser Glu Ala Glu Ala Ala Cys Glu Ala Gln
    2195                2200                2205
Gly Ala Val Leu Ala Ser Phe Pro Gln Leu Ser Ala Ala Gln Gln
    2210                2215                2220
Leu Gly Phe His Leu Cys Leu Met Gly Trp Leu Ala Asn Gly Ser
    2225                2230                2235
Thr Ala His Pro Val Val Phe Pro Val Ala Asp Cys Gly Asn Gly
    2240                2245                2250
Arg Val Gly Ile Val Ser Leu Gly Ala Arg Lys Asn Leu Ser Glu
    2255                2260                2265
Arg Trp Asp Ala Tyr Cys Phe Arg Val Gln Asp Val Ala Cys Arg
    2270                2275                2280
Cys Arg Asn Gly Phe Val Gly Asp Gly Ile Ser Thr Cys Asn Gly
    2285                2290                2295
Lys Leu Leu Asp Val Leu Ala Ala Thr Ala Asn Phe Ser Thr Phe
    2300                2305                2310
Tyr Gly Met Leu Leu Gly Tyr Ala Asn Ala Thr Gln Arg Gly Leu
    2315                2320                2325
Asp Phe Leu Asp Phe Leu Asp Glu Leu Thr Tyr Lys Thr Leu
    2330                2335                2340
Phe Val Pro Val Asn Glu Gly Phe Val Asp Asn Met Thr Leu Ser
    2345                2350                2355
Gly Pro Asp Leu Glu Leu His Ala Ser Asn Ala Thr Leu Leu Ser
    2360                2365                2370
Ala Asn Ala Ser Gln Gly Lys Leu Leu Pro Ala His Ser Gly Leu
    2375                2380                2385
Ser Leu Ile Ile Ser Asp Ala Gly Pro Asp Asn Ser Ser Trp Ala
    2390                2395                2400
Pro Val Ala Pro Gly Thr Val Val Val Ser Arg Ile Ile Val Trp
    2405                2410                2415
Asp Ile Met Ala Phe Asn Gly Ile Ile His Ala Leu Ala Ser Pro
    2420                2425                2430
Leu Leu Ala Pro Pro Gln Pro Gln Ala Val Leu Ala Pro Glu Ala
    2435                2440                2445
Pro Pro Val Ala Ala Gly Val Gly Ala Val Leu Ala Ala Gly Ala
    2450                2455                2460
Leu Leu Gly Leu Val Ala Gly Ala Leu Tyr Leu Arg Ala Arg Gly
    2465                2470                2475
Lys Pro Met Gly Phe Gly Phe Ser Ala Phe Gln Ala Glu Asp Asp
    2480                2485                2490
```

```
Ala Asp Asp Asp Phe Ser Pro Trp Gln Glu Gly Thr Asn Pro Thr
    2495            2500                2505

Leu Val Ser Val Pro Asn Pro Val Phe Gly Ser Asp Thr Phe Cys
    2510            2515                2520

Glu Pro Phe Asp Asp Ser Leu Leu Glu Glu Asp Phe Pro Asp Thr
    2525            2530                2535

Gln Arg Ile Leu Thr Val Lys
    2540            2545

<210> SEQ ID NO 96
<211> LENGTH: 96
<212> TYPE: PRT
<213> ORGANISM: Homo sapiens

<400> SEQUENCE: 96

Arg Ala Gly Val Phe His Leu Gln Ala Thr Ser Gly Pro Tyr Gly Leu
1               5                   10                  15

Asn Phe Ser Glu Ala Glu Ala Ala Cys Glu Ala Gln Gly Ala Val Leu
                20                  25                  30

Ala Ser Phe Pro Gln Leu Ser Ala Ala Gln Leu Gly Phe His Leu
            35                  40                  45

Cys Leu Met Gly Trp Leu Ala Asn Gly Ser Thr Ala His Pro Val Val
50                  55                  60

Phe Pro Val Ala Asp Cys Gly Asn Gly Arg Val Gly Ile Val Ser Leu
65                  70                  75                  80

Gly Ala Arg Lys Asn Leu Ser Glu Arg Trp Asp Ala Tyr Cys Phe Arg
                85                  90                  95

<210> SEQ ID NO 97
<211> LENGTH: 2551
<212> TYPE: PRT
<213> ORGANISM: Homo sapiens

<400> SEQUENCE: 97

Met Met Leu Gln His Leu Val Ile Phe Cys Leu Gly Leu Val Val Gln
1               5                   10                  15

Asn Phe Cys Ser Pro Ala Glu Thr Thr Gly Gln Ala Arg Arg Cys Asp
                20                  25                  30

Arg Lys Ser Leu Leu Thr Ile Arg Thr Glu Cys Arg Ser Cys Ala Leu
            35                  40                  45

Asn Leu Gly Val Lys Cys Pro Asp Gly Tyr Thr Met Ile Thr Ser Gly
50                  55                  60

Ser Val Gly Val Arg Asp Cys Arg Tyr Thr Phe Glu Val Arg Thr Tyr
65                  70                  75                  80

Ser Leu Ser Leu Pro Gly Cys Arg His Ile Cys Arg Lys Asp Tyr Leu
                85                  90                  95

Gln Pro Arg Cys Cys Pro Gly Arg Trp Gly Pro Asp Cys Ile Glu Cys
            100                 105                 110

Pro Gly Gly Ala Gly Ser Pro Cys Asn Gly Arg Gly Ser Cys Ala Glu
        115                 120                 125

Gly Met Glu Gly Asn Gly Thr Cys Ser Cys Gln Glu Gly Phe Gly Gly
    130                 135                 140

Thr Ala Cys Glu Thr Cys Ala Asp Asp Asn Leu Phe Gly Pro Ser Cys
145                 150                 155                 160

Ser Ser Val Cys Asn Cys Val His Gly Val Cys Asn Ser Gly Leu Asp
                165                 170                 175
```

-continued

```
Gly Asp Gly Thr Cys Glu Cys Tyr Ser Ala Tyr Thr Gly Pro Lys Cys
            180                 185                 190

Asp Lys Pro Ile Pro Glu Cys Ala Leu Leu Cys Pro Glu Asn Ser
        195                 200                 205

Arg Cys Ser Pro Ser Thr Glu Asp Glu Asn Lys Leu Glu Cys Lys Cys
    210                 215                 220

Leu Pro Asn Tyr Arg Gly Asp Gly Lys Tyr Cys Asp Pro Ile Asn Pro
225                 230                 235                 240

Cys Leu Arg Lys Ile Cys His Pro His Ala His Cys Thr Tyr Leu Gly
                245                 250                 255

Pro Asn Arg His Ser Cys Thr Cys Gln Glu Gly Tyr Arg Gly Asp Gly
            260                 265                 270

Gln Val Cys Leu Pro Val Asp Pro Cys Gln Ile Asn Phe Gly Asn Cys
        275                 280                 285

Pro Thr Lys Ser Thr Val Cys Lys Tyr Asp Gly Pro Gly Gln Ser His
    290                 295                 300

Cys Glu Cys Lys Glu His Tyr Gln Asn Phe Val Pro Gly Val Gly Cys
305                 310                 315                 320

Ser Met Thr Asp Ile Cys Lys Ser Asp Asn Pro Cys His Arg Asn Ala
                325                 330                 335

Asn Cys Thr Thr Val Ala Pro Gly Arg Thr Glu Cys Ile Cys Gln Lys
            340                 345                 350

Gly Tyr Val Gly Asp Gly Leu Thr Cys Tyr Gly Asn Ile Met Glu Arg
        355                 360                 365

Leu Arg Glu Leu Asn Thr Glu Pro Arg Gly Lys Trp Gln Gly Arg Leu
    370                 375                 380

Thr Ser Phe Ile Ser Leu Leu Asp Lys Ala Tyr Ala Trp Pro Leu Ser
385                 390                 395                 400

Lys Leu Gly Pro Phe Thr Val Leu Leu Pro Thr Asp Lys Gly Leu Lys
                405                 410                 415

Gly Phe Asn Val Asn Glu Leu Val Asp Asn Lys Ala Ala Gln Tyr
            420                 425                 430

Phe Val Lys Leu His Ile Ile Ala Gly Gln Met Asn Ile Glu Tyr Met
        435                 440                 445

Asn Asn Thr Asp Met Phe Tyr Thr Leu Thr Gly Lys Ser Gly Glu Ile
    450                 455                 460

Phe Asn Ser Asp Lys Asp Asn Gln Ile Lys Leu Lys Leu His Gly Gly
465                 470                 475                 480

Lys Lys Lys Val Lys Ile Ile Gln Gly Asp Ile Ile Ala Ser Asn Gly
                485                 490                 495

Leu Leu His Ile Leu Asp Arg Ala Met Asp Lys Leu Glu Pro Thr Phe
            500                 505                 510

Glu Ser Asn Asn Glu Gln Thr Ile Met Thr Met Leu Gln Pro Arg Tyr
        515                 520                 525

Ser Lys Phe Arg Ser Leu Leu Glu Glu Thr Asn Leu Gly His Ala Leu
    530                 535                 540

Asp Glu Asp Gly Val Gly Gly Pro Tyr Thr Ile Phe Val Pro Asn Asn
545                 550                 555                 560

Glu Ala Leu Asn Asn Met Lys Asp Gly Thr Leu Asp Tyr Leu Leu Ser
                565                 570                 575

Pro Glu Gly Ser Arg Lys Leu Leu Glu Leu Val Arg Tyr His Ile Val
            580                 585                 590
```

-continued

Pro Phe Thr Gln Leu Glu Val Ala Thr Leu Ile Ser Thr Pro His Ile
            595                 600                 605

Arg Ser Met Ala Asn Gln Leu Ile Gln Phe Asn Thr Thr Asp Asn Gly
        610                 615                 620

Gln Ile Leu Ala Asn Asp Val Ala Met Glu Glu Ile Glu Ile Thr Ala
625                 630                 635                 640

Lys Asn Gly Arg Ile Tyr Thr Leu Thr Gly Val Leu Ile Pro Pro Ser
                645                 650                 655

Ile Val Pro Ile Leu Pro His Arg Cys Asp Glu Thr Lys Arg Glu Met
            660                 665                 670

Lys Leu Gly Thr Cys Val Ser Cys Ser Leu Val Tyr Trp Ser Arg Cys
        675                 680                 685

Pro Ala Asn Ser Glu Pro Thr Ala Leu Phe Thr His Arg Cys Val Tyr
690                 695                 700

Ser Gly Arg Phe Gly Ser Leu Lys Ser Gly Cys Ala Arg Tyr Cys Asn
705                 710                 715                 720

Ala Thr Val Lys Ile Pro Lys Cys Cys Lys Gly Phe Tyr Gly Pro Asp
                725                 730                 735

Cys Asn Gln Cys Pro Gly Gly Phe Ser Asn Pro Cys Ser Gly Asn Gly
            740                 745                 750

Gln Cys Ala Asp Ser Leu Gly Gly Asn Gly Thr Cys Ile Cys Glu Glu
        755                 760                 765

Gly Phe Gln Gly Ser Gln Cys Gln Phe Cys Ser Asp Pro Asn Lys Tyr
        770                 775                 780

Gly Pro Arg Cys Asn Lys Lys Cys Leu Cys Val His Gly Thr Cys Asn
785                 790                 795                 800

Asn Arg Ile Asp Ser Asp Gly Ala Cys Leu Thr Gly Thr Cys Arg Asp
                805                 810                 815

Gly Ser Ala Gly Arg Leu Cys Asp Lys Gln Thr Ser Ala Cys Gly Pro
            820                 825                 830

Tyr Val Gln Phe Cys His Ile His Ala Thr Cys Glu Tyr Ser Asn Gly
        835                 840                 845

Thr Ala Ser Cys Ile Cys Lys Ala Gly Tyr Glu Gly Asp Gly Thr Leu
850                 855                 860

Cys Ser Glu Met Asp Pro Cys Thr Gly Leu Thr Pro Gly Gly Cys Ser
865                 870                 875                 880

Arg Asn Ala Glu Cys Ile Lys Thr Gly Thr Gly Thr His Thr Cys Val
                885                 890                 895

Cys Gln Gln Gly Trp Thr Gly Asn Gly Arg Asp Cys Ser Glu Ile Asn
            900                 905                 910

Asn Cys Leu Leu Pro Ser Ala Gly Gly Cys His Asp Asn Ala Ser Cys
        915                 920                 925

Leu Tyr Val Gly Pro Gly Gln Asn Glu Cys Glu Cys Lys Lys Gly Phe
        930                 935                 940

Arg Gly Asn Gly Ile Asp Cys Glu Pro Ile Thr Ser Cys Leu Glu Gln
945                 950                 955                 960

Thr Gly Lys Cys His Pro Leu Ala Ser Cys Gln Ser Thr Ser Ser Gly
                965                 970                 975

Val Trp Ser Cys Val Cys Gln Glu Gly Tyr Glu Gly Asp Gly Phe Leu
            980                 985                 990

Cys Tyr Gly Asn Ala Ala Val Glu  Leu Ser Phe Leu Ser  Glu Ala Ala
        995                 1000                 1005

Ile Phe  Asn Arg Trp Ile Asn  Asn Ala Ser Leu Gln  Pro Thr Leu

-continued

```
               1010                1015                1020
Ser Ala Thr Ser Asn Leu Thr Val Leu Val Pro Ser Gln Gln Ala
       1025                1030                1035
Thr Glu Asp Met Asp Gln Asp Glu Lys Ser Phe Trp Leu Ser Gln
       1040                1045                1050
Ser Asn Ile Pro Ala Leu Ile Lys Tyr His Met Leu Leu Gly Thr
       1055                1060                1065
Tyr Arg Val Ala Asp Leu Gln Thr Leu Ser Ser Ser Asp Met Leu
       1070                1075                1080
Ala Thr Ser Leu Gln Gly Asn Phe Leu His Leu Ala Lys Val Asp
       1085                1090                1095
Gly Asn Ile Thr Ile Glu Gly Ala Ser Ile Val Asp Gly Asp Asn
       1100                1105                1110
Ala Ala Thr Asn Gly Val Ile His Ile Ile Asn Lys Val Leu Val
       1115                1120                1125
Pro Gln Arg Arg Leu Thr Gly Ser Leu Pro Asn Leu Leu Met Arg
       1130                1135                1140
Leu Glu Gln Met Pro Asp Tyr Ser Ile Phe Arg Gly Tyr Ile Ile
       1145                1150                1155
Gln Tyr Asn Leu Ala Asn Ala Ile Glu Ala Ala Asp Ala Tyr Thr
       1160                1165                1170
Val Phe Ala Pro Asn Asn Asn Ala Ile Glu Asn Tyr Ile Arg Glu
       1175                1180                1185
Lys Lys Val Leu Ser Leu Glu Glu Asp Val Leu Arg Tyr His Val
       1190                1195                1200
Val Leu Glu Glu Lys Leu Leu Lys Asn Asp Leu His Asn Gly Met
       1205                1210                1215
His Arg Glu Thr Met Leu Gly Phe Ser Tyr Phe Leu Ser Phe Phe
       1220                1225                1230
Leu His Asn Asp Gln Leu Tyr Val Asn Glu Ala Pro Ile Asn Tyr
       1235                1240                1245
Thr Asn Val Ala Thr Asp Lys Gly Val Ile His Gly Leu Gly Lys
       1250                1255                1260
Val Leu Glu Ile Gln Lys Asn Arg Cys Asp Asn Asn Asp Thr Thr
       1265                1270                1275
Ile Ile Arg Gly Arg Cys Arg Thr Cys Ser Ser Glu Leu Thr Cys
       1280                1285                1290
Pro Phe Gly Thr Lys Ser Leu Gly Asn Glu Lys Arg Arg Cys Ile
       1295                1300                1305
Tyr Thr Ser Tyr Phe Met Gly Arg Arg Thr Leu Phe Ile Gly Cys
       1310                1315                1320
Gln Pro Lys Cys Val Arg Thr Val Ile Thr Arg Glu Cys Cys Ala
       1325                1330                1335
Gly Phe Phe Gly Pro Gln Cys Gln Pro Cys Pro Gly Asn Ala Gln
       1340                1345                1350
Asn Val Cys Phe Gly Asn Gly Ile Cys Leu Asp Gly Val Asn Gly
       1355                1360                1365
Thr Gly Val Cys Glu Cys Gly Glu Gly Phe Ser Gly Thr Ala Cys
       1370                1375                1380
Glu Thr Cys Thr Glu Gly Lys Tyr Gly Ile His Cys Asp Gln Ala
       1385                1390                1395
Cys Ser Cys Val His Gly Arg Cys Asn Gln Gly Pro Leu Gly Asp
       1400                1405                1410
```

```
Gly Ser Cys Asp Cys Asp Val Gly Trp Arg Gly Val His Cys Asp
1415                1420                1425

Asn Ala Thr Thr Glu Asp Asn Cys Asn Gly Thr Cys His Thr Ser
1430                1435                1440

Ala Asn Cys Leu Thr Asn Ser Asp Gly Thr Ala Ser Cys Lys Cys
1445                1450                1455

Ala Ala Gly Phe Gln Gly Asn Gly Thr Ile Cys Thr Ala Ile Asn
1460                1465                1470

Ala Cys Glu Ile Ser Asn Gly Gly Cys Ser Ala Lys Ala Asp Cys
1475                1480                1485

Lys Arg Thr Thr Pro Gly Arg Arg Val Cys Thr Cys Lys Ala Gly
1490                1495                1500

Tyr Thr Gly Asp Gly Ile Val Cys Leu Glu Ile Asn Pro Cys Leu
1505                1510                1515

Glu Asn His Gly Gly Cys Asp Lys Asn Ala Glu Cys Thr Gln Thr
1520                1525                1530

Gly Pro Asn Gln Ala Ala Cys Asn Cys Leu Pro Ala Tyr Thr Gly
1535                1540                1545

Asp Gly Lys Val Cys Thr Leu Ile Asn Val Cys Leu Thr Lys Asn
1550                1555                1560

Gly Gly Cys Ser Glu Phe Ala Ile Cys Asn His Thr Gly Gln Val
1565                1570                1575

Glu Arg Thr Cys Thr Cys Lys Pro Asn Tyr Ile Gly Asp Gly Phe
1580                1585                1590

Thr Cys Arg Gly Ser Ile Tyr Gln Glu Leu Pro Lys Asn Pro Lys
1595                1600                1605

Thr Ser Gln Tyr Phe Phe Gln Leu Gln Glu His Phe Val Lys Asp
1610                1615                1620

Leu Val Gly Pro Gly Pro Phe Thr Val Phe Ala Pro Leu Ser Ala
1625                1630                1635

Ala Phe Asp Glu Glu Ala Arg Val Lys Asp Trp Asp Lys Tyr Gly
1640                1645                1650

Leu Met Pro Gln Val Leu Arg Tyr His Val Val Ala Cys His Gln
1655                1660                1665

Leu Leu Leu Glu Asn Leu Lys Leu Ile Ser Asn Ala Thr Ser Leu
1670                1675                1680

Gln Gly Glu Pro Ile Val Ile Ser Val Ser Gln Ser Thr Val Tyr
1685                1690                1695

Ile Asn Asn Lys Ala Lys Ile Ile Ser Ser Asp Ile Ile Ser Thr
1700                1705                1710

Asn Gly Ile Val His Ile Ile Asp Lys Leu Leu Ser Pro Lys Asn
1715                1720                1725

Leu Leu Ile Thr Pro Lys Asp Asn Ser Gly Arg Ile Leu Gln Asn
1730                1735                1740

Leu Thr Thr Leu Ala Thr Asn Asn Gly Tyr Ile Lys Phe Ser Asn
1745                1750                1755

Leu Ile Gln Asp Ser Gly Leu Leu Ser Val Ile Thr Asp Pro Ile
1760                1765                1770

His Thr Pro Val Thr Leu Phe Trp Pro Thr Asp Gln Ala Leu His
1775                1780                1785

Ala Leu Pro Ala Glu Gln Gln Asp Phe Leu Phe Asn Gln Asp Asn
1790                1795                1800
```

-continued

Lys Asp Lys Leu Lys Glu Tyr Leu Lys Phe His Val Ile Arg Asp
    1805                1810                1815

Ala Lys Val Leu Ala Val Asp Leu Pro Thr Ser Thr Ala Trp Lys
    1820                1825                1830

Thr Leu Gln Gly Ser Glu Leu Ser Val Lys Cys Gly Ala Gly Arg
    1835                1840                1845

Asp Ile Gly Asp Leu Phe Leu Asn Gly Gln Thr Cys Arg Ile Val
    1850                1855                1860

Gln Arg Glu Leu Leu Phe Asp Leu Gly Val Ala Tyr Gly Ile Asp
    1865                1870                1875

Cys Leu Leu Ile Asp Pro Thr Leu Gly Gly Arg Cys Asp Thr Phe
    1880                1885                1890

Thr Thr Phe Asp Ala Ser Gly Glu Cys Gly Ser Cys Val Asn Thr
    1895                1900                1905

Pro Ser Cys Pro Arg Trp Ser Lys Pro Lys Gly Val Lys Gln Lys
    1910                1915                1920

Cys Leu Tyr Asn Leu Pro Phe Lys Arg Asn Leu Glu Gly Cys Arg
    1925                1930                1935

Glu Arg Cys Ser Leu Val Ile Gln Ile Pro Arg Cys Cys Lys Gly
    1940                1945                1950

Tyr Phe Gly Arg Asp Cys Gln Ala Cys Pro Gly Pro Asp Ala
    1955                1960                1965

Pro Cys Asn Asn Arg Gly Val Cys Leu Asp Gln Tyr Ser Ala Thr
    1970                1975                1980

Gly Glu Cys Lys Cys Asn Thr Gly Phe Asn Gly Thr Ala Cys Glu
    1985                1990                1995

Met Cys Trp Pro Gly Arg Phe Gly Pro Asp Cys Leu Pro Cys Gly
    2000                2005                2010

Cys Ser Asp His Gly Gln Cys Asp Asp Gly Ile Thr Gly Ser Gly
    2015                2020                2025

Gln Cys Leu Cys Glu Thr Gly Trp Thr Gly Pro Ser Cys Asp Thr
    2030                2035                2040

Gln Ala Val Leu Pro Ala Val Cys Thr Pro Pro Cys Ser Ala His
    2045                2050                2055

Ala Thr Cys Lys Glu Asn Asn Thr Cys Glu Cys Asn Leu Asp Tyr
    2060                2065                2070

Glu Gly Asp Gly Ile Thr Cys Thr Val Val Asp Phe Cys Lys Gln
    2075                2080                2085

Asp Asn Gly Gly Cys Ala Lys Val Ala Arg Cys Ser Gln Lys Gly
    2090                2095                2100

Thr Lys Val Ser Cys Ser Cys Gln Lys Gly Tyr Lys Gly Asp Gly
    2105                2110                2115

His Ser Cys Thr Glu Ile Asp Pro Cys Ala Asp Gly Leu Asn Gly
    2120                2125                2130

Gly Cys His Glu His Ala Thr Cys Lys Met Thr Gly Pro Gly Lys
    2135                2140                2145

His Lys Cys Glu Cys Lys Ser His Tyr Val Gly Asp Gly Leu Asn
    2150                2155                2160

Cys Glu Pro Glu Gln Leu Pro Ile Asp Arg Cys Leu Gln Asp Asn
    2165                2170                2175

Gly Gln Cys His Ala Asp Ala Lys Cys Val Asp Leu His Phe Gln
    2180                2185                2190

Asp Thr Thr Val Gly Val Phe His Leu Arg Ser Pro Leu Gly Gln

```
                2195                2200                2205
Tyr Lys Leu Thr Phe Asp Lys Ala Arg Glu Ala Cys Ala Asn Glu
    2210                2215                2220
Ala Ala Thr Met Ala Thr Tyr Asn Gln Leu Ser Tyr Ala Gln Lys
    2225                2230                2235
Ala Lys Tyr His Leu Cys Ser Ala Gly Trp Leu Glu Thr Gly Arg
    2240                2245                2250
Val Ala Tyr Pro Thr Ala Phe Ala Ser Gln Asn Cys Gly Ser Gly
    2255                2260                2265
Val Val Gly Ile Val Asp Tyr Gly Pro Arg Pro Asn Lys Ser Glu
    2270                2275                2280
Met Trp Asp Val Phe Cys Tyr Arg Met Lys Asp Val Asn Cys Thr
    2285                2290                2295
Cys Lys Val Gly Tyr Val Gly Asp Gly Phe Ser Cys Ser Gly Asn
    2300                2305                2310
Leu Leu Gln Val Leu Met Ser Phe Pro Ser Leu Thr Asn Phe Leu
    2315                2320                2325
Thr Glu Val Leu Ala Tyr Ser Asn Ser Ser Ala Arg Gly Arg Ala
    2330                2335                2340
Phe Leu Glu His Leu Thr Asp Leu Ser Ile Arg Gly Thr Leu Phe
    2345                2350                2355
Val Pro Gln Asn Ser Gly Leu Gly Glu Asn Glu Thr Leu Ser Gly
    2360                2365                2370
Arg Asp Ile Glu His His Leu Ala Asn Val Ser Met Phe Phe Tyr
    2375                2380                2385
Asn Asp Leu Val Asn Gly Thr Thr Leu Gln Thr Arg Leu Gly Ser
    2390                2395                2400
Lys Leu Leu Ile Thr Ala Ser Gln Asp Pro Leu Gln Pro Thr Glu
    2405                2410                2415
Thr Arg Phe Val Asp Gly Arg Ala Ile Leu Gln Trp Asp Ile Phe
    2420                2425                2430
Ala Ser Asn Gly Ile Ile His Val Ile Ser Arg Pro Leu Lys Ala
    2435                2440                2445
Pro Pro Ala Pro Val Thr Leu Thr His Thr Gly Leu Gly Ala Gly
    2450                2455                2460
Ile Phe Phe Ala Ile Ile Leu Val Thr Gly Ala Val Ala Leu Ala
    2465                2470                2475
Ala Tyr Ser Tyr Phe Arg Ile Asn Arg Arg Thr Ile Gly Phe Gln
    2480                2485                2490
His Phe Glu Ser Glu Glu Asp Ile Asn Val Ala Ala Leu Gly Lys
    2495                2500                2505
Gln Gln Pro Glu Asn Ile Ser Asn Pro Leu Tyr Glu Ser Thr Thr
    2510                2515                2520
Ser Ala Pro Pro Glu Pro Ser Tyr Asp Pro Phe Thr Asp Ser Glu
    2525                2530                2535
Glu Arg Gln Leu Glu Gly Asn Asp Pro Leu Arg Thr Leu
    2540                2545                2550

<210> SEQ ID NO 98
<211> LENGTH: 2532
<212> TYPE: PRT
<213> ORGANISM: Homo sapiens

<400> SEQUENCE: 98
```

```
Ser Pro Ala Glu Thr Gly Gln Ala Arg Cys Asp Arg Lys Ser
1               5                   10                  15

Leu Leu Thr Ile Arg Thr Glu Cys Arg Ser Cys Ala Leu Asn Leu Gly
            20                  25                  30

Val Lys Cys Pro Asp Gly Tyr Thr Met Ile Thr Ser Gly Ser Val Gly
        35                  40                  45

Val Arg Asp Cys Arg Tyr Thr Phe Glu Val Arg Thr Tyr Ser Leu Ser
    50                  55                  60

Leu Pro Gly Cys Arg His Ile Cys Arg Lys Asp Tyr Leu Gln Pro Arg
65                  70                  75                  80

Cys Cys Pro Gly Arg Trp Gly Pro Asp Cys Ile Glu Cys Pro Gly Gly
                85                  90                  95

Ala Gly Ser Pro Cys Asn Gly Arg Gly Ser Cys Ala Glu Gly Met Glu
            100                 105                 110

Gly Asn Gly Thr Cys Ser Cys Gln Glu Gly Phe Gly Gly Thr Ala Cys
            115                 120                 125

Glu Thr Cys Ala Asp Asp Asn Leu Phe Gly Pro Ser Cys Ser Ser Val
        130                 135                 140

Cys Asn Cys Val His Gly Val Cys Asn Ser Gly Leu Asp Gly Asp Gly
145                 150                 155                 160

Thr Cys Glu Cys Tyr Ser Ala Tyr Thr Gly Pro Lys Cys Asp Lys Pro
                165                 170                 175

Ile Pro Glu Cys Ala Ala Leu Leu Cys Pro Glu Asn Ser Arg Cys Ser
            180                 185                 190

Pro Ser Thr Glu Asp Glu Asn Lys Leu Glu Cys Lys Cys Leu Pro Asn
        195                 200                 205

Tyr Arg Gly Asp Gly Lys Tyr Cys Asp Pro Ile Asn Pro Cys Leu Arg
    210                 215                 220

Lys Ile Cys His Pro His Ala His Cys Thr Tyr Leu Gly Pro Asn Arg
225                 230                 235                 240

His Ser Cys Thr Cys Gln Glu Gly Tyr Arg Gly Asp Gly Gln Val Cys
                245                 250                 255

Leu Pro Val Asp Pro Cys Gln Ile Asn Phe Gly Asn Cys Pro Thr Lys
            260                 265                 270

Ser Thr Val Cys Lys Tyr Asp Gly Pro Gly Gln Ser His Cys Glu Cys
        275                 280                 285

Lys Glu His Tyr Gln Asn Phe Val Pro Gly Val Gly Cys Ser Met Thr
    290                 295                 300

Asp Ile Cys Lys Ser Asp Asn Pro Cys His Arg Asn Ala Asn Cys Thr
305                 310                 315                 320

Thr Val Ala Pro Gly Arg Thr Glu Cys Ile Cys Gln Lys Gly Tyr Val
                325                 330                 335

Gly Asp Gly Leu Thr Cys Tyr Gly Asn Ile Met Glu Arg Leu Arg Glu
            340                 345                 350

Leu Asn Thr Glu Pro Arg Gly Lys Trp Gln Gly Arg Leu Thr Ser Phe
        355                 360                 365

Ile Ser Leu Leu Asp Lys Ala Tyr Ala Trp Pro Leu Ser Lys Leu Gly
    370                 375                 380

Pro Phe Thr Val Leu Leu Pro Thr Asp Lys Gly Leu Lys Gly Phe Asn
385                 390                 395                 400

Val Asn Glu Leu Leu Val Asp Asn Lys Ala Ala Gln Tyr Phe Val Lys
                405                 410                 415

Leu His Ile Ile Ala Gly Gln Met Asn Ile Glu Tyr Met Asn Asn Thr
```

-continued

```
                420             425             430
Asp Met Phe Tyr Thr Leu Thr Gly Lys Ser Gly Glu Ile Phe Asn Ser
        435             440             445

Asp Lys Asp Asn Gln Ile Lys Leu Lys Leu His Gly Gly Lys Lys Lys
450             455             460

Val Lys Ile Ile Gln Gly Asp Ile Ile Ala Ser Asn Gly Leu Leu His
465             470             475             480

Ile Leu Asp Arg Ala Met Asp Lys Leu Glu Pro Thr Phe Glu Ser Asn
        485             490             495

Asn Glu Gln Thr Ile Met Thr Met Leu Gln Pro Arg Tyr Ser Lys Phe
            500             505             510

Arg Ser Leu Leu Glu Glu Thr Asn Leu Gly His Ala Leu Asp Glu Asp
        515             520             525

Gly Val Gly Gly Pro Tyr Thr Ile Phe Val Pro Asn Asn Glu Ala Leu
    530             535             540

Asn Asn Met Lys Asp Gly Thr Leu Asp Tyr Leu Leu Ser Pro Glu Gly
545             550             555             560

Ser Arg Lys Leu Leu Glu Leu Val Arg Tyr His Ile Val Pro Phe Thr
            565             570             575

Gln Leu Glu Val Ala Thr Leu Ile Ser Thr Pro His Ile Arg Ser Met
        580             585             590

Ala Asn Gln Leu Ile Gln Phe Asn Thr Thr Asp Asn Gly Gln Ile Leu
        595             600             605

Ala Asn Asp Val Ala Met Glu Glu Ile Glu Ile Thr Ala Lys Asn Gly
    610             615             620

Arg Ile Tyr Thr Leu Thr Gly Val Leu Ile Pro Pro Ser Ile Val Pro
625             630             635             640

Ile Leu Pro His Arg Cys Asp Glu Thr Lys Arg Glu Met Lys Leu Gly
            645             650             655

Thr Cys Val Ser Cys Ser Leu Val Tyr Trp Ser Arg Cys Pro Ala Asn
            660             665             670

Ser Glu Pro Thr Ala Leu Phe Thr His Arg Cys Val Tyr Ser Gly Arg
        675             680             685

Phe Gly Ser Leu Lys Ser Gly Cys Ala Arg Tyr Cys Asn Ala Thr Val
        690             695             700

Lys Ile Pro Lys Cys Cys Lys Gly Phe Tyr Gly Pro Asp Cys Asn Gln
705             710             715             720

Cys Pro Gly Gly Phe Ser Asn Pro Cys Ser Gly Asn Gly Gln Cys Ala
            725             730             735

Asp Ser Leu Gly Gly Asn Gly Thr Cys Ile Cys Glu Glu Gly Phe Gln
        740             745             750

Gly Ser Gln Cys Gln Phe Cys Ser Asp Pro Asn Lys Tyr Gly Pro Arg
        755             760             765

Cys Asn Lys Lys Cys Leu Cys Val His Gly Thr Cys Asn Asn Arg Ile
770             775             780

Asp Ser Asp Gly Ala Cys Leu Thr Gly Thr Cys Arg Asp Gly Ser Ala
785             790             795             800

Gly Arg Leu Cys Asp Lys Gln Thr Ser Ala Cys Gly Pro Tyr Val Gln
            805             810             815

Phe Cys His Ile His Ala Thr Cys Glu Tyr Ser Asn Gly Thr Ala Ser
        820             825             830

Cys Ile Cys Lys Ala Gly Tyr Glu Gly Asp Gly Thr Leu Cys Ser Glu
        835             840             845
```

-continued

Met Asp Pro Cys Thr Gly Leu Thr Pro Gly Gly Cys Ser Arg Asn Ala
850                 855                 860

Glu Cys Ile Lys Thr Gly Thr Gly Thr His Thr Cys Val Cys Gln Gln
865                 870                 875                 880

Gly Trp Thr Gly Asn Gly Arg Asp Cys Ser Glu Ile Asn Asn Cys Leu
            885                 890                 895

Leu Pro Ser Ala Gly Gly Cys His Asp Asn Ala Ser Cys Leu Tyr Val
            900                 905                 910

Gly Pro Gly Gln Asn Glu Cys Glu Cys Lys Lys Gly Phe Arg Gly Asn
            915                 920                 925

Gly Ile Asp Cys Glu Pro Ile Thr Ser Cys Leu Glu Gln Thr Gly Lys
            930                 935                 940

Cys His Pro Leu Ala Ser Cys Gln Ser Thr Ser Ser Gly Val Trp Ser
945                 950                 955                 960

Cys Val Cys Gln Glu Gly Tyr Glu Gly Asp Gly Phe Leu Cys Tyr Gly
            965                 970                 975

Asn Ala Ala Val Glu Leu Ser Phe Leu Ser Glu Ala Ala Ile Phe Asn
            980                 985                 990

Arg Trp Ile Asn Asn Ala Ser Leu Gln Pro Thr Leu Ser Ala Thr Ser
            995                 1000                1005

Asn Leu Thr Val Leu Val Pro Ser Gln Gln Ala Thr Glu Asp Met
            1010            1015            1020

Asp Gln Asp Glu Lys Ser Phe Trp Leu Ser Gln Ser Asn Ile Pro
            1025            1030            1035

Ala Leu Ile Lys Tyr His Met Leu Leu Gly Thr Tyr Arg Val Ala
            1040            1045            1050

Asp Leu Gln Thr Leu Ser Ser Ser Asp Met Leu Ala Thr Ser Leu
            1055            1060            1065

Gln Gly Asn Phe Leu His Leu Ala Lys Val Asp Gly Asn Ile Thr
            1070            1075            1080

Ile Glu Gly Ala Ser Ile Val Asp Gly Asp Asn Ala Ala Thr Asn
            1085            1090            1095

Gly Val Ile His Ile Ile Asn Lys Val Leu Val Pro Gln Arg Arg
            1100            1105            1110

Leu Thr Gly Ser Leu Pro Asn Leu Leu Met Arg Leu Glu Gln Met
            1115            1120            1125

Pro Asp Tyr Ser Ile Phe Arg Gly Tyr Ile Ile Gln Tyr Asn Leu
            1130            1135            1140

Ala Asn Ala Ile Glu Ala Ala Asp Ala Tyr Thr Val Phe Ala Pro
            1145            1150            1155

Asn Asn Asn Ala Ile Glu Asn Tyr Ile Arg Glu Lys Lys Val Leu
            1160            1165            1170

Ser Leu Glu Glu Asp Val Leu Arg Tyr His Val Val Leu Glu Glu
            1175            1180            1185

Lys Leu Leu Lys Asn Asp Leu His Asn Gly Met His Arg Glu Thr
            1190            1195            1200

Met Leu Gly Phe Ser Tyr Phe Leu Ser Phe Phe Leu His Asn Asp
            1205            1210            1215

Gln Leu Tyr Val Asn Glu Ala Pro Ile Asn Tyr Thr Asn Val Ala
            1220            1225            1230

Thr Asp Lys Gly Val Ile His Gly Leu Gly Lys Val Leu Glu Ile
            1235            1240            1245

-continued

```
Gln Lys Asn Arg Cys Asp Asn Asn Asp Thr Thr Ile Ile Arg Gly
    1250                1255                1260

Arg Cys Arg Thr Cys Ser Ser Glu Leu Thr Cys Pro Phe Gly Thr
    1265                1270                1275

Lys Ser Leu Gly Asn Glu Lys Arg Arg Cys Ile Tyr Thr Ser Tyr
    1280                1285                1290

Phe Met Gly Arg Arg Thr Leu Phe Ile Gly Cys Gln Pro Lys Cys
    1295                1300                1305

Val Arg Thr Val Ile Thr Arg Glu Cys Cys Ala Gly Phe Phe Gly
    1310                1315                1320

Pro Gln Cys Gln Pro Cys Pro Gly Asn Ala Gln Asn Val Cys Phe
    1325                1330                1335

Gly Asn Gly Ile Cys Leu Asp Gly Val Asn Gly Thr Gly Val Cys
    1340                1345                1350

Glu Cys Gly Glu Gly Phe Ser Gly Thr Ala Cys Glu Thr Cys Thr
    1355                1360                1365

Glu Gly Lys Tyr Gly Ile His Cys Asp Gln Ala Cys Ser Cys Val
    1370                1375                1380

His Gly Arg Cys Asn Gln Gly Pro Leu Gly Asp Gly Ser Cys Asp
    1385                1390                1395

Cys Asp Val Gly Trp Arg Gly Val His Cys Asp Asn Ala Thr Thr
    1400                1405                1410

Glu Asp Asn Cys Asn Gly Thr Cys His Thr Ser Ala Asn Cys Leu
    1415                1420                1425

Thr Asn Ser Asp Gly Thr Ala Ser Cys Lys Cys Ala Ala Gly Phe
    1430                1435                1440

Gln Gly Asn Gly Thr Ile Cys Thr Ala Ile Asn Ala Cys Glu Ile
    1445                1450                1455

Ser Asn Gly Gly Cys Ser Ala Lys Ala Asp Cys Lys Arg Thr Thr
    1460                1465                1470

Pro Gly Arg Arg Val Cys Thr Cys Lys Ala Gly Tyr Thr Gly Asp
    1475                1480                1485

Gly Ile Val Cys Leu Glu Ile Asn Pro Cys Leu Glu Asn His Gly
    1490                1495                1500

Gly Cys Asp Lys Asn Ala Glu Cys Thr Gln Thr Gly Pro Asn Gln
    1505                1510                1515

Ala Ala Cys Asn Cys Leu Pro Ala Tyr Thr Gly Asp Gly Lys Val
    1520                1525                1530

Cys Thr Leu Ile Asn Val Cys Leu Thr Lys Asn Gly Gly Cys Ser
    1535                1540                1545

Glu Phe Ala Ile Cys Asn His Thr Gly Gln Val Glu Arg Thr Cys
    1550                1555                1560

Thr Cys Lys Pro Asn Tyr Ile Gly Asp Gly Phe Thr Cys Arg Gly
    1565                1570                1575

Ser Ile Tyr Gln Glu Leu Pro Lys Asn Pro Lys Thr Ser Gln Tyr
    1580                1585                1590

Phe Phe Gln Leu Gln Glu His Phe Val Lys Asp Leu Val Gly Pro
    1595                1600                1605

Gly Pro Phe Thr Val Phe Ala Pro Leu Ser Ala Ala Phe Asp Glu
    1610                1615                1620

Glu Ala Arg Val Lys Asp Trp Asp Lys Tyr Gly Leu Met Pro Gln
    1625                1630                1635

Val Leu Arg Tyr His Val Val Ala Cys His Gln Leu Leu Leu Glu
```

```
                    1640                1645                 1650

Asn Leu Lys Leu Ile Ser Asn Ala Thr Ser Leu Gln Gly Glu Pro
        1655                1660                 1665

Ile Val Ile Ser Val Ser Gln Ser Thr Val Tyr Ile Asn Asn Lys
        1670                1675                 1680

Ala Lys Ile Ile Ser Ser Asp Ile Ile Ser Thr Asn Gly Ile Val
        1685                1690                 1695

His Ile Ile Asp Lys Leu Leu Ser Pro Lys Asn Leu Leu Ile Thr
        1700                1705                 1710

Pro Lys Asp Asn Ser Gly Arg Ile Leu Gln Asn Leu Thr Thr Leu
        1715                1720                 1725

Ala Thr Asn Asn Gly Tyr Ile Lys Phe Ser Asn Leu Ile Gln Asp
        1730                1735                 1740

Ser Gly Leu Leu Ser Val Ile Thr Asp Pro Ile His Thr Pro Val
        1745                1750                 1755

Thr Leu Phe Trp Pro Thr Asp Gln Ala Leu His Ala Leu Pro Ala
        1760                1765                 1770

Glu Gln Gln Asp Phe Leu Phe Asn Gln Asp Asn Lys Asp Lys Leu
        1775                1780                 1785

Lys Glu Tyr Leu Lys Phe His Val Ile Arg Asp Ala Lys Val Leu
        1790                1795                 1800

Ala Val Asp Leu Pro Thr Ser Thr Ala Trp Lys Thr Leu Gln Gly
        1805                1810                 1815

Ser Glu Leu Ser Val Lys Cys Gly Ala Gly Arg Asp Ile Gly Asp
        1820                1825                 1830

Leu Phe Leu Asn Gly Gln Thr Cys Arg Ile Val Gln Arg Glu Leu
        1835                1840                 1845

Leu Phe Asp Leu Gly Val Ala Tyr Gly Ile Asp Cys Leu Leu Ile
        1850                1855                 1860

Asp Pro Thr Leu Gly Gly Arg Cys Asp Thr Phe Thr Thr Phe Asp
        1865                1870                 1875

Ala Ser Gly Glu Cys Gly Ser Cys Val Asn Thr Pro Ser Cys Pro
        1880                1885                 1890

Arg Trp Ser Lys Pro Lys Gly Val Lys Gln Lys Cys Leu Tyr Asn
        1895                1900                 1905

Leu Pro Phe Lys Arg Asn Leu Glu Gly Cys Arg Glu Arg Cys Ser
        1910                1915                 1920

Leu Val Ile Gln Ile Pro Arg Cys Cys Lys Gly Tyr Phe Gly Arg
        1925                1930                 1935

Asp Cys Gln Ala Cys Pro Gly Gly Pro Asp Ala Pro Cys Asn Asn
        1940                1945                 1950

Arg Gly Val Cys Leu Asp Gln Tyr Ser Ala Thr Gly Glu Cys Lys
        1955                1960                 1965

Cys Asn Thr Gly Phe Asn Gly Thr Ala Cys Glu Met Cys Trp Pro
        1970                1975                 1980

Gly Arg Phe Gly Pro Asp Cys Leu Pro Cys Gly Cys Ser Asp His
        1985                1990                 1995

Gly Gln Cys Asp Asp Gly Ile Thr Gly Ser Gly Gln Cys Leu Cys
        2000                2005                 2010

Glu Thr Gly Trp Thr Gly Pro Ser Cys Asp Thr Gln Ala Val Leu
        2015                2020                 2025

Pro Ala Val Cys Thr Pro Pro Cys Ser Ala His Ala Thr Cys Lys
        2030                2035                 2040
```

-continued

```
Glu Asn Asn Thr Cys Glu Cys Asn Leu Asp Tyr Glu Gly Asp Gly
2045                2050                2055

Ile Thr Cys Thr Val Val Asp Phe Cys Lys Gln Asp Asn Gly Gly
2060                2065                2070

Cys Ala Lys Val Ala Arg Cys Ser Gln Lys Gly Thr Lys Val Ser
2075                2080                2085

Cys Ser Cys Gln Lys Gly Tyr Lys Gly Asp Gly His Ser Cys Thr
2090                2095                2100

Glu Ile Asp Pro Cys Ala Asp Gly Leu Asn Gly Gly Cys His Glu
2105                2110                2115

His Ala Thr Cys Lys Met Thr Gly Pro Gly Lys His Lys Cys Glu
2120                2125                2130

Cys Lys Ser His Tyr Val Gly Asp Gly Leu Asn Cys Glu Pro Glu
2135                2140                2145

Gln Leu Pro Ile Asp Arg Cys Leu Gln Asp Asn Gly Gln Cys His
2150                2155                2160

Ala Asp Ala Lys Cys Val Asp Leu His Phe Gln Asp Thr Thr Val
2165                2170                2175

Gly Val Phe His Leu Arg Ser Pro Leu Gly Gln Tyr Lys Leu Thr
2180                2185                2190

Phe Asp Lys Ala Arg Glu Ala Cys Ala Asn Glu Ala Ala Thr Met
2195                2200                2205

Ala Thr Tyr Asn Gln Leu Ser Tyr Ala Gln Lys Ala Lys Tyr His
2210                2215                2220

Leu Cys Ser Ala Gly Trp Leu Glu Thr Gly Arg Val Ala Tyr Pro
2225                2230                2235

Thr Ala Phe Ala Ser Gln Asn Cys Gly Ser Gly Val Val Gly Ile
2240                2245                2250

Val Asp Tyr Gly Pro Arg Pro Asn Lys Ser Glu Met Trp Asp Val
2255                2260                2265

Phe Cys Tyr Arg Met Lys Asp Val Asn Cys Thr Cys Lys Val Gly
2270                2275                2280

Tyr Val Gly Asp Gly Phe Ser Cys Ser Gly Asn Leu Leu Gln Val
2285                2290                2295

Leu Met Ser Phe Pro Ser Leu Thr Asn Phe Leu Thr Glu Val Leu
2300                2305                2310

Ala Tyr Ser Asn Ser Ser Ala Arg Gly Arg Ala Phe Leu Glu His
2315                2320                2325

Leu Thr Asp Leu Ser Ile Arg Gly Thr Leu Phe Val Pro Gln Asn
2330                2335                2340

Ser Gly Leu Gly Glu Asn Glu Thr Leu Ser Gly Arg Asp Ile Glu
2345                2350                2355

His His Leu Ala Asn Val Ser Met Phe Phe Tyr Asn Asp Leu Val
2360                2365                2370

Asn Gly Thr Thr Leu Gln Thr Arg Leu Gly Ser Lys Leu Leu Ile
2375                2380                2385

Thr Ala Ser Gln Asp Pro Leu Gln Pro Thr Glu Thr Arg Phe Val
2390                2395                2400

Asp Gly Arg Ala Ile Leu Gln Trp Asp Ile Phe Ala Ser Asn Gly
2405                2410                2415

Ile Ile His Val Ile Ser Arg Pro Leu Lys Ala Pro Pro Ala Pro
2420                2425                2430
```

```
Val Thr Leu Thr His Thr Gly Leu Gly Ala Gly Ile Phe Phe Ala
    2435            2440                2445

Ile Ile Leu Val Thr Gly Ala Val Ala Leu Ala Ala Tyr Ser Tyr
    2450            2455                2460

Phe Arg Ile Asn Arg Arg Thr Ile Gly Phe Gln His Phe Glu Ser
    2465            2470                2475

Glu Glu Asp Ile Asn Val Ala Ala Leu Gly Lys Gln Gln Pro Glu
    2480            2485                2490

Asn Ile Ser Asn Pro Leu Tyr Glu Ser Thr Thr Ser Ala Pro Pro
    2495            2500                2505

Glu Pro Ser Tyr Asp Pro Phe Thr Asp Ser Glu Glu Arg Gln Leu
    2510            2515                2520

Glu Gly Asn Asp Pro Leu Arg Thr Leu
    2525            2530

<210> SEQ ID NO 99
<211> LENGTH: 94
<212> TYPE: PRT
<213> ORGANISM: Homo sapiens

<400> SEQUENCE: 99

Gly Val Phe His Leu Arg Ser Pro Leu Gly Gln Tyr Lys Leu Thr Phe
1               5                   10                  15

Asp Lys Ala Arg Glu Ala Cys Ala Asn Glu Ala Ala Thr Met Ala Thr
                20                  25                  30

Tyr Asn Gln Leu Ser Tyr Ala Gln Lys Ala Lys Tyr His Leu Cys Ser
            35                  40                  45

Ala Gly Trp Leu Glu Thr Gly Arg Val Ala Tyr Pro Thr Ala Phe Ala
        50                  55                  60

Ser Gln Asn Cys Gly Ser Gly Val Val Gly Ile Val Asp Tyr Gly Pro
65                  70                  75                  80

Arg Pro Asn Lys Ser Glu Met Trp Asp Val Phe Cys Tyr Arg
                85                  90
```